(12) United States Patent
Barbero Calzado et al.

(10) Patent No.: US 11,207,397 B2
(45) Date of Patent: *Dec. 28, 2021

(54) VIRUS PURIFICATION

(71) Applicant: Valneva SE, Nantes (FR)

(72) Inventors: Jana Barbero Calzado, Vienna (AT);
Mario Nebenführ, Vienna (AT);
Robert Schiegl, Siegenfeld (AT);
Michael Weber, Vienna (AT); Jürgen Heindl-Wruss, Vienna (AT)

(73) Assignee: Valneva SE, Nantes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/702,764

(22) Filed: Dec. 4, 2019

(65) Prior Publication Data

US 2020/0197506 A1 Jun. 25, 2020

Related U.S. Application Data

(63) Continuation of application No. 16/062,245, filed as application No. PCT/EP2016/082662 on Dec. 23, 2016, now Pat. No. 10,537,630.

(30) Foreign Application Priority Data

| Dec. 23, 2015 | (EP) | ................................. 15202585 |
| Mar. 18, 2016 | (EP) | ................................. 16161068 |
| Jun. 23, 2016 | (EP) | ................................. 16176025 |
| Jun. 23, 2016 | (EP) | ................................. 16176049 |
| Aug. 4, 2016 | (EP) | ................................. 16182845 |

(51) Int. Cl.

| *C12N 7/02* | (2006.01) |
| *C12N 7/06* | (2006.01) |
| *A61K 39/39* | (2006.01) |
| *A61P 31/14* | (2006.01) |
| *A61K 39/12* | (2006.01) |
| *C07K 14/18* | (2006.01) |
| *C12N 7/00* | (2006.01) |
| *A61K 39/00* | (2006.01) |

(52) U.S. Cl.
CPC .............. *A61K 39/12* (2013.01); *A61K 39/39* (2013.01); *A61P 31/14* (2018.01); *C07K 14/18* (2013.01); *C07K 14/1825* (2013.01); *C12N 7/00* (2013.01); *C12N 7/02* (2013.01); *C12N 7/06* (2013.01); *A61K 2039/5252* (2013.01); *A61K 2039/5254* (2013.01); *A61K 2039/5258* (2013.01); *A61K 2039/55505* (2013.01); *C12N 2770/24134* (2013.01); *C12N 2770/24151* (2013.01); *C12N 2770/24163* (2013.01); *Y02A 50/30* (2018.01)

(58) Field of Classification Search
CPC ........ A61K 2039/5254; A61K 2236/53; A61K 2300/00; A61K 45/06; A61K 39/12; G01N 2333/185; G01N 2333/183; B01D 15/361; B01D 15/3804

See application file for complete search history.

(56) References Cited

U.S. PATENT DOCUMENTS

| 6,309,650 | B1 | 10/2001 | Kim et al. |
| 7,871,814 | B2 | 1/2011 | Andino-Pavlovsky et al. |
| 8,765,148 | B2 | 7/2014 | Wizel et al. |
| 8,865,184 | B2* | 10/2014 | Ella ...................... C07K 14/005 |
| | | | 424/218.1 |
| 9,499,588 | B2 | 11/2016 | Mason et al. |
| 10,086,061 | B2 | 10/2018 | Thomas et al. |
| 10,537,630 | B2* | 1/2020 | Calzado .................. A61P 31/14 |
| 10,660,950 | B2* | 5/2020 | Calzado ............. C07K 14/1825 |
| 2011/0171249 | A1 | 7/2011 | Frolov et al. |
| 2018/0362936 | A1 | 12/2018 | Calzado et al. |
| 2018/0362937 | A1 | 12/2018 | Calzado et al. |
| 2018/0369359 | A1 | 12/2018 | Calzado et al. |
| 2018/0371027 | A1 | 12/2018 | Calzado et al. |
| 2019/0008945 | A1 | 1/2019 | Calzado et al. |
| 2020/0368342 | A1 | 11/2020 | Calzado et al. |

FOREIGN PATENT DOCUMENTS

| CN | 105749268 A | 7/2016 |
| WO | WO 1999/011762 A1 | 3/1999 |
| WO | WO 2001/092552 A2 | 12/2001 |
| WO | WO 2013/083726 A1 | 6/2013 |
| WO | WO 2016/145149 A1 | 9/2016 |
| WO | WO 2017/109225 A1 | 6/2017 |

OTHER PUBLICATIONS

Powers et al. Journal of General Virology, 2000, vol. 81, pp. 471-479.*
PCT/EP2016/082663, Jul. 5, 2018, International Preliminary Report and Patentability.
PCT/EP2016/082663, Apr. 19, 2017, International Search Report and Written Opinion.
PCT/EP2016/082662, Jul. 5, 2018, International Preliminary Report and Patentability.
PCT/EP2016/082662, Apr. 18, 2018, International Search Report and Written Opinion.
[No Author Listed] Centers for Disease Control and Prevention. Ingredients of vaccines fact sheet; continuously updated; https://www.cdc.gov/vaccines/vac-gen/additives.htm.
[No Author Listed] Japanese Encephalitis Vaccine. Centers for Disease Control and Prevention, 2016. Retrieved from https://www.cdc.gov/japaneseencephalitis/vaccine/on Jun. 16, 2016.

(Continued)

*Primary Examiner* — Bao Q Li
(74) *Attorney, Agent, or Firm* — Wolf, Greenfield & Sacks, P.C.

(57) ABSTRACT

Described herein are improved purification methods for virus vaccines and compositions. Also described are Zika, Chikungunya, dengue and yellow fever vaccines and methods of producing and administering said vaccines to subjects in need thereof.

12 Claims, 35 Drawing Sheets

Specification includes a Sequence Listing.

(56) References Cited

OTHER PUBLICATIONS

[No Author Listed] Pan-American Health Organization, 2015. Number of Reported Cases of Chikungunya Fever in the Americas, by Country or Territory 2013-2014. Cumulative Cases (Updated Oct. 23, 2015).
[No Author Listed] Protamine sulfate. Wikimedia Foundation, Inc., 2015. Retrieved from https://en.wikipedia.org/wiki/Protamine_sulfate; updated Sep. 30, 2015 on Nov. 26, 2015.
[No Author Listed] Valneva Announces Successful Generation of a Highly-purified Zika Vaccine Candidate Using its FDA-EMA Approved Japanese Encephalitis Platform. Press release. Jul. 7, 2016.
[No Author Listed] Valneva Reports Excellent Final Phase 1 Results for its Chikungunya Vaccine Candidate, Confirms Plans. Press release. Nov. 18, 2019.
[No Author Listed] World Health Organization, 2016 Zika Situation Report Feb. 5, 2016.
[No Author Listed] World Health Organization, 2016 Zika Virus Fact Sheet 2016. Retrieved from http://www.who.int/mediacentre/factsheets/zika/en/ on Mar. 11, 2016.
[No Author Listed] Zika virus, strain H/PF/2013. European virus archive, 2016.
Abbink et al., Durability and correlates of vaccine protection against Zika virus in rhesus monkeys. Sci. Transl. Med. 2017;9:eaao4163.
Altschul et al., Basic Local Alignment Search Tool. J. Mol. Biol. 1990;215:403-410.
Altschul et al., Gapped BLAST and PSI-BLAST: a new generation of protein database search programs. Nuc. Acids Res. 1997;25(17):3389-3402.
Baronti et al., Complete Coding Sequence of Zika Virus from a French Polynesia Outbreak in 2013. Genome Announc. May-Jun. 2014; 2(3):e00500-14. Abstract.
Bender et al., Zika Virus Vaccine Candidate VLA1601: Cooperation VALNEVA & EMERGENT. Presentation at World Vaccine Congress Apr. 4, 2018.
Cohen, Infectious Disease. The race for a Zika vaccine is on. Science. Feb. 5, 2016; 351(6273):543-4. doi: 10.1126/science.351.6273.543.
Cox et al., Predicting Zika virus structural biology: Challenges and opportunities for intervention. Antivir Chem Chemother. Aug. 2015;24(3-4): 118-26. doi: 10.1177/2040206616653873. Epub Jun. 13, 2016.
Dowall et al., A susceptible mouse model for Zika virus infection. PLOS Neglected Tropical Diseases.10(5):e0004658. May 5, 2016. DOI:10.1371/journal.pntd.0004658.
Fritsche et al., Vaccine hypersensitivity—update and overview. Swiss Med Wkly. 2010;140(17-18):238-246.
Gardner et al., Deliberate Attenuation of Chikungunya Virus by Adaptation to Heparan Sulfate-Dependent Infectivity: A Model of Rational Arboviral Vaccine Design. PLOS Neglected Tropical Diseases. 2014;8(2):e2719.
Geradin et al., Chikungunya virus-associated encephalitis: A cohort study on La Réunion Island. 2005-2009. Neurology. 86(1):94-102.
Gubler et al., Fields Virology. Knipe DM, Howley PM, editors. Lippincott-Raven Publishers; Philadelphia: 2007:1153-1252.
Haddow et al., Genetic Characterization of Zika Virus Strains: Geographic Expansion of the Asian Lineage. PLoS Negl Trop Dis 6(2): e1477. doi:10.1371/journal.pntd.0001477.
Hallengard et al., Novel Attenuated Chikungunya Vaccine Candidates Elicit Protective Immunity in C57BL/6 mice. J. Virology 88(5):2858-2866.
Hallengard et al., Prime-Boost Immunization Strategies against Chikungunya Virus. J. Virology. 88(22): 13333-13343.
Hombach et al., Report on a WHO consultation on immunological endpoints for evaluation of new Japanese encephalitis vaccines, WHO, Geneva, Sep. 2-3, 2004. Vaccine. 2005; 23(45):5205-5211.
Hutornojs et al., Comparison of ultracentrifugation methods for concentration of recombinant alphaviruses: sucrose and iodixanol cushions. Environmental Experimental Biology. 2012;10:117-123.
Katoh et al., Recent developments in the MAFFT multiple sequence alignment program. Briefings in Bioinformatics. 2008;9(4):286-298.
Kim et al., Design of Chimeric Alphaviruses with a Programmed, Attenuated, Cell Type-Restricted Phenotype. J Virol. 2011;85(9):4363-4376.
Konishi et al., Studies on structural proteins of Chikungunya Virus. I. Separation of three species of proteins and their preliminary characterization. Microbiol Immunol. 1980;24(5):419-28.
Larkin et al., Clustal W and Clustal X version 2.0. Bioinformatics. 2007;23(21):2947-2948.
Larocca et al., Vaccine protection against Zika virus from Brazil. Nature. 2016;536:474-478. doi:10.1038/nature18952. Methods.
Lindenbach et al., Fields Virology. Knipe DM, Howley PM, editors. Lippincott-Raven Publishers; Philadelphia: 2007;1101-1152.
Malone et al., Zika Virus: Medical Countermeasure Development Challenges. PLoS Negl Trop Dis. 2016;10(3):e0004530. doi:10.1371/journal.pntd.0004530.
Modjarrad et al., Preliminary aggregate safety and immunogenicity results from three trials of a purified inactivated Zika virus vaccine candidate: phase 1, randomised, double-blind, placebo-controlled clinical trials. Dec. 4, 2017.
Monath, Yellow fever: an update. Lancet Infect Dis. 2001;1(1):11-20.
Needleman et al., A general method applicable to the search for similarities in the amino acid sequence of two proteins. J. Mol. Biol. 1970;48(3):443-453.
Patkar et al., Yellow Fever virus NS3 plays an essential role in virus assembly independent of its known enzymatic functions. J Virol. Apr. 2008;82(7):3342-52. doi: 10.1128/JVI.02447-07. Epub Jan. 16, 2008.
Pearson et al., Improved tools for biological sequence comparison. Proc. Natl. Acad. Sci. USA. 1988;85(8):2444-8.
Pellerin, Walter Reed Scientists Test Zika Vaccine Candidate. U.S. Department of Defense. Jun. 9, 2016.
Pinto et al., A Temporal Role of Type I Interferon Signaling in CD8+ T Cell Maturation during Acute West Nile Virus Infection. PLoS Pathog. Dec. 2011;7(12):e1002407.
Plevka et al., Maturation of flaviviruses starts from one or more icosahedrally independent nucleation centres. EMBO reports. 2011;12(6):602-606.
Reed et al., A simple method of estimating fifty percent endpoints. American J Hygiene. May 1938;27:493 497.
Rocha et al., Microcephaly: normality parameters and its determinants in northeastern Brazil: a multicentre prospective cohort study. Bull World Health Organ, E-pub: Feb. 8, 2016. doi:http://dx.doi.org/10.2471/BLT.16.171215.
Rozen-Gagnon et al., Alphavirus Mutator Variants Present Host-Specific Defects and Attenuation in Mammalian and Insect Models, PLOS Pathogens, 10(l):e1003877.
Schlegl et al., Influence of elemental impurities in aluminum hydroxide adjuvant on the stability of inactivated Japanese Encephalitis vaccine, IXIARO®. Vaccine. 2015;33(44):5989-5996.
Shustov et al., Efficient, trans-complementing packaging systems for chimeric, pseudoinfectious dengue 2/yellow fever viruses. Virology. Apr. 25, 2010;400(1):8-17. doi:10.1016/j.virol.2009.12.015.
Simizu et al., Structural Proteins of Chikungunya Virus, J Virol. 1984;51(1): 254-258.
Smith et al., Comparison of Biosequences. Adv. Appl. Math. 1981;2:482-489.
Srivastava et al., A purified inactivated Japanese encephalitis virus vaccine made in vero cells. Vaccine. 2001;19:4557-4565.
Tiwari et al., Assessment of immunogenic potential of Vero adapted formalin inactivated vaccine derived from novel ECSA genotype of Chikungunya virus. Vaccine. Apr. 21, 2009;27(18):2513-22. doi: 10.1016/j.vaccine.2009.02.062. Epub Feb. 27, 2009.
Vega-Rua et al., Chikungunya Virus Transmission Potential by Local Aedes Mosquitoes in the Americas and Europe. PLOS Neglected Tropical Diseases. 2015;9(5):e0003780.
Waterhouse et al., Jalview Version 2—a multiple sequence alignment editor and analysis workbench. Bioinformatics. 2009;25(9):1189-1191.

(56) References Cited

OTHER PUBLICATIONS

Way et al., Comparative Studies of some African Arboviruses in Cell Culture and in Mice, J Gen. Virol. 1976;30:123-130.
Weaver, Arrival of Chikungunya Virus in the New Word: Prospects for Spread and Impact on Public Health. PLoS Negl Trop Dis. 2014;8(6):e2921. doi:10.1371/journal.pntd.0002921.
[No Author Listed], Valneva Reports Further Positive Results for Its Chikungunya Vaccine Candidate. Saint Herblain, France. May 22, 2019. 4 pages.
[No Author Listed], Valneva Reports Positive Phase 1 Interim Results for Its Chikungunya Vaccine Candidate. Saint Herblain, France. Jan. 7, 2019. 4 pages.
Anez et al., Passage of dengue virus type 4 vaccine candidates in fetal rhesus lung cells selects heparin-sensitive variants that result in loss of infectivity and immunogenicity in rhesus macaques. J Virol. Oct. 2009;83(20): 10384-94. doi: 10.1128/JVI.01083-09. Epub Aug. 5, 2009.
Athmaram et al., A two step purification strategy for Chikungunya virions purification using sucrose buoyant density gradient separation. J Virology Res. 2013;2(1):18-21.
Aubry et al., Inactivation of Zika virus in plasma with amotosalen and ultraviolet A illumination. Transfusion. Jan. 2016;56(1):33-40. doi: 10.1111/trf.13271. Epub Aug. 18, 2015.
Bender, Chikungunya Virus Vaccine Candidate Valneva's VLA1553. World Vaccine Conference 2019. Washington, D.C.. Apr. 16, 2019. 43 pages.
Eckels et al., Chikungunya virus vaccine prepared by Tween-ether extraction. Appl Microbiol. Feb. 1970;19(2):321-5.
Roques et al., Attenuated and vectored vaccines protect nonhuman primates against Chikungunya virus. JCI Insight. Mar. 23, 2017;2(6):e83527. doi: 10.1172/jci.insight.83527.

\* cited by examiner

- TEV_virus.NC_001672.1
- YFV_ASIBI.AY640589.1
- YFV_17D_vaccine_strain.NC_002031.1
- YFV_virus_isol-Pasteur_17D-204_yellow_fever_vaccine.X15062.1
- YFV_vaccine_strain_17D-213.U17067.1
- JEV_SA14.D90194.1
- JEV_virus.M55506.1
- JEV_SA14-14-2.AF315119.1
- JEV_SA14-14-2.D90195.1
- JEV_virus.NC_001437.1
- WNV_956.NC_001563.2
- WNV_NY99_isol-385-99.NC_009942.1
- WNV_Chin-01.AY490240.2
- ZVV_MR766-NIID.LC002520.1
- ZVV_MR_766.NC_012532.1
- ZVV_MR_766.AY632535.2
- ZVV_ZikaSPH2015.KU321639.1
- DVV_1.NC_001477.1
- DVV_3_isol-D3%H%IMTSSA-SRI%2000%1266.NC_001475.2
- DVV_16681.NC_001474.2
- DVV_4.NC_002640.1

Fig. 1

```
                  ┌─ TEV_virus.NC_001672.1
                  │
                  │        ┌─ YFV_ASIBI.AY640589.1
                  │        ├─ YFV_17D_vaccine_strain.NC_002031.1
                  │        ├─ YFV_vaccine_strain_17D-213.U17067.1
                  │        └─ YFV_Pasteur_17D-204.X15062.1
                  │
                  │              ┌─ JEV_SA14.D90194.1
                  │              ├─ JEV_virus.M55506.1
                  │              ├─ JEV_SA14-14-2.AF315119.1
                  │              ├─ JEV_SA14-14-2.D90195.1
                  │              └─ JEV_virus.NC_001437.1
                  │
                  │              ┌─ WNV_956.NC_001563.2
                  │              ├─ WNV_NY99_isol-385-99.NC_009942.1
                  │              └─ WNV_Chin-01.AY490240.2
                  │
                  │              ┌─ ZVV_MR766-NIID.LC002520.1
                  │              ├─ ZVV_MR_766.NC_012532.1
                  │              ├─ ZVV_MR_766.AY632535.2
                  │              └─ ZVV_ZikaSPH2015.KU321639.1
                  │
                  │              ┌─ DVV_1.NC_001477.1
                  │              ├─ DVV_3.NC_001475.2
                  │              ├─ DVV_16681.NC_001474.2
                  │              └─ DVV_4.NC_002640.1
```

```
                                    subgenomic
                                    promoter non-structural proteins    structural proteins
CHIKV    | nsP1 | nsP2 | nsP3 | nsP4 |—| C | E3 | E2 | 6K | E1 |

Δ5nsP3   | nsP1 | nsP2 | nsP3 | nsP4 |—| C | E3 | E2 | 6K | E1 |
```

Fig. 9

```
Filtration  → Concentration → DNA         → Batch        → Sucrose       → DS
crude         and buffer     reduction      adsorption     gradient        formulation
harvest       exchange       by             by             centrifugation  and final
Day 1 and                    Protamine      CaptoCore                      0.22 µm
Day 2                        sulfate        700                            filtration
```

Fig. 10

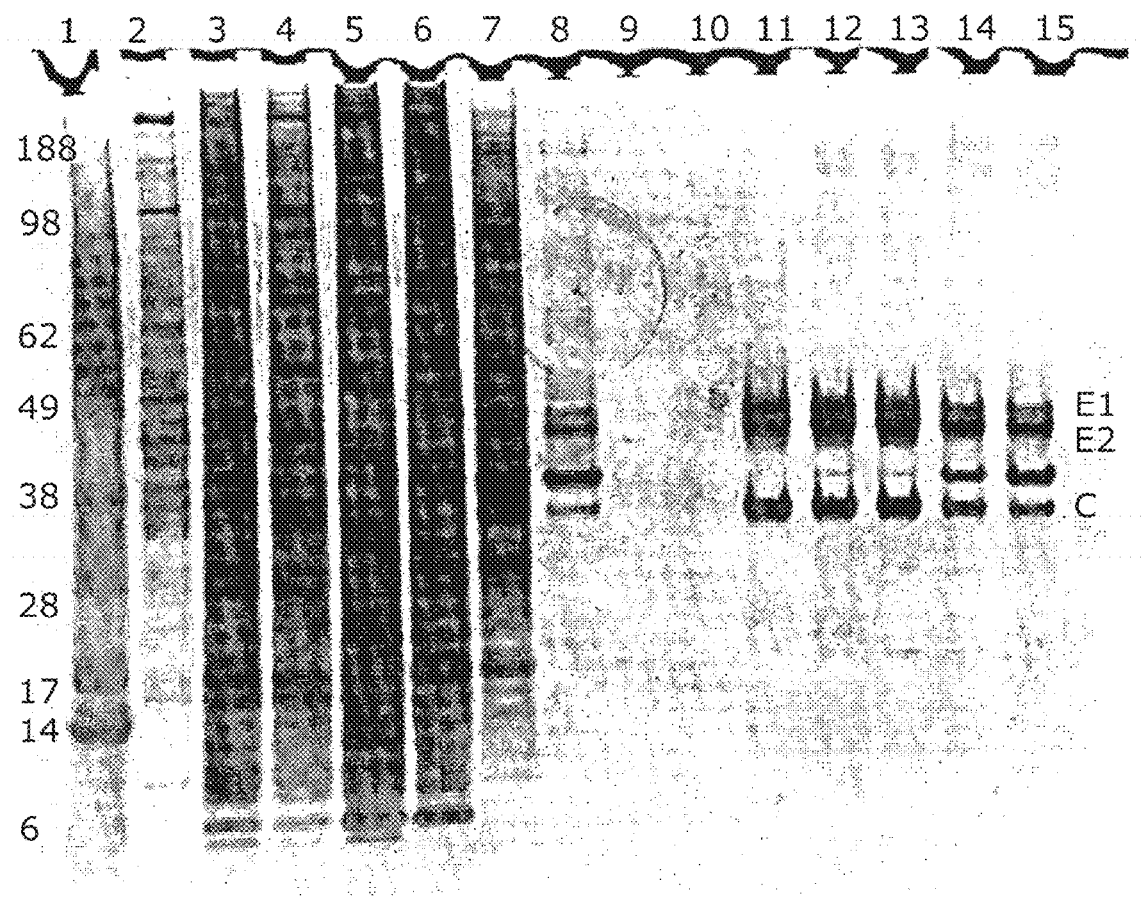

| Lane | Sample |
|------|--------|
| 1 | Marker Seeblueplus2 |
| 2 | CHIKV lot20150812_WVB2015-01_Filtered harvest0.2μ_24hpi |
| 3 | CHIKV lot20150812_WVB2015-01_Filtered harvest0.2μ_48hpi |
| 4 | 20150812_CHIKV_DSP_UF/DF_Load |
| 5 | 20150812_CHIKV_DSP_UF/DF_conc.10x |
| 6 | 20150813_CHIKV_DSP_UF/DF_conc.&dia. 11x |
| 7 | 20150813_CHIKV_DSP_PStreatment |
| 8 | 20150813_CHIKV_DSP_PS&CC700treatment |
| 9 | 20150813_CHIKV_DSP_SGCFrac F5 |
| 10 | 20150813_CHIKV_DSP_SGCFrac F6 |
| 11 | 20150813_CHIKV_DSP_SGCPoolF7-F10 |
| 12 | 20150813_CHIKV_DSP_SGCPoolF7-F11 (final pool) |
| 13 | 20150813_CHIKV_DSP_SGCPoolF7-F12 |
| 14 | 20150813_CHIKV_DSP_SGCFrac F13 |
| 15 | 20150813_CHIKV_DSP_SGCFrac F14 |

VIRUS PURIFICATION

RELATED APPLICATIONS

This application is a continuation of U.S. application Ser. No. 16/062,245, filed Jun. 14, 2018, which is a national stage filing under 35 U.S.C. § 371 of International Patent Application Serial No. PCT/EP2016/082662, filed Dec. 23, 2016, the contents of which is incorporated herein by reference in its entirety.

FIELD OF INVENTION

The disclosure relates to methods for the purification of viruses for use in vaccines and in particular relates to an improved sucrose gradient process step allowing the separation of impurities such as protamine sulphate.

BACKGROUND OF THE INVENTION

Adverse responses to protamine sulfate have been known for many years. Previous exposure to protamine can induce a humoral immune response and predispose susceptible individuals to the development of untoward reactions from the subsequent use of this drug. Patients exposed to protamine through the use of protamine-containing insulin or during heparin neutralization may experience life-threatening reactions and fatal anaphylaxis upon receiving large doses of protamine intravenously. Severe reactions to intravenous protamine can occur in the absence of local or systemic allergic reactions to subcutaneous injection of protamine-containing insulin. Although there is no clear evidence for hypersensitivity reactions of protamine sulphate linked to vaccination, vaccines containing protamine impurities have a precaution and contraindication warning in their labels stating that a serious allergic reaction after a previous dose of such a protamine containing vaccine (e.g. IXIARO®, see CDC site http://www.cdc.gov/japaneseencephalitis/vaccine/) is a contraindication to further doses. Thus elimination of said impurity is a medical request for an improved safety profile. On the other hand protamine sulphate is an excellent tool (and often better than other reagents such as benzonase) to purify crude harvests of viruses grown on cell substrates.

Chikungunya virus (ChikV) is a positive-sense, single-stranded RNA virus from the genus Alphavirus, family Togaviridae. Chikungunya virus disease is mainly an outbreak disease and is associated with high attack rates. The virus is transmitted to humans via a mosquito vector and causes fever, rash, fatigue and severe polyarthralgia. Infections with ChikV generally resolve spontaneously and are not usually fatal, except in rare cases involving CNS infection, where the death rate is from 10-30%. Particularly at risk for ChikV CNS disease are infants under one year and adults over 65 years, with an infection rate of 25-fold and 6-fold higher than the general population, respectively, and with a rate of persistent disabilities estimated at between 30% and 45% (Gerardin, 2016). Furthermore, about 30 percent of all ChikV patients experience arthralgia for months to years after recovery. In some cases, neurological, renal, cardiac, respiratory or hepatic complications can also result.

There are currently no vaccines or medications available for the treatment or prevention of Chikungunya virus disease. Outbreaks in the past have occurred mainly in Africa, but the Central/East/South African (ECSA) genotype has recently expanded its geographical range, resulting in outbreaks in India, Asia, and even temperate Europe (Weaver, S., Arrival of Chikungunya Virus in the New World: Prospects for Spread and Impact on Public Health PLOS Neglected Tropical Diseases (2014) 8(6): e2921). Although ChikV has been repeatedly imported into the Americas since 1995, no autochthonous transmission was reported until 2013 in the Caribbean. By 2015, the epidemic had spread to the mainland and caused more than 1,000,000 suspected cases in 43 countries in the Americas (Pan-American Health Organization (2015) Number of Cumulative Cases of Chikungunya Fever in the Americas). Further epidemics may been aided in part by the spread of the ChikV mosquito vector into non-endemic regions, as well as the ability of ChikV to adapt to local mosquito species (Vega-Rua et al., Chikungunya Virus Transmission Potential by Local Aedes Mosquitoes in the Americas and Europe, May 20, 2015, PLOS Neglected Tropical Diseases DOI:10.1371/journal.pntd.0003780). The high rate of contagion of Chikungunya virus disease, its potential for long-lasting complications, as well as its geographical spread underscore the need for developing preventative measures, such as vaccines.

In 2007, Zika virus was detected for the first time outside of the endemic regions of Asia and Africa since its discovery in a Rhesus monkey in Uganda in 1947. Since then, the virus has caused a large epidemic in French Polynesia, spreading through islands in the Pacific and into South and Central America by 2015 (WHO "Zika Situation Report" Feb. 5, 2016). Evidence suggests that in addition to being transmitted by Aedes species mosquitos, other vectors may exist, and the virus may be transmitted by blood transfusion, transplacentally, and through sexual transmission (WHO Zika Virus Fact Sheet, February 2016). Though the symptoms of Zika virus infection include mild fever, rash, and conjunctivitis, there is a likely correlation between infection and neurological disorders, including Guillain-Barré syndrome and microcephaly in fetuses/neonates subsequent to infection during pregnancy. There is currently no specific treatment or vaccine for Zika virus and the only preventative measures involve control of the mosquito vector. Zika virus presents a substantial public health threat due to the wide circulation of the Aedes mosquito, multiple routes of transmission, and potentially severe neurological effects of infection.

Yellow fever (YF) still represents a constant threat to public health in endemic regions of tropical Africa and South America. The World Health Organization (WHO) estimated that 200,000 cases occur annually with 30,000 fatalities (WHO 2009). Yellow fever virus (YFV), a single-stranded RNA virus, belongs to the family of the Flaviviridae and is transmitted by mosquitoes (Lindenbach B D, Thiel H J, and Rice C M 2007). Yellow fever disease can be divided into three stages. After an incubation period of three to six days, patients develop febrile illness with symptoms like fever, malaise, lower back pain, headache, myalgia, nausea, vomiting, and prostration lasting three to four days. Symptoms disappear for two to forty-eight hours before fifteen to twenty-five percent of the patients enter the third phase, the period of intoxication, characterized by fever, vomiting, epigastric pain, hemorrhagic diathesis, jaundice, and liver and renal failure. Death occurs in twenty to fifty percent of severe YF cases on the seventh to tenth day (Monath 2001; Monath 2004; Gubler, Kuno, and Markoff 2007).

SUMMARY OF THE INVENTION

During the course of virus purification, it was observed that addition of protamine sulfate to a virus harvest produced on a cell substrate removed not only contaminating DNA derived from host cells, as expected, but surprisingly also virtually eliminated immature and otherwise non-infectious virus particles from the preparation. This finding provided a streamlined, gentle, reproducible and broadly-applicable process for obtaining highly-purified infectious virus particles for applications such as vaccine preparation. In addition, it was surprisingly found that said protamine sulfate can be very efficiently separated from the virus fraction allowing for a safer vaccine produced at high yields.

Disclosed herein are virus vaccines and compositions comprising inactivated or attenuated viruses, and related methods of producing said vaccines and compositions. Also provided are methods of administering said virus vaccines for the prevention of virus infection and/or for the production of an anti-virus immune response in subjects, for example subjects at risk of being exposed to virus. In embodiments disclosed herein, "prevention" of a virus infection is equivalent to "protection from" a virus infection; i.e., the vaccine of the invention protects a vaccinated subject from noticeable or serious infection and/or mild or serious sequelae of infection. In particular, the invention is directed to a virus vaccine comprising an optimally inactivated virus particle, wherein the virus particle in an appropriate dose is able to seroconvert a subject that is administered the virus vaccine with at least a 70% probability, preferably an 80% probability; i.e., to confer seroprotection. Another advantage of the invention is that related methods of producing said vaccines and compositions are very efficient and provide pure compositions largely devoid of impurities, in particular protamine sulphate, allowing for high volume production of vaccines. Examples to the above are provided for Zika virus, Chikungunya virus and yellow fever virus.

The herein disclosed in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was unexpectedly higher than the recently reported inactivated Zika virus vaccine candidate (Larocca, et. al, 2016, Nature doi:10.1038/nature18952.). Inactivated viruses are among the safest vaccines and especially preferred for delivery to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Each of the limitations of the invention can encompass various embodiments of the invention. It is therefore anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing, alignments were performed with the multi alignment package Jalview (Waterhouse et al., 2009, Bioinformatics 25 (9) 1189-1191). In the drawings:

FIG. 1: Average distance tree (by % identity, nt), complete genomes.

FIG. 2: Neighbor joining tree (by % identity, nt), complete genomes.

FIG. 6: Pairwise alignment-Jalview (% identity, aa), E-protein.

FIGS. 7A-7C: Alignment (shading: % identity, aa), E-protein.

FIG. 9: Chikungunya virus schematic genome ("CHIKV"), including non-structural (nsP1-4) and structural proteins (C, E3, E2, 6K and E1) as well as a representation of the Δ5nsP3 attenuated Chikungunya virus used to exemplify the purification process of the current invention (labeled "Δ5nsP3"). The black triangle indicates the approximate location of the deletion in the nsP3 coding region. (Figure adapted from Hallengärd et al. 2014, supra.)

FIG. 10: Flow-chart showing an exemplary downstream Δ5nsP3 ChikV virus purification process from the crude harvest to formulation of the (vaccine) drug substance, a preferred embodiment of the process of the invention.

FIGS. 11A-11C: Absorbance at 214 nm, 260 nm and 280 nm of individual sucrose gradient centrifugation (SGC) fractions of a representative purification run of the process of the invention (FIG. 11A); SEC-HPLC analysis of the final pooled fractions containing purified infectious attenuated Δ5nsP3 ChikV virus particles (FIG. 11B); and a silver-stained SDS-PAGE gel showing the protein content of the virus preparation following different steps of the process of the invention (defined in the table below the figure) (FIG. 11C). The sucrose gradient centrifugation (SGC) purified pool consisting of SGC fractions F7-F11 is shown in lane 12.

FIGS. 12A-12B: SEC area (mAU*min; right axis) and TCID$_{50}$ results (log TCID50/mL; left axis) of attenuated Δ5nsP3 ChikV production harvests before and after PS treatment. The grey portions of the bars indicate large losses in SEC area following PS treatment, but no corresponding change in the total number of infectious particles (indicated by black portions of the bars) (FIG. 12A); SEC profile of virus preparation before and after PS addition, showing complete removal of large size virus aggregates by PS treatment as well as a reduction in host cell proteins (HCP) and low molecular weight (LMW) impurities (FIG. 12B).

FIG. 15A: ChikV load material containing 10% sucrose was loaded on top of one 50 (w/w) sucrose layer. Determination of sucrose content in the fractions showed the formation of a linear gradient. SEC showed concentration of ChikV within a sucrose concentration range from 40-30% (w/w) sucrose. PS SEC showed insufficient separation of PS from ChikV. FIG. 15B: ChikV load material containing 10% sucrose was loaded on top of a two layer system consisting of a 50% (w/w) sucrose bottom layer and a second 35% (w/w) sucrose layer. Determination of sucrose content in the fractions showed the formation of a linear gradient. SEC showed concentration of ChikV within a sucrose concentration range from 40-30% (w/w) sucrose. PS SEC showed acceptable separation of PS from ChikV, however a slight overlap is still present. FIG. 15C: ChikV load material containing 10% sucrose was loaded on top of a two layer system consisting of a 50% (w/w) sucrose bottom layer and a second 25% (w/w) sucrose layer. Determination of sucrose content in the fractions showed the formation of a linear gradient. SEC showed concentration of ChikV within a sucrose concentration range from 40-30% (w/w) sucrose. PS SEC showed a good separation of PS from ChikV. FIG. 15D: ChikV load material containing 10% sucrose was loaded on top of a three layer system consisting of a 50% (w/w) sucrose bottom layer as well as a 35% and a 15 (w/w) sucrose layer. Determination of sucrose content in the fractions showed the formation of a linear gradient and SEC showed concentration of ChikV within a sucrose concentration range from 40-30% (w/w) sucrose. PS SEC showed a very good separation of PS and residual contaminants from ChikV. Of the four tested sucrose layer systems the combination of 3 layers (shown in FIG. 16D) showed the best separation of the virus particles from residual contaminants and was therefore used for further DSP development.

DETAILED DESCRIPTION OF THE INVENTION

Figure 3:
FIG. 3: Pairwise alignment-Jalview (% identity, nt), complete genomes.
Figure 4:
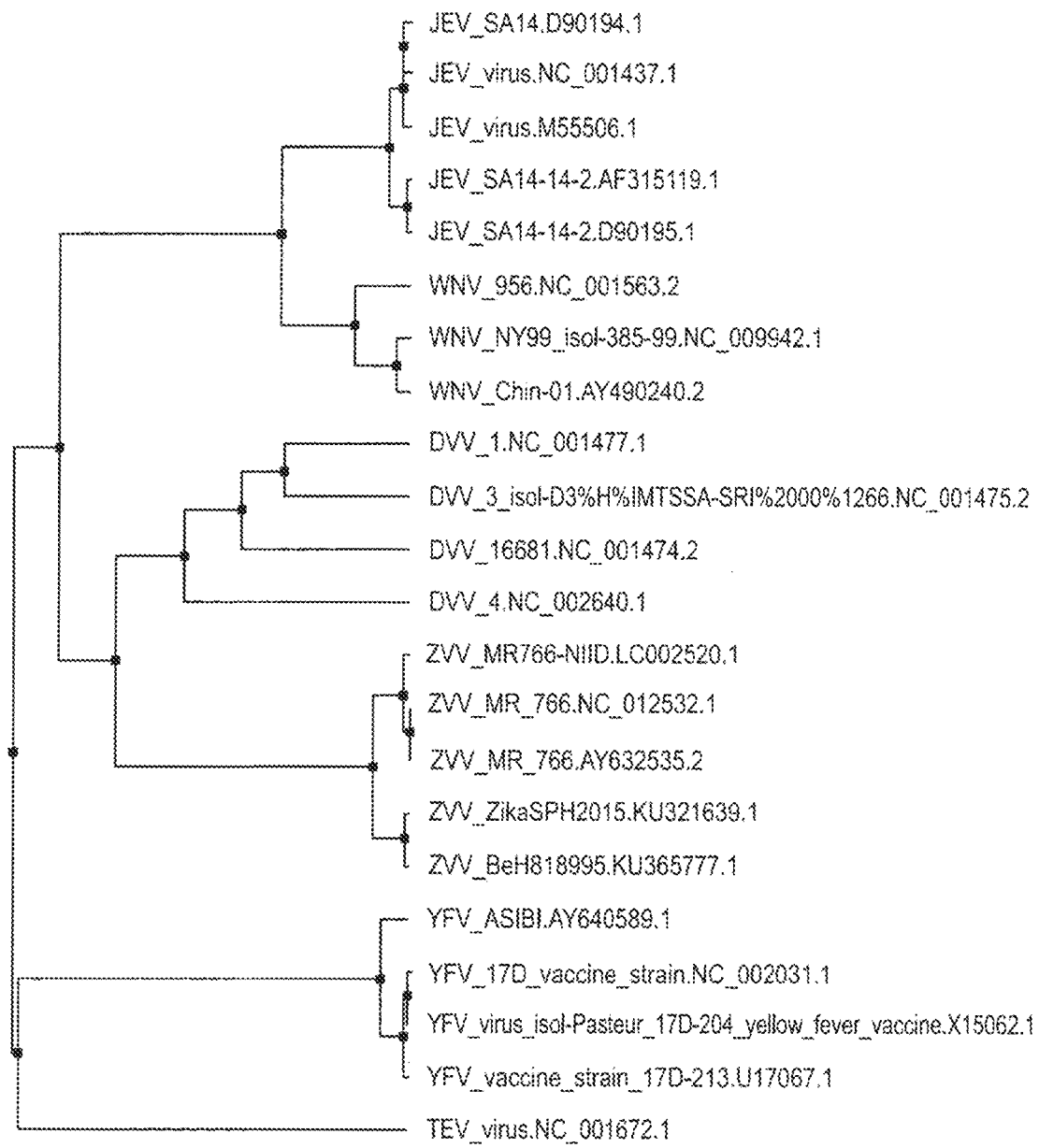
FIG. 4: Average distance tree (by % identity, aa), E-protein.
Figure 5:
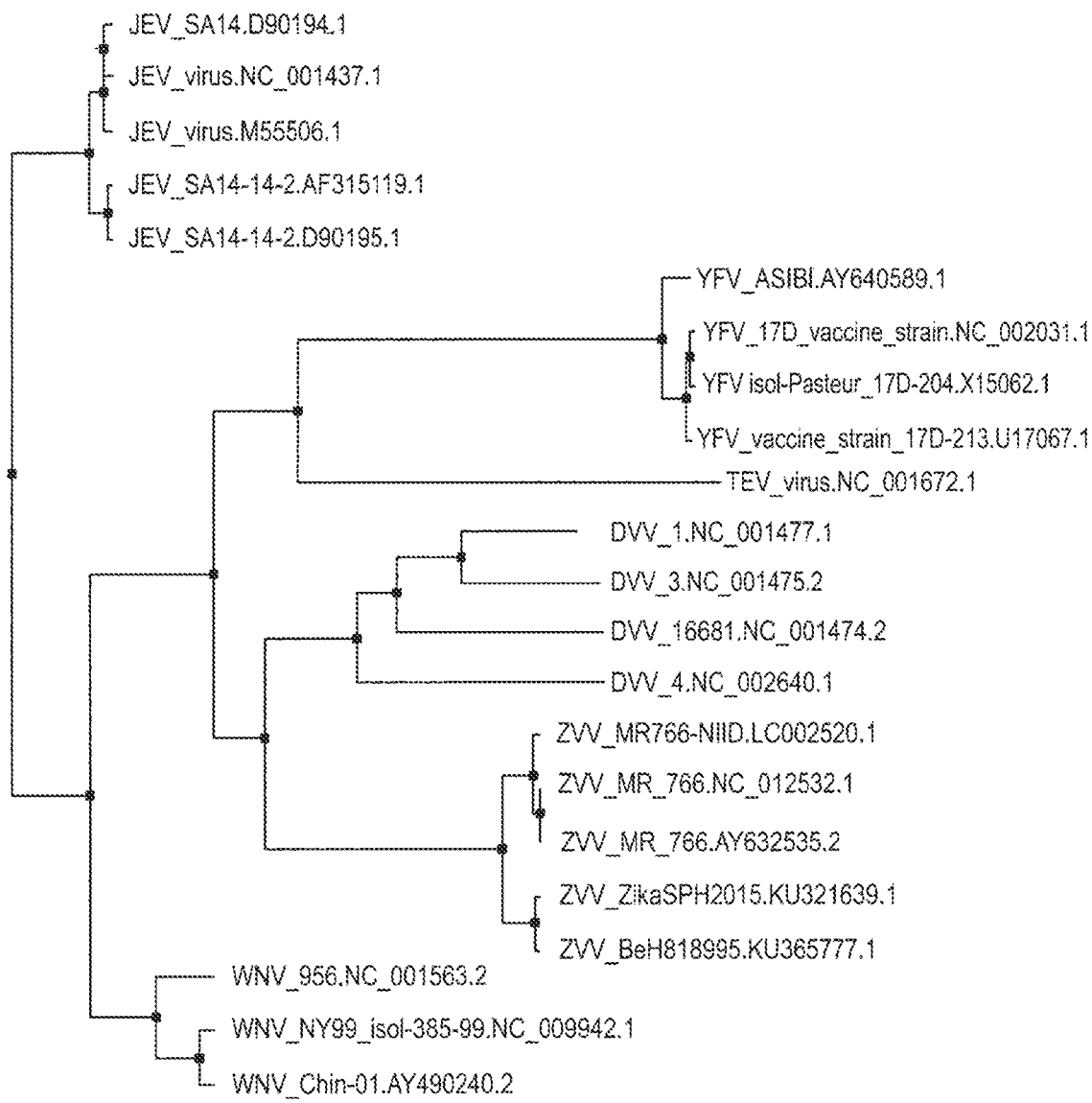
FIG. 5: Neighbor joining tree (by % identity. aa), E-protein.
Figure 8:
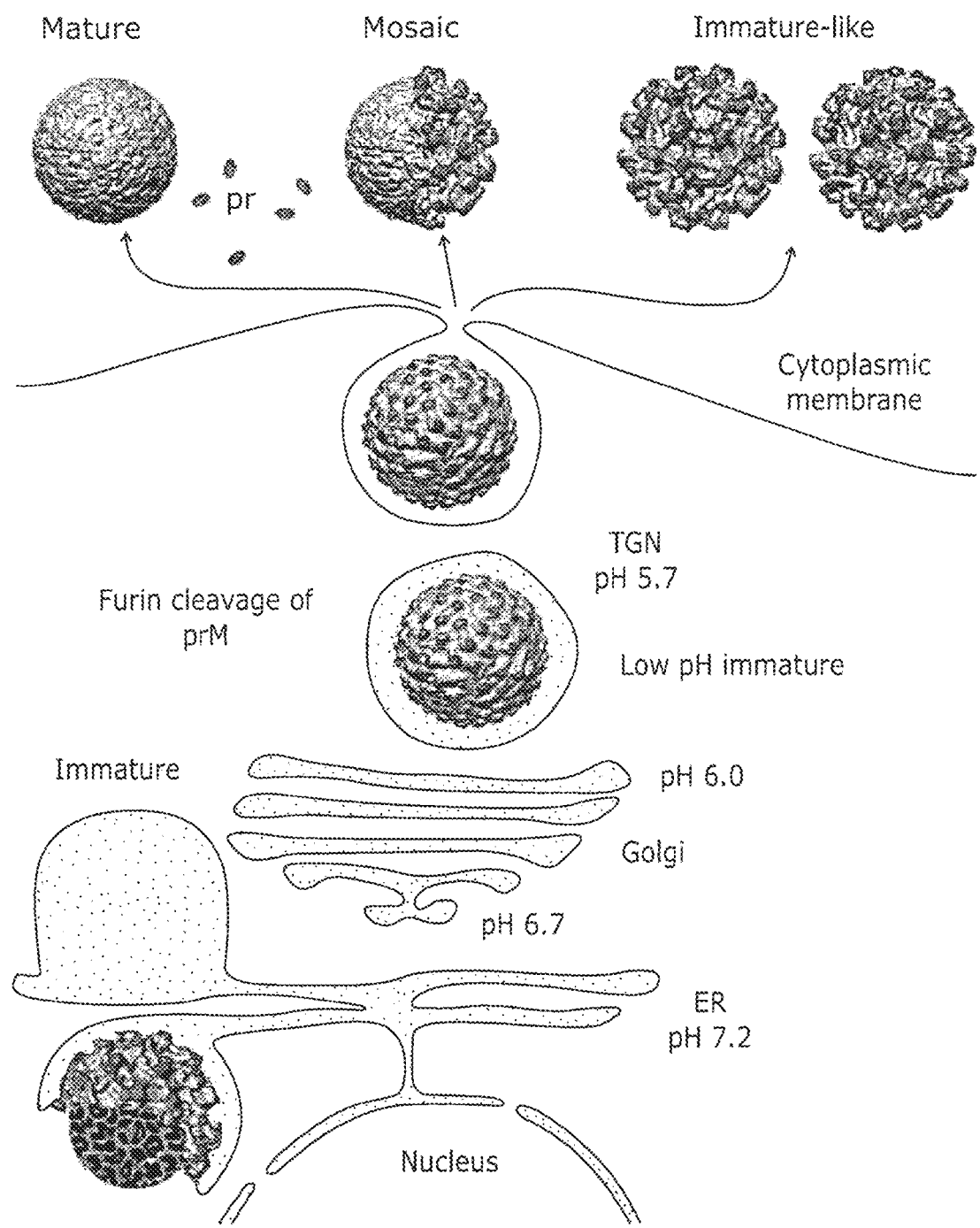
FIG. 8: An example of virus particle maturation in the host cell. As observed in flaviviruses, full maturation of the particles requires proteolytic cleavage of the precursor membrane glycoprotein (prM) by the host protease furin. Not all prM molecules are cleaved, resulting in the release of mature, mosaic or immature-like conformations from the cells. Mosaic and immature forms are generally not infectious—only mature virions are infective and have hemagglutinin (HA)/TCID50 activity. (Figure adapted from Plevka, et al., Maturation of flaviviruses starts from one or more icosahedrally independent nucleation centres, EMBO reports (2011) 12, 602-606).

Disclosed herein are virus vaccines and compositions comprising an inactivated or attenuated virus, and related methods of producing said vaccines and compositions. Also provided are methods of administering said virus vaccines for the prevention of virus infection and/or for the production of an anti-virus immune response in subjects, for example subjects at risk of being exposed to virus. In particular, the invention is directed to a virus vaccine comprising an optimally inactivated or attenuated virus particle, wherein the virus particle in an appropriate dose is able to seroconvert a subject that is administered the virus vaccine with at least a 70% probability, preferably an 80% probability, i.e., is able to confer seroprotection in at least 70% of vaccinated subjects. Another advantage of the invention is that related methods of producing said vaccines and compositions are very efficient and provide pure compositions largely devoid of impurities, in particular protamine sulphate, allowing for high volume production of vaccines. Examples to the above are provided for Zika virus, Chikungunya virus and yellow fever virus.

Disclosed herein are downstream processes for purifying virus particles from a crude preparation. The downstream process can be applied to either a virus which has not adapted for propagation on a particular cell substrate or for a partially/fully cell substrate adapted virus particle.

Aspects of the invention provide processes for the purification of infectious virus particles comprising the steps of (a) providing a crude harvest (a) comprising virus particles and impurities, wherein the impurities are generated from growing said virus particles on a cell substrate; (b) reducing impurities from the crude harvest (a) by precipitation with an agent comprising a protamine salt, preferably a protamine sulphate, to obtain a virus preparation (b); and further purifying the virus preparation (b) by an optimized sucrose density gradient centrifugation to obtain a virus preparation (c) comprising the infectious virus particles.

In some embodiments, the concentration of protamine sulphate in step (b) is about 1 to 10 mg/ml, more preferably about 1 to 5 mg/ml, more preferably about 1 to 2 mg/ml. In one embodiment, the concentration of protamine sulphate in step (b) is about 2 mg/mL. In one embodiment, the concentration of protamine sulphate is 1.2 to 1.8 mg/ml, more preferably 1.4 to 1.6 mg/ml. In a preferred embodiment, the concentration of protamine sulphate in step (b) is about 1.6 mg/ml (for e.g. Chikungunya) or about 2 mg/ml (for e.g. Zika).

In some embodiments, the residual host cell DNA of the virus preparation (c) is less than 1 µg/mL, especially less than 900, 800, 700, 600, 500, 400, 300 or 200 ng/mL, preferably less than 100 ng/mL. In a preferred embodiment, the residual host cell DNA of the virus preparation (c) is less than 10 ng/mL. In some embodiments, the residual host cell protein of the final virus preparation (c) is less than 10 µg/mL, especially less than 9, 8, 7, 6, 5, 4, 3 or 2 µg/mL, preferably less than 1 µg/mL. In a preferred embodiment, the residual host cell protein of the virus preparation (c) is less than 100 ng/mL. In some embodiments, the residual non-infectious virus particles of the final virus preparation (c) is less than 10 µg/mL, especially less than 9, 8, 7, 6, 5, 4, 3 or 2 µg/mL, preferably less than 1 µg/mL. In a preferred embodiment, the residual non-infectious virus particles of the virus preparation (c) is less than 100 ng/mL.

In some embodiments, the residual protamine is less than 1 µg/mL, especially less than 900, 800, 700, 600, 500, 400, 300 or 200 ng/mL, preferably less than 100 ng/mL, more preferably is below the detection limit of HPLC, in particular below the detection limit in the final drug substance. In some embodiments, the PS content is tested by HPLC or size exclusion chromatography (SEC). For example, HPLC is validated for PS determination in JEV sucrose gradient pool samples as a routine release assay and is very sensitive (i.e., LOQ 3 µg/mL; LOD 1 µg/mL). In the current invention, PS content in in virus DS samples was <LOD. In one embodiment, the HPLC assessment of PS content can be performed on a Superdex Peptide 10/300GL column (GE: 17-5176-01) using 30% Acetonitrile, 0.1% Trifluoroacetic acid as solvent with a flow rate of 0.6 ml/min at 25° C. and detection at 214 nm. A more sensitive method of measurement for residual protamine in a purified virus preparation is mass spectrometry (MS). In some embodiments, the residual PS levels in a virus preparation are tested by MS or other such highly sensitive method, e.g. nuclear magnetic resonance (NMR). With this method, residual PS, as well as fragments and/or break-down products of PS, can be detected at trace amounts, such as levels as low as, for example, $10^6$, $10^7$ or $10^8$ molecules per typical sample load. In some embodiments, the PS levels are tested in the sucrose gradient pool. In some embodiments, the PS levels are tested in the drug product. In some embodiments, the PS levels are tested in the drug substance.

In some embodiments, the crude harvest (a) comprising the virus particles and impurities is subjected to one or more pre-purification step(s) prior to step (b). In some embodiments, the one or more pre-purification step(s) comprises digesting host cell genomic DNA in the crude harvest (a) comprising the virus particles and impurities by enzymatic treatment. In some embodiments, the one or more pre-purification step(s) comprises filtration, ultrafiltration, concentration, buffer exchange and/or diafiltration. In some embodiments, the one or more pre-purification steps is filtration using a filter having a pore size equal to or less than 1 µm. In some embodiments, the filter has a pore size equal to or less than 0.2 µm. In a preferred embodiment, the filter has a pore size of 0.2 µm. In some embodiments, the concentration and/or ultra/diafiltration and/or buffer exchange is performed by tangential flow filtration (TFF). In some embodiments, ultra/diafiltration of the crude harvest (a) comprising the virus particles and impurities is performed using a hollow fiber membrane having a cut-off of equal to or less than 300 kDa. In a preferred embodiment, the hollow fiber membrane has a cut-off of about 100 kDa.

The process according to the current invention may also comprise the use of a sucrose gradient, preferably an optimized sucrose gradient. The sucrose gradient is preferably optimized for the removal of protamine sulfate, also for the removal of immature viral particles or other viral particles which are non-infectious or host cell proteins or nucleic acids (DNA, RNA, mRNA, etc) or other host cell debris. In the current invention the optimized sucrose gradient comprises at least two, at least three, at least four layers of sucrose solutions with different densities. In one embodiment, the virus preparation to be purified is provided in a sucrose solution which has a density of about 8%, about 9%, about 10%, about 11%, about 12% sucrose (w/w), preferably about 10%. In one embodiment, one sucrose solution in the gradient has a density of about 45%, about 46%, about 47%, about 48%, about 49%, about 50%, about 51%, about 52%, about 53%, about 54%, about 55% sucrose (w/w), preferably about 50%. In one embodiment, one sucrose solution in the gradient has a density of about 30%, about 31%, about 32%, about 33%, about 34%, about 35%, about 36%, about 37%, about 38%, about 39%, about 40% sucrose (w/w), preferably about 35%. In one embodiment, one sucrose solution in the gradient has a density of about 10%, about 11%, about 12%, about 13%, about 14%, about 15%, about 16%, about 17%, about 18%, about 19%, about 20% sucrose (w/w), preferably about 15% sucrose. In a preferred embodiment, the sucrose gradient comprises three layers of sucrose solutions of about 50%, about 35% and about 15% (w/w) sucrose and the virus composition to be purified is contained in about 10% (w/w) sucrose. Because the invention provided for means to not only test for host cell DNA but also immature viral particles, the skilled person in the art is able to more precisely optimize the sucrose gradient for most efficient purification and include additional tools such as PRNT assay to monitor purification success.

In some embodiments, the virus particle is a live virus, a chimeric virus, an attenuated live virus, a modified live virus, or a recombinant live virus. In a further step, the virus particles of the invention may be optionally inactivated. In some embodiments, the virus particle is an attenuated form of the virus particle. For example, the virus may have reduced infectivity, virulence, and/or replication in a host, as compared to a wild-type virus. In some embodiments, the virus is a mutated or modified virus, for example the nucleic acid of the virus may contain at least one mutation relative to the wild-type virus. In some embodiments, the virus is a recombinant live virus, meaning a virus that is generated recombinantly and may contain nucleic acid from different sources.

In some embodiments, the virus particle is a live virus, an attenuated live virus, a modified live virus, or a recombinant live virus. In some embodiments, the virus belongs to a virus family selected from the group consisting of Paramyxoviridae, Orthomyxoviridae, Flaviviridae, Filoviridae, Arenaviridae, Rhabdoviridae, and Coronaviridae. In some embodiments, the virus belongs to a virus family selected from the group consisting of Togaviridae (being live or inactivated), such as alphaviruses, or Flaviviridae (being live or inactivated). In some embodiments, the virus is a virus of the family Flaviviridae, i.e. a flavivirus. In other embodiments, the virus is a Zika virus or yellow fever virus. In preferred embodiments, the virus is a Zika virus. In a most preferred embodiment, the Zika virus is a Zika virus from the Asian lineage. In a preferred embodiment, the virus is a Chikungunya virus, preferably an attenuated Chikungunya virus. In a most preferred embodiment, the attenuated Chikungunya virus contains a deletion in the non-structural protein 3, such as that provided by e.g. SEQ ID NO: 77. In a preferred embodiment, the virus is a yellow fever virus such as e.g. SEQ ID NO: 76.

In some embodiments, the relative reduction of impurity of the final virus preparation relative to the liquid medium (a) comprising the virus particles and impurities is in a range from 60 to 95%. In some embodiments, the residual impurity of the final virus preparation is less than 1%.

In some embodiments, the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is an EB66 cell line. In a preferred embodiment, said cell line is a Vero cell line.

Aspects of the invention provide a use of any of the processes described herein for manufacturing a composition for immunization against a viral infection. In a preferred embodiment, the composition is a vaccine. In one embodiment, the composition or vaccine is directed against Chikungunya virus, such as an attenuated Chikungunya virus. In one embodiment, the composition or vaccine is directed against a flavivirus. In one embodiment, the composition or vaccine is directed against yellow fever virus. In one embodiment, the composition or vaccine is directed against Zika virus such as e.g. a Zika virus of the Asian lineage.

Other aspects provide compositions comprising the virus particles obtainable by any of the processes described herein for treating and/or preventing a viral infection. In one embodiment, the viral infection is caused by Chikungunya virus. In one embodiment, the viral infection is caused by a flavivirus. In one embodiment, the viral infection is caused by yellow fever virus. In one embodiment, the viral infection is caused by Zika virus such as e.g. a Zika virus of the Asian lineage.

Furthermore, disclosed herein are vaccines and compositions comprising an inactivated Zika virus or yellow fever virus or an attenuated Chikungunya virus and related methods of producing said vaccines and compositions. Also provided are methods of administering the said vaccines for the prevention of Zika, yellow fever or Chikungunya virus infection and/or for the production of an anti-Zika, yellow fever or Chikungunya virus immune response in subjects, for example subjects at risk of being exposed to Zika, yellow fever or Chikungunya virus.

Zika virus is a flavivirus closely related to Dengue virus and is similarly transmitted by the Aedes species mosquito, although other arthropod vectors for Zika virus are possible. Since it was first isolated from a Rhesus monkey in the Zika forest of Uganda in 1947, there were very few reported incidents of human infection, especially outside of the endemic regions of Africa and Asia until a large outbreak in French Polynesia in 2007 (Haddow et al. *PLoS Neglected Tropical Diseases* (2012) 6(2), Malone et al. *PLoS Neglected Tropical Diseases* (2016) 10(3)). The virus has since spread through islands of the Pacific, including Oceania, and into South and Central America (WHO "Zika Situation Report" Feb. 5, 2016).

In addition to being spread by the bite of an infected mosquito, evidence also suggests transmission may occur between individuals, such as from the blood of an infected individual, in utero/transplacental transmission from an infected mother to the fetus, sexual transmission between sexual partners, and possibly by other local transmission routes. There is a possible association between Zika virus infection during pregnancy and microcephaly in the fetus/neonate. Microcephaly is a rare condition in which a baby's head circumference is significantly less than expected based on the average for their age, sex, and ethnicity. This is a result of the brain failing to undergo proper embryonic development, and in 90% of cases is associated with mental retardation (Rocha et al. (2016) *Bull World Health Organ* 8 Feb. 2016).

There is a probable association between individuals having had a prior Zika virus infection and the incidence of Guillain-Barré syndrome, a neurological disorder in which the individual's immune system destroys the myelin sheath surrounding axons of the peripheral nervous system (WHO "Zika Situation Report" Feb. 5, 2016).

No specific treatments or vaccines for Zika virus currently exist, and the only measures at this time to prevent infection are through vector control and avoiding travel to regions experiencing outbreaks.

Described herein are Zika virus vaccines and compositions comprising inactivated Zika virus that provide a safe method for generating an immune response to Zika virus, including virus-neutralizing antibodies, that may help prevent against Zika virus infection.

Any strain of Zika virus may be used in the methods and compositions described herein. In some embodiments, the Zika virus is an isolate from an infected subject during a Zika virus outbreak. In some embodiments, the Zika virus is a strain isolated from Africa or from the African virus lineage. In some embodiments, the Zika virus is a strain isolated from Asia or from the Asian lineage (includes also strains from French Polynesia). In some embodiments, the Zika virus is a strain isolated from the Americas (South America, Central America, or North America), such as a Suriname Zika virus strain. In some embodiments, the Zika virus has an RNA genome corresponding (but not limited) to the DNA sequence provided by GenBank Accession No. AY632535.2, KU321639.1, KU497555.1, KU501215.1, KU509998.1, KU527068.1, KU681081.3, KU681082.3, KU707826.1, KU744693.1, or LC002520.1 or RNA genome disclosed partially or fully herein (SEQ ID NO: 2 to 69). In one embodiment, the Zika virus comprises the RNA sequence corresponding to the DNA sequence provided by SEQ ID NO: 78. In one embodiment, the DNA sequence has at least 95%, 96%, 97%, 98%, at least 99% sequence identity with SEQ ID NO: 78. In one embodiment, the Zika virus contains an RNA molecule encoding the entire polyprotein according to SEQ ID NO: 79 or a polyprotein with at 95%, 96%, 97%, 98%, at least 99% sequence identity with SEQ ID NO: 79. In one embodiment, the In some embodiments, the attenuated form of ChikV is derived from the LR2006-OPY1 ChikV infectious clone (La Reunion isolate). In some embodiments, the attenuated form of ChikV is a Δ5nsP3 mutant similar to the attenuated virus described by Hallengärd et al. (Novel Attenuated Chikungunya Vaccine Candidates Elicit Protective Immunity in C57BL/6 mice (2014) Journal of Virology 88(5):2858-2866) or an immunogenic variant thereof. The immunogenic variant of the Δ5nsP3 ChikV mutant is herein defined as having at least 80% sequence identity to the nucleotide sequence of the Δ5nsP3 mutant sequence (SEQ ID NO: 77), especially at least 81%, 82%, 83%, 84%, 85%, 86%, 87%, 88% 89%, 90%, 91%, 92%, 93%, 94%, 95%, 96%, 97%, 98% or at least 99% sequence identity.

In some embodiments, the process of the invention results in an enrichment of infectious virus particles from the crude harvest comprising infectious virus particles and non-infectious virus particles and other virus products such that the enrichment of the infectious virus particles is at least 50%, at least 60%, at least 70%, at least 80%, at least 90%, at least 95%, preferably at least 80%, especially at least 85% relative to the total virus particle content of the crude harvest (a) comprising the virus particles and impurities.

In some embodiments, the residual impurity of the final virus preparation with respect to all impurities in the crude harvest is less than 10%, 9%, 8%, 7%, 6%, 5%, 4%, 3%, 2%, 1%, preferably less than 5% as determined by SEC-HPLC (Size Exclusion Chromatography—HPLC).

A unique aspect of the current invention is the realization that know-how related to the vaccine design and purification approach used for the Japanese Encephalitis Vaccine (JEV) IXIARO® (see Srivastava A. K. et al., 2001, Vaccine 19, 4557-4565, WO99/11762) may be employed and improved upon in order to expedite the development of a Zika, (or e.g. Chikungunya or yellow fever) virus vaccine and provide it to the subjects in need as soon as possible. The industrial process as disclosed for IXIARO®, providing a very effective vaccine against JEV, was complemented by further significant improvements disclosed herein in order to provide a more efficient (higher yield) and safer (less or no protamine sulphate with its allergic potential) Zika vaccine compared to the available JEV vaccine. A particular innovation of the herein disclosed vaccines is their greatly reduced protamine salt (SEQ ID NO: 1) content in the final drug substance facilitated by the development of an improved sucrose gradient. Said sucrose gradient not only allowed the separation of protamine sulphate but also allowed for a very effective inactivation by formaldehyde and resulted in the case of Zika with over 90% yield with the improved process disclosed herein vs about 35% yield with the published JEV process, see experimental part for comparison). Interestingly, this very efficient process can also be applied to live vaccines as the herein disclosed Chikungunya vaccine. Herein disclosed preliminary results with a yellow fever vaccine are also supportive that this approach can be used. Thus, the invention provides for a robust and widely applicable process for viral vaccines.

Aspects of the disclosure relate to methods of producing a virus in Vero tissue culture cells. Vero cells are a commonly used tissue culture cell line derived from the kidney of an African green monkey. The Vero cells used in the methods described herein are the VERO (WHO) cell line, obtained from the Health Protection Agency general cell collection under catalogue number 88020401.

Vero cells can be grown to confluent monolayers, for example in tissue culture flasks; in suspension (on microcarriers), for example in roller bottles; or in any other cell culture system for viral production. In some embodiments, the Vero cells are grown in a bioreactor for viral production.

For plaque assays or the plaque reduction neutralization test (PRNT), Vero cells are grown in monolayers in tissue culture flasks, dishes, or wells of a plate. To infect the Vero cells with the virus, the culture medium is inoculated with virus and the cells are incubated with the virus for a period of time. The cells may be washed after inoculation to remove any virus that did not adsorb to the cells in a given amount of time.

The methods provided herein involve passaging the virus in Vero cells. As used herein, the terms "passage" or "passaging" refer to infecting a population of Vero cells with virus and subsequently inoculating a second population of Vero cells with virus produced by infection of the first Vero cell population. In some embodiments, a portion of the culture medium from the infected Vero cells (containing virus that was released from the infected cells) is used to inoculate a second population of Vero cells. This is referred to as one passage or one round of passaging. The passaging may be performed serially, for example, a portion of the culture medium from the infected second population of Vero cells is used to inoculate a third population of Vero cells, and so on. In some embodiments, virus obtained from a single plaque is used to inoculate another population of cells.

In some embodiments, the virus is passaged in Vero cells several times, such as at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 times. In some embodiments, the virus is passaged in Vero cells at least 4 times or 5 times. In some embodiments, the virus is passaged in Vero cells at least 30 times. It is important that the virus population, i.e. the virus sequences, stays as much as possible constant over said passaging. If adaption of the virus occurs (i.e. appearance of mutated viruses in the original virus population), it is preferred that said passages are not used in the context of manufacturing of said virus, e.g. for Zika it was found that up to passage 3 and culturing to day 7 can be used without major shifts in virus population, i.e. introduction of virus population with mutations. However this observation needs to be done for each virus strain and may be different.

In some embodiments, the Vero cells are incubated for at least 2 days after inoculation with the virus at e.g. a typical 0.01 MOI (multiplicity of infection), to allow for viral production, prior to passaging. In some embodiments, the Vero cells are incubated for at least 3, 4, 5, 6, 7, 8, 9, 10 or more than 10 days e.g. at least 7 days after inoculation with the virus prior to passaging. The number of days the Vero cells are incubated after viral inoculation may depend on factors such as the multiplicity of infection used to inoculate the cells and the viral titer desired in the culture medium. Serial passaging of the virus in Vero cells may result in generation of a Vero cell adapted virus strain.

The culture medium from the infected Vero cells may be harvested (collected) to obtain the virus. In some embodiments, the culture medium is harvested from infected Vero cells and is replaced with fresh culture medium, which is then harvested after another period of time. In some embodiments, the culture medium harvested from infected Vero cells is pooled from independent Vero cell cultures and/or from independent days. Harvesting can be repeated up to 4 times by 7 or 9 days post infection, for example, and result in a high yield of virus per unit cell culture. In order to minimize the adoption of Zika virus strain to Vero cells, it was found that Vero cell could be incubated for at least 7 days, more preferably 5 days, prior to passaging and subsequently supernatants could be harvested at days 2, 3, 5 and 7 or 2, 3, and 5 (see also experimental part). The harvested culture medium can be stored at +4° C. prior to purification of the virus from the culture medium for up to 2 weeks.

In some embodiments, debris from infected and lysed Vero cells may be removed from the harvested culture medium, referred to as a "clarification" of the culture medium. The harvested culture medium may be clarified by common methods known in the art, such as low-speed centrifugation, for example, at 1500 g for 10 min, and/or by filtration through a filter of pore size of 0.45 µm. The harvested culture medium can be stored at +4° C. prior to concentration.

The inventive processes of this invention can also be applied to the purification of infectious virus particles grown on other cell substrates such as Chick embryo cell (CEF), Sf-9, high five, MRC-5, WI-38, MDCK, PER.C6, and avian cell lines, e.g. the duck cell line EB66 and many others.

To concentrate the titer of the virus in the harvested culture medium, it may be subjected to concentration by any method known in the art. For example, the harvested culture medium may be concentrated by methods including, without limitation, ultrafiltration, ultracentrifugation, centrifugal concentrator, vacuum centrifugation, and lyophilization. In some embodiments, the harvested culture medium is concentrated by ultrafiltration and the retentate containing the virus is collected. In some embodiments, the harvested culture medium is concentrated by precipitation in which polyethylene glycol (PEG) 8000 is dissolved in the culture medium (up to 10%) and the precipitate is dissolved in a buffer, for example phosphate-buffered saline (PBS, pH 7.0).

The harvested culture medium may be precipitated to produce a virus supernatant. In some embodiments, the harvested culture medium is precipitated to remove host cell DNA such as Vero cell DNA and other undesired material, such as Vero cell debris, from the harvested culture medium. In some embodiments, the harvested culture medium is concentrated prior to precipitation. In some embodiments, the harvested culture medium is precipitated by adding protamine sulfate (e.g. SEQ ID NO: 1) to the harvested culture medium and incubating the mixture, for example at +4° C. or on ice. In some embodiments, the harvested culture medium is treated with benzonase to remove host cell DNA e.g. Vero cell DNA and other undesired material, such as Vero cell debris, from the harvested culture medium. However, it was found that the treatment with protamine sulfate is preferred (see experimental part). In some embodiments, the precipitated culture medium is centrifuged to collect precipitated material and the supernatant containing the virus, referred to as a "virus supernatant," is collected.

The virus supernatant may be further purified after precipitation, for example density gradient ultracentrifugation. In some embodiments, the virus supernatant is further purified by sucrose gradient. Fractions may be collected from the sucrose gradients and assayed for presence of the virus. Methods for assaying for virus positive fractions include plaque assay, hemagglutination assay, polyacrylamide gel electrophoresis, and antigen assays such as Western blotting and ELISA. The fractions containing virus may be pooled based on titer of the virus and level of other impurities. The level or amount of impurities present in the virus supernatant can be estimated by testing for host cell DNA e.g. Vero cell DNA, virus aggregates and/or host cell protein e.g. Vero cell protein (see experimental part). A particular embodiment of the invention is the improved sucrose gradient that allows for an efficient protamine separation as shown in the experimental part. It was surprisingly found that the addition of a virus-containing fraction with 10% (w/w) sucrose to a simple three layer sucrose density gradient (e.g. a gradient comprising a 15% (w/w) sucrose solution, a 35% (w/w) sucrose solution, and a 50% (w/w) sucrose solution) resulted in efficient separation of protamine sulphate without much loss of virus. Thus a particularly preferred embodiment of the invention is the use of a sucrose density gradient that is able to efficiently separate protamine sulphate, wherein said sucrose density gradient is used in the purification of virus such as the viruses described herein, e.g. a Zika virus, yellow fever virus or Chikungunya virus.

To achieve a safe vaccine or composition for the administration to subjects, the virus supernatant may be inactivated (see experimental part for Zika virus). According to the current invention, the inactivation step or steps may be performed at any point in the process such as e.g., directly following harvest, before or after PS treatment or sucrose gradient centrifugation or any other permutation thereof. As used herein, the terms "inactivated" and "optimally inactivated" may be used interchangeably and refer to a process (or its result) by which the virus is rendered unable to infect a host cell (non-infectious), but that does not affect or substantially affect the antigenicity of the virus, for example, the immunogenic antigens exposed on the surface of the virus are able to stimulate an immune response in a subject (e.g., antigen-specific antibodies). By "does not affect or substantially affect the antigenicity of the virus" is meant that the inactivated virus retains at least 50%, at least 55%, at least 60%, at least 65%, at least 70%, at least 75%, at least 80%, at least 85%, at least 90%, at least 95%, at least 96%, at least 97%, at least 98%, at least 99%, or even essentially 100% of the antigenicity of a virus that is not subjected to inactivation.

A variety of methods are known in the art for inactivating viruses. In some embodiments, the virus is inactivated by chemical inactivation, thermal inactivation, pH inactivation, or UV inactivation.

In some embodiments, the inactivating is by chemical inactivation and involves contacting the virus with one or more chemical inactivation agents for a period of time under conditions such that the virus is inactivated but the antigenic epitopes are substantially intact. In some embodiments, the virus is inactivated for a period of time that is longer than is required to completely inactivate the virus. In some embodiments, the virus supernatant is inactivated for the number of days required to inactivate the virus plus at least one additional day. Samples of the virus supernatant may be taken at one or more times throughout the inactivation process and assessed for viral viability (infectivity) by any method known in the art, such as by infecting a monolayer of host cells (i.e., plaque assay). Using such a procedure, the period of time that is required to completely inactivate the virus can be determined, and a longer period of time is selected to ensure complete inactivation.

In some embodiments, the virus is contacted with a chemical inactivation agent for between 1 day and 50 days, between 2 days and 40 days, between 2 days and 30 days, between 2 days and 20 days, between 2 days and 10 days, between 3 days and 9 days, between 4 days and 8 days, between 5 days and 7 days, between 2 days and 5 days, or between 5 and 10 days. In some embodiments, the virus is contacted with one or more chemical inactivation agents for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, or at least 50 days.

In some embodiments, the chemical inactivation is performed at about +5° C., +10° C., +15° C., +20° C., +25° C., +30° C., +35° C., +40° C., or about +45° C. In some embodiments, the chemical inactivation is performed at about +4° C. In some embodiments, the chemical inactivation is performed at about +22° C.

Any chemical inactivation agent known in the art may be suitable for inactivating the virus in the methods described herein. It will be appreciated by one of skill in the art that factors such as the chemical inactivation agent and the temperature at which inactivation is performed may affect the length of time (number of days) required to completely inactivate the virus. Examples of chemical inactivation agents include, without limitation, formaldehyde, enzymes, β-propiolactone, ethanol, trifluroacetic acid, acetonitrile, bleach, urea, guanidine hydrochloride, tri-n-butyl phosphate, ethylene-imine or a derivatives thereof, and organic solvents such as Tween, Triton, sodium deoxycholate, and sulfobetaine. A preferred inactivation is the inactivation with formaldehyde at 22° C.+/−2° C. for about 10 days.

In some embodiments, the inactivating agent is neutralized after chemical inactivation of the virus. In some embodiments, the inactivating agent is formaldehyde and is neutralized after chemical inactivation using sodium thiosulphate or sodium metabisulfite.

In some embodiments, the virus is inactivated by thermal inactivation. In some embodiments, the thermal inactivation involves exposing the virus to heat, such as dry heat or vapor heat, for a period of time. In some embodiments, the thermal inactivation involves exposing the virus to temperatures of about +40° C., +45° C., +50° C., +55° C., +60° C., +65° C., +70° C., +75° C., +80° C., +85° C., +90° C., +95° C., or about +100° C. In some embodiments, the virus is exposed to heat for at least 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, about 96 hours, or longer. A preferred thermal inactivation involves exposing the virus to temperatures of about +56° C. for 60 minutes.

In some embodiments, the virus is inactivated by exposing the virus to acidic or alkaline conditions for a period of time such that the virus is completely inactivated. The pH of a virus preparation may be adjusted to a desired pH, for example by the addition of an acid, a base, or a buffer with a particular pH to the virus preparation. In some embodiments, the virus is inactivated at an acidic pH of about 2, 2.5, 3, 3.5, 4, 4.5, 5 or about 5.5. In other embodiments, the virus is inactivated at an alkaline pH of about 8, 8.5, 9, 9.5, 10, or about 10.5.

In some embodiments, the virus is inactivated using UV inactivation. UV inactivation involves exposing the virus to energy-rich radiation, such as UV-A, UV-B, or UV-C light for a period of time.

It will be appreciated that any two or more methods of inactivation may be combined and performed concurrently or serially.

The inactivated virus may be subsequently dialyzed to remove any undesired material, including the inactivating agent and any neutralizing agent, and/or to replace the buffer with a buffer that is pharmaceutically acceptable for administration to subjects. In some embodiments, the inactivated virus is dialyzed with PBS. In addition or alternatively, the inactivated virus may be filtered, such as sterile filtered, through a 0.22 µm filter.

It is believed that the herein described improved process (comprising the PS treatment in combination with the optimized sucrose gradient) is applicable and efficient to any virus purification and in particular efficient for any RNA type virus (such as the herein described Zika and Chikungunya and yellow fever viruses) of similar size (i.e. about 50 to 100 nm). Furthermore, it is believed that the combination of the PS treatment with the optimized sucrose gradient allowing for a complete (or almost complete) separation of PS provides a very efficient virus purification in the very high range, e.g. above 70%, more preferably 75%, 80% or 90%, even more preferably 95%. It is believed that the complete reduction of PS in the virus fraction through the process of the invention allows a very efficient inactivation with almost no or very low viral loss e.g. below 30%, more preferably less than 25%, 20% or 10% loss, even more preferably less than 15% loss.

Any of the methods or uses described herein may be for the prevention of a virus infection in a subject. As used herein, the terms "prevent," and "preventing", include the administration of a virus vaccine or composition to a subject to reduce, or delay the onset of the manifestation of clinical or subclinical symptoms, complications, pathologies or biochemical indicia of a disease or infection, or to reduce or inhibit the spread/transmission of the virus. As used herein, "prevent" may also be construed as "protecting from". As used herein, antigen(s), such as an inactivated virus, that is administered to a subject prophylactically (e.g., prior to infection) may be referred to as a vaccine.

Zika Vaccine

As described herein Zika virus may cause any of a variety of symptoms upon infection of a subject, and is generally characterized by mild fever; rash (exanthema) on face, neck trunk, upper arms; headache; sensitivity to light; non-inflammatory joint pain; conjunctivitis; lack of appetite; diarrhea; abdominal pain; and/or dizziness. Zika virus infection during pregnancy is likely associated with microcephaly in the fetus/neonate. There is also a probable association between the onset of Guillain-Barré syndrome or symptoms thereof. Diagnosis of Zika virus infection in subjects exposed to Zika virus or suspected of being exposed to Zika virus involves detecting the presence of virus-specific antibodies and/or molecular testing, such as PCR or real-time PCR detection of Zika virus.

Provided herein are methods for administering a dose of a therapeutically effective amount of a Zika virus vaccine to a subject in need thereof. In some embodiments, the subject is a mammalian subject, such as a human, non-human primate, rodent, rabbit, sheep, dog, cat, horse, or cow. In some embodiments, the subject is a mouse. In some embodiments, the subject is a human subject, such as a child, an adult, or an elderly adult. In some embodiments, the subject is a female subject. In some embodiments, the subject is pregnant or planning on becoming pregnant. In some embodiments, the subject is at risk of being exposed to Zika virus. In some embodiments, the subject is living in or traveling to an area where Zika virus is present or is thought to be present. In some embodiments, the subject is living in or traveling to an area that is experiencing a Zika virus infection outbreak. In some embodiments, the subject is living in or traveling to an area where an arthropod vector capable of transmitting the Zika virus vector is present or is thought to be present.

Any of the Zika virus vaccines or compositions described herein may be administered to a subject in a therapeutically effective amount or a dose of a therapeutically effective amount. As used herein, a "therapeutically effective amount"

of vaccine is any amount that results in a desired response or outcome in a subject, such as those described herein, including but not limited to prevention of infection, an immune response or an enhanced immune response to Zika virus, or prevention or reduction of symptoms associated with Zika disease.

In some embodiments, the therapeutically effective amount of a Zika virus vaccine or composition described herein is an amount sufficient to generate antigen-specific antibodies (e.g., anti-Zika virus antibodies). In some embodiments, the therapeutically effective amount is sufficient to seroconvert a subject with at least 70% probability. In some embodiments, the therapeutically effective amount is sufficient to seroconvert a subject with at least 75%, 80%, 85% 90%, 95%, 96%, 97%, 98%, or at least 99% probability. Whether a subject has been seroconverted can be assessed by any method known in the art, such as obtaining a serum sample from the subject and performing an assay to detect anti-Zika virus antibodies. In some embodiments, a subject is seroconverted if a serum sample from the subject contains an amount of anti-Zika virus antibodies that surpasses a threshold or predetermined baseline. A subject is generally considered seroconverted if there is at least a 4-fold increase in anti-Zika virus antibodies (i.e., anti-Zika E protein IgG antibodies) present in a serum sample from the subject as compared to a serum sample previously taken from the same subject.

In some embodiments, seroconversion of a subject is assessed by performing a plaque reduction neutralization test (PRNT). Briefly, PRNT is used to determine the serum titer required to reduce the number of Zika virus plaques by 50% (PRNT50) as compared to a control serum/antibody. The PRNT50 may be carried out using monolayers of Vero cells or any other cell type/line that can be infected with Zika virus. Sera from subjects are diluted and incubated with live, non-inactivated Zika virus. The serum/virus mixture may be applied to the Vero cells and incubated for a period of time. Plaques formed on the Vero cell monolayers are counted and compared to the number of plaques formed by the Zika virus in the absence of serum or a control antibody. A threshold of neutralizing antibodies of 1:10 dilution of serum in a PRNT50 is generally accepted as evidence of protection (Hombach et. al. Vaccine (2005) 23:5205-5211).

In some embodiments, the Zika virus may be formulated for administration in a composition, such as a pharmaceutical composition. The term "pharmaceutical composition" as used herein means a product that results from the mixing or combining of at least one active ingredient, such as an inactivated Zika virus, and one or more inactive ingredients, which may include one or more pharmaceutically acceptable excipient.

Pharmaceutical compositions of the invention, including vaccines, can be prepared in accordance with methods well known and routinely practiced in the art (see e.g., Remington: The Science and Practice of Pharmacy, Mack Publishing Co. 20th ed. 2000; and Ingredients of Vaccines—Fact Sheet from the Centers for Disease Control and Prevention, e.g., adjuvants and enhancers such as alum to help the vaccine improve its work, preservatives and stabilizers to help the vaccine remain unchanged (e.g., albumin, phenols, glycine)). Pharmaceutical compositions are preferably manufactured under GMP conditions. Typically a therapeutically effective dose of the inactivated Zika virus preparation is employed in the pharmaceutical composition of the invention. The inactivated Zika virus is formulated into pharmaceutically acceptable dosage forms by conventional methods known to those of skill in the art. Dosage regimens are adjusted to provide the optimum desired response (e.g., the prophylactic response).

Dosages of the active ingredients in the pharmaceutical compositions of the present invention can be varied so as to obtain an amount of the active ingredient which is effective to achieve the desired pharmaceutical response for a particular subject, composition, and mode of administration, without being toxic to the subject. The selected dosage level depends upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the inactivated Zika virus vaccine employed in the pharmaceutical composition at levels lower than that required to achieve the desired therapeutic effect and gradually increase the dosage until the desired effect (e.g., production of anti-Zika virus antibodies) is achieved. In general, effective doses of the compositions of the present invention, for the prophylactic treatment of groups of people as described herein vary depending upon many different factors, including means of administration, target site, physiological state of the patient, whether the patient is human or an animal, other medications administered, and the titer of anti-Zika virus antibodies desired. Dosages need to be titrated to optimize safety and efficacy. In some embodiments, the dosing regimen entails subcutaneous or intramuscular administration of a dose of inactivated Zika virus twice, once at day 0 and once at about day 7. In some embodiments, the dosing regimen entails subcutaneous administration of a dose of inactivated Zika virus twice, once at day 0 and once at about day 14. In some embodiments, the dosing regimen entails subcutaneous administration of a dose of inactivated Zika virus twice, once at day 0 and once at about day 28. In some embodiments, the inactivated Zika virus is administered to the subject once.

Any of the Zika virus vaccines or compositions described herein may be administered to a subject with, prior to, or after administration of one or more adjuvants. An adjuvant is a molecule that enhances a response in a subject, such as an immune response, to an antigen or other molecule. In some embodiments, an adjuvant may stabilize an antigen or other molecule. Determining whether a Zika virus vaccine or compositions thereof are administered with an adjuvant depends on various factors (e.g., type and extent of response desired) and will be evident to one of skill in the art. In some embodiments, administering any of the Zika virus vaccines or compositions described herein with, prior to, or after administration of an adjuvant may enhance the production of virus neutralizing (anti-Zika virus) antibodies. In some embodiments, a subject that is administered any of the Zika virus vaccines or compositions described herein with, prior to, or after administration of an adjuvant may only require a single administration of the Zika virus vaccine or composition to be seroconverted (produce a level of anti-Zika virus antibodies). Examples of adjuvants may include, without limitation, aluminium salt (aluminium hydroxide or aluminium phosphate), calcium phosphate hydroxide, paraffin oil, killed bacteria, bacterial toxins, toxoids, subunits of bacteria, squalene, thimerosal, detergents, IL-1, IL-2, IL-12, 2-component adjuvants, such as 2-component adjuvants containing an antibacterial peptide and a TLR9 agonist (e.g., IC31®), and combinations such as Freund's complete adjuvant and Freund's incomplete adjuvant. In some embodiments, the Zika virus vaccines or compositions is administered with aluminium hydroxide. In some embodiments, the inactivated Zika virus vaccine or composition is administered with aluminium phosphate salt. A preferred aluminium salt is the aluminium hydroxide with reduced Cu content, e.g. lower than 1.25 ppb based on the weight of the Zika composition, an adjuvant described in detail in WO 2013/083726 or Schlegl et al., Vaccine 33 (2015) 5989-5996.

In some embodiments, the adjuvant is comprised of two components. In some embodiments, the 2-component adjuvant comprises an antibacterial peptide and a TLR9 agonist. In some embodiments, the antibacterial peptide is provided by the amino acid sequence KLKL$_5$KLK (SEQ ID NO: 71). In some embodiments, the TLR9 agonist is a deoxyinosine-containing immunostimulatory oligodeoxynucleic acid molecule (I-ODN). In some embodiments, the I-ODN comprises the nucleic acid sequence (dIdC)$_{13}$ (SEQ ID NO: 70). In some embodiments, the adjuvant is IC31®. In some embodiments, the adjuvant is in nanoparticle form (See, e.g., U.S. Pat. No. 8,765,148 B2, incorporated by reference in its entirety). In some embodiments, the adjuvant is IC31®, i.e. KLKL$_5$KLK (SEQ ID NO: 71) and the nucleic acid sequence (dIdC)$_{13}$ (SEQ ID NO: 70), in combination with an aluminium salt such as aluminium hydroxide.

The Zika virus vaccines or compositions described herein may be administered to a subject concomitantly with one or more vaccine to another infectious agent, such as another infectious agent is that present or thought to be present in the same geographic area as Zika virus. In some embodiments, the other infectious agent is one that the subject is also at risk of being in contact with. In some embodiments, the other infectious agent is transmitted by the same arthropod vector as Zika virus. In some embodiments, the other infectious agent is Japanese Encephalitis virus, Yellow Fever virus, Dengue virus and/or Chikungunya virus.

Also within the scope of the present disclosure are kits for use in prophylactically administering to a subject, for example to prevent or reduce the severity of Zika virus infection. Such kits can include one or more containers comprising a composition containing inactivated Zika virus, such as an inactivated Zika virus vaccine. In some embodiments, the kit may further include one or more additional containing comprising a second composition, such as a second vaccine. In some embodiments, the second vaccine is a vaccine for another arbovirus. In some embodiments, the second vaccine is a Dengue virus vaccine and/or a Chikungunya virus vaccine.

In some embodiments, the kit can comprise instructions for use in accordance with any of the methods described herein. The included instructions can comprise a description of administration of the composition containing inactivated Zika virus to prevent, delay the onset, or reduce the severity of Zika virus infection. The kit may further comprise a description of selecting a subject suitable for administration based on identifying whether that subject is at risk for exposure to Zika virus or contracting a Zika virus infection. In still other embodiments, the instructions comprise a description of administering a composition containing inactivated Zika virus to a subject at risk of exposure to Zika virus or contracting Zika virus infection.

The instructions relating to the use of the composition containing inactivated Zika virus generally include information as to the dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine readable instructions are also acceptable.

The kits of the present disclosure are in suitable packaging. Suitable packaging includes, but is not limited to, vials, bottles, jars, flexible packaging, and the like. Also contemplated are packages for use in combination with a specific device, such as a syringe or an infusion device. The container may have a sterile access port, for example the container may be a vial having a stopper pierceable by a hypodermic injection needle. At least one active agent in the composition is an inactivated Zika virus, as described herein.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

TABLE 1

Overview of process buffers and stock solutions.

| Buffer | Composition | Final pH | Final conductivity [mS/cm] |
|---|---|---|---|
| A | 0.5M NaOH | | n.a. |
| B | 0.1M NaOH | | n.a. |
| C | 25 mM Tris, 150 mM NaCl | 7.4 ± 0.2 | 16.5 |
| D | 1M Tris | 7.4 ± 0.2 | n.a. |
| E | 4.5M NaCl | n.a. | n.a. |

TABLE 1-continued

Overview of process buffers and stock solutions.

| Buffer | Composition | Final pH | Final conductivity [mS/cm] |
|---|---|---|---|
| F | 1M NaCl | n.a. | n.a. |
| G | 1% SDS | n.a. | n.a. |
| H | 50% (w/w) Sucrose in 25 mM Tris, 150 mM NaCl | 7.4 ± 0.2 | n.a. |
| I | 35% (w/w) Sucrose in 25 mM Tris, 150 mM NaCl | 7.4 ± 0.2 | n.a. |
| J | 15% (w/w) Sucrose in 25 mM Tris, 150 mM NaCl | 7.4 ± 0.2 | n.a. |
| K | 10 × PBS | 7.4 ± 0.2 | n.a. |
| L | 50 mg/mL Protamine sulphate | 7.4 ± 0.2 | n.a. |
| M | Drug substance formulation buffer (10 mM Tris(hydroxymethyl)-aminomethan, 5% Sucrose, 1% (10 mg/mL) rHSA) | 7.4 ± 0.2 | 1.3 |

TABLE 2

Abbreviations.

| | |
|---|---|
| °Bx | Degrees Brix = sugar content (w/w) of an aqueous solution* |
| BSA | Bovine serum albumin |
| CC700 | Capto ™ Core 700 |
| ChikV | Chikungunya virus |
| CPE | Cytopathic effect |
| EtOH | Ethanol |
| EU | Endotoxin units |
| DS | Drug Substance |
| DP | Drug Product |
| DSP | Downstream Process |
| HCP | Host cell protein |
| hcDNA | Host cell DNA |
| hpi | Hours post infection |
| HPLC | High Performance Liquid Chromatography |
| ID | Inner diameter |
| JEV | Japanese Encephalitis virus |
| LAL | Limulus amebocyte lysate |
| LDS buffer | Lithium dodecyl sulfate sample loading buffer |
| LOD | Limit of detection |
| LOQ | Limit of quantitation |
| MALLS | Multiangle light scattering |
| mAU | Milli absorbance units |
| MS | Mass spectroscopy |
| NIV | Neutralized inactivated virus |
| PBS | Phosphate buffered saline |
| PD | Process development |
| PFU | Plaque forming units |
| p.i. | Post-infection |
| PS | Protamine sulphate or protamine sulfate |
| rcf | Relative centrifugal force |
| rHSA | Recombinant human serum albumin |
| Rms radius | Root mean square radius |
| rMSB | Research master seed bank |
| RSD | Relative standard deviation |
| SEC | Size exclusion chromatography |
| SGC | Sucrose gradient centrifugation |
| SGP | Sucrose gradient purified |
| SDS | Sodium dodecyl sulphate |
| TBS | Tris buffered saline |
| TFF | Tangential flow filtration |
| TCID50 | Tissue culture infectious dose 50% |
| UF/DF | Ultrafiltration/diafiltration |
| WFI | Water for injection |
| ZikaV | Zika virus |

*Degrees Brix (°Bx) is the sugar content of an aqueous solution. One degree Brix is 1 gram of sucrose in 100 grams of solution and represents the strength of the solution as percentage by mass. °Bx corresponds to the sucrose content in percent (w/w), e.g., 45 °Bx equals 45% (w/w) sucrose.

TABLE A

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 1 | 9320_Zika_PF_1F | SEQ ID NO: 80 ttaggatccGTTGTTGATCTGTGTGAAT | 69.9 | 74.6 | 707 |
| | 9321_Zika_PF_1R | SEQ ID NO: 81 taactcgagCGTACACAACCCAAGTT | 69.3 | 75.6 | |
| 2 | 9322_Zika_PF_2F | SEQ ID NO: 82 ttaggatccTCACTAGACGTGGGAGTG | 70 | 73.9 | 704 |
| | 9323_Zika_PF_2R | SEQ ID NO: 83 taactcgagAAGCCATGTCYGATATTGAT | 69.8 | 73.7 | |
| 3 | 9324_Zika_PF_3F | SEQ ID NO: 84 ttaggatccGCATACAGCATCAGGTG | 72.3 | 74.5 | 712 |
| | 9325_Zika_PF_3R | SEQ ID NO: 85 taactcgagTGTGGAGTTCCGGTGTCT | 72 | 76.4 | |
| 4 | 9326_Zika_PF_4F | SEQ ID NO: 86 ttaggatccGAATAGAGCGAARGTTGAGATA | 70.9 | 74 | 712 |
| | 9327_Zika_PF_4R | SEQ ID NO: 87 taactcgAGTGGTGGGTGATCTTCTTCT | 70.5 | 73.7 | |
| 5 | 9328_Zika_PF_5F | SEQ ID NO: 88 ttaggatccCAGTCACAGTGGAGGTACAGTAC | 70.3 | 75 | 704 |
| | 9329_Zika_PF_5R | SEQ ID NO: 89 taactcgagCRCAGATACCATCTTCCC | 71.5 | 77.3 | |

TABLE A-continued

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 6 | 9330_Zika_PF_6F | SEQ ID NO: 90<br>ttaggatCCCTTATGTGCTTGGCCTTAG | 70.7 | 72.7 | 698 |
|   | 9331_Zika_PF_6R | SEQ ID NO: 91<br>taactcgagTCTTCAGCCTCCATGTG | 70.4 | 76.9 | |
| 7 | 9332_Zika_PF_7F | SEQ ID NO: 92<br>ttaggatccAATGCCCACTCAAACATAGA | 71.9 | 75 | 716 |
|   | 9333_Zika_PF_7R | SEQ ID NO: 93<br>taactcgagTCATTCTCTTCTTCAGCCCTT | 71 | 74 | |
| 8 | 9334_Zika_PF_8F | SEQ ID NO: 94<br>ttaggatccAAGGGTGATCGAGGAAT | 70.9 | 75.2 | 703 |
|   | 9335_Zika_PF_8R | SEQ ID NO: 95<br>taactcgagTTCCCTTCAGAGAGGAGC | 71.9 | 73.4 | |
| 9 | 9336_Zika_PF_9F | SEQ ID NO: 96<br>ttaggatccTCTTTTGCAAACTGCGATC | 71.9 | 75 | 699 |
|   | 9337_Zika_PF_9R | SEQ ID NO: 97<br>taactcgagTCCAGCTGCAAAGGGTAT | 71 | 74.9 | |
| 10 | 9338_Zika_PF_10F | SEQ ID NO. 98<br>ttaggatccGTGTGGACATGTACATTGA | 71.4 | 75.8 | 706 |
|   | 9339_Zika_PF_10R | SEQ ID NO: 99<br>taactcgagCCCATTGCCATAAAGTC | 70.4 | 75.8 | |
| 11 | 9340_Zika_PF_11F | SEQ ID NO: 100<br>ttaggatccTCATACTGTGGTCCATGGA | 71.6 | 78.1 | 692 |
|   | 9341_Zika_PF_11R | SEQ ID NO: 101<br>taactcgagGCCCATCTCAACCCTTG | 74 | 78 | |
| 12 | 9342_Zika_PF_12F | SEQ ID NO: 102<br>ttaggatccTAGAGGGCTTCCAGTGC | 70.9 | 74 | 707 |
|   | 9343_Zika_PF_12R | SEQ ID NO: 103<br>taactcgAGATACTCATCTCCAGGTTTGTTG | 70.2 | 72.2 | |
| 13 | 9344_Zika_PF_13F | SEQ ID NO: 104<br>ttaggatccGAAAACAAAACATCAAGAGTG | 70.6 | 75.4 | 726 |
|   | 9345_Zika_PF_13R | SEQ ID NO: 105<br>taactcgagGAATCTCTCTGTCATGTGTCCT | 71.9 | 75.6 | |
| 14 | 9346_Zika_PF_14F | SEQ ID NO: 106<br>ttaggatccTTGATGGCACGACCAAC | 73.1 | 75.6 | 715 |
|   | 9347_Zika_PF_14R | SEQ ID NO: 107<br>ttaggatccGTTGTTGATCTGTGTGAAT | 70.8 | 77.9 | |
| 15 | 9348_Zika_PF_15F | SEQ ID NO: 108<br>taactcgagCAGGTCAATGTCCATTG | 71.9 | 75.4 | 719 |
|   | 9349_Zika_PF_15R | SEQ ID NO: 109<br>ttaggatccTGTTGTGTTCCTATTGCTGGT | 73.9 | 77.2 | |
| 16 | 9350_Zika_PF_16F | SEQ ID NO: 110<br>taactcgaGTGATCAGRGCCCCAGC | 72.3 | 75.4 | 703 |
|   | 9351_Zika_PF_16R | SEQ ID NO: 111<br>ttaggatccTGCTGCCCAGAAGAGAA | 72 | 76.3 | |
| 17 | 9352_Zika_PF_17F | SEQ ID NO: 112<br>taactcgaGCACCAACAYGGGTTCTT | 73.6 | 76 | 705 |
|   | 9353_Zika_PF_17R | SEQ ID NO: 113<br>ttaggatcCTCAAGGACGGTGTGGC | 72 | 75.5 | |
| 18 | 9354_Zika_PF_18F | SEQ ID NO: 114<br>taactcgagCAATGATCTTCATGTTGGG | 71.7 | 75.8 | 699 |
|   | 9355_Zika_PF_18R | SEQ ID NO: 115<br>ttaggatccTATGGGGGAGGACTGGT | 71 | 74.1 | |
| 19 | 9356_Zika_PF_19F | SEQ ID NO: 116<br>taactcGAGCCCAGAACCTTGGATC | 73.3 | 75.5 | 711 |
|   | 9357_Zika_PF_19R | SEQ ID NO: 117<br>ttaggatcCAGACCCCCAAGAAGGC | 71.3 | 76.9 | |

TABLE A-continued

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 20 | 9358_Zika_PF_20F | SEQ ID NO: 118<br>taactcgagCCCCTTTGGTCTTGTCT | 71.7 | 75 | 706 |
|  | 9359_Zika_PF_20R | SEQ ID NO: 119<br>ttaggatccAGGAAGGATGTATGCAGATG | 71.9 | 73.9 |  |
| 21 | 9360_Zika_PF_21F | SEQ ID NO: 120<br>taactcgagACATTTGCGCATATGATTTTG | 70.4 | 75.7 | 709 |
|  | 9361_Zika_PF_21R | SEQ ID NO: 121<br>ttaggatccAGGAAGGACACACAAGAGT | 71.8 | 75 |  |
| 22 | 9362_Zika_PF_22F | SEQ ID NO: 122<br>taactcgagACAGGCTGCACAGCTTT | 70 | 79.1 | 581 |
|  | 9363_Zika_PF_22R | SEQ ID NO: 123<br>ttaggatccTCTCTCATAGGGCACAGAC | 74.8 | 81.1 |  |

SEQUENCES

SEQ ID NO: 1
A typical form of protamine
PRRRRSSSRP VRRRRRPRVS RRRRRRGGRR RR

Provided below are examples of nucleic acid sequences of the genomes of Zika viruses that may be used in the methods, compositions, and/or vaccines described herein.

SEQ ID NO: 2
KU321639.1 Zika virus strain ZikaSPH2015, Brazil, complete genome (SEQ ID NO: 2)
GTTGTTACTGTTGCTGACTCAGACTGCGACAGTTCGAGTTTGAAGCGAAAGCTAGCAACAGTATCAACAGGTTTTATTTGG
ATTTGGAAACGAGAGTTTCTGGTCATGAAAAACCCAAAAAAGAAATCCGGAGGATTCCGGATTGTCAATATGCTAAAACG
CGGAGTAGCCCGTGTGAGCCCCTTTGGGGGCTTGAAGAGGCTGCCAGCCGGACTTCTGCTGGGTCATGGGCCCATCAGG
ATGGTCTTGGCAATTCTAGCCTTTTTGAGATTCACGGCAATCAAGCCATCACTGGGTCTCATCAATAGATGGGGTTCAGTG
GGGAAAAAAGAGGCTATGGAAATAATAAAGAAGTTCAAGAAAGATCTGGCTGCCATGCTGAGAATAATCAATGCTAGGA
AGGAGAAGAAGAGACGGGGCGCAGATACTAGTGTCGGAATTGTTGGCCTCCTGCTGACCACAGCTATGGCAGCGGAGG
TCACTAGACGTGGGAGTGCATACTATATGTACTTGGACAGAAACGATGCTGGGGAGGCCATATCTTTTCCAACCACATTG
GGGATGAATAAGTGTTATATACAGATCATGGATCTTGGACACATGTGTGATGCCACCATGAGCTATGAATGCCCTATGCT
GGATGAGGGGGTGGAACCAGATGACGTCGATTGTTGGTGCAACACGACGTCAACTTGGGTTGTGTACGGAACCTGCCAT
CACAAAAAAGGTGAAGCACGGAGATCTAGAAGAGCTGTGACGCTCCCCTCCCATTCCACTAGGAAGCTGCAAACGCGGT
CGCAAACCTGGTTGGAATCAAGAGAATACACAAAGCACTTGATTAGAGTCGAAAATTGGATATTCAGGAACCCTGGCTTC
GCGTTAGCAGCAGCTGCCATCGCTTGGCTTTTGGGAAGCTCAACGAGCCAAAAAGTCATATACTTGGTCATGATACTGCT
GATTGCCCCGGCATACAGCATCAGGTGCATAGGAGTCAGCAATAGGGACTTTGTGGAAGGTATGTCAGGTGGGACTTGG
GTTGATATTGTCTTGGAACATGGAGGTTGTGTCACCGTAATGGCACAGGACAAACCGACTGTCGACATAGAGCTGGTTAC
AACAACAGTCAGCAACATGGCGGAGGTAAGATCCTACTGCTATGAGGCATCAATATCAGACATGGCTTCGGACAGCCGCT
GCCCAACACAAGGTGAAGCCTACCTTGACAAGCAATCAGACACTCAATATGTCTGCAAAAGAACGTTAGTGGACAGAGGC
TGGGGAAATGGATGTGGACTTTTTGGCAAAGGGAGTCTGGTGACATGCGCTAAGTTTGCATGCTCCAAGAAAATGACCG
GGAAGAGCATCCAGCCAGAGAATCTGGAGTACCGGATAATGCTGTCAGTTCATGGCTCCCAGCACAGTGGGATGATCGT
TAATGACACAGGACATGAAACTGATGAGAATAGAGCGAAGGTTGAGATAACGCCCAATTCACCAAGAGCCGAAGCCACC
CTGGGGGGTTTTGGAAGCCTAGGACTTGATTGTGAACCGAGGACAGGCCTTGACTTTTCAGATTTGTATTACTTGACTATG
AATAACAAGCACTGGTTGGTTCACAAGGAGTGGTTCCACGACATTCCATTACCTTGGCACGCTGGGGCAGACACCGGAAC
TCCACACTGGAACAACAAAGAAGCACTGGTAGAGTTCAAGGACGCACATGCCAAAAGGCAAACTGTCGTGGTTCTAGGG
AGTCAAGAAGGAGCAGTTCACACGGCCCTTGCTGGAGCTCTGGAGGCTGAGATGGATGGTGCAAAGGGAAGGCTGTCCT
CTGGCCACTTGAAATGTCGCCTGAAAATGGATAAACTTAGATTGAAGGGCGTGTCATACTCCTTGTGTACCGCAGCGTTCA
CATTCACCAAGATCCCGGCTGAAACACTGCACGGGACAGTCACAGTGGAGGTACAGTACGCAGGGACAGATGGACCTTG
CAAGGTTCCAGCTCAGATGGCGGTGGACATGCAAACTCTGACCCCAGTTGGGAGGTTGATAACCGCTAACCCCGTAATCA
CTGAAAGCACTGAGAACTCTAAGATGATGCTGGAACTTGATCCACCATTTGGGGACTCTTACATTGTCATAGGAGTCGGG
GAGAAGAAGATCACCCACCACTGGCACAGGAGTGGCAGCACCATTGGAAAAGCATTTGAAGCCACTGTGAGAGGTGCCA
AGAGAATGGCAGTCTTGGGAGACACAGCCTGGGACTTTGGATCAGTTGGAGGCGCTCTCAACTCATTGGGCAAGGGCAT
CCATCAAATTTTTGGAGCAGCTTTCAAATCATTGTTTGGAGGAATGTCCTGGTTCTCACAAATTCTCATTGGAACGTTGCTG
ATGTGGTTGGGTCTGAACACAAAGAATGGATCTATTTCCCTTATGTGCTTGGCCTTAGGGGGAGTGTTGATCTTCTTATCC
ACAGCCGTCTCTGCTGATGTGGGGTGCTCGGTGGACTTCTCAAAGAAGGAGACGAGATGCGGTACAGGGGTGTTCGTCT
ATAACGACGTTGAAGCCTGGAGGGACAGGTACAAGTACCATCCTGACTCCCCCCGTAGATTGGCAGCAGCAGTCAAGCA
AGCCTGGGAAGATGGTATCTGCGGGATCTCCTCTGTTTCAAGAATGGAAAACATCATGTGGAGATCAGTAGAAGGGGAG
CTCAACGCAATCCTGGAAGAGAATGGAGTTCAACTGACGGTCGTTGTGGGATCTGTAAAAAACCCCATGTGGAGAGGTC
CACAGAGATTGCCCGTGCCTGTGAACGAGCTGCCCCACGGCTGGAAGGCTTGGGGGAAATCGCACTTCGTCAGAGCAGC
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGATTATTCATTAGAGTGTGAT
CCAGCCGTTATTGGAACAGCTGTTAAGGGAAAGGAGGCTGTACACAGTGATCTAGGCTACTGGATTGAGAGTGAGAAGA
ATGACACATGGAGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATACCAGAGAGGGCT
ACAGGACCCAAATGAAAGGGCCATGGCACAGTGAAGAGCTTGAAATTCGGTTTGAGGAATGCCCAGGCACTAAGGTCCA

| SEQUENCES |
|---|
| CGTGGAGGAAACATGTGGAACAAGAGGACCATCTCTGAGATCAACCACTGCAAGCGGAAGGGTGATCGAGGAATGGTG |
| CTGCAGGGAGTGCACAATGCCCCCACTGTCGTTCCGGGCTAAAGATGGCTGTTGGTATGGAATGGAGATAAGGCCCAGG |
| AAAGAACCAGAAAGCAACTTAGTAAGGTCAATGGTGACTGCAGGATCAACTGATCACATGGATCACTTCTCCCTTGGAGT |
| GCTTGTGATTCTGCTCATGGTGCAGGAAGGGCTGAAGAAGAGAATGACCACAAAGATCATCATAAGCACATCAATGGCA |
| GTGCTGGTAGCTATGATCCTGGGAGGATTTTCAATGAGTGACCTGGCTAAGCTTGCAATTTTGATGGGTGCCACCTTCGC |
| GGAAATGAACACTGGAGGAGATGTAGCTCATCTGGCGCTGATAGCGGCATTCAAAGTCAGACCAGCGTTGCTGGTATCTT |
| TCATCTTCAGAGCTAATTGGACACCCCGTGAAAGCATGCTGCTGGCCTTGGCCTCGTGTCTTTTGCAAACTGCGATCTCCG |
| CCTTGGAAGGCGACCTGATGGTTCTCATCAATGGTTTTGCTTTGGCCTGGTTGGCAATACGAGCGATGGTTGTTCCACGCA |
| CTGATAACATCACCTTGGCAATCCTGGCTGCTCTGACACCACTGGCCCGGGGCACACTGCTTGTGGCGTGGAGAGCAGGC |
| CTTGCTACTTGCGGGGGGTTTATGCTCCTCTCTCTGAAGGGAAAAGGCAGTGTGAAGAAGAACTTACCATTTGTCATGGC |
| CCTGGGACTAACCGCTGTGAGGCTGGTCGACCCCATCAACGTGGTGGGGCTGCTGTTGCTCACAAGGAGTGGGAAGCGG |
| AGCTGGCCCCCTAGCGAAGTACTCACAGCTGTTGGCCTGATATGCGCATTGGCTGGAGGGTTCGCCAAGGCAGATATAGA |
| GATGGCTGGGCCCATGGCCGCGGTCGGTCTGCTAATTGTCAGTTACGTGGTCTCAGGAAAGAGTGTGGACATGTACATTG |
| AAAGAGCAGGTGACATCACATGGGAAAAAGATGCGGAAGTCACTGGAAACAGTCCCCGGCTCGATGTGGCGCTAGATG |
| AGAGTGGTGATTTCTCCTGGTGGAGGATGACGGTCCCCCCATGAGAGAGATCATACTCAAGGTGGTCCTGATGACCATC |
| TGTGGCATGAACCCAATAGCCATACCCTTTGCAGCTGGAGCGTGGTACGTATACGTGAAGACTGGAAAAAGGAGTGGTG |
| CTCTATGGGATGTGCCTGCTCCCAAGGAAGTAAAAAAGGGGGAGACCACAGATGGAGTGTACAGAGTAATGACTCGTAG |
| ACTGCTAGGTTCAACACAAGTTGGAGTGGGAGTTATGCAAGAGGGGGTCTTTCACACTATGTGGCACGTCACAAAAGGA |
| TCCGCGCTGAGAAGCGGTGAAGGGAGACTTGATCCATACTGGGGAGATGTCAAGCAGGATCTGGTGTCATACTGTGGTC |
| CATGGAAGCTAGATGCCGCCTGGGACGGGCACAGCGAGGTGCAGCTCTTGGCCGTCCCCCGGAGAGAGAGCGAGGA |
| ACATCCAGACTCTGCCCGGAATATTTAAGACAAAGGATGGGGACATTGGAGCGGTTGCGCTGGATTACCCAGCAGGAAC |
| TTCAGGATCTCCAATCCTAGACAAGTGTGGGAGAGTGATAGGACTTTATGGCAATGGGGTCGTGATCAAAAATGGGAGT |
| TATGTTAGTGCCATCACCCAAGGGAGGAGGGAGGAAGAGACTCCTGTTGAGTGCTTCAGCCTTCGATGCTGAAGAAGA |
| AGCAGCTAACTGTCTTAGACTTGCATCCTGGAGCTGGGAAAACCAGGAGAGTTCAAGAGAGTTAGGACGGAGCAAAGGAGCCATA |
| AAAACAAGACTCCGTACTGTGATCTTAGCTCCAACCAGGGTTGTCGCTGCTGAAATGGAGGAAGCCCTTAGAGGGCTTCC |
| AGTGCGTTATATGACAACAGCAGTCAATGTCACCCACTCTGGAACAGAAATCGTCGACTTAATGTGCCATGCCACCTTCAC |
| TTCACGTCTACTACAGCCAATCAGAGTCCCCAACTATAATCTGTATATTATGGATGAGGCCCACTTCACAGATCCCTCAAGT |
| ATAGCAGCAAGAGGATACATTTCAACAAGGGTTGAGATGGGCAGGCGGCTGCCATCTTCATGACCGCCACGCCACCAG |
| GAACCCGTGACGCATTTCCGGACTCCAACTCACCAATTATGGACACCGAAGTGGAAGTCCCAGAGAGAGCCTGGAGCTCA |
| GGCTTTGATTGGGTGACGGATTATTCTGGAAAAACAGTTTGGTTTGTTCCAAGCGTGAGGAACGGCAATGAGATCGCAGC |
| TTGTCTGACAAAGGCTGGAAAACGGGTCATACAGCTCAGCAGAAAGACTTTTGAGACAGAGTTCCAGAAAACAAAACATC |
| AAGAGTGGGACTTTGTCGTGACAACTGACATTTCAGAGATGGGCGCCAACTTTAAAGCTGACCGTGTCATAGATTCCAGG |
| AGATGCCTAAAGCCGGTCATACTTGATGGCGAGAGAGTCATTCTGGCTGGACCCATGCCTGTCACACATGCCAGCGCTGC |
| CCAGAGGAGGGGCGCATAGGCAGGAATCCCAACAAACCTGGAGATGAGTATCTGTATGGAGGTGGGTGCGCAGAGAC |
| TGACGAAGACCATGCACACTGGCTTGAAGCAAGAATGCTCCTTGACAATATTTACCTCCAAGATGGCCTCATAGCCTCGCT |
| CTATCGACCTGAGGCCGACAAAGTAGCAGCCATTGAGGGAGAGTTCAAGCTTAGGACGGAGCAAAGGAAGACCTTTGTG |
| GAACTCATGAAAAGAGGAGATCTTCCTGTTTGGCTGGCCTATCAGGTTGCATCTGCCGGAATAACCTACACAGATAGAAG |
| ATGGTGCTTTGATGGCACGACCAACAACACCATAATGGAAGACAGTGTGCCGGCAGAGGTGTGGACCAGACACGGAGA |
| GAAAAGAGTGCTCAAACCGAGGTGGATGGACGCCAGAGTTTGTTCAGATCATGCGGCCCTGAAGTCATTCAAGGAGTTT |
| GCCGCTGGGAAAAGAGGAGCGGCTTTTTGGAGTGATGGAAGCCCTGGGAACACTGCCAGGACACATGCAGAGAGATTC |
| CAGGAAGCCATTGACAACCTCGCTGTGCTCATGCGGGCAGAGACTGGAAGCAGGCCTTACAAAGCCGCGGCGGCCCAAT |
| TGCCGGAGACCCTAGAGACCATTATGCTTTTGGGGTTGCTGGGAACAGTCTCGCTGGGAATCTTTTTCGTCTTGATGAGG |
| AACAAGGGCATAGGGAAGATGGGCTTTGGAATGGTGACTCTTGGGGCCAGCGCATGGCTCATGTGGCTCTCGGAAATTG |
| AGCCAGCCAGAATTGCATGTGTCCTCATTGTTGTGTTCCTATTGCTGGTGGTGCTCATACCTGAGCCAGAAAAGCAAAGAT |
| CTCCCCAGGACAACCAAATGGCAATCATCATCATGGTAGCAGTAGGTCTTCTGGGCTTGATTACCGCCAATGAACTCGGAT |
| GGTTGGAGAGAACAAAGAGTGACCTAAGCCATCTAATGGGAAGGAGAGAGGAGGGGGCAACCATGGGATTCTCAATGG |
| ACATTGACCTGCGGCCAGCCTCAGCTTGGGCCATCTATGCTGCCTTGACAACTTTCATTACCCCAGCCGTCAACATGCAGT |
| GACCACTTCATACAACAACTACTCCTTAATGGCGATGGCCACGCAAGCTGGAGTGTTGTTTGGTATGGGCAAAGGGATGC |
| CATTCTACGCATGGACTTTGAGTCCCGCTGCTAATGATAGGTTGCTACTCACAATTAACGCCCCCTGACCCTAATAGTGG |
| CCATCATTTTGCTCGTGGCGCACTACATGTACTTGATCCCAGGGCTGCAGGCAGCAGCTGCGCGTGCTGCCCAGAAGAGA |
| ACGGCAGCTGGCATCATGAAGAACCCTGTTGTGGATGGAATAGTGGTGACTGACATTGACACAATGACAATTGACCCCCA |
| AGTGGAGAAAAAGATGGGACAGGTGCTACTCATGGCAGTAGCCGTCTCCAGCGCCATACTGTCGCGGACCGCCTGGGGG |
| TGGGGGGAGGCTGGGCCTGATCACAGCCGCCAACTTCCACTTTGTGGAAGGCTCTCCGAACAAGTACTGGAACTCCTC |
| TACAGCCACTTCACTGTGTAACATTTTTAGGGGAAGTTACTTGGCTGGAGCTTCTCTAATCTACACAGTAACAAGAAACGC |
| TGGCTTGGTCAAGAGACGTGGGGGTGGAACAGGAGAGACCCTGGGAGAGAAATGGAAGGCCCGCTTGAACCAGATGTC |
| GG CCCTGGAGTCTACTCCTACAAAAAGTCAGGCATCACCGAGGTGTGCAGAGAAGAGGCCCGCCGCGCCCTCAAGGAC |
| GGTGTGGCAACGGGAGGCCATGCTGTGTCCCGAGGAAGTGCAAAGCTGAGATGGTTGGTGGAGCGGGGATACCTGCAG |
| CCCTATGGAAAGGTCATTGATCTTGGATGTGGCAGAGGGGGCTGGAGTTACTACGCCGCCACCATCCGCAAAGTTCAAGA |
| AGTGAAAGGATACACAAAAGGAGGCCCTGGTCATGAAGAACCCGTGTTGGTGCAAAGCTATGGGTGGAACATAGTCCGT |
| CTTAAGAGTGGGGTGGACGTCTTTCATATGGCGGCTGAGCCGTGTGACACGTTGCTGTGTGACATAGGTGAGTCATCATC |
| TAGTCCTGAAGTGGAAGAAGCACGGACGCTCAGAGTCCTCTCCATGGTGGGGATTGGCTTGAAAAAGACCAGGACC |
| TTTTGTATAAAAGTGTTGTGCCCATACACCAGCACTATGATGAAACCCTGGAGGCAGCTGCAGGTAGGTATGGGGGAG |
| GACTGGTCAGAGTGCCACTCTCCCGCAACTCTACACATGAGATGTACTGGGTCTCTGGAGCGAAAAGCAACACCATAAA |
| AGTGTGTCCACCACGAGCCAGCTCCTCTTGGGCGCATGGACGGGCCTAGGAGGCCAGTGAAATATGAGGAGGATGTGA |
| ATCTCGGCTCTGGCACGCGGGCTGTGGTAAGCTGCGCTGAAGCTCCCAACATGAAGATCATTGGTAACCGCATTGAAAGG |
| ATCCGCAGTGAGCACGCGGAAACGTGGTTCTTTGACGAGAACCACCCATATAGGACATGGGCTTACCATGGAAGCTATGA |
| GGCCCCCACACAAGGGTCAGCGTCCTCTCTAATAAACGGGGTTGTCAGGCTCCTGTCAAAACCCTGGGATGTGGTGACTG |
| GAGTCACAGGAATAGCCATGACCGACACCACACCGTATGGTCAGCAAAGAGTTTTCAAGGAAAAAGTGGACACTAGGGT |
| GCCAGACCCCCAAGAAGGTACTCGTCAGGTTATGAGCATGGTCTCTTCCTGGTTGTGGAAAGAGTAGGCAAACACAAAC |
| GGCCACGAGTCTGTACCAAAGAAGAGTTCATCAACAAGGTTCGTAGCAATGCAGCATTAGGGGCAATATTTGAAGAGGA |
| AAAAGAGTGGAAGACTGCAGTGGAAGCTGTGAACGATCCAAGGTTCTGGGCTCTAGTGGACAAGGAAAGAGAGCACCA |
| CCTGAGAGGAGAGTGCCAGAGTTGTGTGTACAACATGATGGGAAAAAGAGAAAAGAAAACAAGGGGAATTTGGAAAGGC |
| CAAGGGCAGCCGCGCCATCTGGTATATGTGGCTAGGGGCTAGATTTCTAGAGTTCGAAGCCCTTGGATTCTTGAACGAGG |
| ATCACTGGATGGGGAGAGAACTCAGGAGGTGGTGTTGAAGGGCTGGATTACAAAGACTCGGATATGTCCTAGAAG |
| AGATGAGTCGCATACCAGGAGGAAGGATGTATGCAGATGACACTGCTGGCTGGGACACCCGCATCAGCAGGTTTGATCT |
| GGAGAATGAAGCTCTAATCACCAACCAAATGGAGAAAGGGCACAGGGCCTTGGCATTGGCCATAATCAAGTACACATAC |
| CAAAACAAAGTGGTAAAGGTCCTTAGACCAGCTGAAAAAGGGAAAACAGTTATGGACATTATTTCGAGACAAGACCAAA |

GGGGGAGCGGACAAGTTGTCACTTACGCTCTTAACACATTTACCAACCTAGTGGTGCAACTCATTCGGAATATGGAGGCT
GAGGAAGTCCTAGAGATGCAAGACTTGTGGCTGCTGCGGAGGTCAGAGAAAGTGACCAACTGGTTGCAGAGCAACGGA
TGGGATAGGCTCAAACGAATGGCAGTCAGTGGAGATGATTGCGTTGTGAAGCCAATTGATGATAGGTTTGCACATGCCCT
CAGGTTCTTGAATGATATGGGAAAAGTTAGGAAGGACACACAAGAGTGGAAACCCTCAACTGGATGGGACAACTGGGAA
GAAGTTCCGTTTTGCTCCCACCACTTCAACAAGCTCCATCTCAAGGACGGGAGGTCCATTGTGGTTCCCTGCCGCCACCAA
GATGAACTGATTGGCCGGGCCCGCGTCTCTCCAGGGGCGGGATGGAGCATCCGGGAGACTGCTTGCCTAGCAAAATCAT
ATGCGCAAATGTGGCAGCTCCTTTATTTCCACAGAAGGGACCTCCGACTGATGGCCAATGCCATTTGTTCATCTGTGCCAG
TTGACTGGGTTCCAACTGGGAGAACTACCTGGTCAATCCATGGAAAGGGAGAATGGATGACCACTGAAGACATGCTTGT
GGTGTGGAACAGAGTGTGGATTGAGGAGAACGACCACATGGAAGACAAGACCCCAGTTACGAAATGGACAGACATTCCC
TATTTGGGAAAAAGGGAAGACTTGTGGTGTGGATCTCTCATAGGGCACAGACCGCGCACCACCTGGGCTGAGAACATTA
AAAACACAGTCAACATGGTGCGCAGGATCATAGGTGATGAAGAAAAGTACATGGACTACCTATCCACCCAAGTTCGCTAC
TGGGTGAAGAAGGGTCTACACCTGGAGTGCTGTAAGCACCAATCTTAATGTTGTCAGGCCTGCTAGTCAGCCACAGCTT
GGGGAAAGCTGTGCAGCCTGTGACCCCCCAGGAGAAGCTGGGAAACCAAGCCTATAGTCAGGCCGAGAACGCCATGG
CACGGAAGAAGCCATGCTGCCTGTGAGCCCCTCAGAGGACACTGAGTCAAAAAACCCCACGCGCTGGAGGCGCAGGAT
GGGAAAAGAAGGTGGCGACCTTCCCCACCCTTCAATCTGGGGCCTGAACTGGAGATCAGCTGTGGATCTCCAGAAGAGG
GACTAGTGGTTAGAGGAGA

SEQ ID NO: 3
KU497555.1 Zika virus isolate Brazil-ZKV2015, Brazil, complete genome
CCAATCTGTGAATCAGACTGCGACAGTTCGAGTTTGAAGCGAAAGCTAGCAACAGTATCAACAGGTTTTATTTTGGATTTG
GAAACGAGAGTTTCTGGTCATGAAAAACCCAAAAAGAAATCCGGAGGATTCCGGATTGTCAATATGCTAAAACGCGGA
GTAGCCCGTGTGAGCCCCTTTGGGGGCTTGAAGAGGCTGCCAGCCGGACTTCTGCTGGGTCATGGGCCCATCAGGATGG
TCTTGGCCGATTCTAGCCTTTTTGAGATTCACGGCAATCAAGCCATCACTGGGTCTCATCAATAGATGGGGTTCAGTGGGA
AAAAAGAGGCTATGGAAATAATAAAGAAGTTCAAGAAAGATCTGGCTGCCATGCTGAGAAATATCAATGCCAGGAAGGA
GAAGAAGAGACGAGGCGCAGATACTAGTGTCGGAATCGTTGGCCTCCTGCTGACCACAGCTATGGCAGCGGAGGTCACT
AGACGTGGGAGTGCATACTATATGTACTTGGACAGAAACGATGCTGGGGAGGCCATATCTTTTCCAACCACATTGGGGAT
GAATAAGTGTTATATACAGATCATGGATCTTGGACACATGTGTGATGCCACCATGAGCTATGAATGCCCTATGCTGGATG
AGGGGGTGGAACCAGATGACGTCGATTGTTGGTGCAACACGACGTCAACTTGGGTTGTGTACGGAACCTGCCATCACAA
AAAAGGTGAAGCACGGAGATCTAGAAGAGCTGTGACGCTCCCCTCCCATTCCACTAGGAAGCTGCAAACGCGGTCGCAA
ACCTGGTTGGAATCAAGAGAATACACAAAGCACTTGATTAGAGTCGAAAATTGGATATTCAGGAACCCTGGCTTCGCGTT
AGCAGCAGCTGCCATCGCTTGGCTTTTGGGAAGCTCAACGAGCCAAAAAGTCATATACTTGGTCATGACTACTGCTGATTGC
CCCGGCATACAGCATCAGGTGCATAGGAGTCAGCAATAGGGACTTTGTGGAAGGTATGTCAGGTGGGACTTGGGTTGAT
GTTGTCTTGGAACATGGGGGTTGTGTCACCGTAATGGCACAGGACAAAACCGACTGTCGACATAGAGCTGGTTACAACAAC
AGTCAGCAACATGGCGGAGGTAAGATCCTACTGCTATGAGGCATCAATATCAGACATGGCTTCGGACAGCCGCTGCCCAA
CACAAGGTGAAGCCTACCTTGACAAGCAATCAGACACTCAATATGTCTGCAAAAGAACGTTAGTGGACAGAGGCTGGGG
AAATGGATGTGGACTTTTTGGCCAAAGGGAGCCTGGTGACATGCGCTAAGTTTGCATGCTCCAAGAAAATGACCGGGAAG
AGCATCCAGCCAGAGAATCTGGAGTACCGGATAATGCTGTCAGTTCATGGCTCCCAGCACAGTGGGATGATCGTTAATGA
CACAGGACATGAAACTGATGAGAATAGAGCGAAGGTTGAGATAACGCCCAATTCACCAAGAGCCGAAGCCACCCTGGGG
GGTTTTGGAAGCTTAGGACTTGATTGTGAACCGAGGACAGGCCTTGACTTTTCAGATTTGTATTACTTGACTATGAATAAC
AAGCACTGGTTGGTTCACAAGGAGTGGTTCCACGACATTCCATTACCTTGGCACGCTGGGGCAGACACCGGAACTCCACA
CTGGAACAACAAAGAAGCACTGGTAGAGTTCAAGGACGCACATGCCAAAAGGCAAACTGTCGTGGTTCTAGGGACTCAA
GAAGGAGCAGTTCACACGCCCCTTGCTGGAGCTCTGGAGGCTGAGATGGATGGTGCAAAGGGAAGGCTGTCCTCTGGCC
ACTTGAAATGTCGCCTGAAAATGGATAAACTTAGATTGAAGGGCGTGTCATACTCCTTGTGTACCGCAGCGTTCACATTCA
CCAAGATCCCGGCTGAAACACTGCACGGGACAGTCACAGTGGAGGTACAGTACGCAGGGACAGATGGACCTTGCAAGGT
TCCAGCTCAGATGGCGGTGGACATGCAAACTCTGACCCCAGTTGGGAGGTTGATAACCGCTAACCCCGTAATCACTGAAA
GCACTGAGAACTCTAAGATGATGCTGGAACTTGATCCACCATTTGGGGACTCTTACATTGTCATAGGAGTCGGGGAGAAG
AAGATCACCCACCACTGGCACAGGAGTGGCAGCACCATTGGAAAAGCATTTGAAGCCACTGTGAGAGGTGCCAAGAGAA
TGGCAGTCTTGGGAGACACAGCCTGGGACTTTGGATCAGTTGGAGGCGCTCTCAACTCATTGGGCAAGGGCATCCATCAA
ATTTTTGGAGCAGCTTTCAAATCATTGTTTGGAGGAATGTCCTGGTTCTCACAAATTCTCATTGGAACGTTGCTGATGTGGT
TGGGTCTGAACACAAAGAATGGATCTATTTCCCTTATGTGCTTGGCCTTAGGGGGAGTGTTGATCTTCTTATCCACAGCCG
TCTCTGCTGATGTGGGGTGCTCGGTGGACTTCTCAAAGAAGGAGACGAGATGTGGTACAGGGGTGTTCGTCTATAACGA
CGTTGAAGCCTGGAGGGACAGGTACAAGTACCATCCTGACTCTCCCCGTAGATTGGCAGCAGCAGTCAAGCAAGCCTGG
GAAGATGGTATCTGCGGGATCTCCTCTGTTTCAAGAATGGAAAACATCATGTGGGATCAGTAGAAGGGGAGCTTAACG
CAATCCTGGAAGAGAATGGAGTTCAACTGACGGTCGTTGTGGGATCTGTAAAAAACCCCATGTGGAGAGGTCCACAGGA
ATTGCCCGTGCCTGTGAACGAGCTGCCCCACGGCTGGAAGGCTTGGGGGAAATCGTACTTCGTCAGAGCAGCAAAGACA
AATAACAGCTTTGTCGTGGATGGTGACACACTGAAGGAATGCCCACTCAAACATAGAGCATGGAACAGCTTTCTTGTGGA
GGATCATGGGTTCGGGGTATTTCACACTAGTGTCTGGCTCAAGGTTAGAGAAGATTATTCATTAGAGTGTGATCCAGCCG
TTATTGGAACAGCTGTTAAGGGAAAGGAGGCTGTACACAGTGATCTAGGCTACTGGATTGAGAGTGAGAAGAATGACAC
ATGGAGGCTGAAGAGGGCCCATCTGATCGAGATGAAAACATGTGAATGGCCAAAGTCCCACACATTGTGGACAGATGGA
ATAGAAGAGAGTGATCTGATCATACCCAAGTCTTTAGCTGGGCCACTCAGCCATCACAATACCAGAGAGGGCTACAGGAC
CCAAATGAAAGGGCCATGGCACAGTGAAGAGCTTGAAATTCGGTTTGAGGAATGCCCAGGCACTAAGGTCCACGTGGAG
GAAACATGTGGAACAAGAGGACCATCTCTGAGATCAACCACTGCTCAAGCGGAAGGGTGATCGAGGAATGGTGCTGCAGG
GAGTGCACAATGCCCCACTGTCGTTCCGGGCTAAAGATGGCTGTTGGTATGGAATGGAGATAAGGCCCAGGAAAGAAC
CAGAAAGCAACTTAGTAAGGTCAATGGTGACTGCAGGATCAACTGATCACATGGATCACTTCTCCCTTGGAGTGCTTGTG
ATTCTGCTCATGGTGCAGGAAGGGCTGAAGAAGAGAATGACCACAAAGATCATCATAAGCACATCAATGGCAGTGCTGG
TAGCTATGATCCTGGGAGGATTTTCAATGAGTGACCTGGCTAAGCTTGCAATTTTGATGGGTGCCACCTTCGCGGAAATG
AACACTGGAGGAGATGTAGCTCATCTGGCGCTGATAGCGGCATTCAAAGTCAGACCAGCGTTGCTGGTATCTTTCATCTTC
AGAGCTAATTGGACACCCCGTGAAAGCATGCTGCTGGCCTTGGCCTCGTGTTTTTTGCAAACTGCGATCTCCGCCTTGGAA
GGCGACCTGATGGTTCTCATCAATGGTTTGCTTTGGCCTGGTTGCAATAGAGCGATGGTTGTTCCACGCACTGACAAC
ATCACCTTGGCAATCCTGGCTGCTCTGACACCACTGGCCCGGGGCACACTGCTTGTGGCGTGGAGAGCAGGCCTTGCTAC
TTGCGGGGGTTTATGCTCCTCTCTCTGAAGGGAAAAGGCAGTGTGGAAGAGAACTTACCATTTGTCATGGCCCTGGGAC
TAACCGCTGTGAGGCTGGTCGACCCCATCAACGTGGTGGGACTGCTGTTGCTCACAAGGAGTGGGAAGCGGAGCTGGCC
CCCTAGCGAAGTACTCACAGCTGTTGGCCTGATATGCGCATTGGCTGGAGGGTTCGCCAAGGCAGATATAGAGATGGCT
GGGCCCATGGCCGCGGTCGGTCTGCTAATTGTCAGTTACGTGGTCTCAGGAAAGAGTGTGGACATGTACATTGAAAGAG
CAGGTGACATCACATGGGAAAAAGATGCGGAAGTCACTGGAAACAGTCCCCGGCTCGATGTGGCGCTAGATGAGAGTG
GTGACTTCTCCCTGGTGGAGGATGACGGTCCCCCCATGAGAGAGATCATACTCAAGGTGGTCCTGATGACCATCTGTGGC
ATGAACCCAATAGCCATACCCTTTGCAGCTGGAGCGTGGTACGTATACGTGAAGACTGGAAAAAGGAGTGGTGCTCTATG

| SEQUENCES |
|---|
| GGATGTGCCTGCTCCCAAGGAAGTAAAAAAGGGGGAGACCACAGATGGAGTGTACAGAGTAATGACTCGTAGACTGCTA |
| GGTTCAACACAAGTTGGAGTGGGAGTTATGCAAGAGGGGGTCTTTCACACTATGTGGCACGTCACAAAAGGATCCGCGC |
| TGAGAAGCGGTGAAGGGAGACTTGATCCATACTGGGGAGATGTCAAGCAGGATCTGGTGTCATACTGTGGTCCATGGAA |
| GCTAGATGCCGCCTGGGACGGGCACAGCGAGGTGCAGCTCTTGGCCGTGCCCCCCGGAGAGAGAGCGAGGAACATCCA |
| GACTCTGCCCGGAATATTTAAGACAAAGGATGGGGACATTGGAGCGGTTGCGCTGGATTACCCAGCAGGAACTTCAGGA |
| TCTCCAATCCTAGACAAGTGTGGGAGAGTGATAGGACTTTATGGCAATGGGGTCGTGATAAAAAATGGGAGTTATGTTA |
| GTGCCATCACCCAAGGGAGGAGGGAGGAAGAAGACTCCTGTTGAGTGCTTCGAGCCTTCGATGCTGAAGAAGAAGCAGCT |
| AACTGTCTTAGACTTGCATCCTGGAGCTGGGAAAACCAGGAGAGTTCTTCCTGAAATAGTCCGTGAAGCCATAAAAACAA |
| GACTCCGTACTGTGATCTTAGCTCCAACCAGGGTTGTCGCTGCTGAAATGGAGGAAGCCCTTAGAGGGCTTCCAGTGCGT |
| TATATGACAACAGCAGTCAATGTCACCCACTCTGGAACAGAAATCGTCGACTTAATGTGCCATGCCACCTTCACTTCACGT |
| CTACTACAGCCAATCAGAGTCCCCAACTATAATCTGTATATTATGGATGAGGCCCACTTCACAGATCCCTCAAGCATAGCA |
| GCAAGAGGATACATTTCAACAAGGGTTGAGATGGGCGAGGCGGCTGCCATCTTCATGACCGCCACGCCACCAGGAACCC |
| GTGACGCATTTCCGGACTCCAACTCACCAATTATGGACACCGAAGTGGAAGTCCCAGAGAGAGCCTGGAGCTCAGGCTTT |
| GATTGGGTGACGGATCATTCTGGAAAAACAGTTTGGTTTGTTCCAAGCGTGAGGAACGGCAATGAGATCGCAGCTTGTCT |
| GACAAAGGCTGGAAAACGGGTCATACAGCTCAGCAGAAAGACTTTTGAGACAGAGTTCCAGAAAACAAAACATCAAGAG |
| TGGGACTTTGTCGTGACAACTGACATTTCAGAGATGGGCGCCAACTTTAAAGCTGACCGTGTCATAGATTCCAGGAGATG |
| CCTAAAGCCGGTCATACTTGATGGCGAGAGAGTCATTCTGGCTGGACCCATGCCTGTCACACATGCCAGCGCTGCCCAGA |
| GGAGGGGGCGCATAGGCAGGAATCCCAACAAACCTGGAGATGAGTACCTGTATGGAGGTGGGTGCGCAGAGACTGACG |
| AAGACCATGCACACTGGCTTGAAGCAAGAATGCTCCTTGACAATATTTACCTCCAAGATGGCCTCATAGCCTCGCTCTATC |
| GACCTGAGGCCGACAAAGTAGCAGCCATTGAGGGAGAGTTCAAGCTTAGGACGGAGCAAAGGAAGACCTTTGTGGAAC |
| TCATGAAAAGAGGAGATCTTCCTGTTTGGCTGGCCTATCAGGTTGCATCTGCCGGAATAACCTACACAGATAGAAGATGG |
| TGCTTTGATGGCACGACCAACAACACCATAATGGAAGACAGTGTGCCGGCAGAGGTGTGGACCAGACACGGAGAGAAA |
| AGAGTGCTCAAACCGAGGTGGATGGACGCCAGAGTTTGTTCAGATCATGCGGCCCTGAAGTCATTCAAGGAGTTTGCCGC |
| TGGGAAAAGAGGAGCGGCTTTTGGAGTGATGAAGCCCTGGGAACGCTGCCAGGACACATGCAGAGAGAGATTCCAGGA |
| AGCCATTGACAACCTCGCTGTGCTCATGCGGGCAGAGACTGGAAGCAGGCCTTACAAAGCGCGGCGGCCCAATTGCCG |
| GAGACCCTAGAGACCATTATGCTTTTGGGGTTGCTGGGAACAGTCTCGCTGGGAATCTTTTTCGTCTTGATGAGGAACAA |
| GGGCATAGGGAAGATGGGCTTTGGAATGGTGACTCTTGGGGCCAGCGCATGGCTCATGTGGCTCTCGGAAATTGAGCCA |
| GCCAGAATTGCATGTGTCCTCATTGTTGTTCCTATTGCTGGTGGTGCTCATACCGTGAGCCAGAAAAGCAAAGATCTCCC |
| CAGGACAACCAAATGGCAATCATCATCATGGTAGCAGTAGGTCTTCTGGGCTTGATTACCGCCAATGAACTCGGATGGTT |
| GGAGAGAACAAAGAGTGACCTAAGCCATCTAATGGGAAGGAGAGAGGGAGGGGGCAACCATAGGATTCTCAATGGACAT |
| TGACCTGCGGCCAGCCTCAGCTTGGGCCATCTATGCTGCCTTGACAACTTTCATTACCCCAGCCGTCCAACATGCAGTGAC |
| CACTTCATACAACAACTACTCCTTAATGGCGATGGCCACGCAAGCTGGAGTGTTGTTTGGTATGGGCAAAGGGATGCCAT |
| TCTACGCATGGGACTTTGGAGTCCCGCTGCTAATGATAGGTTGCTACTCACAATTAACACCCCTGACCCTAATAGTGGCCA |
| TCATTTTGCTCGTGGCGCACTACATGTACTTGATCCCAGGGCTGCAGGCAGCAGCTGCGCGTGCTGCCCAGAAGAGAACG |
| GCAGCTGGCATCATGAAGAACCCTGTTGTGGATGGAATAGTGGTGACTGACATTGACACAATGACAATTGACCCCCAAGT |
| GGGAGAAAAGATGGGACAGGTGCTACTCATAGCAGTAGCCGTCTCCAGCGCCATACTGTCGCGGACCGCCTGGGGTGG |
| GGGGAGGCTGGGGCCCTGATCACAGCCGCAACTTCCACTTTGTGGGAAGGCTCTCCGAACAAGTACTGGAACTCCTCTAC |
| AGCCACTTCACTGTGTAACATTTTTAGGGGAAGTTACTTGGCTGGAGCTTCTCTAATCTACACAGTAACAAGAAACGCTGG |
| CTTGGTCAAGAGACGTGGGGGTGGAACAGGAGAGACCCTGGGAGAGAAATGGAAGGCCCGCTTGAACCAGATGTCGGC |
| CCTGGAGTTCTACTCCTACAAAAAGTCAGGCATCACCGAGGTGTGCAGAGAAGAGGCCCGCCGCGCCCTCAAGGACGGT |
| GTGGCAACGGGAGGCCATGCTGTGTCCCGAGGAAGTGCAAAGCTGAGATGGTTGGTGGAGCGGGGATACCTGCAGCCC |
| TATGGAAAGGTCATTGATCTTGGATGTGGCAGAGGGGGCTGGAGTTACTACGCCGCCACCATCCGCAAAGTTCAAGAAG |
| TGAAAGGATACACAAAAGGAGGCCCTGGTCATGAAGAACCCGTGTTGGTGCAAAGCTATGGGTGGAACATAGTCCGTCT |
| TAAGAGTGGGGTGGACGTCTTTCATATGGCGGCTGAGCCGTGTGACACGTTGCTGTGTGACATAGGTGAGTCATCATCTA |
| GTCCTGAAGTGGAAGAAGCACGGACGCTCAGAGTCCTCTCCATGGTGGGGATTGGCTTGAAAAAAGACCAGGAGCM |
| TTGCATAAAAGTGTTGTGCCCATACACCAGCACTATGATGGAAACCCTGGAGCGACTGCAGCGTAGGTATGGGGGAGGA |
| CTGGTCAGAGTGCCACTCTCCCGCAACTCTACACATGAGATGTACTGGGTCTCTGGAGCGAAAAGCAACACCATAAAAG |
| TGTGTCCACCACGAGCCAGCTCCTCTTGGGGCGCATGGACGGGCCTAGGAGGCCAGTGAAATATGAGGAGGATGTGAAT |
| CTCGGCTCTGGCACGCGGGCTGTGGTAAGCTGCGCTGAAGCTCCCAACATGAAGATCATTGGTAACGCATTGAAAGGAT |
| CCGCAGTGAGCACGCGGAAACGTGGTTCTTTGACGAAAACCACCCATATAGGACATGGGCTTACCATGGAAGCTATGTG |
| GCCCCCACACAAGGGTCAGCGTCCTCTCTAATAAACGGGGTTGTCAGGCTCCTGTCAAAACCCTGGGATGTGGTGACTGG |
| AGTCACAGGAATAGCCATGACCGACACCACACCGTATGGTCAGCAAAGAGTTTTCAAGGAAAAAGTGGACACTAGGGTG |
| CCAGACCCCCAAGAAGGCACTCGTCAGGTTATGAGCATGGTCTCTTCCTGGTTGTGGAAAGAGCTAGGCAAACACAAACG |
| ACCAGAGTCTGTACCAAAGAAGAGTTCATCAACAAGGTTCGTAGCAATGACAGCATTAGGGGCAATATTTGAAGAGGAA |
| AAAGAGTGGAAGACTGCAGTGGAAGCTGTGAACGATCCAAGGTTCTGGGCTCTAGTGGACAAGGAAAGAGAGCACCAC |
| CTGAGAGGAGAGTGCCAGAGTTGTGTGTACAACATGATGGGAAAAAGAGAAAAGAAACAAGGGGAATTTGGAAAGGCC |
| AAGGGCAGCCGCGCCATCTGGTATATGTGGCTAGGGGCTAGATTTCTAGAGTTCGAAGCCCTTGGATTCTTGAACGAGGA |
| TCACTGGATGGGAGAGAGAACTCAGGAGGTGGTGTTGAAGGCTGGGATTACAAAGACTCGGATATGTCCTAGAAGA |
| GATGAGTCGCATACCAGGAGGAAGGATGTATGCAGATGACACTGCTGGCTGGGACACCCGCATCAGCAGGTTTGATCTG |
| GAGAATGAAGCTCTAATCACCCAACCAAATGGAGAAAGGGCACAGGGCCTTGGCATTGGCCATAATCAAGTACACATACC |
| AAAACAAAGTGGTAAAGGTCCTTAGACCAGCTGAAAAAGGGAAAACAGTTATGGACATTATTTCGAGACAAGACCAAAG |
| GGGGAGCGGACAAGTTGTCACTTACGCTCTTAACACATTTACCAACCTAGTGGTGCAACTCATTCGGAATATGGAGGCTG |
| AGGAAGTTCTAGAGATGCAAGACTTGTGGCTGCTGCGGAGGTCAGAGAAAGTGACCAACTGGTTGCAGAGCAACGGAT |
| GGGATAGGCTCAAACGAATGGCAGTCAGTGGAGATGATTGCGTTGTGAAGCCAATTGATGATAGGTTTGCACATGCCCTC |
| AGGTTCTTGAATGATATGGGAAAAGTTAGGAAGGACACACAAGAGTGGAAACCCTCAACTGGATGGGACAACTGGGAA |
| GAAGTTCCGTTTTGCTCCCACCACTTCAACAAGCTCCATCTCAAGGACGGGAGGTCCATTGTGGTTCCCTGCCGCCACCAA |
| GATGAACTGATTGGCCGGGCCCGCGTCTCTCAGGGGCGGGATGGAGCATCCGGGAGACTGCTTGCCTAGCAAAATCAT |
| ATGCGCAAATGTGGCAGCTCCTTTATTTCCACAGAAGGGACCTCCGACTGATGGCCAATGCCATTTGTTCATCTGTGCCAG |
| TTGACTGGGTTCCAACTGGGAGAACTACCTGGTCAATCATGGAAAGGGAGAATGGATGACCATGAAGACATGCATTGT |
| GGTGTGGAACAGAGTGTGGATTGAGGAGAACGACCACATGGAAGACAAGACCCCAGTTACGAAATGACAGACATTCCC |
| TATTTGGGAAAAAGGGAAGACTTGTGGTGTGGATCTCTCATAGGGCACAGACCGCGCACCACCTGGGCTGAGAACATTA |
| AAAATACAGTCAACATGGTGCGCAGGATCATAGGTGATGAAGAAAGTACATGGACTACCTATCCACCCAAGTTCGCTAC |
| TTGGGTGAAGAAGGGTCTACACCTGGAGTGCTGTGAGCACCAATCTTAATGTTGTCAGGCCTGCTAGTCAGCCACAGCTT |
| GGGGAAAGCTGTGCAGCCTGTGACCCCTCCAGGAGAAGCTGGGTAACCAAGCCTATAGTCAGGCCGAGAACGCCATGGC |
| ACGGAAGAAGCCATGCTGCCTGTGAGCCCCTCAGAGGACACTGAGTCAAAAAACCCCACGCGCTTGGAGGCGCAGGATG |

| SEQUENCES |
|---|
| GGAAAAGAAGGTGGCGACCTTCCCCACCCTTCAATCTGGGGCCTGAACTGGAGATCAGCTGTGGATCTCCAGAAGAGGG
ACTAGTGGTTAGAGGAGACCCCCCGGAAAACGCAAAACAGCATATTGACGCTGGGAAAGACCAGAGACTCCATGAGTTT
CCACCACGCTGGCCGCCAGGCACAGATCGCCGAATAGCGGCGGCCGGTGTGGGGAAATCCA |
| SEQ ID NO: 4
KU501215.1 Zika virus strain PRVABC59, Puerto Rico, complete genome
GTTGTTGATCTGTGTGAATCAGACTGCGACAGTTCGAGTTTGAAGCGAAAGCTAGCAACAGTATCAACAGGTTTTATTTTG
GATTTGGAAACGAGAGTTTCTGGTCATGAAAAACCCAAAAAAGAAATCCGGAGGATTCCGGATTGTCAATATGCTAAAAC
GCGGAGTAGCCCGTGTGAGCCCCTTTGGGGGCTTGAAGAGGCTGCCAGCCGGACTTCTGCTGGGTCATGGGCCCATCAG
GATGGTCTTGGCGATTCTAGCCTTTTTGAGATTCACGGCAATCAAGCCATCACTGGGTCTCATCAATAGATGGGGTTCAGT
GGGGAAAAAAGAGGCTATGGAAACAATAAAGAAGTTCAAGAAAGATCTGGCTGCCATGCTGAGAATAATCAATGCTAGG
AAGGAGAAGAAGAGACGAGGCGCAGATACTAGTGTCGGAATTGTTGGCCTCCTGCTGACCACAGCTATGGCAGCGGAG
GTCACTAGACGTGGGAGTGCATACTATATGTACTTGGACAGAAACGATGCTGGGGAGGCCATATCTTTTCCAACCACATT
GGGGATGAATAAGTGTTATATACAGATCATGGATCTTGGACACATGTGTGATGCCACCATGAGCTATGAATGCCCTATGC
TGGATGAGGGGGTGGAACCAGATGACGTCGATTGTTGGTGCAACACGACGTCAACTTGGGTTGTGTACGGAACCTGCCA
TCACAAAAAAGGTGAAGCACGGAGATCTAGAAGAGCTGTGACGCTCCCCTCCCATTCCACCAGGAAGCTGCAAACGCGG
TCGCAAACCTGGTTGGAATCAAGAGAATACACAAAGCACTTGATTAGAGTCGAAAATTGGATATTCAGGAACCCTGGCTT
CGCGTTAGCAGCAGCTGCCATCGCTTGGCTTTTGGGAAGCTCAACGAGCCAAAAGTCATATACTTGGTCATGATACTGCT
GATTGCCCCGGCATACAGCATCAGGTGCATAGGAGTCAGCAATAGGGACTTTGTGGAAGGTATGTCAGGTGGGACTTGG
GTTGATGTTGTCTTGGAACATGGAGGTTGTGTCACCGTAATGGCACAGGACAAACCGACTGTCGACATAGAGCTGGTTAC
AACAACAGTCAGCAACATGGCGGAGGTAAGATCCTACTGCTATGAGGCATCAATAAGTCAGACATGGCTTCTGACAGCCGCT
GCCCAACACAAGGTGAAGCCTACCTTGACAAGCAATCAGACACTCAATATGCTGCAAAAGAACGTTAGTGGACAGAGGC
TGGGGAAATGGATGTGGACTTTTTGGCAAAGGGAGCCTGGTGACATGCGCTAAGTTTGCATGCTCCAAGAAAATGACCG
GGAAGAGCATCCAGCCAGAGAATCTGGAGTACCGGATAATGCTGTCAGTTCATGGCTCCCAGCACAGTGGGATGATCGT
TAATGACACAGGACATGAAACTGATGAGAATAGAGCGAAAGTTGAGATAACGCCCAATTCACCGAGAGCCGAAGCCACC
CTGGGGGGTTTTGGAAGCCTAGGACTTGATTGTGAACCGAGGACAGGCCTTGACTTTTCAGATTTGTATTACTTGACTATG
AATAACAAGCACTGGTTGGTTCACAAGGAGTGGTTCCACGACATTCCATTACCTTGGCACGCTGGGGCAGACACCGGAAC
TCCACACTGGAACAACAAAGAAGCACTGGTAGAGTTCAAGGACGCACATGCCAAAAGGCAAACTGTCGTGGTTCTAGGG
AGTCAAGAAGGAGCAGTTCACACGGCCCTTGCTGGAGCTCTGGAGGCTGAGATGGATGGTGCAAAGGGAAGGCTGTCCT
CTGGCCACTTGAAATGTCGCCTGAAAATGGATAAACTTAGATTGAAGGGCGTGTCATACTCCTTGTGTACTGCAGCGTTCA
CATTCACCAAGATCCCGGCTGAAACACTGCACGGGACAGTCACAGTGGAGGTACAGTACGCAGGGACAGATGGACCTTG
CAAGGTTCCAGCTCAGATGGCGGTGGACATGCAAACTCTGACCCCAGTTGGGAGGTTGATAACCGCTAACCCCGTAATCA
CTGAAAGCACTGAGAACTCTAAGATGATGCTGGAACTTGATCCACCATTTGGGGACTCTTACATTGTCATAGGAGTCGGG
GAGAAGAAGATCACCCACCACTGGCACAGGAGTGGCAGCACCATTGGAAAAGCATTTGAAGCCACTGTGAGAGGTGCCA
AGAGAATGGCAGTCTTGGGAGACACAGCCTGGGACTTTGGATCAGTTGGAGGCGCTCTCAACTCATTGGGCAAGGGCAT
CCATCAAATTTTTGGACAGCAGCTTTCAAATCATTGTTTGGAGGAATGTCCTGGTTCTCACAAATTCTCATTGGAACGTTGCTG
ATGTGGTTGGGTCTGAACACAAAGAATGGATCTATTTCCCTTATGTGCTTGGCCTTAGGGGGAGTGTTGATCTTCTTATCC
ACAGCCGTCTCTGCTGATGTGGGGTGCTCGGTGGACTTCTCAAAGAAGGAGACGAGATGCGGTACAGGGGTGTTCGTCT
ATAACGACGTTGAAGCCTGGAGGGACAGGTACAAGTACCATCCTGACTCCCCCCGTAGATTGGCAGCAGCAGTCAAGCA
AGCCTGGGAAGATGGTATCTGCGGGATCTCCTCTGTTTCAAGAATGGAAAACATCATGTGGAGATCAGTAGAAGGGGAG
CTCAACGCAATCCTGGAAGAGAATGGAGTTCAACTGACGGTCGTTGTGGGATCTGTAAAAAACCCCATGTGGAGAGGTC
CACAGAGATTGCCCGTGCCTGTGAACGAGCTGCCCCACGGCTGGAAGGCTTGGGGGAAATCGTATTTCGTCAGAGCAGC
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGATTATTCATTAGAGTGTGAT
CCAGCCGTTATTGGAACAGCTGTTAAGGGAAAGGAGGCTGTACACAGTGATCTGTCGTACTGGATTGAGAGTGAGAAGA
ATGACACATGGAGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATACCAGAGAGGGCT
ACAGGACCCAAATGAAAGGGCCATGGCACAGTGAAGAGCTTGAAATTCGGTTTGAGGAATGCCCAGGCACTAAGGTCCA
CGTGGAGGAAACATGTGGAACAAGAGGACCATCTCTGAGATCAACCACTGCAAGCGGAAGGGTGATCGAGGAATGGTG
CTGCAGGAGTGCACAATGCCCCCACTGTCGTTCCGGGCTAAAGATGGCTGTTGGTATGGAATGGAGATAAGGCCCAGG
AAAGAACCAGAAAGCAACTTAGTAAGGTCAATGGTGACTGCAGGATCAACTGATCACATGGACCACTTCTCCCTTGGAGT
GCTTGTGATCCTGCTCATGGTGCAGGAAGGGCTGAAGAAGAGAATGACCACAAAGATCATCATAAGCACATCAATGGCA
GTGCTGGTAGCTATGATCCTGGGAGGATTTTCAATGAGTGACCTGGCTAAGCTTGCAATTTTGATGGGTGCCACCTTCGC
GGAAATGAACACTGGAGGAGATGTAGCTCATCTGGCGCTGATAGCGGCATTCAAAGTCAGACCAGCGTTGCTGGTATCTT
TCATCTTCAGAGCTAATTGGACACCCCGTGAAAGCATGCTGCTGGCCTTGGCCTCGTGTCTTTTGCAAACTGCGATCTCCG
CCTTGGAAGGCGACCTGATGGTTCTCATCAATGGTTTTGCTTTGGCCTGGTTGGCAATACGAGCGATGGTTGTTCCACGCA
CTGATAACATCACCTTGGCAATCCTGGCTGCTGTGACACCACTGGCCCGGGGCACACTGCTTGTGGCGTGGAGAGCAGGC
CTGCTACTTGCGGGGGTTTATGCTCCTCTCTCTGAAGGGAAAAGGCAGTGTGAAGAAGAACTTACCATTTGTCATGGC
CCTGGGACTAACCGCTGTGAGGCTGGTCGACCCCATCAACGTGGTGGGACTGCTGTTGCTCACAAGGAGTGGGAAGCGG
AGCTGGCCCCCTAGCGAAGTACTCACAGCTGTTGGCCTGATATGCGCATTGGCTGGAGGGTTCGCCAAGGCAGATATAGA
GATGGCTGGGCCCATGGCCGCGGTCGGTCTGCTAATTGTCAGTTACGTGGTCTCAGGAAAGAGTGTTGACATGTACATTG
AAAGAGCAGGTGACATCACATGGGAAAAAGATGCGGAAGTCACTGGAAACAGTCCCCGGCTCGATGTGGCGCTAGATG
AGAGTGGTGATTTCTCCCTGGTGGAGGATGACGGTCCCCCCATGAGAGAGATATACTCAAGGTGGTCCTGATGACCATC
TGTGGCATGAACCCAATAGCCATACCCTTTGCAGCTGGAGCGTGGTACGTATACGTGAAGACTGGAAAAAGGAGTGGTG
CTCCTATGGGATGTGCCTGCTCCCAAGGAAGTAAAAAGGGGGAGACCACAGATGGAGTGTACAGAGTAATGACTCGTAG
ACTGCTAGGTTCAACACAAGTTGGAGTGGGAGTTATGCAAGAGGGGGTCTTTCACACTATGTGGCACGTCACAAAAGGA
TCCGCGCTGAGAAGCGGTGAAGGGAGACTTGATCCATACTGGGGAGATGTCAAGCAGGATCTGGTGTCATACTGTGGTC
CATGGAAGCTAGATGCCGCCTGGGATGGGCACAGCGAGGTGCAGCTCTTGGCCGTGCCCCCCGGAGAGAGAGCGAGGA
ACATCCAGACTCTGCCCGGAATATTTAAGACAAAGGATGGGGACATTGGAGCGGTTGCGCTGGATTACCCAGCAGGAAC
TTCAGGATCTCCAATCCTAGACAAGTGTGGGAGAGTGATAGGACTTTATGGCAATGGGGTCGTGATCAAAAACGGGAGT
TATGTTAGTGCCATCACCCAAGGAGGGAGGAAGGAAGAGACTCCTGTTGAGCTTGCTTCGAGCCCTCGAGCCATA
AGCAGCTAACTGTCTTAGACTTGCATCCTGGAGCTGGGAAAACCAGGAGAGTTCTTCCTGAAATAGTCCGTGAAGCCATA
AAAACAAGACTCCGTACTGTGATCTTAGCTCCAACCAGGGTTGTCGCTGCTGAAATGGAGGAGGCCCTTAGAGGGCTTCC
AGTGCGTTATATGACAACAGCAGTCAATGTCACCCACTCTGGAACAGAAATCGTCGACTTAATGTGCCATGCCACCTTCAC
TTCACGTCTACTACAGCCAATCAGAGTCCCCAACTATAATCTGTATATTATGGATGAGGCCCACTTCACAGATCCCTCAAGT
ATAGCAGCAAGAGGATACATTTCAACAAGGGTTGAGATGGGCGAGGCGGCTGCCATCTTCATGACCGCCACGCCACCAG
GAACCCGTGACGCATTTCCGGACTCCAACTCACCAATTATGGACACCGAAGTGGAAGTCCCAGAGAGAGCCTGGAGCTCA |

| SEQUENCES |
|---|
| GGCTTTGATTGGGTGACGGATCATTCTGGAAAAACAGTTTGGTTTGTTCCAAGCGTGAGGAACGGCAATGAGATCGCAGC |
| TTGTCTGACAAAGGCTGGAAAACGGGTCATACAGCTCAGCAGAAAGACTTTTGAGACAGAGTTCCAGAAAACAAAACATC |
| AAGAGTGGGACTTTGTCGTGACAACTGACATTTCAGAGATGGGCGCCAACTTTAAAGCTGACCGTGTCATAGATTCCAGG |
| AGATGCCTAAAGCCGGTCATACTTGATGGCGAGAGAGTCATTCTGGCTGGACCCATGCCTGTCACACATGCCAGCGCTGC |
| CCAGAGGAGGGGGCGCATAGGCAGGAATCCCAACAAACCTGGAGATGAGTATCTGTATGGAGGTGGGTGCGCAGAGAC |
| TGACGAAGACCATGCACACTGGCTTGAAGCAAGAATGCTCCTTGACAATATTTACCTCCAAGATGGCCTCATAGCCTCGCT |
| CTATCGACCTGAGGCCGACAAAGTAGCAGCCATTGAGGGAGAGTTCAAGCTTAGGACGGAGCAAAGGAAGACCTTTGTG |
| GAACTCATGAAAAGAGGGAGATCTTCCTGTTTGGCTGGCCTATCAGGTTGCATCTGCCGGAATAACCTACACAGATAGAAG |
| ATGGTGCTTTGATGGCACGACCAACAACACCATAATGGAAGACAGTGTGCCGGCAGAGGTGTGGACCAGACACGGAGA |
| GAAAAGAGTGCTCAAACCGAGGTGGATGGACGCCAGAGTTTGTTCAGATCATGCGGCCCTGAAGTCATTCAAGGAGTTT |
| GCCGCTGGGAAAAGAGGAGCGGCTTTTGGAGTGATGGAAGCCCTGGGAACACTGCCAGGACACATGACAGAGAGATTC |
| CAGGAAGCCATTGACAACCTCGCTGTGCTCATGCGGGCAGAGACTGGAAGCAGGCCTTACAAAGCCGCGGCGGCCCAAT |
| TGCCGGAGACCCTAGAGACCATAATGCTTTTGGGGTTGCTGGGAACAGTCTCGCTGGGAATCTTCTTCGTCTTGATGAGG |
| AACAAGGGCATAGGGAAGATGGGCTTTGGAATGGTGACTCTTGGGGCAGCGCATGGCTCATGTGGCTCTCGGAAATTG |
| AGCCAGCCAGAATTGCATGTGTCCTCATTGTTGTGTTCCTATTGCTGGTGGTGCTCATACCTGAGCCAGAAAAGCAAAGAT |
| CTCCCCAGGACAACCAAATGGCAATCATCATCATGGTAGCAGTAGGTCTTCTGGGCTTGATTACCGCCAATGAACTCGGAT |
| GGTTGGAGAGAACAAAGAGTGACCTAAGCCATCTAATGGGAAGGAGAGAGGGAGGGGGCAACCATAGGATTCTCAATGG |
| ACATTGACCTGCGGCCAGCCTCAGCTTGGGCCATCTATGCTGCCTTGACAACTTTCATTACCCCAGCCGTCCAACATGCAGT |
| GACCACCTCATACAACAACTACTCCTTAATGGCGATGGCCACGCAAGCTGGAGTGTTGTTTGGCATGGGCAAAGGGATGC |
| CATTCTACGCATGGGACTTTGGAGTCCCGCTGCTAATGATAGGTTGCTACTCACAATTAACACCCCTGACCCTAATAGTGG |
| CCATCATTTTGCTCGTGGCGCACTACATGTACTTGATCCCAGGGCTGCAGGCAGCAGCTGCGCGTGCTGCCCAGAAGAGA |
| ACGGCAGCTGGCATCATGAAGAACCCTGTTGTGGATGGAATAGTGGTGACTGACATTGACACAATGACAATTGACCCCCA |
| AGTGGAGAAAAAGATGGGACAGGTGCTACTCATAGCAGTAGCCGTCTCCAGCGCCATACTGTCGCGGACCGCCTGGGGG |
| TGGGGGGAGGCTGGGGCTCTGATCACAGCCGCAACTTCCACTTTGTGGGAAGGCTCTCCGACAAGTACTGGAACTCCTC |
| TACAGCCACTTCACTGTGTAACATTTTTAGGGGAAGTTACTTGGCTGGAGCTTCTCTAATCTACACAGTAACAAGAAACGC |
| TGGCTTGGTCAAGAGACGTGGGGGTGGAACAGGAGAGACCCTGGGAGAGAAATGGAAGGCCCGCTTGAACCAGATGTC |
| GGCCCTGGAGTCTACTCCTACAAAAAGTCAGGCATCACCGAGGTGTGCAGAGAAGAGGCCCGCCGCGCCCTCAAGGAC |
| GGTGTGGCAACGGGAGGCCATGCTGTGTCCCGAGGAAGTGCAAAGCTGGAGTGGTTGGAGCGGGGATACCTGCAG |
| CCCTATGGAAAGGTCATTGATCTTGGATGTGGCAGAGGGGGCTGGAGTTACTACGTCGCCACCATCCGCAAAGTTCAAGA |
| AGTGAAAGGATACACAAAAGGAGGCCCTGGTCATGAAGAACCCGTGTTGGTGCAAAGCTATGGGTGGAACATAGTCCGT |
| CTTAAGAGTGGGGTGGACGTCTTTCATATGGCGGCTGAGCCGTGTGACACGTTGCTGTGTGACATAGGTGAGTCATCATC |
| TAGTCCTGAAGTGGAAGAAGCACGGACGCTCAGAGTCCTCTCCATGGTGGGGATTGGCTTGAAAAAAGACCAGGAGCC |
| TTTTGTATAAAAGTGTTGTGCCCATACACCAGCACTATGATGGAAACCCTGGAGCGACTGCAGCGTAGGTATGGGGGAG |
| GACTGGTCAGAGTGCCACTCTCCCGCAACTCTACACATGAGATGTACTGGGTCTCTGGAGCGAAAAGCAACACCATAAAA |
| AGTGTGTCCACCACGAGCCAGCTCCTCTTGGGGCGCATGGACGGGCCTAGGAGGCCAGTGAAATATGAGGAGGATGTGA |
| ATCTCGGCTCTGGCACGCGGGCTGTGGTAAGCTGCGCTGAAGCTCCCAACATGAAGATCATTGGTAACCGCATTGAAAGG |
| ATCCGCAGTGAGCACGCGGAAACGTGGTTCTTTGACGAGAACCACCCATATAGGACATGGGCTTACCATGGAAGCTATGA |
| GGCCCCCACACAAGGGTCAGCGTCCTCTCTAATAAACGGGGTTGTCAGGCTCCTGTCAAAACCCTGGGATGGTGACTG |
| GAGTCACAGGAATAGCCATGACCGACACCACACCGTATGGTCAGCAAAGAGTTTTCAAGGAAAAAGTGGACACTAGGGT |
| GCCAGACCCCAAGAAGGCACTCGTCAGGTTATGAGCAGCATGGTCTCTTCCTGGTTGTGGAAAGAGCTAGGCAAACACAAAC |
| GGCCACGAGTCTGCACCAAAAGAAGAGTTCATCAACAAGGTTCGTAGCAATGCAGCATTAGGGGCAATATTTGAAGAGGA |
| AAAAGACTGGAAGACTGCAGTGGAAGCTGTGAACGATCCAAGGTTCTGGGCTCTAGTGGACAAGGAAAGAGAGCACCA |
| CCTGAGGAGGAGTGCCAGAGCTGTGTGTACAACATGATGGGAAAAAGAGAAAAGAAACAAGGGGAATTTGGAAAGGC |
| CAAGGGCAGCCGCGCCATCTGGTATATGTGGCTAGGGGCTAGATTTCTAGAGTTCGAAGCCCTTGGATTCTTGAACGAGG |
| ATCACTGGATGGGGAGAGAACTCAGGAGGTGGTGTTGAAGGGCTGGGATTACAAAGACTCGGATATGTCCTAGAAG |
| AGATGAGTCGTATACCAGGAGGAAGGATGTATGCAGATGACACTGCTGGCTGGGACACCCGCATTAGCAGGTTTGATCT |
| GGAGAATGAAGCTCTAATCACCAACCAAATGGAGAAAGGCACAGGGCCTTGGCATTGGCCATAATCAAGTACACATAC |
| CAAAACAAAGTGGTAAAGGTCCTTAGACCAGCTGAAAAAGGGAAAACAGTTATGGACATTATTTCGAGACAAGACCCAAA |
| GGGGGAGCGGACAAGTTGTCACTTACGCTCTTAACACATTTACCAACCTAGTGGTGCAACTCATTCGGAATATGGAGGCT |
| GAGGAAGTTCTAGAGATGCAAGACTTGTGGCTGCTGCGGAGGTCAGAGAAAGTGACCAACTGGTTGCAGAGCAACGGA |
| TGGGATAGGCTCAAACGAATGGCAGTCAGTGGAGATGATTGCGTTGTGAAGCCAATTGATGATAGGTTTGCACATGCCCT |
| CAGGTTCTTGAATGATATGGGAAAAGTTAGGAAGGACACACAAGAGTGGAAACCCTCAACTGGATGGACAACTGGGAA |
| GAAGTTCCGTTTTGCTCCCACCACTTCAACAAGCTCCATCTCAAGGACGGAGGTCCATTGTGGTTCCCTGCCGCCACCAA |
| GATGAACTGATTGGCCGGGCCCGCGTCTCTCAGGGGCGGGATGGACATCCGGGAGACTGCTTGCCTAGCAAAATCAT |
| ATGCGCAAATGTGGCAGCTCCTTTATTTCACAGAAGGGACCTCCGACTGATGGCCAATGCCATTTGTTCATCTGTGCCAG |
| TTGACTGGGTTCCAACTGGGAGAACTACCTGGTCAATCCATGGAAAGGGAGAATGGATGACCACTGAAGACATGCTTGT |
| GGTGTGGAACAGAGTGTGGATTGAGGAGAACGACCACATGGAAGACAAGACCCCAGTTACGAAATGGACAGACATTCCC |
| TATTTGGGAAAAAGGGGAAGACTTGTGGTGTGGATCTCTCATAGGGCACAGACCGCGCACCACCTGGGCTGAGAACATTA |
| AAAACACAGTCAACATGGTGCGCAGGATCATAGGTGATGAAGAAAGTACATGGACTACCTATCACCCAAGTTCGCTAC |
| TGGGTGAAGAAGGGTCTACACCTGGAGTGCTGTAAGCACCAATCTTAATGTTGTCAGGCCTGCTAGTCAGCCACAGCTT |
| GGGGAAAGCTGTGCAGCCTGTGACCCCCCAGGAGAAGCTGGGAAACCAAGCCTATAGTCAGGCCGGAGAACGCCATGG |
| CACGGAAGAAGCCATGCTGCCTGTGAGCCCCTCAGAGGACACTGAGTCAAAAAACCCCACGCGCTGGAGGCGCAGGAT |
| GGGAAAAGAAGGTGGCGACCTTCCCCACCCTTCAATCTGGGGCCTGAACTGGAGATCAGCTGTGGATCTCCAGAAGAGG |
| GACTAGTGGTTAGAGGA |

SEQ ID NO: 5
KU509998.1 Zika virus strain Haiti/1225/2014, Haiti, complete genome
GTTGTTACTGTTGCTGACTCAGACTGCGACAGTTCGAGTTTGAAGCGAAAGCTAGCAACAGTATCAACAGGTTTTATTTGG
ATTTGGAAACGAGAGTTTCTGGTCATGAAAAACCCAAAAAAGAAATCCGGAGGATTCCGGATTGTCAATATGCTAAAACG
CGGAGTAGCCCGTGTGAGCCCCTTTGGGGGCTTGAAGAGGCTGCCAGCCGGACTTCTGCTGGGTCATGGGCCCATCAGG
ATGGTCTTGGCAATTCTAGCCTTTTTGAGATTCACGGCAATCAAGCCATCACTGGGTCTCATCAATAGATGGGGTTCAGTG
GGGAAAAAAGAGGCTATGGAAATAATAAAGAAGTTCAAGAAAGATCTGGCTGCCATGCTGAGAATAATCAATGCTAGGA
AGGAGAAGAAGAGACGAGGCGCAGATACTAGTGTCGGAATTGTTGGCCTCCTGCTGACCACAGCTATGGCAGCGGAGG
TCACTAGACGTGGGAGTGCATACTATATGTACTTGGACAGAAACGATGCTGGGGAGGCCATATCTTTTCCAACCACATTG
GGGATGAATAAGTGTTATATACAGATCATGGATCTTGGACACATGTGTGATGCCACCATGAGCTATGAATGCCCTATGCT
GGATGAGGGGGTGGAACCAGATGACGTCGATTGTTGGTGCAACACGACGTCAACTTGGGTTGTGTACGGAACCTGCCAT
CACAAAAAGGTGAAGCACGGAGATCTAGAAGAGCTGTGACGCTCCCCTCCCATTCCACTAGGAAGCTGCAAACGCGGT

| SEQUENCES |
|---|
| CGCAAACCTGGTTGGAATCAAGAGAATACACAAAGCACTTGATTAGAGTCGAAAATTGGATATTCAGGAACCCTGGCTTC |
| GCGTTAGCAGCAGCTGCCATCGCTTGGCTTTTGGGAAGCTCAACGAGCCAAAAAGTCATATACTTGGTCATGATACTGCT |
| GATTGCCCCGGCATACAGCATCAGGTGCATAGGAGTCAGCAATAGGGACTTTGTGGAAGGTATGTCAGGTGGGACTTGG |
| GTTGATGTTGTCTTGGAACATGGAGGTTGTGTCACCGTAATGGCACAGGACAAACCGACTGTCGACATAGAGCTGGTTAC |
| AACAACAGTCAGCAACATGGCGGAGGTAAGATCCTACTGCTATGAGGCATCAATATCAGACATGGCTTCGGACAGCCGCT |
| GCCCAACACAAGGTGAAGCCTACCTTGACAAGCAATCAGACACTCAATATGTCTGCAAAAGAACGTTAGTGGACAGAGGC |
| TGGGGAAATGGATGTGGACTTTTTGGCAAAGGGAGTCTGGTGACATGCGCTAAGTTTGCATGCTCCAAGAAAATGACCG |
| GGAAGAGCATCCAGCCAGAGAATCTGGAGTACCGGATAATGCTGTCAGTTCATGGCTCCCAGCACAGTGGGATGATCGT |
| TAATGACACAGGACATGAAACTGATGAGAATAGAGCGAAGGTTGAGATAACGCCCAATTCACCAAGAGCCGAAGCCACC |
| CTGGGGGGTTTTGGAAGCCTAGGACTTGATTGTGAACCGAGGACAGGCCTTGACTTTTCAGATTTGTATTACTTGACTATG |
| AATAACAAGCACTGGTTGGTTCACAAGGAGTGGTTCCACGACATTCCATTACCTTGGCACGCTGGGGCAGACACCGGAAC |
| TCCACACTGGAACAACAAAGAAGCACTGGTAGAGTTCAAGGACGCACATGCCAAAAGGCAAACTGTCGTGGTTCTAGGG |
| AGTCAAGAAGGAGCAGTTCACACGGCCCTTGCTGGAGCTCTGGAGGCTGAGATGGATGGTGCAAAGGGAAGGCTGTCCT |
| CTGGCCACTTGAAATGTCGCCTGAAAATGGATAAACTTAGATTGAAGGGCGTGTCATACTCCTTGTGTACCGCAGCGTTCA |
| CATTCACCAAGATCCCGGCTGAAACACTGCACGGGACAGTCACAGTGGAGGTACAGTACGCAGGGACAGATGGACCTTG |
| CAAGGTTCCAGCTCAGATGGCGGTGGACATGCAAACTCTGACCCCAGTTGGGAGGTTGATAACCGCTAACCCCGTAATCA |
| CTGAAAGCACTGAGAACTCTAAGATGATGCTGGAACTTGATCCACCATTTGGGGACTCTTACATTGTCATAGGAGTCGGG |
| GAGAAGAAGATCACCCACCACTGGCACAGGAGTGGCAGCACCATTGGAAAAGCATTTGAAGCCACTGTGAGAGGTGCCA |
| AGAGAATGGCAGTCTTGGGAGACACAGCCTGGGACTTTTGGATCAGTTGGAGGCGCTCTCAACTCATTGGGCAAGGGCAT |
| CCATCAAATTTTTGGAGCAGCTTTCAAATCATTGTTTGGAGGAATGTCCTGGTTCTCACAAATTCTCATTGGAACGTTGCTG |
| ATGTGGTTGGGTCTGAACACAAAGAATGGATCTATTTCCCTTATGTGCTTGGCCTTAGGGGAGTGTTGATCTTCTTATCC |
| ACAGCCGTCTCTGCTGATGTGGGGTGCTCGGTGGACTTCTCAAAGAAGGAGACGAGATGCGGTACAGGGGTGTTCGTCT |
| ATAACGACGTTGAAGCCTGGAGGGACAGGTACAAGTACCATCCTGACTCCCCCCGTAGATTGGCAGCAGCAGTCAAGCA |
| AGCCTGGGAAGATGGTATCTGCGGGATCTCCTCTGTTTCAAGAATGGAAACATCATGTGGAGATCAGTAGAAGGGGAG |
| CTCAACGCAATCCTGGAAGAGAATGGAGTTCAACTGACGGTCGTTGTGGGATCTGTAAAAAACCCCATGTGGAGAGGTC |
| CACAGAGATTGCCCGTGCCTGTGAACGAGCTGCCCCACGGCTGGAAGGCTTGGGGGAAATCGCACTTCGTCAGAGCAGC |
| AAAGACAAATAACAGCTTTGTCGTGGATGGTGACACACTGAAGGAATGCCCACTCAAACATAGAGCATGGAACAGCTTTC |
| TTGTGGAGGATCATGGGTTCGGGGTATTTCACACTAGTGTCTGGCTCAAGGTTAGAGAAGATTATTCATTAGAGTGTGAT |
| CCAGCCGTTATTGGAACAGCTGTTAAGGGAAAGGAGGCTGTACACAGTGATCTAGGCTACTGGATTGAGAGTGAGAAGA |
| ATGCACATGGAGGCTGAAGAGGGCCCATCTGATCGAGATGAAAACATGTGAATGGCCAAAGTCCCACACATTGTGGAC |
| AGATGGAATAGAAGAGAGTGATCTGATCATACCCAAGTCTTTAGCTGGGCCACTCAGCCATCACAATACCAGAGAGGGCT |
| ACAGGACCCAAATGAAAGGGCCATGGCACAGTGAAGAGCTTGAAATTCGGTTTGAGGAATGCCCAGGCACTAAGGTCCA |
| CGTGGAGGAAACATGTGGAACAAGAGGACCATCTCTGAGATCAACCACTGCAAGCGGAAGGGTGATCGAGGAATGGTG |
| CTGCAGGGAGTGCACAATGCCCCACTGTCGTTCCGGGCTAAAGATGGCTGTTGGTATGGAATGGAGATAAGGCCCAGG |
| AAAGAACCAGAAAGCAACTTAGTAAGGTCAATGGTGACTGCAGGATCAACTGATCACATGGATCACTTCTCCCTTGGAGT |
| GCTTGTGATTCTGCTCATGGTGCAGGAAGGGCTGAAGAAGAGAATGACCACAAAGATCATCATAAGCACATCAATGGCA |
| GTGCTGGTAGCTATGATCCTGGGAGGATTTTCAATGAGTGACCTGGCTAAGCTTGCAATTTTGATGGGTGCCACCTTCGC |
| GGAAATGAACACTGGAGGAGATGTAGCTCATCTGGCGCTGATAGCGGCATTCAAAGTCAGACCAGCGTTGCTGGTATCTT |
| TCATCTTCAGAGCTAATTGGACACCCCGTGAAAGCATGCTGCTGGCCTTGGCCTCGTGTCTTTTGCAAACTGCGATCTCCG |
| CCTTGGAAGGCGACCTGATGGTTCTCATCAATGGTTTTGCTTTGGCCTGGTTGGCAATACGAGCGATGGTTGTTCCACGCA |
| CTGATAACATCACCTTGGCAATCCTGGCTGCTCTGACACCACTGGCCCGGGGCACACTGCTTGTGGCGTGGAGAGCAGGC |
| CTTGCTACTTGCGGGGGGTTTATGCTCCTCTCTCTGAAGGGAAAAGGCAGTGTGAAGAAGAACTTACCATTTGTCATGGC |
| CCTGGGACTAACCGCTGTGAGGCTGGTCGACCCCATCAACGTGGTGGGGCTGCTGTTGCTCACAAGGAGTGGGAAGCGG |
| AGCTGGCCCCCTAGCGAAGTACTCACAGCTGTTGGCCTGATATGCGCATTGGCTGGAGGGTTCGCCAAGGCAGATATAGA |
| GATGGCTGGGCCCATGGCCGCGGTCGGTCTGCTAATTGTCAGTTACGTGGTCTCAGGAAAGAGTGTGGACATGTACATTG |
| AAAGAGCAGGTGACATCACATGGGAAAAAGATGCGGAAGTCACTGGAAACAGTCCCCGGCTCGATGTGGCGCTAGATG |
| AGAGTGGTGATTTCTCCCTGGTGGAGGATGACGGTCCCCCCATGAGAGAGATCATACTCAAGGTGGTCCTGATGACCATC |
| TGTGGCATGAACCCAATAGCCATACCCTTTGCAGCTGGAGCGTGGTACGTATACGTGAAGACTGGAAAAAGGAGTGGTG |
| CTCTATGGGATGTGCCTGCTCCCAAGGAAGTAAAAAAGGGGGAGACCACAGATGGAGTGTACAGAGTAATGACTCGTAG |
| ACTGCTAGGTTCAACAAGTTGGAGTGGGAGTTATGCAAGAGGGGGTCTTTCACACTATGTGGCACGTCACAAAAGGA |
| TCCGCGCTGAGAAGCGGTGAAGGGAGACTTGATCCATACTGGGGAGATGTCAAGCAGGATCTGGTGTCATACTGTGGTC |
| CATGGAAGCTAGATGCCGCCTGGGACGGGCACAGCGAGGTGCAGCTCTTGGCCGTGCCCCCCGGAGAGAGAGCGAGGA |
| ACATCCAGACTCTGCCCGGAATATTTAAGACAAAGGATGGGGACATTGGAGCGGTTGCTGGTGGATTACCCAGCAGGAAC |
| TTCAGGATCTCCAATCCTAGACAAGTGTGGGAGAGTGATAGGACTTTATGGCAATGGGGTCGTGATCAAAAATGGGAGT |
| TATGTTAGTGCCATCACCCAAGGGAGGAGGGAGGAAGAGACTCCTGTTGAGTGCTTCGAGCCTTCGATGCTGAAGAAGA |
| AGCAGCTAACTGTCTTAGACTTGCATCCTGGAGCTGGGAAAACCAGGAGAGTTCTTCCTGAAATAGTCCGTGAAGCCATA |
| AAAACAAGACTCCGTACTGTGATCTTAGCTCCAACCAGGGTTTGTCGCTGCTGAAATGGAGGAAGCCCTTAGAGGGCTTCC |
| AGTGCGTTATATGACAACAGCAGTCAATGTCACCCACTCTGGAACAGAAATCGTCGACTTAATGTGCCATGCCACCTTCAC |
| TTCACGTCTACTACAGCCAATCAGAGTCCCCAACTATAATCTGTATATTATGGATGAGGCCCACTTCACAGATCCCTCAAGT |
| ATAGCAGCAAGAGGATACATTTCAACAAGGGTTGAGATGGGCGAGGCGGCTGCCATCTTCATGACCGCCACGCCACCAG |
| GAACCCGTGACGCATTTCCGGACTCCAACTCACCAATTATGGACACCGAAGTGGAAGTCCCAGAGAGACCTGGAGCTCA |
| GGCTTTGATTGGGTGACGGATTATTCTGGAAAAACAGTTTGGTTTGTTCCAAGCGTGAGGAACGGCAATGAGATCGCAGC |
| TTGTCTGACAAAGGCTGGAAAACGGGTCATACAGCTCAGCAGAAAGACTTTTGAGACAGAGTTCCAGAAAACAAAACATC |
| AAGAGTGGGACTTTGTCGTGACAACTGACATTTCAGAGATGGGCGCCAACTTTAAAGCTGACCGTGTCATAGATTCCAGG |
| AGATGCCTAAAGCCGGTCATACTTGATGGCGAGAGAGTCATTCTGGCTGGACCCATGCCTGTCACACATGCCAGCGCTGC |
| CCAGAGGAGGGGCGCATAGGCAGGAATCCCAACAAACCTGGAGATGGAGTATCTGTATGGAGGTGGGTGCGCAGAGAC |
| TGACGAAGACCATGCACACTGGCTTGAAGCAAGAATGCTCCTTGACAATATTTACCTCCAAGATGGCCTCATAGCCTCGCT |
| CTATCGACCTGAGGCCGACAAAGTAGCAGCCATTGAGGGAGAGTTCAAGCTTAGGCGGAGCAAAGGAAGACCTTTGTG |
| GAACTCATGAAAAGAGGAGATCTTCCTGTTTGGCTGGCCTATCAGGTTGCATCTGCCGGAATAACCTACACAGATAGAAG |
| ATGGTGCTTTGATGGCACGACCAACAACACCATAATGGAAGACAGTGTGCCGGCAGAGGTGTGGACCAGACACGGAGA |
| GAAAAGAGTGCTCAAACCGAGGTGGATGGACGCCAGAGTTTGTTCAGATCATGCGGCCCTGAAGTCATTCAAGGAGTTT |
| GCCGCTGGGAAAAGAGGAGCGGCTTTTTGGAGTGATGGAAGCCTCTGGGAACACTGCCAGGACACATGACAGAGAGATTC |
| CAGGAAGCCATTGACAACCTCGCTGTGCTCATGCGGGCAGAGACTGGAAGCAGGCCTTACAAAGCCGCGGCGGCCCAAT |
| TGCCGGAGACCCTAGAGACCATTATGCTTTTGGGGTTGCTGGGAACAGTCTCGCTGGGAATCTTTTTCGTCTTGATGAGG |
| AACAAGGGCATAGGGAAGATGGGCTTTGGAATGGTGACTCTTGGGGCCAGCGCATGGCTCATGTGGCTCTCGGAAATTG |
| AGCCAGCCAGAATTGCATGTGTCCTCATTGTTGTGTTCCTATTGCTGGTGGTGCTCATACCTGAGCCAGAAAAGCAAAGAT |
| CTCCCCAGGACAACCAAATGGCAATCATCATCATGGTAGCAGTAGGTCTTCTGGGCTTGATTACCGCCAATGAACTCGGAT |

-continued

SEQUENCES

GGTTGGAGAGAACAAAGAGTGACCTAAGCCATCTAATGGGAAGGAGAGAGGAGGGGGCAACCATGGGATTCTCAATGG
ACATTGACCTGCGGCCAGCCTCAGCTTGGGCCATCTATGCTGCCTTGACAACTTTCATTACCCCAGCCGTCCAACATGCAGT
GACCACTTCATACAACAACTACTCCTTAATGGCGATGGCCACGCAAGCTGGAGTGTTGTTTGGTATGGGCAAAGGGATGC
CATTCTACGCATGGGACTTTGGAGTCCCGCTGCTAATGATAGGTTGCTACTCACAATTAACGCCCCTGACCCTAATAGTGG
CCATCATTTTGCTCGTGGCGCACTACATGTACTTGATCCCAGGGCTGCAGGCAGCAGCTGCGCGTGCTGCCCAGAAGAGA
ACGGCAGCTGGCATCATGAAGAACCCTGTTGTGGATGGAATAGTGGTGACTGACATTGACACAATGACAATTGACCCCCA
AGTGGAGAAAAAGATGGGACAGGTGCTACTCATGGCAGTAGCCGTCTCCAGCGCCATACTGTCGCGGACCGCCTGGGGG
TGGGGGGAGGCTGGGGCCCTGATCACAGCCGCAACTTCCACTTTGTGGGAAGGCTCTCCGAACAAGTACTGGAACTCCTC
TACAGCCACTTCACTGTGTAACATTTTTAGGGGAAGTTACTTGGCTGGAGCTTCTCTAATCTACACAGTAACAAGAAACGC
TGGCTTGGTCAAGAGACGTGGGGGTGGAACAGGAGAGACCCTGGGAGAGAAATGGAAGGCCCGCTTGAACCAGATGTC
GG CCCTGGAGTCTACTCCTACAAAAAGTCAGGCATCACCGAGGTGTGCAGAGAAGAGGCCCGCCGCGCCCTCAAGGAC
GGTGTGGCAACGGGAGGCCATGCTGTGTCCCGAGGAAGTGCAAAGCTGAGATGGTTGGTGGAGCGGGGATACCTGCAG
CCCTATGGAAAGGTCATTGATCTTGGATGTGGCAGAGGGGCTGGAGTTACTACGCCGCCACCATCCGCAAAGTTCAAGA
AGTGAAAGGATACACAAAAGGAGGCCCTGGTCATGAAGAACCCTGTTGGTGCAAAGCTATGGGTGGAACATAGTCCGT
CTTAAGAGTGGGGTGGACGTCTTTCATATGGCGGCTGAGCCGTGTGACACGTTGCTGTGTGACATAGGTGAGTCATCATC
TAGTCCTGAAGTGGAAGAAGCACGGACGCTCAGAGTCCTCTCCATGGTGGGGATTGGCTTGAAAAAAGACCAGGAGCC
TTTTGTATAAAAGTGTTGTGCCCATACACCAGCACTATGATGGAAACCCTGGAGCGACTGCAGCGTAGGTATGGGGGAG
GACTGGTCAGAGTGCCACTCTCCCGCAACTCTACACATGAGATGTACTGGGTCTCTGGAGCGAAAAGCAACACCATAAAA
AGTGTGTCCACCACGAGCCAGCTCCTCTTGGGGCGCATGGACGGGCCTAGGAGGCCAGTGAAATATGAGGAGGATGTGA
ATCTCGGCTCTGGCACGCGGGCTGTGGTAAGCTGCGCTGAAGCTCCCAACATGAAGATCATTGGTAACCGCATTGAAAGG
ATCCGCAGTGAGCACGCGGAAACGTGGTTCTTTGACGAGAACACCCATATAGGACATGGGCTTACCATGGAAGCTATGA
GGCCCCCACACAAGGGTCAGCGTCCTCTCTAATAAACGGGGTTGTCAGGCTCCTGTCAAAACCCTGGGATGTGGTGACTG
GAGTCACAGGAATAGCCATGACCGACACCACACCGTATGGTCAGCAAAGAGTTTTCAAGGAAAAAGTGGACACTAGGGT
GCCAGACCCCCAAGAAGGCACTCGTCAGGTTATGAGCAGGCTGTCTCTTCCTGGTTGTGGAAAGAGCTAGGCAAACACAAAC
GGCCACGAGTCTGTACCAAAGAAGAGTTCATCAACAAGGTTCGTAGCAATGCAGCATTAGGGGCAATATTTGAAGAGGA
AAAAGAGTGGAAGACTGCAGTGGAAGCTGTGAACGATCCAAGGTTCTGGGCTCTAGTGGACAAGGAAAGAGAGCACCA
CCTGAGAGGAGAGTGCCAGAGTTGTGTGTACAACATGATGGGAAAAAGAGAAAAGAAACAAGGGGAATTTGGAAAGGC
CAAGGGCGCCGCGCCATCTGGTATATGTGGCTAGGGGCTAGATTTCTAGAGTTCGAAGCCCTTGGATTCTTGAACGAGG
ATCACTGGATGGGGAGAGAGAACTCAGGAGGTGGTGTTGAAGGGCTGGGATTACAAAGACTCGGATATGTCCTAGAAG
AGATGAGTCGCATACCAGGAGGAAGGATGTATGCAGATGACACTGCTGGCTGGGACACCCGCATCAGCAGGTTTGATCT
GGAGAATGAAGCTCTAATCACCAACCAAATGGAGAAAGGGCACAGGGCCTTGGCATTGGCCATAATCAAGTACACATAC
CAAAACAAAGTGGTAAAGGTCCTTAGACAGCTGAAAAAGGGAAGACAGTTATGGACATTATTTCGAGACAAGACCAA
GGGGGAGCGGACAAGTTGTCACTTACGCTCTTAACACATTTACCAACCTAGTGGTGCAACTCATTCGGAATATGGAGGCT
GAGGAAGTTCTAGAGATGCAAGACTTGTGGCTGCTGCGGAGGTCAGAGAAAGTGACCAACTGGTTGCAGAGCAACGGA
TGGGATAGGCTCAAACGAATGGCAGTCAGTGGAGATGATTGCGTTGTGAAGCCAATTGATGATAGGTTTGCACATGCCCT
CAGGTTCTTGAATGATATGGGAAAAGTTAGGAAGGACACACAAGAGTGGAAACCCTCAACTGGATGGGACAACTGGGAA
GAAGTTCCGTTTTGCTCCCACCACTTCAACAAGCTCCATCTCAAGGACGGGAGGTCCATTGTGGTTCCCTGCCGCCACCAA
GATGAACTGATTGGCCGGGCCCGCGTCTCTCAGGGGCGGGATGAGCATCCGGGAGACTGCTTGCCTAGCAAAATCAT
ATGCGCAAATGTGGCAGCTCCTTTATTTCCACAGAAGGGACCTCCGACTGATGGCCAATGCCATTTGTTCATCTGTGCCAG
TTGACTGGGTTCCAACTGGGAGAACTACCTGGTCAATCCATGGAAAGGGGAGAATGGATGACCACTGAAGACATGCTTGT
GGTGTGGAACAGAGTGTGGATTGAGGAGAACGACCACATGGAAGACAAGACCCCAGTTACGAAATGGACAGACATTCCC
TATTTGGGAAAAAGGGAAGACTTGTGGTGTGGATCTCTCATAGGGCACAGACCGCGCACCACCTGGGCTGAGAACATTA
AAAACACAGTCAACATGGTGCGCAGGATCATAGGTGATGAAGAAAGTACATGGACTACCTATCCACCCAAGTTCGCTAC
TTGGGTGAAGAAGGGTCTACACCTGGAGTGCTGTAAGCACCAATCTTAATGTTGTCAGGCCTGCTAGTCAGCCACAGCTT
GGGGAAAGCTGTGCAGCCTGTGACCCCCCCAGGAGAACGTGGGAAACCAAGCCTATAGTCAGGCCGAGAACGCCCATGG
CACGGAAGAAGCCATGCTGCCTGTGAGCCCCTCAGAGGACACTGAGTCAAAAAACCCCACGCGCTTGGAGGCGCAGGAT
GGGAAAAGAAGGTGGCGACCTTCCCCACCCTTCAATCTGGGGCCTGAACTGGAGATCAGCTGTGGATCTCCAGAAGAGG
GACTAGTGGTTAGAGGAGA

SEQ ID NO: 6
KU527068.1 Zika virus strain Natal RGN, Brazil: Rio Grande do Norte, Natal, complete
genome
AGTTGTTGATCTGTGTGAATCAGACTGCGACAGTTCGAGTTTGAAGCGAAAGCTAGCAACAGTATCAACAGGTTTTATTTT
GGATTTGGAAACGAGAGTTTCTGGTCATGAAAAACCCAAAAAAGAAATCCGGAGGATTCCGGATTGTCAATATGCTAAAA
CGCGGAGTAGCCCGTGTGAGCCCCTTTGGGGGCTTGAAGAGGCTGCCAGCCGGACTTCTGCTGGGTCATGGGCCCATCA
GGATGGTCTTGGCAATTCTAGCCTTTTTGAGATTCACGGCAATCAAGCCATCACTGGGTCTCATCAATAGATGGGGTTCAG
TGGGGAAAAAAGAGGCTATGGAAATAATAAAGAAGTTCAAGAAAGATCTGGCTGCCATGCTGAGAATAATCAATGCTAG
GAAGGAGAAGAAGAGACGAGGCGCAGATACTAGTGTCGGAATTGTTGGCCTCCTGCTGACCACAGCTATGGCAGCGGA
GGTCACTAGACGTGGGAGTGCATACTATATGTACTTGGACAGAAACGATGCTGGGGAGGCCATATCTTTTCCAACCACAT
TGGGGATGAATAAGTGTTATATACAGATCATGGATCTTGGACACATGTGTGATGCCACCATGAGCTATGAATGCCCTATG
CTGGATGAGGGGGTGGAACCAGATGACGTCGATTGTTGGTGCAACACAACCGACACTTGGGTTGTGTACGGAACCTGC
ATCACAAAAAAGGTGAAGCACGGAGATCTAGAAGAGCTGTGACGCTCCCCTCCATTCCACTAGGAAGCTGAAACGCG
GTCGCAAACCTGGTTGGAATCAAGAGAATACACAAAGCACTTGATTAGAGTCGAAAATTGGATATTCAGGAACCCTGGCT
TCGCGTTAGCAGCAGCTGCCATCGCTTGGCTTTTGGGAAGCTCAACGAGCCAAAAAGTCATATACTTGGTCATGATACTGC
TGATTGCCCCGGCATACAGCATCAGGTGCATAGGAGTCAGCAATAGGGACTTTGTGGAAGGTATGTCAGGTGGGACTTG
GGTTGATGTTGTCTTGGAACATGGAGGTTGTGTCACCGTAATGGCACAGGACAAACCGACTGTCGACATAGAGCTGGTTA
CAACAACAGTCAGCAACATGGCGGAGGTAAGATCCTACTGCTATGAGGCATCAATATCAGACATGGCTTCGGACAGCCGC
TGCCCAACACAAGGTGAAGCCTACCTTGACAAGCAATCAGACACTCAATATGTCTGCAAAAGAACGTTAGTGGACAGAGG
CTGGGGAAATGGATGTGGACTTTTTGGCAAAGGGAGCCTGGTGACATGCGCTAAGTTTGCATGCTCCAAGAAAATGACC
GGGAAGAGCATCCAGCCAGAGAATCTGGAGTACCGGATAATGCTGTCAGTTCATGGCTCCCAGCACAGTGGGATGATCG
TTAATGACAACATGATGAGAATAGAGCCAAGCTGGCTGATAACGAGGAAGATAACGCCCAATTCACCAAGAGCCAAGCAC
CCTGGGGGTTTTGGAAGCCTAGGACTTGATTGTGAACCGAGGACAGGCCTTGACTTTTCAGATTTGTATTACTTGACTAT
GAATAACAAGCACTGGTTGGTCCACAAGGAGTGGTTCCACGACATTCCATTACCTTGGCACGCTGGGGCAGACACCGGAA
CTCCACACTGGAACAACAAAGAAGCACTGGTAGAGTTCAAGGACGCACATGCCAAAAGGCAAACTGTCGTGGTTCTAGG
GAGTCAAGAAGGAGCAGTTCACACGGCCCTTGCTGGAGCTCTGGAGGCTGAGATGGATGGTGCAAAGGGAAGGCTGTC
CTCTGGCCACTTGAAATGTCGCCTGAAAATGGATAAACTTAGATTGAAGGGCGTGTCATACTCCTTGTGTACCGCAGCGTT
CACATTCACCAAGATCCCGGCTGAAACACTGCACGGGACAGTCACAGTGGAGGTACAGTACGCAGGGACAGATGGACCT

| SEQUENCES |
|---|
| TGCAAGGTTCCAGCTCAGATGGCGGTGGACATGCAAACTCTGACCCCAGTTGGGAGGTTGATAACCGCTAACCCCGTAAT |
| CACTGAAAGCACTGAGAACTCTAAGATGATGCTGGAACTTGATCCACCATTTGGGGACTCTTACATTGTCATAGGAGTCG |
| GGGAGAAGAAGATCACCCACCACTGGCACAGGAGTGGCAGCCACCATTGGAAAAGCATTTGAAGCCACTGTGAGAGGTG |
| CCAAGAGAATGGCAGTCTTGGGAGACACAGCCTGGGACTTTGGATCAGTTGGAGGCGCTCTCAACTCATTGGGCAAGGG |
| CATCCATCAAATTTTTGGAGCAGCTTTCAAATCATTGTTTGGAGGAATGTCCTGGTTCTCACAAATCCTCATTGGAACGTTG |
| CTGATGTGGTTGGGTCTGAACACAAAGAATGGATCTATTTCCCTTATGTGCTTGGCCTTAGGGGGAGTGTTGATCTTCTTA |
| TCCACAGCCGTCTCTGCTGATGTGGGGTGCTCGGTGGACTTCTCAAAGAAGGAGACGAGATGCGGTACAGGGGTGTTCG |
| TCTATAACGACGTTGAAGCCTGGAGGGACAGGTACAAGTACCATCCTGACTCCCCCCGTAGATTGGCAGCAGCAGTCAAG |
| CAAGCCTGGGAAGATGGTATCTGCGGGATCTCCTCTGTTTCAAGAATGGAGAACATCATGTGGAGATCAGTAGAAGGGG |
| AGCTCAACGCAATCTTGGAAGAGAATGGAGTTCAACTGACGGTCGTTGTGGGATCTGTAAAAAACCCCATGTGGAGAGG |
| TCCACAGAGATTGCCCGTGCCTGTGAACGAGCTGCCCCACGGCTGGAAGGCTTGGGGGAAATCGTACTTCGTCAGAGCA |
| GCAAAGACAAATAACAGCTTTGTCGTGGATGGTGACACACTGAAGGAATGCCCACTCGAACATAGAGCATGGAACAGCT |
| TTCTTGTGGAGGATCATGGGTTCGGGGTATTTCACACTAGTGTCTGGCTCAAGGTTAGAGAAGATTATTCATTAGAGTGT |
| GATCCAGCCGTTATTGGAACAGCTGTTAAGGGGAAGGAGGCTGTACACAGTGATCTAGGCTACTGGATTGAGAGTGAGA |
| AGAATGACACATGGAGGCTGAAGAGGGCCCATCTAATCGAGATGAAAACATGTGAATGGCCAAAGTCCCACACATTGTG |
| GGCAGATGGAATAGAAGAGAGTGATCTGATCATTCCCAAGTCTTTAGCTGGGCCACTCAGCCATCACAATACCAGAGAGG |
| GCTACAGGACCCAAATGAAAGGGCCATGGCACAGTGAAGAGCTTGAAATTCGGTTTGAGGAATGCCCGGGCACTAAGGT |
| CCACGTGGAGGAAACATGTGGAACAAGAGGACCATCTCTGAGATCAACCACTGCAAGCGGAAGGGTGATCGAGGAATG |
| GTGCTGCAGGGAGTGCACAATGCCCCCACTGTCGTTCCGGGCTAAAGATGGCTGTTGGTATGGAATGGAGATAAGGCCC |
| AGGAAAGAACCAGAAAGCAACTTAGTAAGGTCAGTGGTGACTGCAGGATCAACTGATCACATGGATCACTTCTCCCTTGG |
| AGTGCTTGTGATTCTGCTCATGGTGCAGGAAGGGCTGAAGAAGAGAATGACCACAAAGATCATCATAAGCACATCAATG |
| GCAGTGCTGGTAGCTATGATCCTGGGAGGATTTTCAATGAGTGACCTGGCTAAGCTTGCAATTTTGATGGGCGCCACCTT |
| CGCGGAAATGAACACTGGAGGAGATGTAGCTCATCTGGCGCTGATAGCGGCATTCAAAGTCAGACCAGCGTTGCTGGTA |
| TCTTTCATCTTCAGAGCTAATTGGACACCCCGTGAAAGCATGCTGCTGGCCTTGGCCTCGTGTCTTTTGCAAACTGCGATCT |
| CCGCCTTGGAAGGCGACCTGATGGTTCTCATCAATGGTTTTGCTTTGGCCTGGTTGGCAATACGAGCGATGGTTGTTCCAC |
| GCACTGATAACATCACCTTGGCAATCCTGGCTGCTCTGACACCACTGGCCCGGGGCACACTGCTTGTGGCGTGGAGAGCA |
| GGCCTTGCTACTTGCGGGGGTTTATGCTCCTCTCTCTGAAGGGAAAAGGCAGTGTGAAGAAGAACTTACCATTTGTCAT |
| GGCCCTGGGACTAACCGCTGTGAGGCTGGTCGACCCCATCAACGTGGTGGGACTGCTGTTGCTCACAAGGAGTGGGAAG |
| CGGAGCTGGCCCCCTAGCGAAGTACTCACAGCTGTTGGCCTGATATGCGCATTGGCTGGAGGGTTCGCCAAGGCAGATAT |
| AGAGATGGCTGGGCCCATGGCCGCGGTCGGTCTGCTAATTGTCAGTTACGTGGTCTCAGGAAAGAGTGTGGACATGTAC |
| ATTGAAAGAGCAGGTGACATCACATGGGAAAAAGATGCGGAAGTCACTGGAAACAGTCCCCGGCTCGATGTGGCGCTAG |
| ATGAGAGTGGTGATTTCTCCCTGGTGGAGGATGACGGTCCCCCCATGAGAGATATCATCTCAAGGTGGTCCTGATGACC |
| ATCTGTGGCATGAACCCAATAGCCATACCCTTTGCAGCTGGAGCGTGGTACGTATACGTGAAGACTGGAAAAAGGAGTG |
| GTGCTCTATGGGATGTGCCTGCTCCCAAGGAAGTAAAAAAGGGGGAGACCACAGATGGAGTGTACAGAGTAATGACTCG |
| TAGACTGCTAGGTTCAACACAAGTTGGAGTGGGAGTTATGCAAGAGGGGGTCTTTCACACTATGTGGCACGTCACAAAA |
| GGATCCGCGCTGAGAAGCGGTGAAGGGAGACTTGATCCATACTGGGGAGATGTCAAGCAGGATCTGGTGTCATACTGTG |
| GTCCATGGAAGCTAGATGCCGCCTGGGACGGGCACAGCGAGGTGCAGCTCTTGGCCGTGCCCCCCGGAGAGAGAGCGA |
| GGAACATCCAGACTCTGCCCGGAATATTTAAGACAAAGGATGGGGACATTGGAGCGGTTGCGCTGGATTACCCAGCAGG |
| AACTTCAGGATCTCCAATCCTAGACAAGTGTGGGAGAGTGATAGGACTTTATGGCAATGGGGTCGTGATCAAAAATGGG |
| AGTTATGTTAGTGCCATCACCCAAGGGAGGAGGGAGGAAGAGACTCCTGTTGAGTGCTTCGAGCCTTCGATGCTGAAGA |
| AGAAGCAGCTAACTGTCTTAGACTTGCATCCTGGAGCTGGGAAAACCAGGAGAGTTCTTCCTGAAATAGTCCGTGAAGCC |
| ATAAAAACAAGACTCCGTACTGTGATCTTAGCTCCAACCAGGGTTGTCGCTGCTGAAATGGAGGAAGCCCTTAGAGGGCT |
| TCCAGTGCGTTATATGACAACAGCAGTCAATGTCACCCACTCTGGAACAGAAATCGTCGACTTAATGTGCCATGCCACCTT |
| CACTTCACGTCTACTACAGCCAATCAGAGTCCCCAACTATAATCTGTATATTATGGATGAGGCCCACTTCACAGATCCCTCA |
| AGTATAGCAGCAAGAGGATACATTTCAACAAGGGTTGAGATGGGCGAGGCGGCTGCCATCTTCATGACCGCCACGCCAC |
| CAGGAACCCGTGACGCATTCCGGACTCCAACTCACCAATATGGACACCGAAGTGGAAGTCCCAGAGAGAGCCTGGAG |
| CTCAGGCTTTGATTGGGTGACGGATCATTCTGGAAAAACAGTTTGGTTTGTTCCAAGCGTGAGGAACGGCAATGAGATCG |
| CAGCTTGTCTGACAAAGGCTGGAAAACGGGTCATACAGCTCAGCAGAAAGACTTTTGAGACAGAGTTCCAGAAAACAAA |
| ACATCAAGAGTGGGACTTTGTCGTGACAACTGACATTTCAGAGATGGGCGCCAACTTTAAAGCTGACCGTGTCATAGATT |
| CCAGGAGATGCCTAAAGCCGGTCATACTTGATGGCGAGAGAGTCATTTTGGCTGGACCCATGCCTGTCACACATGCCAGC |
| GCTGCCCAGAGGAGGGGCGCATAGGCAGGAATCCCAACAAACCTGGAGATGAGTATCTGTATGGAGGTGGGTGCGCA |
| GAGACTGACGAAGACCATGCACACTGGCTTGAAGCAAGAATGCTCCTTGACAATATTTACCTCCAAGATGGCCTCATAGC |
| CTCGCTCTATCGACCTGAGGCCGACAAAGTAGCAGCCATTGAGGGAGAGTTCAAGCTTAGGACGGAGCAAAGGAAGACC |
| TTTGTGGAACTCATGAAAAGAGGGAGATCTTCCTGTTTGGCTGGCCTATCAGGTTGCATCTGCCGGAATAACCTACACAGAT |
| AGAAGATGGTGCTTTGATGGCACGACCAACAACACCATAATGGAAGACAGTGTGCCGGCAGAGGTGTGGACCAGACAC |
| GGGAGAGAAAAGAGTGCTCAAACCGAGGTGGATGGACGCCAGAGTTTGTTCAGATCATGCGGCCCTGAAGTCATTCAAGG |
| AGTTTGCCGCTGGGAAAAGAGGAGCGGCTTTTGGAGTGATGAAGGCCCTGGGAACATGCCAGGACACATGACAGAGA |
| GATTCCAGGAAGCCATTGACAACCTCGCTGTGCTCATGCGGGCAGAGACTGGAAGCAGGCCTTACAAAGCGCGGCGGC |
| CCAATTGCCGGAGACCCTAGAGACCATTATGCTTTTGGGGTTGCTGGGAACAGTCTCGCTGGGAATCTTTTCGTCTTGAT |
| GAGGAACAAGGGCATAGGGAAGATGGGCTTTGGAATGGTGACTCTTGGGGCCAGCGCATGGCTCATGTGGCTCTCGGA |
| AATTGAGCCAGCCAGAATTGCATGTGTCCTCATTGTTGTTCCTATTGCTGGTGGTGCTCATACCTGAGCCAGAAAAGCA |
| AAGATCTCCCCAGGACAACCAAATGGCAATCATCATCATGGTAGCAGTAGGTCTTCTGGGCTTGATTACCGCCAATGAACT |
| CGGATGGTTGGAGAGAACAAAGAGTGACCTAAGCCATCTAATGGGAAGGAGAGAGGAGGGAGCAACCATAGGATTCTC |
| AATGGACATTGACCTGCGCCAGCCTCAGCTTGGGCCATCTATGCTGCCTTGACAACTTCATTACCCCAGCCGTCCAACA |
| TGCAGTGACCACTTCATACAACAACTACTCCTTAATGGCGATGGCCACGCAAGCTGGAGTGTTGTTTGGTATGGGCAAAG |
| GGATGCCATTCTACGCATGGGACTTTGGAGTCCCGCTGCTAATGATAGGTTGCTACTCACAATTAACACCCCTGACCCTAA |
| TAGTGGCCATCATTTTGCTCGTGGCGCACTACATGTACTTGATCCCAGGGCTGCAGGCAGCAGCTGCGCGTGCTGCCCAG |
| AAGAGAACGGCAGCTGGCATCATGAAGAACCCTGTTGTGGATGGAATAGTGGTGACTGACATTGACACAATGACAATTG |
| ACCCCCAAGTGGAGAAAAAGATGGGACAGGTGCTACTCATAGCAGTAGCAGTCTCCAGCGCCATACTGTCGCGGACCGC |
| CTGGGGGTGGGGGAGGCTGGGGCCCTGATCACAGCCGCAACTTCCACTTTGTGGGAAGGCTCTCCGAACAAGTACTGG |
| AACTCCTCTACAGCCACTTCACTGTGTAACATTTTTAGGGGAAGTTACTTGGCTGGAGCTTCTCTAATCTACACATAGTAACAA |
| GAAACGCTGGCTTGGTCAAGAGACGTGGGGGTTGGAACAGGAGAGACCCTGGGAGAAATGGAAGGCCCGCTTGAAC |
| CAGATGTCGGCCCTGGAGTTCTACTCCTACAAAAAGTCAGGCATCACCGAGGTGTGCAGAGAAGAGGCCCGCCGCGCCC |
| TCAAGGATGGTGTGGCAACGGGAGGCCATGCTGTGTCCCGAGGAAGTGCAAAGCTGAGATGGTTGGTGGAGCGGGGAT |
| ACCTGCAGCCCTATGGAAAGGTCATTGATCTTGGATGTGGCAGAGGGGGCTGGAGTTACTACGCCGCCACCATCCGCAAA |
| GTTCAAGAAGTGAAAGGATACACAAAAGGAGGCCCTGGTCATGAAGAACCCGTGTTGGTGCAAAGCTATGGGTGAAC |
| ATAGTCCGTCTTAAGAGTGGGGTGGACGTCTTTCATATGGCGGCTGAGCCGTGTGACACGTTGCTGTGTGACATAGGTGA |

| SEQUENCES |
|---|
| GTCATCATCTAGTCCTGAAGTGGAAGAAGCACGGACGCTCAGAGTCCTCTCCATGGTGGGGATTGGCTTGAAAAAAGA
CCAGGAGCCTTTTGTATAAAAGTGTTGTGCCCATACACCAGCACTATGATGGAAACCCTGGAGCGACTGCAGCGTAGGTA
TGGGGGAGGACTGGTCAGAGTGCCACTCTCCCGCAACTCTACACATGAGATGTACTGGGTCTCTGGAGCGAAAAGCAAC
ACCATAAAAAGTGTGTCCACCACGAGCCAGCTCCTCTTGGGGCGCATGGACGGGCCTAGGAGGCCAGTGAAATATGAGG
AGGATGTGAATCTCGGCTCTGGCACGCGGGCTGTGGTAAGCTGCGCTGAAGCTCCCAACATGAAGATCATTGGTAACCGC
ATTGAAAGGATCCGCAGTGAGCACGCGGAAACGTGGTTCTTTGACGAGAACCACCCATATAGGACATGGGCTTACCATG
GAAGCTATGAGGCCCCCACACAAGGGTCAGCGTCCTCTCTAATAAACGGGGTTGTCAGGCTCCTGTCAAAACCCTGGGAT
GTGGTGACTGGAGTCACAGGAATAGCCATGACCGACACCACACCGTATGGTCAGCAAAGAGTTTTCAAGGAAAAAGTGG
ACACTAGGGTGCCAGACCCCCAAGAAGGCACTCGTCAGGTTATGAGCATGGTCTCTTCCTGGTTGTGGAAAGAGCTAGGC
AAACACAAACGGCCACGAGTCTGTACCAAAGAAGAGTTCATCAACAAGGTTCGTAGCAATGCAGCATTAGGGGCAATATT
TGAAGAGGAAAAAGAGTGGAAGACTGCAGTGGAAGCTGTGAACGATCCAAGGTTCTGGGCTCTAGTGGACAAGGAAAG
AGAGCACCACCTGAGAGGAGAGTGCCAGAGTTGTGTGTACAACATGATGGGAAAAAGAGAAAAGAAACAAGGGGAATT
TGGAAAGGCCAAGGGCAGCCGCGCCATCTGGTATATGTGGCTAGGGGCTAGATTTCTAGAGTTCGAAGCCCTTGGATTCT
TGAACGAGGATCACTGGATGGGGAGAGAGAACTCAGGAGGTGGTGTTGAAGGGCTGGGATTACAAAGACTCGGATATG
TCCTAGAAGAGATGAGTCGCATACCAGGAGGAAGGATGTATGCAGATGACACTGGCTGGCTGGGACACCCGCATCAGCAG
GTTCGATCTGGAGAATGAAGCTCTAATCACCAACCAAATGGAGAAAGGGCATAGGGCCTTGGCATTGGCCATAATCAAGT
ACACATACCAAAACAAAGTGGTAAAGGTCCTTAGACCAGCTGAAAAGGGAAAACAGTTATGGACATTATTTCGAGACAA
GACCAAAGGGGGAGCGGACAAGTTGTCACTTACGCTCTTAACACATTTACCAACCTAGTGGTGCA

| SEQUENCES |
|---|
| GAACGACACATGGAGGCTGAGGAGGGCCCACCTGATCGAGATGAAAACATGTGAATGGCCAAAGTCCCACACATTGTGG |
| ACAGATGGAATAGAAGAGAGTGATCTGATCATACCCAAGTCTTTAGCTGGGCCACTCAGCCATCACAACACCAGAGAGG |
| GCTACAGGACCCAAATGAAAGGGCCATGGCACAGTGAAGAGCTTGAAATTCGGTTTGAGGAATGCCCAGGCACTAAGGT |
| CCACGTGGAGGAAACATGTGGAACAAGAGGACCATCTCTGAGATCAACCACTGCAAGCGGAAGGGTGATCGAGGAATG |
| GTGCTGCAGGGAGTGCACAATGCCCCACTGTCGTTCCGGGCTAAAGATGGCTGTTGGTATGGAATGGAGATAAGGCCC |
| AGGAAAGAACCAGAAAGTAACTTAGTAAGGTCAATGGTGACTGCAGGATCAACTGATCACATGGATCACTTTTCCCTTGG |
| AGTGCTTGTGATTCTGCTCATGGTGCAGGAAGGGCTGAAGAAGAGAATGACCACAAAGATCATCATAAGCACATCAATG |
| GCAGTGCTGGTAGCTATGATCCTGGGAGGATTTTCAATGAGTGATCTGGCTAAGCTTGCAATTTTGATGGGTGCCACCTTT |
| GCGGAAATGAACACTGGAGGAGATGTAGCTCATCTGGCGCTGGTAGCGGCATTCAAAGTCAGACCAGCGTTGCTGGTAT |
| CTTTCATCTTCAGAGCTAATTGGACACCCCGTGAAAGCATGCTGCTGGCCTTGGCCTCGTGTCTTTTGCAAACTGCGATCTC |
| CGCCTTGGAAGGCGACCTGATGGTTCTCATCAATGGTTTTGCTTTGGCCTGGTTGGCAATACGAGCGATGGTTGTTCCACG |
| CACTGACAATATCCACCTTGGCAATCCTGGCTGCTCTGACACCACTGGCCCGGGGCACACTGCTTGTGGCGTGGAGAGCAG |
| GCCTTGCTACTTGCGGGGGGTTCATGCTCCTCTCTCTGAAGGGGAAAGGCAGTGTGAAGAAGAACTTACCATTTGTCATG |
| GCCCTGGGACTAACCGCTGTGAGGCTGGTCGACCCCATCAACGTGGTGGGACTGCTGTTGCTCACAAGGAGTGGGAAGC |
| GGAGCTGGCCCCCTAGCGAAGTACTCACAGCTGTTGGCCTGACTGTGATATCGCATTGGCTGGAGGGTTCGCCAAGGCAGATAT |
| AGAGATGGCTGGGCCCATGGCCGCGGTCGGTCTGCTAATTGTCAGTTACGTGGTCTCAGGAAAGAGTGTGGACATGTAC |
| ATTGAAAGAGCAGGTGACATCACATGGGAAAAAGATGCGGAAGTTACTGGAAACAGTCCCCGGCTCGATGTGGCACTAG |
| ATGAGAGTGGTGATTTCTCCCTGGTGGAGGATGACGGTCCCCCCATGAGAGAGATCATACTCAAAGTGGTCCTGATGACC |
| ATCTGTGGCATGAACCCAATAGCCATACCCTTTGCAGCTGGAGCGTGGTACGTATACGTGAAAACTGGAAAAAGGAGTG |
| GTGCTCTATGGGATGTGCCTGCTCCCAAGGAAGTAAAAAAGGGGAGACCACAGATGGAGTGTACAGAGTAATGACTCG |
| TAGACTGCTAGGTTCAACACAAGTTGGAGTGGGAGTTATGCAAGAGGGGGTCTTTCACACTATGTGGCATGTCACAAAAG |
| GATCCGCGCTGAGAAGCGGTGAAGGGAGACTTGATCCATACTGGGGAGATGTCAAGCAGGATCTGGTGTCATACTGTGG |
| TCCATGGAAGCTAGATGCCGCCTGGGACGGGCACAGCGAGGTGCAGCTCTTGGCCGTGCCCCCCGGAGAGAGAGCGAG |
| GAACATCCAGACTCTGCCCGGAATATTTAAGACAAAGGATGGGGACATTGGAGCGGTTGCGCTGGACTATCCAGCAGGA |
| ACTTCAGGATCTCCAATCCTAGACAAGTGTGGGAGAGTGATAGGACTCTATGGCAATGGGGTCGTGATCAAGAATGGGA |
| GTTATGTCAGTGCCATCACCCAAGGGAGGAGGGAGGAAGAGACTCCTGTTGAGTGCTTCGAGCCTTCGATGCTGAAGAA |
| GAAGCAGCTAACTGTCTTAGACTTGCATCCTGGAGCTGGGAAAACCAGGAGAGTTCTTCCTGAAATAGTCCGTGAAGCCA |
| TAAAAACGAGACTCCGTACTGTGATCTTAGCTCCAACCAGGGTTGTCGCTGCTGAAATGGAGGAAGCCCTTAGAGGGCTT |
| CCAGTGCGTTATATGACAACAGCAGTCAATGTCACCCATTCTGGGACAGAAATCGTTGACTTAATGTGCCATGCCACCTTC |
| ACTTCACGTCTACTACAGCCAATCAGAGTCCCCAACTATAATCTGTATATTATGGATGAGGCCCACTTCACAGATCCCTCAA |
| GTATAGCAGCAAGAGGATACATTTCAACAAGGGTTGAGATGGGCGAGGCAGCTGCCATCTTCATGACCGCCACGCCACC |
| AGGAACCCGTGACGCATTCCCGGACTCCAACTCACCAATTATGGACACCGAAGTGGAAGTCCCAGAGAGAGCCTGGAGC |
| TCAGGCTTTGATTGGGTGACGGATCATTCTGGAAAAACAGTTTGGTTTGTCCCAAGCGTGAGGAACGGCAATGAGATCGC |
| AGCTTGTCTGACAAAGGCTGGAAAACGGGTCATACAGCTCAGCAGAAAGACTTTTGAGACAGAGTTCCAGAAAACAAAA |
| CATCAAGAGTGGGACTTCGTCGTGACAACTGACATTTCAGAGATGGGCGCCAACTTTAAAGCTGACCGTGTCATAGATTC |
| CAGGAGATGCCTAAAGCCGGTCATACTTGATGGCGAGAGAGTCATTCTGGCTGGACCCATGCCTGTCACACATGCCAGCG |
| CTGCCCAGAGGAGGGGGCGCATAGGCAGGAATCCCAACAAACCTGGAGATGAGTATCTGTATGGAGGTGGGTGCGCAG |
| AGACTGATGAAGACCATGCACACTGGCTTGAAGCAAGAATGCTCCTTGACAATATTTACCTCCAAGATGGCCTCATAGCCT |
| CGCTCTATCGACCTGAGGCCGACAAAGTAGCAGCCATTGAGGGAGAGTTCAAGCTTAGGACGGAGCAAAGGAAGACCTT |
| TGTGGAACTCATGAAAAGAGGAGATCTTCCTGTTTGGCTGGCCTATCAGGTTGCATCTGCCGGAATAACCTACACAGATA |
| GAAGATGGTGCTTTGATGGCATGACCAACAACACCATAATGGAAGACAGTGTGCCGCAGAGGTGTGACCAGACACG |
| GAGAGAAAAGAGTGCTCAAACCGAGGTGGATGGACGCCAGAGTTTGTTCAGATCATGCGGCCCTGAAGTCATTCAAGGA |
| GTTTGCCGCTGGGAAAAGAGGAGCGGCTTTTGGAGTGATGGAAGCCCTGGGAACACTGCCAGGACACATGACGGAGAG |
| ATTCCAGGAAGCCATTGACAACCTCGCTGTGCTCATGCGGGCAGAGACTGGAAGCAGGCCTTACAAAGCCGCGGCGGCC |
| CAATTGCCGGAGACCCTAGAGACCATTATGCTTTTGGGGTTGCTGGGAACAGTCCTGCTGGGAATCTTTTTCGTCTTGATG |
| CGGAACAAGGGCATAGGGAAGATGGGCTTTGGAATGGTGACTCTTGGGGCCAGCGCATGGCTCATGTGGCTCTCGGAAA |
| TTGAGCCAGCCAGAATTGCATGCGTCCTCATTGTTGTGTTCCTATTGCTGGTGGTGCTCATACCTGAGCCAGAAAGCAAA |
| GATCCCCCCAGGACAACCAAATGGCAATCATCATCATGGTAGCAGTAGGTCTTCTGGGCTTGATTACCGCCAATGAACTCG |
| GATGGTTGGAGAGAACAAAGAGTGACCTAAGCCATCTAATGGGAAGGAGAGAGGAGGGGCAACCATAGGATTCTCAA |
| TGGACATTGACCTGCGGCCAGCCTCGGCCTGGGCCATCTATGCTGCCCTGACAACTTTCATTACCCCAGCCGTCCAACATG |
| CAGTGACCACTTCATCAACAACTACTCCTTAATGGCGATGGCCACGCAAGCTGGAGTGTTGTTGGTATGGGCAAAGGG |
| ATGCCATTCTACGCATGGGACTTTGGAGTCCCGCTGCTAATGATAGGTTGCTACTCACAATTAACACCCCTGACCCTAATA |
| GTGGCTATCATTTTGCTCGTGGCGCACTACATGTACTTGATCCCAGGGCTGCAGGCAGCAGCTGCGCGTGCTGCCCAGAA |
| GAGAACGGCAGCTGGCATCATGAAGAACCCTGTTGTGGATGGAATAGTGGTGACTGACATTGACACAATGACTATTGAC |
| CCCCAAGTGGAGAAAAAGATGGGACAGGTGCTACTCATAGCAGTAGCCGTCCCAGCGCCATACTGTCGCGGACCGCCT |
| GGGGGTGGGGGAAGCTGGGCCCTGATCACAGCTGCAACTTCCACTTTGTGGGAAGGCTCTCCGAACAAGTACTGGAA |
| CTCCTCTACAGCCACTTCACTGTGCAACATTTTTAGGGGAAGTTACTTGGCTGGAGCTTCTCTAATCTACACAGTAACAAGA |
| AACGCTGGCTTGGTCAAGAGACGTGGGGGTGGAACAGGAGAGACCTGGGAGAGAAATGAAGGCCCGCTTGAACCA |
| GATGTCGGCCCTGGAGTTCTACTCCTACAAAAAGTCAGGCATCACCGAGGTGTGCAGAGAAGAGGCCCGCCGCGCCCTC |
| AAGGACGGTGTGGCAACGGGAGGCCATGCTGTGTCCCGAGGAAGTGCAAAGCTGAGATGGTTGGTGGAGCGGGGATAC |
| CTGCAGCCCTATGGAAAGGTCATTGATCTTGGATGTGGCAGAGGGGGTTGGAGTTACTACGCCGCCACCATCCGCAAGT |
| TCAAGAAGTGAAAGGATACACAAAAGGAGGCCCTGGTCATGAAGAACCCATGTTGGTGCAAAGCTATGGGTGGAACATA |
| GTCCGTCTTAAGAGTGGGGTGGACGTCTTTCATATGGCGGCTGAGCCGTGTGACACGTTGCTGTGTGACATAGGTGAGTC |
| ATCATCAGTCCTGAAGTGGAAGAAGCACGGACGCTCAGAGTCCTCTCCATGGTGGGGATTGGCTTGAAAAAAGACCA |
| GGAGCCTTTTGTGTAAAAGTGTTGTGCCCATACACCAGCACTATGATGGAAACCCTGGAGCGACTGCAGCGTAGGTATGG |
| GGGAGGACTGGTCAGAGTGCCACTCTCCCGCAACTCTACACATGAGATGTACGGTCTCTGGAGCGAAAAGCAACACC |
| ATAAAAAGTGTGTCCACCACGAGCCAGCTCCTCTTGGGGCGCATGGACGGGCCCAGGAGGCCAGTGAAATATGAGGAG |
| GATGTGAATCTCGGCTCTGGCACGCGGGCTGTGGTAAGCTGCGCTGAAGCTCCCAACATGAAGATCATTGGTAACCGCAT |
| TGAAAGGATCCGCAGTGAGCACGCGGAAACGTGGTTCTTTGACGAGAACCACCCATATAGGACATGGGCTTACCATGGA |
| AGCTATGAGGCCCCTACACAAGGGTCAGCGTCCTCTCTAATAAACGGGGTTGTCAGGCTCCTGTCAAACCCTGGGATGT |
| GGTGACTGGAGTCACAGGAATAGCCATGACCGACACCACACCGTATGGTCAGCAAAGAGTTTTCAAGGAAAAAGTGGAC |
| ACCAGGGTGCCAGACCCCCAAGAAGGCACTCGTCAGGTTATGAGCATGGTCTCTTCCTGGTTGTGGAAAGAGCTAGGCA |
| AACACAAACGGCCACGAGTCTGTACCAAAGAAGAGTTCATCAACAAGGTTCGTAGCAATGCAGCATTAGGGGCAATATTT |
| GAAGAGGAAAAAGAGTGGAAGACCGCAGTGGAAGCTGTGAACGATCCAAGGTTCTGGGCTCTAGTGGACAAGGAAAGA |
| GAGCACCACCTGAGAGGAGAGTGCCAGAGCTGTGTGTACAACATGATGGGAAAAAGAGAAAAGAAACAAGGGGAATTT |
| GGAAAGGCCAAGGGCAGCCGCGCCATCTGGTATATGTGGCTAGGGGCTAGATTTCTAGAGTTCGAAGCCCTTGGATTCTT |
| AAATGAGGATCACTGGATGGGGAGAGAACTCAGGAGGTGGTGTTGAAGGGCTGGGATTACAAAGACTCGGATATGT |

-continued

SEQUENCES

CCTAGAAGAGATGAGTCGCATACCAGGAGGAAGGATGTATGCAGATGACACTGCTGGCTGGGACACCCGCATCAGCAG
GTTTGATCTGGAGAATGAAGCTTTAATCACCAACCAAATGGAGAAAGGGCACAGGGCCTTAGCATTGGCCATAATCAAGT
ACACATACCAAAACAAAGTGGTAAAGGTCCTTAGACCAGCTGAAAAAGGGAAGACAGTTATGGACATTATTTCAAGACAA
GACCAAAGGGGGAGCGGACAAGTTGTCACTTACGCTCTTAACACATTTACCAACCTAGTGGTGCAACTCATTCGGAATAT
GGAGGCTGAGGAAGTTCTAGAGATGCAAGACTTGTGGCTGCTGCGGAGGTCAGAGAAAGTGACCAACTGGTTGCAGAG
CAACGGATGGGATAGGCTCAAACGAATGGCAGTCAGTGGAGATGATTGCGTTGTGAAGCCAATTGATGATAGGTTTGCA
CATGCCCTCAGGTTCTTGAATGATATGGGAAAAGTTAGGAAGGACACACAAGAGTGGAAACCCTCAACTGGATGGGACA
ACTGGGAAGAAGTTCCGTTTTGTTCCCACCACTTCAACAAGCTCCATCTCAAGGACGGGAGGTCCATTGTGGTTCCCTGCC
GCCACCAAGATGAACTGATTGGCCGGGCCCGTGTCTCTCCAGGGGCGGATGGAGCATCCGGGAGACTGCTTGCCTAGC
AAAGTCATATGCGCAAATGTGGCAGCTCCTTTATTTCCACAGAAGGGACCTCCGACTGATGGCCAATGCCATCTGTTCATC
TGTGCCAGTTGACTGGGTTCCAACTGGGAGAACTACCTGGTCAATCCATGGAAAGGGAGAATGGATGACCACTGAAGAC
ATGCTTGTGGTGTGGAACAGAGTGTGGATTGAGGAGAACGACCACATGGAAGACAAGACCCCAGTTACGAAATGGACA
GACATTCCCTATCTGGGAAAAAGGGAAGACTTGTGGTGTGGATCTCTCATAGGGCACAGACCGCGCACCACCTGGGCTG
AGAACATTAAAAACACAGTCAACATGGTGCGCAGGATCATAGGTGATGAAGAAAAGTACATGGACTACCTATCCACCCAA
GTTCGCTACTTGGGTGAAGAAGGGTCTACACCTGGAGTGCTATAAGCACCAATCTTAGTGTTGTCAGGCCTGCTAGTCAG
CCACAGCTTGGGGAAAGCTGTGCAGCCTGTGACCCCCCCAGGAGAGGCTGGGAAACCAAGCCCATAGTCAGGCCGAGAA
CGCCATGGCACGGAAGAAGCCATGCTGCCTGTGAGCCCCTCAGAGGACACTGAGTCAAAAAACCCCACGCGCTTGGAGG
CGCAGGATGGGAAAAGAAGGTGGCGACCTTCCCCACCCTTCAATCTGGGGCCTGAACTGGAGATCAGCTGTGGATCTCC
AGAAGAGGGACTAGTGGTTAGAGGAGACCCCCCGGAAAACGCAAAACAGCATATTGACGCTGGGAAAGACCAGAGACT
CCATGAGTTTCCACCACGCTGGCCGCCAGGCACAGATCGCCGAATAGCGGCGGCCGGTGTGGGGAAATCCATGGGTCT

SEQ ID NO: 8
KU681082.3 Zika virus isolate Zika virus/*H.sapiens*-tc/PHL/2012/CPC-0740, Philippines, complete genome
AGTTGTTGATCTGTGTGAATCAGACTGCGACAGTTCGAGTTTGAAGCGAAAGCTAGCAACAGTATCAACAGGTTTTATTTT
GGATTTGGAAACGAGAGTTTCTGGTCATGAAAAACCCAAAAAAGAAATCCGGAGGATTCCGGATTGTCAATATGCTAAAA
CGCGGAGTAGCCCGTGTGAGCCCCTTTGGGGGCTTGAAGAGGCTGCCAGCCGGACTTCTGCTGGGCCATGGGCCCATCA
GGATGGTCTTGGCGATACTAGCCTTTTTGAGATTCACGGCAATCAAGCCATCACTGGGTCTCATCAATAGATGGGGTTCA
GTGGGGAAAAAAGAGGCTATGGAAATAATAAAGAAGTTCAAGAAAGATCTGGCTGCCATGCTGAGAATAATCAATGCTA
GGAAGGAGAAGAAGAGACGAGGCGCAGATACTAGCGTCGGAATTGTTGGCCTCCTCCTGACCACAGCCATGGCAGTAG
AGGTCACTAGACGTGGGAGTGCATACTATATGTACTTGGACAGAAGCGATGCTGGGGAGGCCATATCTTTTCCAACCACA
CTGGGGATGAATAAGTGTTACATACAAATCATGGATCTTGGACACATGTGTGATGCCACCATGAGCTATGAATGCCCTAT
GTTGGATGAGGGGGTAGAACCAGATGACGTCGATTGCTGGTGCAACACGACATCAACTTGGGTTGTGTATGGAACCTGC
CACCACAAAAAAGGTGAAGCACGGAGATCTAGAAGAGCTGTGACGCTCCCCTCCCATTCCACTAGGAAGCTGCAAACGC
GGTCGCAGACCTGGTTGGAATCAAGAGAATACACAAAGCACCTGATTAGAGTTGAAAATTGGATATTCAGGAACCCTGG
CTTCGCGTTAGCAGCAGCTGTCATCGCTTGGCTTTTGGGAAGTTCAACGAGCCAAAAAGTCATATATCTGGTCATGATACT
GCTGATTGCCCCGGCATACAGCATCAGGTGCATAGGAGTCAGCAATAGGGACTTTGTGGAAGGTATGTCAGGTGGGACT
TGGGTTGATGTTGTCTTGGAACATGGAGGTTGTGTTACCGTAATGGCACAGGACAAACCGACTGTCGACATAGAGCTGGT
TACAACAACAGTCAGCAACATGGCGGAGGTAAGATCCTACTGCTATGAGGCATCAATATCGGATATGGCTTCGGACAGCC
GCTGCCCAACACAAGGTGAGGCCTACCTTGACAAGCAGTCAGACACTCAATATGTCTGCAAAAGAACGTTAGTGGACAGA
GGCTGGGGAAATGGATGTGGACTTTTTGGCAAAGGGAGCCTGGTGACATGCGCTAAGTTTGCATGCTCCAAGAAAATGA
CCGGGAAGAGCATCCAGCCAGAGAATCTGGAGTACCGGATAATGCTGTCAGTTCATGGCTCCCAGCACAGTGGGATGAT
CGTTAATGACACAGGACATGAAACTGATGAGAATAGAGCGAAGGTTGAGATAACGCCCAATTCACCAAGAGCCGAAGCC
ACCCTGGGGGGTTTTGGGAGCCTAGGACTTGATTGTGAACCGAGGACAGGCCTTGACTTTTCAGATTTGTATTACCTGACT
ATGAATAACAAGCACTGGTTGGTTCACAAGGAGTGGTTCCACGACATTCCATTACCTTGGCATGCTGGGGCAGACACTGG
AACTCCACATTGGAACAACAAAGAAGCACTGGTAGAGTTCAAGGACGCACATGCAAAAAGGCAAACTGTCGTGGTTCTA
GGGAGTCAAGAAGGAGCAGTTCACACGGCCCTTGCTGGAGCTCTGGAGGCTGAGATGGATGGAGCCAAGGGAAGGCTG
TCCTCTGGCCACTTGAAATGTCGCCTGAAAATGGATAAACTTAGATTGAAGGGCGTGTCATACTCCTTGTGCACTGCAGCG
TTCACATTCACCAAGATCCCGGCTGAAACACTGCACGGGACAGTCACAGTGGAGGTACAGTACGCAGGGACAGATGGAC
CTGCAAGGTTCCAGCTCAGATGGCGGTGGATATGCAAACTCTGACCCCAGTTGGGAGGTTGATAACCGCTAACCCTGTA
ATCACTGAAAGCACCGAGAACTCTAAGATGATGCTGGAACTTGATCCACCATTTGGGGACTCTTACATTGTCATAGGAGTC
GGGGAGAAGAAGATCACCCATCACTGGCACAGGAGTGGCAGCACCATTGGAAAAGCATTTGAAGCCACTGTGAGAGGT
GCCAAGAGAATGGCAGTCTTGGGAGACACAGCCTGGGACTTTGGATCAGTTGGGGGTGCTCTCAACTCATTGGGCAAGG
GCATCCATCAAATTTTTGGAGCAGCTTTCAAATCATTGTTCGGAGGAATGTCCTGGTTCTCACAAATTCTCATTGGAACGTT
GCTGGTGTGGTTGGGTCTGAATACAAAGAATGGATCTATTTCCCTTACGTGCTTGGCCTTAGGGGGAGTGTTGATCTTCTT
ATCCACAGCCGTTTCTGCTGATGTGGGGTGCTCGGTGGACTTCTCAAAGAAGGAAACGAGATGCGGTACAGGGGTGTTC
GTCTATAACGACGTTGAAGCCTGGAGGGACAGGTACAAGTACCATCCTGACTCCCCTCGTAGATTGGCAGCAGCAGTCAA
GCAAGCCTGGGAAGATGGGATCTGTGGGATCTCCTCTGTCTCAAGAATGGAAAACATCATGTGGAGATCAGTAGAAGGG
GAGCTCAACGCAATCCTGGAAGAGAATGGAGTTCAACTGACGGTCGTTGTGGGATCTGTAAAAAACCCCATGTGGAGAG
GTCCACAGAGATTGCCCGTGCCTGTGAACGAGCTGCCCCACGGCTGGAAGGCTTGGGGGAAATCGTACTTCGTCAGAGC
AGCAAAGACAAATAACAGCTTTGTCGTGGATGGTGACACACTGAAGGAATGCCCACTCAAACATAGAGCATGGAACAGC
TTTCTTGTGGAGGATCATGGGTTTGGGGTATTTCACACTAGTGTCTGGCTCAAGGTTAGAGAAGATTATTCATTAGAGTGT
GATCCAGCCGTCATTGGAACAGCTGCTAAGGGAAAGGAGGCTGTGCACAGCGATCTAGGCTACTGGATTGAGAGTGAGA
AGAACGACACATGGAGGCTGAAGAGGGCCCACCTGATCGAGATGAAAACATGTGAATGGCCAAAGTCCCACACATTGTG
GACAGATGGAGTAGAAGAAAGTGATCTGATCATACCCAAGTCTTTAGCTGGGCCACTCAGCCATCACAACACCAGAGAG
GGCTACAGGACTCAAATGAAAGGGCCATGGCACAGTGAAGAGCTTGAAATTCGGTTTGAGGAATGCCCAGGCACTAAGG
TCCACGTGGAGGAAACATGTGGGACAAGAGGACCATCCCTGAGATCAACCACTGCAAGCGGAAGGGTGATCGAGGAAT
GGTGCTGCAGGGAATGCACAATGCCCCCACTGTCGTTCCGAGCTAAAGATGGCTGTTGGTATGGAATGGAGATAAGGCC
CAGGAAAGAACCAGAAAGTAACTTAGTAAGGTCAATGGTGACTGCAGGATCAACTGATCACATGGATCACTTCTCTCTTG
GAGTGCTTGTGATTTTGCTCATGGTGCAGGAAGGGCTGAAGAAGAGAATGACCACAAAGATCATCATAAGCACATCAAT
GGCAGTGCTGGTAGCCATGATCCTGGGAGGATTTTCAATGAGTGACCTGGCTAAGCTTGCAATTTTGATGGGTGCCACCT
TCGCGGAAATGAACACTGGAGGAGATGTAGCTCATTTGGCGCTGATAGCGGCATTCAAAGTCAGACCTGCGTTGCTGGTA
TCTTTCATCTTCAGAGCTAATTGGACACCCCGTGAGAGCATGCTGCTGGCCTTGGCCTCGTGTCTTCTGCAAACTGCGATCT
CCGCCTTGGAAGGCGACCTGATGGTTCTCATCAATGGTTTTGCTTTGGCCTGGTTGGCAATACGAGCGATGGTTGTTCCAC
GCACTGACAACATCACCTTGGCAATCCTGGCTGCTCTGACACCACTGGCCCGGGGCACACTGCTTGTGGCGTGGAGAGCA
GGCCTTGCTACTTGCGGGGGGTTCATGCTCCTCTCTCTGAAGGGGAAAGGCAGTGTGAAGAAGAACCTACCATTTGTCAT
GGCCTTGGGACTAACTGCTGTGAGGCTGGTCGACCCCATCAACGTGGTGGGACTGCTGTTGCTCACAAGGAGTGGGAAG

| SEQUENCES |
|---|
| CGGAGCTGGCCCCCTAGTGAAGTACTCACAGCTGTTGGCCTGATATGCGCATTGGCTGGAGGGTTCGCCAAGGCGGATA |
| TAGAGATGGCTGGGCCCATGGCCGCGGTCGGTCTGCTAATTGTCAGTTACGTGGTCTCAGGAAAGAGTGTGGACATGTA |
| CATTGAAAGAGCAGGTGACATCACATGGGAAAAAGATGCGGAAATCACTGGAAACAGTCCCCGGCTCGATGTGGCACTA |
| GATGAGAGTGGTGATTTCTCCCTAGTGGAGGATGATGGTCCACCCATGAGAGAGATCATACTCAAAGTGGTCCTGATGAC |
| CATCTGCGGCATGAACCCAATAGCCATACCCTTTGCAGCTGGAGCGTGGTACGTGTATGTGAAGACTGGAAAAGGAGT |
| GGTGCTCTATGGGATGTGCCTGCTCCCAAGGAAGTAAAAAAGGGGGAGACCACAGATGGAGTGTACAGAGTAATGACTC |
| GTAGACTGCTTGGTTCAACACAAGTTGGAGTGGGAGTCATGCAAGAGGGGGTCTTCCACACTATGTGGCACGTCACAAA |
| AGGATCCGCGCTGAGAAGCGGTGAAGGGAGACTTGATCCATACTGGGGAGATGTCAAGCAGGATCTGGTGTCATACTGT |
| GGTCCGTGGAAGCTAGACGCCGCCTGGGACGGGCACAGCGAGGTGCAGCTCTTGGCCGTGCCCCCGGAGAGAGAGCG |
| AGGAACATCCAGACTCTGCCCGGAACATTTAAGACAAAGGATGGGGACATTGGAGCAGTTGCGCTGGACTACCCAGCAG |
| GAACTTCAGGATCTCCAATCCTAGACAAGTGTGGGAGAGTGATAGGACTCTATGGTAATGGGGTCGTGATAAAAAATGG |
| GAGTTATGTTAGTGCCATCACCCAAGGGAGGAGGGAGGAAGAGACTCCTGTTGAGTGCTTCGAGCCTTCGATGCTGAAG |
| AAGAAGCAGCTAACTGTCTTAGACCTGCATCCTGGAGCCGGGAAAACCAGGAGAGTTCTTCCTGAAATAGTCCGTGAAGC |
| CATAAAAACAAGACTCCGTACTGTGATCTTAGCTCCAACCAGGGTCGTCGCTGCTGAAATGGAGGAAGCCCTTAGAGGGC |
| TTCCAGTTCGTTATATGACAACAGCAGTCAATGTCACCCATTCTGGGACAGAAATCGTTGACTTAATGTGCCATGCTACCTT |
| CACTTCACGCCTACTACAACCAATCAGAGTCCCCAACTATAATTTGTATATTATGGATGAGGCCCACTTCACAGATCCCTCA |
| AGTATAGCAGCAAGAGGATACATTTCAACAAGGGTTGAGATGGGCGAGGCGGCTGCCATCTTCATGACCGCCACGCCAC |
| CAGGAACCCGTGACGCATTCCCGGACTCCAACTCACCAATTATGGACACCGAGGTGGAAGTCCCAGAGAGAGCCTGGAG |
| CACAGGCTTTGATTGGGTGACGGATCATTCTGGGAAAACAGTCTGGTTTGTTCCAAGCGTGAGGAACGGCAATGAGATC |
| GCAGCTTGTCTGACAAAGGCTGGAAAACGGGTCATACAGCTCAGCAGAAGACTTTTGAGACAGAGTTCCAGAAAACGA |
| AAAATCAAGAGTGGGACTTCGTCGTGACAACCGACATTTCAGAGATGGGCGCCAACTTTAAAGCTGACCGTGTCATAGAT |
| TCCAGGAGATGCTTAAAGCCGGTCATACTTGATGGCGAGAGAGTCATTTTGGCTGGACCCATGCCTGTCACACATGCCAG |
| CGCTGCTCAGAGGAGGGGCGCATAGGCAGGAATCCCAACAAACCTGGAGATGAGTATCTGTATGGAGGTGGGTGCGC |
| AGAGACTGATGAAGATCACGCACACTGGCTTGAAGCAAGAATGCTTCTTGACAACATTTACCTCCAAGATGGCCTCATAG |
| CTTCGCTCTATCGACCTGAGGCCGACAAAGTAGCAGCTATTGAGGGAGAGTTCAAGCTTAGGACGGAGCAAAGGAAGAC |
| CTTTGTGGAACTCATGAAAAGAGGAGATCTTCCGGTTTGGTTGGCCTATCAGGTTGCATCTGCCGGAATAACCTACACAG |
| ATAGAAGATGGTGCTTTGATGGCATGACCAACAACACCATAATGGAAGACAGTGTGCCGGCAGAGGTGTGGACCAGATA |
| CGGAGAGAAAAGAGTGCTCAAACCGAGGTGGATGGACGCCAGAGTTTGTTCAGATCATGCGGCCCTGAAGTCATTCAAA |
| GAGTTTGCCGCTGGGAAAAGAGGAGCGGCCTTTGGAGTGATAGAAGCCCTGGGAACACTGCCAGGACACATGACAGAG |
| AGATTCCAGGAAGCCATTGACAACCTCGCTGTGCTCATGCGGGCAGAGACTGGAAGCAGGCCTTACAAAGCGCGGCGG |
| CCCAATTGCCGGAGACCCTAGAGACCATTATGCTTTTGGGGTTGCTGGGAACAGTCTCGCTGGGAATCTTTTCGTCTTGA |
| TGCGGACAAGGGCATGGGGAAGATGGGCTTTGGAATGGTGACTCTTGGGGCCAGCGCATGGCTTATGTGGCTCTCGGA |
| AATTGAGCCAGCCAGAATTGCATGTGTCCTCATTGTCGTGTTCCTATTGCTGGTGGTGCTCATACCTGAGCCAGAAAAGCA |
| AAGATCTCCTCAGGACAACCAAATGGCAATCATCATCATGGTAGCAGTGGGTCTTCGGGCTTGATTACCGCCAATGAACT |
| CGGATGGTTGGAGAGAACAAAAAGTGACCTAAGCCATCTAATGGGAAGGAGAGAGGAGGGGGCAACCACAGGATTCTC |
| AATGGACATTGACCTGCGGCCAGCCTCAGCTTGGGCTATCTATGCTGGTCTCTGACAACTTTCATCACCCCAGCCGTCCAACA |
| TGCGGTGACCACTTCATACAACAACTACTCCTTAATGGCGATGGCCACGCAAGCTGGGGTGTTGTTTGGTATGGGCAAAG |
| GGATGCCATTCTACGCATGGGACTTTGGAGTCCCGCTGCTAATGATGGGTTGCTACTCACAATTAACACCTCTGACCCTAA |
| TAGTGGCCATCATTTTGCTCGTGGCGCACTACATGTACTTGATCCCAGGGCTGCAGGCAGCAGCTGCGCGGGCTGCCCAG |
| AAGAGAACGGCAGCTGGCATCATGAAGAACCCTGTTGTGGATGGAATAGTGGTGACTGACATTGACACAATGACAATTG |
| ACCCCCAAGTGGAAAAAAAGATGGGGGCAGGTGCTACTCATAGCAGTAGCCGTCTCCAGCGCCATACTGTCGCGGACCGC |
| CTGGGGGTGGGGGAGGCTGGGGCCCTGATCACAGCTGCAACTTCCACCTTGTGGGAAGGCTCTCCGAACAAGTACTGG |
| AACTCCTCCACAGCCACTTCACTGTGTAACATTTTTAGGGGAAGTTACTTGGCTGGAGCTTCTCTAATCTACACAGTAACAA |
| GAAACGCTGGCTTGGTCAAGAGACGTGGGGGTGGAACGGGAGAGACCCTGGGAGAGAAATGGAAGGCCCGCCTGAAC |
| CAGATGTCGGCCCTGGAGTTCTACTCCTACAAAAAGTCAGGCATCACCGAGGTGTGCAGAGAAGAGGCCCGCCGTGCCCT |
| CAAGGACGGTGTGGCAACAGGAGGCCATGCTGTGTCCCGAGGAAGTGCAAAGCTTAGATGGCTGGTGGAGAGAGGATA |
| CCTGCAGCCCTATGGAAAGGTCATTGATCTTGGATGTGGCAGAGGGGGCTGGAGTTACTATGCCGCCACCATCCGCAAAG |
| TTCAGGAAGTGAAAGGATACACAAAAGGAGGCCCTGGTCATGAAGAACCCATGTTGGTGCAAAGCTATGGGTGGAACAT |
| AGTCCGTCTTAAGAGTGGGGTGGACGTCTTTCACATGGCGGCTGAGCCGTGTGACACTTTGCTGTGTGATATAGGTGAGT |
| CATCATCTAGTCCTGAAGTGGAAGAAGCACGGACGCTCAGAGTCCTCTCCATGGTGGGGGATTGGCTTGAAAAAAGACC |
| AGGAGCCTTTTGTATAAAAGTGTTGTGCCCATACACCAGCACTATGATGGAAACCCTGGAGCGACTGCAGCGTAGGTATG |
| GGGGAGGACTGGTCAGGGTGCCACTCTCCCGCAACTCTACACATGAGATGTACTGGGTCTCTGGAGCGAAAAGCAACAC |
| CATAAAAAGTGTGTCCACCACGAGCCAGCTCCTCTTGGGGCGCATGGACGGGCCCAGGAGGCCAGTGAAATATGAGGAG |
| GATGTGAATCTCGGCTCTGGCACGCGGGCTGTGGTAAGCTGCGCTGAAGCTCCCAACATGAAGATCATTGGTAACCGCAT |
| TGAGAGGATCCGCAGTGAGCACGCGGAAACGTGGTTCTTTGACGAGAACCACCCATATAGGACATGGGCTTACCATGGA |
| AGCTATGAGGCCCCTACACAAGGGTCAGCGTCCTCTCTAATAAACGGGGTTGTCAGGCTCCTGTCAAACCCTGGGATGT |
| GGTGACTGGAGTCACAGGAATAGCCATGACTGACACCACACCGTATGGTCAGCAAAGAGTTTTCAAGGAAAAAGTGGAC |
| ACTAGGGTGCCAGACCCCCAAGAAGGCACTCGTCAGGTTATGAGCATGGTCTCTTCCTGGTTATGGAAGGAGCTAGGCAA |
| ACACAAACGGCCACGAGTCTGTACCAAAGAAGAGTTCATCAACAAGGTTCGTAGCAATGCAGCATTAGGGGCAATATTTG |
| AAGAGGAAAAAGAGTGGAAGACTGCAGTGGAAGCTGTGAATGATCCAAGGTTCTGGGCTCTAGTGGACAAGGAAAGAG |
| AGCATCACCTGAGAGGAGAGTGTCAGACGTGTGTATACAACATGATGGGAAAAAGAGAAAAGAAACAAGGGGAATTTG |
| GAAAGGCCAAGGGCAGCCGCGCCATCTGGTATATGTGGCTAGGGGCTAGATTCCTAGAGTTCGAAGCCCTTGGATTCTTG |
| AATGAGGATCATTGGATGGGGAGAGAATTCAGGAGGTGGTGTTGAAGGACTGGGATTACAAAGACTCGGATATGTC |
| CTAGAAGAGATGAGTCGCATACCAGGAGGAAGGATGTATGCAGATGATACTGCTGGCTGGGACACCCGCATCAGCAGGT |
| TTGATCTGGAGAATGAAGCTCTAATCACCAACCAAATGGAGAAAGGGCACAGGGCCTTGGCATTGGCCATAATCAAGTAC |
| ACATACCAAAACAAAGTGGTAAAGGTCCTTAGACCAGCTGAAAAAGGGAAGACAGTTATGGACATTATTTCAAGACAAG |
| ACCAAAGGGGGAGCGGACAAGTTGTCACTTACGCTCTTAATACATTCACCAACCTGGTGGTGCAGCTCATTCGGAATATG |
| GAGGCTGAGGAAGTTCTAGAGATGCAAGACTTGTGGCTGCTGCGGAGGCCAGAGAAAGTGACCAACTGGTTGCAAAGC |
| AACGGATGGGATAGGCTCAAAAGAATGGCAGTCAGTGGAGATGATTGCGTTGTGAAACCAATTGATGATAGGTTTGCAC |
| ATGCCCTCAGGTTCTTGAATGATATGGGAAAAGTTAGGAAGGACACACAAGAGTGGAAACCCTCAACTGGATGGGACAA |
| CTGGGAAGAAGTTCCGTTTTGCTCCCACCACTTCAACAAACTCCATCTTAAGGACGGGAGGTCCATTGTGGTTCCCTGCCG |
| CCACCAAGATGAACTGATTGGCCGAGCCCGCGTATCACCAGGGGCGGGATGGAGCATCCGGGAGACTGCTTGCCTAGCA |
| AAATCATATGCGCAAATGTGGCAGCTCCTTTATTTCCACAGAAGGGACCTCCGACTGATGGCCAATGCCATTTGTTCATCT |
| GTGCCAGTTGATTGGGTTCCAACTGGGAGAACTACCTGGTCAATCCATGGAAAGGGAGAATGGATGACCACTGAAGACA |
| TGCTTGTGGTATGGAACAGAGTGTGGATTGAGGAAAACGACCACATGGAAGACAAGACCCCAGTTACAAAATGGACAGA |
| CATTCCCTATTTGGGAAAAAGAGAAGACTTGTGGTGTGGATCTCTCATAGGGACAGACCGCGTACTACCTGGGCTGAGA |
| ACATCAAAAATACAGTCAACATGATGCGCAGGATCATAGGTGATGAAGAAAAGTACATGGACTACCTATCCACCCAGGTT |

| SEQUENCES |
|---|
| CGCTACTTGGGTGAAGAAGGGTCCACACCTGGAGTGCTGTAAGCACCAATCTTAGTGTTGTCAGGCCTGCTAGTCAGCCA
CAGCTTGGGGAAAGCTGTGCAGCCTGTGACCCCCCAGGAGAAGCTGGGAAACCAAGCCTATAGTCAGGCCGAGAACGC
CATGGCACGGAAGAAGCCATGCTGCCTGTGAGCCCCTCAGAGGACACTGAGTCAAAAAACCCCACGCGCTTGGAGGCGC
AGGATGGGAAAAGAAGGTGGCGACCTTCCCCACCCTTCAATCTGGGGCCTGAACTGGAGATCAGCTGTGGATCTCCAGA
AGAGGGACTAGTGGTTAGAGGAGACCCCCGGAAAACGCAAACAGCATATTGACGCTGGGAAGACCAGAGACTCCA
TGAGTTTCCACCACGCTGGCCGCCAGGCACAGATCGCCGAATAGCGGCGGCCGGTGTGGGGAAATCCATGGGTCT

SEQ ID NO: 9
KU707826.1 Zika virus isolate SSABR1, Brazil, complete genome
GACAGTTCGAGTTTGAAGCGAAAGCTAGCAACAGTATCAACAGGTTTTATTTGGATTTGGAAACGAGAGTTTCTGGTCAT
GAAAAACCCAAAAAAGAAATCCGGAGGATTCCGGATTGTCAATATGCTAAAACGCGGAGTAGCCCGTGTGAGCCCCTTT
GGGGGCTTGAAGAGGCTGCCAGCCGGACTTCTGCTGGGTCATGGGCCCATCAGGATGGTCTTGGCGATTCTAGCCTTTTT
GAGATTCACGGCAATCAAGCCATCACTGGGTCTCATCAATAGATGGGGTTCAGTGGGGAAAAAAGAGGCTATGGAAATA
ATAAAGAAGTTCAAGAAAGATCTGGCTGCCATGCTGAGAATAATCAATGCTAGGAAGGAGAAGAAGAGACGAGGCGCA
GATACTAGTGTCGGAATTGTTGGCCTCCTGCTGACCACAGCTATGGCAGCGGAGGTCACTAGACGTGGGAGTGCATACTA
TATGTACTTGGACAGAAACGATGCTGGGGAGGCCATATCTTTTCCAACCACATTGGGGATGAATAAGTGTTATATACAGA
TCATGGATCTTGGACACATGTGTGATGCCACCCATGAGCTATGAATGCCCTATGCTGGATGAGGGGGTGGAACCAGATGAC
GTCGATTGTTGGTGCAACACGACGTCAACTTGGGTTGTGTACGGAACCTGCCATCACAAAAAAGGTGAAGCACGGAGAT
CTAGAAGAGCTGTGACGCTCCCCTCCCATTCCACTAGGAAGCTGCAAACGCGGTCGCAAACCTGGTTGGAATCAAGAGAA
TACACAAAGCACTTGATTAGAGTCGAAAATTGGATATTCAGGAACCCTGGCTTCGCGTTAGCAGCAGCTGCCATCGCTTG
GCTTTTGGGAAGCTCAACGAGCCAAAAAGTCATATACTTGGTCATGATACTGCTGATTGCCCCGGCATACAGCATCAGGT
GCATAGGAGTCAGCAATAGGGACTTTGTGGAAGGTATGTCAGGTGGGACCTGGGTTGATGTTGTCTTGGAACATGGAGG
TTGTGTCACCGTAATGGCACAGGACAAACCGACTGTCGACATAGAGCTGGTTACAACAACAGTCAGCAACATGGCGGAG
GTAAGATCCTACTGCTATGAGGCATCAATATCAGACATGGCTTCGGACAGCCGCTGCCCAACACAAGGTGAAGCCTACCT
TGACAAGCAATCAGACACTCAATATGTCTGCAAAAGAACGTTAGTGGACAGAGGCTGGGGAAATGGATGTGGACTTTTT
GGCAAAGGGAGCCTGGTGACATGCGCTAAGTTTGCATGCTCCAAGAAAATGACCGGGAAGAGCATCCAGCCAGAGAATC
TGGAGTACCGGATAATGCTGTCAGTTCATGGCTCCCAGCACAGTGGGATGATTGTTAATGACACAGGACATGAAACTGAT
GAGAATAGAGCGAAAGTTGAGATAACGCCCAATTCACCAAGAGCCGAAGCCTGCGCACCCTGGGGGGTTTTGGAAGCCTAGGAC
TTGATTGTGAACCGAGGACAGGCCTTGACTTTTCAGATTTGTATTACTTGACTATGAATAACAAGCACTGGTTGGTTCACA
AGGAGTGGTTCCACGACATTCATTACCTTGGCACGCTGGGCAGACACCGGAACTCCACACTGGAACAACAAAGAAGC
ACTGGTAGAGTTCAAGGACGCACATGCCAAAAGGCAAACTGTCGTGGTTCTAGGGAGTCAAGAAGGAGCAGTTCACACG
GCCCTTGCTGGAGCTCTGGAGGCTGAGATGGATGGTGCAAAGGGAAAGGCTGTCCTCTGGACCACTTGAAATGTCGCCTGA
AAATGGATAAACTTAGATTGAAGGGCGTGTCATACTCCTTGTGTACTGCAGCGTTCACATTCACCAAGATCCCGGCTGAAA
CACTGCACGGGACAGTCACAGTGGAGGTACAGTACGCAGGGACAGATGGACCTTGCAAGGTTCCAGCTCAGATGGCGGT
GGACATGCAAACTCTGACCCCAGTTGGGAGGTTGATAACGCTAACCCCGTAATCACTGAAAGCACTGAGAACTCTAAGA
TGATGCTGGAACTTGATCCACCCATTTGGGGACTCTTACATTGTCATGTCATAGGAGTCGGGGAGAAGAAGATCACCCACCACTGG
CACAGGAGTGGCAGCACCATTGGAAAAGCATTTGAAGCCACTGTGAGAGGTGCCAAGAGAATGGCAGTCTTGGGAGAC
ACAGCCTGGGACTTTGGATCAGTTGGAGGCGCTCTCAACTCATTGGGCAAGGGCATCCATCAAATTTTTGGAGCAGCTT
CAAATCATTGTTTGGAGGAATGTCCTGGTTCTCACAAATTCTCATTGGAACGTTGCTGATGTGGTTGGGTCTGAACACAAA
GAATGGATCTATTTCCCTTATGTGCTTGGCCTTAGGGGGAGTGTTGATCTTCTTATCCACAGCCGTCTCTGCTGATGTGGG
GTGCTCGGTGGACTTCTCAAAGAAGGAGACGAGATGCGGTACAGGGGTGTTGTCTATAACGACGTCTGAAGCCTGGAGG
GACAGGTACAAGTACCATCCTGACTCCCCCCGTAGATTGGCAGCAGCAGTCAAGCAAGCCTGGGAAGATGGTATCTGCG
GGATCTCCTCTGTTTCAAGAATGGAAAACATCATGTGGAGATCAGTAGAAGGGGAGCTCAACGCAATCCTGGAAGAGAA
TGGAGTTCAACTGACGGTCGTTGTGGGATCTGTAAAAAACCCCATGTGGAGAGGTCCACAGAGATTGCCCGTGCCTGTGA
ACGAGCTGCCCCACGGCTGGAAGGCTTGGGGAAATCGTACTTCGTCAGAGCAGCAAAGACAAATAACAGCTTTGTCGT
GGATGGTGACACACTGAAGGAATGCCCACTCAAACATAGAGCATGGAACAGCTTTCTTGTGGAGGATCATGGGTTCGGG
GTATTTCACACTAGTGTCTGGCTCAAGGTTAGAGAAGATTATTCATTAGAGTGTGATCCAGCCGTTATTGGAACAGCTGTT
AAGGGAAAGGAGGCTGTACACAGTGATCTAGGCTACTGGATTGAGAGTGAGAAGAATGACACATGGAGGCTGAAGAGG
GCCCATCTGATCGAGATGAAAACATGTGAATGGCCAAAGTCCCACAACATTGTGAACATAGGAGAATAGAAGAGAGTGATC
TGATCATACCCAAGTCTTTAGCTGGGCCACTCAGCCATCACAATACCAGAGAGGGCTACAGGACCCAATTGAAAGGGCCA
TGGCACAGTGAAGAGCTTGAAATTCGGTTTGAGGAATGCCCAGGCACTAAGGTCCACGTGGAGGAAACATGTGGAACAA
GAGGACCATCTCTGAGATCAACCACTGCAAGCGGAAGGGTGATCGAGGAATGGTGCTGCAGGGAGTGCACAATGCCCCC
ACTGTCGTTCCGGGCTAAAGATGGCTGTTGGTATGGAATGGAGATAAGGCCCAGGAAGGAACCAGAAGCAACTTAGTA
AGGTCAATGGTGACTGCAGGATCAACTGATCACATGGACCACTTCTCCCTTGGAGTGCTTGTGATTCTGCTCATGGTGCAG
GAAGGGCTGAAGAAGAGAATGACCACAAAGATCATCATAAGCACATCAATGGCAGTGCTGGTAGCTATGATCCTGGGAG
GATTTTCAATGAGTGACCTGGCTAAGCTTGCAATTTTGATGGGTGCCACCTTCGCGGAAATGAACACTGGAGGAGATGTA
GCTCATCTGGCGCTGATAGCGGCATTCAAAGTCAGACCAGCGTTGCTGGTATCTTTTATCTTCAGAGCTAATTGGACACCC
CGTGAAAGCATGCTGCTGGCCTTGGCCTCGTGTCTTTTGCAAACTGCGATCTCCGCCCTTGAAGGCGACCTGATGGTTCTC
ATCAATGGTTTTGCTTTGGCCTGGTTGGCAATACGAGCGATGGTTGTTCCACGCACTGATAACATCACCTTGGCAATCCTG
GCTGCTCTGACACCACTGGCCCGGGGCACACTGCTTGTGGCGTGGAGAGCAGGCCTTGCTACTTGCGGGGGGTTTATGCT
CCTCTCTCTGAAGGGAAAAGGCAGTGTGAAGAAGAACTTACCATTTGTCATGGCCCTGGGACTAACCGCTGTGAGGCTGG
TCGACCCCATCAACGTGGTGGGACTGCTGTTGCTCACAAGGAGTGGGAAGCGGAGCTGGCCCCCTAGCGAAGTACTCAC
AGCTGTTGGCCTGATATGCGCATTGGCTGGAGGGTTCGCAAGGCAGATATAGAGATGGCTGGGCCCATGGCCGCGGTC
GGTCTGCTAATTGTCAGTTACGTGGTCTCAGGAAAGAGTGTGGACATGTACATTGAAAGAGCAGGTGACATCACATGGG
AAAAAGATGCGGAAGTCACTGGAAACAGTCCCCGGCTCGATGTGGCGCTAGATGAGAGTGGTGATTTCTCCCTGGTGGA
GGATGACGGTCCCCCCATGAGAGAGATCATACTCAAGGTGGTCCTGATGGCCATCTGTGGCATGAACCCAATAGCCATAC
CCTTTGCAGCTGGAGCGTGGTACGTATACGTGAAGACTGGAAAAAGGAGTGGTGCTCTATGGATGTGCTGCTCCCAA
GGAAGTAAAAAGGGGGAGACCACAGATGGAGTGTACAGAGTAATGACTCGTAGACTGCTAGGTTCAACACAAGTTGG
AGTGGGAGTTATGCAAGAGGGGGTCTTTCACACTATGTGGCACGTCACAAAAGGATCCGCGCTGAGAAGCGGTGAAGG
GAGACTTGATCCATACTGGGGAGATGTCAAGCAGGATCTGGTGTCATACTGTGGTCCATGGAAGCTAGATGCCGCCTGG
GACGGGCACAGCGAGGTGCAGCTCTTGGCCGTGCCCCCCGGAGAGAGAGCGAGGAACATCCAGACTCTGCCCGGAATAT
TTAAGACAAAGGATGGGGACATTGGAGCGGTTGCGCTGGATTACCCAGCAGGAACTTCAGGATCTCCAATCCTAGACAA
GTGTGGGAGAGTGATAGGACTTTATGGCAATGGGGTCGTGATCAAAAATGGGAGTTATGTTAGTGCCATCACCCAAGGG
AGGAGGGAGGAAGAGACTCCTGTTGAGTGCTTCGAGCCTTCGATGCTGAAGAAGAAGCAGCTAACTGTCTTAGACTTGC
ATCCTGGAGCTGGGAAAACCAGGAGAGTTCTTCCTGAAATAGTCCGTGAAGCCATAAAAACAAGACTCCGTACTGTGATC
TTAGCTCCAACCAGGGTTGTCGCTGCTGAAATGGAGGAGGCCCTTAGAGGGCTTCCAGTGCGTTATATGACAACAGCAGT
CAATGTCACCCACTCTGGAACAGAAATCGTCGACTTAATGTGCCATGCCACCTTCACTTCACGTCTACTACAGCCAATCAGA |

| SEQUENCES |
|---|
| GTCCCCAACTATAATCTGTATATTATGGATGAGGCCCACTTCACAGATCCCTCAAGTATAGCAGCAAGAGGATACATTTCA |
| ACAAGGGTTGAGATGGGCGAGGCGGCTGCCATCTTCATGACCGCCACGCCACCAGGAACCCGTGACGCATTTCCGGACT |
| CCAACTCACCAATTATGGACACCGAAGTGGAAGTCCCAGAGAGAGCCTGGAGCTCAGGCTTTGATTGGGTGACGGATCA |
| TTCTGGAAAAACAGTTTGGTTTGTTCCAAGCGTGAGGAACGGCAATGAGATCGCAGCTTGTCTGACAAAGGCTGGAAAAC |
| GGGTCATACAGCTCAGCAGAAAGACTTTTGAGACAGAGTTCCAGAAAACAAAACATCAAGAGTGGGACTTTGTCGTGAC |
| AACTGACATTTCAGAGATGGGCGCCAACTTTAAAGCTGACCGTGTCATAGATTCCAGGAGATGCCTAAAGCCGGTCATAC |
| TTGATGGCGAGAGAGTCATTCTGGCTGGACCCATGCCTGTCACACATGCCAGCGCTGCCCAGAGGAGGGGGCGCATAGG |
| CAGGAATCCCAACAAACCTGGAGATGAGTATCTGTATGGAGGTGGGTGCGCAGAGACTGACGAAGACCATGCACACTGG |
| CTTGAAGCAAGAATGCTCCTTGACAATATTTACCTCCAAGATGGCCTCATAGCCTCGCTCTATCGACCTGAGGCCGACAA |
| GTAGCAGCCATTGAGGGAGAGTTCAAGCTTAGGACGGAGCAAAGGAAGACCTTTGTGGAACTCATGAAAAGAGGAGAT |
| CTTCCTGTTTGGCTGGCCTATCAGGTTGCATCTGCCGGAATAACCTACACAGATAGAAGATGGTGCTTTGATGGCACGACC |
| AACAACACCATAATGGAAGACAGTGTGCCGGCAGAGGTGTGGACAGACACGGAGAGAAAAGAGTGCTCAAACCGAGG |
| TGGATGGACGCCAGAGTTTGTTCAGATCATGCGGCCCTGAAGTCATTCAAGGAGTTTGCCGCTGGGAAAGAGGAGCGG |
| CTTTTGGAGTGATGGAAGCCCTGGGAACACTGCCAGGACACATGACAGAGAGATTCCAGGAAGCCATTGACAACCTCGC |
| TGTGCTCATGCGGGCAGAGACTGGAAGCAGGCCTTACAAAGCCGCGGCGGCCCAATTGCCGGAGACCCTAGAGACCATT |
| ATGCTTTTGGGGTTGCTGGGAACAGTCTCGCTGGGAATCTTCTTCGTCTTGATGAGGAACAAGGGCATAGGGAAGATGG |
| GCTTTGGAATGGTGACTCTTGGGGCCAGCGCATGGCTCATGTGGCTCTCGGAAATTGAGCCAGCCAGAATTGCATGTGTC |
| CTCATTGTTGTGTTTCTATTGCTGGTGGTGCTCATACCTGAGCCAGAAAAGCAAAGATCTCCCCAGGACAACCAAATGGCA |
| ATCATCATCATGGTAGCAGTAGGTCTTCTGGGCTTGATTACCGCCAATGAACTCGGATGGTTGGAGAGAACAAAGAGTGA |
| CCTAAGCCATCAATGGAAGGAGAGAGGAGGGGGCAACCATAGGATTCTCAAGGATTCTGCACCATGCATTGACCTGCGGCCAGCCTCA |
| GCTTGGGCCATCTATGCTGCCTTGACAACTTTCATTACCCCAGCCGTCCAACATGCAGTGACCACTTCATACAACAACTACT |
| CCTTAATGGCGATGGCCACGCAAGCTGGAGTGTTGTTTGGTATGGGCAAAGGGATGCCATTCTACGCATGGGACTTTGGA |
| GTCCCGCTGCTAATGATAGGTTGCTACTCACAATTAACACCCCTGACCCTAATAGTGGCCATCATTTTGCTCGTGGCGCACT |
| ACATGTACTTGATCCCAGGGCTGCAGGCAGCAGCTGCGCGTGCTGCCCAGAAGAGAACGGCAGCTGGCATCATGAAGAA |
| CCCTGTTGTGGATGGAATAGTGGTGACTGACATTGACACAATGACAATTGACCCCCAAGTGGAGAAAAAGATGGGACAG |
| GTGCTACTCATAGCAGTAGCCGTCTCCAGCGCCATACTGTCGCGGACCGCCTGGGGGTGGGGGGAGGCTGGGGCCCTGA |
| TCACAGCCGCAACTTCCACTTTGTGGGAAGGCTCTCCGAACAAGTACTGGAACTCCTCTACAGCCACTTCACTGTGTAACA |
| TTTTAGGGGAAGTTACTTGGCTGGAGCTTCTCTAATCTACACAGTAACAAGAAACGCTGGCTTGGTCAAGAGACGTGGG |
| GGTGGAACAGGAGAGACCCTGGGAGAGAAATGGAAGGCCCGCTTGAACCAGATGTCGGCCCTGGAGTTCTACTCCTACA |
| AAAAGTCAGGCATCACCGAGGTGTGCAGAGAAGAGGCCCGCCGCGCCCTCAAGGACGGTGTGGCAACGGGAGGCCATG |
| CTGTGTCCCGAGGAAGTGCAAAGCTGAGATGGTTGGTGGAGCGGGGATACCTGCAGCCCTATGGAAAGGTCATTGATCT |
| TGGATGTGGCAGAGGGGGCTGGAGTTACTACGCCGCCACCATCCGCAAAGTTCAAGAAGTGAAAGGATACACACAAAGG |
| AGGCCCTGGTCATGAAGAACCCGTGTTGGTGCAAAGCTATGGGTGGAACATAGTCCGTCTTAAGAGTGGGGTGGACGTC |
| TTTCATATGGCGGCTGAGCCGTGTGACACGTTGCTGTGTGACATAGGTGAGTCATCATCTAGTCCTGAAGTGGAAGAAGC |
| ACGGACGCTCAGAGTCCTCTCCATGGTGGGGATTGGCTTGAAAAAAGACCAGGAGCCTTTTGTATAAAGGTGTTGTGCC |
| CATACACCAGCACTATGATGGAAACCCTGGAGCGACTGCAGCGTAGGTATGGGGGAGGACTGGTCAGAGTGCCACTCTC |
| CCGCAACTCTACACATGAGATGTATTGGGTCTCTGGAGCGAAAAGCAACACCATAAAAAGTGTGTCCACCACGAGCCAGC |
| TCCTCTTGGGGCGCATGGACGGGCCTAGGAGGCCAGTGAAATATGAGGAGGATGTGAATCTCGGCTCTGGCACGCGGGC |
| TGTGGTAAGCTGCGCTGAAGCTCCCAACATGAAGATCATTGGTAACCGCATTGAAAGGATCCGCAGTGAGCACGCGGAA |
| ACGTGGTTCTTTGACGAGAACCACCCATATAGGACATGGGCTTACCATGGAAGCTATGAGGCCCCCACACAAGGGTCAGC |
| GTCCTCTCTAATAAACGGGGTTGTCAGGCTCCTGTCAAAACCCTGGGATGTGGTGACTGGAGTCACAGGAATAGCCATGA |
| CCGACACCACACCGTATGGTCAGCAAAGAGTTTTCAAGGAAAAAGTGGACACTAGGGTGCCAGACCCCAAGAAGGCAC |
| TCGTCAGGTTATGAGCATGGTCTCTTCCTGGTTGTGGAAAGAGCTAGGCAAACACAAACGGCCACGAGTCTGTACCAAAG |
| AAGAGTTCATCAACAAGGTTCGTAGCAATGCAGCATTAGGGGCAATATTTGAAGAGGAAAAAGAGTGGAAGACTGCAGT |
| GGAAGCTGTGAACGATCCAAGGTTCTGGGCTCTAGTGGATAAGGAAAGAGAGCACCACCTGAGAGGAGAGTGCCAGAG |
| TTGTGTGTACAACATGATGGGAAAAAGAGAAAAGAAACAAGGGGAATTTGGAAAGGCCAAGGGCAGCCGCGCCATCTG |
| GTATATGTGGCTAGGGGCTAGATTTCTAGAGTTCGAAGCCCTTGGATTCTTGAACGAGGATCACTGGATGGGGAGAGAG |
| AACTCAGGAGGTGGTGTTGAAGGGCTGGGATTACAAAGACTCGGATATGTCCTAGAAGAGATGAGTCGTATACCAGGAG |
| GAAGGATGTATGCAGATGACACTGCTGGCTGGGACACCCGCATCAGCAGGTTTGATCTGGAGAATGAAGCTCTAATCACC |
| AACCAAATGGAAAAAGGGCACAGGGCCTTGGCATTGGCCATAATCAAGTACACATACCAAAACAAAGTGGTAAAGGTCC |
| TTAGACCAGCTGAAAAAGGGAAAACAGTTATGGACATTATTTCGAGACAAGACCAAAGGGGGAGCGGACAAGTTGTCAC |
| TTACGCTCTTAACACATTTACCAACCTAGTGGTGCAACTCATTCGGAATATGGAGGCTGAGGAAGTTCTAGAGATGCAAG |
| ACTTGTGGCTGCTGCGGAGGTCAGAGAAAGTGACCAACTGGTTGCAGAGCAACGGATGGGATAGGCTCAAACGAATGG |
| CAGTCAGTGGAGATGATTGCGTTGTGAAGCCAATTGATGATAGGTTTGCACATGCCCTCAGGTTCTTGAATGATATGGGA |
| AAAGTTAGGAAGGACACACAAGAGTGGAAACCCTCAACTGGATGGGACAACTGGGAAGAAGTTCCGTTTTGCTCCCACC |
| ACTTCAACAAGCTCCATCTCAAGGACGGGAGGTCCATTGTGGTTCCCTGCCGCCACCAAGATGAACTGATTGGCCGGGCC |
| CGCGTCTCTCCAGGGGCGGGATGGAGCATCCGGGAGACTGCTTGCCTAGCAAAATCATATGCGAAATGGGCAGCTCCT |
| TTATTTCCACAGAAGGGACCTCCGACTGATGGCCAATGCCATTTGTTCATCTGTGCCAGTTGACTGGGTTCCAACTGGGAG |
| AACTACCTGGTCAATCCATGGAAAGGGAGAATGGATGACCACTGAAGACATGCTTGGTGTGGAACAGAGTGTGGATT |
| GAGGAGAACGACCACATGGAAGACAAGACCCCAGTTACGAAATGGACAGACATCCCCTATTTGGGAAAAAGGGAAGACT |
| TGTGGTGGATCTCTCATAGGGCACAGACCGCGCACCACCTGGGCTGAGACATTAAAAACACAGTCAACATGGTGCGC |
| AGGATCATAGGTGATGAAGAAAAGTACATGGACTACCTATCCACCCAAGTTCGCTACTTGGGTGAAGAAGGGTCTACACC |
| TGGAGTGCTGTAAGCACCAGTCTTAATGTTGTCAGGCCTGCTAGTCAGCCACAGCTTGGGGAAAGCTGTGCAGCCTGTGA |
| CCCCCCCAGGAGAAGCTGGGAAACCAAGCCTATAGTCAGGCCGAGAACGCCATGGCACGAAGAAGCCATGCTGCCTGT |
| GAGCCCCTCAGAGGACACTGAGTCAAAAAACCCCACGCGCTTGGAGGCGCAGGATGGGAAAGAAGGTGGCGACCTTC |
| CCCACCCTTCAATCTGGGGCCTGAACTGGAGATCAGCTGTGGATCTCCAGAAGAGGGACTAGTGGTTAGAGGAG |

SEQ ID NO: 10
KU744693.1 Zika virus isolate VE_Ganxian, China, complete genome
GTTGTTACTGTTGCTGACTCAGACTGCGACAGTTCGAGTTTGAAGCGAAAGCTAGCAACAGTATCAACAGGTTTTATTTGG
ATTTGGAAACGAGAGTTTCTGGTCATGAAAAACCCAAAAAAGAAATCCGGAGGATTCCGGATTGTCAATATGCTAAAACG
CGGAGTAGCCCGTGTGAGCCCCTTTGGGGGCTTGAAGAGGCTGCCAGCCGGACTTCTGCTGGGTCATGGGCCCATCAGG
ATGGTCTTGGCAATTCTAGCCTTTTTGAGATTCACGGCAATCAAGCCATCACTGGGTCTCATCAATAGATGGGGTTCAGTG
GGGAAAAAGATGCTATGGAATAATAAAGGAGTTCAAGAAAGATCTGGCTGCCATGCTGAGAATAATCAATGCTAGGA
AGGAGAAGAAGAGACGAGGCGCAGATACTAGTGTCGGAATTGTTGGCCTCCTGCTGACCACAGCTATGGCAGCGGAGG
TCACTAGACGTGGGAGTGCATACTATATGTACTTGGACAGAAACGATGCTGGGAGGCCATATCTTTTCCAACCACATTG
GGGATGAATAAGTGTTATATACAGATCATGGATCTTGGACACATGTGTGATGCCACCATGAGCTATGAATGCCCTATGCT

| SEQUENCES |
|---|
| GGATGAGGGGGTGGAACCAGATGACGTCGATTGTTGGTGCAACACGACGTCAACTTGGGTTGTGTACGGAACCTGCCAT |
| CACAAAAAAGGTGAAGCACGGAGATCTAGAAGAGCTGTGACGCTCCCTTCCCATTCCACTAGGAAGCTGCAAACGCGGT |
| CGCAAACCTGGTTGGAATCAAGAGAATACACAAAGCACTTGATTAGAGTCGAAAATTGGATATTCAGGAACCCTGGCTTC |
| GCGTTAGCAGCAGCTGCCATCGCTTGGCTTTTGGGAAGCTCAACGAGCCAAAAAGTCATATACTTGGTCATGATACTGCT |
| GATTGCCCCGGCATACAGCATCAGGTGCATAGGAGTCAGCAATAGGGACTTTGTGGAAGGTATGTCAGGTGGGACTTGG |
| GTTGATGTTGTCTTGGAACATGGAGGTTGTGTCACCGCAATGGCACAGGACAAACCGACTGTCGACATAGAGCTGGTTAC |
| AACAACAGTCAGCAACATGGCGGAGGTAAGATCCTACTGCTATGAGGCATCAATATCAGACATGGCTTCGGACAGCCGCT |
| GCCCAACACAAGGTGAAGCCTACCTTGACAAGCAATCAGACACTCAATATGTTTGCAAAAGAACGTTAGTGGACAGAGGC |
| TGGGGAAATGGATGTGGACTTTTTGGCAAAGGGAGTCTGGTGACATGCGCTAAGTTTGCATGCTCCAAGAAAATGACCG |
| GGAAGAGCATCCAGCCAGAGAATCTGGAGTACCGGATAATGCTGTCAGTTCATGGCTCCCAGCACAGTGGGATGCTCGTT |
| AATGACACAGGACATGAAACTGATGAGAATAGAGCGAAGGTTGAGATAACGCCCAATTCACCAAGAGCCGAAGCCACCC |
| TGGGGGGTTTTGGAAGCCTAGGACTTGATTGTGAACCGAGGACAGGCCTTGACTTTTCAGATTTGTATTACTTGACTATGA |
| ATAACAAGCACTGGTTGGCTCACAAGGAGTGGTTCCACGACATTCCATTACCTTGGCACGCTGGGGCAGCCACCGGAACT |
| CCACACTGGAACAACAAAGAAGCACTGGTAGAGTTCAAGGACGCACATGCCAAAAGGCAAACTGTCGTGGTTCTAGGGA |
| GTCAAGAAGGAGCAGTTCACACGGCCCTTGCTGGAGCTCTGGAGGCTGAGATGGATGGTGCAAAGGGAAGGCTGTCCTC |
| TGGCCACTTGAAATGTCGCCTGAAAATGGATAAACTTAGATTGAAGGGCGTGTCATACTCCTTGTGTACCGCAGCGTTCAC |
| ATTCACCAAGATCCCGGCTGAAACAGTGGACGGGACAGTCACAGTGGAGGGACAGTACGGAGGGACAGATGGACCTTG |
| CAAGGTTCCAGCTCAGATGGCGGTGGACATGCAGACTCTGACCCCAGTTGGGAGGTTGATAACCGCTAACCCCGTAATCA |
| CTGAAAGCACTGAGAACTCTAAGATGATGCTGGAACTTGATCCACCATTTGGGGACTCTTACATTGTCATAGGAGTCGGG |
| GAGAAGAAGATCACCCACCACTGGCACAGGAGTGGCAGCACCATTGGAAAAGCATTTGAAGCCACTGTGAGAGGTGCCA |
| AGAGAATGGCAGTCTTGGGAGACACAGCCTGGGACTTTGATCAGTTGGAGGCGCTCTCAACTCATTGGGCAAGGGCAT |
| CCATCAAATTATTGGAGCAGCTTTCAAATCATTGTTTGGAGGAATGTCCTGGTTCTCACAAATTCTCATTGGGACGTTGCTG |
| ATGTGGTTGGGTCTGAACACAAAGAATGGATCTATTTCCCTTATGTGCTTGGCCTTAGGGGAGTGTTGATCTTCTTATCC |
| ACAGCCGTCTCAGGTGGTGTGGGGTGCTCGGTGGACTTCTCAAAGAAGGAGACGAGATGCGGTACAGGGGTGTTCGTCT |
| ATAACGATGTTGAAGCCTGGAGGGACAGGTACAAGTACCATCCTGACTCCCCCCGTAGATTGGCAGCAGCAGTCAAGCA |
| AGCCTGGGAAGATGGTATCTGCGGGATCTCCTCTGTTTCAAGAATGGAAAACATCATGTGGAGATCAGTAGAAGGGGAG |
| CTCAACGCAATCCTGGAAGAGAATGGAGTTCAACTGACGGTCGTTGTGGGATCTGTAAAAAACCCCATGTGGAGAGGTC |
| CACAGAGATTGCCCGTGCCTGTGAACGAGCTGCCCCCACGGCTGGAAGGCTTGGGGGAAATCGTACTTCGTCAGAGCAGC |
| AAAGACAAATAACAGCTTTGTCGTGGATGGTGACACACTGAAGGAATGCCCACTCAAACATAGAGCATGGAACAGCTTTC |
| TTGTGGAGGATCATGGGTTCGGGGTATTTCACACTAGTGTCTGGCTCAAGGTTAGAGAAGACTATTGTTAGAGTGTGAT |
| CCAGCCGTTATTGGAACAGCTGTTAAGGGAAAGGAGGCTGTACACAGTGATCTAGGCTACTGGATTGAGAGTGAGAAGA |
| ATGACACATGGTGGCTGAAGAGGGCCCATCTGATCGAGATGAAAACATGTGAATGGCCAAAGTCCCACACATTGTGGAC |
| AGATGGAATAGAAGAGAGTGATCTGATCATACCCAAGTCTTTAGCTGGGCCACTCAGCCATCACAATGCCAGAGAGGGCT |
| ACAGGACCCAAATGAAAGGGCCATGGCACAGTGAAGAGCTTGAAATTCGGTTTGAGGAATGCCCAGGCACTAAGGTCCA |
| CGTGGAGGAAACATGTGGAACAAGAGGACCATCTCTGAGATCAACCACTGCAAGCGGAAGGGTGATCGAGGAATGGTG |
| CTCCAGGGAGTGCACAATGCCCCCACTGTCCTTCCAGGCTAAAGATGGCTGTTGGTATGGAATGGAGATAAGGCCCAGG |
| AAAGAACCAGAAAGCAACTTAGTAAGGTCAATGGTGACTGCAGGATCAACTGATCACATGGATCACTTCTCCCTTGGAGT |
| GCTTGTGATTCTGCTCATGGTGCAGGAAGGGCTGAAGAAGAGAATGACCACAAAGATCATCATAAGCACATCAATGGCA |
| GTGCTGGTAGCTATGATCCTGGGAGGATTTTCAATGAGTGACCTGGCTAAGCTTGCAATTTTGATGGGTGCCACCTTCGC |
| GGAAATGAACACTGGAGGAGATGTAGCTCATCTGGCGCTGATAGCGGCATTCAAAGTCAGACCAGCGTTGCTGGTATCTT |
| TCATCTTCAGAGCTAATTGGACACCCCGTGAAAGCATGCTGCTGGCCTTGGCCTCGTGTCTTTTGCAAACTGCGATCTCCG |
| CCTTGGAAGGCGACCTGATGGTTCTCATCAATGGTTTTGCTTTGGCTCGTTGGCAATACGAGCGATGGTTGTTCCACGCA |
| CTGATAACATCACCTTAGCAATCCTGGCTGCTCTGACACCACTGGCCCGGGGCACACTGCTTGTGGCGTGGAGAGCAGGC |
| CTTGCTACTTGCGGGGGTTTATGCTCCTCTCTCTGAAGGGAAAAGGCAGTGTGAAGAAGAACTTACCATTTGTCATGGC |
| CCTGGGACTAACCGCTGTGAGGCTGGTCGACCCCCATCAACGTGGTGGGACTGCTGTTGCTCACAAGGAGTGGGAAGCGG |
| AGCTGGCCCCCTAGCGAAGTACTCACAGCTGTTGGCCTGATATGCGCATTGGCTGGAGGGTTCGCCAAGGCAGATATAGA |
| GATGGCTGGGCCCATGGCCGCGGTCGGTCTGCTAATTGTCAGTTACGTGGTCTCAGGAAAGAGTGTGGACATGTACATTG |
| AAAGAGCAGGTGACATCACATGGGAAAAGATGCGGAAGTCACTGGAAACAGTCCCCGGCTCGATGTGGCGCTAGATG |
| AGAGTGGTGATTTCTCCTGGTGGAGGATGACGGTCCCCCCATGAGAGAGATCATACTCAAGGTGGTCCTGATGACCATC |
| TGTGGCATGAACCCAATAGCCATACCCTTTGCAGCTGGAGCTGGTACGTATACGTGAAGACTGGAAAAAGGAGTGGTG |
| CTCTATGGGATGTGCCTGCTCCCAAGGAAGTAAAAAAGGGGGAGACCACAGATGGAGTGTACAGAGTAATGACTCGCAG |
| ACTGCTAGGTTCAACACAAGTTGGAGTGGGAGTTATGCAAGAGGGGGTCTTTCACACTATGTGGCACGTCACAAAAGGA |
| TCCGCGCTGAGAAGCGGTGAAGGGAGACTTGATCCATACTGGGGAGATGTCAAGCAGGATCTGGTGTCATACTGTGGTC |
| CATGGAAGCTAGATGCCGCCTGGGACGGGCACAGCAGAGGTGCAGCTCTTGGCCGTGCCCCCCGGAGAGAGAGCGAGGA |
| ACATCCAGACTCTGCCCGGAATATTAAGCAAAGGATGGGGACATTGGAGCGGTTGCACTGGATTACCCAGCAGGAAC |
| TTCAGGATCTCCAATCCTAGACAAGTGTGGGAGAGTGATAGGACTTTATGGCAATGGGTCGTGATCAAAAATGGGAGT |
| TATGTTAGTGCCATCACCCAAGGGAGGAGGGAGGAAGAACATCCTGTTGAGTGCTCTGAGGCCCTCGATGCTGAAGAGA |
| AGCAGCTAACTGTCTTAGACTTGCATCCTGGAGCTGGGAAAACAGGAGAGTTCTTCCTGAAATAGTCCGTGAAGCCATA |
| AAAACAAGACTCCGTACTGTGATCTTGGCTCCAACCAGGGTTGTCGCTGCTGAAATGGAGGAGGCCCTTAGAGGGCTTCC |
| AGTGCGTTATATGACAACAGCAGTCAATGTCACCCACTCTGGAACAGAAATCGTCGACTTAATGTGCCATGCCACCTTCAC |
| TTCACGTCTACTACAGCCAATTAGAGTCCCCAACTATAATCTGTATATTATGGATGAGGCCCACTTCACAGATCCCTCAAGT |
| ATAGCAGCAAGAGGATACATTTCAACAAGGGTTGAGATGGGCGAGGCGGCTGCCATCTTCATGACCGCCACGCCACCAG |
| GAACCCGTGACGCATTTCCGGACTCCAACTCACCAATTATGGACACCGAAGTGGAAGTCCCAGAGAGAGCCTGGAGCTCA |
| GGCTTTGATTGGGTGACGGAGTATTCTGGAAAAACAGTTTGGTTTGTTCCACGCGTGAGGAACGGCAATGAGATCGCAG |
| CTTGTCTGACAAAGGCTGGAAAACGGGTCATACAGCTCAGCAGAAAGACTTTTGAGACAGAGTTCCAGAAAACAAAACAT |
| CAAGAGTGGGACTTTGTCGTGACAACTGACATTTCAGAGATGGGCGCCAACTTTAAAGCTGACCGTGTCATAGATTCCAG |
| GAGATGCCTAAAGCCGGTCATACTTGGTGGCGAGAGAGTCATTCTGGCTGGACCCATGCCTGTCACACATGCCAGCGCTG |
| CCCAGAGGAGGGGCGCATAGGCAGGAATCCCAACAAACCTGGAGATGAGTATCTGTATGGAGGTGGGTGCGCAGAGA |
| CTGACGAAGACCATGCACACTGGCTTGAAGCAAGAATGCTCCTTGACAATATTTACCTCCAAGATGGCCTCATAGCCTCGC |
| TCTATCGACCTGAGGCCGACAAAGTAGCAGCCATTGAGGGAGAGTTCAAGCTTAGGACGGAGCAAAGGAAGACCTTTGT |
| GGAACTCATGAAAAGAGGAGATCTTCCTGTTTGGCTGGCCTATCAGGTTGCATCTGCCGGAATAACCTACACAGATAGAA |
| GATGGTGCTTTGATGGCACGACCAACAACACCATAATGGAAGACAGTGTGCCGGCAGAGGTGTGACCAGACACGGAG |
| AGAAAAGAGTGCTCAAACCGAGGTGGATGGACGCCAGAGTTTGTTCAGATCATGCGGCCCTGAAGTCATTCAAGGAGTT |
| TGCCGCTGGGAAAAGAGGAGCGGCTTTTGGAGTGATGGAAGCCCTGGGAACACTGCCAGGACACATGACAGAGATT |
| CCAGGAAGCCATTGACAACCTCGCTGTGCTCATGCGGGCAGAGACTGGAAGCAGGCCTTACAAAGCCGCGGCGGCCCAA |
| TTGCCGGAGACCCTAGAGACCATTATGCTTTTGGGGTTGCTGGGAACAGTCTCGCTGGGAATCTTTTCGTCTTGATGAGG |
| AACAAGGGCATAGGGAAGATGGGCTTTGGAATGGTGACTCTTGGGGCCAGCGCATGGCTCATGTGGCTCTCGGAAATTG |

-continued

SEQUENCES

AGCCAGCCAGAATTGCATGTGTCCTCATTGTTGTGTTCCTATTGCTGGTGGTGCTCATACCTGAGCCAGAAAAGCAAAGAT
CTCCCCAGGACAACCAAATGGCCATCATCATCATGGTAGCAGTAGGTCTTCTGGGCTTGATTACCGCCAATGAACTCGGAT
GGTTGGAGAGAACAAAGAGTGACCTAAGCCATCTAATGGGAAGGAGAGAGGAGGGGGCAACCATGGGATTCTCAATGG
ACATTGACCTGCCGGCCAGCCTCAGCTTGGGCCATCTATCCTGCCTTGACATCTTTCATTACCCCAGCCGTCCAACATGCAGT
GACCCACTTCATACAACAACTACTCCTTAATGGCGATGGCCACGCAAGCTGGAGTGTTGTTGGTATGGGCAAAGGGATGC
CATTCTACGCATGGGACTTTGGAGTCCCGCTGCTAATGATAGGTTGCTACTCACAATTAACGCCCCTGACCCTAATAGTGG
CCATCATTTTGCTCGTGGCGCACTACATGTACTTGATCCCAGGGCTGCAGGCAGCAGCTGCGCGTGCTGCCCAGAAGAGA
ACGGCAGCTGGCATCATGAAGAACCCTGTTGTGGAGGGAATAGTGGTGACTGACATTGACACAATGACAATTGACCCCC
AAGTGGAGAAAAGATGGGACAGGTGCTACTCATGGCAGTAGCCGTCTCCAGCGCCATACTGTCGAGGACCGCCTGGGG
GTGGGGGAGGCTGGGGCCCTGATCACAGCCGCAACTTCCACTTTGTGGGAAGGCTCTCCGAACAAGTACTGGAACTCC
TCTACAGCCACCTCACTGTGTAACATTTTTAGGGGAAGTTACTTGGCTGGAGCTTCTCTAATCTACACAGTAACAAGAAAC
GCTGGCTTGGTCAAGAGACGTGGGGGTGGAACAGGAGAGACCCTGGGAGAGAAATGGAAGGCCCGCTTGAACCAGAT
GTCGGCCCTGGAGTTCTACTCCTACAAAAAGTCAGGCATCACCGAGGTGTGCAGAGAAGAGGCCCGCCGCGCCCTCAAG
GACGGTGTGGCAACGGGAGGCCATGCTGTGTCCCGAGGAAGTGCAAAGCTGAGATGGTTGGTGGAGCGGGGATACCTG
CAGCCCTATGGAAAGGTCATTGATCTTGGATGTGGCAGAGGGGGCTGGAGTTACTACGCCGCCACCATCCGCAAAGTTCA
AGAAGTGAAAGGATACACAAAAGGAGGCCCTGGTCATGAAGAACCCGTGTTGGTGCAAAGCTATGGGTGGAACATAGT
CCGTCTTAAGAGTGGGGTGGACGTCTTTCATATGGCGGCTGAGCCGTGTGACACGTTGCTGTGTGACATAGGTGAGTCAT
CATCTAGTCCTGAAGTGGAAGAAGCACGGACGCTCAGAGTCCTCTCCATGGTGGGGATTGGCTTGAAAAAGACCAGG
AGCCTTTTGTATAAAAGTGTTGTGCCCATACACCAGCACTATGATGGAAACCCTGGAGCGACTGCAGCGTAGGTATGGGG
GAGGACTGGTCAGAGTGCCACTCTCCCGCAACTCTACACATGAGATGTACTGGGTCTCTGGAGCGAAAAGCAACACCATA
AAAAGTGTGTCCACCACGAGCCAGCTCCTCTTGGGGCGCATGGACGGGCTAGGAGGCCAGTGAAATATGAGGAGGAT
GTGAATCTCGGCTCTGGCACGGGCTGTGGTAAGCTGCGCTGAAGCTCCCAACATGAAGATCATTGGTAACCGCATTGA
AAGGATCCGCGCTGAGAAAGCGGAAACGTGGTTCTTTGACGAGAACCACCCATATAGGACATGGGCTTACCATGGAAGC
TATGATGCCGCCACACAAGGGTCAGCGTCCTCTCTAATAAACAGGGGTTGTCAGGCTCCTGTCAAAACCCTGGGATGTGGT
GACTGGAGTCACAGGAATAGCCATGACCGACACCACACCGTATGGTCAGCAAAGAGTTTTCAAGGAAAAAGTGGACACT
AGGGTGCCAGACCCCCAAGAAGGCACTCGTCAGGTTATGAGCATGGTCTCTTCCTGGTTGTGGAAAGAGCTAGGCAAAC
ACAAACGGCCACGAGTCTGTACCAAAGAAGAGTTCATCAACAAGGTTCGTAGCAATGCAGCATTAGGGGCAATATTTGAA
GAGGAAAAAGAGTGGAAGACTGCAGTGGAAGCTGTGAACGATCCAAGGTTCTGGGCTCTAGTGGACAAGGAAAGAGA
CACCACCTGAGAGGAGAGTGCCAGAGTTGTGTGTACATCACAATGGGAAAAAGAGAAAAGAAACAAGGGGAATTTGGA
AAGGCCAAGGGCAGCCGCGCCATCTGGTATATGTGGCTAGGGGCTAGATTTCTAGAGTTCGAAGCCCTTGGATTCTTGAA
CGAGGATCACTGGATGGGGAGAGAGAACTCAGGAGGTGGTGTTGAAGGGCTGGGATTACAAAGACTCGGATATGTCCT
AGAAGAGATGAGTCGCATACCAGGAGGAAGGATGTATGCAGATGACCTGCTGGCTGGGACACCCGCATCAGCAGGTTT
GATCTGGAGAATGAAGCTCTAATCACCAACCAAATGGAGAAAGGGCACAGGGCCTTGGCATTGGCCATAATCAAGTACA
CATACCAAAACAAAGTGGTAAAGGTCCTTAGACCAGCTGAAAAAGGGAAGACAGTTATGGACATTATTCGAGACAAGA
CCAAAGGGGAGCGGACAAGTTGTCACTTACGCTCTCAACACATTTACCAACCTAGTGGTGCAACTCATTCGGAATATGG
AGGCTGAGGAAGTTCTAGAGATGCAAGACTTGTGGCTGCTGCGGAGGTCAGAGAAGTGACCAACTGGTTGCAGAGCA
ACGGATGGGATAGGCTCAAACGAATGGCGGTCAGTGGAGATGATTGCGTTGTGAAACCAATTGATGATAGGTTTGCACA
TGCCCTCAGGTTCTTGAATGATATGGGAAAAGTTAGGAAGGACACACAAGAGTGGAAACCCTCAACTGGATGGGACAAC
TGGGAAGAAGTTCCCTTCTGCTCCCACCACTTCAACAAGCTCCATCTCAAGGACGGGAGGTCCATTGTGGTTCCCTGCCGC
CACCAAGATGAACTGATTGGCCGGGCCCGCGTCTCTCCAGGGGCGGGATGGAGCATCCGGGAGACTGCTTGCCTAGCAA
AATCATATGCGCAAATGTGGCAGCTCCTTTATTTCCACAGAAGGGACCTCCGACTGATGGCCAATGCCATTTGTTCATCTG
TGCCAGTTGACTGGGTTCCAACTGGGAGAACTACCTGGTCAATCCATGGAAAGGGAGAATGGATGACCACTGAAGACAT
GCTTGTGGCGTGGAACAGAGTGTGGATTGAGGAGAACGACCACATGGAAGACAAGACCCCAGTCACGAAATGGACAGA
CATTCCCTATTTGGGAAAAAGGGGAAGACTTGTGGTGTGGATCTCTCATAGGGCACAGACCGCGCACCACCTGGGCTGAGA
ACATTAAAAACACAGTCAACATGGTGCGCAGGATCATAGGTGATGAAGAAAAGTACATGGACTACCTATCCACCCAAGTT
CGCTACTTGGGTGAAGAAGGGTCTACACCTGGAGTGCTGTAAGCACCAATCTTAATGTTGTCAGGCCTGCTAGTCAGCCA
CAGCTTGGGGAAAGCTGTGCAGCCTGTGACCCCCCAGGAGAAGCTGGGAAACCAAGCCTATAGTCAGGCCGAGAACGC
CATGGCACGGAAGAAGCCATGCTGCCTGTGAGCCCCTCAGAGGACACTGAGTCAAAAACCCCACGCGCTTGGAGGCGC
AGGATGGGAAAGAAGGTGGCGACCTTCCCCACCCTTCAATCTGGGGCCTGAACTGGAGATCAGCTGTGGATCTCCAGA
AGAGGGACTAGTGGTTAGAGGAGA

SEQ ID NO: 11
LC002520.1 Zika virus genomic RNA, strain: MR766-NIID, Uganda, complete genome
AGTTGTTGATCTGTGTGAGTCAGACTGCGACAGTTCGAGTCTGAAGCGAGAGCTAACAACAGTATCAACAGGTTTAATTT
GGATTTGGAAACGAGAGTTTCTGGTCATGAAAAACCCAAAGAAGAAATCCGGAGGATTCCGGATTGTCAATATGCTAAA
ACGCGGAGTAGCCCGTGTAAACCCCTTGGGAGGTTTGAAGAGGTTGCCAGCCGGACTTCGCTGGGTCATGGACCCATCA
GAATGGTTTTGGCGATACTAGCCTTTTTGAGATTTACAGCAATCAAGCCATCACTGGGCCTTATCAACAGATGGGGTTCCG
TGGGAAAAAAGAGGCTATGGAAATAATAAAGAAGTTCAAGAAAGATCTTGCTGCCATGTTGAGAATAATCAATGCTAG
GAAAGAGAGGAAGAGACGTGGCGCAGACACCAGCATCGGAATCATTGGCCTCCTGCTGACTACAGCCATGGCAGCAGA
GATCACTAGACGCGGGAGTGCATACTACATGTACTTGGATAGGAGCGATGCCGGAAGGCCATTTCGTTTGCTACCACAT
TGGGAGTGAACAAGTGCCACGTACAGATCATGGACCTCGGGCACATGTGTGACGCCACCATGAGTTATGAGTGCCCTATG
CTGGATGAGGGAGTGGAACCAGATGATGTCGATTGCTGGTGCAACACGACATCAACTTGGGTTGTGTACGGAACCTGTC
ATCACAAAAAAGGTGAGGCACGGCGATCTAGAAGAGCCGTGACGCTCCCTTCTCACTCTACAAGGAAGTTGCAAACGCG
GTCGCAGACCTGGTTAGAATCAAGAGAATACACGAAGCACTTGATCAAGGTTGAAACTGGATATTCAGGAACCCCGGG
TTTGCGCTAGTGGCCGTTGCCATTGCCTGGCTTTTGGGAAGCTCGACGAGCCAAAAAGTCATATACTTGGTCATGATACTG
CTGATTGCCCCGGCATACAGTATCAGGTGCATTGGAGTCAGCAATAGAGACTTTGTGGAGGGCATGTCAGGTGGGACCT
GGGTTGATGTTGTCTTGGAACATGGAGGCTGCGTTACCGTGATGGCACAGGACAAGCCAACAGTTGACATAGAGTTGGT
CACGACGACGGTTAGTAACATGGCCGAGGTAAGATCCTATTGCTACGAGGCATCGATATCGGACATGGCTTCGGACAGTC
GTTGCCCAACACAAGGTGAAGCCTACCTTGACAAGCAATCAGACACTCAATATGTCTGCAAAAGAACATTAGTGGACAGA
GGTTGGGGAAACGGTTGTGGACTTTTTGGCAAAGGGAGCTTGGTGACATGTGCCAAGTTTACGTGTTCTAAGAAGATGA
CCGGGAAGAGCATTCAACCGGAAAATCTGGAGTATCGGATAATGCTGTCTGTACACGGGTCTCCAGCATAGCGGGATGAC
TGTCAATGATATAGGATATGAAACTGACGAAAATAGAGCGAAAGTCGAGGTTACGCCTAATTCACCAAGAGCGGAAGCA
ACCTTGGGAGGCTTTGGAAGCTTAGGACTTGACTGTGAACCAAGGACAGGCCTTGACTTTTCAGATCTGTATTACCTGACC
ATGAACAATAAGCATTGGTTGGTCACAAAGAGTGGTTTCATGACATCCCATTGCCTTGGCATGCTGGGCAGACACTGG
AACTCCACACTGGAACAACAAAGAGGCATTGGTAGAATTCAAGGATGCCCACGCCAAGAGGCAAACCGTCGTCGTTCTG
GGGAGCCAGGAAGGAGCCGTTCACACGGCTCTCGCTGGAGCTCTAGAGGCTGAGATGGATGGTGCAAAGGGAAAGCTG
TTCTCTGGCCATTTGAAATGCCGCCTAAAAATGGACAAGCTTAGATTGAAGGCGTGTCATATTCCTTGTGCACTGCGGCA

| SEQUENCES |
|---|
| TTCACATTCACCAAGGTCCCAGCTGAAACACTGCATGGAACAGTCACAGTGGAGGTGCAGTATGCAGGGACAGATGGAC |
| CCTGCAAGATCCCAGTCCAGATGGCGGTGGACATGCAGACCCTGACCCCAGTTGGAAGGCTGATAACCGCCAACCCCGTG |
| ATTACTGAAAGCACTGAGAACTCAAAGATGATGTTGGAGCTTGACCCACCATTTGGGGATTCTTACATTGTCATAGGAGTT |
| GGGGACAAGAAAATCACCCACCACTGGCATAGGAGTGGTAGCACCATCGGAAAGGCATTTGAGGCCACTGTGAGAGGC |
| GCCAAGAGAATGGCAGTCCTGGGGGATACAGCCTGGGACTTCGGATCAGTCGGGGGTGTGTTCAACTCACTGGGTAAGG |
| GCATTCACCAGATTTTTGGAGCAGCCTTCAAATCACTGTTTGGAGGAATGTCCTGGTTCTCACAGATCCTCATAGGCACGC |
| TGCTAGTGTGGTTAGGTTTGAACACAAAGAATGGATCTATCTCCCTCACATGCTTGGCCCTGGGGGGAGTGATGATCTTCC |
| TCTCCACGGCTGTTTCTGCTGACGTGGGGTGCTCAGTGGACTTCTCAAAAAAGGAAACGAGATGTGGCACGGGGGTATTC |
| ATCTATAATGATGTTGAAGCCTGGAGGGACCGGTACAAGTACCATCCTGACTCCCCCCGCAGATTGGCAGCAGCAGTCAA |
| GCAGGCCTGGGAAGAGGGGATCTGTGGGATCTCATCCGTTTCAAGAATGGAAAACATCATGTGGAAATCAGTAGAAGGG |
| GAGCTCAATGCTATCCTAGAGGAGAATGGAGTTCAACTGACAGTTGTTGTGGGATCTGTAAAAAACCCCATGTGGAGAG |
| GTCCACAAAGATTGCCAGTGCCTGTGAATGAGCTGCCCCATGGCTGGAAAGCCTGGGGGAAATCGTATTTTGTTAGGGCG |
| GCAAAGACCAACAACAGTTTTGTTGTCGACGGTGACACACTGAAGGAATGTCCGCTTGAGCACAGAGCATGGAATAGTTT |
| TCTTGTGGAGGATCACGGGTTTGGAGTCTTCCACACCAGTGTCTGGCTTAAGGTCAGAGAAGATTACTCATTAGAATGTG |
| ACCCAGCCGTCATAGGAACAGCTGTTAAGGGAAGGGAGGCCGCGCACAGTGATCTGGGCTATTGGATTGAAAGTGAAAA |
| GAATGACACATGGAGGCTGAAGAGGGCCCACCTGATTGAGATGAAAACATGTGAATGGCCAAAGTCTCACACATTGTGG |
| ACAGATGGAGTAGAAGAAAGTGATCTTATCATACCCAAGTCTTTAGCTGGTCCACTCAGCCACCACAACACCAGAGAGGG |
| TTACAGAACCCAAGTGAAAGGGCCATGGCACAGTGAAGAGCTTGAAATCCGGTTTGAGGAATGTCCAGGCACCAAGGTT |
| TACGTGGAGGAGACATGCGGAACTAGAGGACCATCTCTGAGATCAACTACTGCAAGTGGAAGGGTCATTGAGGAATGGT |
| GCTGTAGGGAATGCACAATGCCCCCACTATCGTTTCGAGCAAAAGACGGCTGCTGGTATGGAATGGAGATAAGGCCCAG |
| GAAAGAACCAGAGAGCAACTTAGTGAGGTCAATGGTGACAGCGGGGTCAACCGATCATATGGACCACTTCTCTCTTGGA |
| GTGCTTGTGATTCTACTCATGGTGCAGGAGGGGTTGAAGAAGAGAATGACCACAAAGATCATCATGAGCACATCAATGG |
| CAGTGCTGGTAGTCATGATCTTGGGAGGATTTTCAATGAGTGACCTGGCCAAGCTTGTGATCCTGATGGGTGCTACTTTCG |
| CAGAAATGAACACTGGAGGAGATGTAGCTCACTTGGCATTGGTAGCGGCATTTAAAGTCAGACCAGCCTTGCTGGTCTCC |
| TTCATTTTCAGAGCCAATTGGACACCCCGTGAGAGCATGCTGCTAGCCCTGGCTTCGTGTCTTCTGCAAACTGCGATCTCT |
| GCTCTTGAAGGTGACTTGATGGTCCTCATTAATGGATTTGCTTTGGCCTGGTTGGCAATTCGAGCAATGGCCGTGCCACGC |
| ACTGACAACATCGCTCTACCAATCTTGGCTGCTCTAACACCACTAGCTCGAGGCACACTGCTCGTGGCATGGAGAGCGGG |
| CCTGGCTACTTGTGGAGGGATCATGCTCCTCTCCCTGAAAGGGAAAGGTAGTGTGAAGAAGAACCTGCCATTTGTCATGG |
| CCCTGGGATTGACAGCTGTGAGGGTAGTAGACCCTATTAATGTGGTAGGACTACTGTTACTCACAAGGAGTGGGAAGCG |
| GAGCTGGCCCCCTAGTGAAGTTCTCACAGCCGTTGGCCTGATATGTGCACTGGCCGGAGGGTTTGCCAAGGCAGACATTG |
| AGATGGCTGGACCCATGGCTGCAGTAGGCTTGCTAATTGTCAGCTATGTGGTCTCGGGAAAGAGTGTGGACATGTACATT |
| GAAAGAGCAGGTGACATCACATGGGAAAAGGACGCGGAAGTCACTGGAACAAGTCCTCGGCTTGACGTGGCACTGGAT |
| GAGAGTGGTGATTTCTCCTTGGTAGAGGAAGATGGTCCACCCATGAGAGAGATCATACTTAAGGTGGTCCTGATGGCCAT |
| CTGTGGCATGAACCCAATAGCTATACCTTTTGCTGCAGGAGCGTGGTATGTGTATGTGAAGACTGGGAAAAGGAGTGGC |
| GCCCTCTGGGACGTGCCTGCTCCCAAAGAAGTGAAGAAAGGAGAGACCACAGATGGAGTGTACAGAGTGATGACTCGCA |
| GACTGCTAGGTTCAACACAGGTTGGAGTGGGAGTCATGCAAGAGGGAGTTCTTCACACCATGTGGCACGTTACAAAAGG |
| AGCCGCACTGAGGAGCGGTGAGGGAAGACTTGATCCATACTGGGGGGATGTCAAGCAGGACTTGGTGTCATACTGTGG |
| GCCTTGGAAGTTGGATGCAGCTTGGGATGGACTCAGCGAGGTACAGCTTTTGGCCGTACCTCCCGGAGAGGGCCAGA |
| AACATTCAGACCCTGCCTGGAATATTCAAGACAAAGGACGGGGACATCGGAGCAGTTGCTCTGGACTACCCTGCAGGGA |
| CCTCAGGATCTCCGATCCTAGACAAATGTGGAAGAGTGATAGGACTCTATGGCAATGGGGTTGTGATCAAGAATGGAAG |
| CTATGTTAGTGCTATAACCCAGGGAAAGAGGGAGGAGGAGACTCCGGTTGAATGTTTCGAACCCTCGATGCTGAAGAAG |
| AAGCAGCTAACTGTCTTGGATCTGCATCCAGGAGCCGGAAAAACCAGGAGAGTTCTTCCTGAAATAGTCCGTGAAGCCAT |
| AAAAAAGAGACTCCGGACAGTGATCTTGGCACCAACTAGGGTTGTCGCTGCTGAGATGGAGGAGGCCTTGAGAGGACTT |
| CCGGTGCGTTACATGACAACAGCAGTCAACGTCACCCATTCTGGGACAGAAATCGTTGATTTGATGTGCCATGCCACTTTC |
| ACTTCACGCTTACTACAACCCATCAGATGCCCTAATTACAATCTCTACATCATGGATGAAGCCCACTTCACAGACCCCTCAA |
| GTATAGCTGCAAGAGGATATATATCAACAAGGGTTGAAATGGGCGAGGCGGCTGCCATTTTTATGACTGCCACACCACCA |
| GGAACCCGTGATGCGTTTCCTGACTCTAACTCACCAATCATGGACACAGAAGTGGAAGTCCCAGAGAGAGCCTGGAGCTC |
| AGGCTTTGATTGGGTGACAGACCATTCTGGGAAAACAGTTTGGTTCGTTCCAAGCGTGAGAAACGGAAATGAAATCGCA |
| GCCTGTCTGACAAAGGCTGGAAAGCGGGTCATACAGCTCAGCAGGAAGACTTTTGAGACAGAATTTCAGAAAACAAAAA |
| ATCAAGAGTGGGACTTTGTCATAACAACTGACATCTCAGAGATGGGCGCCAACTTCAAGGCTGACCGGGTCATAGACTCT |
| AGGAGATGCCTAAAACCAGTCATACTTGATGGTGAGAGAGTCATCTTGGCTGGGCCCATGCCTGTCACGCATGCTAGTGC |
| TGCTCAGAGGAGAGGACGTATAGGCAGGAACCCTAACAAACCTGGAGATGAGTACATGTATGGAGGTGGGTGTGCAGA |
| GACTGATGAAGGCCATGCACACTGGCTTGAAGCAAGAATGCTTCTTGACAACATCTACCTCCAGGATGGCCTCATAGCCTC |
| GCTCTATCGGCCTGAGGCCGATAAGGTAGCCGCCATTGAGGGAGAGTTTAAGCTGAGGACAGAGCAAAGGAAGACCTTC |
| GTGGAACTCATGAAGAGAGGAGACCTTCCCGTCTGGCTAGCCTATCAGGTTGCATCTGCCGGAATAACTTACACAGACAG |
| AAGATGGTGCTTTGATGGCACAACCAACAACACCATAATGGAAGACAGCGTACCAGCAGAGGTGTGGACAAAGTATGGA |
| GAGAAGAGAGTGCTCAAACCGAGATGGATGGATGCTAGGGTCTGTTCAGACCATGCGGCCCTGAAGTCCTTCAAAGAAT |
| TCGCCGCTGGAAAAAGAGGAGCGGCTTTGGGAGTAATGGAGGCCCTGGGAACACTGCCAGGACACATGACAGAGAGGT |
| TTCAGGAAGCCATTGACAACCTCGCCGTGCTCATGCGAGCAGAGACTGGAAGCAGGCCTTATAAGGCAGCGGCAGCCCA |
| ACTGCCGGAGACCCTAGAGACCATTATGCTCTTAGGTTTGCTGGGAACAGTTTCACTGGGGATCTTCTTCGTCTTGATGCG |
| GAATAAGGGCATCGGGAAGATGGGCTTTGGAATGGTAACCCTTGGGGCCAGTGCATGGCTGATGTGGCTTTCGGAAATT |
| GAACCAGCCAGAATTGCATGTGTCCTCATTGTTGTGTTTTTATTACTGGTGGTGCTCATACCCGAGCCAGAGAAGCAAAGA |
| TCTCCCCAAGATAACCAGATGGCAATTATCATCATGGTGGCAGTGGGCCTTCTAGGTTTGATAACTGCAAACGAACTTGGA |
| TGGCTGGAAAGAACAAAAAATGACATAGCTCATCTAATGGGAAGGAGAGAAGAAGGAGCAACCATGGGATTCTCAATG |
| GACATTGATCTGCGGCCAGCCTCCGCCTGGGCTATCTATGCCGCATTGACAACTCTCATCACCCCAGCTGTCCAACATGCG |
| GTAACCACTTCATACAACAACTACTCCTTAATGGCGATGGCCACACAAGCTGGAGTGCTGTTTGGCATGGGCAAAGGGAT |
| GCCATTTTATGCATGGGACCTTGGAGTCCCGCTGCTAATGATGGGTTGCTATTCACAATTAACACCCCTGACTCTGATAGT |
| AGCTATCATTCTGCTTGTGGCGCACTACATGTACTTGATCCCAGGCCTACAAGCGGCAGCAGCGCGTGCTGCCCAGAAAA |
| GGACAGCAGCTGGCATCATGAAGAATCCCGTTGTGGATGGAATAGTGGTAACTGACATTGACACAATGACAATAGACCCC |
| CCAGGTGGAAGAAGATGGGCAAGTGTTACTCATAGCAGTAGCCATCTCCAGTGCTGTGCTGCTGCGGACCGCCTGG |
| GGATGGGGAGGCTGGAGCTCTGATCACAGCAGCCCTCCACCTTGTGGGAAGGCTCTCCAAAATACTGGAACT |
| CCTCTACGACCACCTCACTGTGCAACATCTTCAGAGGAAGCTATCTGGCAGGAGCTTCCCTTATCTATACAGTGACGAGAA |
| ACGCTGGCCTGGTTAAGAGACGTGGAGGTGGGACGGGAGAGACTCTGGGAGAAGTGGAAAGCTCGTCTGAATCAGA |
| TGTCGGCCCTGGAGTTCTACTCTTATAAAAAGTCAGGTATCACTGAAGTGTGTAGAGGAGGCTCGCCGTGCCCTCAAG |
| GATGGAGTGGCCACAGGAGGACATGCCGTATCCCGGGGAAGTGCAAAGCTCAGATGGTTGGTGGAGAGGGGATATCTG |
| CAGCCCTATGGGAAGGTTGTTGACCTCGGATGTGGCAGAGGGGGCTGGAGCTATTATGCCGCCACCATCCGCAAAGTGC |
| AGGAGGTGAGAGGATACACAAAGGGAGGTCCCGGTCATGAAGAACCCATGCTGGTGCAAAGCTATGGGTGGAACATAG |

TTCGTCTCAAGAGTGGAGTGGACGTCTTCCACATGGCGGCTGAGCCGTGTGACACTCTGCTGTGTGACATAGGTGAGTCA
TCATCTAGTCCTGAAGTGGAAGAGACACGAACACTCAGAGTGCTCTCTATGGTGGGGGACTGGCTTGAAAAAAGACCAG
GGGCCTTCTGTATAAAGGTGCTGTGCCCATACACCAGCACTATGATGGAAAACCATGGAGCGACTGCAACGTAGGCATGG
GGGAGGATTAGTCAGAGTGCCATTGTCTCGCAACTCCACACATGAGATGTACTGGGTCTCTGGGGCAAAGAGCAACATCA
TAAAAAGTGTGTCCACCACAAGTCAGCTCCTCCTGGGACGCATGGATGGCCCCAGGAGGCCAGTGAAATATGAGGAGGA
TGTGAACCTCGGCTCGGGTACACGAGCTGTGGCAAGCTGTGCTGAGGCTCCTAACATGAAAATCATCGGCAGGCGCATTG
AGAGAATCCGCAATGAACATGCAGAAACATGGTTTCTTGATGAAAACCACCCATACAGGACATGGGCCTACCATGGGAGC
TACGAAGCCCCCACGCAAGGATCAGCGTCTTCCCTCGTGAACGGGGTTGTTAGACTCCTGTCAAAGCCTTGGGACGTGGT
GACTGGAGTTACAGGAATAGCCATGACTGACACCACACCATACGGCCAACAAAGAGTCTTCAAAGAAAAAGTGGACACC
AGGGTGCCAGATCCCCAAGAAGGCACTCGCCAGGTAATGAACATAGTCTCTTCCTGGCTGTGGAAGGAGCTGGGGAAAC
GCAAGCGGCCACGCGTCTGCACCAAAGAAGAGTTTATCAACAAGGTGCGCAGCAATGCAGCACTGGGAGCAATATTTGA
AGAGGAAAAAGAATGGAAGACGGCTGTGGAAGCTGTGAATGATCCAAGGTTTTGGGCCCTAGTGGATAGGGAGAGAGA
ACACCACCTGAGAGGAGAGTGTCACAGCTGTGTGTACAACATGATGGGAAAAAGAGAAAAGAAGCAAGGAGAGTTCGG
GAAAGCAAAAGGTAGCCGCGCCATCTGGTACATGTGGTTGGGAGCCAGATTCTTGGAGTTTGAAGCCCTTGGATTCTTGA
ACGAGGACCATTGGATGGGAAGAGAAAACTCAGGAGGTGGAGTCGAAGGGTTAGGATTGCAAAGACTTGGATACATTC
TAGAAGAAATGAATCGGGCACCAGGAGGAAAGATGTACGCAGATGACACTGCTGGCTGGCTGGGACACCCGCATTAGTAAGTT
TGATCTGGAGAATGAAGCTCTGATTACCAACCAAATGGAGGAAGGGCACAGAACTCTGGCGTTGGCCGTGATTAAATAC
ACATACCAAACAAAGTGGTGAAGGTTCTCAGACCAGCTGAAGGAGGAAAAACAGTTATGGACATCATTTCAAGACAAG
ACCAGAGAGGGAGTGGACAAGTTGTCACTTATGCTCTCAACACATTCACCAACTTGGTGGTGCAGCTTATCCGGAACATG
GAAGCTGAGGAAGTGTTAGAGATGCAAGACTTATGGTTGTTGAGGAAGCCAGAGAAAGTGACCAGATGGTTGCAGAGC
AATGGATGGGATAGACTCAAACGAATGGCGGTCAGTGGAGATGACTGCGTTGTGAAGCCAATCGATGATAGGTTTGCAC
ATGCCCTCAGGTTCTTGAATGACATGGGAAAAGTTAGGAAAGACACACAGGAGTGGAAACCCTCGACTGGATGGAGCAA
TTGGGAAGAAGTCCCGTTCTGCTCCCACCACTTCAACAAGCTGTACCTCAAGGATGGGAGATCCATTGTGGTCCCTTGCCG
CCACCAAGATGAACTGATTGGCCGAGCTCGCGTCTCACCAGGGCAGGATGGAGCATCCGGGAGACTGCCTGTCTTGCA
AAATCATATGCGCAGATGTGGCAGCTCCTTTATTTCCACAGAAGAGACCTTCGACTGATGGCTAATGCCATTTGCTCGGCT
GTGCCAGTTGACTGGGTACCAACTGGGAGAACCACCTGGTCAATCCATGGAAAGGGAGAATGGATGACCACTGAGGACA
TGCTCATGGTGTGGAATAGAGTGTGGATTGAGGAGAACGACCATATGGAGGACAAGACTCCTGTAACAAAATGGACAGA
CATTCCCTATCTAGGAAAAAGGGGAGGACTTATGGTGTGGAATCCCTTATAGGGCACAGACCCCGCACCACTTGGGCTGAAA
ACATCAAAGACACAGTCAACATGGTGCGCAGGATCATAGGTGATGAAGAAAAGTACATGGACTATCTATCCACCCAAGTC
CGCTACTTGGGTGAGGAAGGGTCCACACCCGGAGTGTTGTAAGCACCAATTTTAGTGTTGTCAGGCCTGCTAGTCAGCCA
CAGTTTGGGGAAAGCTGTGCAGCCTGTAACCCCCCAGGAGAAGCTGGGAAACCAAGCTCATAGTCAGGCCGAGAACGC
CATGGCACGGAAGAAGCCATGCTGCCTGTGAGCCCTCAGAGGACACTGAGTCAAAAAACCCCACGCGCTTGAAGCGC
AGGATGGGAAAAGAAGGTGGCGACCTTCCCCACCCTTCAATCTGGGCCTGAACTGGAGACTAGCTGTGAATCTCCAGC
AGAGGGACTAGTGGTTAGAGGAGACCCCCCGGAAAACGCAAAACAGCATATTGACGCTGGGAAAGACCAGAGACTCCA
TGAGTTTCCACCACGCTGGCCGCCAGGCACAGATCGCCGAACAGCGGCGGCCGGTGTGGGGAAATCCATGGTTTCT

SEQ ID NO: 12
AY632535.2 NC_012532.1 Zika virus strain MR 766, Uganda, complete genome
AGTTGTTGATCTGTGTGAGTCAGACTGCGACAGTTCGAGTCTGAAGCGAGAGCTAACAACAGTATCAACAGGTTTAATTT
GGATTTGGAAACGAGAGTTTCTGGTCATGAAAAACCCCAAAGAAGAAATCCGGAGGATTCCGGATTGTCAATATGCTAAA
ACGCGGAGTAGCCCGTGTAAACCCCTTGGGAGGTTTGAAGAGGTTGCCAGCCGGACTTCTGCTGGGTCATGGACCCATCA
GAATGGTTTTGGCGATACTAGCCTTTTTGAGATTTACAGCAATCAAGCCATCACTGGGCCTTATCAACAGATGGGGTTCCG
TGGGGAAAAAAGAGGCTATGGAAATAATAAAGAAGTTCAAGAAAGATCTTGCTGCCATGTTGAGAATAATCAATGCTAG
GAAAGAGAGGAAGAGACGTGGCGCAGACACCAGCATCGGAATCATTGGCCTCCTGCTGACTACAGCCATGGCAGCAGA
GATCACTAGACGCGGGAGTGCCATACTACATGTCTTGGATAGGAGCGATGCCGGAAGGCCATTTCGTTTGCTACCACAT
TGGGAGTGAACAAGTGCCACGTACAGATCATGGACCTCGGGCACATGTGTGACGCCACCATGAGTTATGAGTGCCCTATG
CTGGATGAGGGAGTGGAACCAGATGATGTCGATTGCTGGTGCAACACGACATCAACTTGGGTTGTGTACGGAACCTGTC
ATCACAAAAAGGTGAGGCACGGCGATCTAGAAGAGCCGTGACGCTCCCTTCTCACTCTACAAGGAAGTTGCAAACGCG
GTCGCAAGCTGGTTAGAATCAAGAGAATACACGAAGCATTGTTGATCAAGGTTGAAAACTGGATATTCAGGAACCCCGGG
TTTGCGCTAGTGGCCGTTGCCATTGCCTGGCTTTTGGGAAGCTCGACGAGCCAAAAAGTCATATACTTGGTCATGATACTG
CTGATTGCCCCGGCATACAGTATCAGGTGCATTGAGTCAGCAATAGAGACTTCGTGGAGGGCATGTCAGGTGGGACCT
GGGTTGATGTTGTCTTGGAACATGGAGGCTGCGTTACCGTGATGGCACAGGACAAGCCAACAGTCGACATAGAGTTGGT
CACGACGACGGTTAGTAACATGGCCGAGGTAAGATCCTATTGCTACGAGGCATCGATATCGGACATGGCTTCGGACAGTC
GTTGCCCAACACAAGGTGAAGCCTACCTTGACAAGCAATCAGACACTCAATATGTCTGCAAAAGAACATTAGTGGACAGA
GGTTGGGGAAACGGTTGTGGACTTTTTGGCAAAGGGAGCTTGGTGACATGTGCCAAGTTTACGTGTTCTAAGAAGATGA
CCGGGAAGAGCATTCAACCGGAAAATCTGGAGTATCGGATAATGCTATCAGTGCATGGCTCCCAGCATAGCGGGATGAT
TGGATATGAAACTGACGAAGATAGAGCCAAAGTTGAGGTTACGCCTAATTCACCAAGAGCGGAAGCAACCTTGGGAGGC
TTTGGAAGCTTAGGACTTGACTGTGAACCAAGGACAGGCCTTGACTTTTCAGATCTGTATTACCTGACCATGAACAATAAG
CATTGGTTGGTGCACAAAGAGTGGTTTCATGACATCCCATTGCCTTGGCATGCTGGGGCAGACACCGGAACTCCACACTG
GAACAACAAAGAGGCATTGGTAGAATTCAAGGATGCCCACGCCAAGAGGCAAACCGTCGTCGTTCTGGGGAGCCAGGAA
GGAGCCGTTCACACGGCTCTCGCTGGAGCTCTAGAGGCTGAGATGGATGGTGCAAAGGGAAGGCTGTTCTCTGGCCATT
TGAAATGCCGCCTAAAAATGGACAAGCTTAGATTGAAGGGCGTGTCATATTCCTTGTGCACTGCGGCATTCACATTCACCA
AGGTCCCAGCTGAAACACTGCATGGAACAGTCACAGTGGAGGTGCAGTATGCAGGGACAGATGGACCCTGCAAGATCCC
AGTCCAGATGGCGGTGGACATGCAGACCCTGACCCCAGTTGGAAGGCTGATAACCGCCAACCCCGTGATTACTGAAAGC
ACTGAGAACTCAAAGATGATGTTGGAGCTTGACCCACCATTTGGGGATTCTTACATTGTCATAGGAGTTGGGGACAAGAA
AATCACCCACCACTGGCATAGGAGTGGTAGCACCATCGGAAAAGGCCATTCGGAAAGGCCACTGTGAGAGGCGCCAAGAATG
GCAGTCCTGGGGGATACAGCCTGGGACTTCGATCAGTCGGGGGTGTGTTCAACTCACTGGGTAAGGGCATTCACCAGA
TTTTTGGAGCAGCCTTCAAATCACTGTTTGGAGGAATGTCCTGGTTCTCACAGATCCTCATAGGCACGCTGCTAGTGTGGT
TAGGTTTGAACACAAAGAATGGATCTATCTCCCTCACATGCTTGGCCCTGGGGGAGTGATGATCTTCCTCTCCACGGCTG
TTTCTGCTGACGTGGGGTGCTCAGTGGACTTCTCAAAAAAGGAAACGAGATGTGGCACGGGGTATTCATCTATAATGAT
GTTGAAGCCTGGAGGGGACCGGTACAAGTACCATCCTGACTCCTCCCCGCAGTTGGCACAGCAGTCAAGCAGGCCTGGG
AAGAGGGGATCTGTGGGATCTCATCCGTTTCAAGAATGAAAACATCATGTGGAAATCAGTAGAAGGGGAGCTCAATGC
TATCCTAGAGGAGAATGGAGTTCAACTGACAGTTGTTGTGGGATCTGTAAAAAACCCCATGTGGAGAGGTCCACAAAGAT
TGCCAGTGCCTGTGAATGAGCTGCCCCATGGCTGGAAAGCCTGGGGGAAATCGTATTTTGTTAGGGCGGCAAAGACCAA
CAACAGTTTTGTTGTCGACGGTGACACACTGAAGGAATGTCCGCTTGAGCACAGAGCATGGAATAGTTTTCTTGTGGAGG
ATCACGGGTTTGGAGTCTTCCACACCAGTGTCTGGCTTAAGGTCAGAGAAGATTACTCATTAGAATGTGACCCAGCCGTCA
TAGGAACAGCTGTTAAGGGAAGGGGAGGCCGCGCACAGTGATCTGGGCTATTGGATTGAAAGTGAAAAGAATGACACAT

SEQUENCES

```
GGAGGCTGAAGAGGGCCCACCTGATTGAGATGAAAACATGTGAATGGCCAAAGTCTCACACATTGTGGACAGATGGAGT
AGAAGAAAGTGATCTTATCATACCCAAGTCTTTAGCTGGTCCACTCAGCCACCACAACACCAGAGAGGGTTACAGAACCC
AAGTGAAAGGGCCATGGCACAGTGAAGAGCTTGAAATCCGGTTTGAGGAATGTCCAGGCACCAAGGTTTACGTGGAGG
AGACATGCGGAACTAGAGGACCATCTCTGAGATCAACTACTGCAAGTGGAAGGGTCATTGAGGAATGGTGCTGTAGGGA
ATGCACAATGCCCCACTATCGTTTCGAGCAAAAGACGGCTGCTGGTATGGAATGGAGATAAGGCCCAGGAAAGAACCA
GAGAGCAACTTAGTGAGGTCAATGGTGACAGCGGGGTCAACCGATCATATGGACCACTTCTCTCTTGGAGTGCTTGTGAT
TCTACTCATGGTGCAGGAGGGGTTGAAGAAGAGAATGACCACAAAGATCATCATGAGCACATCAATGGCAGTGCTGGTA
GTCATGATCTTGGGAGGATTTTCAATGAGTGACCTGGCCAAGCTTGTGATCCTGATGGGTGCTACTTTCGCAGAAATGAA
CACTGGAGGAGATGTAGCTCACTTGGCATTGGTAGCGGCATTTAAAGTCAGACCAGCCTTGCTGGTCTCCTTCATTTTCAG
AGCCAATTGGACACCCCGTGAGAGCATGCTGCTAGCCCTGGCTTCGTGTCTTCTGCAAACTGCGATCTCTGCTCTTGAAGG
TGACTTGATGGTCCTCATTAATGGATTTGCTTTGGCCTGGTTGGCAATTCGAGCAATGGCCGTGCCACGCACTGACAACAT
CGCTCTACCAATCTTGGCTGCTCTAACACCACTAGCTCGAGGCACACTGCTCGTGGCATGGAGAGCGGGCCTGGCTACTT
GTGGAGGGATCATGCTCCTCTCCCTGAAAGGGAAAGGTAGTGTGAAGAAGAACCTGCCATTTGTCATGGCCCTGGGATT
GACAGCTGTGAGGGTAGTAGACCCTATTAATGTGGTAGGACTACTGTTACTCACAAGGAGTGGGAAGCGGAGCTGGCCC
CCTAGTGAAGTTCTCACAGCCGTTGGCCTGATATGTGCACTGGCCGGAGGGTTTGCCAAGGCAGACATTGAGATGGCTG
GACCCATGGCTGCAGTAGGCTTGCTAATTGTCAGCTATGTGGTTCGGGAAAGAGTGTGGACATGTACATTGAAAGAGCA
GGTGACATCACATGGGAAAAGGACGCGGAAGTCACTGGAAACAGTCCTCGGCTTGACGTGGCACTGGATGAGAGTGGT
GACTTCTCCTTGGTAGAGGAAGATGGTCCACCCATGAGAGAGATCATACTCAAGGTGGTCCTGATGGCCATCTGTGGCAT
GAACCCAATAGCTATACCTTTTGCTGCAGGAGCGTGGTATGTGTATGTGAAGACTGGGAAAGGGAGTGGCGCCCTCTGG
GACGTGCCTGCTCCCAAAGAAGTGAAGAAAGGAGAGACCACAGATGGATCTGCAGAGTGAGTGTACAGAGTGATGACTCGCAGACTGCTA
GGTTCAACACAGGTTGGAGTGGGAGTCATGCAAGAGGGAGTCTTCCACACCATGTGGCACGTTACAAAAGGAGCCGCAC
TGAGGAGCGGTGAGGGAAGACTTGATCCATACTGGGGGGATGTCAAGCAGGACTTGGTGTCATACTGTGGGCCTTGGAA
GTTGGATGCAGCTTGGGATGGACTCAGCGAGGTACAGCTTTTGGCCGTACCTCCCGGAGAGAGGGCCAGAAACATTCAG
ACCCTGCCTGGAATATTCAAGACAAAGGACGGGGACATCGGAGCAGTTGCTCTGGACTACCCTGCAGGGACCTCAGGAT
CTCCGATCCTAGACAAATGTGGAAGAGTGATAGGACTCTATGGCAATGGGGTTGTGATCAAGAATGGAAGCTATGTTAGT
GCTATAACCCAGGGAAAGAGGGAGGAGGAGACTCCGGTTGAATGTTTCGAACCCTCGATGCTGAAGAAGAAGCAGCTA
ACTGTCTTGGATCTGCATCCAGGAGCCGGAAAAACCAGGAGAGTTCTTCCTGAAATAGTCCGTGAAGCCATAAAAAAGAG
ACTCCGGACAGTGATCTTGGCCACCAACTAGGGTTGTCGCTGCTGAGATGGAGGAGGCCTTGAGAGGACTTCCGGTGCGT
TACATGACAACAGCAGTCAACGTCACCCATTCTGGGACAGAAATCGTTGATTTGATGTGCCATGCCACTTTCACTTCACGC
TTACTACAACCCATCAGAGTCCCTAATTACAATCTCAACATCATGGATGAAGCCCACTTCACAGACCCCTCAAGTATAGCTG
CAAGAGGATACATATCAACAAGGGTTGAAATGGGCGAGGCGGCTGCCATTTTTATGACTGCCACACCACCAGGAACCCGT
GATGCGTTTCCTGACTCTAACTCACCAATCATGGACACAGAAGTGGAAGTCCCAGAGAGAGCCTGGAGCTCAGGCTTTGA
TTGGGTGACAGACCATTCTGGGAAAACAGTTTGGTTCGTTCCAAGCGTGAGAAACGGAAATGAAATCGCAGCCTGTCTGA
CAAAGGCTGGAAAGCGGGTCATACAGCTCAGCAGGAAGACTTTTGAGACAGAATTTCAGAAAACAAAAAATCAAGAGTG
GGACTTTGTCATAACAACTGACATCTCAGAGATGGGCGCCAACTTCAAGGCTGACCGGGTCATAGACTCTAGGAGATGCC
TAAAACCAGTCATACTTGATGGTGAGAGAGTCATCTTGGCTGGGCCCATGCCTGTCACGCATGCTAGTGCTGCTCAGAGG
AGAGGACGTATAGGCAGGAACCCTAACAAACCTGGAGATGAGTACATGTATGGAGGTGGGTGTGCAGAGACTGATGAA
GGCCATGCACACTGGCTTGAAGCAAGAATGCTTCTTGACAACATCTACCTCCAGGATGGCCTCATAGCCTCGCTCTATCGG
CCTGAGGCCGATAAGGTAGCCGCCATTGAGGGAGAGTTTAAGCTGAGGACAGAGCAAAGGAAGACCTTCGTGGAACTC
ATGAAGAGAGGAGACCTTCCCGTCTGGCTAGCCTATCAGGTTGCATCTGCCGGAATAACTTACACAGACAGAAGATGGTG
CTTTGATGGCACAACCAACAACACCATAATGGAAGACAGTGTACCAGCAGAGGTTTGGACAAAGTATGGAGAGAAGAGA
GTGCTCAAACCGAGATGGATGGATGCTAGGGTCTGTTCAGACCATGCGGCCCTGAAGTCGTTCAAAGAATTCGCCGCTGG
AAAAAGAGGAGCGGCTTTGGGAGTAATGGAGGCCCTGGGAACACTGCCAGGACACATGACAGAGAGGTTTCAGGAAGC
CATTGACAACCTCGCCGTGCTCATGCGAGCAGAGACTGGAAGCAGGCCTTATAAGGCAGCGGCAGCCCAACTGCCGGAG
ACCCTAGAGACCATTATGCTCTTAGGTTTGCTGGGAACAGTTTCACTGGGGATCTTCTTCGTCTTTGATGCGGAATAAGGGC
ATCGGGAAGATGGGCTTTGGAATGGTAACCCTTGGGGCCAGTGCATGGCTCATGTGGCTTTCGGAAATTGAACCAGCCA
GAATTGCATGTGTCCTCATTGTTGTGTTTTTATTACTGGTGGTGCTCATACCCGAGCCAGAGAAGCAAAGATCTCCCCAAG
ATAACCAGATGGCAATTATCATCATGGTGGCAGTGGGCCTTCTAGGTTTGATAACTGCAAACGAACTTGGATGGCTGGAA
AGAACAAAAAATGACATAGCTCATCTAATGGGAAGGAGAGAAGAAGGAGCAACCATGGATTCTCAATGGACATTGATC
TGCGGCCAGCCTCCGCCTGGGCTATCTATGCCGCATTGACAACTCTCATCACCCCAGCTGTCCAACATGCGGTAACCACTT
CATACAACAACTACTCCTTAATGGCGATGGCCACACAAGCTGGAGTGCTGTTTGGCATGGGCAAAGGGATGCCATTTATG
CATGGGGACCTTGGAGTCCCGCTGCTAATGATGGGTTGCTATTCACAATTAACACCCCTGACTCTGATAGTAGCTATCATT
CTGCTTGTGGCGCACTACATGTACTTGATCCCAGGCCTACAAGCGGCAGCAGGTCTGCCCAGAAAGGACAGCAG
CTGGCATCATGAAGAATCCCGTTGTGGATGGAATAGTGGTAACTGACATTGACACAATGACAATAGACCCCCAGGTGGA
GAAGAAGATGGGACAAGTGTTACTCATAGCAGTAGCCATCTCCAGTGCTGTGCTGCTGCGGACCGCCTGGGGATGGGG
GAGGCTGGAGCTCTGATCACAGCAGCGACCTCCACCTTGTGGGAAGGCTCTCCAAACAAATACTGGAACTCCTCTACAGC
CACCTCACTGTGCAACATCTTCAGAGGAAGCTATCTGGCAGGAGCTTCCCTTATCTATACAGTGACGAGAAACGCTGGCCT
GGTTAAGAGACGTGGAGGTGGGACGGGAGAGACTCTGGGAGAGAAGTGGAAAGCTCGTCTGAATCAGATGTCGGCCCT
GGAGTTCTACTCTTATAAAAAGTCAGGTATCACTGAAGTGTGTAGAGAGGGCTCGCCGTGCCCTCAAGGATGGAGTG
GCCACAGGAGGACATGCCGTATCCCGGGGAAGTGCAAAGATCAGATGGTTGGAGGAGAGAGGATATCTGCAGCCCTAT
GGGAAGGTTGTTGACCTCGGATGTGGCAGAGGGGGCTGGAGCTATTATGCCGCCACCATCCGCAAAGTGCAGGAGGTG
AGAGGATACACAAAGGGAGGTCCCGGTCATGAAGAACCCATGCTGGTGCAAAGCTATGGGTGGAACATAGTTCGTCTCA
AGAGTGGAGTGGACGTCTTCCACATGGCGGCTGAGCCGTGTGACACTCTGCTGTGTGACATAGGTGAGTCATCATCTAGT
CCTGAAGTGGAAGAGACACGAACACTCAGAGTGCTCTCTATGGTGGGGACTGGCTTGAAAAAAGACCAGGGGCCTTCT
GTATAAAGGTGCTGTGCCCATACACCAGCACTATGATGGAAACCATGGAGCGACTGCAACGTAGGCATGGGGAGGATT
AGTCAGAGTGCCATTGTGTCGCAACTCCACACATGAAGATGGTTCCTGGGGCAAAGAGCAACATCATAAAAAGTG
TGTCCACCACAAGTCAGCTCCTCCTGGGACGCATGGATGGCCCCAGGAGGCCAGTGAAATATGAGGAGGATGTGAACCT
CGGCTCGGGTACACGAGCTGTGGCAAGCTGTGCTGAGGCTCCTAACATGAAAATCATCGGCAGGCGCATTGAGAGAATC
CGCAATGAACATGCAGAAACATGGTTTCTTGATGAAAACCACCCATACAGGACATGGGCCTACCATGGGAGCTACGAAGC
CCCCACGCAAGGATCAGCGTCTTCCCTCGTGAACGGGGTTGTTAGACTCCTGTCAAAGCCTTGGGACGTGGTGACTGGAG
TTACAGGAATAGCCATGACTGACACCACACCATACGGCCAACAAAGGGTCTTCAAAGAAAAGTGGACACCAGGGTGCC
AGATCCCCAAGAAGGCACTCGCCAGGTAATGAACATAGTCTCTTCCTGGCTGTGGAAGAGCTGGGGAAACGCAAGCGG
CCACGCGTCTGCACCAAAGAAGAGTTTATCAACAAGGTGCGCAGCAATGCAGCACTGGGAGCAATATTTGAAGAGGAAA
AAGAATGGAAGACGGCTGTGGAAGCTGTGAATGATCCAAGGTTTTGGGCCCTAGTGGATAGGGAGAGAGAACACCACC
TGAGAGGAGAGTGTCACAGCTGTGTGTACAACATGATGGGAAAAAGAGAAAAGAAGCAAGGAGAGTTCGGGAAAGCA
AAAGGTAGCCGCGCCATCTGGTACATGTGGTTGGGAGCCAGATTCTTGGAGTTTGAAGCCCTTGGATTCTTGAACGAGGA
CCATTGGATGGGAAGAGAAAACTCAGGAGGTGGAGTCGAAGGGTTAGGATTGCAAAGACTTGGATACATTCTAGAAGA
```

-continued

SEQUENCES

AATGAATCGGGCACCAGGAGGAAAGATGTACGCAGATGACACTGCTGGCTGGGACACCCGCATTAGTAAGTTTGATCTG
GAGAATGAAGCTCTGATTACCAACCAAATGGAGGAAGGGCACAGAACTCTGGCGTTGGCCGTGATTAAATACACATACC
AAAACAAAGTGGTGAAGGTTCTCAGACCAGCTGAAGGAGGAAAAACAGTTATGGACATCATTTCAAGACAAGACCAGAG
AGGGAGTGGACAAGTTGTCACTTATGCTCTCAACACATTCACCAACTTGGTGGTGCAGCTTATCCGGAACATGGAAGCTG
AGGAAGTGTTAGAGATGCAAGACTTATGGTTGTTGAGGAAGCCAGAGAAAGTGACCAGATGGTTGCAGAGCAATGGAT
GGGATAGACTCAAACGAATGGCGGTCAGTGGAGATGACTGCGTTGTGAAGCCAATCGATGATAGGTTTGCACATGCCCT
CAGGTTCTTGAATGACATGGGAAAAGTTAGGAAAGACACACAGGAGTGGAAACCCTCGACTGGATGGAGCAATTGGGA
AGAAGTCCCGTTCTGCTCCCACCACTTCAACAAGCTGTACCTCAAGGATGGGAGATCCATTGTGGTCCCTTGCCGCCACCA
AGATGAACTGATTGGCCGAGCTCGCGTCTCACCAGGGGCAGGATGGAGCATCCGGGAGACTGCCTGTCTTGCAAAATCA
TATGCGCAGATGTGGCAGCTCCTTTATTTCCACAGAAGAGACCTTCGACTGATGGCTAATGCCATTTGCTCGGCTGTGCCA
GTTGACTGGGTACCAACTGGGAGAACCACCTGGTCAATCCATGGAAAGGGAGAATGGATGACCACTGAGGACATGCTCA
TGGTGTGGAATAGAGTGTGGATTGAGGAGAACGACCATATGGAGGACAAGACTCCTGTAACAAAATGGACAGACATTCC
CTATCTAGGAAAAAGGGAGGACTTATGGTGTGGATCCCTTATAGGGCACAGACCCCGCACCACTTGGGCTGAAAACATCA
AAGACACAGTCAACATGGTGCGCAGGATCATAGGTGATGAAGAAAAGTACATGGACTATCTATCCACCCAAGTCCGCTAC
TTGGGTGAGGAAGGGTCCACACCCGGAGTGTTGTAAGCACCAATTTTAGTGTTGTCAGGCCTGCTAGTCAGCCACAGTTT
GGGGAAAGCTGTGCAGCCTGTAACCCCCCCAGGAGAAGCTGGGAAACCAAGCTCATAGTCAGGCCGAGAACGCCATGG
CACGGAAGAAGCCATGCTGCCTGTGAGCCCCTCAGAGGACACTGAGTCAAAAAACCCCACGCGCTTGGAAGCGCAGGAT
GGGAAAAGAAGGTGGCGACCTTCCCCACCCTTCAATCTGGGGCCTGAACTGGAGACTAGCTGTGAATCTCCAGCAGAGG
GACTAGTGGTTAGAGGAGACCCCCCGGAAAACGCAAAACAGCATATTGACGTGGGAAAGACCAGAGACTCCATGAGTTT
CCACCACGCTGGCCGCCAGGCACAGATCGCCGAACTTCGGCGGCCGGTGTGGGGAAATCCATGGTTTCT

SEQ ID NO: 13
KJ776791.1, Zika virus strain H/PF/2013 polyprotein gene, complete cds
AGTATCAACAGGTTTTATTTTGGATTTGGAAACGAGAGTTTCTGGTCATGAAAAACCCAAAAAAGAAATCCGGAGGATTC
CGGATTGTCAATATGCTAAAACGCGGAGTAGCCCGTGTGAGCCCCTTTGGGGGCTTGAAGAGGCTGCCAGCCGGACTTCT
GCTGGGTCATGGGCCCATCAGGATGGTCTTGGCGATTCTAGCCTTTTTGAGATTCACGGCAATCAAGCCATCACTGGGTCT
CATCAATAGATGGGGTTCAGTGGGGAAAAAAGAGGCTATGGAAATAATAAAGAAGTTCAAGAAAGATCTGGCTGCCATG
CTGAGAATAATCAATGCTAGGAAGGAGAAGAAGAGACGAGGCGCAGATACTAGTGTCGGAATTGTTGGCCTCCTGCTGA
CCACAGCTATGGCAGCGGAGGTCACTAGACGTGGGAGTGCATACTATATGTACTTGGACAGAAACGACGCTGGGGAGGC
CATATCTTTTCCAACCACATTGGGGATGAATAAGTGTTATATACAGATCATGGATCTTGGACACATGTGTGATGCCACCAT
GAGCTATGAATGCCCTATGCTGGATGAGGGGGTGGAACCAGATGACGTCGATTGTTGGTGCAACACGACGTCAACTTGG
GTTGTGTACGGAACCTGCCATCACAAAAAAGGTGAAGCACGGAGATCTAGAAGAGCTGTGACGCTCCCCTCCCATTCCAC
TAGGAAGCTGCAAACGCGGTCGCAAACCTGGTTGGAATCAAGAGAATACACAAAGCACTTGATTAGAGTCGAAAATTGG
ATATTCAGGAACCCTGGCTTCGCGTTAGCAGCAGCTGCCATCGCTTGGCTTTTGGGAAGCTCAACGAGCCAAAAAGTCAT
ATACTTGGTCATGATACTGCTGATTGCCCCGGCATACAGCATCAGGTGCATAGGAGTCAGCAATAGGGACTTTGTGGAAG
GTATGTCAGGTGGGACTTGGGTTGATGTTGTCTTGGAACATGGAGGTTGTGTCACCGTAATGGCACAGGACAAACCGACT
GTCGACATAGAGCTGGTTACAACAACAGTCAGCAACATGGCGGAGGTAAGATCCTACTGCTATGAGGCATCAATATCGG
ACATGGCTTCGGACAGCCGCTGCCCAACACAAGGTGAAGCCTACCTTGACAAGCAATCAGACACTCAATATGTCTGCAAA
AGAACGTTAGTGGACAGAGGCTGGGGAAATGGATGTGGACTTTTTGGCAAAGGGAGCCTGGTGACATGCGCTAAGTTTG
CATGCTCCAAGAAAATGACCGGGAAGAGCATCCAGCCAGAGAATCTGGAGTACCGGATAATGCTGTCAGTTCATGGCTCC
CAGCACAGTGGGATGATCGTTAATGACACAGGACATGAAACTGATGAGAATAGAGCGAAGGTTGAGATAACGCCCAATT
CACCAAGAGCCGAAGCCACCCTGGGGGGTTTTGGAAGCCTAGGACTTGATTGTGAACCGAGGACAGGCCTTGACTTTTCA
GATTTGTATTACTTGACTATGAATAACAAGCACTGGTTGGTTCACAAGGAGTGGTTCCACGACATTCCATTACCTTGGCAC
GCTGGGGCAGACACCGGAACTCCACACTGGAACAACAAAGAAGCACTGGTAGAGTTCAAGGACGCACATGCCAAAAGG
CAAACTGTCGTGGTTCTAGGGAGTCAAGAAGGAGCAGTTCACACGGCCCTTGCTGGAGCTCTGGAGGCTGAGATGGATG
GTGCAAAGGGAAGGCTGTCCTCTGGCCACTTGAAATGTCGCCTGAAAATGGATAAACTTAGATTGAAGGGCGTGTCATAC
TCCTTGTGTACCGCAGCGTTCACATTCACCAAGATCCCGGCTGAAACACTGCACGGGACAGTCACAGTGGAGGTACAGTA
CGCAGGGACAGATGGACCTTGCAAGGTTCCAGCTCAGATGGCGGTGGACATGCAAACTCTGACCCCAGTTGGGAGGTTG
ATAACCGCTAACCCCGTAATCACTGAAAGCACTGAGAACTCTAAGATGATGCTGGAACTTGATCCACCATTTGGGGACTCT
TACATTGTCATAGGAGTCGGGGAGAAGAAGATCACCCACCACTGGCACAGGAGTGGCAGCACCATTGGAAAAGCATTTG
AAGCCACTGTGAGAGGTGCCAAGAGAATGGCAGTCTTGGGAGACACAGCCTGGGACTTTGGATCAGTTGGAGGCGCTCT
CAACTCATTGGGCAAGGGCATCCATCAAATTTTTGGAGCAGCTTTCAAATCATTGTTTGGAGGAATGTCCTGGTTCTCACA
AATTCTCATTGGAACGTTGCTGATGTGGTTGGGTCTGAACACAAAGAATGGATCTATTTCCCTTATGTGCTTGGCCTTAGG
GGGAGTGTTGATCTTCTTATCCACAGCTGTCTCTGCTGATGTGGGGTGCTCGGTGGACTTCTCAAAGAAGGAGACGAGAT
GCGGTACAGGGGTGTTCGTCTATAACGACGTTGAAGCCTGGAGGGACAGGTACAAGTACCATCCTGACTCCCCCCGTAGA
TTGGCAGCAGCAGTCAAGCAAGCCTGGGAAGATGGTATCTGTGGGATCTCCTCTGTTTCAAGAATGGAAAACATCATGTG
GAGATCAGTAGAAGGGGAGCTCAACGCAATCCTGGAAGAGAATGGAGTTCAACTGACGGTCGTTGTGGGATCTGTAAAA
AACCCCATGTGGAGAGGTCCACAGAGATTGCCCGTGCCTGTGAACGAGCTGCCCCACGGCTGGAAGGCTTGGGGGAAAT
CGTACTTCGTCAGAGCAGCAAAGACAAATAACAGCTTTGTCGTGGATGGTGACACACTGAAGGAATGCCCACTCAAACAT
AGAGCATGGAACAGCTTTCTTGTGGAGGATCATGGGTTCGGGGTATTTCACACTAGTGTCTGGCTCAAGGTTAGAGAAGA
TTATTCATTAGAGTGTGATCCAGCCGTTATTGGAACAGCTGTTAAGGGAAAGGAGGCTGTACACAGTGATCTAGGCTACT
GGATTGAGAGTGAGAAGAATGACACATGGAGGCTGAAGAGGGCCCATCTGATCGAGATGAAAACATGTGAATGGCCAA
AGTCCCACACATTGTGGACAGATGGAATAGAAGAGAGTGATCTGATCATACCCAAGTCTTTAGCTGGGCCACTCAGCCAT
CACAATACCAGAGAGGGCTACAGGACCCAAATGAAAGGGCCATGGCACAGTGAAGAGCTTGAAATTCGGTTTGAGGAAT
GCCCAGGCACTAAGGTCCACGTGGAGGAAACATGTGGAACAAGAGGACCATCTCTGAGATCAACCACTGCAAGCGGAAG
GGTGATCGAGGAATGGTGCTGCAGGGAGTGCACAATGCCCCCACTGTCGTTCCGGGCTAAAGATGGCTGTTGGTATGGA
ATGGAGATAAGGCCCAGGAAAGAACCAGAAAGTAACTTAGTAAGGTCAATGGTGACTGCAGGATCAACTGATCACATGG
ATCACTTCTCCCTTGGAGTGCTTGTGATTCTGCTCATGGTGCAGGAAGGGCTGAAGAAGAGAATGACCACAAAGATCATC
ATAAGCACATCGATGGCAGTGCTGGTAGCTATGATCCTGGGAGGATTTTCAATGAGTGACCTGGCTAAGCTTGCAATTTT
GATGGGTGCCACCTTCGCGGAAATGAACACTGGAGGAGATGTAGCTCATCTGGCGCTGATAGCGGCATTCAAAGTCAGA
CCAGCGTTGCTGGTATCTTTCATCTTCAGAGCTAATTGGACACCCCGTGAAAGCATGCTGCTGGCCTTGGCCTCGTGTCTTT
TGCAAACTGCGATCTCCGCCTTGGAAGGCGACCTGATGGTTCTCATCAATGGTTTTGCTTTGGCCTGGTTGGCAATACGAG
CGATGGTTGTTCCACGCACTGATAACATCACCTTGGCAATCCTGGCTGCTCTGACACCACTGGCCCGGGGCACACTGCTTG
TGGCGTGGAGAGCAGGCCTTGCTACTTGCGGGGGGTTTATGCTCCTCTCTCTGAAGGGAAAAGGCAGTGTGAAGAAGAA
CTTACCATTTGTCATGGCCCTGGGACTAACCGCTGTGAGGCTGGTCGACCCCATCAACGTGGTGGGACTGCTGTTGCTCAC
AAGGAGTGGGAAGCGGAGCTGGCCCCCTAGCGAAGTACTCACAGCTGTTGGCCTGATATGCGCATTGGCTGGAGGGTTC
GCCAAGGCAGATATAGAGATGGCTGGGCCCATGGCCGCGGTCGGTCTGCTAATTGTCAGTTACGTGGTCTCAGGAAAGA

| SEQUENCES |
|---|
| GTGTGGACATGTACATTGAAAGAGCAGGTGACATCACATGGGAAAAAGATGCGGAAGTCACTGGAAACAGTCCCCGGCT |
| CGATGTGGCGCTAGATGAGAGTGGTGATTTCTCCCTGGTGGAGGATGACGGTCCCCCCATGAGAGAGATCATACTCAAG |
| GTGGTCCTGATGACCATCTGTGGCATGAACCCAATAGCCATCCCTTTGCAGCTGGAGCGTGGTACGTATACGTGAAGAC |
| TGGAAAAAGGAGTGGTGCTCTATGGGATGTGCCTGCTCCCAAGGAAGTAAAAAAGGGGGAGACCACAGATGGAGTGTA |
| CAGAGTAATGACTCGTAGACTGCTAGGTTCAACACAAGTTGGAGTGGGAGTTATGCAAGAGGGGGTCTTTCACACTATGT |
| GGCACGTCACAAAAGGATCCGCGCTGAGAAGCGGTGAAGGGAGACTTGATCCATACTGGGGAGATGTCAAGCAGGATC |
| TGGTGTCATACTGTGGTCCATGGAAGCTAGATGCCGCCTGGGACGGGCACAGCGAGGTGCAGCTCTTGGCCGTGCCCCC |
| CGGAGAGAGAGCGAGGAACATCCAGACTCTGCCCGGAATATTTAAGACAAAGGATGGGGACATTGGAGCGGTTGCGCT |
| GGATTACCCAGCAGGAACTTCAGGATCTCCAATCCTAGACAAGTGTGGGAGAGTGATAGGACTTTATGGCAATGGGGTC |
| GTGATCAAAAATGGGAGTTATGTTAGTGCCATCACCCAAGGGAGGAGGGAGGAAGAGACTCCTGTTGAGTGCTTCGAGC |
| CTTCGATGCTGAAGAAGAAGCAGCTAACTGTCTTAGACTTGCATCCTGGAGCTGGGAAAACCAGGAGAGTTCTTCCTGAA |
| ATAGTCCGTGAAGCCATAAAAACAAGACTCCGTACTGTGATCTTAGCTCCAACCAGGGTTGTCGCTGCTGAAATGGAGGA |
| AGCCCTTAGAGGGCTTCCAGTGCGTTATATGACAACAGCAGTCAATGTCACCCACTCTGGAACAGAAATCGTCGACTTAAT |
| GTGCCATGCCACCTTCACTTCACGTCTACTACAGCCAATCAGAGTCCCCAACTATAATCTGTATATTATGGATGAGGCCCAC |
| TTCACAGATCCCTCAAGTATAGCAGCAAGAGGATACATTTCAACAAGGGTTGAGATGGGCGAGGCGGCTGCCATCTTCAT |
| GACCGCCACGCCACCAGGAACCCGTGACGCATTTCCGGACTCCAACTCACCAATTATGGACACCGAAGTGGAAGTCCCAG |
| AGAGAGCCTGGAGCTCAGGCTTTGATTGGGTGACGGATCATTCTGGAAAAACAGTTTGGTTTGTTCCAAGCGTGAGGAAC |
| GGCAATGAGATCGCAGCTTGTCTGACAAAGGCTGGAAAACGGGTCATACAGCTCAGCAGAAAGACTTTTGAGACAGAGT |
| TCCAGAAAACAAAACATCAAGAGTGGGACTTTGTCGTGACAACTGACATTTCAGAGATGGGCGCCAACTTTAAAGCTGAC |
| CGTGTCATAGATTCCAGGAGATGCCTAAAGCCGGTCATACTTGATGGCGAGAGAGTCATTCTGGCTGGACCCATGCCTGT |
| CACACATGCCAGCGCTGCCCAGAGGAGGGGGCGCATAGGCAGGAATCCCAACAAACCTGGAGATGAGTATCTGTATGGA |
| GGTGGGTGCGCAGAGACTGACGAAGACCATGCACACTGGCTTGAAGCAAGAATGCTCCTTGACAATATTTACCTCCAAGA |
| TGGCCTCATAGCCTCGCTCTATCGACCTGAGGCCGACAAAGTAGCAGCCATTGAGGGAGAGTTCAAGCTTAGGACGGAG |
| CAAAGGAAGACCTTTGTGGAACTCATGAAAAGAGGAGATCTTCCTGTTTGGCTGGCCTATCAGGTTGCATCTGCCGGAAT |
| AACCTACACAGATAGAAGATGGTGCTTTGATGGCACGACCAACACACCATAATGGAAGACAGTGTGCCGGCAGAGGTG |
| TGGACCAGACACGGAGAGAAAAGAGTGCTCAAACCGAGGTGGATGGACGCCAGAGTTTGTTCAGATCATGCGGCCCTGA |
| AGTCATTCAAGGAGTTTGCCGCTGGGAAAAGAGGAGCGGCTTTTGGAGTGATGGAAGCCCTGGGAACACTGCCAGGACA |
| CATGACAGAGAGATTCCAGGAAGCCATTGACAACCTCGCTGTGCCTCATGCGGGCAGAGACTGGAAGCAGGCCTTACAAA |
| GCCGCGGCGGCCCAATTGCCGGAGACCCTAGAGACCATTATGCTTTTGGGGTTGCTGGGAACAGTCTCGCTGGGAATCTT |
| TTTCGTCTTGATGAGGAACAAGGGCATAGGGAAGATGGGCTTTGGAATGGTGACTCTTGGGCCAGCGCATGGCTCATG |
| TGGCTCTCGGAAATTGAGCCAGCCAGAATTGCATGTGTCCTCATTGTTGTGTTCCTATTGCTGGTGGTGCTCATACCTGAG |
| CCAGAAAAGCAAAGATCTCCCCAGGACAACCAAATGGCAATCATCATCATGTGGCAGTAGGTCTTCTGGGCTTGATTAC |
| CGCCAATGAACTCGGATGGTTGGAGAGAACAAAGAGTGACCTAAGCCATCTAATGGGAAGGAGAGAGGAGGGGGCAAC |
| CATAGGATTCTCAATGGACATTGACCTGCGGCCAGCCTCAGCTTGGGCCATCTATGCTGCCTTGACAACTTTCATTACCCCA |
| GCCGTCCAACATGCAGTGACCACTTCATACAACAACTACTCCTTAATGGCGATGGCCACGCAAGCTGGAGTGTTGTTTGGT |
| ATGGGCAAAGGGATGCCATTCTACGCATGGGACTTTGGAGTCCCGCTGCTAATGATAGGTTGCTACTCACAATTAACACC |
| CCTGACCCTAATAGTGGCCATCATTTTGCTCGTGGCGCACTACATGTACTTGATCCCAGGGCTGCAGGCAGCAGCTGCGC |
| GTGCTGCCCAGAAGAGAACGGCAGCTGGCATCATGAAGAACCCTGTTGTGGATGGAATAGTGGTGACTGACATTGACAC |
| AATGACAATTGACCCCCAAGTGGAGAAAAAGATGGGACAGGTGCTACTCATAGCAGTAGCCGTCTCCAGCGCCATACTGT |
| CGCGGACCGCCTGGGGTGGGGGAGGCTGGGGCCCTGATCACAGCGGCAACTTCCACTTTGTGGGAAGGCTCTCCGA |
| ACAAGTACTGGAACTCCTCTACAGCCACTTCACTGTGTAACATTTTTAGGGGAAGTTACTTGGCTGGAGCTTCTCTAATCTA |
| CACAGTAACAAGAAACGCTGGCTTGGTCAAGAGACGTGGGGGTGGAACAGGAGAGACCCTGGGAGAGAAATGGAAGG |
| CCCGCTTGAACCAGATGTCGGCCCTGGAGTTCTACTCCTACAAAAAGTCAGGCATCACCGAGGTGTGCAGAGAAGAGGCC |
| CGCCGCGCCCTCAAGGACGGTGTGGCAACGGGAGGCCATGCTGTGTCCCGAGGAAGTGCAAAGCTGAGATGGTTGGTG |
| GAGCGGGGATACCTGCAGCCCTATGGAAAGGTCATTGATCTTGGATGTGGCAGAGGGGGCTGGAGTTACTACGCCGCCA |
| CCATCCGCAAAGTTCAAGAAGTGAAAGGATACACAAAAGGAGGCCCTGGTCATGAAGAACCCATGTTGGTGCAAAGCTA |
| TGGGTGGAACATAGTCCGTCTTAAGAGTGGGGTGGACGTCTTTCATATGGCGGCTGAGCCGTGTGACACGTTGCTGTGTG |
| ACATAGGTGAGTCATCATCTAGTCCTGAAGTGGAAGAAGCACGGACGCTCAGAGTCCTCTCCATGGTGGGGATTGGCTT |
| GAAAAAAGACCAGGAGCCTTTTGTATAAAAGTGTTGTGCCCATACACGACTATGATGGAAACCCTGGAGCGACTGCA |
| GCGTAGGTATGGGGGAGGACTGGTCAGAGTGCCACTCTCCCGCAACTCTACACATGAGATGTACTGGGTCTCTGGAGCC |
| AAAAGCAACACCATAAAAGTGTGTCCACCACGAGCCAGCTCCTCTTGGGGCGCATGGACGGGCCCAGGAGGCCAGTGA |
| AATATGAGGAGGATGTGAATCTCGGCTCTGGCACGCGGGCTGTGGTAAGCTGCGCTGAAGCTCCCAACATGAAGATCAT |
| TGGTAACCGCATTGAAAGGATCCGCAGTGAGCACGCGGAAACGTGGTTCTTTGACGAGAACCACCCATATAGGACATGG |
| GCTTACCATGGAAGCTATGAGGCCCCACACAAGGGTCAGCGTCCTCTCTAATAAACGGGGTTGTCAGGCTCCTGTCAAA |
| ACCCTGGGATGTGGTGACTGGAGTCACAGGAATAGCCATGACCGACACCACACCGTATGGTCAGCAAAGAGTTTTCAAG |
| GAAAAAGTGGACACTAGGGTGCCAGACCCCCAAGAAGGCACTCGTCAGGTTATGAGCATGGTCTCTTCCTGGTTGTGGA |
| AAGAGCTAGGCAAACACAAACGGCCACAGTTCTGTACAAAGAAGAGTTCATCAACAAGGTTCGTAGCAATGCAGCAU |
| AGGGGCAATATTTGAAGAGGAAAAAGAGTGGAAGACTGCAGTGGAAGCTGTGAACGATCCAAGGTTCTGGGCTCTAGT |
| GGACAAGGAAAGAGCACCACCTGAGAGGAGAGTGCCAGAGTTGTGTACAACATGATGGGAAAAAGAGAAAGA |
| AACAAGGGGAATTTGGAAAGGCCAAGGGCAGCCGCGCCATCTGGTATATGTGGCTAGGGCTAGATTTCTAGAGTTCGA |
| AGCCCTTGGATTCTTGAACGAGGATCACTGGATGGGGAGAGGAACTCAGGAGGTGGTGTTGAAGGGCTGGGATTACA |
| AAGACTCGGATATGTCCTAGAAGAGATGAGTCGCATACCAGGAGGAAGGATGTATGCAGATGACACTGCTGGCTGGGAC |
| ACCCGCATCAGCAGGTTTGATCTGGAGAATGAAGCTCTAATCACCAACCAAATGGAGAAAGGGCACAGGGCCTTGGCAT |
| TGGCCATAATCAAGTACACATACCAAAACAAAGTGGTAAAGGTCCTTAGACCAGCTGAAAAAGGGAAGACAGTTATGGA |
| CATTATTTCGAGACAAGACCAAAGGGGGAGCGGACAAGTTGTCACTTACGCTCTTAACACATTTACCAACCTAGTGGTGC |
| AACTCATTCGGAATATGGAGGCTGAGGAAGTTCTAGAGATGCAAGACTTGTGGCTGCTGCGCAGGGTCAGAGAAAGTGAC |
| CAACTGGTTGCAGAGCAACGGATGGGATAGGCTCAAACGAATGGCAGTCAGTGGAGATGATTGCGTTGTGAAGCCAATT |
| GATGATAGGTTTGCACATGCCCTCAGGTTCTTGAATGATATGGGAAAAGTTAGGAAGGACACACAAGAGTGGAAACCCT |
| CAACTGGATGGGACAACTGGGAAGAAGTTCCGTTTTGCTCCCACCACTTCAACAAGCTCCATCTCAAGGACGGGAGGTCC |
| ATTGTGGTTCCCTGCCGCCACCAAGATGAACTGATTGGCCGGGCCCGCGTCTCTCCAGGGCGGGATGGAGCATCCGGG |
| AGACTGCTTAGCAAAATCATATGCGCAAATGTGGCAGCTCCTTTATTCCACAGAAGGGACCTCCGACTGATGGCCA |
| ATGCCATTTGTTCATCTGTCCAGTTGACTGGGTTCCAACTGGGAGAACTACCTGGTCAATCCATGGAAGGGAGAATGG |
| ATGACCACTGAAGACATGCTTGTGGTGTGGAACAGAGTGTGGATTGAGGAGAACGACCACATGGAAGACAAGACCCCA |
| GTTACGAAATGGACAGACATTCCCTATTTGGGAAAAAGGGAAGACTTGTGGTGTGGATCTCTCATAGGGCACAGACCGC |
| GCACCACCTGGGCTGAGAACATTAAAAACACAGTCAACATGGTGCGCAGGATCATAGGTGATGAAGAAAGTACATGGA |
| CTACCTATCCACCCAAGTTCGCTACTTGGGTGAAGAAGGGTCTACACCTGGAGTGCTGTAAGCACCAATCTTAGTGTTGTC |
| AGGCCTGCTAGTCAGCCACAGCTTGGGGAAAGCTGTGCAGCCTGTGACCCCCCAGGAGAAGCTGGGAAACCAAGCCTA |

| SEQUENCES |
|---|
| TAGTCAGGCCGAGAACGCCATGGCACGGAAGAAGCCATGCTGCCTGTGAGCCCCTCAGAGGACACTGAGTCAAAAAACC<br>CCACGCGCTTGGAGGCGCAGGATGGGAAAAGAAGGTGGCGACCTTCCCCACCCTTCAATCTGGGGCCTGAACTGGAGAT<br>CAGCTGTGGATCTCCAGAAGAGGGACTAGTGGTTAGAGGAG |

In some embodiments, the Zika virus has a RNA genome corresponding to the DNA sequence provided by the nucleic acid sequence of any one of SEQ ID NOs: 2-13 or 78. In some embodiments, the Zika virus has a variant genome that is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-13 or 78.

Provided below are amino acid sequences of the E-proteins of Zika strains that may be used in the methods, compositions, and/or vaccines described herein.

```
isol-ARB15076.AHF49784.1.Central_African_Republic/291-788 Flavivirus envelope glycoprotein E.
                                                                             SEQ ID NO: 14
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDENRAKVEVT PNSPRAEATLGGFGSLGLDCEPRTGLDFSDLYYLTMNNKHWLVHKEWFHDIPLPWHAGADTGTPHWNNKEALVEFKDAHAK RQTVVVLGSQEGAVHTALAGALEAEMDGAKGRLFSGHLKCRLKMDKLRLKGVSYSLCTAAFTFTKVPAETLHGTVTVEVQYAG TDGPCKVPAQMAVDMQTLTPVGRLITANPVITESTENSKMMLELDPPFGDSYIVIGVGDKKITHHWHRSGSTIGKAFEATVRG AKRMAVLGDTAWDFGSVGGVFNSLGKGIHQIFGAAFKSLFGGMSWFSQILIGTLLVWLGLNTKNGSISLTCLALGGVMIFLSTA

VSA isol-IbH_30656.AEN75265.1.Nigeria/291-788 Flavivirus envelope glycoprotein E.
                                                                             SEQ ID NO: 15
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDENRAKVEVT PNSPRAEATLGGFGSLGLDCEPRTGLDFSDLYYLTMNNKHWLVHKEWFHDIPLPWHSGADTETPHWNNKEALVEFKDAHAK RQTVVVLGSQEGAVHTALAGALEAEMDGAKGRLSSGHLKCRLKMDKLRLKGVSYSLCTAAFTFTKVPAETLHGTVTVEVQYAG RDGPCKVPAQMAVDMQTLTPVGRLITANPVITESTENSKMMLELDPPFGDSYIVIGVGDKKITHHWHRSGSIIGKAFEATVRG AKRMAVLGDTAWDFGSVGGVFNSLGKGIHQIFGAAFKSLFGGMSWFSQILIGTLLVWLGLNTKNGSISLTCLALGGVMIFLSTA

VSA

ArB1362.AHL43500.1.1291-794 Flavivirus envelope glycoprotein E.
                                                                             SEQ ID NO: 16
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDXXXXXXXNR AEVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLFSGHLKCRLKMDKLRLKGVSYSLCTAAFTFTKVPAETLHGTVTV EVQYAGTDGPCKVPAQMAVDMQTLTPVGRLITANPVITESTENSKMMLELDPPFGDSYIVIGVGDKKITHHWHRSGSTIGKAF EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

ArD128000.AHL43502.1.-1291-794 Flavivirus envelope glycoprotein E.
                                                                             SEQ ID NO: 17
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMXXXXXGHETDEN RAKVEVTPNSPRAEATLGGFGSLGLDCEPRTGLDFSDLYYLTMNNKHRLVRKEWFHDIPLPWHAGADTGTPHWNNKEALVEF KDAHAKRQTVVVLGSQEGAVHTALAGALEAEMDGAKGRLFSGHLKCRLKMDKLRLKGVSYSLCTAAFTFTKVPAETLHGTVTV EVQYAGTDGPCKVPAQMAVDMQTLTPVGRLITANPVITESTENSKMMLELDPPFGDSYIVIGVGDKKITHHWLKKGSSIGKAF EATVRGAKRMAVLGDTAWDFGSVGGVFNSLGKGVHQIFGAAFKSLFGGMSWFSQILIGTLLVWLGLNTKNGSISLTCLALGG

VMIFLSTAVSA
```

ArD158095.AHL43505.1.1291-794 Flavivirus envelope glycoprotein E.

SEQ ID NO: 18

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIVNDIGHETDENR

AKVEVTPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLFSGHLKCRLKMDKLRLKGVSYSLCTAAFTFTKVPAETLHGTVTV

EVQYAGTDGPCKVPAQMAVDMQTLTPVGRLITANPVITESTENSKMMLELDPPFGDSYIVIGVGDKKITHHWHRSGSTIGKAF

EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

ArD158084.AHL43504.1.-1291-794 Flavivirus envelope glycoprotein E.

SEQ ID NO: 19

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIVNDIGHETDENR

AKVEVTPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLFSGHLKCRLKMDKLRLKGVSYSLCTAAFTFTKVPAETLHGTVTV

EVQYAGTDGPCKVPAQMAVDMQTLTPVGRLITANPVITESTENSKMMLELDPPFGDSYIVIGVGDKKITHHWHRSGSTIGKAF

EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA isol-ARB13565.AHF49783.1.Central_African_Republic/291-794 Flavivirus envelope glycoprotein E.

SEQ ID NO: 20

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIVNDIGHETDENR

AKVEVTPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLFSGHLKCRLKMDKLRLKGVSYSLCTAAFTFTKVPAETLHGTVTV

EVQYAGTDGPCKVPAQMAVDMQTLTPVGRLITANPVITESTENSKMMLELDPPFGDSYIVIGVGDKKITHHWHRSGSTIGKAF

EATVRGAKRMAVLGDTAWDFGSVGGVFNSLGKGVHQIFGAAFKSLFGGMSWFSQILIGTLLVWLGLNTKNGSISLTCLALGG

VMIFLSTAVSA isol-ARB7701.AHF49785.1.Central_African_Republic/291-794 Flavivirus envelope glycoprotein E.

SEQ ID NO: 21

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIVNDIGHETDENR

AKVEVTPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLFSGHLKCRLKMDKLRLKGVSYSLCTAAFTFTKVPAETLHGTVTV

EVQYAGTDGPCKVPAQMAVDMQTLTPVGRLITANPVITESTENSKMMLELDPPFGDSYIVIGVGDKKITHHWHRSGSTIGKAF

EATVRGAKRMAVLGDTAWDFGSVGGVFNSLGKGVHQIFGAAFKSLFGGMSWFSQILIGTLLVWLGLNTKNGSISLTCLALGG

VMIFLSTAVSA isol-ArD_41519.AEN75266.1.Senegal/291-794 Flavivirus envelope glycoprotein E.

SEQ ID NO: 22

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIVNDTGHETDEN

RAKVEVTPNSPRAEATLGGFGSLGLDCEPRTGLDFSDLYYLTMNNKHWLVHKEWFHDIPLPWHAGADTGTPHWNNKEALVE

FKDAHAKRQTVVVLGSQEGAVHTALAGALEAEMDGAKGRLFSGHLKCRLKMDKLRLKGVSYSLCTAAFTFTKVPAETLHGTVT

VEVQYAGTDGPCKVPAQMAVDMQTLTPVGRLITANPVITESTENSKMMLELDPPFGDSYIVIGVGDKKITHHWHRSGSTIGKA

FEATVRGAKRMAVLGDTAWDFGSVGGVFNSLGKGIHQIFGAAFKSLFGGMSWFSQILIGTLLVWLGLNTKNGSISLTCLALGG

VMIFLSTAVSA

-continued

MR766-NIID.BAP47441.1.Uganda/291-794 Flavivirus envelope glycoprotein E.

SEQ ID NO: 23

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMTVNDIGYETDENR

AKVEVTPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGKLFSGHLKCRLKMDKLRLKGVSYSLCTAAFTFTKVPAETLHGTVTV

EVQYAGTDGPCKIPVQMAVDMQTLTPVGRLITANPVITESTENSKMMLELDPPFGDSYIVIGVGDKKITHHWHRSGSTIGKAF

EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

LC002520.1/326-829 Zika virus genomic RNA, strain: MR766-NIID, Uganda, Flavivirus envelope glycoprotein E.

SEQ ID NO: 24

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMTVNDIGYETDENR

AKVEVTPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGKLFSGHLKCRLKMDKLRLKGVSYSLCTAAFTFTKVPAETLHGTVTV

EVQYAGTDGPCKIPVQMAVDMQTLTPVGRLITANPVITESTENSKMMLELDPPFGDSYIVIGVGDKKITHHWHRSGSTIGKAF

EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA isol-MR_766.AEN75263.1.Uganda/291-794 Flavivirus envelope glycoprotein E.

SEQ ID NO: 25

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIVNDTGYETDENR

AKVEVTPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGKLFSGHLKCRLKMDKLRLKGVSYSLCTAAFTFTKVPAETLHGTVTV

EVQYAGTDGPCKIPVQMAVDMQTLTPVGRLITANPVITESTENSKMMLELDPPFGDSYIVIGVGDKKITHHWHRSGSTIGKAF

EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

ArD7117.AHL43501.1.1291-794 Flavivirus envelope glycoprotein E.

SEQ ID NO: 26

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIVNDIGHETDENR

AKVEVTPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLFSGHLKCRLKMDKLRLKGVSYSLCTAVCTAAKVPAETLHGTVT

VEVQYAGTDGPCKVPAQMAVDMQTLTPVGRLITANPVITESTENSKMMLELDPPFGDSYIVIGVGDKKITHHWHRSGSTIGKA

FEATVRGAKRMAVLGDTAWDFGSVGGVFNSLGKGIHQIFGAAFKSLFGGMSWFSQILIGTLLVWLGLNTKNGSISLTCLALGG

VMIFLSTAVSA

AY632535.2/326-825 NC_012532.1 Zika virus strain MR 766, Uganda, Flavivirus envelope glycoprotein E.

SEQ ID NO: 27

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIGYETDEDRAKVE

VTPNSPRAEATLGGFGSLGLDCEPRTGLDFSDLYYLTMNNKHWLVHKEWFHDIPLPWHAGADTGTPHWNNKEALVEFKDAH

AKRQTVVVLGSQEGAVHTALAGALEAEMDGAKGRLFSGHLKCRLKMDKLRLKGVSYSLCTAAFTFTKVPAETLHGTVTVEVQY

AGTDGPCKIPVQMAVDMQTLTPVGRLITANPVITESTENSKMMLELDPPFGDSYIVIGVGDKKITHHWHRSGSTIGKAFEATV

RGAKRMAVLGDTAWDFGSVGGVFNSLGKGIHQIFGAAFKSLFGGMSWFSQILIGTLLVWLGLNTKNGSISLTCLALGGVMIFL

STAVSA

MR_766.AAV34151.1.Uganda/291-790 Flavivirus envelope glycoprotein E. |Q32ZE1|Q32ZE1_9FL

SEQ ID NO: 28

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIGYETDEDRAKVE

VTPNSPRAEATLGGFGSLGLDCEPRTGLDFSDLYYLTMNNKHWLVHKEWFHDIPLPWHAGADTGTPHWNNKEALVEFKDAH

AKRQTVVVLGSQEGAVHTALAGALEAEMDGAKGRLFSGHLKCRLKMDKLRLKGVSYSLCTAAFTFTKVPAETLHGTVTVEVQY

AGTDGPCKIPVQMAVDMQTLTPVGRLITANPVITESTENSKMMLELDPPFGDSYIVIGVGDKKITHHWHRSGSTIGKAFEATV

RGAKRMAVLGDTAWDFGSVGGVFNSLGKGIHQIFGAAFKSLFGGMSWFSQILIGTLLVWLGLNTKNGSISLTCLALGGVMIFL

STAVSA

MR_766.YP_009227198.1.Uganda/1-500 envelope protein E [Zika virus]

SEQ ID NO: 29

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIGYETDEDRAKVE

VTPNSPRAEATLGGFGSLGLDCEPRTGLDFSDLYYLTMNNKHWLVHKEWFHDIPLPWHAGADTGTPHWNNKEALVEFKDAH

AKRQTVVVLGSQEGAVHTALAGALEAEMDGAKGRLFSGHLKCRLKMDKLRLKGVSYSLCTAAFTFTKVPAETLHGTVTVEVQY

AGTDGPCKIPVQMAVDMQTLTPVGRLITANPVITESTENSKMMLELDPPFGDSYIVIGVGDKKITHHWHRSGSTIGKAFEATV

RGAKRMAVLGDTAWDFGSVGGVFNSLGKGIHQIFGAAFKSLFGGMSWFSQILIGTLLVWLGLNTKNGSISLTCLALGGVMIFL

STAVSA

KU681081.3/308-811 Zika virus isolate Zika virus/*H.sapiens*-tc/THA/2014/SV0127-14, Thailand,
Flavivirus envelope glycoprotein E.

SEQ ID NO: 30

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHTGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITEGTENSKMMLELDPPFGDSYIVIGVGEKKITHHWHRSGSTIGKAF

EATVRGAKRMAVLGDTAWDFGSVGGVLNSLGKGIHQIFGAAFKSLFGGMSWFSQILIGTLLMWLGLNTKNGSISLMCLALGG

VLIFLSTAVSA isol-Zika_virus%*H.sapiens*-tc%THA%2014%SV0127-_14.AMD61710.1.Thailand/291-794 Flavivirus
envelope glycoprotein E.

SEQ ID NO: 31

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHTGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITEGTENSKMMLELDPPFGDSYIVIGVGEKKITHHWHRSGSTIGKAF

EATVRGAKRMAVLGDTAWDFGSVGGVLNSLGKGIHQIFGAAFKSLFGGMSWFSQILIGTLLMWLGLNTKNGSISLMCLALGG

VLIFLSTAVSA

CK-ISL_2014.AIC06934.1.Cook_Islands/1-504 Flavivirus envelope glycoprotein E. (Fragment)
OS = Zika virus GN = E PE = 4 SV = 1

SEQ ID NO: 32

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

-continued

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

Natal_RGN.AMB18850.1.Brazik_Rio_Grande_do_Norte,_Natal/291-794 Flavivirus envelope
glycoprotein E.
SEQ ID NO: 33

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA isol-Si323.AMC37200.1.Colombia/1-504 Flavivirus envelope glycoprotein E.
SEQ ID NO: 34

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

KU707826.1/317-820 Zika virus isolate SSABR1, Brazil, Flavivirus envelope glycoprotein E.
SEQ ID NO: 35

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

KU509998.1/326-829 Zika virus strain Haiti/1225/2014, Haiti, Flavivirus envelope
glycoprotein E.
SEQ ID NO: 36

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA isol-GDZ16001.AML82110.1.China/291-794 Flavivirus envelope glycoprotein E.
SEQ ID NO: 37

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

BeH819015.AMA12085.1.Brazil/291-794 Flavivirus envelope glycoprotein E.
SEQ ID NO: 38

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

MRS_OPY_Martinique_PaRi_2015.AMC33116.1.Martinique/291-794 Flavivirus envelope glycoprotein E.
SEQ ID NO: 39

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

KU501215.1/308-811 Zika virus strain PRVABC59, Puerto Rico, Flavivirus envelope glycoprotein E.
SEQ ID NO: 40

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

Haiti%1225%2014.AMB37295.1.Haiti/291-794 Flavivirus envelope glycoprotein E.
SEQ ID NO: 41

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

KU527068.1/308-811 Zika virus strain Natal RGN, Brazil: Rio Grande do Norte, Natal, Flavivirus envelope glycoprotein E.
SEQ ID NO: 42

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

-continued

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA isol-Z1106027.ALX35662.1.Suriname/5-508 Flavivirus envelope glycoprotein E.
SEQ ID NO: 43

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA isol-FLR.AMM39804.1.Colombia:_Barranquilla/291-794 Flavivirus envelope glycoprotein E.
SEQ ID NO: 44

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

PLCal_ZV_isol-From_Vero_E6_cells.AHL37808.1.Canada/254-757 Flavivirus envelope glycoprotein E.
SEQ ID NO: 45

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

BeH818995.AMA12084.1.Brazil/291-794 Flavivirus envelope glycoprotein E. [Zika virus].
SEQ ID NO: 46

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

H/PF/2013.AHZ13508.1.French_Polynesia/291-794 Flavivirus envelope glycoprotein E.
SEQ ID NO: 47

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

-continued

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

PRVABC59.AMC13911.1.Puerto_Rico/291-794 Flavivirus envelope glycoprotein E.
SEQ ID NO: 48

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

KU321639.1/326-829 Zika virus strain ZikaSPH2015, Brazil, Flavivirus envelope glycoprotein E.
SEQ ID NO: 49

IRCIGVSNRDFVEGMSGGTWVDIVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

ZikaSPH2015.ALU33341.1.Brazil/291-794 Flavivirus envelope glycoprotein E.
SEQ ID NO: 50

IRCIGVSNRDFVEGMSGGTWVDIVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

103344.AMC13912.1.Guatemala/291-794 polyprotein [Zika virus]. 103344.AMC13912.1.Guatemala
Flavivirus envelope glycoprotein E.
SEQ ID NO: 51

IRCIGVSNRDFVEGMSGGTWVDVVLEHGGCVTVMAQDKPTVDIELVTTTVSNMAEIRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA isol-Brazil-ZKV2015.AMD16557.1.Brazil/291-794 Flavivirus envelope glycoprotein E.
SEQ ID NO: 52

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGTQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

-continued

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

KU497555.1/308-811 Zika virus isolate Brazil-ZKV2015, Flavivirus envelope glycoprotein E.
SEQ ID NO: 53

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGTQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA isol-ZJ03.AMM39806.1.China/291-794 Flavivirus envelope glycoprotein E.
SEQ ID NO: 54

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGARRMAVLGDTAWDFGSVGGALNSLGKGIHQIFGAAFKSLFGGMSWFSQILIGTLLMWLGLNTKNGSISLMCLALGG

VLIFLSTAVSA isol-FSS13025.AFD30972.1.Cambodia/291-794 Flavivirus envelope glycoprotein E.
SEQ ID NO: 55

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLVWLGLNTKNGSISLMCLALGG

VLIFLSTAVSA isol-Z1106032.ALX35660.1.Suriname/291-794 Flavivirus envelope glycoprotein E. [Zika virus]
SEQ ID NO: 56

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNAKNGSISLMCLALGG

VLIFLSTAVSA isol-Z1106033.ALX35659.1.Suriname/291-794 Flavivirus envelope glycoprotein E. [Zika virus]
SEQ ID NO: 57

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

-continued

EATVRGAKRMAVLGDTAWDFGSVGGALNSLGKGIHQIFGAAFKSLFGGMSWFSQILIGTLLMWLGLNAKNGSISLMCLALGG

VLIFLSTAVSA isol-BeH828305.AMK49165.1.Brazil/291-794 Flavivirus envelope glycoprotein E.

SEQ ID NO: 58

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDTQTLTPVGRLITANPVITESTENSKMMLELDPPFGDSYIVIGVGEKKITHHWHRSGSTIGKAFE

ATVRGAKRMAVLGDTAWDFGSVGGALNSLGKGIHQIFGAAFKSLFGGMSWFSQILIGTLLMWLGLNTKNGSISLMCLALGGV

LIFLSTAVSA isol-GD01.AMK79468.1.China/291-794 Flavivirus envelope glycoprotein E.

SEQ ID NO: 59

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNGTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA isol-ZI106031.ALX35661.1.Suriname/291-794 Flavivirus envelope glycoprotein E.

SEQ ID NO: 60

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVLAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

ACD75819.1.Micronesia/291-794 Flavivirus envelope glycoprotein E.

SEQ ID NO: 61

IRCIGVSNRDFVEGMSGGTWVDVVLEHGGCVTVMAQDKPAVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLVWLGLNTKNGSISLTCLALGGV

LIFLSTAVSA

KU681082.3/308-811 Zika virus isolate Zika virus/*H. sapiens*-tc/PHL/2012/CPC-0740, Philippines,
Flavivirus envelope glycoprotein E.

SEQ ID NO: 62

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLVWLGLNTKNGSISLTCLALGGV

LIFLSTAVSA isol-Zika_virus%H.sapiens-tc%PHL%2012%CPC-0740.AM D61711.1.Philippines/291-794 Flavivirus
envelope glycoprotein E.
SEQ ID NO: 63

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLVWLGLNTKNGSISLTCLALGGV

LIFLSTAVSA isol-BeH823339.AMK49164.2.Brazil/291-794 Flavivirus envelope glycoprotein E.
SEQ ID NO: 64

IRCIGVSNRDFVEGMSGGTWVDVVLEHGGCVTVMAQDKPTVDIELVSTTVSNMAEVRSYCYEATISDIASDSRCPTQGEAYLD

KQSDTQYVCKRTLVDRGWGNGCGLFGKGSLVTCAKFACSKKMTGKSIQPENLEYRIMLSVHGSQHSGMIVNDTGHETDENR

AKVEITPNSPRAEATLGGFGSLGLDCEPRTGLDFSDLYYLTMNNKHWLVHKEWFHDIPLPWHAGADTGTPHWNNKEALVEFK

DAHAKRQTAVVLGSQEGAVHTALAGALEAEMDGAKGRLSSGHLKCRLKMDKLRLKGVSYSLCTAAFTFTKIPAETLHGTVTVE

VQYAGTDGPCKVPAQMAVDMQTLTPVGRLITANPVITESTENSKMMLELDPPFGDSYIVIGVGEKKITHHWHRSGSTIGKAFE

ATVRGAKRMAVLGDTAWDFGSVGGALNSLGKGIHQIFGAAFKSLFGGMSWFSQILIGTLLMWLGLNTKNGSISLMCLALGGV

LIFLSTAVSA isol-P6-740.AEN75264.1.Malaysia/291-794 Flavivirus envelope glycoprotein E.
SEQ ID NO: 65

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDXGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGDKKITHHWXRSGSTIGKAF

EATVRGAKRMAVLGDTAWDFGSVGGALNSLGKGIHQIFGAAFKSLFGGMSWFSQILIGTLLVWLGLNTKNGSISLTCLALGGV

LIFLSTAVSA

KU744693.1/326-829 Zika virus isolate VE_Ganxian, China, Flavivirus envelope glycoprotein E.
SEQ ID NO: 66

IRCIGVSNRDFVEGMSGGTWVDVVLEHGGCVTAMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMLVNDTGHETDEN

RAKVEITPNSPRAEATLGGFGSLGLDCEPRTGLDFSDLYYLTMNNKHWLAHKEWFHDIPLPWHAGAATGTPHWNNKEALVEF

KDAHAKRQTVVVLGSQEGAVHTALAGALEAEMDGAKGRLSSGHLKCRLKMDKLRLKGVSYSLCTAAFTFTKIPAETVDGTVTV

EGQYGGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIIGAAFKSLFGGMSWFSQILIGTLLMWLGLNTKNGSISLMCLALGG

VLIFLSTAVSG isol-VE_Ganxian.AMK79469.1.China/291-794 Flavivirus envelope glycoprotein E.
SEQ ID NO: 67

IRCIGVSNRDFVEGMSGGTWVDVVLEHGGCVTAMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMLVNDTGHETDEN

RAKVEITPNSPRAEATLGGFGSLGLDCEPRTGLDFSDLYYLTMNNKHWLAHKEWFHDIPLPWHAGAATGTPHWNNKEALVEF

KDAHAKRQTVVVLGSQEGAVHTALAGALEAEMDGAKGRLSSGHLKCRLKMDKLRLKGVSYSLCTAAFTFTKIPAETVDGTVTV

EGQYGGTDGPCKVPAQMAVDMQTLTPVGRLITANPVITESTENSKMMLELDPPFGDSYIVIGVGEKKITHHWHRSGSTIGKAF

-continued

ArD157995.AHL43503.1.1291-794 Flavivirus envelope glycoprotein E.
SEQ ID NO: 68
```
EATVRGAKRMAVLGDTAWDFGSVGGALNSLGKGIHQIIGAAFKSLFGGMSWFSQILIGTLLMWLGLNTKNGSISLMCLALGG
VLIFLSTAVSG
```

ArD157995.AHL43503.1.1291-794 Flavivirus envelope glycoprotein E.
SEQ ID NO: 68
```
ISCIGVSNRDLVEGMSGGTWVDVVLEHGGCVTEMAQDKPTVDIELVTMTVSNMAEVRSYCYEASLSDMASASRCPTQGEPSL
DKQSDTQSVCKRTLGDRGWGNGCGIFGKGSLVTCSKFTCCKKMPGKSIQPENLEYRIMLPVHGSQHSGMIVNDIGHETDENR
AKVEVTPNSPRAEATLGGFGSLGLDCEPRTGLDFSDLYYLTMNNKHWLVHKEWFHDIPLPWHAGADTGTPHWNNKEALVEF
KDAHAKRQTVVVLGSQEGAVHTALAGALEAEMDGAKGRLFSGHLKCRLKMDKLRLKGVSYSLCTAAFTFTKVPAETLHGTVTV
EVQSAGTDGPCKVPAQMAVDMQTLTPVGRLITANPVITESTENSKMMLELDPPFGDSYIVIGVGDKKITHHWHRSGSTIGKAF
EATVRGAKRMAVLGDTAWDFGSVGGVFNSLGKGIHQIFGAAFKSLFGGMSWFSQILIGTLLVWLGLNTKNGSISLTCLALGGV
MIFLSTAVSA
```

MR_766.ABI54475.1.Uganda/291-788 Flavivirus envelope glycoprotein E.
SEQ ID NO: 69
```
IRCIGVSNRDFVEGMSGGTWVDVVLEHGGCVTVMAQDKPTVDIELVTTTVSNMAEVRSYCYEASISDMASDSRCPTQGEAYL
DKQSDTQYVCKRTLVDRGWGNGCGLFGKGSLVTCAKFTCSKKMTGKSIQPENLEYRIMLSVHGSQHSGMIVNDENRAKVEVT
PNSPRAEATLGGFGSLGLDCEPRTGLDFSDLYYLTMNNKHWLVHKEWFHDIPLPWHAGADTGTPHWNNKEALVEFKDAHAK
RQTVVVLGSQEGAVHTALAGALEAEMDGAKGRLFSGHLKCRLKMDKLRLKGVSYSLCTAAFTFTKVPAETLHGTVTVEVQYAG
TDGPCKVPAQMAVDMQTLTPVGRLITANPVITESTENSKMMLELDPPFGDSYIVIGVGDKKITHHWHRSGSTIGKAFEATVRG
AKRMAVLGDTAWDFGSVGGVFNSLGKGIHQIFGAAFKSLFGGMSWFSQILIGTLLVWLGLNTKNGSISLTCLALGGVMIFLSTA
VSA
```

SEQ ID NO: 70
```
5'-(dIdC)13-3'
dIdC dIdC dIdC dIdC dIdC dIdC dIdC dIdC dIdC dIdC dIdC dIdC dIdC
```

SEQ ID NO: 71
```
KLK peptide
KLKLLLLLKLK
```

Provided below are examples of nucleic acid sequences of the genomes of Chikungunya, Japanese Encephalitis and yellow fever viruses that may be used in the methods, compositions, and/or vaccines described herein.

Chikungunya virus strain LR2006_OPY1, complete genome ACCESSION: DQ443544
SEQ ID NO: 72
```
ATGGCTGCGTGAGACACACGTAGCCTACCAGTTTCTTACTGCTCTACTCTGCAAAGCAAGAGATTAATAACCCATCATG
GATCCTGTGTACGTGGACATAGACGCTGACAGCGCCTTTTTGAAGGCCCTGCAACGTGCGTACCCCATGTTTGAGGTGG
AACCAAGGCAGGTCACACCGAATGACCATGCTAATGCTAGAGCGTTCTCGCATCTAGCTATAAAACTAATAGAGCAGG
AAATTGACCCCGACTCAACCATCCTGGATATCGGCAGTGCGCCAGCAAGGAGGATGATGTCGGACAGGAAGTACCACT
GCGTCTGCCCGATGCGCAGTGCGGAAGATCCCGAGAGACTCGCCAATTATGCGAGAAAGCTAGCATCTGCCGCAGGAA
AAGTCCTGGACAGAAACATCTCTGGAAAGATCGGGGACTTACAAGCAGTAATGGCCGTGCCAGACACGGAGACGCCA
ACATTCTGCTTACACACAGACGTCTCATGTAGACAGAGAGCAGACGTCGCTATATACCAAGACGTCTATGCTGTACACG
CACCCACGTCGCTATACCACCAGGCGATTAAAGGGGTCCGAGTGGCGTACTGGGTTGGGTTCGACACAACCCCGTTCAT
GTACAATGCCATGGCGGGTGCCTACCCCTCATACTCGACAAACTGGGCAGATGAGCAGGTACTGAAGGCTAAGAACAT
AGGATTATGTTCAACAGACCTGACGGAAGGTAGACGAGGCAAGTTGTCTATTATGAGAGGGAAAAAGCTAAAACCGT
GCGACCGTGTGCTGTTCTCAGTAGGGTCAACGCTCTACCCGGAAAGCCGCAAGCTACTTAAGAGCTGGCACCTGCCATC
GGTGTTCCATTTAAAGGGCAAACTCAGCTTCACATGCCGCTGTGATACAGTGGTTTCGTGTGAGGGCTACGTCGTTAAG
AGAATAACGATGAGCCCAGGCCTTTATGGAAAAACCACAGGGTATGCGGTAACCCACCACGCAGACGGATTCCTGATG
TGCAAGACTACCGACACGGTTGACGGCGAAAGARTGTCATTCTCGGTGTGCACATACGTGCCGGCGACCATTTGTGATC
AAATGACCGGCATCCTTGCTACAGAAGTCACGCCGGAGGATGCACAGAAGCTGTTGGTGGGGCTGAACCAGAGAATA
GTGGTTAACGGCAGAACGCAACGGAATACGAACACCATGAAAAATTATCTGCTTCCCGTGGTCGCCCAAGCCTTCAGTA
```

-continued

```
AGTGGGCAAAGGAGTGCCGGAAAGACATGGAAGATGAAAAACTCCTGGGGGTCAGAGAAAGAACACTGACCTGCTG
CTGTCTATGGGCATTCAAGAAGCAGAAAACACACACGGTCTACAAGAGGCCTGATACCCAGTCAATTCAGAAGGTTCA
GGCCGAGTTTGACAGCTTTGTGGTACCGAGTCTGTGGTCGTCCGGGTTGTCAATCCCTTTGAGGACTAGAATCAAATGG
TTGTTAAGCAAGGTGCCAAAAACCGACCTGATCCCATACAGCGGAGACGCCCGAGAAGCCCGGGACGCAGAAAAAGA
AGCAGAGGAAGAACGAGAAGCAGAACTGACTCGCGAAGCCCTACCACCTCTACAGGCAGCACAGGAAGATGTTCAGG
TCGAAATCGACGTGGAACAGCTTGAGGACAGAGCGGGCGCAGGAATAATAGAGACTCCGAGAGGAGCTATCAAAGTT
ACTGCCCAACCAACAGACCACGTCGTGGGAGAGTACCTGGTACTCTCCCCGCAGACCGTACTACGTAGCCAGAAGCTCA
GTCTGATTCACGCTTTGGCGGAGCAAGTGAAGACGTGCACGCACAACGGACGAGCAGGGAGGTATGCGGTCGAAGCG
TACGACGGCCGAGTCCTAGTGCCCTCAGGCTATGCAATCTCGCCTGAAGACTTCCAGAGTCTAAGCGAAAGCGCAACG
ATGGTGTATAACGAAAGAGAGTTCGTAAACAGAAAGCTACACCATATTGCGATGCACGGACCAGCCCTGAACACCGAC
GAAGAGTCGTATGAGCTGGTGAGGGCAGAGAGGACAGAACACGAGTACGTCTACGACGTGGATCAGAGAAGATGCT
GTAAGAAGGAAGAAGCCGCAGGACTGGTACTGGTGGGCGACTTGACTAATCCGCCCTACCACGAATTCGCATATGAAG
GGCTAAAAATCCGCCCTGCCTGCCCATACAAAATTGCAGTCATAGGAGTCTTCGGAGTACCGGGATCTGGCAAGTCAGC
TATTATCAAGAACCTAGTTACCAGGCAGGACCTGGTGACTAGCGGAAAGAAAGAAAACTGCCAAGAAATCACCACCGA
CGTGATGAGACAGAGAGGTCTAGAGATATCTGCACGTACGGTTGACTCGCTGCTCTTGAATGGATGCAACAGACCAGT
CGACGTGTTGTACGTAGACGAGGCGTTTGCGTGCCACTCTGGAACGCTACTTGCTTTGATCGCCTTGGTGAGACCAAGG
CAGAAAGTTGTACTTTGTGGTGACCCGAAGCAGTGCGGCTTCTTCAATATGATGCAGATGAAAGTCAACTATAATCACA
ACATCTGCACCCAAGTGTACCACAAAAGTATCTCCAGGCGGTGTACACTGCCTGTGACCGCCATTGTGTCATCGTTGCAT
TACGAAGGCAAAATGCGCACTACGAATGAGTACAACAAGCCGATTGTAGTGGACACTACAGGCTCAACAAAACCTGAC
CCTGGAGACCTCGTGTTAACGTGCTTCAGAGGGTGGGTTAAACAACTGCAAATTGACTATCGTGGATACGAGGTCATG
ACAGCAGCCGCATCCCAAGGGTTAACCAGAAAAGGAGTTTACGCAGTTAGACAAAAGTTAATGAAAACCCGCTCTAT
GCATCAACGTCAGAGCACGTCAACGTACTCCTAACGCGTACGGAAGGTAAACTGGTATGGAAGACACTTTCCGGCGAC
CCGTGGATAAAGACGCTGCAGAACCCACCGAAAGGAAACTTCAAAGCAACTATTAAGGAGTGGGAGGTGGAGCATGC
ATCAATAATGGCGGGCATCTGCAGTCACCAAATGACCTTCGATACATTCCAAAATAAAGCCAACGTTTGTTGGGCTAAG
AGCTTGGTCCCTATCCTCGAAACAGCGGGGATAAAACTAAATGATAGGCAGTGGTCTCAGATAATTCAAGCCTTCAAAG
AAGACAAAGCATACTCACCTGAAGTAGCCCTGAATGAAATATGTACGCGCATGTATGGGGTGGATCTAGACAGCGGGC
TATTTTCTAAACCGTTGGTGTCTGTGTATTACGCGGATAACCACTGGGATAATAGGCCTGGAGGGAAAATGTTCGGATT
TAACCCCGAGGCAGCATCCATTCTAGAAAGAAAGTATCCATTCACAAAAGGGAAGTGGAACATCAACAAGCAGATCTG
CGTGACTACCAGGAGGATAGAAGACTTTAACCCTACCACCAACATCATACCGGCCAACAGGAGACTACCACACTCATTA
GTGGCCGAACACCGCCCAGTAAAAGGGGAAAGAATGGAATGGCTGGTTAACAAGATAAACGGCCACCACGTGCTCCT
GGTCAGTGGCTATAACCTTGCACTGCCTACTAAGAGAGTCACTTGGGTAGCGCCGTTAGGTGTCCGCGGAGCGGACTA
CACATACAACCTAGAGTTGGGTCTGCCAGCAACGCTTGGTAGGTATGACCTAGTGGTCATAAACATCCACACACCTTTTC
GCATACACCATTACCAACAGTGCGTCGACCACGCAATGAAACTGCAAATGCTCGGGGGTGACTCATTGAGACTGCTCAA
ACCGGGCGGCTCTCTATTGATCAGAGCATATGGTTACGCAGATAGAACCAGTGAACGAGTCATCTGCGTATTGGGACG
CAAGTTTAGATCGTCTAGAGCGTTGAAACCACCATGTGTCACCAGCAACACTGAGATGTTTTTCCTATTCAGCAACTTTG
ACAATGGCAGAAGGAATTTCACAACTCATGTCATGAACAATCAACTGAATGCAGCCTTCGTAGGACAGGTCACCCGAG
CAGGATGTGCACCGTCGTACCGGGTAAAACGCATGGACATCGCGAAGAACGATGAAGAGTGCGTAGTCAACGCCGCT
AACCCTCGCGGGTTACCGGGTGRCGGTGTTTGCAAGGCAGTATACAAAAAATGGCCGGAGTCCTTTAAGAACAGTGCA
ACACCAGTGGGAACCGCAAAAACAGTTATGTGCGGTACGTATCCAGTAATCCACGCTGTTGGACCAAACTTCTCTAATT
ATTCGGAGTCTGAAGGGGACCGGGAATTGGCAGCTGCCTATCGAAGTCGCAAAGGAAGTAACTAGGCTGGGAGTA
AATAGTGTAGCTATACCTCTCCTCTCCACAGGTGTATACTCAGGAGGGAAAGACAGGCTGACCCAGTCACTGAACCACC
```

-continued

```
TCTTTACAGCCATGGACTCGACGGATGCAGACGTGGTCATCTACTGCCGCGACAAAGAATGGGAGAAGAAAATATCTG

AGGCCATACAGATGCGGACCCAAGTAGAGCTGCTGGATGAGCACATCTCCATAGACTGCGATATTGTTCGCGTGCACC

CTGACAGCAGCTTGGCAGGCAGAAAAGGATACAGCACCACGGAAGGCGCACTGTACTCATATCTAGAAGGGACCCGTT

TTCATCAGACGGCTGTGGATATGGCGGAGATACATACTATGTGGCCAAAGCAAACAGAGGCCAATGAGCAAGTCTGCC

TATATGCCCTGGGGGAAAGTATTGAATCGATCAGGCAGAAATGCCCGGTGGATGATGCAGACGCATCATCTCCCCCCA

AAACTGTCCCGTGCCTTTGCCGTTACGCTATGACTCCAGAACGCGTCACCCGGCTTCGCATGAACCACGTCACAAGCATA

ATTGTGTGTTCTTCGTTTCCCCTCCCAAAGTACAAAATAGAAGGAGTGCAAAAAGTCAAATGCTCTAAGGTAATGCTATT

TGACCACAACGTGCCATCGCGCGTAAGTCCAAGGGAATATAKATCTTCCCAGGAGTCTGCACAGGAGGCGAGTACAAT

CACGTCACTGACGCATAGTCAATTCGACCTAAGCGTTGATGGCGAGATACTGCCCGTCCCGTCAGACCTGGATGCTGAC

GCCCCAGCCCTAGAACCAGCACTAGACGACGGGGCGACACACACGCTGCCATCCACAACCGGAAACCTTGCGGCCGTG

TCTGATTGGGTAATGAGCACCGTACCTGTCGCGCCGCCCAGAAGAAGGCGAGGGAGAAACCTGACTGTGACATGTGAC

GAGAGAGAAGGGAATATAACACCCATGGCTAGCGTCCGATTCTTTAGGGCAGAGCTGTGTCCGGTCGTACAAGAAACA

GCGGAGACGCGTGACACAGCAATGTCTCTTCAGGCACCACCGAGTACCGCCACGGAACCGAATCATCCGCCGATCTCCT

TCGGAGCATCAAGCGAGACGTTCCCCATTACATTTGGGGACTTCAACGAAGGAGAAATCGAAAGCTTGTCTTCTGAGCT

ACTAACTTTCGGAGACTTCTTACCAGGAGAAGTGGATGACTTGACAGACAGCGACTGGTCCACGTGCTCAGACACGGA

CGACGAGTTATGACTAGACAGGGCAGGTGGGTATATATTCTCGTCGGACACCGGTCCAGGTCATTTACAACAGAAGTC

AGTACGCCAGTCAGTGCTGCCGGTGAACACCCTGGAGGAAGTCCACGAGGAGAAGTGTTACCCACCTAAGCTGGATGA

AGCAAAGGAGCAACTATTACTTAAGAAACTCCAGGAGAGTGCATCCATGGCCAACAGAAGCAGGTATCAGTCGCGCAA

AGTAGAAAACATGAAAGCAGCAATCATCCAGAGACTAAAGAGAGGCTGTAGACTATACTTAATGTCAGAGACCCCAAA

AGTCCCTACTTACCGGACTACATATCCGGCGCCTGTGTACTCGCCTCCGATCAACGTCCGATTGTCCAATCCCGAGTCCG

CAGTGGCAGCATGCAATGAGTTCTTAGCTAGAAACATATCCAACTGTCTCATCATACCAAATTACCGACGAGTATGATGC

ATATCTAGACATGGTGGACGGGTCGGAGAGTTGCCTGGACCGAGCGACATTCAATCCGTCAAAACTCAGGAGCTACCC

GAAACAGCACGCTTACCACGCGCCCTCCATCAGAAGCGCTGTACCGTCCCCATTCCAGAACACACTACAGAATGTACTG

GCAGCAGCCACGAAAAGAAACTGCAACGTCACACAGATGAGGGAATTACCCACTTTGGACTCAGCAGTATTCAACGTG

GAGTGTTTCAAAAAATTCGCATGCAACCAAGAATACTGGGAAGAATTTGCTGCCAGCCCTATTAGGATAACAACTGAGA

ATTTAGCAACCTATGTTACTAAACTAAAAGGGCCAAAAGCAGCAGCGCTATTCGCAAAAACCCATAATCTACTGCCACT

ACAGGAAGTACCAATGGATAGGTTCACAGTAGATATGAAAAGGGACGTAAAGGTGACTCCTGGTACAAAGCATACAG

AGGAAAGACCTAAGGTGCAGGTTATACAGGCGGCTGAACCCTTGGCGACAGCATACCTATGTGGGATTCACAGAGAG

CTGGTTAGGAGGCTGAACGCCGTCCTCCTACCCAATGTACATACACTATTTGACATGTCTGCCGAGGATTTCGATGCCAT

CATAGCCGCACACTTTAAGCCAGGAGACACTGTTTTGGAAACGGACATAGCCTCCTTTGATAAGAGCCAAGATGATTCA

CTTGCGCTTACTGCTTTGATGCTGTTAGAGGATTTAGGGGTGGATCACTCCCTGCTGGACTTGATAGAGGCTGCTTTCG

GAGAGATTTCCAGCTGTCACCTACCGACAGGTACGCGCTTCAAGTTCGGCGCCATGATGAAATCAGGTATGTTCCTAAC

TCTGTTCGTCAACACATTGTTAAACATCACCATCGCCAGCCGAGTGCTGGAAGATCGTCTGACAAAATCCGCGTGCGCG

GCCTTCATCGGCGACGACAACATAATACATGGAGTCGTCTCCGATGAATTGATGGCAGCCAGATGTGCCACTTGGATGA

ACATGGAAGTGAAGATCATAGATGCAGTTGTATCCTTGAAAGCCCCTTACTTTTGTGGAGGGTTTATACTGCACGATAC

TGTGACAGGAACAGCTTGCAGAGTGGCAGACCCGCTAAAAAGGCTTTTTAAACTGGGCAAACCGCTAGCGGCAGGTG

ACGAACAAGATGAAGATAGAAGACGAGCGCTGGCTGACGAAGTGATCAGATGGCAACGAACAGGGCTAATTGATGAG

CTGGAGAAAGCGGTATACTCTAGGTACGAAGTGCAGGGTATATCAGTTGTGGTAATGTCCATGGCCACCTTTGCAAGCT

CCAGATCCAACTTCGAGAAGCTCAGAGGACCCGTCATAACTTTGTACGGCGGTCCTAAATAGGTACGCACTACAGCTAC

CTATTTTGCAGAAGCCGACAGCAAGTATCTAAACACTAATCAGCTACAATGGAGTTCATCCCAACCCAAACTTTTTACAA

TAGGAGGTACCAGCCTCGACCCTGGACTCCGCGCCCTACTATCCAAGTCATCAGGCCCAGACCGCGCCCTCAGAGGCAA
```

-continued

```
GCTGGGCAACTTGCCCAGCTGATCTCAGCAGTTAATAAACTGACAATGCGCGCGGTACCCCAACAGAAGCCACGCAGG
AATCGGAAGAATAAGAAGCAAAAGCAAAAACAACAGGCGCCACAAAACAACACAAATCAAAAGAAGCAGCCACCTAA
AAAGAAACCGGCTCAAAAGAAAAGAAGCCGGGCCGCAGAGAGAGGATGTGCATGAAAATCGAAATGATTGTATTT
TCGAAGTCAAGCACGAAGGTAAGGTAACAGGTTACGCGTGCCTGGTGGGGACAAAGTAATGAAACCAGCACACGTA
AAGGGGACCATCGATAACGCGGACCTGGCCAAACTGGCCTTTAAGCGGTCATCTAAGTATGACCTTGAATGCGCGCAG
ATACCCGTGCACATGAAGTCCGACGCTTCGAAGTTCACCCATGAGAAACCGGAGGGGTACTACAACTGGCACCACGGA
GCAGTACAGTACTCAGGAGGCCGGTTCACCATCCCTACAGGTGCTGGCAAACCAGGGGACAGCGGCAGACCGATCTTC
GACAACAAGGGACGCGTGGTGGCCATAGTCTTAGGAGGAGCTAATGAAGGAGCCCGTACAGCCCTCTCGGTGGTGAC
CTGGAATAAAGACATTGTCACTAAAATCACCCCCGAGGGGGCCGAAGAGTGGAGTCTTGCCATCCCAGTTATGTGCCT
GTTGGCAAACACCACGTTCCCCTGCTCCCAGCCCCCTTGCACGCCCTGCTGCTACGAAAAGGAACCGGAGGAAACCCTA
CGCATGCTTGAGGACAACGTCATGAGACCTGGGTACTATCAGCTGCTACAAGCATCCTTAACATGTTCTCCCCACCGCCA
GCGACGCAGCACCAAGGACAACTTCAATGTCTATAAAGCCACAAGACCATACTTAGCTCACTGTCCCGACTGTGGAGAA
GGGCACTCGTGCCATAGTCCCGTAGCACTAGAACGCATCAGAAATGAAGCGACAGACGGGACGCTGAAAATCCAGGT
CTCCTTGCAAATCGGAATAAAGACGGATGACAGCCACGATTGGACCAAGCTGCGTTATATGGACAACCACATGCCAGC
AGACGCAGAGAGGGCGGGGCTATTTGTAAGAACATCAGCACCGTGTACGATTACTGGAACAATGGGACACTTCATCCT
GGCCCGATGTCCAAAAGGGGAAACTCTGACGGTGGGATTCACTGACAGTAGGAAGATTAGTCACTCATGTACGCACCC
ATTTCACCACGACCCTCCTGTGATAGGTCGGGAAAAATTCCATTCCCGACCGCAGCACGGTAAAGAGCTACCTTGCAGC
ACGTACGTGCAGAGCACCGCCGCAACTACCGAGGAGATAGAGGTACACATGCCCCAGACACCCCTGATCGCACATTA
ATGTCACAACAGTCCGGCAACGTAAAGATCACAGTCAATGGCCAGACGGTGCGGTACAAGTGTAATTGCGGTGGCTCA
AATGAAGGACTAACAACTACAGACAAAGTGATTAATAACTGCAAGGTTGATCAATGTCATGCCGCGGTCACCAATCACA
AAAGTGGCAGTATAACTCCCCTCTGGTCCCGCGTAATGCTGAACTTGGGGACCGAAAAGGAAAAATTCACATCCCGTT
TCCGCTGGCAAATGTAACATGCAGGGTGCCTAAAGCAAGGAACCCCACCGTGACGTACGGGAAAAACCAAGTCATCAT
GCTACTGTATCCTGACCACCCAACACTCCTGTCCTACCGGAATATGGGAGAAGAACCAAACTATCAAGAAGAGTGGGT
GATGCATAAGAAGGAAGTCGTGCTAACCGTGCCGACTGAAGGGCTCGAGGTCACGTGGGGCAACAACGAGCCGTATA
AGTATTGGCCGCAGTTATCTACAAACGGTACAGCCCATGGCCACCCGCATGAGATAATTCTGTATTATTATGAGCTGTAC
CCCACTATGACTGTAGTAGTTGTGTCAGTGGCCACGTTCATACTCCTGTCGATGGTGGGTATGGCAGCGGGGATGTGCA
TGTGTGCACGACGCAGATGCATCACACCGTATGAACTGACACCAGGAGCTACCGTCCCTTTCCTGCTTAGCCTAATATGC
TGCATCAGAACAGCTAAAGCGGCCACATACCAAGAGGCTGCGATATACCTGTGGAACGAGCAGCAACCTTTGTTTTGG
CTACAAGCCCTTATTCCGCTGGCAGCCCTGATTGTTCTATGCAACTGTCTGAGACTCTTACCATGCTGCTGTAAAACGTT
GGCTTTTTTAGCCGTAATGAGCGTCGGTGCCCACACTGTGAGCGCGTACGAACACGTAACAGTGATCCCGAACACGGT
GGGAGTACCGTATAAGACTCTAGTCAATAGACCTGGCTACAGCCCCATGGTATTGGAGATGGAACTACTGTCAGTCACT
TTGGAGCCAACACTATCGCTTGATTACATCACGTGCGAGTACAAAACCGTCATCCCGTCTCCGTACGTGAAGTGCTGCG
GTACAGCAGAGTGCAAGGACAAAAACCTACCTGACTACAGCTGTAAGGTCTTCACCGGCGTCTACCCATTTATGTGGGG
CGGCGCCTACTGCTTCTGCGACGCTGAAAACACGCAGTTGAGCGAAGCACACGTGGAGAAGTCCGAATCATGCAAAAC
AGAATTTGCATCAGCATACAGGGCTCATACCGCATCTGCATCAGCTAAGCTCCGCGTCCTTTACCAAGGAAATAACATC
ACTGTAACTGCCTATGCAAACGGCGACCATGCCGTCACAGTTAAGGACGCCAAATTCATTGTGGGGCCAATGTCTTCAG
CCTGGACACCTTTCGACAACAAAATTGTGGTGTACAAAGGTGACGTCTATAACATGGACTACCCGCCCTTTGGCGCAGG
AAGACCAGGACAATTTGGCGATATCCAAAGTCGCACACCTGAGAGTAAAGACGTCTATGCTAATACACAACTGGTACT
GCAGAGACCGGCTGTGGGTACGGTACACGTGCCATACTCTCAGGCACCATCTGGCTTTAAGTATTGGCTAAAAGAACG
CGGGGCGTCGCTGCAGCACACAGCACCATTTGGCTGCCAAATAGCAACAAACCCGGTAAGAGCGGTGAACTGCGCCGT
AGGGAACATGCCCATCTCCATCGACATACCGGAAGCGGCCTTCACTAGGGTCGTCGACGCGCCCTCTTTAACGGACATG
```

```
TCGTGCGAGGTACCAGCCTGCACCCATTCCTCAGACTTTGGGGGCGTCGCCATTATTAAATATGCAGCCAGCAAGAAAG

GCAAGTGTGCGGTGCATTCGATGACTAACGCCGTCACTATTCGGGAAGCTGAGATAGAAGTTGAAGGGAATTCTCAGC

TGCAAATCTCTTTCTCGACGGCCTTAGCCAGCGCCGAATTCCGCGTACAAGTCTGTTCTACACAAGTACACTGTGCAGCC

GAGTGCCACCCCCGAAGGACCACATAGTCAACTACCCGGCGTCACATACCACCCTCGGGGTCCAGGACATCTCCGCTA

CGGCGATGTCATGGGTGCAGAAGATCACGGGAGGTGTGGGACTGGTTGTTGCTGTTGCCGCACTGATTCTAATCGTGG

TGCTATGCGTGTCGTTCAGCAGGCACTAACTTGACAATTAAGTATGAAGGTATATGTGTCCCCTAAGAGACACACTGTA

CATAGCAAATAATCTATAGATCAAAGGGCTACGCAACCCCTGAATAGTAACAAAATACAAAATCACTAAAAATTATAAA

AACAGAAAAATACATAAATAGGTATACGTGTCCCCTAAGAGACACATTGTATGTAGGTGATAAGTATAGATCAAAGGG

CCGAATAACCCCTGAATAGTAACAAAATATGAAAATCAATAAAAATCATAAAATAGAAAAACCATAAACAGAAGTAGTT

CAAAGGGCTATAAAACCCCTGAATAGTAACAAAACATAAAATTAATAAAAATCAAATGAATACCATAATTGGCAAACGG

AAGAGATGTAGGTACTTAAGCTTCCTAAAAGCAGCCGAACTCACTTTGAGAAGTAGGCATAGCATACCGAACTCTTCCA

CGATTCTCCGAACCCACAGGGACGTAGGAGATGTTATTTTGTTTTTAATATTTCAAAAAAAAAAAAAAAAAAAAAAAA

AAAA

Japanese encephalitis virus strain SA14-14-2, complete genome, ACCESSION: KC517497
                                                                    SEQ ID NO: 73
TTTAAACAGTTTTTTAGAACGGAAGATAACCATGACTAAAAAACCAGGAGGGCCCGGTAAAAACCGGGCTATCAATAT

GCTGAAACGCGGCCTACCCCGCGTATTCCCACTAGTGGGAGTGAAGAGGGTAGTAATGAGCTTGTTGGACGGCAGAG

GGCCAGTACGTTTCGTGCTGGCTCTTATCACGTTCTTCAAGTTTACAGCATTAGCCCCGACCAAGGCGCTTTTAGGCCGA

TGGAAAGCAGTGGAAAAGAGTGTGGCAATGAAACATCTTACTAGTTTCAAACGAGAACTTGGAACACTCATTGACGCC

GTGAACAAGCGGGGCAGAAAGCAAACAAAGAGGAGGAAATGAAGGCTCAATCATGTGGCTCGCGAGCTTGGCAG

TTGTCATAGCTTGTGCAGGAGCCATGAAGTTGTCGAATTTCCAGGGGAAGCTTTTGATGACCATCAACAACACGGACAT

TGCAGACGTTATCGTGATTCCCACCTCAAAAGGAGAGAACAGATGCTGGGTCCGGGCAATCGACGTCGGCTACATGTG

TGAGGACACTATCACGTACGAATGTCCTAAGCTTACCATGGGCAATGATCCAGAGGATGTGGATTGCTGGTGTGACAA

CCAAGAAGTCTACGTCCAATATGGACGGTGCACGCGGACCAGGCATTCCAAGCGAAGCAGGAGATCCGTGTCGGTCCA

AACACATGGGAGAGTTCACTAGTGAATAAAAAAGAGGCTTGGCTGGATTCAACGAAAGCCACACGATATCTCATGAA

AACTGAGAACTGGATCATAAGGAATCCTGGCTATGCTTTCCTGGCGGCGGTACTTGGCTGGATGCTTGGCAGTAACAAC

GGTCAACGCGTGGTATTTACCATCCTCCTGCTGTTGGTCGCTCCGGCTTACAGTTTTAATTGTCTGGGAATGGGCAATCG

TGACTTCATAGAAGGAGCCAGTGGAGCCACTTGGGTGGACTTGGTGCTAGAAGGAGATAGCTGCTTGACAATCATGGC

AAACGACAAACCAACATTGGACGTCCGCATGATTAACATCGAAGCTAGCCAACTTGCTGAGGTCAGAAGTTACTGCTAT

CATGCTTCAGTCACTGACATCTCGACGGTGGCTCGGTGCCCCACGACTGGAGAAGCCCACAACGAGAAGCGAGCTGAT

AGTAGCTATGTGTGCAAACAAGGCTTCACTGACCGTGGGTGGGCAACGGATGTGGACTTTTCGGGAAGGGAAGCAT

TGACACATGTGCAAAATTCTCCTGCACCAGTAAAGCGATTGGGAGAACAATCCAGCCAGAAAACATCAAATACGAAGTT

GGCATTTTTGTGCATGGAACCACCACTTCGGAAAACCATGGGAATTATTCAGCGCAAGTTGGGGCGTCCCAGGCGGCA

AAGTTTACAGTAACACCCAATGCTCCTTCGATAACCCTCAAACTTGGTGACTACGGAGAAGTCACACTGGACTGTGAGC

CAAGGAGTGGACTGAACACTGAAGCGTTTTACGTCATGACCGTGGGGTCAAAGTCATTTCTGGTCCATAGGGAGTGGT

TTCATGACCTCGCTCTCCCCTGGACGTCCCCTTCGAGCACAGCGTGGAGAAACAGAGAACTCCTCATGGAATTTGAAGG

GGCGCACGCCACAAAACAGTCCGTTGTTGCTCTTGGGTCACAGGAAGGAGGCCTCCATCAGGCGTTGGCAGGAGCCAT

CGTGGTGGAGTACTCAAGCTCAGTGAAGTTAACATCAGGCCACCTGAAATGTAGGCTGAAAATGGACAAACTGGCTCT

GAAAGGCACAACCTATGGCATGTGTACAGAAAAATTCTCGTTCGCGAAAAATCCGGCGGACACTGGTCACGGAACAGT

TGTCATTGAACTCTCCTACTCTGGGAGTGATGGCCCCTGCAAAATTCCGATTGTTTCCGTTGCGAGCCTCAATGACATGA

CCCCCGTTGGGCGGCTGGTGACAGTGAACCCCTTCGTCGCGACTTCCAGTGCCAACTCAAAGGTGCTGGTCGAGATGG

AACCCCCCTTCGGAGACTCCTACATCGTAGTTGGAAGGGGAGACAAGCAGATCAACCACCATTGGCACAAAGCTGGAA
```

-continued

```
GCACGCTGGGCAAGGCCTTTTCAACAACTTTGAAGGGAGCTCAAAGACTGGCAGCGTTGGGCGACACAGCCTGGGACT
TTGGCTCTATTGGAGGGGTCTTCAACTCCATAGGAAAAGCCGTTCACCAAGTGTTTGGTGGTGCCTTCAGAACACTCTTT
GGGGGAATGTCTTGGATCACACAAGGGCTAATGGGTGCCCTACTGCTCTGGATGGGCGTCAACGCACGAGACCGATCA
ATTGCTTTGGCCTTCTTAGCCACAGGGGGTGTGCTCGTGTTCTTAGCGACCAATGTGCATGCTGACACTGGATGTGCCA
TTGACATCACAAGAAAAGAGATGAGATGTGGAAGTGGCATCTTCGTGCACAACGACGTGGAAGCCTGGGTGGATAGG
TATAAATATTTGCCAGAAACGCCCAGATCCCTAGCGAAGATCGTCCACAAAGCGCACAAGGAAGGCGTGTGCGGAGTC
AGATCTGTCACTAGACTGGAGCACCAAATGTGGGAAGCCGTACGGGACGAATTGAACGTCCTGCTCAAAGAGAATGCA
GTGGACCTCAGTGTGGTTGTGAACAAGCCCGTGGGAAGATATCGCTCAGCCCCTAAACGCCTATCCATGACGCAAGAG
AAGTTTGAAATGGGCTGGAAAGCATGGGGAAAAAGCATTCTCTTTGCCCCGGAATTGGCTAACTCCACATTTGTCGTAG
ATGGACCTGAGACAAAGGAATGCCCTGATGAGCACAGAGCTTGGAACAGCATGCAAATCGAAGACTTCGGCTTTGGCA
TCACATCAACCCGTGTGTGGCTGAAAATTAGAGAGGAGAGCACTGACGAGTGTGATGGAGCGATCATAGGCACGGCT
GTCAAAGGACATGTGGCAGTCCATAGTGACTTGTCGTACTGGATTGAGAGTCGCTACAACGACACATGGAAACTTGAG
AGGGCAGTCTTTGGAGAGGTCAAATCTTGCACTTGGCCAGAGACACACACCCTTTGGGGAGATGATGTTGAGGAAAGT
GAACTCATCATTCCGCACACCATAGCCGGACCAAAAAGCAAGCACAATCGGAGGGAAGGGTATAAGACACAAAACCA
GGGACCTTGGGATGAGAATGGCATAGTCTTGGACTTTGATTATTGCCCAGGGACAAAAGTCACCATTACAGAGGATTG
TGGCAAGAGAGGCCCTTCGGTCAGAACCACTACTGACAGTGGAAAGTTGATCACTGACTGGTGCTGTCGCAGTTGCTC
CCTTCCGCCCCTACGATTCCGGACAGAAAATGGCTGCTGGTACGAATGGAAATCAGACCTGTTAGGCATGATGAAAC
AACACTCGTCAGATCACAGGTTGATGCTTTCAATGGTGAAATGGTTGACCCTTTTCAGCTGGGCCTTCTGGTGATGTTTC
TGGCCACCCAGGAGGTCCTTCGCAAGAGGTGGACGGCCAGATTGACCATTCCTGCGGTTTTGGGGGCCCTACTTGTGC
TGATGCTTGGGGGCATCACTTACACTGATTTGGCGAGGTATGTGGTGCTAGTCGCTGCTGCTTTCGCAGAGGCCAACAG
TGGAGGAGACGTCCTGCACCTTGCTTTGATTGCCGTTTTTAAGATCCAACCAGCATTTCTAGTGATGAACATGCTTAGCA
CGAGATGGACGAACCAAGAAAACGTGGTTCTGGTCCTAGGGGCTGCCTTTTTCCAATTGGCCTCAGTAGATCTGCAAAT
AGGAGTCCACGGAATCCTGAATGCCGCCGCTATAGCATGGATGATTGTCCGAGCGATCACCTTCCCCACAACCTCCTCC
GTCACCATGCCAGTCTTAGCGCTTCTAACTCCGGGATGAGGGCTCTATACCTAGACACTTACAGAATCATCCTCCTCGT
CATAGGGATTTGCTCCCTGCTGCACGAGAGGAAAAAGACCATGGCAAAAAAGAAAGGAGCTGTACTCTTGGGCTTAGC
GCTCACATCCACTGGATGGTTCTCGCCCACCACTATAGCTGCCGGACTAATGGTCTGCAACCCAAACAAGAAGAGAGG
GTGGCCAGCTACTGAGTTTTTGTCGGCAGTTGGATTGATGTTTGCCATCGTAGGTGGTTTGGCCGAGTTGGATATTGAA
TCCATGTCAATACCCTTCATGCTGGCAGGTCTCATGGCAGTGTCCTACGTGGTGTCAGGAAAAGCAACAGATATGTGGC
TTGAACGGGCCGCCGACATCAGCTGGGAGATGGATGCTGCAATCACAGGAAGCAGTCGGAGGCTGGATGTGAAACTG
GATGATGACGGAGATTTTCACTTGATTGATGATCCCGGTGTTCCATGGAAGGTCTGGGTCCTGCGCATGTCTTGCATTG
GCTTAGCCGCCCTCACGCCTTGGGCCATCGTTCCCGCCGCTTTTCGGTTATTGGCTCACTTTAAAAACAACAAAAAGAGG
GGGCGTGTTTTGGGACACGCCATCCCCAAAACCTTGCTCAAAAGGAGACACCACTACAGGAGTCTACCGAATTATGGCT
AGAGGGATTCTTGGCACTTACCAGGCCGGCGTCGGAGTCATGTACGAGAATGTTTTCCACACACTATGGCACACAACTA
GAGGAGCAGCCATTATGAGTGGAGAAGGAAAATTGACGCCATACTGGGGTAGTGTGAGAGAAGACCGCATAGCTTAC
GGAGGCCCATGGAGGTTTGACCGAAAATGGAATGAACAGATGACGTGCAAGTGATCGTGGTAGAACCGGGGAAGG
CTGCAGTAAACATCCAGACAAAACCAGGAGTGTTTCGGACTCCCTTCGGGGAGGTTGGGGCTGTTAGTCTGGATTACCC
GCGAGGAACATCCGGCTCACCCATTCTGGATTCCAATGGAGACATTATAGGCCTATACGGCAATGGAGTTGAGCTTGG
CGATGGCTCATACGTCAGCGCCATCGTGCAGGGTGACCGTCAGGAGGAACCAGTCCCAGAAGCTTACACCCCAAACAT
GTTGAGAAAGAGACAGATGACTGTGCTAGATTTGCACCCTGGTTCAGGGAAAACCAGGAAAATTCTGCCACAAATAAT
TAAGGACGCTATCCAGCAGCGCCTAAGAACAGCTGTGTTGGCACCGACGCGGGTGGTAGCAGCAGAAATGGCAGAAG
CTTTGAGAGGGCTCCCAGTACGATATCAAACTTCAGCAGTGCAGAGAGAGCACCAAGGGAATGAAATAGTGGATGTG
```

```
-continued
ATGTGCCACGCCACTCTGACCCATAGACTGATGTCACCGAACAGAGTGCCCAACTACAACCTATTTGTCATGGATGAAG

CTCATTTCACCGACCCAGCCAGTATAGCCGCACGAGGATACATTGCTACCAAGGTGGAATTAGGGGAGGCAGCAGCCA

TCTTTATGACAGCGACCCCGCCTGGAACCACGGATCCTTTTCCTGACTCAAATGCCCCAATCCATGATTTGCAAGATGAG

ATACCAGACAGGGCATGGAGCAGTGGATACGAATGGATCACAGAATATGCGGGTAAAACCGTGTGGTTTGTGGCGAG

CGTAAAAATGGGGAATGAGATTGCAATGTGCCTCCAAAGAGCGGGGAAAAAGGTCATCCAACTCAACCGCAAGTCCTA

TGACACAGAATACCCAAAATGTAAGAATGGAGACTGGGATTTTGTCATTACCACCGACATCTCTGAAATGGGGCCAA

CTTCGGTGCGAGCAGGGTCATCGACTGTAGAAAGAGCGTGAAACCCACCATCTTAGAAGAGGGAGAAGGCAGAGTCA

TCCTCGGAAACCCATCTCCCATAACCAGTGCAAGCGCAGCTCAACGGAGGGGCAGAGTAGGCAGAAACCCCAACCAAG

TTGGAGATGAATACCACTATGGGGGGGCTACCAGTGAAGATGACAGTAACCTAGCCCATTGGACAGAGGCAAAGATC

ATGTTAGACAACATACACATGCCCAATGGACTGGTGGCCCAGCTCTATGGACCAGAGAGGGAAAAGGCTTTCACAATG

GATGGCGAATACCGTCTCAGAGGTGAAGAAAAGAAAAACTTCTTAGAGCTGCTTAGGACGGCTGACCTCCCGGTGTGG

CTGGCCTACAAGGTGGCGTCCAATGGCATTCAGTACACCGACAGAAAGTGGTGTTTTGATGGGCCGCGTACGAATGCC

ATACTGGAGGACAACACCGAGGTAGAGATAGTCACCCGGATGGGTGAGAGGAAAATCCTCAAGCCGAGATGGCTTGA

TGCAAGAGTTTATGCAGATCACCAAGCCCTCAAGTGGTTCAAAGACTTTGCAGCAGGGAAGAGATCAGCCGTTAGCTTC

ATAGAGGTGCTCGGTCGCATGCCTGAGCATTTCATGGGAAAGACGCGGGAAGCTTTAGACACCATGTACTTGGTTGCA

ACGGCTGAGAAAGGTGGGAAAGCACACCGAATGGCTCTCGAAGAGCTGCCAGATGCACTGGAAACCATCACACTTATT

GTCGCCATTACTGTGATGACAGGAGGATTCTTCCTACTAATGATGCAGCGAAAGGGTATAGGGAAGATGGGTCTTGGA

GCTCTAGTGCTCACGCTAGCTACCTTCTTCCTGTGGGCGGCAGAGGTTCCTGGAACCAAAATAGCAGGGACCCTGCTGA

TCGCCCTGCTGCTGATGGTGGTTCTCATCCCAGAACCGGAAAAACAGAGGTCACAGACAGATAACCAACTGGCGGTGT

TTCTCATCTGTGTCTTGACCGTGGTTGGAGTGGTGGCAGCAAACGAGTACGGGATGCTAGAAAAAACCAAAGCAGATC

TCAAGAGCATGTTTGGCGGAAAGACGCAGGCATCAGGACTGACTGGATTGCCAAGCATGGCACTGGACCTGCGTCCAG

CCACAGCCTGGGCACTGTATGGGGGAGCACAGTCGTGCTAACCCCTCTTCTGAAGCACCTGATCACGTCGGAATACGT

CACCCACATCGCTAGCCTCAATTAACTCACAAGCTGGCTCATTATTCGTCTTGCCACGAGGCGTGCCTTTTACCGACCTAG

ACTTGACCGTTGGCCTCGTCTTCCTTGGCTGTTGGGGTCAAATCACCCTCACAACGTTTCTGACAGCCATGGTTCTGGCG

ACACTTCACTATGGGTACATGCTCCCTGGATGGCAAGCAGAAGCACTCAGGGCTGCCCAGAGAAGGACAGCGGCTGG

AATAATGAAGAATGCCGTTGTTGACGGAATGGTCGCCACTGATGTGCCTGAACTGGAAAGGACTACTCCTCTGATGCA

AAAGAAAGTCGGACAGGTGCTCCTCATAGGGGTAAGCGTGGCAGCGTTCCTCGTCAACCCTAATGTCACCACTGTGAG

AGAAGCAGGGGTGTTGGTGACGGCGGCTACGCTTACTTTGTGGGACAATGGAGCCAGTGCCGTTTGGAATTCCACCAC

AGCCACGGGACTCTGCCATGTCATGCGAGGTAGCTACCTGGCTGGAGGCTCCATTGCTTGGACTCTCATCAAGAACGCT

GATAAGCCCTCCTTGAAAAGGGGAAGGCCTGGGGGCAGGACGCTAGGGGAGCAGTGGAAGGAAAAACTAAATGCCA

TGAGCAGAGAAGAGTTTTTTAAATACCGGAGAGAGGCCATAATCGAGGTGGACCGCACTGAAGCACGCAGGGCCAGA

CGTGAAAATAACATAGTGGGAGGACATCCGGTTTCGCGAGGCTCAGCAAAACTCCGTTGGCTCGTGGAGAAAGGATTT

GTCTCGCCAATAGGAAAAGTCATTGATCTAGGGTGTGGGCGTGGAGGATGGAGCTACTACGCAGCAACCCTGAAGAA

GGTCCAGGAAGTCAGAGGATACACGAAAGGTGGGGCGGGACATGAAGAACCGATGCTCATGCAGAGCTACGGCTGG

AACCTGGTCTCCCTGAAGAGTGGAGTGGACGTGTTTTACAAACCTTCAGAGCCCAGTGACACCCTGTTCTGTGACATAG

GGGAATCCTCCCCAAGTCCAGAAGTAGAAGAACAACGCACACTACGCGTCCTAGAGATGACATCTGACTGGTTGCACC

GAGGACCTAGAGAGTTCTGCATTAAAGTTCTCTGCCCTTACATGCCCAAGGTTATAGAAAAAATGGAAGTTCTGCAGCG

CCGCTTCGGAGGTGGGCTAGTGCGTCTCCCCCTGTCCCGAAACTCCAATCACGAGATGTATTGGGTTAGTGGAGCCGCT

GGCAATGTGGTGCACGCTGTGAACATGACCAGCCAGGTACTACTGGGGCGAATGGATCGCACAGTGTGGAGAGGGCC

AAAGTATGAGGAAGATGTCAACCTAGGGAGCGGAACAAGAGCCGTGGGAAAGGGAGAAGTCCATAGCAATCAGGAG

AAAATCAAGAAGAGAATCCAGAAGCTTAAAGAAGAATTCGCCACAACGTGGCACAAAGACCCTGAGCATCCATACCGC
```

```
ACTTGGACATACCACGGAAGCTATGAAGTGAAGGCTACTGGCTCAGCCAGCTCTCTCGTCAACGGAGTGGTGAAGCTC
ATGAGCAAACCTTGGGACGCCATTGCCAACGTCACCACCATGGCCATGACTGACACCACCCCTTTTGGACAGCAAAGAG
TTTTCAAGGAGAAAGTTGACACGAAGGCTCCTGAGCCACCAGCTGGAGCCAAGGAAGTGCTCAACGAGACCACCAACT
GGCTGTGGGCCCACTTGTCACGGGAAAAAAGACCCCGCTTGTGCACCAAGGAAGAATTCATAAAGAAAGTCAACAGCA
ACGCGGCTCTTGGAGCAGTGTTCGCTGAACAGAATCAATGGAGCACGGCGCGTGAGGCTGTGGATGACCCGCGGTTTT
GGGAGATGGTTGATGAAGAGAGGGAAAACCATCTGCGAGGAGAGTGTCACACATGTATCTACAACATGATGGGAAAA
AGAGAGAAGAAGCCTGGAGAGTTTGGAAAAGCTAAGGAAGCAGGGCCATTTGGTTCATGTGGCTTGGAGCACGGTA
TCTAGAGTTTGAAGCTTTGGGGTTCCTGAATGAAGACCATTGGCTGAGCCGAGAGAATTCAGGAGGTGGAGTGGAAG
GCTCAGGCGTCCAAAAGCTGGGATACATCCTCCGTGACATAGCAGGAAAGCAAGGAGGGAAAATGTACGCTGATGAT
ACCGCCGGGTGGGACACTAGAATTACCAGAACTGATTTAGAAAATGAAGCTAAGGTACTGGAGCTCCTAGACGGTGAA
CACCGCATGCTCGCCCGAGCCATAATTGAACTGACTTACAGGCACAAAGTGGTCAAGGTCATGAGACCTGCAGCAGAA
GGAAAGACCGTGATGGACGTGATATCAAGAGAAGATCAAAGGGGGAGTGGACAGGTGGTCACTTATGCTCTTAACAC
TTTCACGAACATCGCTGTCCAGCTCGTCAGGCTGATGGAGGCTGAGGGGGTCATTGGACCACAACACTTGGAACAGCT
ACCTAGGAAAAACAAGATAGCTGTCAGGACCTGGCTCTTTGAGAATGGAGAGGAGAGAGTGACCAGGATGGCGATCA
GCGGAGACGACTGTGTCGTCAAGCCGCTGGACGACAGATTCGCCACAGCCCTCCACTTCCTCAACGCAATGTCAAAGGT
CAGAAAAGACATCCAGGAATGGAAGCCTTCGCATGGCTGGCACGATTGGCAGCAAGTTCCCTTCTGCTCTAACCATTTT
CAGGAGATTGTGATGAAAGATGGAAGGAGTATAGTTGTCCCGTGCAGAGGACAGGATGAGCTGATAGGCAGGGCTCG
CATCTCTCCAGGAGCTGGATGGAATGTGAAGGACACAGCTTGCCTGGCCAAAGCATATGCACAGATGTGGCTACTCCT
ATACTTCCATCGCAGGGACTTGCGTCTCATGGCAAATGCGATTTGCTCAGCAGTGCCAGTGGATTGGGTGCCCACAGGC
AGGACATCCTGGTCAATACACTCGAAAGGAGAGTGGATGACCACGGAAGACATGCTGCAGGTCTGGAACAGAGTCTG
GATTGAAGAAAATGAATGGATGATGGACAAGACTCCAATCACAAGCTGGACAGACGTTCCGTATGTGGGAAAGCGTG
AGGACATCTGGTGTGGCAGCCTCATCGGAACGCGATCCAGAGCAACCTGGGCTGAGAACATCTATGCGGCGATAAACC
AGGTTAGAGCTGTCATTGGGAAAGAAAATTATGTTGACTACATGACCTCACTCAGGAGATACGAAGACGTCTTGATCCA
GGAAGACAGGGTCATCTAGTGTGATTTAAGGTAGAAAAGTAGACTATGTAAATAATGTAAATGAGAAAATGCATGCAT
ATGGAGTCAGGCCAGCAAAAGCTGCCACCGGATACTGGGTAGACGGTGCTGCCTGCGTCTCAGTCCCAGGAGGACTG
GGTTAACAAATCTGACAACAGAAAGTGAGAAAGCCCTCAGAACCGTCTCGGAAGTAGGTCCCTGCTCACTGGAAGTTG
AAAGACCAACGTCAGGCCACAAATTTGTGCCACTCCGCTAGGGAGTGCGGCCTGCGCAGCCCCAGGAGGACTGGCTTA
CCAAAGCCGTTGAGGCCCCCACGGCCCAAGCCTCGTCTAGGATGCAATAGACGAGGTGTAAGGACTAGAGGTTAGAG
GAGACCCCGTGGAAACAACAACATGCGGCCCAAGCCCCCTCGAAGCTGTAGAGGAGGTGGAAGGACTAGAGGTTAGA
GGAGACCCCGCATTTGCATCAAACAGCATATTGACACCTGGGAATAGACTGGGAGATCTTCTGCTCTATCTCAACATCA
GCTACTAG
```

Japanese encephalitis virus strain SA14-14-2, complete genome, ACCESSION: JN604986

SEQ ID NO: 74

```
AGAAGTTTATCTGTGTGAACTTCTTGGCTTAGTATCGTAGAGAAGAATCGAGAGATTAGTGCAGTTTAAACAGTTTTTA
GAACGGAAGATAACCATGACTAAAAAACCAGGAGGGCCCGGTAAAAACCGGGCTATCAATATGCTGAAACGCGGCCT
ACCCCGCGTATTCCCACTAGTGGGAGTGAAGAGGGTAGTAATGAGCTTGTTGGACGGCAGAGGGCCAGTACGTTCGT
GCTGGCTCTTATCACGTTCTTCAAGTTTACAGCATTAGCCCCGACCAAGGCGCTTTCAGGCCGATGGAAAGCAGTGGAA
AAGAGTGTGGCAATGAAACATCTTACTAGTTTCAAACGAGAACTTGGAACACTCATTGACGCCGTGAACAAGCGGGGC
AGAAAGCAAACAAAGAGGAGGAAATGAAGGCTCAATCATGTGGCTCGCGAGCTTGGCAGTTGTCATAGCTTGTGC
AGGAGCCATGAAGTTGTCGAATTTCCAGGGGAAGCTTTTGATGACCATCAACAACACGGACATTGCAGACGTTATCGT
GATTCCCACCTCAAAAGGAGAGAACAGATGCTGGGTCCGGGCAATCGACGTCGGCTACATGTGTGAGGACACTATCAC
GTACGAATGTCCTAAGCTTACCATGGGCAATGATCCAGAGGATGTGGATTGCTGGTGTGACAACCAAGAAGTCTACGT
```

-continued

```
CCAATATGGACGGTGCACGCGGACCAGGCATTCCAAGCGAAGCAGGAGATCCGTGTCGGTCCAAACACATGGGAGA

GTTCACTAGTGAATAAAAAAGAGGCTTGGCTGGATTCAACGAAAGCCACACGATATCTCATGAAAACTGAGAACTGGA

TCATAAGGAATCCTGGCTATGCTTTCCTGGCGGCGGTACTTGGCTGGATGCTTGGCAGTAACAACGGTCAACGCGTGGT

ATTTACCATCCTCCTGCTGTTGGTCGCTCCGGCTTACAGTTTTAATTGTCTGGGAATGGGCAATCGTGACTTCATAGAAG

GAGCCAGTGGAGCCACTTGGGTGGACTTGGTGCTAGAAGGAGACAGCTGCTTGACAATCATGGCAAACGACAAACCA

ACATTGGACGTCCGCATGATTAACATCGAAGCTAGCCAACTTGCTGAGGTCAGAAGTTACTGCTATCATGCTTCAGTCA

CTGACATCTCGACGGTGGCTCGGTGCCCCACGACTGGAGAAGCCCACAACGAGAAGCGAGCTGATAGTAGCTATGTGT

GCAAACAAGGCTTCACTGACCGTGGGTGGGGCAACGGATGTGGATTTTTCGGGAAGGGAAGCATTGACACATGTGCA

AAATTCTCCTGCACCAGTAAAGCGATTGGGAGAACAATCCAGCCAGAAAACATCAAATACAAAGTTGGCATTTTTGTGC

ATGGAACCACCACTTCGGAAAACCATGGGAATTATTCAGCGCAAGTTGGGGCGTCCCAGGCGGCAAAGTTTACAGTAA

CACCCAATGCTCCTTCGGTAGCCCTCAAACTTGGTGACTACGGAGAAGTCACACTGGACTGTGAGCCAAGGAGTGGAC

TGAACACTGAAGCGTTTTACGTCATGACCGTGGGGTCAAAGTCATTTCTGGTCCATAGGGAGTGGTTTCATGACCTCGC

TCTCCCCTGGACGTCCCCTTCGAGCACAGCGTGGAGAAACAGAGAACTCCTCATGGAATTTGAAGGGGCGCACGCCAC

AAAACAGTCCGTTGTTGCTCTTGGGTCACAGGAAGGAGGCCTCCATCATGCGTTGGCAGGAGCCATCGTGGTGGAGTA

CTCAAGCTCAGTGATGTTAACATCAGGCCACCTGAAATGTAGGCTGAAAATGGACAAACTGGCTCTGAAAGGCACAAC

CTATGGCATGTGTACAGAAAAATTCTCGTTCGCGAAAAATCCGGTGGACACTGGTCACGGAACAGTTGTCATTGAACTC

TCCTACTCTGGGAGTGATGGCCCCTGCAAAATTCCGATTGTTTCCGTTGCGAGCCTCAATGACATGACCCCCGTTGGGC

GGCTGGTGACAGTGAACCCCTTCGTCGCGACTTCCAGTGCCAACTCAAAGGTGCTGGTCGAGATGGAACCCCCCTTCG

GAGACTCCTACATCGTAGTTGGAAGGGGAGACAAGCAGATCAACCACCATTGGCACAAAGCTGGAAGCACGCTGGGC

AAGGCCTTTTCAACAACTTTGAAGGGAGCTCAAAGACTGGCAGCGTTGGGCGACACAGCCTGGGACTTTGGCTCTATT

GGAGGGGTCTTCAACTCCATAGGAAGAGCCGTTCACCAAGTGTTTGGTGGTGCCTTCAGAACACTCTTTGGGGGAATG

TCTTGGATCACACAAGGGCTAATGGGTGCCCTACTGCTCTGGATGGGCGTCAACGCACGAGACCGATCAATTGCTTTGG

CCTTCTTAGCCACAGGAGGTGTGCTCGTGTTCTTAGCGACCAATGTGCATGCTGACACTGGATGTGCCATTGACATCAC

AAGAAAAGAGATGAGATGTGGAAGTGGCATCTTCGTGCACAACGACGTGGAAGCCTGGGTGGATAGGTATAAATATT

TGCCAGAAACGCCCAGATCCCTAGCGAAGATCGTCCACAAAGCGCACAAGGAAGGCGTGTGCGGAGTCAGATCTGTCA

CTAGACTGGAGCACCAAATGTGGGAAGCCGTAAGGGACGAATTGAACGTCCTGCTCAAAGAGAATGCAGTGGACCTC

AGTGTGGTTGTGAACAAGCCCGTGGGAAGATATCGCTCAGCCCCTAAACGCCTATCCATGACGCAAGAGAAGTTTGAA

ATGGGCTGGAAAGCATGGGGAAAAAGCATCCTCTTTGCCCCGGAATTGGCTAACTCCACATTTGTCGTAGATGGACCTG

AGACAAAGGAATGCCCTGATGAGCACAGAGCTTGGAACAGCATGCAAATCGAAGACTTCGGCTTTGGCATCACATCAA

CCCGTGTGTGGCTGAAAATTAGAGAGGAGAGCACTGACGAGTGTGATGGAGCGATCATAGGCACGGCTGTCAAAGGA

CATGTGGCAGTCCATAGTGACTTGTCGTACTGGATTGAGAGTCGCTACAACGACACATGGAAACTTGAGAGGGCAGTC

TTTGGAGAGGTCAAATCTTGCACTTGGCCAGAGACACACACCCTTTGGGGAGATGATGTTGAGGAAAGTGAACTCATC

ATTCCGCACACCATAGCCGGACCAAAAAAGCAAGCACAATCGGAGGGAAGGGTATAAGACACAAACCAGGGACCTTG

GGATGAGAATGGCATAGTCTTGGACTTTGATTATTGCCCAGGGACAAAAGTCACCATTACAGAGGATTGTAGCAAGAG

AGGCCCTTCGGTCAGAACCACTACTGACAGTGGAAAGTTGATCACTGACTGGTGCTGTCGCAGTTGCTCCCTTCCGCCC

CTACGATTCCGGACAGAAAATGGCTGCTGGTACGAATGGAAATCAGACCTGTTATGCATGATGAAACAACACTCGTC

AGATCACAGGTTCATGCTTTCAAAGGTGAAATGGTTGACCCTTTTCAGCTGGGCCTTCTGGTGATGTTTCTGGCCACCCA

GGAAGTCCTTCGCAAGAGGTGGACGGCCAGATTGACCATTCCTGCGGTTTTGGGGGTCCTACTTGTGCTGATGCTTGG

GGGTATCACTTACACTGATTTGGCGAGGTATGTGGTGCTAGTCGCTGCTGCTTTCGCAGAGGCCAACAGTGGAGGAGA

CGTCCTGCACCTTGCTTTGATTGCTGTTTTTAAGATCCAACCAGCATTTTTAGTGATGAACATGCTTAGCACGAGATGGA

CGAACCAAGAAAACGTGGTTCTGGTCCTAGGGGCTGCCTTTTTCCAATTGGCCTCAGTAGATCTGCAAATAGGAGTCCA
```

-continued

```
CGGAATCCTGAATGCCGCCGCTATAGCATGGATGATTGTCCGAGCGATCACCTTCCCCACAACCTCCTCCGTCACCATGC
CAGTCTTAGCGCTTCTAACTCCGGGGATGAGGGCTCTATACCTAGACACTTACAGAATCATCCTCCTCGTCATAGGGATT
TGCTCCCTGCTGCACGAGAGGAAAAAGACCATGGCGAAAAGAAAGGAGCTGTACTCTTGGGCTTAGCGCTCACATCC
ACTGGATGGTTCTCGCCCACCACTATAGCTGCCGGACTAATGGTCTGCAACCCAAACAAGAAGAGAGGGTGGCCAGCT
ACTGAGTTTTTGTCGGCAGTTGGATTGATGTTTGCCATCGTAGGTGGTTTGGCCGAGTTGGATATTGAATCCATGTCAAT
ACCCTTCATGCTGGCAGGTCTCATGGCAGTGTCCTACGTGGTGTCAGGAAAAGCAACAGATATGTGGCTTGAACGGGC
CGCCGACATCAGCTGGGATATGGGTGCTGCAATCACAGGAAGCAGTCGGAGGCTGGATGTGAAACTGGATGATGACG
GAGATTTTCACTTGATTGATGATCCCGGTGTTCCATGGAAGGTCTGGGTCCTGCGCATGTCTTGCATTGGCTTAGCCGCC
CTCACGCCTTGGGCCATCGTTCCCGCCGCTTTCGGTTATTGGCTCACTTTAAAAACAACAAAAAGAGGGGGCGTGTTTT
GGGACACGCCATCCCCAAAACCTTGCTCAAAAGGAGACACCACTACAGGAGTCTACCGAATTATGGCTAGAGGGATTC
TTGGCACTTACCAGGCCGGCGTCGGAGTCATGTACGAGAATGTTTTCCACACACTATGGCACACAACTAGAGGAGCAG
CCATTGTGAGTGGAGAAGGAAAATTGACGCCATACTGGGGTAGTGTGAAAGAAGACCGCATAGCTTACGGAGGCCCA
TGGAGGTTTGACCGAAAATGGAATGGAACAGATGACGTGCAAGTGATCGTGGTAGAACCGGGGAAGGGCGCAGTAA
ACATCCAGACAAAACCAGGAGTGTTTCGGACTCCCTTCGGGGAGGTTGGGGCTGTTAGTCTGGATTACCCGCGAGGAA
CATCCGGCTCACCCATTCTGGATTCCAATGGAGACATTATAGGCCTATACGCAATGGAGTTGAGCTTGGCGATGGCTC
ATACGTCAGCGCCATCGTGCAGGGTGACCGTCAGGAGGAACCAGTCCCAGAAGCTTACACCCCAAACATGTTGAGAAA
GAGACAGATGACTGTGCTAGATTTGCACCCTGGTTCAGGGAAAACCAGGAAAATTCTGCCACAAATAATTAAGGACGC
TATCCAGCAGCGCCTAAGAACAGCTGTGTTGGCACCGACGCGGGTGGTAGCAGCAGAAATGGCAGAAGCTTTGAGAG
GGCTCCCAGTACGATATCAAACTTCAGCAGTGCAGAGAGAGCACCAAGGGAATGAAATAGTGGATGTGATGTGCCAC
GCCACTCTGACCCATAGACTGATGTCACCGAACAGAGTGCCCAACTACAACCTATTTGTCATGGATGAAGCTCATTTCAC
CGACCCAGCCAGTATAGCCGCACGAGGATACATTGCTACCAAGGTGGAATTAGGGGAGGCAGCAGCCATCTTTATGAC
AGCGACCCCGCCTGGAACCACGGATCCTTTTCCTGACTCAAATGCCCCAATCCATGATTTGCAAGATGAGATACCAGAC
AGGGCATGGAGCAGTGGATACGAATGGATCACAGAATATGCGGGTAAAACCGTGTGGTTTGTGGCGAGCGTAAAAAT
GGGGAATGAGATTGCAATGTGCCTCCAAAGAGCGGGGAAAAAGGTCATCCAACTCAACCGCAAGTCCTATGACACAG
AATACCCAAAATGTAAGAATGGAGACTGGGATTTTGTCATTACCACCGACATCTCTGAAATGGGGGCCAACTTCGGTGC
GAGCAGGGTCATCGACTGTAGAAAGAGCGTGAAACCCACCATCTTAGAAGAGGGAGAAGGCAGAGTCATCCTCGGAA
ACCCATCTCCCATAACCAGTGCAAGCGCAGCTCAACGGAGGGGCAGAGTAGGCAGAAACCCCAATCAAGTTGGAGAT
GAATACCACTATGGGGGGGCTACCAGTGAAGATGACAGTAACCTAGCCCATTGGACAGAGGCAAAGATCATGTTAGAC
AACATACACATGCCCAATGGACTGGTGGCCCAGCTCTATGGACCAGAGAGGGAAAAGGCTTTCACAATGGATGGCGAA
TACCGTCTCAGAGGTGAAGAAAAGAAAAACTTCTTAGAGCTGCTTAGGACGGCTGACCTCCCGGTGTGGCTGGCCTAC
AAGGTGGCGTCCAATGGCATTCAGTACACCGACAGAAAGTGGTGTTTTGATGGGCCGCGTACGAATGCCATACTGGAG
GACAACACCGAGGTAGAGATAGTCACCCGGATGGGTGAGAGGAAAATCCTCAAGCCGAGATGGCTTGATGCAAGAGT
TTATGCAGATCACCAGGCCCTCAAGTGGTTCAAAGACTTTGCAGCAGGGAAGAGATCAGCCGTTAGCTTCATAGAGGT
GCTCGGTCGCATGCCTGAGCATTTCATGGGAAAGACGCGGGAAGCTTTAGACACCATGTACTTGGTTGCAACGGCTGA
GAAAGGTGGGAAAGCACACCGAATGGCTCTCGAAGAGCTGCCAGATGCACTGGAAACCATCACACTTATTGTCGCCAT
TACTGTGATGACAGGAGGATTCTTCCTACTAATGATGCAGCGAAAGGGTATAGGGAAGATGGGTCTTGGAGCTCTAGT
GCTCACACTAGCTACCTTCTTCCTGTGGGCGGCAGAGGTTCCTGGAACCAAAATAGCAGGGACCCTGCTGATCGCCCTG
CTGCTGATGGTGGTTCTCATCCCAGAACCGGAAAACAGAGGTCACAGACAGATAACCAACTGGCGGTGTTTCTCATCT
GTGTCTTGACCGTGGTTGGAGTGGTGGCAGCAAACGAGTACGGGATGCTAGAAAAAACCAAAGCGGATCTCAAGAGC
ATGTTTGGCGGAAAGACGCAGGCATCAGGACTGACTGGATTGCCAAGCATGGCACTGGACCTGCGTCCAGCCACAGCC
TGGGCACTGTATGGGGGAGCACAGTCGTGCTAACCCCTCTTCTGAAGCACCTGATCACGTCGGAATACGTCACCACAT
```

-continued

```
CGCTAGCTTCAATTAACTCACAAGCTGGCTCATTATTCGTCTTGCCACGAGGCGTGCCTTTTACCGACCTAGACTTGACT
GTTGGCCTCGTCTTCCTTGGCTGTTGGGGTCAAGTCACCCTCACAACGTTTCTGACAGCCATGGTTCTGGCGACACTTCA
CTATGGGTACATGCTCCCTGGATGGCAAGCAGAAGCACTCAGGGCTGCCCAGAGAAGGACAGCGGCTGGAATAATGA
AGAATGCCGTTGTTGACGGAATGGTCGCCACTGATGTGCCTGAACTGGAAAGGACTACTCCTCTGATGCAAAAGAAAG
TCGGACAGGTGCTCCTCATAGGGGTAAGCGTGGCAGCGTTCCTCGTCAACCCTAATGTCACCACTGTGAGAGAAGCAG
GGGTGTTGGTGACGGCGGCTACGCTTACTTTGTGGGACAATGGAGCCAGTGCCGTTTGGAATTCCACCACAGCCACGG
GACTCTGCCATGTCATGCGAGGTAGCTACCTGGCTGGAGGCTCCATTGCTTGGACTCTCATCAAGAACGCTGATAAGCC
CTCCTTGAAAAGGGGAAGGCCTGGGGCAGGACGCTAGGGGAGCAGTGGAAGGAAAAACTAAATGCCATGAGTAGA
GAAGAGTTTTTAAATACCGGAGAGAGGCCATAATCGAGGTGGACCGCACTGAAGCACGCAGGGCCAGACGTGAAAA
TAACATAGTGGGAGGACATCCGGTTTCGCGAGGCTCAGCAAAACTCCGTTGGCTCGTGGAGAAAGGATTTGTCTCGCC
AATAGGAAAAGTCATTGATCTAGGGTGTGGGCGTGGAGGATGGAGCTACTACGCAGCAACCCTGAAGAAGGTCCAGG
AAGTCAGAGGATACACGAAAGGTGGGGCGGGACATGAAGAACCGATGCTCATGCAGAGCTACGGCTGGAACCTGGTC
TCCCTGAAGAGTGGAGTGGACGTGTTTTACAAACCTTCAGAGCCCAGTGATACCCTGTTCTGTGACATAGGGGAATCCT
CCCCAAGTCCAGAAGTAGAAGAACAACGCACACTACGCGTCCTAGAGATGACATCTGACTGGTTGCACCGAGGACCTA
GAGAGTTCTGCATTAAAGTTCTCTGCCCTTACATGCCCAAGGTTATAGAAAAAATGGAAGTTCTGCAGCGTCGCTTCGG
AGGTGGGCTAGTGCGTCTCCCCCTGTCCCGAAACTCCAATCACGAGATGTATTGGGTTAGTGGAGCCGCTGGCAATGT
GGTGCACGCTGTGAACATGACCAGCCAGGTATTACTGGGGCAATGGATCGCACAGTGTGGAGAGGGCCAAAGTATG
AGGAAGATGTCAACCTAGGGAGCGGAACAAGAGCCGTGGGAAAGGGAGAAGTCCATAGCAATCAGGAGAAAATCAA
GAAGAGAATCCAGAAGCTTAAAGAAGAATTCGCCACAACGTGGCACAAAGACCCTGAGCATCCATACCGCACTTGGAC
ATACCACGGAAGCTATGAAGTGAAGGCTACTGGCTCAGCCAGCTCTCTCGTCAACGGAGTGGTGAAGCTCATGAGCAA
ACCTTGGGACGCCATTGCCAACGTCACCACCATGGCCATGACTGACACCACCCCTTTTGGACAGCAAAGAGTTTTCAAG
GAGAAAGTTGACACGAAGGCTCCTGAGCCACCAGCTGGAGCCAAGGAAGTGCTCAACGAGACCACCAACTGGCTGTG
GGCCTACTTGTCACGGGAAAAAGACCCCGCTTGTGCACCAAGGAAGAATTCATTAAGAAAGTTAACAGCAACGCGGC
TCTTGGAGCAGTGTTCGCTGAACAGAATCAATGGAGCACGGCGCGTGAGGCTGTGGATGACCCGCGGTTTTGGGAGA
TGGTTGATGAAGAGAGGGAAAACCATCTGCGAGGAGAGTGTCACACATGTATCTACAACATGATGGGAAAAGAGAG
AAGAAGCCTGGAGAGTTTGGAAAAGCTAAAGGAAGCAGGGCCATTTGGTTCATGTGGCTTGGAGCACGGTATCTAGA
GTTTGAAGCTTTGGGGTTCCTGAATGAAGACCATTGGCTGAGCCGAGAGAATTCAGGAGGTGGAGTGGAAGGCTCAG
GCGTCCAAAAGCTGGGATACATCCTCCGTGACATAGCAGGAAAGCAAGGAGGGAAAATGTACGCTGATGATACCGCC
GGGTGGGACACTAGAATTACCAGAACTGATTTAGAAAATGAAGCTAAGGTACTGGAGCTCCTAGACGGTGAACACCGC
ATGCTCGCCCGAGCCATAATTGAACTGACTTACAGGCACAAAGTGGTCAAGGTCATGAGACCTGCAGCAGAAGGAAAG
ACCGTGATGGACGTGATATCAAGAGAAGATCAAAGGGGGAGTGGACAGGTGGTCACTTATGCTCTTAACACTTTCACG
AACATCGCTGTCCAGCTCGTCAGGCTGATGGAGGCTGAGGGGTCATTGGACCACAACACTTGGAACATCTACCTAGG
AAAAACAAGATAGCTGTCAGGACCTGGCTCTTTGAGAATGGAGAGGAGAGTGACCAGGATGGCGATCAGCGGAG
ACGACTGTGCCGTCAAACCGCTGGACGACAGATTCGCCACAGCCCTCCACTTCCTCAACGCAATGTCAAAGGTCAGAAA
AGACATCCAGGAATGGAAGCCTTCGCATGGCTGGCACGATTGGCAGCAAGTTCCCTTCTGTTCTAACCATTTTCAGGAG
ATTGTGATGAAAGATGGAAGGAGTATAGTTGTCCCGTGCAGAGGACAGGATGAGCTGATAGGCAGGGCTCGCATCTC
TCCTGGAGCTGGATGGAATGTGAAGGACACAGCTTGCCTGGCCAAAGCATATGCACAGATGTGGCTACTCCTATACTTC
CATCGCAGGGACTTGCGTCTCATGGCAAATGCGATTTGCTCAGCAGTGCCAGTAGATTGGGTGCCCACAGGCAGGACA
TCCTGGTCAATACACTCGAAAGGAGAGTGGATGACCACGGAAGACATGCTGCAGGTCTGGAACAGAGTTTGGATTGAA
GAAAATGAATGGATGATGGACAAGACTCCAATCACAAGCTGGACAGACGTTCCGTATGTGGGAAAGCGCGAGGACAT
CTGGTGTGGCAGCCTCATCGGAACGCGATCCAGAGCAACCTGGGCTGAGAACATCTATGCGGCGATAAACCAGGTTAG
```

-continued

AGCTGTCATTGGGAAAGAAAATTATGTTGACTACATGACCTCACTCAGGAGATACGAAGACGTCTTGATCCAGGAAGA
CAGGGTCATCTAGTGTGATTTAAGGTAGAAAAGTAGACTATGTAAACAATGTAAATGAGAAAATGCATGCATATGGAG
TCAGGCCAGCAAAAGCTGCCACCGGATACTGGGTAGACGGTGCTGCCTGCGTCTCAGTCCCAGGAGGACTGGGTTAAC
AAATCTGACAACAGAAAGTGAGAAAGCCCTCAGAACCGTCTCGGAAGTAGGTCCCTGCTCACTGGAAGTTGAAAGACC
AACGTCAGGCCACAAATTTGTGCCACTCCGCTAGGGAGTGCGGCCTGCGCAGCCCCAGGAGGACTGGGTTACCAAAGC
CGTTGAGGCCCCCACGGCCCAAGCCTCGTCTAGGATGCAATAGACGAGGTGTAAGGACTAGAGGTTAGAGGAGACCC
CGTGGAAACAACAACATGCGGCCCAAGCCCCCTCGAAGCTGTAGAGGAGGTGGAAGGACTAGAGGTTAGAGGAGACC
CCGCATTTGCATCAAACAGCATATTGACACCTGGGAATAGACTGGGAGATCTTCTGCTCTATCTCAACATCAGCTACTAG
GCACAGAGCGCCGAAGTATGTAGCTGGTGGTGAGGAAGAACACAGGATCT

Japanese encephalitis virus strain SA14-14-2, complete genome, ACCESSION: AF315119
SEQ ID NO: 75
AGAAGTTTATCTGTGTGAACTTCTTGGCTTAGTATCGTAGAGAAGAATCGAGAGATTAGTGCAGTTTAAACAGTTTTTA
GAACGGAAGATAACCATGACTAAAAACCAGGAGGGCCCGGTAAAAACCGGGCTATCAATATGCTGAAACGCGGCCT
ACCCCGCGTATTCCCACTAGTGGGAGTGAAGAGGGTAGTAATGAGCTTGTTGGACGGCAGAGGGCCAGTACGTTTCGT
GCTGGCTCTTATCACGTTCTTCAAGTTTACAGCATTAGCCCCGACCAAGGCGCTTTCAGGCCGATGGAAAGCAGTGGAA
AAGAGTGTGGCAATGAAACATCTTACTAGTTTCAAACGAGAACTTGGAACACTCATTGACGCCGTGAACAAGCGGGGC
AGAAAGCAAAACAAAAGAGGAGGAAATGAAGGCTCAATCATGTGGCTCGCGAGCTTGGCAGTTGTCATAGCTTGTGC
AGGAGCCATGAAGTTGTCGAATTTCCAGGGGAAGCTTTTGATGACCATCAACAACACGGACATTGCAGACGTTATCGT
GATTCCCACCTCAAAAGGAGAGAACAGATGCTGGGTCCGGGCAATCGACGTCGGCTACATGTGTGAGGACACTATCAC
GTACGAATGTCCTAAGCTTACCATGGGCAATGATCCAGAGGATGTGGATTGCTGGTGTGACAACCAAGAAGTCTACGT
CCAATATGGACGGTGCACGCGGACCAGGCATTCCAAGCGAAGCAGGAGATCCGTGTCGGTCCAAACACATGGGAGA
GTTCACTAGTGAATAAAAAGAGGCTTGGCTGGATTCAACGAAAGCCACACGATATCTCATGAAAACTGAGAACTGGA
TCATAAGGAATCCTGGCTATGCTTTCCTGGCGGCGGTACTTGGCTGGATGCTTGGCAGTAACAACGGTCAACGCGTGGT
ATTTACCATCCTCCTGCTGTTGGTCGCTCCGGCTTACAGTTTTAATTGTCTGGGAATGGGCAATCGTGACTTCATAGAAG
GAGCCAGTGGAGCCACTTGGGTGGACTTGGTGCTAGAAGGAGACAGCTGCTTGACAATCATGGCAAACGACAAACCA
ACATTGGACGTCCGCATGATTAACATCGAAGCTAGCCAACTTGCTGAGGTCAGAAGTTACTGCTATCATGCTTCAGTCA
CTGACATCTCGACGGTGGCTCGGTGCCCCACGACTGGAGAAGCCCACAACGAGAAGCGAGCTGATAGTAGCTATGTGT
GCAAACAAGGCTTCACTGACCGTGGGTGGGCAACGGATGTGGATTTTTCGGGAAGGGAAGCATTGACACATGTGCA
AAATTCTCCTGCACCAGTAAAGCGATTGGGAGAACAATCCAGCCAGAAAACATCAAATACAAAGTTGGCATTTTTGTGC
ATGGAACCACCACTTCGGAAAACCATGGGAATTATTCAGCGCAAGTTGGGGCGTCCCAGGCGGCAAAGTTTACAGTAA
CACCCAATGCTCCTTCGGTAGCCCTCAAACTTGGTGACTACGGAGAAGTCACACTGGACTGTGAGCCAAGGAGTGGAC
TGAACACTGAAGCGTTTTACGTCATGACCGTGGGGTCAAAGTCATTTCTGGTCCATAGGGAGTGGTTTCATGACCTCGC
TCTCCCCTGGACGTCCCCTTCGAGCACAGCGTGGAGAAACAGAGAACTCCTCATGGAATTTGAAGGGGCGCACGCCAC
AAAACAGTCCGTTGTTGCTCTTGGGTCACAGGAAGGAGGCCTCCATCATGCGTTGGCAGGAGCCATCGTGGTGGAGTA
CTCAAGCTCAGTGATGTTAACATCAGGCCACCTGAAATGTAGGCTGAAAATGGACAAACTGGCTCTGAAAGGCACAAC
CTATGGCATGTGTACAGAAAAATTCTCGTTCGCGAAAAATCCGGTGGACACTGGTCACGGAACAGTTGTCATTGAACTC
TCCTACTCTGGGAGTGATGGCCCCTGCAAAATTCCGATTGTTTCCGTTGCGAGCCTCAATGACATGACCCCCGTTGGGC
GGCTGGTGACAGTGAACCCCTTCGTCGCGACTTCCAGTGCCAACTCAAAGGTGCTGGTCGAGATGGAACCCCCCTTCG
GAGACTCCTACATCGTAGTTGGAAGGGGAGACAAGCAGATCAACCACCATTGGCACAAAGCTGGAAGCACGCTGGGC
AAGGCCTTTTCAACAACTTTGAAGGGAGCTCAAAGACTGGCAGCGTTGGGCGACACAGCCTGGGACTTTGGCTCTATT
GGAGGGGTCTTCAACTCCATAGGAAGAGCCGTTCACCAAGTGTTTGGTGATGCCTTCAGAACACTCTTTGGGGGAATG
TCTTGGATCACACAAGGGCTAATGGGTGCCCTACTGCTCTGGATGGGCGTCAACGCACGAGACCGATCAATTGCTTTGG -continued

```
CCTTCTTAGCCACAGGAGGTGTGCTCGTGTTCTTAGCGACCAATGTGCATGCTGACACTGGATGTGCCATTGACATCAC
AAGAAAAGAGATGAGATGTGGAAGTGGCATCTTCGTGCACAACGACGTGGAAGCCTGGGTGGATAGGTATAAATATT
TGCCAGAAACGCCCAGATCCCTAGCGAAGATCGTCCACAAAGCGCACAAGGAAGGCGTGTGCGGAGTCAGATCTGTCA
CTAGACTGGAGCACCAAATGTGGGAAGCCGTAAGGGACGAATTGAACGTCCTGCTCAAAGAGAATGCAGTGGACCTC
AGTGTGGTTGTGAACAAGCCCGTGGGAAGATATCGCTCAGCCCCTAAACGCCTATCCATGACGCAAGAGAAGTTTGAA
ATGGGCTGGAAAGCATGGGGAAAAAGCATCCTCTTTGCCCCGGAATTGGCTAACTCCACATTTGTCGTAGATGGACCTG
AGACAAAGGAATGCCCTGATGAGCACAGAGCTTGGAACAGCATGCAAATCGAAGACTTCGGCTTTGGCATCACATCAA
CCCGTGTGTGGCTGAAAATTAGAGAGGAGAGCACTGACGAGTGTGATGGAGCGATCATAGGCACGGCTGTCAAAGGA
CATGTGGCAGTCCATAGTGACTTGTCGTACTGGATTGAGAGTCGCTACAACGACACATGGAAACTTGAGAGGGCAGTC
TTTGGAGAGGTCAAATCTTGCACTTGGCCAGAGACACACACCCTTTGGGGAGATGATGTTGAGGAAAGTGAACTCATC
ATTCCGCACACCATAGCCGGACCAAAAAGCAAGCACAATCGGAGGGAAGGGTATAAGACACAAAACCAGGGACCTTG
GGATGAGAATGGCATAGTCTTGGACTTTGATTATTGCCCAGGGACAAAAGTCACCATTACAGAGGATTGTAGCAAGAG
AGGCCCTTCGGTCAGAACCACTACTGACAGTGGAAAGTTGATCACTGACTGGTGCTGTCGCAGTTGCTCCCTTCCGCCC
CTACGATTCCGGACAGAAAATGGCTGCTGGTACGGAATGGAAATCAGACCTGTTATGCATGATGAAACAACACTCGTC
AGATCACAGGTTCATGCTTTCAAAGGTGAAATGGTTGACCCTTTTCAGCTGGGCCTTCTGGTGATGTTTCTGGCCACCCA
GGAAGTCCTTCGCAAGAGGTGGACGGCCAGATTGACCATTCCTGCGGTTTTGGGGGTCCTACTTGTGCTGATGCTTGG
GGGTATCACTTACACTGATTTGGCGAGGTATGTGGTGCTAGTCGCTGCTGCTTTCGCAGAGGCCAACAGTGGAGGAGA
CGTCCTGCACCTTGCTTTGATTGCTGTTTTTAAGATCCAACCAGCATTTTTAGTGATGAACATGCTTAGCACGAGATGGA
CGAACCAAGAAAACGTGGTTCTGGTCCTAGGGGCTGCCTTTTTCCAATTGGCCTCAGTAGATCTGCAAATAGGAGTCCA
CGGAATCCTGAATGCCGCCGCTATAGCATGGATGATTGTCCGAGCGATCACCTTCCCCACAACCTCCTCCGTCACCATGC
CAGTCTTAGCGCTTCTAACTCCGGGGATGAGGGCTCTATACCTAGACACTTACAGAATCATCCTCCTCGTCATAGGGATT
TGCTCCCTGCTGCACGAGAGGAAAAAGACCATGGCGAAAAGAAAGGAGCTGTACTCTTGGGCTTAGCGCTCACATCC
ACTGGATGGTTCTCGCCCACCACTATAGCTGCCGGACTAATGGTCTGCAACCCAAACAAGAAGAGAGGGTGGCCAGCT
ACTGAGTTTTTGTCGGCAGTTGGATTGATGTTTGCCATCGTAGGTGGTTTGGCCGAGTTGGATATTGAATCCATGTCAAT
ACCCTTCATGCTGGCAGGTCTCATGGCAGTGTCCTACGTGGTGTCAGGAAAAGCAACAGATATGTGGCTTGAACGGGC
CGCCGACATCAGCTGGGATATGGGTGCTGCAATCACAGGAAGCAGTCGGAGGCTGGATGTGAAACTGGATGATGACG
GAGATTTTCACTTCATTGATGATCCCGGTGTTCCATGGAAGGTCTGGGTCCTGCGCATGTCTTGCATTGGCTTAGCCGCC
CTCACGCCTTGGGCCATCGTTCCCGCCGCTTTCGGTTATTGGCTCACTTTAAAAACAACAAAAAGAGGGGGCGTGTTTT
GGGACACGCCATCCCCAAAACCTTGCTCAAAAGGAGACACCACTACAGGAGTCTACCGAATTATGGCTAGAGGGATTC
TTGGCACTTACCAGGCCGGCGTCGGAGTCATGTACGAGAATGTTTTCCACACACTATGGCACACAACTAGAGGAGCAG
CCATTGTGAGTGGAGAAGGAAATTGACGCCATACTGGGGTAGTGTGAAAGAAGACCGCATAGCTTACGGAGGCCCA
TGGAGGTTTGACCGAAAATGGAATGGAACAGATGACGTGCAAGTGATCGTGGTAGAACCGGGGAAGGGCGCAGTAA
ACATCCAGACAAAACCAGGAGTGTTTCGGACTCCCTTCGGGGAGGTTGGGGCTGTTAGTCTGGATTACCCGCGAGGAA
CATCCGGCTCACCCATTCTGGATTCCAATGGAGACATTATAGGCCTATACGGCAATGGAGTTGAGCTTGGCGATGGCTC
ATACGTCAGCGCCATCGTGCAGGGTGACCGTCAGGAGGAACCAGTCCCAGAAGCTTACACCCCAAACATGTTGAGAAA
GAGACAGATGACTGTGCTAGATTTGCACCCTGGTTCAGGGAAAACCAGGAAAATTCTGCCACAAATAATTAAGGACGC
TATCCAGCAGCGCCTAAGAACAGCTGTGTTGGCACCGACGCGGGTGGTAGCAGCAGAAATGGCAGAAGTTTTGAGAG
GGCTCCCAGTACGATATCAAACTTCAGCAGTGCAGAGAGAGCACCAAGGGAATGAAATAGTGGATGTGATGTGCCAC
GCCACTCTGACCCATAGACTGATGTCACCGAACAGAGTGCCCAACTACAACCTATTTGTCATGGATGAAGCTCATTTCAC
CGACCCCAGCCAGTATAGCCGCACGAGGATACATTGCTACCAAGGTGGAATTAGGGGAGGCAGCAGCCATCTTTATGAC
AGCGACCCCGCCTGGAACCACGGATCCTTTTCCTGACTCAAATGCCCCAATCCATGATTTGCAAGATGAGATACCAGAC
```

-continued

```
AGGGCATGGAGCAGTGGATACGAATGGATCACAGAATATGCGGGTAAAACCGTGTGGTTTGTGGCGAGCGTAAAAAT

GGGGAATGAGATTGCAATGTGCCTCCAAAGAGCGGGGAAAAAGGTCATCCAACTCAACCGCAAGTCCTATGACACAG

AATACCCAAAATGTAAGAATGGAGACTGGGATTTTGTCATTACCACCGACATCTCTGAAATGGGGGCCAACTTCGGTGC

GAGCAGGGTCATCGACTGTAGAAAGAGCGTGAAACCCACCATCTTAGAAGAGGGAGAAGGCAGAGTCATCCTCGGAA

ACCCATCTCCCATAACCAGTGCAAGCGCAGCTCAACGGAGGGGCAGAGTAGGCAGAAACCCCAATCAAGTTGGAGAT

GAATACCACTATGGGGGGGCTACCAGTGAAGATGACAGTAACCTAGCCCATTGGACAGAGGCAAAGATCATGTTAGAC

AACATACACATGCCCAATGGACTGGTGGCCCAGCTCTATGGACCAGAGAGGGAAAAGGCTTTCACAATGGATGGCGAA

TACCGTCTCAGAGGTGAAGAAAAGAAAAACTTCTTAGAGCTGCTTAGGACGGCTGACCTCCCGGTGTGGCTGGCCTAC

AAGGTGGCGTCCAATGGCATTCAGTACACCGACAGAAAGTGGTGTTTTGATGGGCCGCGTACGAATGCCATACTGGAG

GACAACACCGAGGTAGAGATAGTCACCCGGATGGGTGAGAGGAAAATCCTCAAGCCGAGATGGCTTGATGCAAGAGT

TTATGCAGATCACCAGGCCCTCAAGTGGTTCAAAGACTTTGCAGCAGGGAAGAGATCAGCCGTTAGCTTCATAGAGGT

GCTCGGTCGCATGCCTGAGCATTTCATGGGAAAGACGCGGGAAGCTTTAGACACCATGTACTTGGTTGCAACGGCTGA

GAAAGGTGGGAAAGCACACCGAATGGCTCTCGAAGAGCTGCCAGATGCACTGGAAACCATCACACTTATTGTCGCCAT

TACTGTGATGACAGGAGGATTCTTCCTACTAATGATGCAGCGAAAGGGTATAGGGAAGATGGGTCTTGGAGCTCTAGT

GCTCACACTAGCTACCTTCTTCCTGTGGGCGGCAGAGGTTCCTGAACCAAAATAGCAGGGACCCTGCTGATCGCCCTG

CTGCTGATGGTGGTTCTCATCCCAGAACCGGAAAAACAGAGGTCACAGACAGATAACCAACTGGCGGTGTTTCTCATCT

GTGTCTTGACCGTGGTTGGAGTGGTGGCAGCAAACGAGTACGGGATGCTAGAAAAACCAAAGCGGATCTCAAGAGC

ATGTTTGGCGGAAAGACGCAGGCATCAGGACTGACTGGATTGCCAAGCATGGCACTGGACCTGCGTCCAGCCACAGCC

TGGGCACTGTATGGGGGAGCACAGTCGTGCTAACCCCTCTTCTGAAGCACCTGATCACGTCGGAATACGTCACCACAT

CGCTAGCTTCAATTAACTCACAAGCTGGCTCATTATTCGTCTTGCCACGAGGCGTGCCTTTTACCGACCTAGACTTGACT

GTTGGCCTCGTCTTCCTTGGCTGTTGGGGTCAAGTCACCCTCACAACGTTTCTGACAGCCATGGTTCTGGCGACACTTCA

CTATGGGTACATGCTCCCTGGATGGCAAGCAGAAGCACTCAGGGCTGCCCAGAGAAGGACAGCGGCTGGAATAATGA

AGAATGCCGTTGTTGACGGAATGGTCGCCACTGATGTGCCTGAACTGGAAAGGACTACTCCTCTGATGCAAAAGAAAG

TCGGACAGGTGCTCCTCATAGGGGTAAGCGTGGCAGCGTTCCTCGTCAACCCTAATGTCACCACTGTGAGAGAAGCAG

GGGTGTTGGTGACGGCGGCTACGCTTACTTTGTGGGACAATGGAGCCAGTGCCGTTTGGAATTCCACCACAGCCACGG

GACTCTGCCATGTCATGCGAGGTAGCTACCTGGCTGGAGGCTCCATTGCTTGGACTCTCATCAAGAACGCTGATAAGCC

CTCCTTGAAAAGGGAAGGCCTGGGGCAGGACGCTAGGGGAGCAGTGGAAGGAAAAACTAAATGCCATGAGTAGA

GAAGAGTTTTTTAAATACCGGAGAGAGGGCATAATCGAGGTGGACCGCACTGAAGCACGCAGGGCCAGAAGTGAAAA

TAACATAGTGGGAGGACATCCGGTTTCGCGAGGCTCAGCAAAACTCCGTTGGCTTGTGGAGAAAGGATTTGTCTCGCC

AATAGGAAAAGTCATTGATCTAGGGTGTGGGCGTGGAGGATGGAGCTACTACGCAGCAACCCTGAAGAAGGTCCAGG

AAGTCAGAGGATACACGAAAGGTGGGGCGGGACATGAAGAACCGATGCTCATGCAGAGCTACGGCTGGAACCTGGTC

TCCCTGAAGAGTGGAGTGGACGTGTTTTACAAACCTTCAGAGCCCAGTGATACCCTGTTCTGTGACATAGGGGAATCCT

CCCCAAGTCCAGAAGTAGAAGAACAACGCACACTACGCGTCCTAGAGATGACATCTGACTGGTTGCACCGAGGACCTA

GAGAGTTCTGCATTAAAGTTCTCTGCCCTTACATGCCCAAGGTTATAGAAAAAATTGAAGTTCTGCAGCGCCGCTTCGG

AGGTGGGCTAGTGCGTCTCCCCCTGTCCCGAAACTCCAATCACGAGATGTATTGGGTTAGTGGAGCCGCTGGCAATGT

GGTGCACGCTGTGAACATGACCAGCCAGGTATTACTGGGGCGAATGGATCGCACAGTGTGGGAGAGGGCCAAAGTATG

AGGAAGATGTCAACCTAGGGAGCGGAACAAGAGCCGTGGGAAAGGGAGAAGTCCATAGCAATCAGGAGAAAATCAA

GAAGAGAATCCAGAAGCTTAAAGAAGAATTCGCCACAACGTGGCACAAAGACCCTGAGCATCCATACCGCACTTGGAC

ATACCACGGAAGCTATGAAGTGAAGGCTACTGGCTCAGCCAGCTCTCTCGTCAACGGAGTGGTGAAGCTCATGAGCAA

ACCTTGGGACGCCATTGCCAACGTCACCACCATGGCCATGACTGACACCACCCCTTTTGGACAGCAAAGAGTTTTCAAG

GAGAAAGTTGACACGAAGGCTCCTGAGCCACCAGCTGGAGCCAAGGAAGTGCTCAACGAGACCACCAACTGGCTGTG
```

-continued

```
GGCCTACTTGTCACGGGAAAAAAGACCCCGCTTGTGCACCAAGGAAGAATTCATTAAGAAAGTTAACAGCAACGCGGC

TCTTGGAGCAGTGTTCGCTGAACAGAATCAATGGAGCACGGCGCGTGAGGCTGTGGATGACCCGCGGTTTTGGGAGA

TGGTTGATGAAGAGAGGGAAAACCATCTGCGAGGAGAGTGTCACACATGTATCTACAACATGATGGGAAAAAGAGAG

AAGAAGCCTGGAGAGTTTGGAAAAGCTAAAGGAAGCAGGGCCATTTGGTTCATGTGGCTTGGAGCACGGTATCTAGA

GTTTGAAGCTTTGGGGTTCCTGAATGAAGACCATTGGCTGAGCCGAGAGAATTCAGGAGGTGGAGTGGAAGGCTCAG

GCGTCCAAAAGCTGGGATACATCCTCCGTGACATAGCAGGAAAGCAAGGAGGGAAAATGTACGCTGATGATACCGCC

GGGTGGGACACTAGAATTACCAGAACTGATTTAGAAAATGAAGCTAAGGTACTGGAGCTCCTAGACGGTGAACACCGC

ATGCTCGCCCGAGCCATAATTGAACTGACTTACAGGCACAAAGTGGTCAAGGTCATGAGACCTGCAGCAGAAGGAAAG

ACCGTGATGGACGTGATATCAAGAGAAGATCAAAGGGGGAGTGGACAGGTGGTCACTTATGCTCTTAACACTTTCACG

AACATCGCTGTCCAGCTCGTCAGGCTGATGGAGGCTGAGGGGGTCATTGGACCACAACACTTGGAACATCTACCTAGG

AAAAACAAGATAGCTGTCAGGACCTGGCTCTTTGAGAATGGAGAGGAGAGAGTGACCAGGATGGCGATCAGCGGAG

ACGACTGTGCCGTCAAACCGCTGGACGACAGATTCGCCACAGCCCTCCACTTCCTCAACGCAATGTCAAAGGTCAGAAA

AGACATCCAGGAATGGAAGCCTTCGCATGGCTGGCACGATTGGCAGCAAGTTCCCTTCTGTTCTAACCATTTTCAGGAG

ATTGTGATGAAAGATGGAAGGAGTATAGTTGTCCCCGTGCAGAGGACAGGATGAGCTGATAGGCAGGGCTCGCATCTC

TCCAGGAGCTGGATGGAATGTGAAGGACACAGCTTGCCTGCCCAAAGCATATGCACAAATGTGGGTACTCCTATACTTC

CACCGCAGGGACTTGCGTCTCATGGCAAATGCGATTTGCTCAGCAGTGCCAGTAGATTGGGTGCCCACAGGCAGGACA

TCCTGGTCAATACACTCGAAAGGAGAGTGGATGACCACGGAAGACATGCTGCAGGTCTGGAACAGAGTTTGGATTGAA

GAAAATGAATGGATGATGGACAAGACTCCAATCACAAGCTGGACAGACGTTCCGTATGTGGGAAAGCGCGAGGACAT

CTGGTGTGGCAGCCTCATCGGAACGCGATCCAGAGCAACCTGGGCTGAGAACATCTATGCGGCGATAAACCAGGTTAG

AGCTGTCATTGGGAAAGAAAATTATGTTGACTACATGACCTCACTCAGGAGATACGAAGACGTCTTGATCCAGGAAGA

CAGGGTCATCTAGTGTGATTTAAGGTAGAAAAGTAGACTATGTAAACAATGTAAATGAGAAAATGCATGCATATGGAG

TCAGGCCAGCAAAAGCTGCCACCGGATACTGGGTAGACGGTGCTGCCTGCGTCTCAGTCCCAGGAGGACTGGGTTAAC

AAATCTGACAACAGAAAGTGAGAAAGCCCTCAGAACTGTCTCGGAAGTAGGTCCCTGCTCACTGGAAGTTGAAAGACC

AACGTCAGGCCACAAATTTGTGCCACTCCGCTAGGGAGTGCGGCCTGCGCAGCCCCAGGAGGACTGGGTTACCAAAGC

CGTTGAGCCCCCACGGCCCAAGCCTCGTCTAGGATGCAATAGACGAGGTGTAAGGACTAGAGGTTAGAGGAGACCCC

GTGGAAACAACAACATGCGGCCCAAGCCCCCTCGAAGCTGTAGAGGAGGTGGAAGGACTAGAGGTTAGAGGAGACCC

CGCATTTGCATCAAACAGCATATTGACACCTGGGAATAGACTGGGAGATCTTCTGCTCTATCTCAACATCAGCTACTAGG

CACAGAGCGCCGAAGTATGTACGTGGTGGTGAGGAAGAACACAGGATCT
```

>gi|564014614|gb|KF769015.1| Yellow fever virus strain 17D-204, complete genome
SEQ ID NO: 76

```
GTGCTAATTGAGGTGCATTGGTCTGCAAATCGAGTTGCTAGGCAATAAACACATTTGGATTAATTTTAATCGTTCGTTGAG

CGATTAGCAGAGAACTGACCAGAACATGTCTGGTCGTAAAGCTCAGGGAAAAACCCTGGGCGTCAATATGGTACGACGA

GGAGTTCGCTCCTTGTCAAACAAAATAAAACAAAAAACAAAACAAATTGGAAACAGACCTGGACCTTCAAGAGGTGTTCA

AGGATTTATCTTTTCTTTTTGTTCAACATTTTGACTGGAAAAAAGATCACAGCCCACCTAAAGAGGTTGTGGAAAATGCTG

GACCCAAGACAAGGCTTGGCTGTTCTAAGGAAAGTCAAGAGAGTGGTGGCCAGTTTGATGAGAGGATTGTCCTCAAGGA

AACGCCGTTCCCATGATGTTCTGACTGTGCAATTCCTAATTTTGGGAATGCTGTTGATGACGGGTGGAGTGACCTTGGTGC

GGAAAAACAGATGGTTGCTCCTAAATGTGACATCTGAGGACCTCGGGAAAACATTCTCTGTGGGCACAGGCAACTGCACA

ACAAACATTTTGGAAGCCAAGTACTGGTGCCCAGACTCAATGGAATACAACTGTCCCAATCTCAGTCCAAGAGAGGAGCC

AGATGACATTGATTGCTGGTGCTATGGGGTGGAAAACGTTAGAGTCGCATATGGTAAGTGTGACTCAGCAGGCAGGTCT

AGGAGGTCAAGAAGGGCCATTGACTTGCCTACGCATGAAAACCATGGTTTGAAGACCCGGCAAGAAAATGGATGACTG

GAAGAATGGGTGAAAGGCAACTCCAAAAGATTGAGAGATGGTTCGTGAGGAACCCCTTTTTTGCAGTGACGGCTCTGAC

CATTGCCTACCTTGTGGGAAGCAACATGACGCAACGAGTCGTGATTGCCCTACTGGTCTTGGCTGTTGGTCCGGCCTACTC
```

-continued
```
AGCTCACTGCATTGGAATTACTGACAGGGATTTCATTGAGGGGGTGCATGGAGGAACTTGGGTTTCAGCTACCCTGGAGC
AAGACAAGTGTGTCACTGTTATGGCCCCTGACAAGCCTTCATTGGACATCTCACTAGAGACAGTAGCCATTGATAGACCTG
CTGAGGTGAGGAAAGTGTGTTACAATGCAGTTCTCACTCATGTGAAGATTAATGACAAGTGCCCCAGCACTGGAGAGGCC
CACCTAGCTGAAGAGAACGAAGGGGACAATGCGTGCAAGCGCACTTATTCTGATAGAGGCTGGGGCAATGGCTGTGGCC
TATTTGGGAAAGGGAGCATTGTGGCATGCGCCAAATTCACTTGTGCCAAATCCATGAGTTTGTTTGAGGTTGATCAGACC
AAAATTCAGTATGTCATCAGAGACACAATTGCATGTAGGGGCCAAGCAGGAAAATTGGACTACCGACATTAAGACTCTCAA
GTTTGATGCCCTGTCAGGCTCCCAGGAAGTCGAGTTCATTGGGTATGGAAAAGCTACACTGGAATGCCAGGTGCAAACTG
CGGTGGACTTTGGTAACAGTTACATCGCTGAGATGGAAACAGAGAGCTGGATAGTGGACAGACAGTGGGCCCAGGACTT
GACCCTGCCATGGCAGAGTGGAAGTGGCGGGGTGTGGAGAGAGATGCATCATCTTGTCGAATTTGAACCTCCGCATGCC
GCCACTATCAGAGTACTGGCCCTGGGAAACCAGGAAGGCTCCTTGAAAACAGCTCTTACTGGCGCAATGAGGGTTACAAA
GGACACAAATGACAACAACCTTTACAAACTACATGGTGGACATGTTTCTTGCAGAGTGAAATTGTCAGCTTTGACACTCAA
GGGGACATCCTACAAAATATGCACTGACAAAATGTTTTTTGTCAAGAACCCAACTGACACTGGCCATGGCACTGTTGTGAT
GCAGGTGAAAGTGTCAAAAGGAGCCCCCTGCAGGATTCCAGTGATAGTAGCTGATGATCTTACAGCGGCAATCAATAAA
GGCATTTTGGTTACAGTTAACCCCATCGCCTCAACCAATGATGATGAAGTGCTGATTGAGGTGAACCCACCTTTTGGAGAC
AGCTACATTATCGTTGGGAGAGGAGATTCACGTCTCACTTACCAGTGGCACAAAGAGGGAAGCTCAATAGGAAAGTTGTT
CACTCAGACCATGAAAGGCGTGGAACGCCTGGCCGTCATGGGAGACACCGCCTGGGATTTCAGCTCCGCTGGAGGGTTC
TTCACTTCGGTTGGGAAAGGAATTCATACGGTGTTTGGCTCTGCCTTTCAGGGGCTATTTGGCGGCTTGAACTGGATAACA
AAGGTCATCATGGGGGCGGTACTTATATGGGTTGGCATCAACACAAGAAACATGACAATGTCCATGAGCATGATCTTGGT
AGGAGTGATCATGATGTTTTTGTCTCTAGGAGTTGGGGCGGATCAAGGATGCGCCATCAACTTTGGCAAGAGAGAGCTCA
AGTGCGGAGATGGTATCTTCATATTTAGAGACTCTGATGACTGGCTGAACAAGTACTCATACTATCCAGAAGATCCTGTGA
AGCTTGCATCAATAGTGAAAGCCTCTTTTGAAGAAGGGAAGTGTGGCCTAAATTCAGTTGACTCCCTTGAGCATGAGATG
TGGAGAAGCAGGGCAGATGAGATCAATGCCATTTTTGAGGAAAACGAGGTGGACATTTCTGTTGTCGTGCAGGATCCAA
AGAATGTTTACCAGAGAGGAACTCATCCATTTTCCAGAATTCGGGATGGTCTGCAGTATGGTTGGAAGACTTGGGGTAAG
AACCTTGTGTTCTCCCCAGGGAGGAAGAATGGAAGCTTCATCATAGATGGAAAGTCCAGGAAAGAATGCCCGTTTTCAAA
CCCGGGTCTGGAATTCTTTCCAGATAGAGGAGTTTGGGACGGGAGTGTTCACCACACGCGTGTACATGGACGCAGTCTTTG
AATACACCATAGACTGCGATGGATCTATCTTGGGTGCAGCGGTGAACGGAAAAAAGAGTGCCCATGGCTCTCCAACATTT
TGGATGGGAAGTCATGAAGTAAATGGGACATGGATGATCCACACCTTGGAGGCATTAGATTACAAGGAGTGTGAGTGGC
CACTGACACATACGATTGGAACATCAGTTGAAGAGAGTGAAATGTTCATGCCGAGATCAATCGGAGGCCCAGTTAGCTCT
CACAATCATATCCCTGGATACAAGGTTCAGACGAACGGACCTTGGATGCAGGTACCACTAGAAGTGAAGAGAGAAGCTT
GCCCAGGGACTAGCGTGATCATTGATGGCAACTGTGATGGACGGGGAAAATCAACCAGATCCACCACGGATAGCGGGAA
AGTTATTCCTGAATGGTGTTGCCGCTCCTGCACAATGCCGCCTGTGAGCTTCCATGGTAGTGATGGGTGTTGGTATCCCAT
GGAAATTAGGCCAAGGAAAACGCATGAAAGCCATCTGGTGCGCTCCTGGGTTACAGCTGGAGAAATACATGCTGTCCCTT
TTGGTTTGGTGAGCATGATGATAGCAATGGAAGTGGTCCTAAGGAAAAGACAGGGACCAAAGCAAATGTTGGTTGGAG
GAGTAGTGCTCTTGGGAGCAATGCTGGTCGGGCAAGTAACTCTCCTTGATTTGCTGAAACTCACAGTGGCTGTGGGATTG
CATTTCCATGAGATGAACAATGGAGGAGACGCCATGTATATGGCGTTGATTGCTGCCTTTTCAATCAGACCAGGGCTGCTC
ATCGGCTTTGGGCTCAGGACCCTATGGAGCCCTCGGGAACGCCTTGTGCTGACCCTAGGAGCAGCCATGGTGGAGATTG
CCTTGGGTGGCGTGATGGGCGGCCTGTGGAAGTATCTAAATGCAGTTTCTCTCTGCATCCTGACAATAAATGCTGTTGCTT
CTAGGAAAGCATCAAATACCATCTTGCCCCTCATGGCTCTGTTGACACCTGTCACTATGGCTGAGGTGAGACTTGCCGCAA
TGTTCTTTTGTGCCGTGGTTATCATAGGGGTCCTTCACCAGAATTTCAAGGACACCTCCATGCAGAAGACTATACCTCTGGT
GGCCCTCACACTCACATCTTACCTGGGCTTGACACAACCTTTTTTGGGCCTGTGTGCATTTCTGGCAACCCGCATATTTGGG
CGAAGGAGTATCCCAGTGAATGAGGCACTCGCAGCAGCTGGTCTAGTGGGAGTGCTGGCAGGACTGGCTTTTCAGGAGA
```

-continued

```
TGGAGAACTTCCTTGGTCCGATTGCAGTTGGAGGACTCCTGATGATGCTGGTTAGCGTGGCTGGGAGGGTGGATGGGCT

AGAGCTCAAGAAGCTTGGTGAAGTTTCATGGGAAGAGGAGGCGGAGATCAGCGGGAGTTCCGCCCGCTATGATGTGGC

ACTCAGTGAACAAGGGGAGTTCAAGCTGCTTTCTGAAGAGAAAGTGCCATGGGACCAGGTTGTGATGACCTCGCTGGCC

TTGGTTGGGGCTGCCCTCCATCCATTTGCTCTTCTGCTGGTCCTTGCTGGGTGGCTGTTTCATGTCAGGGGAGCTAGGAGA

AGTGGGGATGTCTTGTGGGATATTCCCACTCCTAAGATCATCGAGGAATGTGAACATCTGGAGGATGGGATTTATGGCAT

ATTCCAGTCAACCTTCTTGGGGGCCTCCCAGCGAGGAGTGGGAGTGGCACAGGGAGGGGTGTTCCACACAATGTGGCAT

GTCACAAGAGGAGCTTTCCTTGTCAGGAATGGCAAGAAGTTGATTCCATCTTGGGCTTCAGTAAAGGAAGACCTTGTCGC

CTATGGTGGCTCATGGAAGTTGGAAGGCAGATGGGATGGAGAGGAAGAGGTCCAGTTGATCGCGGCTGTTCCAGGAAA

GAACGTGGTCAACGTCCAGACAAAACCGAGCTTGTTCAAAGTGAGGAATGGGGGAGAAATCGGGGCTGTCGCTCTTGAC

TATCCGAGTGGCACTTCAGGATCTCCTATTGTTAACAGGAACGGAGAGGTGATTGGGCTGTACGGCAATGGCATCCTTGT

CGGTGACAACTCCTTCGTGTCCGCCATATCCCAGACTGAGGTGAAGGAAGAAGGAAAGGAGGAGCTCCAAGAGATCCCG

ACAATGCTAAAGAAAGGAATGACAACTGTCCTTGATTTTCATCCTGGAGCTGGGAAGACAAGACGTTTCCTCCCACAGAT

CTTGGCCGAGTGCGCACGGAGACGCTTGCGCACTCTTGTGTTGGCCCCCACCAGGGTTGTTCTTTCTGAAATGAAGGAGG

CTTTTCACGGCCTGGACGTGAAATTCCACACACAGGCTTTTTCCGCTCACGGCAGCGGGAGAGAAGTCATTGATGCTATGT

GCCATGCCACCCTAACTTACAGGATGTTGGAACCAACTAGGGTTGTTAACTGGGAAGTGATCATTATGGATGAAGCCCAT

TTTTTGGATCCAGCTAGCATAGCCGCTAGAGGTTGGGCAGCGCACAGAGCTAGGGCAAATGAAAGTGCAACAATCTTGAT

GACAGCCACACCGCCTGGGACTAGTGATGAATTTCCACATTCAAATGGTGAAATAGAAGATGTTCAAACGGACATACCCA

GTGAGCCCTGGAACACAGGGCATGACTGGATCCTGGCTGACAAAAGGCCCACGGCATGGTTCCTTCCATCCATCAGAGCT

GCAAATGTCATGGCTGCCTCTTTGCGTAAGGCTGGAAAGAGTGTGGTGGTCCTGAACAGGAAAACCTTTGAGAGAGAAT

ACCCCACGATAAAGCAGAAGAAACCTGACTTTATATTGGCCACTGACATAGCTGAAATGGGAGCCAACCTTTGCGTGGAG

CGAGTGCTGGATTGCAGGACGGCTTTTAAGCCTGTGCTTGTGGATGAAGGGAGGAAGGTGGCAATAAAAGGGCCACTTC

GTATCTCCGCATCCTCTGCTGCTCAAAGGAGGGGCGCATTGGGAGAAATCCCAACAGAGATGGAGACTCATACTACTAT

TCTGAGCCTACAAGTGAAAATAATGCCCACCACGTCTGCTGGTTGGAGGCCTCAATGCTCTTGGACAACATGGAGGTGAG

GGGTGGAATGGTCGCCCCACTCTATGGCGTTGAAGGAACTAAAACACCAGTTTCCCCTGGTGAAATGAGACTGAGGGAT

GACCAGAGGAAAGTCTTCAGAGAACTAGTGAGGAATTGTGACCTGCCCGTTTGGCTTTCGTGGCAAGTGGCCAAGGCTG

GTTTGAAGACGAATGATCGTAAGTGGTGTTTTGAAGGCCCTGAGGAACATGAGATCTTGAATGACAGCGGTGAAACAGT

GAAGTGCAGGGCTCCTGGAGGAGCAAAGAAGCCTCTGCGCCCAAGGTGGTGTGATGAAAGGGTGTCATCTGACCAGAG

TGCGCTGTCTGAATTTATTAAGTTTGCTGAAGGTAGGAGGGGAGCTGCTGAAGTGCTAGTTGTGCTGAGTGAACTCCCTG

ATTTCCTGGCTAAAAAAGGTGGAGAGGCAATGGATACCATCAGTGTGTTTCTCCACTCTGAGGAAGGCTCTAGGGCTTAC

CGCAATGCACTATCAATGATGCCTGAGGCAATGACAATAGTCATGCTGTTTATACTGGCTGGACTACTGACATCGGGAAT

GGTCATCTTTTTCATGTCTCCCAAAGGCATCAGTAGAATGTCTATGGCGATGGGCACAATGGCCGGCTGTGGATATCTCAT

GTTCCTTGGAGGCGTCAAACCCACTCACATCTCCTATATCATGCTCATATTCTTTGTCCTGATGGTGGTTGTGATCCCCGAG

CCAGGGCAACAAAGGTCCATCCAAGACAACCAAGTGGCATACCTCATTATTGGCATCCTGACGCTGGTTTCAGCGGTGGC

AGCCAACGAGCTAGGCATGCTGGAGAAAACCAAAGAGGACCTCTTTGGGAAGAAGAACTTAATTCCATCTAGTGCTTCAC

CCTGGAGTTGGCCGGATCTTGACCTGAAGCCAGGAGCTGCCTGGACAGTGTACGTTGGCATTGTTACAATGCTCTCTCCA

ATGTTGCACCACTGGATCAAAGTCGAATATGGCAACCTGTCTCTGTCTGGAATAGCCCAGTCAGCCTCAGTCCTTTCTTTCA

TGGACAAGGGGATACCATTCATGAAGATGAATATCTCGGTCATAATGCTGCTGGTCAGTGGCTGGAATTCAATAACAGTG

ATGCCTCTGCTCTGTGGCATAGGGTGCGCCATGCTCCACTGGTCTCTCATTTTACCTGGAATCAAAGCGCAGCAGTCAAAG

CTTGCACAGAGAAGGGTGTTCCATGGCGTTGCCAAGAACCCTGTGGTTGATGGGAATCCAACAGTTGACATTGAGGAAG

CTCCTGAAATGCCTGCCCTTTATGAGAAGAAACTGGCTCTATATCTCCTTCTTGCTCTCAGCCTAGCTTCTGTTGCCATGTGC

AGAACGCCCTTTTCATTGGCTGAAGGCATTGTCCTAGCATCAGCTGCCCTAGGGCCGCTCATAGAGGGAAACACCAGCCT
```

-continued

```
TCTTTGGAATGGACCCATGGCTGTCTCCATGACAGGAGTCATGAGGGGGAATCACTATGCTTTTGTGGGAGTCATGTACA
ATCTATGGAAGATGAAAACTGGACGCCGGGGGAGCGCGAATGGAAAAACTTTGGGTGAAGTCTGGAAGAGGGAACTGA
ATCTGTTGGACAAGCGACAGTTTGAGTTGTATAAAAGGACCGACATTGTGGAGGTGGATCGTGATACGGCACGCAGGCA
TTTGGCCGAAGGGAAGGTGGACACCGGGGTGGCGGTCTCCAGGGGGACCGCAAAGTTAAGGTGGTTCCATGAGCGTGG
CTATGTCAAGCTGGAAGGTAGGGTGATTGACCTGGGGTGTGGCCGCGGAGGCTGGTGTTACTACGCTGCTGCGCAAAAG
GAAGTGAGTGGGGTCAAAGGATTTACTCTTGGAAGAGACGGCCATGAGAAACCCATGAATGTGCAAAGTCTGGGATGG
AACATCATCACCTTCAAGGACAAAACTGATATCCACCGCCTAGAACCAGTGAAATGTGACACCCTTTTGTGTGACATTGGA
GAGTCATCATCGTCATCGGTCACAGAGGGGGAAAGGACCGTGAGAGTTCTTGATACTGTAGAAAAATGGCTGGCTTGTG
GGGTTGACAACTTCTGTGTGAAGGTGTTAGCTCCATACATGCCAGATGTTCTCGAGAAACTGGAATTGCTCCAAAGGAGG
TTTGGCGGAACAGTGATCAGGAACCCTCTCTCCAGGAATTCCACTCATGAAATGTACTACGTGTCTGGAGCCCGCAGCAAT
GTCACATTTACTGTGAACCAAACATCCCGCCTCCTGATGAGGAGAATGAGGCGTCCAACTGGAAAAGTGACCCTGGAGGC
TGACGTCATCCTCCCAATTGGGACACGCAGTGTTGAGACAGACAAGGGACCCCTGGACAAAGAGGCCATAGAAGAAAGG
GTTGAGAGGATAAAATCTGAGTACATGACCTCTTGGTTTTATGACAATGACAACCCCTACAGGACCTGGCACTACTGTGGC
TCCTATGTCACAAAAACCTCAGGAAGTGCGGCGAGCATGGTAAATGGTGTTATTAAAATTCTGACATATCCATGGGACAG
GATAGAGGAGGTCACAAGAATGGCAATGACTGACACAACCCCTTTTGGACAGCAAAGAGTGTTTAAAGAAAAGTTGAC
ACCAGAGCAAAGGATCCACCAGCGGGAACTAGGAAGATCATGAAAGTTGTCAACAGGTGGCTGTTCCGCCACCTGGCCA
GAGAAAAGAACCCCAGACTGTGCACAAAGGAAGAATTTATTGCAAAAGTCCGAAGTCATGCAGCCATTGGAGCTTACCTG
GAAGAACAAGAACAGTGGAAGACTGCCAATGAGGCTGTCCAAGACCCAAAGTTCTGGGAACTGGTGGATGAAGAAAGG
AAGCTGCACCAACAAGGCAGGTGTCGGACTTGTGTGTACAACATGATGGGGAAAAGAGAGAAGAAGCTGTCAGAGTTT
GGGAAAGCAAAGGGAAGCCGTGCCATATGGTATATGTGGCTGGGAGCGCGGTATCTTGAGTTTGAGGCCCTGGGATTCC
TGAATGAGGACCATTGGGCTTCCAGGGAAAACTCAGGAGGAGGAGTGGAAGGCATTGGCTTACAATACCTAGGATATGT
GATCAGAGACCTGGCTGCAATGGATGGTGGTGGATTCTACGCGGATGACACCGCTGGATGGGACACGCGCATCACAGAG
GCAGACCTTGATGATGAACAGGAGATCTTGAACTACATGAGCCCACATCACAAAAAACTGGCACAAGCAGTGATGGAAA
TGACATACAAGAACAAAGTGGTGAAAGTGTTGAGACCAGCCCCAGGAGGGAAAGCCTACATGGATGTCATAAGTCGACG
AGACCAGAGAGGATCCGGGCAGGTAGTGACTTATGCTCTGAACACCATCACCAACTTGAAAGTCCAATTGATCAGAATGG
CAGAAGCAGAGATGGTGATACATCACCAACATGTTCAAGATTGTGATGAATCAGTTCTGACCAGGCTGGAGGCATGGCTC
ACTGAGCACGGATGTAACAGACTGAAGAGGATGGCGGTGAGTGGAGACGACTGTGTGGTCCGGCCCATCGATGACAGG
TTCGGCCTGGCCCTGTCCCATCTCAACGCCATGTCCAAGGTTAGAAAGGACATATCTGAATGGCAGCCATCAAAAGGGTG
GAATGATTGGGAGAATGTGCCCTTCTGTTCCCACCACTTCCATGAACTACAGCTGAAGGATGGCAGGAGGATTGTGGTGC
CTTGCCGAGAACAGGACGAGCTCATTGGGAGAGGAAGGGTGTCTCCAGGAAACGGCTGGATGATCAAGGAAACAGCTT
GCCTCAGCAAAGCCTATGCCAACATGTGGTCACTGATGTATTTTCACAAAAGGGACATGAGGCTACTGTCATTGGCTGTTT
CCTCAGCTGTTCCCACCTCATGGGTTCCACAAGGACGCACAACATGGTCGATTCATGGGAAAGGGGAGTGGATGACCACG
GAAGACATGCTTGAGGTGTGGAACAGAGTATGGATAACCAACAACCCACACATGCAGGACAAGACAATGGTGAAAAAAT
GGAGAGATGTCCCTTATCTAACCAAGAGACAAGACAAGCTGTGCGGATCACTGATTGGAATGACCAATAGGGCCACCTG
GGCCTCCCACATCCATTTGGTCATCCATCGTATCCGAACGCTGATTGGACAGGAGAAATACACTGACTACCTAACAGTCAT
GGACAGGTATTCTGTGGATGCTGACCTGCAACTGGGTGAGCTTATCTGAAACACCATCTAACAGGAATAACCGGATACA
AACCACGGGTGGAGAACCGGACTCCCCACAACCTGAAACCGGGATATAAACCACGGCTGGAGAACCGGACTCCGCACTT
AAAATGAAACAGAAACCGGATAAAAACTACGGATGGAGAACCGGACTCCACACATTGAGACAGAAGAAGTTGTCAGCC
CAGAACCCCACACGAGTTTTGCCACTGCTAAGCTGTGAGGCAGTGCAGGCTGGGACAGCCGACCTCCAGGTTGCGAAAA
ACCTGGTTTCTGGGACCTCCCACCCCAGAGTAAAAAGAACGGAGCCTCCGCTACCACCCTCCCACGTGGTGGTAGAAAGA
```

-continued

CGGGGTCTAGAGGTTAGAGGAGACCCTCCAGGGAACAAATAGTGGGACCATATTGACGCCAGGGAAAGACCGGAGTGG

TTCTCTGCTTTTCCTCCAGAGGTCTGTGAGCACAGTTTGCTCAAGAATAAGCAGACCTTTGGATGACAAA

Attenuated Chikungunya "Delta5nsP3" sequence

SEQ ID NO: 77

GATGGCTGCGTGAGACACACGTAGCCTACCAGTTTCTTACTGCTCTACTCTGCAAAGCAAGAGATTAATAACCCATCATGG

ATCCTGTGTACGTGGACATAGACGCTGACAGCGCCTTTTTGAAGGCCCTGCAACGTGCGTACCCCATGTTTGAGGTGGAA

CCAAGGCAGGTCACACCGAATGACCATGCTAATGCTAGAGCGTTCTCGCATCTAGCTATAAAACTAATAGAGCAGGAAAT

TGACCCCGACTCAACCATCCTGGATATCGGCAGTGCGCCAGCAAGGAGGATGATGTCGGACAGGAAGTACCACTGCGTC

TGCCCGATGCGCAGTGCGGAAGATCCCGAGAGACTCGCCAATTATGCGAGAAAGCTAGCATCTGCCGCAGGAAAAGTCC

TGGACAGAAACATCTCTGGAAAGATCGGGGACTTACAAGCAGTAATGGCCGTGCCAGACACGGAGACGCCAACATTCTG

CTTACACACAGACGTCTCATGTAGACAGAGAGCAGACGTCGCTATATACCAAGACGTCTATGCTGTACACGCACCCACGTC

GCTATACCACCAGGCGATTAAAGGGGTCCGAGTGGCGTACTGGGTTGGGTTCGACACAACCCCGTTCATGTACAATGCCA

TGGCGGGTGCCTACCCCTCATACTCGACAAACTGGGCAGATGAGCAGGTACTGAAGGCTAAGAACATAGGATTATGTTCA

ACAGACCTGACGGAAGGTAGACGAGGCAAGTTGTCTATTATGAGAGGGAAAAAGCTAAAACCGTGCGACCGTGTGCTGT

TCTCAGTAGGGTCAACGCTCTACCCGAAAAGCCGCAAGCTACTTAAGAGCTGGCACCTGCCATCGGTGTTCCATTTAAAG

GGCAAACTCAGCTTCACATGCCGCTGTGATACAGTGGTTTCGTGTGAGGGCTACGTCGTTAAGAGAATAACGATGAGCCC

AGGCCTTTATGGAAAAACCACAGGGTATGCGGTAACCCACCACGCAGACGGATTCCTGATGTGCAAGACTACCGACACG

GTTGACGGCGAAAGAATGTCATTCTCGGTGTGCACATACGTGCCGGCGACCATTTGTGATCAAATGACCGGCATCCTTGC

TACAGAAGTCACGCCGGAGGATGCACAGAAGCTGTTGGTGGGGCTGAACCAGAGAATAGTGGTTAACGGCAGAACGCA

ACGGAATACGAACACCATGAAAAATTATCTGCTTCCCGTGGTCGCCCAAGCCTTCAGTAAGTGGGCAAAGGAGTGCCGGA

AAGACATGGAAGATGAAAAACTCCTGGGGGTCAGAGAAAGAACACTGACCTGCTGCTGTCTATGGGCATTCAAGAAGCA

GAAAACACACACGGTCTACAAGAGGCCTGATACCCAGTCAATTCAGAAGGTTCAGGCCGAGTTTGACAGCTTTGTGGTAC

CGAGTCTGTGGTCGTCCGGGTTGTCAATCCCTTTGAGGACTAGAATCAAATGGTTGTTAAGCAAGGTGCCAAAAACCGAC

CTGATCCCATACAGCGGAGACGCCCGAGAAGCCCGGGACGCAGAAAAAGAAGCAGAGGAAGAACGAGAAGCAGAACT

GACTCGCGAAGCCCTACCACCTCTACAGGCAGCACAGGAAGATGTTCAGGTCGAAATCGACGTGGAACAGCTTGAGGAC

AGAGCGGGCGCAGGAATAATAGAGACTCCGAGAGGAGCTATCAAAGTTACTGCCCAACCAACAGACCACGTCGTGGGA

GAGTACCTGGTACTCTCCCCGCAGACCGTACTACGTAGCCAGAAGCTCAGTCTGATTCACGCTTTGGCGGAGCAAGTGAA

GACGTGCACGCACAACGGACGAGCAGGGAGGTATGCGGTCGAAGCGTACGACGGCCGAGTCCTAGTGCCCTCAGGCTA

TGCAATCTCGCCTGAAGACTTCCAGAGTCTAAGCGAAAGCGCAACGATGGTGTATAACGAAAGAGAGTTCGTAAACAGA

AAGCTACACCATATTGCGATGCACGGACCAGCCCTGAACACCGACGAAGAGTCGTATGAGCTGGTGAGGGCAGAGAGG

ACAGAACACGAGTACGTCTACGACGTGGATCAGAGAAGATGCTGTAAGAAGGAAGAAGCCGCAGGACTGGTACTGGTG

GGCGACTTGACTAATCCGCCCTACCACGAATTCGCATATGAAGGGCTAAAAATCCGCCCTGCCTGCCCATACAAATTGCA

GTCATAGGAGTCTTCGGAGTACCGGGATCTGGCAAGTCAGCTATTATCAAGAACCTAGTTACCAGGCAGGACCTGGTGAC

TAGCGGAAAGAAAGAAAACTGCCAAGAAATCACCACCGACGTGATGAGACAGAGAGGTCTAGAGATATCTGCACGTACG

GTTGACTCGCTGCTCTTGAATGGATGCAACAGACCAGTCGACGTGTTGTACGTAGACGAGGCGTTTGCGTGCCACTCTGG

AACGCTACTTGCTTTGATCGCCTTGGTGAGACCAAGGCAGAAAGTTGTACTTTGTGGTGACCCGAAGCAGTGCGGCTTCT

TCAATATGATGCAGATGAAAGTCAACTATAATCACAACATCTGCACCCAAGTGTACCACAAAAGTATCTCCAGGCGGTGTA

CACTGCCTGTGACCGCCATTGTGTCATCGTTGCATTACGAAGGCAAAATGCGCACTACGAATGAGTACAACAAGCCGATT

GTAGTGGACACTACAGGCTCAACAAAACCTGACCCTGGAGACCTCGTGTTAACGTGCTTCAGAGGGTGGGTTAAACAACT

GCAAATTGACTATCGTGGATACGAGGTCATGACAGCAGCCGCATCCCAAGGGTTAACCAGAAAAGGAGTTTACGCAGTT

AGACAAAAAGTTAATGAAAACCCGCTCTATGCATCAACGTCAGAGCACGTCAACGTACTCCTAACGCGTACGGAAGGTAA

ACTGGTATGGAAGACACTTTCCGGCGACCCGTGGATAAAGACGCTGCAGAACCCACCGAAAGGAAACTTCAAAGCAACT

```
ATTAAGGAGTGGGAGGTGGAGCATGCATCAATAATGGCGGGCATCTGCAGTCACCAAATGACCTTCGATACATTCCAAAA
TAAAGCCAACGTTTGTTGGGCTAAGAGCTTGGTCCCTATCCTCGAAACAGCGGGGATAAAACTAAATGATAGGCAGTGGT
CTCAGATAATTCAAGCCTTCAAAGAAGACAAAGCATACTCACCTGAAGTAGCCCTGAATGAAATATGTACGCGCATGTAT
GGGGTGGATCTAGACAGCGGGCTATTTTCTAAACCGTTGGTGTCTGTGTATTACGCGGATAACCACTGGGATAATAGGCC
TGGAGGGAAAATGTTCGGATTTAACCCCGAGGCAGCATCCATTCTAGAAAGAAAGTATCCATTCACAAAAGGGAAGTGG
AACATCAACAAGCAGATCTGCGTGACTACCAGGAGGATAGAAGACTTTAACCCTACCACCAACATCATACCGGCCAACAG
GAGACTACCACACTCATTAGTGGCCGAACACCGCCCAGTAAAAGGGGAAAGAATGGAATGGCTGGTTAACAAGATAAAC
GGCCACCACGTGCTCCTGGTCAGTGGCTATAACCTTGCACTGCCTACTAAGAGAGTCACTTGGGTAGCGCCGTTAGGTGT
CCGCGGAGCGGACTACACATACAACCTAGAGTTGGGTCTGCCAGCAACGCTTGGTAGGTATGACCTAGTGGTCATAAACA
TCCACACACCTTTTCGCATACACCATTACCAACAGTGCGTCGACCACGCAATGAAACTGCAAATGCTCGGGGGTGACTCAT
TGAGACTGCTCAAACCGGGCGGCTCTCTATTGATCAGAGCATATGGTTACGCAGATAGAACCAGTGAACGAGTCATCTGC
GTATTGGGACGCAAGTTTAGATCGTCTAGAGCGTTGAAACCACCATGTGTCACCAGCAACACTGAGATGTTTTTCCTATTC
AGCAACTTTGACAATGGCAGAAGGAATTTCACAACTCATGTCATGAACAATCAACTGAATGCAGCCTTCGTAGGACAGGT
CACCCGAGCAGGATGTGCACCGTCGTACCGGGTAAAACGCATGGACATCGCGAAGAACGATGAAGAGTGCGTAGTCAAC
GCCGCTAACCCTCGCGGGTTACCGGGTGGCGGTGTTTGCAAGGCAGTATACAAAAAATGGCCGGAGTCCTTTAAGAACA
GTGCAACACCAGTGGGAACCGCAAAAACAGTTATGTGCGGTACGTATCCAGTAATCCACGCTGTTGGACCAAACTTCTCT
AATTATTCGGAGTCTGAAGGGGACCGGGAATTGGCAGCTGCCTATCGAGAAGTCGCAAAGGAAGTAACTAGGCTGGGA
GTAAATAGTGTAGCTATACCTCTCCTCTCCACAGGTGTATACTCAGGAGGGAAAGACAGGCTGACCCAGTCACTGAACCA
CCTCTTTACAGCCATGGACTCGACGGATGCAGACGTGGTCATCTACTGCCGCGACAAAGAATGGGAGAAGAAAATATCTG
AGGCCATACAGATGCGGACCCAAGTAGAGCTGCTGGATGAGCACATCTCCATAGACTGCGATATTGTTCGCGTGCACCCT
GACAGCAGCTTGGCAGGCAGAAAAGGATACAGCACCACGGAAGGCGCACTGTACTCATATCTAGAAGGGACCCGTTTTC
ATCAGACGGCTGTGGATATGGCGGAGATACATACTATGTGGCCAAAGCAAACAGAGGCCAATGAGCAAGTCTGCCTATA
TGCCCTGGGGGAAAGTATTGAATCGATCAGGCAGAAATGCCCGGTGGATGATGCAGACGCATCATCTCCCCCCAAAACTG
TCCCGTGCCTTTGCCGTTACGCTATGACTCCAGAACGCGTCACCCGGCTTCGCATGAACCACGTCACAAGCATAATTGTGT
GTTCTTCGTTTCCCCTCCCAAAGTACAAAATAGAAGGAGTGCAAAAAGTCAAATGCTCTAAGGTAATGCTATTTGACCACA
ACGTGCCATCGCGCGTAAGTCCAAGGGCTTATAGAGGTGCCGCTGCCGGTAACCTTGCGGCCGTGTCTGATTGGGTAATG
AGCACCGTACCTGTCGCGCCGCCCAGAAGAAGGCGAGGGAGAAACCTGACTGTGACATGTGACGAGAGAGAAGGGAAT
ATAACACCCATGGCTAGCGTCCGATTCTTTAGGGCAGAGCTGTGTCCGGTCGTACAAGAAACAGCGGAGACGCGTGACA
CAGCAATGTCTCTTCAGGCACCACCGAGTACCGCCACGGAACCGAATCATCCGCCGATCTCCTTCGGAGCATCAAGCGAG
ACGTTCCCCATTACATTTGGGGACTTCAACGAAGGAGAAATCGAAAGCTTGTCTTCTGAGCTACTAACTTTCGGAGACTTC
TTACCAGGAGAAGTGGATGACTTGACAGACAGCGACTGGTCCACGTGCTCAGACACGGACGACGAGTTAAGACTAGACA
GGGCAGGTGGGTATATATTCTCGTCGGACACCGGTCCAGGTCATTTACAACAGAAGTCAGTACGCCAGTCAGTGCTGCCG
GTGAACACCCTGGAGGAAGTCCACGAGGAGAAGTGTTACCCACCTAAGCTGGATGAAGCAAAGGAGCAACTATTACTTA
AGAAACTCCAGGAGAGTGCATCCATGGCCAACAGAAGCAGGTATCAGTCGCGCAAAGTAGAAAACATGAAAGCAGCAAT
CATCCAGAGACTAAAGAGAGGCTGTAGACTATACTTAATGTCAGAGACCCCAAAAGTCCCTACTTACCGGACTACATATCC
GGCGCCTGTGTACTCGCCTCCGATCAACGTCCGATTGTCCAATCCCGAGTCCGCAGTGGCAGCATGCAATGAGTTCTTAGC
TAGAAACTATCCAACTGTCTCATCATACCAAATTACCGACGAGTATGATGCATATCTAGACATGGTGGACGGGTCGGAGA
GTTGCCTGGACCGAGCGACATTCAATCCGTCAAAACTCAGGAGCTACCCGAAACAGCACGCTTACCACGCGCCCTCCATC
AGAAGCGCTGTACCGTCCCCATTCCAGAACACACTACAGAATGTACTGGCAGCAGCCACGAAAAGAAACTGCAACGTCAC
ACAGATGAGGGAATTACCCACTTTGGACTCAGCAGTATTCAACGTGGAGTGTTTCAAAAAATTCGCATGCAACCAAGAAT
ACTGGGAAGAATTTGCTGCCAGCCCTATTAGGATAACAACTGAGAATTTAGCAACCTATGTTACTAAACTAAAAGGGCCA
```

-continued
```
AAAGCAGCAGCGCTATTCGCAAAAACCCATAATCTACTGCCACTACAGGAAGTACCAATGGATAGGTTCACAGTAGATAT
GAAAAGGGACGTAAAGGTGACTCCTGGTACAAAGCATACAGAGGAAAGACCTAAGGTGCAGGTTATACAGGCGGCTGA
ACCCTTGGCGACAGCATACCTATGTGGGATTCACAGAGAGCTGGTTAGGAGGCTGAACGCCGTCCTCCTACCCAATGTAC
ATACACTATTTGACATGTCTGCCGAGGATTTCGATGCCATCATAGCCGCACACTTTAAGCCAGGAGACACTGTTTTGGAAA
CGGACATAGCCTCCTTTGATAAGAGCCAAGATGATTCACTTGCGCTTACTGCTTTGATGCTGTTAGAGGATTTAGGGGTGG
ATCACTCCCTGCTGGACTTGATAGAGGCTGCTTTCGGAGAGATTTCCAGCTGTCACCTACCGACAGGTACGCGCTTCAAGT
TCGGCGCCATGATGAAATCAGGTATGTTCCTAACTCTGTTCGTCAACACATTGTTAAACATCACCATCGCCAGCCGAGTGC
TGGAAGATCGTCTGACAAAATCCGCGTGCGCGGCCTTCATCGGCGACGACAACATAATACATGGAGTCGTCTCCGATGAA
TTGATGGCAGCCAGATGTGCCACTTGGATGAACATGGAAGTGAAGATCATAGATGCAGTTGTATCCTTGAAAGCCCCTTA
CTTTTGTGGAGGGTTTATACTGCACGATACTGTGACAGGAACAGCTTGCAGAGTGGCAGACCCGCTAAAAAGGCTTTTTA
AACTGGGCAAACCGCTAGCGGCAGGTGACGAACAAGATGAAGATAGAAGACGAGCGCTGGCTGACGAAGTGATCAGAT
GGCAACGAACAGGGCTAATTGATGAGCTGGAGAAAGCGGTATACTCTAGGTACGAAGTGCAGGGTATATCAGTTGTGGT
AATGTCCATGGCCACCTTTGCAAGCTCCAGATCCAACTTCGAGAAGCTCAGAGGACCCGTCATAACTTTGTACGGCGGTCC
TAAATAGGTACGCACTACAGCTACCTATTTTGCAGAAGCCGACAGCAAGTATCTAAACACTAATCAGCTACAATGGAGTTC
ATCCCAACCCAAACTTTTTACAATAGGAGGTACCAGCCTCGACCCTGGACTCCGCGCCCTACTATCCAAGTCATCAGGCCC
AGACCGCGCCCTCAGAGGCAAGCTGGGCAACTTGCCCAGCTGATCTCAGCAGTTAATAAACTGACAATGCGCGCGGTACC
ACAACAGAAGCCACGCAGGAATCGGAAGAATAAGAAGCAAAAGCAAAACAACAGGCGCCACAAAACAACACAAATCA
AAAGAAGCAGCCACCTAAAAAGAAACCGGCTCAAAAGAAAAAGAAGCCGGGCCGCAGAGAGAGGATGTGCATGAAAAT
CGAAAATGATTGTATTTTCGAAGTCAAGCACGAAGGTAAGGTAACAGGTTACGCGTGCCTGGTGGGGACAAAGTAATG
AAACCAGCACACGTAAAGGGGACCATCGATAACGCGGACCTGGCCAAACTGGCCTTTAAGCGGTCATCTAAGTATGACCT
TGAATGCGCGCAGATACCCGTGCACATGAAGTCCGACGCTTCGAAGTTCACCCATGAGAAACCGGAGGGGTACTACAACT
GGCACCACGGAGCAGTACAGTACTCAGGAGGCCGGTTCACCATCCCTACAGGTGCTGGCAAACCAGGGGACAGCGGCA
GACCGATCTTCGACAACAAGGGACGCGTGGTGGCCATAGTCTTAGGAGGAGCTAATGAAGGAGCCCGTACAGCCCTCTC
GGTGGTGACCTGGAATAAAGACATTGTCACTAAAATCACCCCCGAGGGGGCCGAAGAGTGGAGTCTTGCCATCCCAGTT
ATGTGCCTGTTGGCAAACACCACGTTCCCCTGCTCCCAGCCCCCTTGCACGCCCTGCTGCTACGAAAAGGAACCGGAGGA
AACCCTACGCATGCTTGAGGACAACGTCATGAGACCTGGGTACTATCAGCTGCTACAAGCATCCTTAACATGTTCTCCCCA
CCGCCAGCGACGCAGCACCAAGGACAACTTCAATGTCTATAAAGCCACAAGACCATACTTAGCTCACTGTCCCGACTGTG
GAGAAGGGCACTCGTGCCATAGTCCCGTAGCACTAGAACGCATCAGAAATGAAGCGACAGACGGGACGCTGAAAATCCA
GGTCTCCTTGCAAATCGGAATAAAGACGGATGACAGCCACGATTGGACCAAGCTGCGTTATATGGACAACCACATGCCAG
CAGACGCAGAGAGGGCGGGGCTATTTGTAAGAACATCAGCACCGTGTACGATTACTGGAACAATGGGACACTTCATCCT
GGCCCGATGTCCAAAAGGGGAAACTCTGACGGTGGGATTCACTGACAGTAGGAAGATTAGTCACTCATGTACGCACCCAT
TTCACCACGACCCTCCTGTGATAGGTCGGGAAAAATTCCATTCCCGACCGCAGCACGGTAAAGAGCTACCTTGCAGCACG
TACGTGCAGAGCACCGCCGCAACTACCGAGGAGATAGAGGTACACATGCCCCCAGACACCCCTGATCGCACATTAATGTC
ACAACAGTCCGGCAACGTAAAGATCACAGTCAATGGCCAGACGGTGCGGTACAAGTGTAATTGCGGTGGCTCAAATGAA
GGACTAACAACTACAGACAAAGTGATTAATAACTGCAAGGTTGATCAATGTCATGCCGCGGTCACCAATCACAAAAAGTG
GCAGTATAACTCCCCTCTGGTCCCGCGTAATGCTGAACTTGGGGACCGAAAAGGAAAAATTCACATCCCGTTTCCGCTGGC
AAATGTAACATGCAGGGTGCCTAAAGCAAGGAACCCCACCGTGACGTACGGGAAAAACCAAGTCATCATGCTACTGTATC
CTGACCACCCAACACTCCTGTCCTACCGGAATATGGGAGAAGAACCCAAACTATCAAGAAGAGTGGGTGATGCATAAGAA
GGAAGTCGTGCTAACCGTGCCGACTGAAGGGCTCGAGGTCACGTGGGGCAACAACGAGCCGTATAAGTATTGGCCGCAG
TTATCTACAAACGGTACAGCCCATGGCCACCCGCATGAGATAATTCTGTATTATTATGAGCTGTACCCCACTATGACTGTA
GTAGTTGTGTCAGTGGCCACGTTCATACTCCTGTCGATGGTGGGTATGGCAGCGGGGATGTGCATGTGTGCACGACGCA
```

-continued

GATGCATCACACCGTATGAACTGACACCAGGAGCTACCGTCCCTTTCCTGCTTAGCCTAATATGCTGCATCAGAACAGCTA
AAGCGGCCACATACCAAGAGGCTGCGATATACCTGTGGAACGAGCAGCAACCTTTGTTTTGGCTACAAGCCCTTATTCCG
CTGGCAGCCCTGATTGTTCTATGCAACTGTCTGAGACTCTTACCATGCTGCTGTAAAACGTTGGCTTTTTTAGCCGTAATGA
GCGTCGGTGCCCACACTGTGAGCGCGTACGAACACGTAACAGTGATCCCGAACACGGTGGGAGTACCGTATAAGACTCT
AGTCAATAGACCTGGCTACAGCCCCATGGTATTGGAGATGGAACTACTGTCAGTCACTTTGGAGCCAACACTATCGCTTGA
TTACATCACGTGCGAGTACAAAACCGTCATCCCGTCTCCGTACGTGAAGTGCTGCGGTACAGCAGAGTGCAAGGACAAAA
ACCTACCTGACTACAGCTGTAAGGTCTTCACCGGCGTCTACCCATTTATGTGGGCGGCGCCTACTGCTTCTGCGACGCTG
AAAACACGCAGTTGAGCGAAGCACACGTGGAGAAGTCCGAATCATGCAAAACAGAATTTGCATCAGCATACAGGGCTCA
TACCGCATCTGCATCAGCTAAGCTCCGCGTCCTTTACCAAGGAAATAACATCACTGTAACTGCCTATGCAAACGGCGACCA
TGCCGTCACAGTTAAGGACGCCAAATTCATTGTGGGGCCAATGTCTTCAGCCTGGACACCTTTCGACAACAAAATTGTGGT
GTACAAAGGTGACGTCTATAACATGGACTACCCGCCCTTTGGCGCAGGAAGACCAGGACAATTTGGCGATATCCAAAGTC
GCACACCTGAGAGTAAAGACGTCTATGCTAATACACAACTGGTACTGCAGAGACCGGCTGTGGGTACGGTACACGTGCC
ATACTCTCAGGCACCATCTGGCTTTAAGTATTGGCTAAAAGAACGCGGGGCGTCGCTGCAGCACACAGCACCATTTGGCT
GCCAAATAGCAACAAACCCGGTAAGAGCGGTGAACTGCGCCGTAGGGAACATGCCCATCTCCATCGACATACCGGAAGC
GGCCTTCACTAGGGTCGTCGACGCGCCCTCTTTAACGGACATGTCGTGCGAGGTACCAGCCTGCACCCATTCCTCAGACTT
TGGGGGCGTCGCCATTATTAAATATGCAGCCAGCAAGAAAGGCAAGTGTGCGGTGCATTCGATGACTAACGCCGTCACTA
TCGGGAAGCTGAGATAGAAGTTGAAGGGAATTCTCAGCTGCAAATCTCTTTCTCGACGGCCTTAGCCAGCGCCGAATTC
CGCGTACAAGTCTGTTCTACACAAGTACACTGTGCAGCCGAGTGCCACCCCCCGAAGGACCACATAGTCAACTACCCGGC
GTCACATACCACCCTCGGGGTCCAGGACATCTCCGCTACGGCGATGTCATGGGTGCAGAAGATCACGGGAGGTGTGGGA
CTGGTTGTTGCTGTTGCCGCACTGATTCTAATCGTGGTGCTATGCGTGTCGTTCAGCAGGCACTAACTTGACAATTAAGTA
TGAAGGTATATGTGTCCCCTAAGAGACACACTGTACATAGCAAATAATCTATAGATCAAAGGGCTACGCAACCCCTGAAT
AGTAACAAAATACAAAATCACTAAAAATTATAAAAACAGAAAAATACATAAATAGGTATACGTGTCCCCTAAGAGACACA
TTGTATGTAGGTGATAAGTATAGATCAAAGGGCCGAATAACCCCTGAATAGTAACAAAATATGAAAATCAATAAAAATCA
TAAAATAGAAAAACCATAAACAGAAGTAGTTCAAAGGGCTATAAAACCCCTGAATAGTAACAAAACATAAAATTAATAAA
AATCAAATGAATACCATAATTGGCAAACGGAAGAGATGTAGGTACTTAAGCTTCCTAAAAGCAGCCGAACTCACTTTGAG
AAGTAGGCATAGCATACCGAACTCTTCCACGATTCTCCGAACCCACAGGGACGTAGGAGATGTTATTTTGTTTTTAATATTT
CAAAAAAAAAAAAAAAAAAAAAAAA

ZIKV Sequence H/PF/2013 as sequenced

SEQ ID NO: 78

CAGACTGCGACAGTTCGAGTTTGAAGCGAAAGCTAGCAACAGTATCAACAGGTTTTATTTTGGATTTGGAAACGAGAGTT
TCTGGTCATGAAAAACCCAAAAAGAAATCCGGAGGATTCCGGATTGTCAATATGCTAAAACGCGGAGTAGCCCGTGTG
AGCCCCTTTGGGGGCTTGAAGAGGCTGCCAGCCGGACTTCTGCTGGGTCATGGGCCCATCAGGATGGTCTTGGCGATTCT
AGCCTTTTTGAGATTCACGGCAATCAAGCCATCACTGGGTCTCATCAATAGATGGGGTTCAGTGGGGAAAAAGAGGCTA
TGGAAATAATAAAGAAGTTCAAGAAAGATCTGGCTGCCATGCTGAGAATAATCAATGCTAGGAAGGAGAAGAAGAGAC
GAGGCGCAGATACTAGTGTCGGAATTGTTGGCCTCCTGCTGACCACAGCTATGGCAGCGGAGGTCACTAGACGTGGGAG
TGCATACTATATGTACTTGGACAGAAACGACGCTGGGGAGGCCATATCTTTTCCAACCACATTGGGGATGAATAAGTGTT
ATATACAGATCATGGATCTTGGACACATGTGTGATGCCACCATGAGCTATGAATGCCCTATGCTGGATGAGGGGGTGGAA
CCAGATGACGTCGATTGTTGGTGCAACACGACGTCAACTTGGGTTGTGTACGGAACCTGCCATCACAAAAAAGGTGAAGC
ACGGAGATCTAGAAGAGCTGTGACGCTCCCCTCCCATTCCACTAGGAAGCTGCAAACGCGGTCGCAAACCTGGTTGGAAT
CAAGAGAATACACAAAGCACTTGATTAGAGTCGAAAATTGGATATTCAGGAACCCTGGCTTCGCGTTAGCAGCAGCTGCC
ATCGCTTGGCTTTTGGGAAGCTCAACGAGCCAAAAAGTCATATACTTGGTCATGATACTGCTGATTGCCCCGGCATACAGC
ATCAGGTGCATAGGAGTCAGCAATAGGGACTTTGTGGAAGGTATGTCAGGTGGGACTTGGGTTGATGTTGTCTTGGAAC

-continued

```
ATGGAGGTTGTGTCACCGTAATGGCACAGGACAAACCGACTGTCGACATAGAGCTGGTTACAACAACAGTCAGCAACAT
GGCGGAGGTAAGATCCTACTGCTATGAGGCATCAATATCGGACATGGCTTCGGACAGCCGCTGCCCAACACAAGGTGAA
GCCTACCTTGACAAGCAATCAGACACTCAATATGTCTGCAAAAGAACGTTAGTGGACAGAGGCTGGGGAAATGGATGTG
GACTTTTTGGCAAAGGGAGCCTGGTGACATGCGCTAAGTTTGCATGCTCCAAGAAAATGACCGGGAAGAGCATCCAGCC
AGAGAATCTGGAGTACCGGATAATGCTGTCAGTTCATGGCTCCCAGCACAGTGGGATGATCGTTAATGACACAGGACATG
AAACTGATGAGAATAGAGCGAAGGTTGAGATAACGCCCAATTCACCAAGAGCCGAAGCCACCCTGGGGGGTTTTGGAAG
CCTAGGACTTGATTGTGAACCGAGGACAGGCCTTGACTTTTCAGATTTGTATTACTTGACTATGAATAACAAGCACTGGTT
GGTTCACAAGGAGTGGTTCCACGACATTCCATTACCTTGGCACGCTGGGGCAGACACCGGAACTCCACACTGGAACAACA
AAGAAGCACTGGTAGAGTTCAAGGACGCACATGCCAAAAGGCAAACTGTCGTGGTTCTAGGGAGTCAAGAAGGAGCAG
TTCACACGGCCCTTGCTGGAGCTCTGGAGGCTGAGATGGATGGTGCAAAGGGAAGGCTGTCCTCTGGCCACTTGAAATG
TCGCCTGAAAATGGATAAACTTAGATTGAAGGGCGTGTCATACTCCTTGTGTACCGCAGCGTTCACATTCACCAAGATCCC
GGCTGAAACACTGCACGGGACAGTCACAGTGGAGGTACAGTACGCAGGGACAGATGGACCTTGCAAGGTTCCAGCTCAG
ATGGCGGTGGACATGCAAACTCTGACCCCAGTTGGGAGGTTGATAACCGCTAACCCCGTAATCACTGAAAGCACTGAGAA
CTCTAAGATGATGCTGGAACTTGATCCACCATTTGGGGACTCTTACATTGTCATAGGAGTCGGGGAGAAGAAGATCACCC
ACCACTGGCACAGGAGTGGCAGCACCATTGGAAAAGCATTTGAAGCCACTGTGAGAGGTGCCAAGAGAATGGCAGTCTT
GGGAGACACAGCCTGGGACTTTGGATCAGTTGGAGGCGCTCTCAACTCATTGGGCAAGGGCATCCATCAAATTTTTGGAG
CAGCTTTCAAATCATTGTTTGGAGGAATGTCCTGGTTCTCACAAATTCTCATTGGAACGTTGCTGATGTGGTTGGGTCTGA
ACACAAAGAATGGATCTATTTCCCTTATGTGCTTGGCCTTAGGGGGAGTGTTGATCTTCTTATCCACAGCTGTCTCTGCTGA
TGTGGGGTGCTCGGTGGACTTCTCAAAGAAGGAGACGAGATGCGGTACAGGGGTGTTCGTCTATAACGACGTTGAAGCC
TGGAGGGACAGGTACAAGTACCATCCTGACTCCCCCCGTAGATTGGCAGCAGCAGTCAAGCAAGCCTGGGAAGATGGTA
TCTGTGGGATCTCCTCTGTTTCAAGAATGGAAAACATCATGTGGAGATCAGTAGAAGGGGAGCTCAACGCAATCCTGGAA
GAGAATGGAGTTCAACTGACGGTCGTTGTGGGATCTGTAAAAAACCCCATGTGGAGAGGTCCACAGAGATTGCCCGTGC
CTGTGAACGAGCTGCCCCACGGCTGGAAGGCTTGGGGGAAATCGTACTTCGTCAGAGCAGCAAAGACAAATAACAGCTT
TGTCGTGGATGGTGACACACTGAAGGAATGCCCACTCAAACATAGAGCATGGAACAGCTTTCTTGTGGAGGATCATGGGT
TCGGGGTATTTCACACTAGTGTCTGGCTCAAGGTTAGAGAAGATTATTCATTAGAGTGTGATCCAGCCGTTATTGGAACAG
CTGTTAAGGGAAAGGAGGCTGTACACAGTGATCTAGGCTACTGGATTGAGAGTGAGAAGAATGACACATGGAGGCTGA
AGAGGGCCCATCTGATCGAGATGAAAACATGTGAATGGCCAAAGTCCCACACATTGTGGACAGATGGAATAGAAGAGAG
TGATCTGATCATACCCAAGTCTTTAGCTGGGCCACTCAGCCATCACAATACCAGAGAGGGCTACAGGACCCAAATGAAAG
GGCCATGGCACAGTGAAGAGCTTGAAATTCGGTTTGAGGAATGCCCAGGCACTAAGGTCCACGTGGAGGAAACATGTGG
AACAAGAGGACCATCTCTGAGATCAACCACTGCAAGCGGAAGGGTGATCGAGGAATGGTGCTGCAGGGAGTGCACAAT
GCCCCCACTGTCGTTCCGGGCTAAAGATGGCTGTTGGTATGGAATGGAGATAAGGCCCAGGAAAGAACCAGAAAGTAAC
TTAGTAAGGTCAATGGTGACTGCAGGATCAACTGATCACATGGATCACTTCTCCCTTGGAGTGCTTGTGATTCTGCTCATG
GTGCAGGAAGGGCTGAAGAAGAGAATGACCACAAAGATCATCATAAGCACATCGATGGCAGTGCTGGTAGCTATGATCC
TGGGAGGATTTTCAATGAGTGACCTGGCTAAGCTTGCAATTTTGATGGGTGCCACCTTCGCGGAAATGAACACTGGAGGA
GATGTAGCTCATCTGGCGCTGATAGCGGCATTCAAAGTCAGACCAGCGTTGCTGGTATCTTTCATCTTCAGAGCTAATTGG
ACACCCCGTGAAAGCATGCTGCTGGCCTTGGCCTCGTGTCTTTTGCAAACTGCGATCTCCGCCTTGGAAGGCGACCTGATG
GTTCTCATCAATGGTTTTGCTTTGGCCTGGTTGGCAATACGAGCGATGGTTGTTCCACGCACTGATAACATCACCTTGGCA
ATCCTGGCTGCTCTGACACCACTGGCCCGGGGCACACTGCTTGTGGCGTGGAGAGCAGGCCTTGCTACTTGCGGGGGGTT
TATGCTCCTCTCTCTGAAGGGAAAAGGCAGTGTGAAGAAGAACTTACCATTTGTCATGGCCCTGGGACTAACCGCTGTGA
GGCTGGTCGACCCCATCAACGTGGTGGGACTGCTGTTGCTCACAAGGAGTGGGAAGCGGAGCTGGCCCCCTAGCGAAGT
ACTCACAGCTGTTGGCCTGATATGCGCATTGGCTGGAGGGTTCGCCAAGGCAGATATAGAGATGGCTGGGCCCATGGCC
```

```
GCGGTCGGTCTGCTAATTGTCAGTTACGTGGTCTCAGGAAAGAGTGTGGACATGTACATTGAAAGAGCAGGTGACATCAC
ATGGGAAAAAGATGCGGAAGTCACTGGAAACAGTCCCCGGCTCGATGTGGCGCTAGATGAGAGTGGTGATTTCTCCCTG
GTGGAGGATGACGGTCCCCCCATGAGAGAGATCATACTCAAGGTGGTCCTGATGACCATCTGTGGCATGAACCCAATAGC
CATACCCTTTGCAGCTGGAGCGTGGTACGTATACGTGAAGACTGGAAAAAGGAGTGGTGCTCTATGGGATGTGCCTGCTC
CCAAGGAAGTAAAAAAGGGGGAGACCACAGATGGAGTGTACAGAGTAATGACTCGTAGACTGCTAGGTTCAACACAAGT
TGGAGTGGGAGTTATGCAAGAGGGGGTCTTTCACACTATGTGGCACGTCACAAAAGGATCCGCGCTGAGAAGCGGTGAA
GGGAGACTTGATCCATACTGGGGAGATGTCAAGCAGGATCTGGTGTCATACTGTGGTCCATGGAAGCTAGATGCCGCCT
GGGACGGGCACAGCGAGGTGCAGCTCTTGGCCGTGCCCCCCGGAGAGAGAGCGAGGAACATCCAGACTCTGCCCGGAA
TATTTAAGACAAAGGATGGGGACATTGGAGCGGTTGCGCTGGATTACCCAGCAGGAACTTCAGGATCTCCAATCCTAGAC
AAGTGTGGGAGAGTGATAGGACTTTATGGCAATGGGGTCGTGATCAAAAATGGGAGTTATGTTAGTGCCATCACCCAAG
GGAGGAGGGAGGAAGAGACTCCTGTTGAGTGCTTCGAGCCTTCGATGCTGAAGAAGAAGCAGCTAACTGTCTTAGACTT
GCATCCTGGAGCTGGGAAAACCAGGAGAGTTCTTCCTGAAATAGTCCGTGAAGCCATAAAAACAAGACTCCGTACTGTGA
TCTTAGCTCCAACCAGGGTTGTCGCTGCTGAAATGGAGGAAGCCCTTAGAGGGCTTCCAGTGCGTTATATGACAACAGCA
GTCAATGTCACCCACTCTGGAACAGAAATCGTCGACTTAATGTGCCATGCCACCTTCACTTCACGTCTACTACAGCCAATCA
GAGTCCCCAACTATAATCTGTATATTATGGATGAGGCCCACTTCACAGATCCCTCAAGTATAGCAGCAAGAGGATACATTT
CAACAAGGGTTGAGATGGGCGAGGCGGCTGCCATCTTCATGACCGCCACGCCACCAGGAACCCGTGACGCATTTCCGGA
CTCCAACTCACCAATTATGGACACCGAAGTGGAAGTCCCAGAGAGAGCCTGGAGCTCAGGCTTTGATTGGGTGACGGATC
ATTCTGGAAAAACAGTTTGGTTTGTTCCAAGCGTGAGGAACGGCAATGAGATCGCAGCTTGTCTGACAAAGGCTGGAAA
ACGGGTCATACAGCTCAGCAGAAAGACTTTTGAGACAGAGTTCCAGAAAACAAAACATCAAGAGTGGGACTTTGTCGTG
ACAACTGACATTTCAGAGATGGGCGCCAACTTTAAAGCTGACCGTGTCATAGATTCCAGGAGATGCCTAAAGCCGGTCAT
ACTTGATGGCGAGAGAGTCATTCTGGCTGGACCCATGCCTGTCACACATGCCAGCGCTGCCCAGAGGAGGGGCGCATA
GGCAGGAATCCCAACAAACCTGGAGATGAGTATCTGTATGGAGGTGGGTGCGCAGAGACTGACGAAGACCATGCACACT
GGCTTGAAGCAAGAATGCTCCTTGACAATATTTACCTCCAAGATGGCCTCATAGCCTCGCTCTATCGACCTGAGGCCGACA
AAGTAGCAGCCATTGAGGGAGAGTTCAAGCTTAGGACGGAGCAAAGGAAGACCTTTGTGGAACTCATGAAAAGAGGAG
ATCTTCCTGTTTGGCTGGCCTATCAGGTTGCATCTGCCGAATAACCTACACAGATAGAAGATGGTGCTTTGATGGCACGA
CCAACAACACCATAATGGAAGACAGTGTGCCGGCAGAGGTGTGGACCAGACACGGAGAGAAAAGAGTGCTCAAACCGA
GGTGGATGGACGCCAGAGTTTGTTCAGATCATGCGGCCCTGAAGTCATTCAAGGAGTTTGCCGCTGGGAAAAGAGGAGC
GGCTTTTGGAGTGATGGAAGCCCTGGGAACACTGCCAGGACACATGACAGAGAGATTCCAGGAAGCCATTGACAACCTC
GCTGTGCTCATGCGGGCAGAGACTGGAAGCAGGCCTTACAAAGCCGCGGCGGCCCAATTGCCGGAGACCCTAGAGACCA
TTATGCTTTTGGGGTTGCTGGGAACAGTCTCGCTGGGAATCTTTTTCGTCTTGATGAGGAACAAGGGCATAGGGAAGATG
GGCTTTGGAATGGTGACTCTTGGGGCCAGCGCATGGCTCATGTGGCTCTCGGAAATTGAGCCAGCCAGAATTGCATGTGT
CCTCATTGTTGTGTTCCTATTGCTGGTGGTGCTCATACCTGAGCCAGAAAAGCAAAGATCTCCCCAGGACAACCAAATGGC
AATCATCATCATGGTAGCAGTAGGTCTTCTGGGCTTGATTACCGCCAATGAACTCGGATGGTTGGAGAGAACAAAGAGTG
ACCTAAGCCATCTAATGGGAAGGAGAGGAGGGGGCAACCATAGGATTCTCAATGGACATTGACCTGCGGCCAGCCTC
AGCTTGGGCCATCTATGCTGCCTTGACAACTTTCATTACCCCAGCCGTCCAACATGCAGTGACCACTTCATACAACAACTAC
TCCTTAATGGCGATGGCCACGCAAGCTGGAGTGTTGTTTGGTATGGGCAAAGGGATGCCATTCTACGCATGGGACTTTGG
AGTCCCGCTGCTAATGATAGGTTGCTACTCACAATTAACACCCCTGACCCTAATAGTGGCCATCATTTTGCTCGTGGCGCAC
TACATGTACTTGATCCCAGGGCTGCAGGCAGCAGCTGCGCGTGCTGCCCAGAAGAGAACGGCAGCTGGCATCATGAAGA
ACCCTGTTGTGGATGGAATAGTGGTGACTGACATTGACACAATGACAATTGACCCCCAAGTGGAGAAAAAGATGGGACA
GGTGCTACTCATAGCAGTAGCCGTCTCCAGCGCCATACTGTCGCGGACCGCCTGGGGGTGGGGGGAGGCTGGGGCCCTG
ATCACAGCGGCAACTTCCACTTTGTGGGAAGGCTCTCCGAACAAGTACTGGAACTCCTCTACAGCCACTTCACTGTGTAAC
```

-continued
```
ATTTTTAGGGGAAGTTACTTGGCTGGAGCTTCTCTAATCTACACAGTAACAAGAAACGCTGGCTTGGTCAAGAGACGTGG
GGGTGGAACAGGAGAGACCCTGGGAGAGAAATGGAAGGCCCGCTTGAACCAGATGTCGGCCCTGGAGTTCTACTCCTAC
AAAAAGTCAGGCATCACCGAGGTGTGCAGAGAAGAGGCCCGCCGCGCCCTCAAGGACGGTGTGGCAACGGGAGGCCAT
GCTGTGTCCCGAGGAAGTGCAAAGCTGAGATGGTTGGTGGAGCGGGGATACCTGCAGCCCTATGGAAAGGTCATTGATC
TTGGATGTGGCAGAGGGGGCTGGAGTTACTACGCCGCCACCATCCGCAAAGTTCAAGAAGTGAAAGGATACACAAAAGG
AGGCCCTGGTCATGAAGAACCCATGTTGGTGCAAAGCTATGGGTGGAACATAGTCCGTCTTAAGAGTGGGGTGGACGTC
TTTCATATGGCGGCTGAGCCGTGTGACACGTTGCTGTGTGACATAGGTGAGTCATCATCTAGTCCTGAAGTGGAAGAAGC
ACGGACGCTCAGAGTCCTCTCCATGGTGGGGGATTGGCTTGAAAAAAGACCAGGAGCCTTTTGTATAAAAGTGTTGTGCC
CATACACCAGCACTATGATGGAAACCCTGGAGCGACTGCAGCGTAGGTATGGGGAGGACTGGTCAGAGTGCCACTCTC
CCGCAACTCTACACATGAGATGTACTGGGTCTCTGGAGCGAAAAGCAACACCATAAAAAGTGTGTCCACCACGAGCCAGC
TCCTCTTGGGGCGCATGGACGGGCCCAGGAGGCCAGTGAAATATGAGGAGGATGTGAATCTCGGCTCTGGCACGCGGG
CTGTGGTAAGCTGCGCTGAAGCTCCCAACATGAAGATCATTGGTAACCGCATTGAAAGGATCCGCAGTGAGCACGCGGA
AACGTGGTTCTTTGACGAGAACCACCCATATAGGACATGGGCTTACCATGGAAGCTATGAGGCCCCCACACAAGGGTCAG
CGTCCTCTCTAATAAACGGGGTTGTCAGGCTCCTGTCAAAACCCTGGGATGTGGTGACTGGAGTCACAGGAATAGCCATG
ACCGACACCACACCGTATGGTCAGCAAAGAGTTTTCAAGGAAAAAGTGGACACTAGGGTGCCAGACCCCCAAGAAGGCA
CTCGTCAGGTTATGAGCATGGTCTCTTCCTGGTTGTGGAAAGAGCTAGGCAAACACAAACGGCCACGAGTCTGTACCAAA
GAAGAGTTCATCAACAAGGTTCGTAGCAATGCAGCATTAGGGGCAATATTTGAAGAGGAAAAAGAGTGGAAGACTGCAG
TGGAAGCTGTGAACGATCCAAGGTTCTGGGCTCTAGTGGACAAGGAAAGAGAGCACCACCTGAGAGGAGAGTGCCAGA
GTTGTGTGTACAACATGATGGGAAAAAGAGAAAAGAAACAAGGGGAATTTGGAAAGGCCAAGGGCAGCCGCGCCATCT
GGTATATGTGGCTAGGGGCTAGATTTCTAGAGTTCGAAGCCCTTGGATTCTTGAACGAGGATCACTGGATGGGGAGAGA
GAACTCAGGAGGTGGTGTTGAAGGGCTGGGATTACAAAGACTCGGATATGTCCTAGAAGAGATGAGTCGCATACCAGGA
GGAAGGATGTATGCAGATGACACTGCTGGCTGGGACACCCGCATCAGCAGGTTTGATCTGGAGAATGAAGCTCTAATCA
CCAACCCAAATGGAGAAAGGGCACAGGGCCTTGGCATTGGCCATAATCAAGTACACATACCAAAACAAAGTGGTAAAGGT
CCTTAGACCAGCTGAAAAAGGGAAGACAGTTATGGACATTATTTCGAGACAAGACCAAAGGGGGAGCGGACAAGTTGTC
ACTTACGCTCTTAACACATTTACCAACCTAGTGGTGCAACTCATTCGGAATATGGAGGCTGAGGAAGTTCTAGAGATGCAA
GACTTGTGGCTGCTGCGGAGGTCAGAGAAAGTGACCAACTGGTTGCAGAGCAACGGATGGGATAGGCTCAAACGAATG
GCAGTCAGTGGAGATGATTGCGTTGTGAAGCCAATTGATGATAGGTTTGCACATGCCCTCAGGTTCTTGAATGATATGGG
AAAAGTTAGGAAGGACACACAAGAGTGGAAACCCTCAACTGGATGGGACAACTGGGAAGAAGTTCCGTTTTGCTCCCAC
CACTTCAACAAGCTCCATCTCAAGGACGGGAGGTCCATTGTGGTTCCCTGCCGCCACCAAGATGAACTGATTGGCCGGGC
CCGCGTCTCTCCAGGGGCGGGATGGAGCATCCGGGAGACTGCTTGCCTAGCAAAATCATATGCGCAAATGTGGCAGCTC
CTTTATTTCCACAGAAGGGACCTCCGACTGATGGCCAATGCCATTTGTTCATCTGTGCCAGTTGACTGGGTTCCAACTGGG
AGAACTACCTGGTCAATCCATGGAAAGGGAGAATGGATGACCACTGAAGACATGCTTGTGGTGTGGAACAGAGTGTGGA
TTGAGGAGAACGACCACATGGAAGACAAGACCCCAGTTACGAAATGGACAGACATTCCCTATTTGGGAAAAAGGGAAGA
CTTGTGGTGTGGATCTCTCATAGGGCACAGACCGCGCACCACCTGGGCTGAGAACATTAAAAACACAGTCAACATGGTGC
GCAGGATCATAGGTGATGAAGAAAAGTACATGGACTACCTATCCACCCAAGTTCGCTACTTGGGTGAAGAAGGGTCTACA
CCTGGAGTGCTGTAAGCACCAATCTTAGTGTTGTCAGGCCTGCTAGTCAGCCACAGCTTGGGGAAAGCTGTGCAGCCTGT
GACCCCCCCAGGAGAAGCTGGGAAACCAAGCCTATAGTCAGGCCGAGAACGCCATGGCACGGAAGAAGCCATGCTGCCT
GTGAGCCCCTCAGAGGACACTGAGTCAAAAAACCCCACGCGCTTGGAGGCGCAGGATGGGAAAAGAAGGTGGCGACCT
TCCCCACCCTTCAATCTGGGGCCTGAACTGGAGATCAGCTGTGGATCTCCAGAAGAGGGACTAGTGGTTAGAGGAGACCC
CCCGGAAAACGCAAAACAGCATATTGACGCTGGGAAAGACCAGAGACTCCATGAGTTTCCACCACGCTGGCCGCCAGGC
ACAGATCGCCGAATAGCGGCGGCCGGTGTGGGG
```

-continued

AHZ13508.1, Zika virus polyprotein from Polynesian outbreak (H/PF/2013)
SEQ ID NO: 79

MKNPKKKSGGFRIVNMLKRGVARVSPFGGLKRLPAGLLLGHGPIRMVLAILAFLRFTAIKPSLGLINRWGSVGKKEAMEIIKKFK

KDLAAMLRIINARKEKKRRGADTSVGIVGLLLTTAMAAEVTRRGSAYYMYLDRNDAGEAISFPTTLGMNKCYIQIMDLGHMCD

ATMSYECPMLDEGVEPDDVDCWCNTTSTWVVYGTCHHKKGEARRSRRAVTLPSHSTRKLQTRSQTWLESREYTKHLIRVEN

WIFRNPGFALAAAAIAWLLGSSTSQKVIYLVMILLIAPAYSIRCIGVSNRDFVEGMSGGTWVDVVLEHGGCVTVMAQDKPTVD

IELVTTTVSNMAEVRSYCYEASISDMASDSRCPTQGEAYLDKQSDTQYVCKRTLVDRGWGNGCGLFGKGSLVTCAKFACSKKM

TGKSIQPENLEYRIMLSVHGSQHSGMIVNDTGHETDENRAKVEITPNSPRAEATLGGFGSLGLDCEPRTGLDFSDLYYLTMNNK

HWLVHKEWFHDIPLPWHAGADTGTPHWNNKEALVEFKDAHAKRQTVVVLGSQEGAVHTALAGALEAEMDGAKGRLSSGH

LKCRLKMDKLRLKGVSYSLCTAAFTFTKIPAETLHGTVTVEVQYAGTDGPCKVPAQMAVDMQTLTPVGRLITANPVITESTENS

KMMLELDPPFGDSYIVIGVGEKKITHHWHRSGSTIGKAFEATVRGAKRMAVLGDTAWDFGSVGGALNSLGKGIHQIFGAAFK

SLFGGMSWFSQILIGTLLMWLGLNTKNGSISLMCLALGGVLIFLSTAVSADVGCSVDFSKKETRCGTGVFVYNDVEAWRDRYK

YHPDSPRRLAAAVKQAWEDGICGISSVSRMENIMWRSVEGELNAILEENGVQLTVVVGSVKNPMWRGPQRLPVPVNELPHG

WKAWGKSYFVRAAKTNNSFVVDGDTLKECPLKHRAWNSFLVEDHGFGVFHTSVWLKVREDYSLECDPAVIGTAVKGKEAVH

SDLGYWIESEKNDTWRLKRAHLIEMKTCEWPKSHTLWTDGIEESDLIIPKSLAGPLSHHNTREGYRTQMKGPWHSEELEIRFEE

CPGTKVHVEETCGTRGPSLRSTTASGRVIEEWCCRECTMPPLSFRAKDGCWYGMEIRPRKEPESNLVRSMVTAGSTDHMDHF

SLGVLVILLMVQEGLKKRMTTKIIISTSMAVLVAMILGGFSMSDLAKLAILMGATFAEMNTGGDVAHLALIAAFKVRPALLVSFIF

RANWTPRESMLLALASCLLQTAISALEGDLMVLINGFALAWLAIRAMVVPRTDNITLAILAALTPLARGTLLVAWRAGLATCGG

FMLLSLKGKGSVKKNLPFVMALGLTAVRLVDPINVVGLLLLTRSGKRSWPPSEVLTAVGLICALAGGFAKADIEMAGPMAAVGL

LIVSYVVSGKSVDMYIERAGDITWEKDAEVTGNSPRLDVALDESGDFSLVEDDGPPMREIILKVVLMTICGMNPIAIPFAAGAW

YVYVKTGKRSGALWDVPAPKEVKKGETTDGVYRVMTRRLLGSTQVGVGVMQEGVFHTMWHVTKGSALRSGEGRLDPYWG

DVKQDLVSYCGPWKLDAAWDGHSEVQLLAVPPGERARNIQTLPGIFKTKDGDIGAVALDYPAGTSGSPILDKCGRVIGLYGNG

VVIKNGSYVSAITQGRREEETPVECFEPSMLKKKQLTVLDLHPGAGKTRRVLPEIVREAIKTRLRTVILAPTRVVAAEMEEALRGLP

VRYMTTAVNVTHSGTEIVDLMCHATFTSRLLQPIRVPNYNLYIMDEAHFTDPSSIAARGYISTRVEMGEAAAIFMTATPPGTRD

AFPDSNSPIMDTEVEVPERAWSSGFDWVTDHSGKTVWFVPSVRNGNEIAACLTKAGKRVIQLSRKTFETEFQKTKHQEWDFV

VTTDISEMGANFKADRVIDSRRCLKPVILDGERVILAGPMPVTHASAAQRRGRIGRNPNKPGDEYLYGGGCAETDEDHAHWLE

ARMLLDNIYLQDGLIASLYRPEADKVAAIEGEFKLRTEQRKTFVELMKRGDLPVWLAYQVASAGITYTDRRWCFDGTTNNTIME

DSVPAEVWTRHGEKRVLKPRWMDARVCSDHAALKSFKEFAAGKRGAAFGVMEALGTLPGHMTERFQEAIDNLAVLMRAET

GSRPYKAAAAQLPETLETIMLLGLLGTVSLGIFFVLMRNKGIGKMGFGMVTLGASAWLMWLSEIEPARIACVLIVVFLLLVVLIPE

PEKQRSPQDNQMAIIIMVAVGLLGLITANELGWLERTKSDLSHLMGRREEGATIGFSMDIDLRPASAWAIYAALTTFITPAVQH

AVTTSYNNYSLMAMATQAGVLFGMGKGMPFYAWDFGVPLLMIGCYSQLTPLTLIVAIILLVAHYMYLIPGLQAAAARAAQKR

TAAGIMKNPVVDGIVVTDIDTMTIDPQVEKKMGQVLLIAVAVSSAILSRTAWGWGEAGALITAATSTLWEGSPNKYWNSSTA

TSLCNIFRGSYLAGASLIYTVTRNAGLVKRRGGGTGETLGEKWKARLNQMSALEFYSYKKSGITEVCREEARRALKDGVATGGH

AVSRGSAKLRWLVERGYLQPYGKVIDLGCGRGGWSYYAATIRKVQEVKGYTKGGPGHEEPMLVQSYGWNIVRLKSGVDVFH

MAAEPCDTLLCDIGESSSSPEVEEARTLRVLSMVGDWLEKRPGAFCIKVLCPYTSTMMETLERLQRRYGGGLVRVPLSRNSTHE

MYWVSGAKSNTIKSVSTTSQLLLGRMDGPRRPVKYEEDVNLGSGTRAVVSCAEAPNMKIIGNRIERIRSEHAETWFFDENHPY

RTWAYHGSYEAPTQGSASSLINGVVRLLSKPWDVVTGVTGIAMTDTTPYGQQRVFKEKVDTRVPDPQEGTRQVMSMVSSW

LWKELGKHKRPRVCTKEEFINKVRSNAALGAIFEEEKEWKTAVEAVNDPRFWALVDKEREHHLRGECQSCVYNMMGKREKK

QGEFGKAKGSRAIWYMWLGARFLEFEALGFLNEDHWMGRENSGGGVEGLGLQRLGYVLEEMSRIPGGRMYADDTAGWDT

RISRFDLENEALITNQMEKGHRALALAIIKYTYQNKVVKVLRPAEKGKTVMDIISRQDQRGSGQVVTYALNTFTNLVVQLIRNM

EAEEVLEMQDLWLLRRSEKVTNWLQSNGWDRLKRMAVSGDDCVVKPIDDRFAHALRFLNDMGKVRKDTQEWKPSTGWD

NWEEVPFCSHHFNKLHLKDGRSIVVPCRHQDELIGRARVSPGAGWSIRETACLAKSYAQMWQLLYFHRRDLRLMANAICSSV

-continued

PVDWVPTGRTTWSIHGKGEWMTTEDMLVVWNRVWIEENDHMEDKTPVTKWTDIPYLGKREDLWCGSLIGHRPRTTWAE
NIKNTVNMVRRIIGDEEKYMDYLSTQVRYLGEEGSTPGVL

9320_Zika_PF_1F  SEQ ID NO: 80
ttaggatccGTTGTTGATCTGTGTGAAT

9321_Zika_PF_1R  SEQ ID NO: 81
taactcgagCGTACACAACCCAAGTT

9322_Zika_PF_2F  SEQ ID NO: 82
ttaggatccTCACTAGACGTGGGAGTG

9323_Zika_PF_2R  SEQ ID NO: 83
taactcgagAAGCCATGTCYGATATTGAT

9324_Zika_PF_3F  SEQ ID NO: 84
ttaggatccGCATACAGCATCAGGTG

9325_Zika_PF_3R  SEQ ID NO: 85
taactcgagTGTGGAGTTCCGGTGTCT

9326_Zika_PF_4F  SEQ ID NO: 86
ttaggatccGAATAGAGCGAARGTTGAGATA

9327_Zika_PF_4R  SEQ ID NO: 87
taactcgAGTGGTGGGTGATCTTCTTCT

9328_Zika_PF_5F  SEQ ID NO: 88
ttaggatcCAGTCACAGTGGAGGTACAGTAC

9329_Zika_PF_5R  SEQ ID NO: 89
taactcgagCRCAGATACCATCTTCCC

9330_Zika_PF_6F  SEQ ID NO: 90
ttaggatCCCTTATGTGCTTGGCCTTAG

9331_Zika_PF_6R  SEQ ID NO: 91
taactcgagTCTTCAGCCTCCATGTG

9332_Zika_PF_7F  SEQ ID NO: 92
ttaggatccAATGCCCACTCAAACATAGA

9333_Zika_PF_7R  SEQ ID NO: 93
taactcgagTCATTCTCTTCTTCAGCCCTT

9334_Zika_PF_8F  SEQ ID NO: 94
ttaggatccAAGGGTGATCGAGGAAT

9335_Zika_PF_8R  SEQ ID NO: 95
taactcgagTTCCCTTCAGAGAGAGGAGC

9336_Zika_PF_9F  SEQ ID NO: 96
ttaggatccTCTTTTGCAAACTGCGATC

9337_Zika_PF_9R  SEQ ID NO: 97
taactcgagTCCAGCTGCAAAGGGTAT

9338_Zika_PF_10F  SEQ ID NO: 98
ttaggatccGTGTGGACATGTACATTGA

-continued

| | |
|---|---|
| 9339_Zika_PF_10R<br>taactcgagCCCATTGCCATAAAGTC | SEQ ID NO: 99 |
| 9340_Zika_PF_11F<br>ttaggatccTCATACTGTGGTCCATGGA | SEQ ID NO: 100 |
| 9341_Zika_PF_11R<br>taactcgagGCCCATCTCAACCCTTG | SEQ ID NO: 101 |
| 9342_Zika_PF_12F<br>ttaggatccTAGAGGGCTTCCAGTGC | SEQ ID NO: 102 |
| 9343_Zika_PF_12R<br>taactcgAGATACTCATCTCCAGGTTTGTTG | SEQ ID NO: 103 |
| 9344_Zika_PF_13F<br>ttaggatccGAAAACAAAACATCAAGAGTG | SEQ ID NO: 104 |
| 9345_Zika_PF_13R<br>taactcgagGAATCTCTCTGTCATGTGTCCT | SEQ ID NO: 105 |
| 9346_Zika_PF_14F<br>ttaggatccTTGATGGCACGACCAAC | SEQ ID NO: 106 |
| 9347_Zika_PF_14R<br>ttaggatccGTTGTTGATCTGTGTGAAT | SEQ ID NO: 107 |
| 9348_Zika_PF_15F<br>taactcgagCAGGTCAATGTCCATTG | SEQ ID NO: 108 |
| 9349_Zika_PF_15R<br>ttaggatccTGTTGTGTTCCTATTGCTGGT | SEQ ID NO: 109 |
| 9350_Zika_PF_16F<br>taactcgaGTGATCAGRGCCCCAGC | SEQ ID NO: 110 |
| 9351_Zika_PF_16R<br>ttaggatccTGCTGCCCAGAAGAGAA | SEQ ID NO: 111 |
| 9352_Zika_PF_17F<br>taactcgaGCACCAACAYGGGTTCTT | SEQ ID NO: 112 |
| 9353_Zika_PF_17R<br>ttaggatcCTCAAGGACGGTGTGGC | SEQ ID NO: 113 |
| 9354_Zika_PF_18F<br>taactcgagCAATGATCTTCATGTTGGG | SEQ ID NO: 114 |
| 9355_Zika_PF_18R<br>ttaggatccTATGGGGGAGGACTGGT | SEQ ID NO: 115 |
| 9356_Zika_PF_19F<br>taactcGAGCCCAGAACCTTGGATC | SEQ ID NO: 116 |
| 9357_Zika_PF_19R<br>ttaggatcCAGACCCCCAAGAAGGC | SEQ ID NO: 117 |
| 9358_Zika_PF_20F<br>taactcgagCCCCTTTGGTCTTGTCT | SEQ ID NO: 118 |

```
9359_Zika_PF_20R
                                                                SEQ ID NO: 119
ttaggatccAGGAAGGATGTATGCAGATG 9360_Zika_PF_21F
                                                                SEQ ID NO: 120
taactcgagACATTTGCGCATATGATTTTG 9361_Zika_PF_21R
                                                                SEQ ID NO: 121
ttaggatccAGGAAGGACACACAAGAGT 9362_Zika_PF_22F
                                                                SEQ ID NO: 122
taactcgagACAGGCTGCACAGCTTT 9363_Zika_PF_22R
                                                                SEQ ID NO: 123
ttaggatccTCTCTCATAGGGCACAGAC
```

In some embodiments, the Zika virus has a polyprotein including an envelope (E) protein with an amino acid sequence provided by any one of SEQ ID NOs: 14-69. In some embodiments, the polyprotein or E protein sequence is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-69.

The terms "identical" or "percent identity" in the context of two or more nucleic acids or amino acid sequences refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, or 99% identity) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. In some embodiments, the identity exists over the length of a protein, such as the E protein.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman. Proc. Natl. Acad. Sci. USA 85:2444, 1988, by computerized implementations of these algorithms (GAP, BESTFIT, FASTA, Jalview and TFASTA in the Wisconsin Genetics Software Package, Genetics Computer Group. 575 Science Dr., Madison. Wis.), by multi sequence alignment implementation using e.g. CLUSTALW (Larkin et al., (2007). Bioinformatics, 23, 2947-2948) or MAFFT (Katoh & Toh, 2008, Briefings in Bioinformatics 9:286-298), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977 and Altschul et al., J. Mol. Biol. 215:403-410, 1990, respectively.

EXAMPLES

Example 1

Development of a Purification Process for Live Attenuated Chikungunya Virus Vaccine Produced in Vero Cells A downstream process was developed for the purification of infectious Chikungunya virus particles whereby non-infectious virus particles and aggregates are removed by the addition of protamine sulphate. The unexpected and novel purification properties of protamine sulphate (PS) were evaluated in purification processes for Chikungunya Virus (ChikV) as follows:

A downstream purification process for the attenuated Chikungunya virus mutant "Δ5nsP3" (as described by Hallengärd et al., 2014, supra) produced under standard cell culture conditions in Vero cells was developed. The attenuated Δ5nsP3 Chikungunya virus was derived from the strain LR2006-OPY1, the complete genome of which is provided herein as SEQ ID NO: 72. Briefly, the downstream process consists of crude harvest filtration followed by concentration and diafiltration on a tangential flow filtration (TFF) system. Host cell DNA and host cell proteins were reduced by precipitation with protamine sulphate and by batch adsorption, respectively. Sucrose density gradient centrifugation was done as a final polishing step. Out of 16 roller bottles $1\times10^{12}$ total PFU were purified with an overall DSP process yield of 10-15% (~1 log 10 TCID50 loss). Sucrose gradient pool samples were characterized with regard to product-related impurities, such as hcDNA, HCP and endotoxins and met safety criteria.

Harvest of Vero Cell Culture Medium Containing ChikVΔ5nsP3

ChikV Δ5nsP3 was grown on Vero cells in roller bottles. A first harvest was performed after 24 hours post infection (hpi; day 1 harvest) and stored at 2-8° C. until further processing. After the first harvest, fresh medium was added and the roller bottles were returned to the incubator. A second harvest was done after 48 hours post infection (day 2 harvest) and stored at 2-8° C.

Filtration of Crude Cell Culture Harvest

At both harvest timepoints, the crude harvest was immediately filtered using a 0.2 μm filter capsule (GE ULTA™

CG, 2 inch). The filtered harvest after 48 hpi was pooled together with the 24 hpi harvest and the pooled filtered harvest material was immediately further processed by ultrafiltration.

Purification of ChikV Δ5nsP3 by Tangential Flow Filtration (TFF)

The pooled filtered harvest material was further processed by tangential flow filtration (TFF) in order to concentrate the harvest, reduce host cell proteins and replace the depleted cell culture medium with a defined buffer system (buffer exchange). A Millipore TFF system (Millipore Pellicon II mini membrane holder) equipped with a 100 kDa cutoff PES membrane module (Pellicon2 Biomax, 1000 cm$^2$) was used for concentration and buffer exchange. A Pellicon2 Biomax membrane module was mounted on the Pellicon II mini filter holder and the device was connected to a peristaltic pump. The system was first rinsed with ultra-pure water and then sanitized by recirculation of 0.1 M NaOH for 60 min. In case the system was not used immediately, it was stored in 0.1 M NaOH until use. Prior to use the system was rinsed with 1 L of RO-water followed by buffer A until the permeate pH value was constant at pH 7.4±0.2.

Adjustment of the ChikV 45nsP3 Harvest (pH, Salt)

The pooled filtered harvest material was adjusted to a final concentration of 25 mM Tris and 150 mM NaCl using stock solutions of both components (see Table 1). This adjustment was done to increase buffering capacity and to reduce unspecific adsorption to the membrane. The necessary volumes of stock solutions D (1 M Tris, pH 7.4) and E (4.5 M NaCl) were calculated as follows:

Volume of stock solution D (1 M Tris, pH 7.4) added to pooled harvest=Volume of pooled filtered harvest/40

Volume of stock solution E (4.5 M NaCl) added to pooled harvest=Volume of pooled filtered harvest/30

Example: 4 L harvest obtained from 20 RB (850 cm$^2$) would require addition of 100 mL stock solution D (1 M Tris, pH 7.4) and 133 mL stock solution E (4.5 M NaCl).

The calculated volumes of stock solution D and Buffer E were added to the pooled filtered harvest under gentle stirring. The adjusted harvest was then stirred using a magnetic stirrer for 5 minutes at room temperature.

Concentration and Diafiltration of the ChikV Δ5nsP3 Harvest by TFF

In a first step, the adjusted harvest material was concentrated approximately 10 fold. The feed flowrate was approximately 220 mL/min. The transmembrane flux at a transmembrane pressure of approximately 0.6 bar was in the range of 90±5 mL/min per 1000 cm$^2$ membrane. After concentration, the cell culture medium was exchanged against 25 mM Tris, 150 mM NaCl, pH 7.5, by continuous diafiltration with 6 volume exchanges. The diafiltration buffer was supplied to the feed vessel from a measuring cylinder by a second peristaltic pump set to a flowrate of approximately 90 mL/min. Minor flowrate adjustments of the second peristaltic pump in the range of ±10 mL/min were done manually to ensure a constant volume of harvest in the feed vessel. After 6 volume exchanges, diafiltration was stopped. The liquid remaining in the membrane module was recovered by pumping the module empty with air.

Sucrose Addition to Diafiltrated ChikV Δ5nsP3 Material

After diafiltration, sucrose stock solution H (50% (w/w) sucrose solution) was added to the diafiltrated material to achieve a final sucrose concentration of 10% (w/w). The volume of buffer H was calculated as follows:

Volume of stock solution H added (mL)=Volume (mL) of diafiltrated ChikV material×0.25(dilution factor=1:4)(i.e., final sucrose concentration is 10%)

Example: 400 mL diafiltrated ChikV solution would require addition of 100 mL stock solution H (50% sucrose).

The calculated volume of solution H was added to the diafiltrated ChikV Δ5nsP3 material under gentle stirring and the solution was then stirred using a magnetic stirrer for a further 5 minutes at room temperature. (At this stage of the process the material can be either immediately further processed or stored frozen (<−65° C., hold step).)

DNA Reduction by Protamine Sulphate Precipitation

A DNA precipitation step using protamine sulphate (PS) was performed to reduce hcDNA. Protamine sulphate stock solution L (50 mg/mL PS in PBS) was added to the diafiltrated ChikV Δ5nsP3 material to a final nominal concentration of ~1.6 mg/mL. The necessary volume of stock solution L was calculated as follows:

Volume of stock solution L (50 mg/mL PS) added=Volume of diafiltrated ChikV Δ5nsP3 material in 10% sucrose/31

Example: 500 mL diafiltrated ChikV Δ5nsP3 solution in 10% sucrose would require addition of 16 mL stock solution L (50 mg/mL PS in PBS).

The protamine sulphate stock solution was added while stirring the ChikV Δ5nsP3 material using a magnetic stirrer followed by incubation at 2-8° C. for 30 minutes. After incubation, the precipitate was not removed. The material was immediately further processed by batch adsorption with Capto™ Core 700 chromatography media.

Batch Adsorption with Capto™ Core 700

To reduce HCPs, a batch adsorption step with Capto™ Core 700 (CC700) chromatography medium was performed after DNA precipitation. CC700 slurry (50% slurry in buffer A) was added directly to the protamine sulphate treated material. The required slurry volume was determined based on the volume of Δ5nsP3 ChikV harvest material (d1+d2) and was calculated as follows:

Volume of CC700 slurry added to PS-treated concentrated harvest (mL)=Volume of Δ5nsP3 ChikV harvest material (mL)×0.02(dilution factor=1:50)(i.e., final concentration of CC700 is 1%)

After slurry addition, the material was incubated at 4° C. for 15 minutes under constant agitation using a magnetic stirrer. After incubation, the CC700 solid matter was allowed to settle by gravity for 10 minutes. The Δ5nsP3 ChikV material was then removed from the top of the solution in order to avoid blocking of the filter by the CaptoCore particles. The remaining CaptoCore particles and the DNA precipitate were then removed from the solution by filtration using a 0.2 μm Mini Kleenpak EKV filter capsule (Pall). The resulting filtrate was further processed by sucrose density gradient centrifugation.

Sucrose Density Gradient Centrifugation

Sucrose density gradient centrifugation (SGC) was used for final concentration and polishing of the Δ5nsP3 ChikV material. The Δ5nsP3 ChikV material was loaded on top of a solution consisting of three layers of sucrose with different densities. The three sucrose layers were selected based on a preliminary study which showed the formation of a linear sucrose gradient and good separation of the virus particles from residual contaminants. The optimal volumes of the sucrose solutions were determined empirically. The volumes of individual layers for a centrifugation at 500 mL scale are shown in Table 3.

TABLE 3

Sucrose concentrations and volumes (500 mL scale).

| Solution | Volume (mL) |
| --- | --- |
| Harvest with 10% sucrose | 360 |
| 15% sucrose | 40 |
| 35% sucrose | 40 |
| 50% sucrose | 60 |
| Total volume | 500 |

Preparation of the Sucrose Gradient

Figure 14:
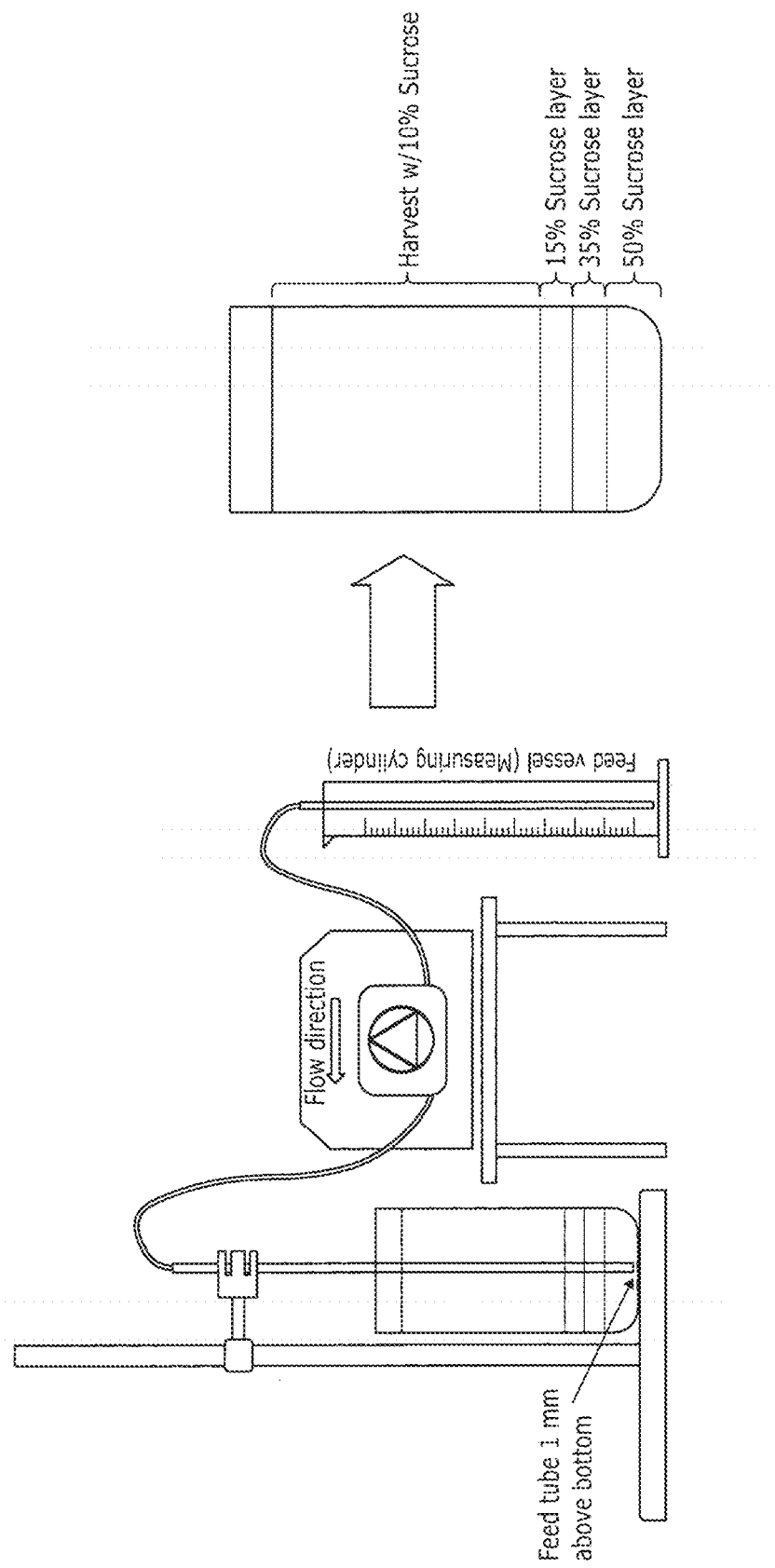
FIG. 14: Preparation of the optimized sucrose gradient of the invention.

The sucrose gradient bottles (500 mL) were prepared by underlaying the individual sucrose layers. A 3.5 mm ID plastic tube was attached to 60 cm of peristaltic pump tubing. The plastic tube was mounted on a laboratory stand using a clamp and placed into the centrifuge bottle. The nozzle of the plastic tube was placed at the bottom of the bottle. Using a peristaltic pump set to a flow rate of 25 mL per minute, the Δ5nsP3 ChikV material and the sucrose solutions were pumped into the cylinder. A measuring cylinder was used as a feed vessel. The first solution pumped was the Δ5nsP3 ChikV material as it had the lowest density (10% sucrose (w/w)). Following the addition of the Δ5nsP3 ChikV material, the sucrose solutions were pumped in ascending order starting with the lowest (15%), followed by the 35% sucrose solution and finishing with the highest density sucrose solution (50%). After all sucrose solutions were transferred, the plastic tubing was carefully removed in order not to disturb the layers. An illustration of a completed gradient is shown in FIG. 14.

Centrifugation

Prior to centrifugation a Beckman Avanti JXN-26 centrifuge equipped with rotor Beckman 10.500 was pre-cooled to 4° C. The prepared SG bottles were carefully transferred into the pre-cooled (4° C.) rotor so as to not to disturb the sucrose layers. The bottles were centrifuged at 10,000 rpm (~18,500 rcf) at 4° C. for 17-20 hours. (In case a different centrifuge system with a different rotor would be used, the necessary speed and centrifugation times would need to be calculated based on the k-factor in order to achieve comparable centrifugation efficiency.)

Sucrose Gradient Harvest

Harvesting of the sucrose gradient following centrifugation was done manually using a peristaltic pump. A 3.5 mm ID plastic tube attached to 60 cm of peristaltic pump tubing was used for harvesting the sucrose gradient. The 500 mL bottle containing the centrifuged gradient was mounted onto a laboratory stand in a tilted position (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14). Using a peristaltic pump set to a flow rate of 60 mL per minute, the gradient was harvested and manually split into 5 mL fractions. A third of the bottle volume was harvested and the rest was discarded. The fractions were immediately tested by measuring UV absorbance in a plate reader as described below.

Analysis of Fractions by UV Absorbance and SEC-HPLC

Figure 11A:
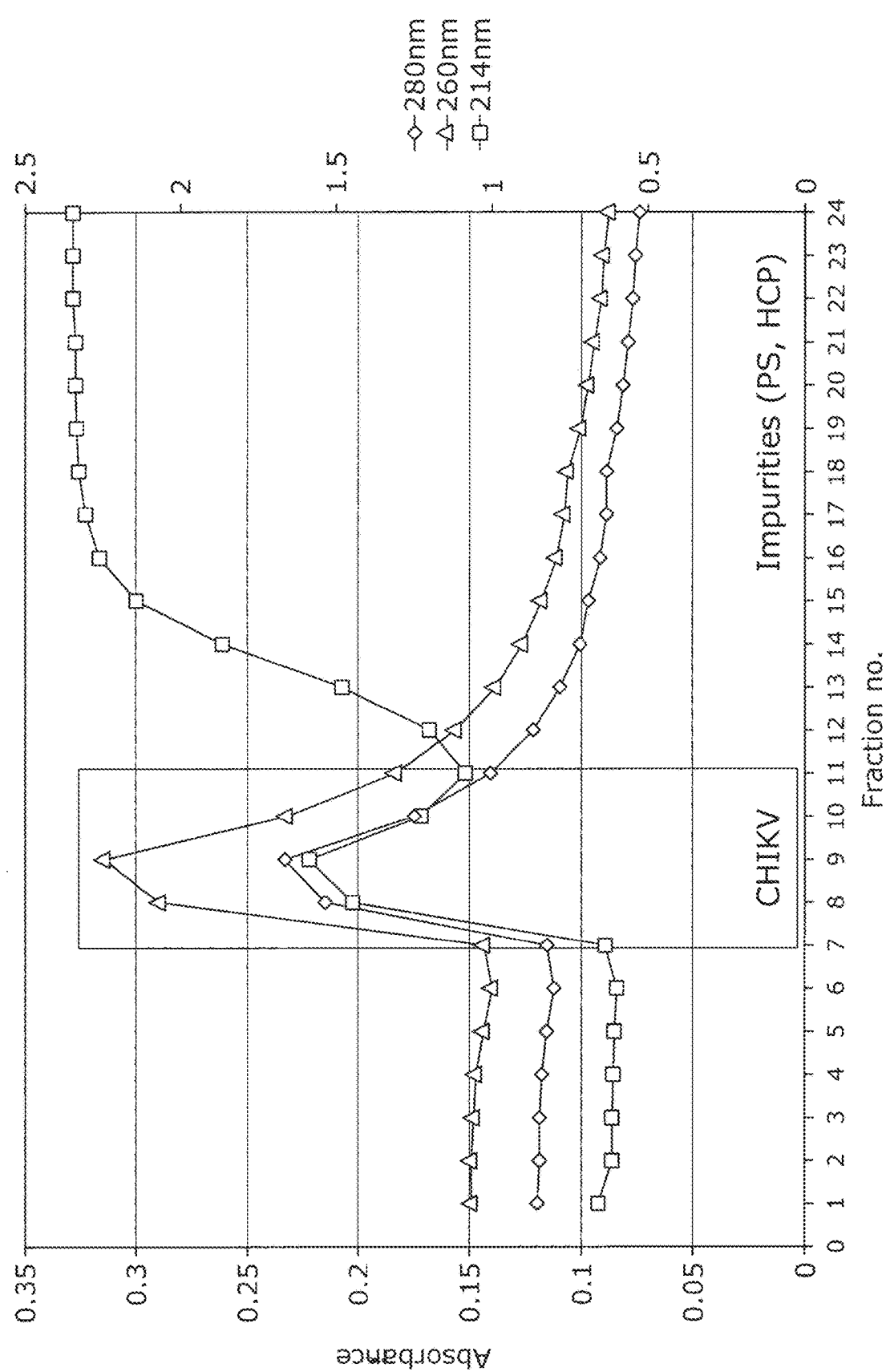

UV absorbance measurement was used as primary method for analysis of the sucrose gradient fractions. Absorbance at 214, 280 and 260 nm was tested immediately after fractionation was completed. Briefly, a 100 μL sample of each fraction was transferred into a 96 well plate and absorbance at 214, 260 and 280 nm was measured using a plate reader. The absorbance values were plotted against the fraction number. A representative profile is shown in FIG. 11A. The Δ5nsP3 ChikV containing fractions were indicated by a peak in all three measured wavelengths (FIG. 11A, grey shaded area). The presence of impurities was indicated by an increase of the UV214 signal after the main peak. The fractions comprising the main peak were pooled from the peak start to the valley of the 214 nm curve. This method can be used as single method for pooling Δ5nsP3 ChikV fractions.

After identification of the virus containing fractions, the respective fractions were pooled. Pooling criteria for SGC fractions were based on UV 260 nm data, e.g. start of pooling at ~10% of peak maximum, end of pooling at ~30% of peak maximum. (Final pooling criteria at a manufacturing scale may need to be determined empirically.) The sucrose gradient pool was either stored at <−65° C. or immediately further formulated to drug substance (DS).

Size Exclusion Chromatography

The final pooled SGC fractions containing purified infectious Δ5nsP3 ChikV particles were analyzed for purity by SEC-HPLC. In brief, SEC was performed as follows: a Superose 610/300 Increase column (GE Healthcare) equilibrated with PBS+250 mM NaCl, pH 7.4 at 1 ml/min and 25° C., was used to detect ChikV particles at 214 nm detection wavelength in the pooled samples. SEC-HPLC is a semi-quantitative (relative yield) and qualitative (purity) method that separates intact virus particles from virus aggregates and host cell proteins (HCPs). The method cannot distinguish between infectious and non-infectious virus particles due to their identical retention time.

Figure 11B:
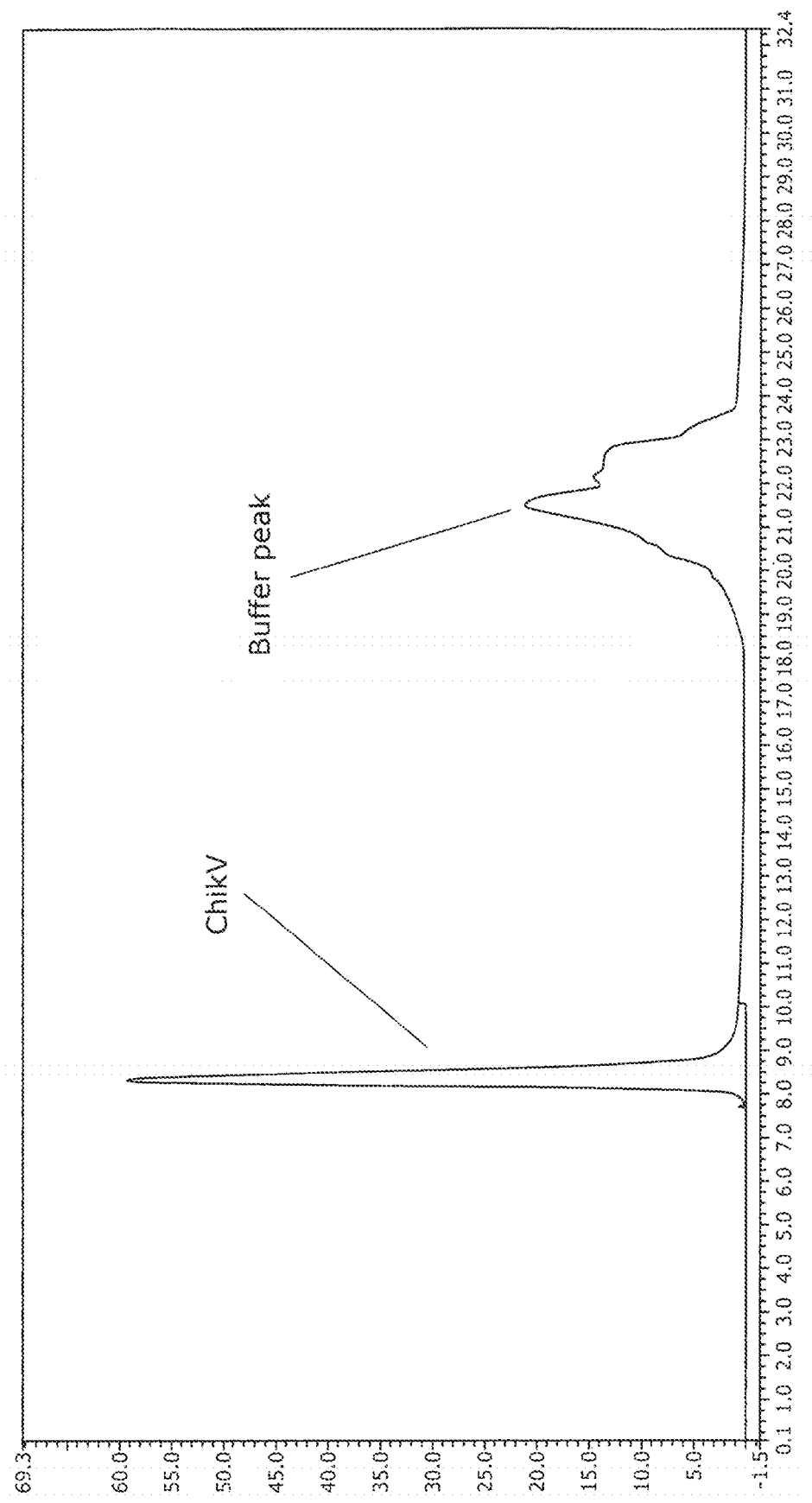

As shown in FIG. 11B, there were two defined peaks identified by SEC: the Δ5nsP3 ChikV peak and a peak corresponding to buffer components. The SGC step yield based on SEC-HPLC data for pooled fractions F6-F11 was estimated at ~70%. The final purity of the Δ5nsP3 ChikV SGC pool, based on SEC-HPLC analysis, was estimated at >95%.

SDS-PAGE and Silver Stain

SDS-PAGE silver stain was performed in order to qualitatively assess sample purity throughout the purification process from the first crude harvest through SGC. Briefly, ChikV process samples analyzed by SDS-PAGE/silver stain were diluted 1:1.33 with LDS buffer and were heated to 70° C. for 5 minutes.

The samples were loaded onto 4-12% Bis-Tris Gels (NuPAGE). Silver staining was done using the Silver Express staining kit (Invitrogen).

A silver-stained gel of a representative ChikV Δ5nsP3 purification is shown in FIG. 11C. The viral proteins E1, E2 and C are marked on the right-hand side of the gel. The final SGC pool (fraction 7-fraction 11) is shown in lane 12. Note that a defined HCP band migrating between ChikV protein E2 and C still appears after CaptoCore700 treatment that has been identified as a single band in SDS-PAGE. This impurity is removed by sucrose gradient centrifugation, but can still be seen in fractions 13 and 14 (corresponding to lanes 14 and 15 of FIG. 11C).

Enrichment of infectious Δ5nsP3 ChikV particles by PS treatment Although generally used as a method of removing contaminating hcDNA, it was observed in the course of the present invention that PS treatment also removes virus aggregates and HCPs. Size exclusion chromatography (SEC-HPLC, as described above) was used throughout the purification process to determine the purity of the ChikV virus relative to impurities which also generate UV absorption.

Figure 12A:
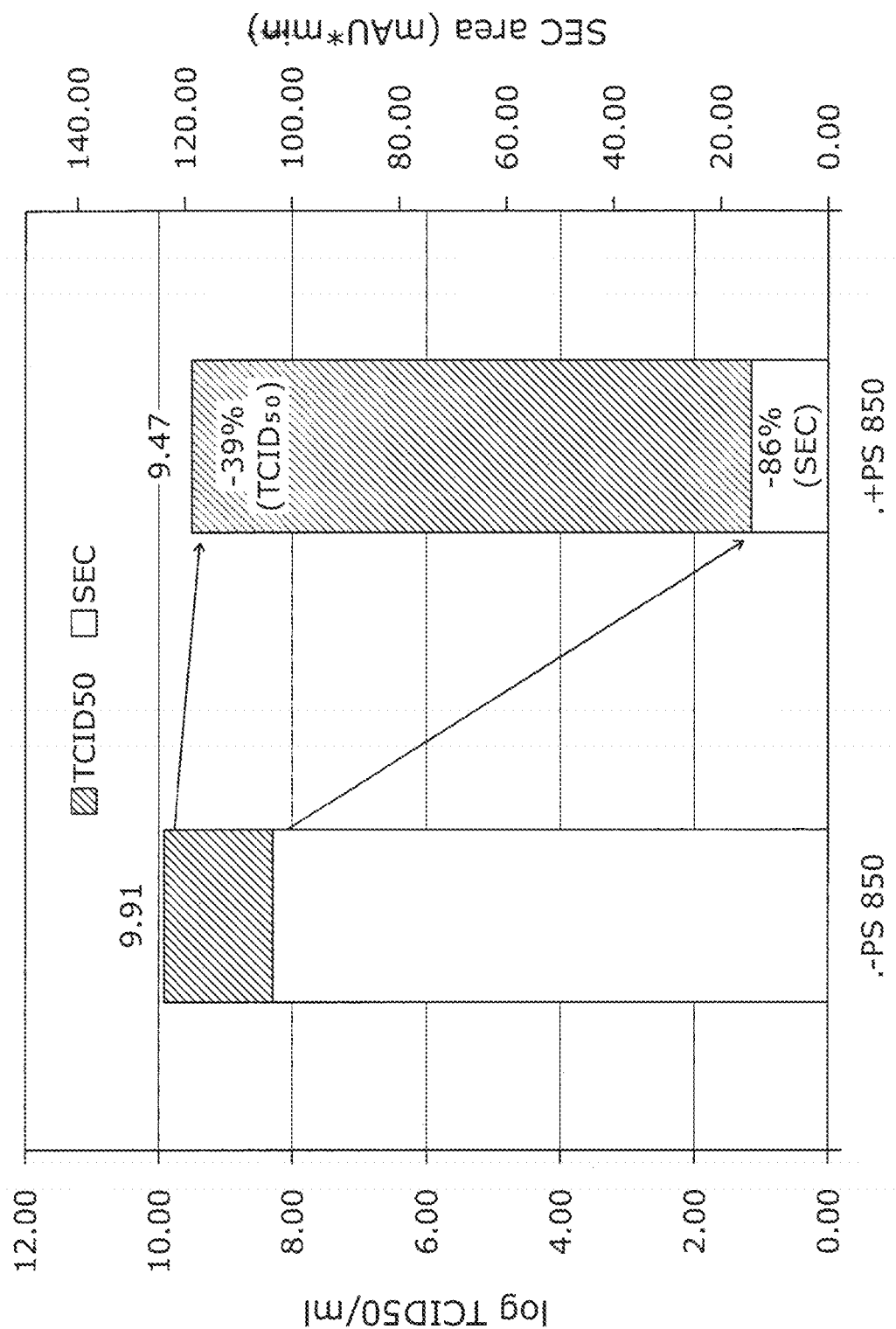

As can be seen in FIG. 12B, treatment with PS reduces not only host cell proteins and low molecular weight contaminants of the Δ5nsP3 ChikV preparation, but also reduces the SEC area corresponding to virus products, including aggregates as indicated. A surprising finding, however, was that even a reduction of the total SEC area by 86% (in a representative experiment shown in FIG. 12A, grey portion of bars) did not result in a concomitant reduction in infectious virus particles as measured by TCID50 (FIG. 12A, left axis). Instead, even though a large percentage of virus particles were removed by PS treatment, the majority of infectious particles remained. This observation indicates that PS treatment selectively enriches infectious virus particles from a larger pool of total virus particles present in the crude harvest.

Figure 13:
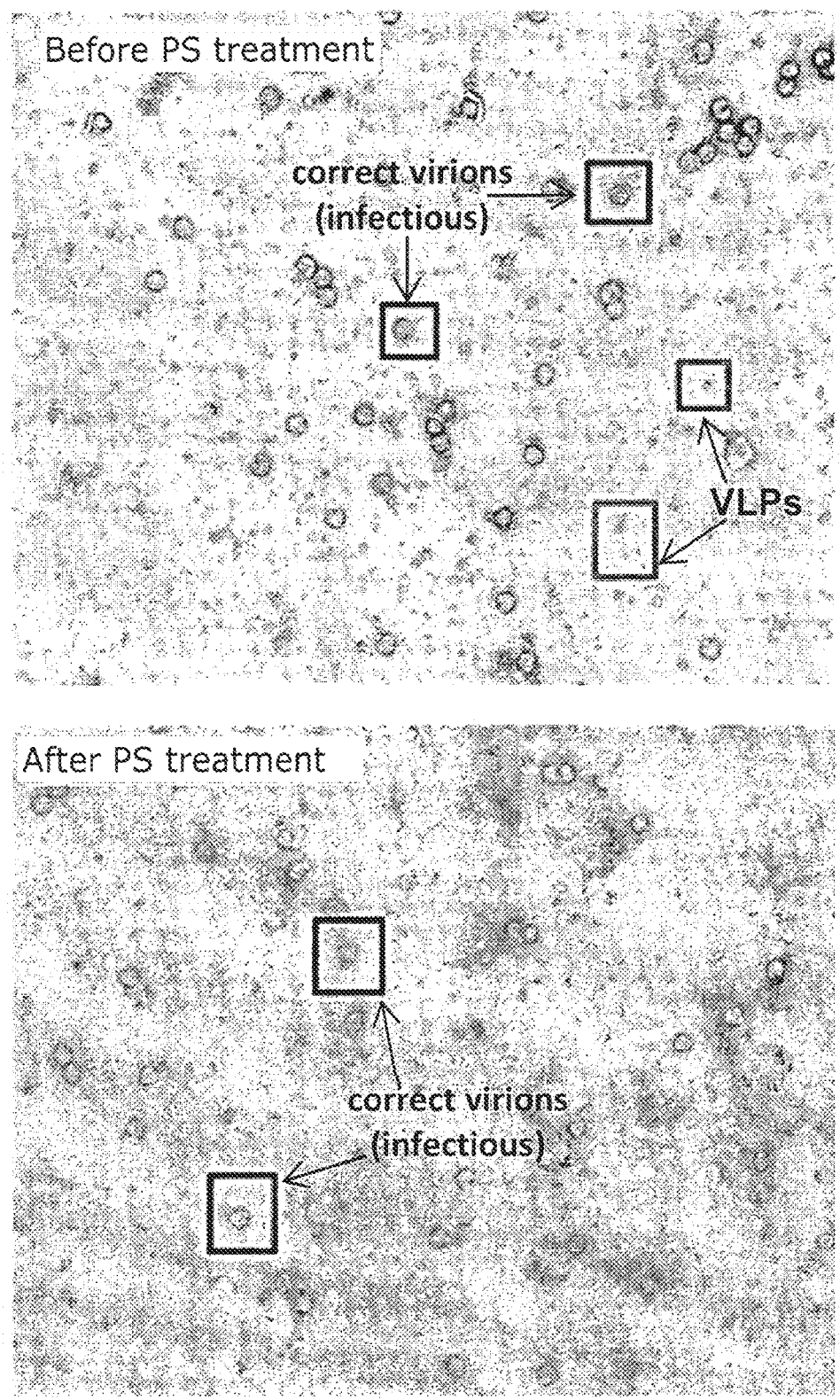
FIG. 13: Electron micrographs of attenuated Δ5nsP3 ChikV harvest before and after PS treatment.

TCID50 was performed to quantify infectious virus particles during the course of the purification process and to assign an active virus titer to final drug substance and drug product samples. Briefly, Vero cells were seeded at 2×10⁴ cells per well in 100 μL medium (EMEM with 2 mM L-Glutamine+5 FBS+1 antibiotic/antimycotic) in 96-well TC-treated flat-bottom plates and incubated overnight at 35° C./5% CO$_2$. On day two, Vero cell monolayers were infected by adding 100 μL of 1:10 serial dilutions of test samples to each of quintuplicate wells seeded with Vero cells and incubated at 35° C./5% CO$_2$. On day seven, plaques were counted by visualization under a microscope. The TCID50 was calculated according to the Reed & Munch endpoint calculation method (Reed, L. J.; Muench, H. (1938) A simple method of estimating fifty percent endpoints, The American Journal of Hygiene 27: 493-497). Furthermore, electron microscopy of Δ5nsP3 ChikV samples before and after PS treatment showed that not only large aggregates but also smaller non-infectious virus-like particles (essentially not fully assembled particles lacking the RNA genome) were effectively removed by PS (FIG. 13).

This enrichment of infectious virus particles was also observed when analyzing day one and day two crude harvests separately. As presented in Table 4, the SEC area (total virus particles) of the day 1 harvest remains roughly the same after PS treatment; whereas a large decrease in virus peak area is seen for the day 2 harvest after PS treatment. This observation was confirmed by MALLS analysis of the virus preparation, wherein it was seen that a higher percentage of virus particles were of the correct size following PS treatment. Similarly to the results shown in FIG. 12, day 1 and day 2 harvests showed no reduction in infectious particles as measured by TCID50 following PS treatment, indicating that mainly non-infectious, immature and/or aggregated virus particles are removed during the PS treatment and infectious particles are enriched in the preparation.

Figure 15A:
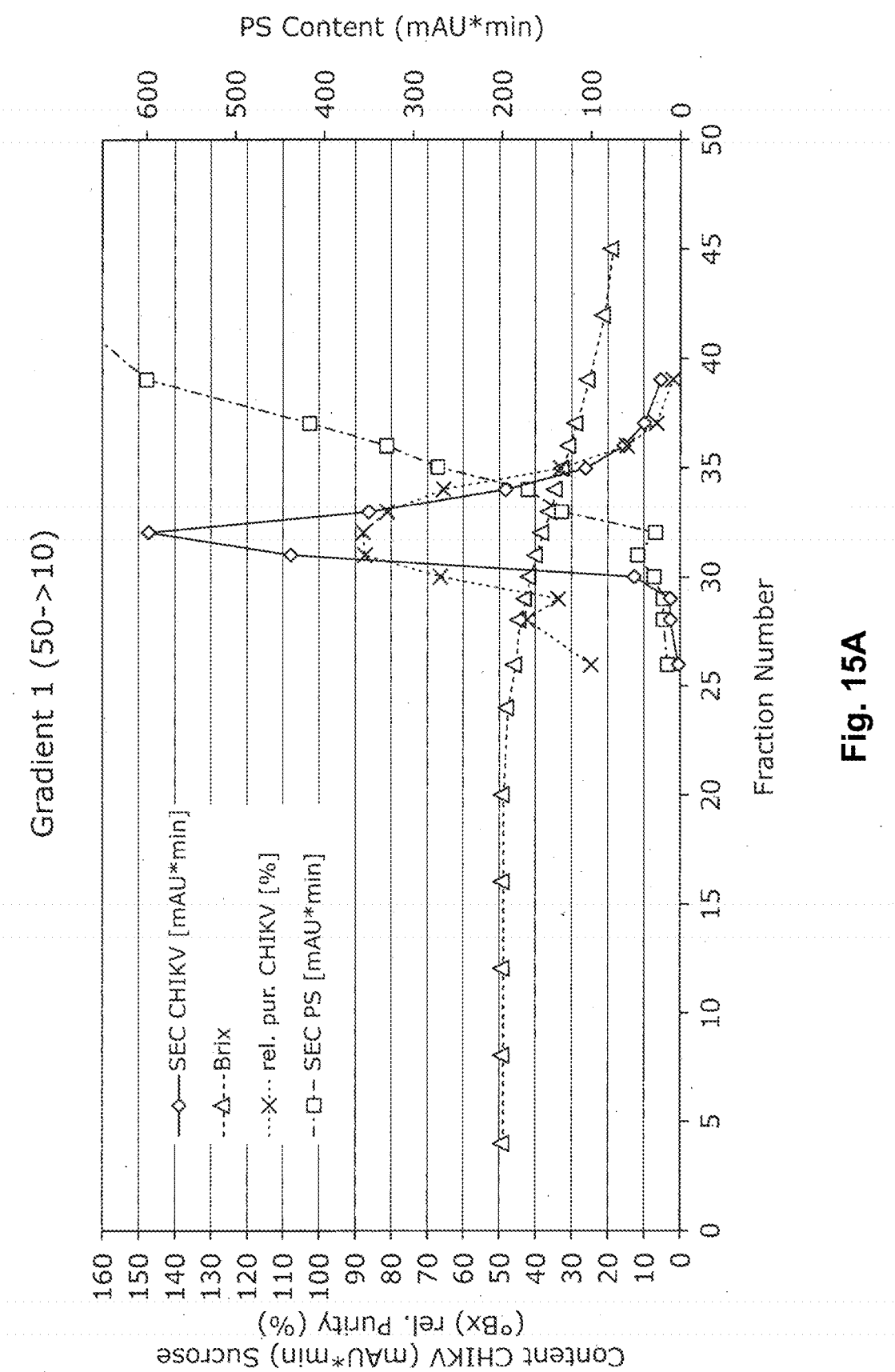
FIGS. 15A-15D: Comparison of four different sucrose gradient centrifugation experiments performed to empirically determine the optimal combination of sucrose layers for an exemplary purification of ChikV. The ChikV content in the gradient fractions was determined by SEC. The sucrose content in the gradient fractions was determined by refractometry as °Bx (sucrose weight percentage). Protamine sulphate (PS) content was determined by SEC. PS was separated within the sucrose gradient alongside host cell derived residual contaminants and was therefore used to assess the quality of ChikV separation from residual contaminants in the tested gradients.
Figure 15B:
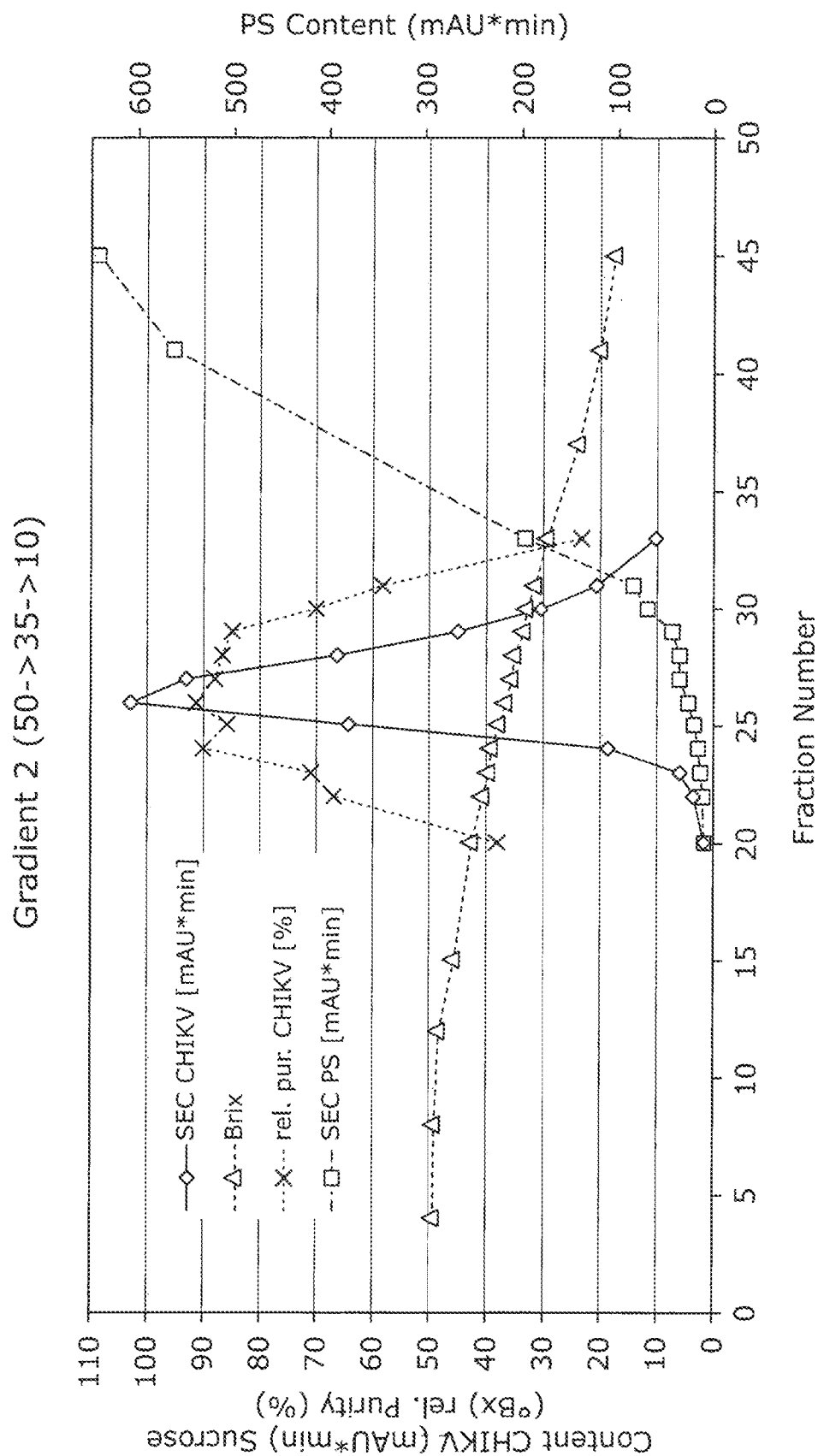
Figure 15C:
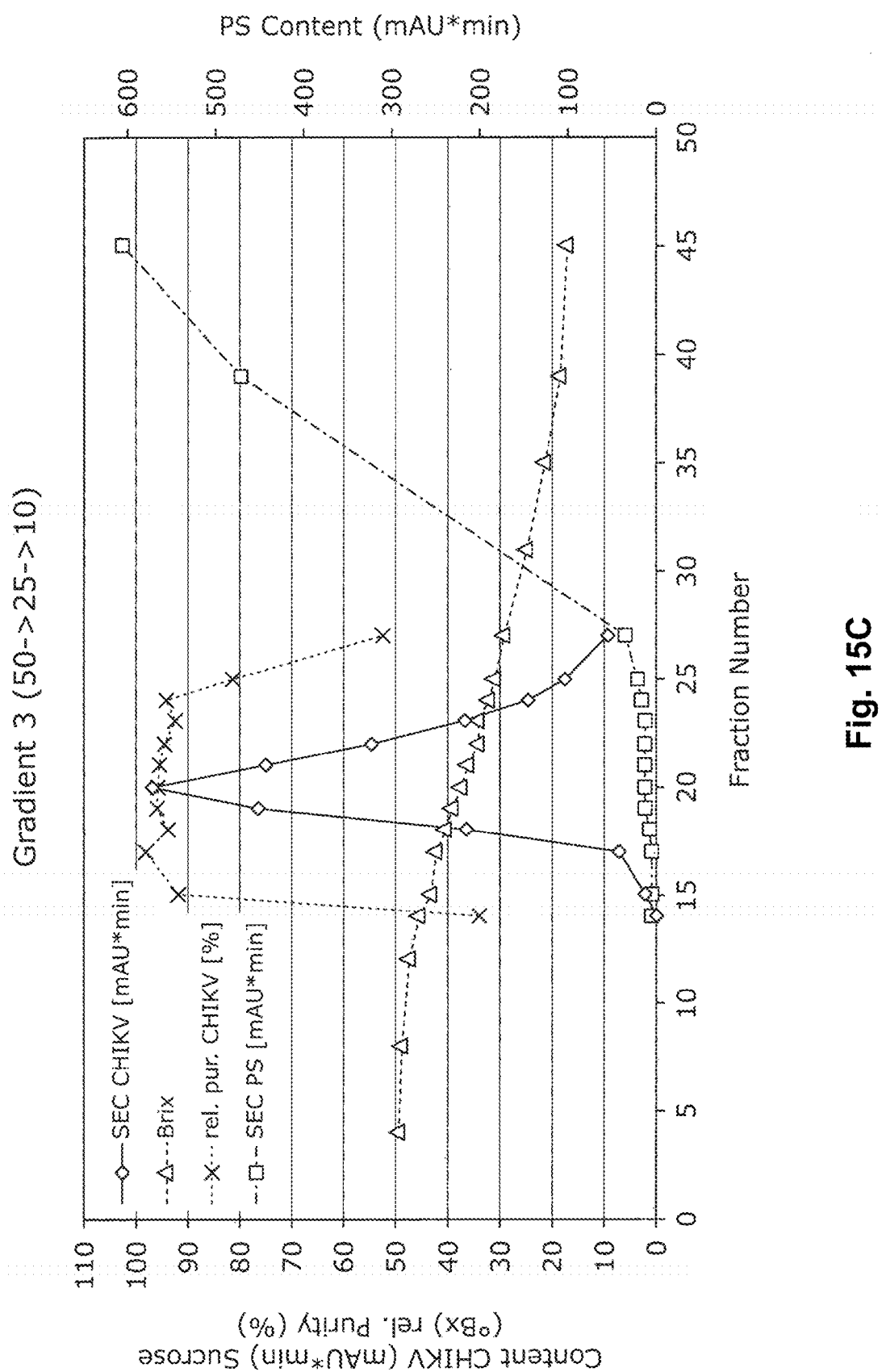
Figure 15D:
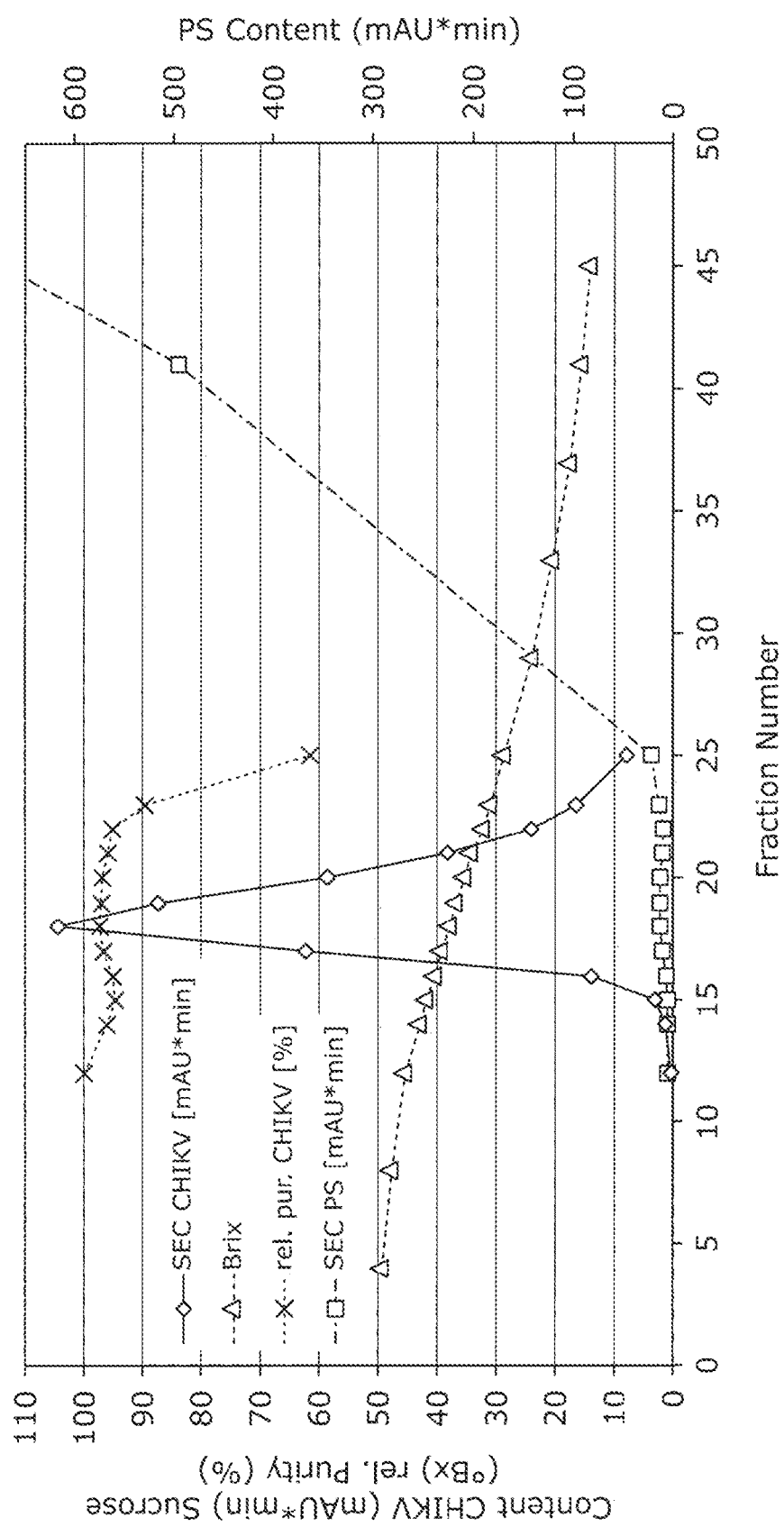
Figure 16A:
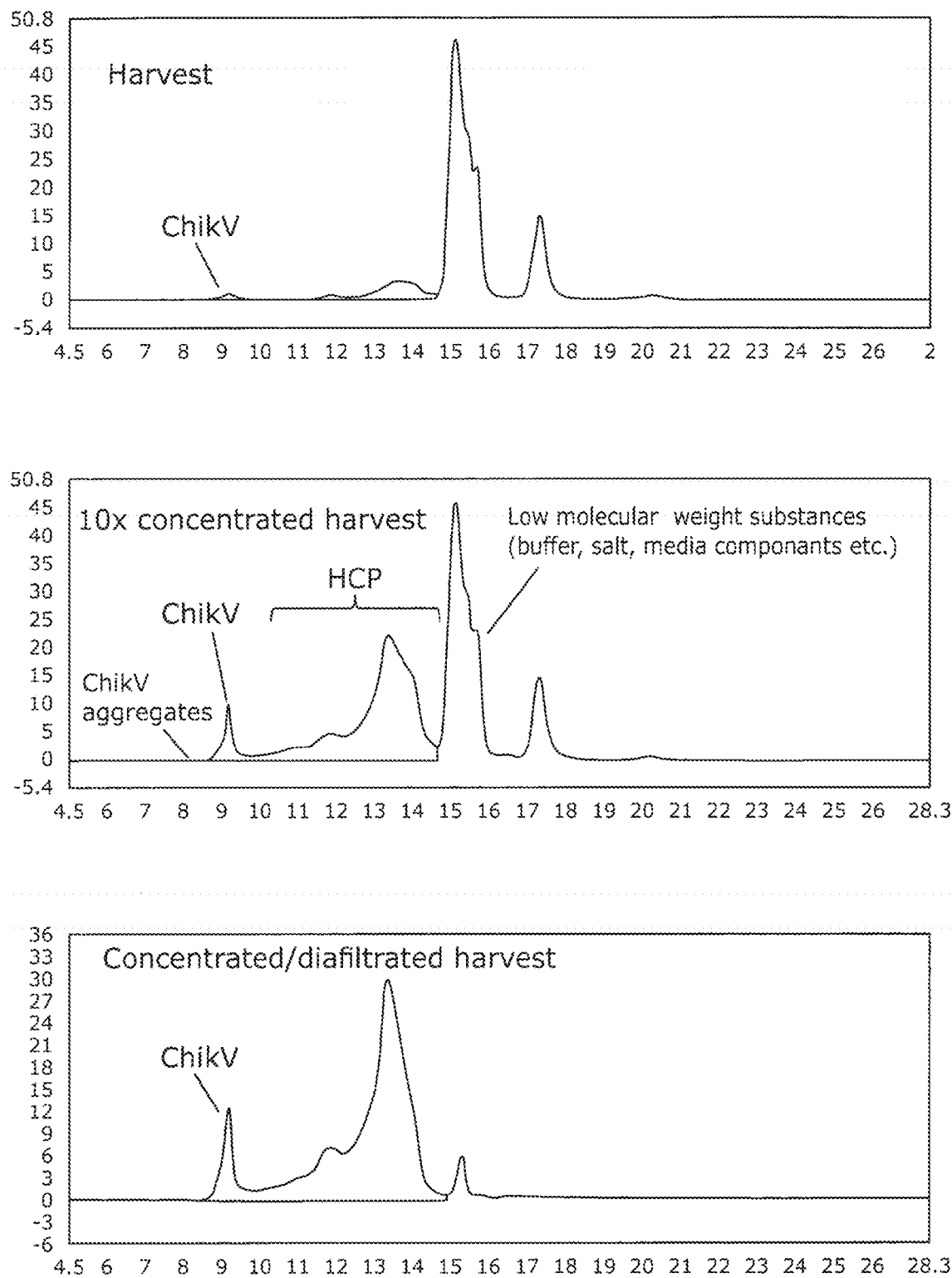
FIGS. 16A-16B: Relative amounts of attenuated Δ5nsP3 ChikV particles and other components as measured by SEC-HPLC analysis at the different steps of the process of the invention including, from top to bottom: crude harvest (a); 10× concentrated harvest; diafiltrated concentrated harvest; PS treated material; CC700-treated material and SGC purified pool.
Figure 16B:
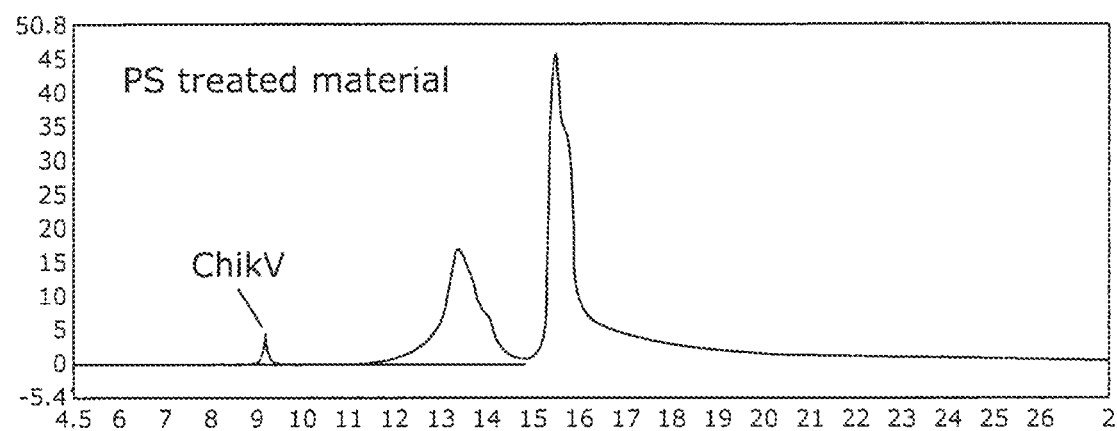
Figure 16B:
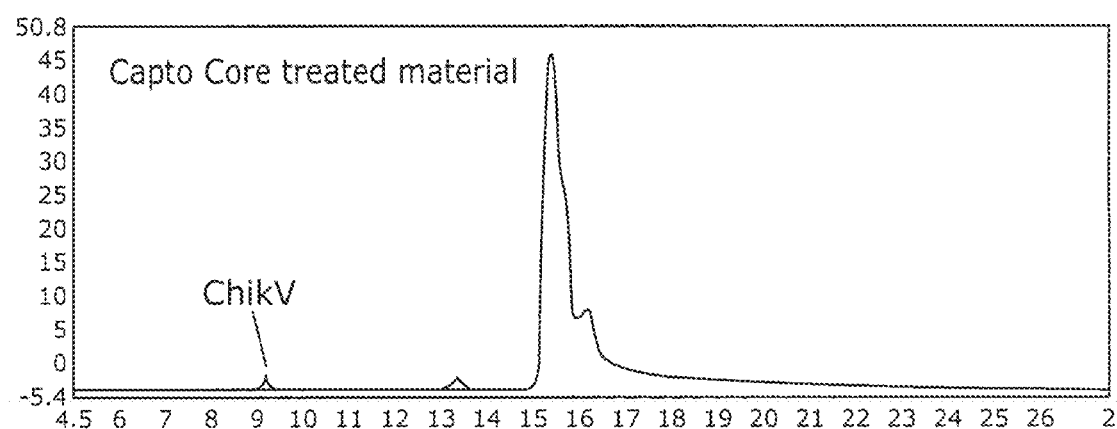
Figure 16B:
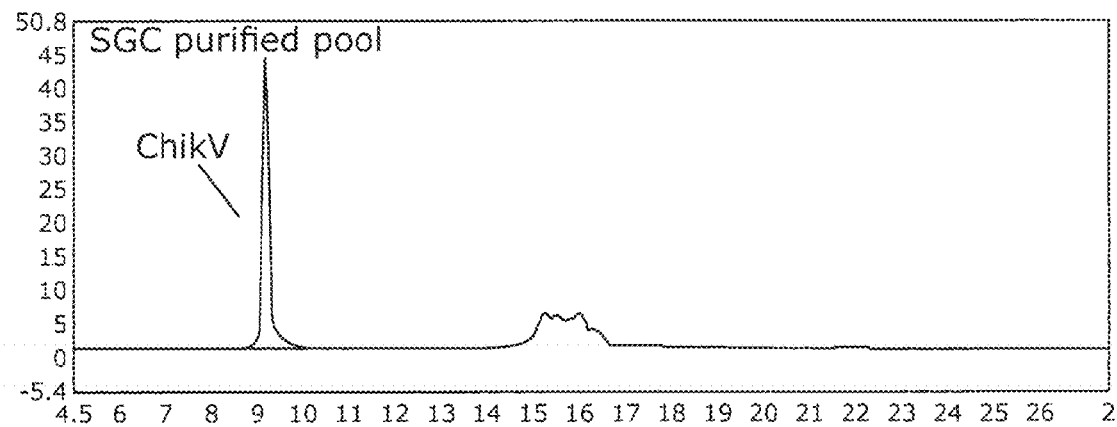

The PS-treated samples were further purified by sucrose gradient centrifugation (see FIG. 14 for a schematic preparation of an optimized sucrose gradient). An optimal sucrose gradient was determined experimentally as shown in FIG. 15. Results of the further purification of PS-treated ChikV on the optimized sucrose gradient of the invention are shown in FIG. 15D.

TABLE 4

Overview of the process of Δ5nsP3 ChikV purification as described in Example 1. SEC-MALLS analysis of harvests before and after PS treatment shows the removal of larger virus particles (aggregates), an effect that is particularly pronounced for day 2 harvests.

|  | SEC Area [mAU*min] | MALLS Total particles/ mL | % correct size (20-40 nm) | Infectious particles TCID50 log 10 |
|---|---|---|---|---|
| Harvest 1 (H1) | 57 | 1.17E+11 | 49% | 10.2 |
| H1 + protamine sulphate | 53 | 1.33E+11 | 81% | 10.0 |
| Harvest 2 (H2) | 36 | 4.60E+09 | 3% | 7.9 |
| H2 + protamine sulphate | 2 | 8.80E+09 | 59% | 7.9 |
| Combined Harvests (C) | 67 | 2.60E+10 | 14% | 9.9 |
| C + protamine sulphate | 24 | 8.00E+10 | 72% | 10.1 |

Finally, an overview of the relative amounts of Δ5nsP3 ChikV particles and other components as measured by SEC-HPLC at various steps throughout the entire virus purification process from crude harvest (a) to the final SGC purified pool is presented in FIG. 16. In sum, not only are the vast majority of contaminants and undesired products removed by the process, infectious ChikV particles are highly purified. As shown by the previously presented data, the final preparation is a highly enriched preparation of infectious ChikV particles.

Drug Substance (DS) Formulation

The pooled SGC fractions are diluted with DS formulation buffer M (10 mM Tris, 5% Sucrose (w/w), 1% (10 mg/mL) rHSA, pH 7.4±0.2). The final target volume of DS should be in the range of approximately 2 L. Based on current data the estimated range of the dilution factor might be 1:20 to 1:50.

Final DS Sterile Filtration

The final DS was filtered under aseptic conditions in a laminar flow hood using a sterility grade 0.2 μm syringe filter (e.g. 0.2 μm Mini Kleenpak EKV filter capsule with 220 cm² filter surface, Pall).

Quantification of Host Cell DNA (hcDNA) Host Cell Protein (HCP) and Endotoxin

The residual host cell DNA content of the sucrose gradient pool samples was determined by using the qPCR based assay. The DNA content in SGC pool was determined to be ≤0.002 ng/mL. The presence of residual host cell protein (HCP) from Vero cells was determined by ELISA. Residual host cell proteins present in the sucrose gradient pool samples were quantified using the Vero Cell HCP ELISA kit (Cygnus, F500). The residual host cell protein content in SGC pool was determined to be ≤200 ng/mL.

Endotoxin content of the SGC pool and DS was measured by Endosafe®-PTS™ system (Charles River). The system uses Limulus Amembocyte Lysate (LAL) reagents by a kinetic chromogenic methodology to measure color intensity directly related to the endotoxin content in a sample. Each cartridge contains precise amounts of a licensed LAL reagent, chromogenic substrate and an endotoxin control standard. Samples were diluted 1:100 in WFI. The SGC Pool F7-F11 was determined to be <5.00 EU/mL; likewise, the Drug Substance was also determined to have <5.00 EU/mL.

The following specifications for impurities in final Drug product were proposed: hcDNA<10 ng/dose; Endotoxins<50 EU/dose; HCP<200 ng/dose. These residual specifications would already be met in the highly concentrated SGC pool (~10 log TCID50/mL), which provides a high margin of safety considering the high dilution factor of SGC pool to final DP of >1:1000.

Example 2

Figure 17A:
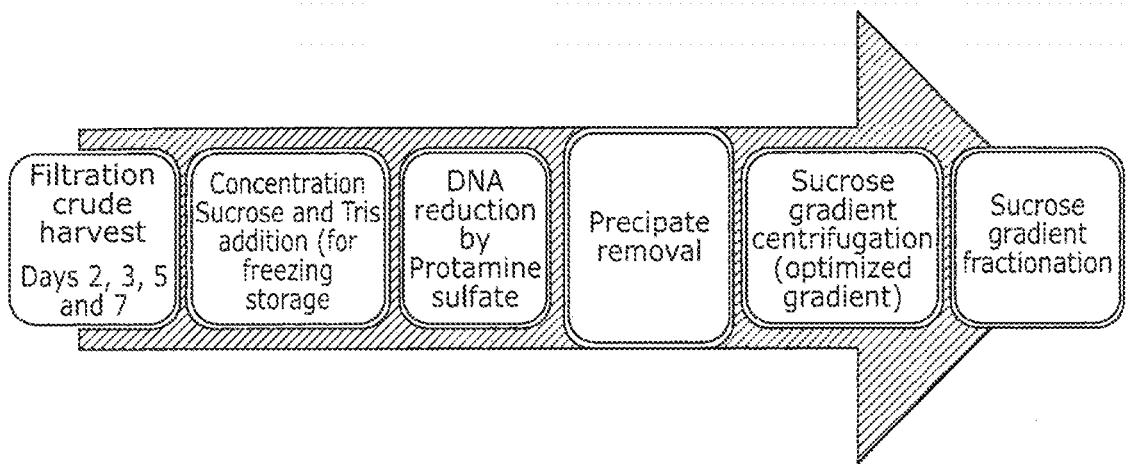
FIGS. 17A-17B: An exemplary downstream virus purification process from the crude harvest to formulation of the drug substance (vaccine), a preferred embodiment of the process of the invention (A). A flow-chart of an exemplary virus inactivation process is shown in (B). Both processes were exemplified in detail with Zika virus.
Figure 17B:
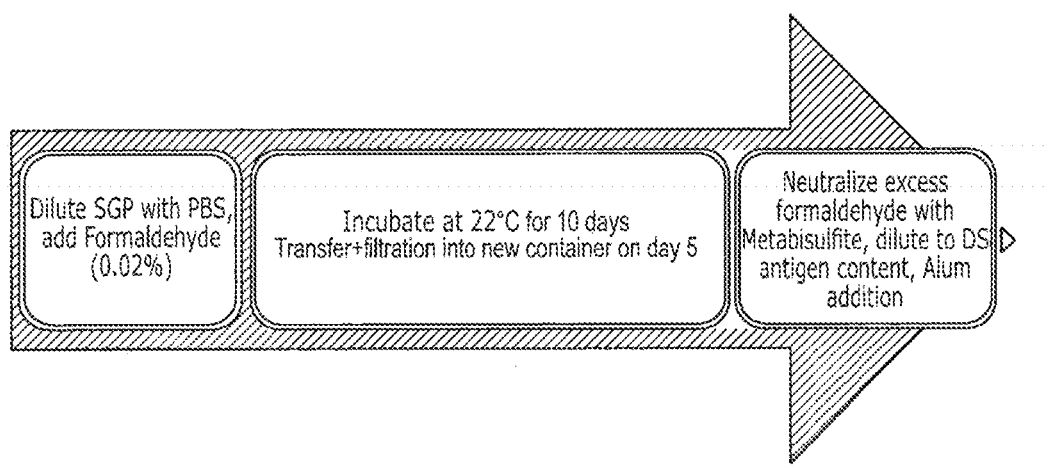
Figure 18:
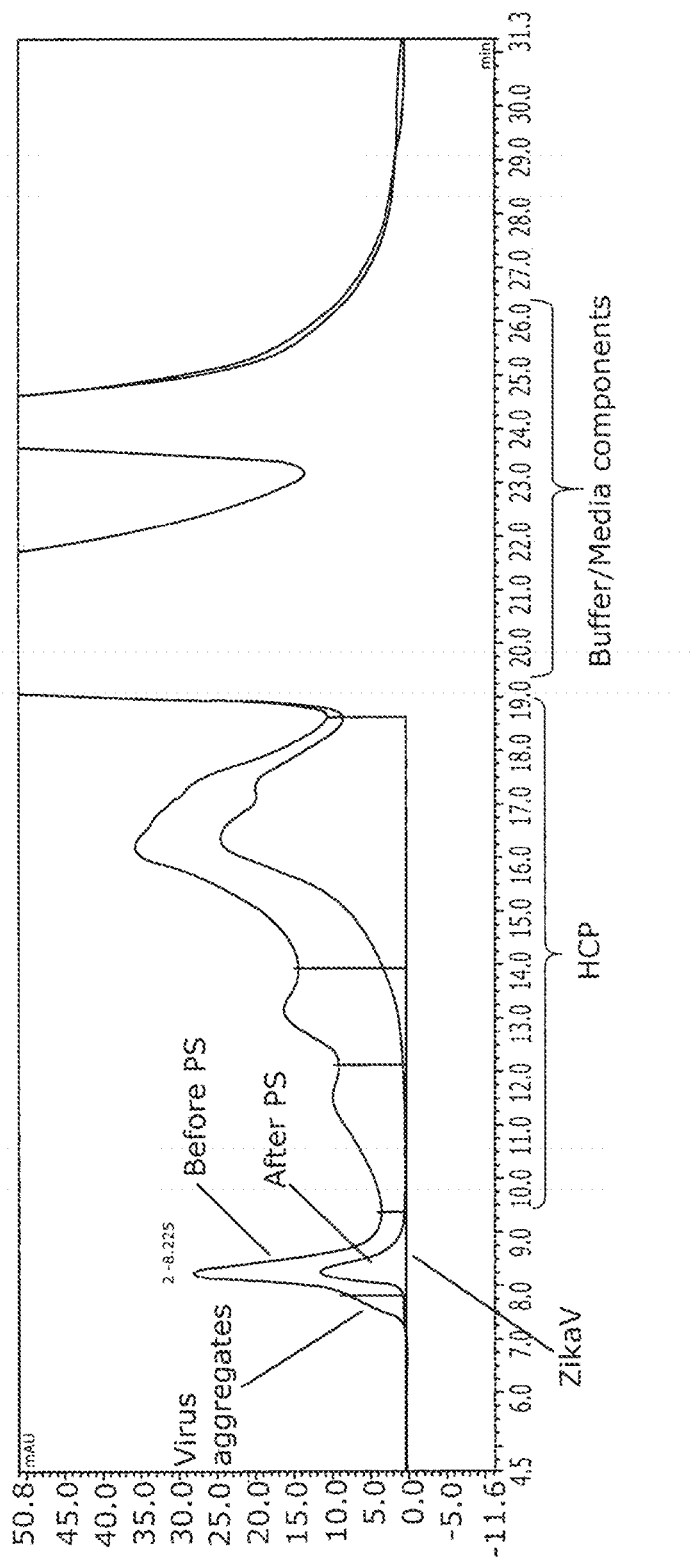
FIG. 18: PS treatment resulted in selective removal of Zika virus aggregates and Vero HCP and LMW impurities (SEC-HPLC of 30× concentrated Zika Virus harvest day 5).
Figure 19:
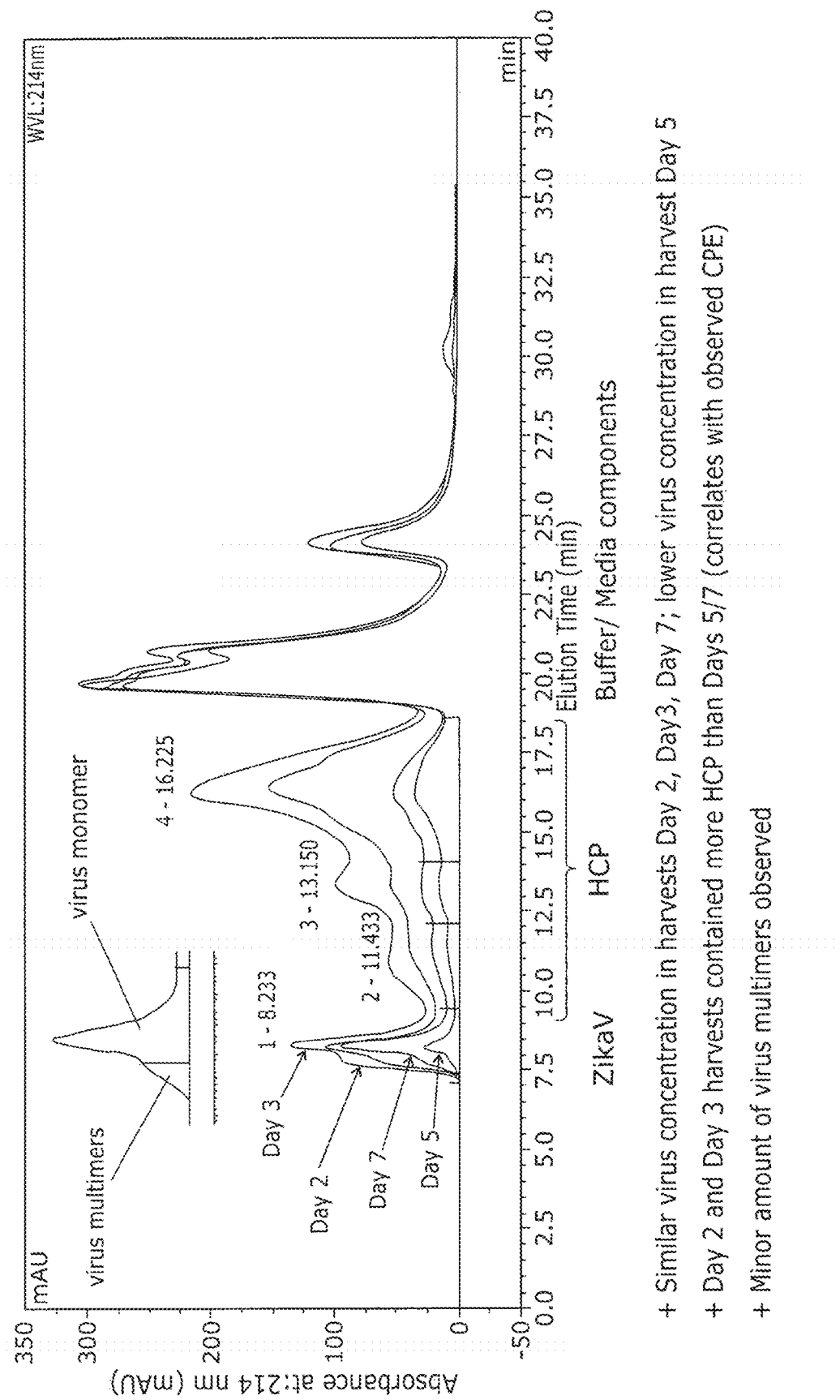
FIG. 19: SEC-HPLC of individual 30× concentrated Zika harvest prior PS treatment at different time points.
Figure 20:
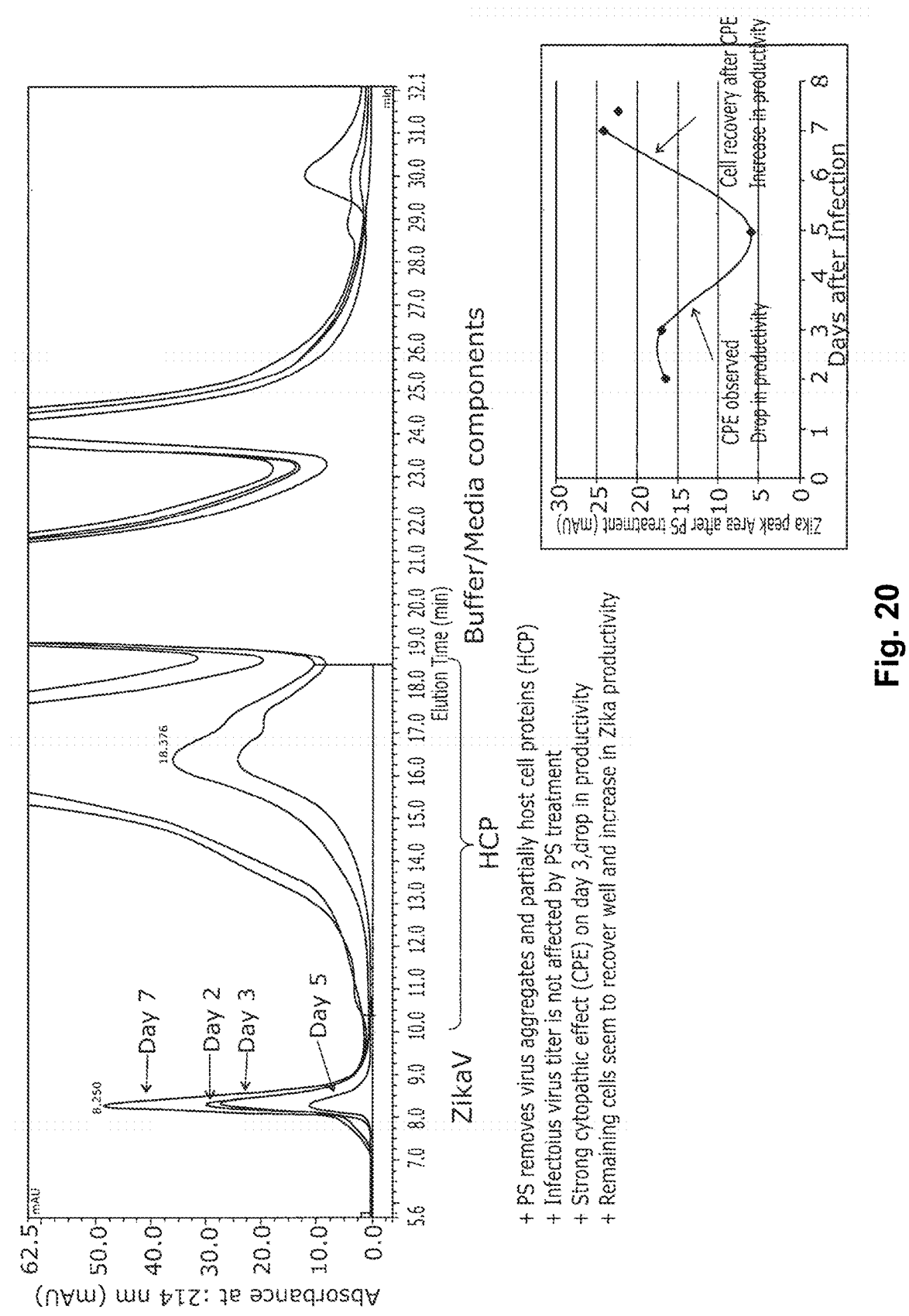
FIG. 20: SEC-HPLC of individual 30× concentrated Zika harvest post PS treatment at different time points. The smaller graph indicates the observed cytopathic effect (CPE) over time.

Production of a Zika Drug Substance Suitable for Application as a Vaccine In Humans and Animals Materials and Methods:

For the production of ZikaV the JEV process platform (Srivastava et al., Vaccine 19 (2001) 4557-4565; U.S. Pat. No. 6,309,650B1) was used as a basis Small changes of certain process steps were adapted to ZikaV properties and to improve purity. A short summary of the process steps is outlined below (see also FIGS. 17A and B). Briefly, the unexpected and novel purification properties of protamine sulphate (PS) were evaluated in purification processes for Zika Virus similarly as found above. Again non-infectious virus particle aggregates, HCP and other LMW impurities were removed by PS precipitation as shown by removal of aggregate shoulder in SEC-HPLC and no loss of infectious virus titer by PS treatment (FIG. 18). Further optimization of the Zika purification protocol is provided below.

Upstream:
Roller Bottle based Vero cell expansion (25×850 cm2 CellBind):
5% $CO_2$, 35° C., MEM+2 mM L-Glutamine+10% FBS
Infection with ZikaV research Master Seed Bank (rMSB) at MOI 0.01
Virus Production without serum
5% $CO_2$, 35° C., MEM+2 mM L-Glutamine
Multiple harvests (days 2, 3, 5 and 7) with re-feed
Sterile filtration of harvests and storage at 2-8° C. until further processing Downstream:
Pooling of harvests and concentration by ultrafiltration (100 kDa)
Stabilization of concentrated harvest (Tris/10% sucrose) for storage if required (−80° C.)
Removal of hcDNA by Protamine Sulphate (2 mg/mL)
Sucrose Gradient Purification (optimized three layered gradient)
Formaldehyde Inactivation (0.02%, 22° C., 10 days), neutralization with Na-metabisulfite
Dilution to DS antigen target content and formulation with Aluminium hydroxide (0.5 mg Al/mL)

Zika Virus Strain H/PF/2013 was originally isolated from a 51-year-old woman (accession number KJ776791.1, also SEQ ID NO: 13 herein) from French Polynesia. A sample was obtained from the European Virus Archive (EVAg; Ref-SKU: 001v-EVA1545). Based on this material, a research master seed bank (rMSB) was prepared on Vero cells as the cell substrate and the genomic sequence was checked by sequencing. Because the genomic sequence at the 5' and 3' flanking sequences of Zika virus strain H/PF/2013 was unknown, primers for sequencing were designed in those regions based on other Zika virus strains whereas the internal primers were designed from the published sequence (SEQ ID NOs: 80 to 123, see also Table A). The sequence obtained from the rMSB by use of these primers is provided by SEQ ID NO: 78. There was 100% overlap of the sequence with the published sequence of Zika Virus Strain H/PF/2013 (SEQ ID NO: 13). However, we sequenced additional regions 5' (an additional 40 bp) and 3 (an additional 160 bp) represented in SEQ ID NO: 78. In a preferred embodiment, the Zika virus of the invention comprises SEQ ID NO: 78. The genomic RNA is somewhat longer than the sequence according to SEQ ID NO: 78 (perhaps an additional 200 bp). Additionally, a Zika virus adapted to a host cell such as e.g. Vero cells may be expected to contain one or more mutations. For these reasons, the Zika virus of the current invention comprises the sequence of SEQ ID NO: 78 or, preferably, a sequence with at least 95%, 96%, 97%, 98%, or at least 99% sequence identity to the sequence provided by SEQ ID NO: 78. Furthermore, because the viral genome is likely to contain even further flanking regions to SEQ ID NO: 78; in one embodiment, the Zika virus of the invention contains the sequence of SEQ ID NO: 78 and optionally further comprises extensions at the 5' and/or 3' ends of at least 10, at least 20, at least 30, at least 40, at least 50, at least 60, at least 70, at least 80, at least 90, at least 100, at least 110, at least 120 or at least 130 nucleotides. In a preferred embodiment, the Zika virus comprises at least the coding sequence for the entire polyprotein of Zika Virus Strain H/PF/2013 of the invention i.e. the amino acid sequence of SEQ ID NO: 79 or a polyprotein with at least 95%, 96%, 97%, 98%, or at least 99% sequence identity to the sequence provided by SEQ ID NO: 79. Furthermore, the Zika virus comprises at least the coding sequence for the E-protein of Zika Virus Strain H/PF/2013 of the invention SEQ ID NO: 47 or an E-protein thereof with at least 95%, 96%, 97%, 98%, or at least 99% sequence identity to the sequence provided by SEQ ID NO: 47.

Virus Growth on Vero Cells

Vero cells were grown in Eagle's minimal essential medium (EMEM) containing 10% fetal bovine serum (FBS). Roller bottle cultures of Vero cell monolayers were infected with Zika Virus Strain H/PF/2013 at a multiplicity of infection (moi) of 0.01 plaque forming units (pfu) per cell. After 2 hours of virus adsorption, the cultures were washed 3 times with PBS and fed with EMEM without FBS and incubated at +35° C. with 5% $CO_2$. Infected Vero cell cultures were incubated until the virus titer reaches a desired level.

The culture medium was harvested at days 2, 3, 5 and 7 and were pooled from those harvest days and then centrifuged in a standard centrifuge. The supernatants were then filtered. Virus culture supernatants were concentrated by TFF ultrafiltration to remove cell culture media components and to reduce batch volume.

Evaluation of Harvest Procedure

The current JEV harvest process has scheduled harvests on days 3, 5, 7 and 9 post infection. To mimic the JEV process roller bottles were infected with ZIKV bank P4-FBS at an MOI of 0.01 in infection medium (MEM with 2% FBS+2 mM L-glutamine) for 2 hours. After removing the inoculum the cells were washed twice with PBS and 200 mL production medium (MEM+2 mM L-glutamine) was added.

After taking a sample on day 2 the first virus harvest was conducted on day 3 after infection. At this point significantly higher CPE could be observed compared to cells where virus was removed on day 2. Plaque assay analysis showed that the viral titers on day 2 were in the same range as for the standard harvesting schedule. However, starting with the day 3 harvest, the observed titers were significantly lower correlating with the increased CPE observed compared to the standard harvest schedule. On day 5 post infection no more living cells could be observed at all and the experiment was terminated with a final day 5 harvest.

TABLE 5

The calculated titers per plaque assay are summarized in the list below.

| | Log 10 PFU/mL |
|---|---|
| sample day2 | 7.02 |
| harvest day 3 | 6.66 |
| harvest day 5 | 6.26 |

Figure 23:
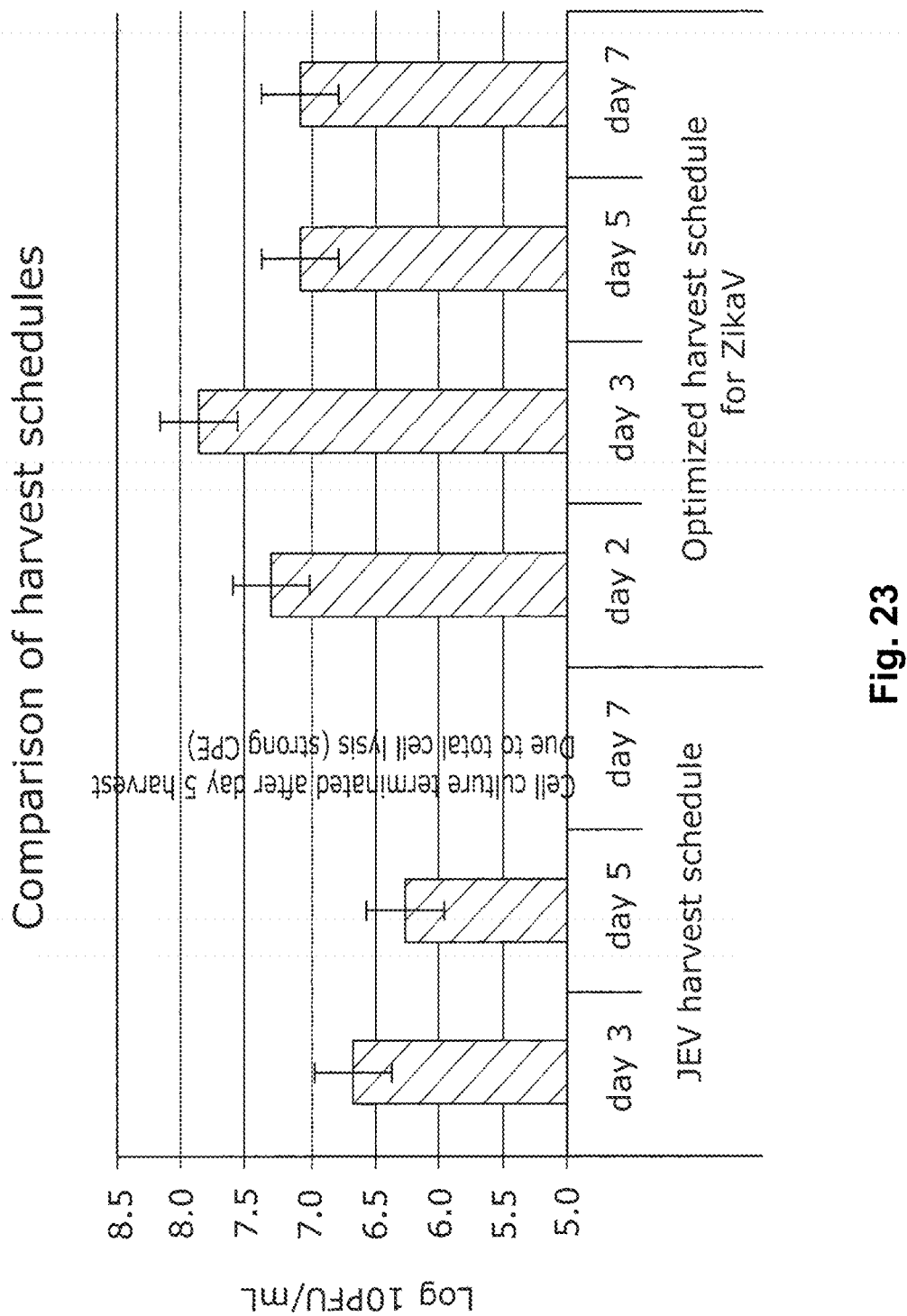
FIG. 23: Comparison of JEV and ZikaV harvest yields at different time points.
Figure 24:
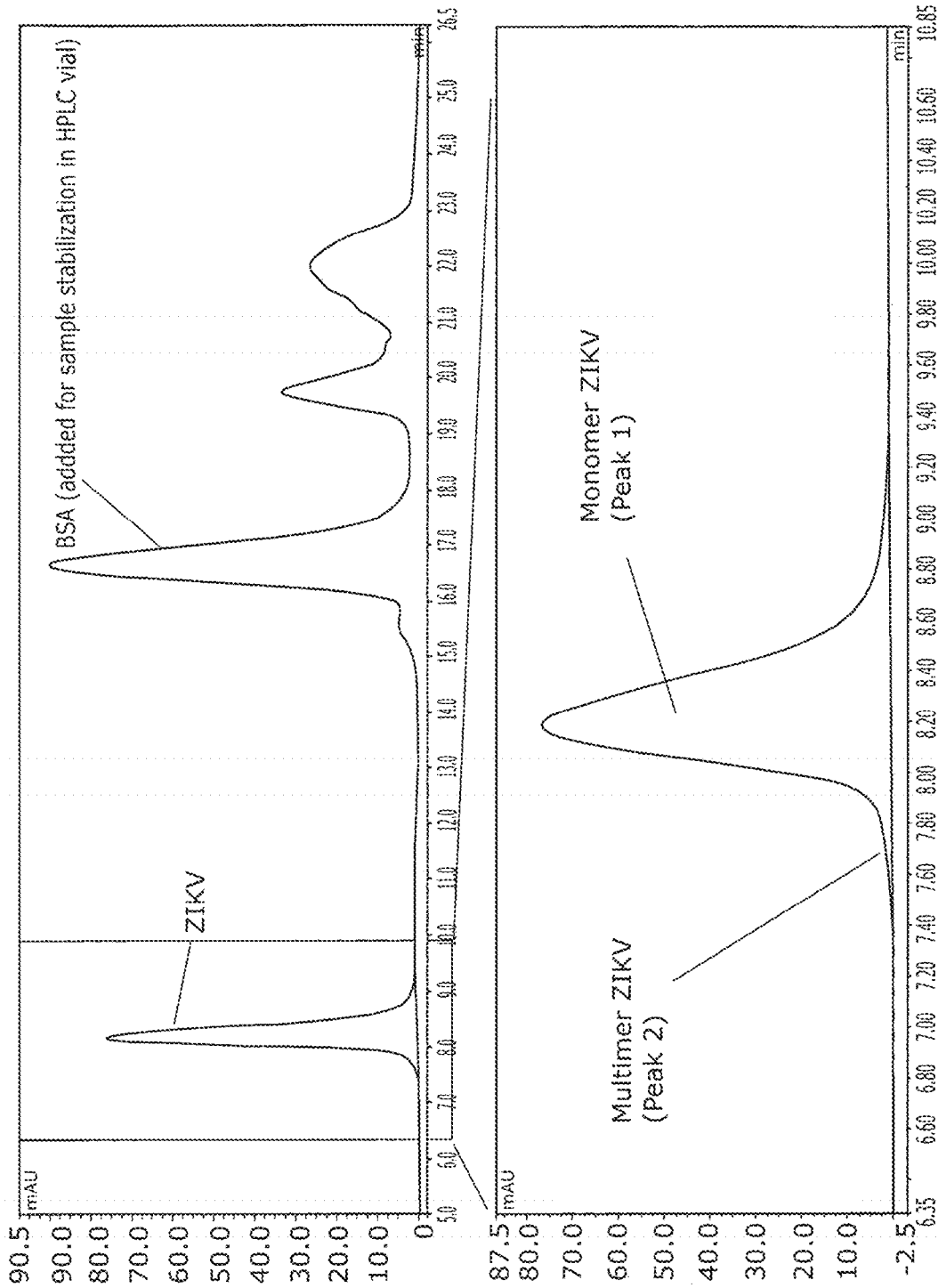
FIG. 24: SEC-HPLC elution profile of ZikaV NIV. Data were processed on Dionex Ultimate 3000/Superose 6 Increase column. Both panels are from the same chromatogram. The upper graph is the complete elution profile; the lower graph is an enlargement of the ZIKA virus elution peak.
Figure 25:
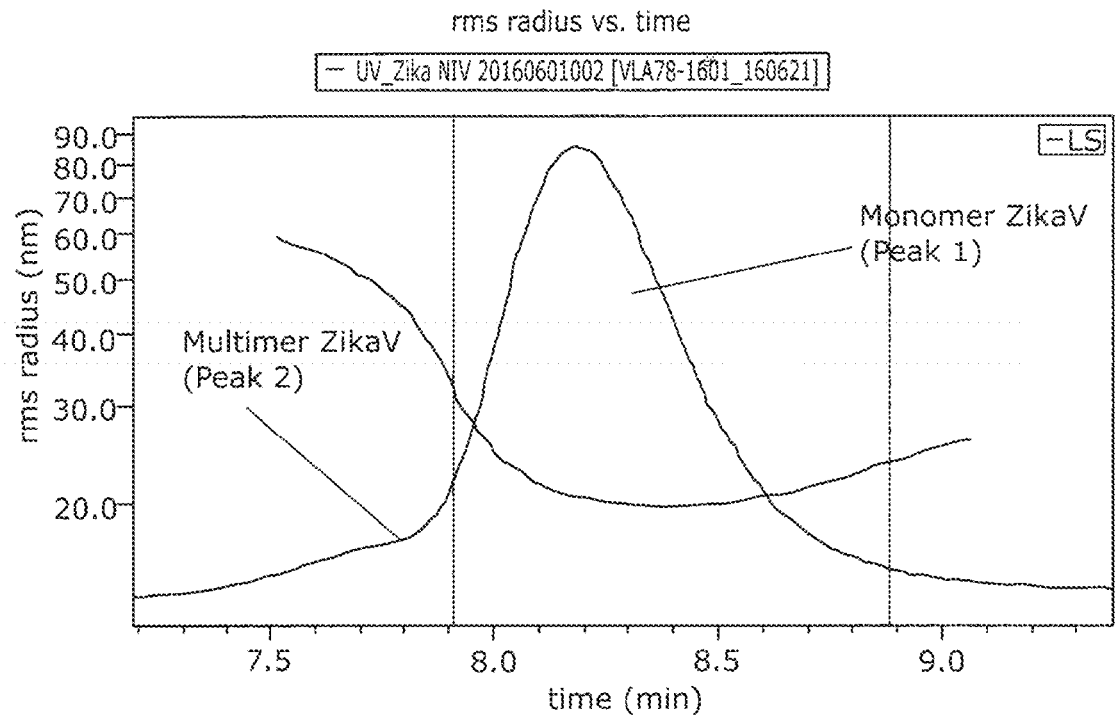
FIG. 25: SEC-MALLS analysis of inactivated ZikaV.
Figure 26:
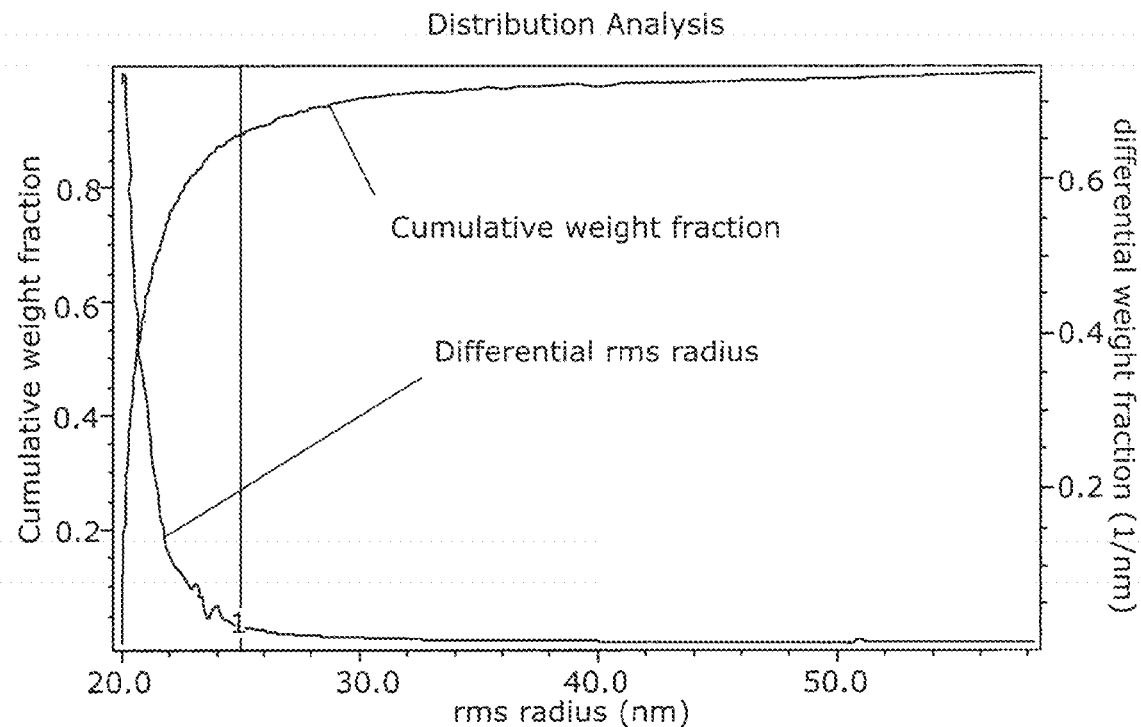
FIG. 26: Cumulative particle size distribution of Zika NIV.
Figure 27:
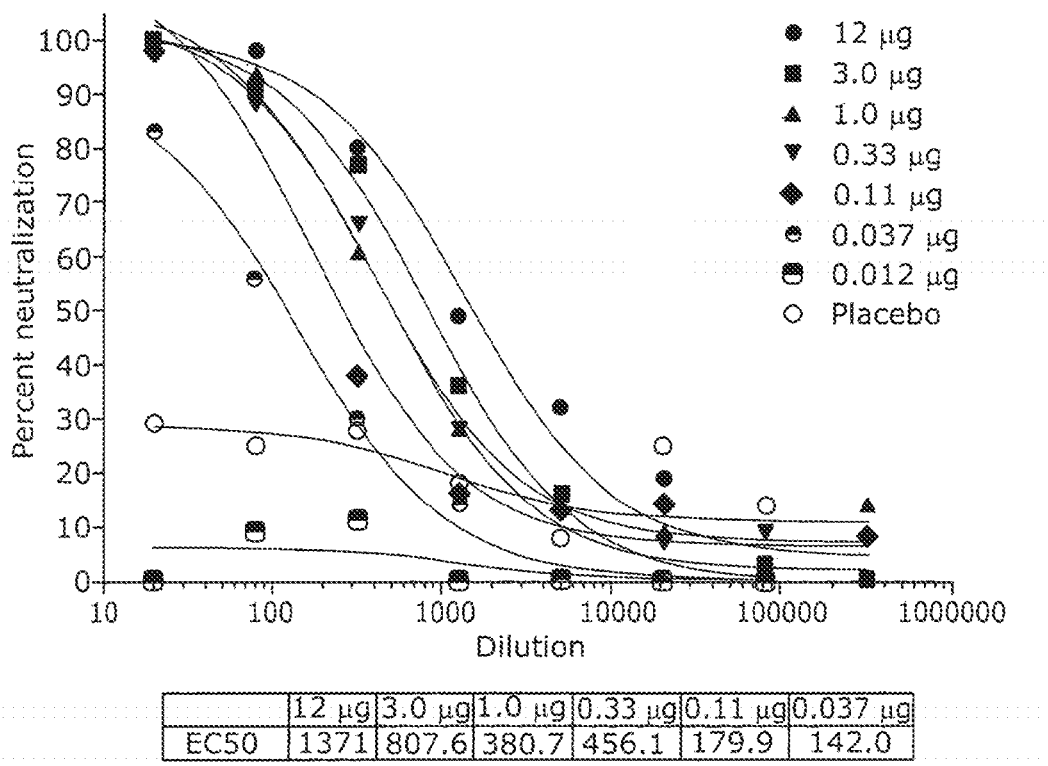
FIG. 27: Graphical representation of the neutralization of the Zika virus H/PF/2013 with pooled immunized mouse sera. The number of plaques without serum was set to 100%. The EC50 was calculated using the 3-parameter method.
Figure 28:
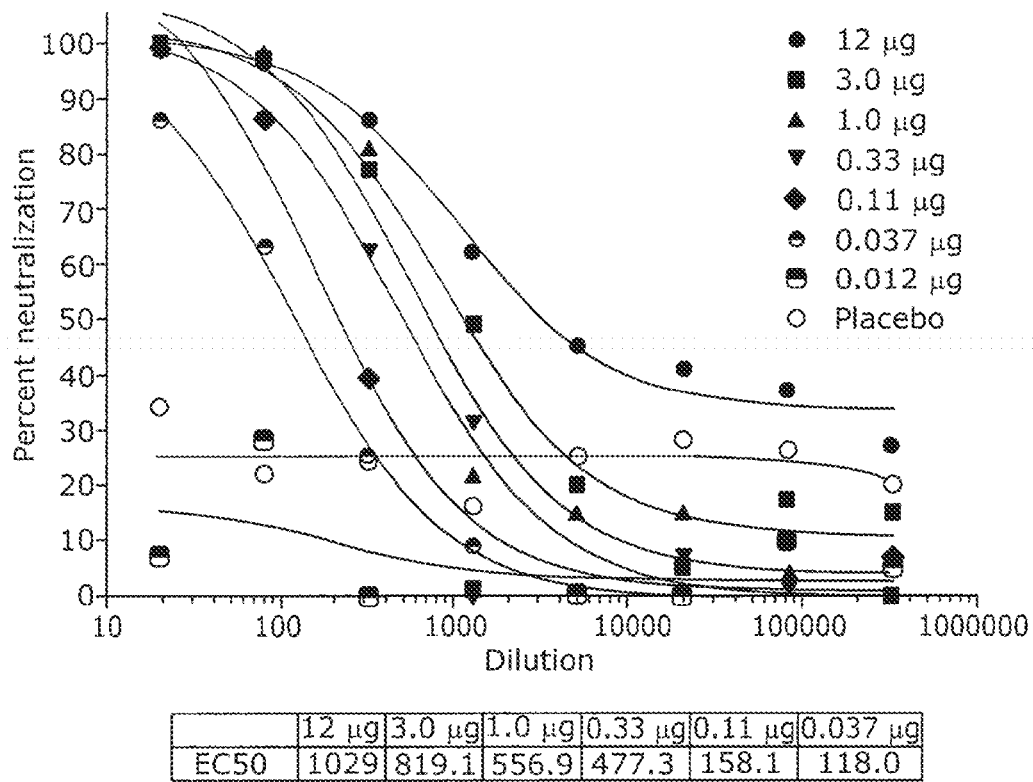
FIG. 28: Graphical representation of the neutralization of the Zika virus MR766 with pooled immunized mouse sera. The number of plaques without serum was set to 100%. The EC50 was calculated using the 3-parameter method.

This finding led to an optimized harvest schedule to better control of CPE and allow additional harvest day 5 and 7, see FIG. 23. For both harvest days the optimized ZikaV protocol yield significant higher virus titers compared to the modified protocol showing that the time of the first harvest is crucial for production yields. Additionally first harvesting at day 3 results in maximum 2 harvest points whereas first harvesting at day 2 allows for 4 harvest points further increasing the yield gain.

Downstream Purification of Zika Virus

The purification process was carried out at room temperature (18-22° C.) unless stated otherwise. Virus purification started with concentration of filtered combined harvest using 100 kDa cut-off TFF ultrafiltration modules to remove cell culture media components and reduce batch volume. After concentration, the pooled filtered harvest material was adjusted to a final concentration of 25 mM Tris pH 7.5 and 10% sucrose (w/w) using stock solution of both components (see FIG. 19 for SEC-HPLC of different harvests prior to PS treatment). This allowed for freezing the concentrated harvest at <−65° C. if required.

Host cell DNA and protein reduction as well reduction of non-infectious virus aggregates in the concentrated material was achieved by precipitation with protamine sulphate (2 mg/mL) followed by sucrose density centrifugation (2-8° C.) as final polishing step (see FIG. 20 for SEC-HPLC of different harvests post PS treatment). The purification process was designed to be completed within 2 working days with SGC starting on end of day 1 followed by fractionation and SDS-PAGE analysis on day 2. The sucrose gradient fractions were stored at 2-8° C. during the SDS-PAGE analysis (Silver staining) to identify the pure fractions containing ZikaV (see FIG. 21). After pooling the relevant fractions, the pool was diluted and inactivated by Formalin After pooling the relevant fractions of sucrose gradient centrifugation, the pool was diluted 1:3 in PBS and inactivated by Formalin (0.02% v/v, 200 ppm). Fractions were subjected to analysis by SDS-PAGE.

Effect of PS Treatment on Virus Recovery

Samples of individual 30× concentrated harvests days 2, 3, 5 and 7 were analysed before (FIG. 19) and after PS (FIG. 20) treatment by SEC-HPLC and plaque assay. SEC-HPLC was used for determination of relative total ZikaV content (active+inactive) expressed as peak area, whereas the rel. ZikaV peak purity is given as relative content of virus monomer population to total virus peak. Plaque assay states the content of total active virus particles in each sample. Experimental results are summarized in Table 1. The virus peak recovery by SEC-HPLC was only between 12 to 36% with peak purity after PS treatment in the range of >90% (no virus aggregates detected). The recovery of active virus particles by plaque assay was all >100% (130-700%, range within the variability of the assay) showing that no active virus particles were lost during PS treatment. These results show that during PS treatment only non-infective (immature and/or aggregated virus) particles were removed.

TABLE 6

ZikaV recovery by SEC-HPLC and plaque assay before and after PS treatment.

SEC-HPLC

| Harvest day | Peak area mAU*min 30x conc | 30x + PS | SEC Recovery (%) | rel. virus monomer content after PS (%) |
|---|---|---|---|---|
| Day 2 | 101.36 | 18.63 | 18 | 89% |
| Day 3 | 144.51 | 17.48 | 12 | 90% |
| Day 5 | 19.97 | 5.92 | 30 | 96% |
| Day 7 | 68.80 | 24.43 | 36 | 99% |

TABLE 6-continued

Plaque Assay

| Harvest day | PFU/mL 30x conc | 30x + PS | Plaque Recovery (%) |
|---|---|---|---|
| Day 2 | 3E+08 | 5E+08 | 179 |
| Day 3 | 2E+08 | 4E+08 | 193 |
| Day 5 | 1E+08 | 9E+08 | 700 |
| Day 7 | 3E+08 | 4E+08 | 132 |

Sucrose Gradient Centrifugation

The PS treated harvest was split in two parts and loaded on two centrifuge bottles. Sucrose density gradient centrifugation (SGC) was used for final concentration and polishing of the ZikaV material. The ZikaV PS treated concentrated harvest was loaded on top of a solution consisting of three layers of sucrose with different densities. The three sucrose layers were selected based on a preliminary study which showed the formation of a linear sucrose gradient and complete separation of the virus particles from residual contaminants as demonstrated for ChikV (FIG. 15D). The optimal volumes of the sucrose solutions were determined empirically. The volumes of individual layers for a centrifugation in 100 mL bottle scale are shown in Table 2.

TABLE 7

Individual layers/volumes for a centrifugation in bottle.

| Solution | Volume (mL) |
|---|---|
| PS treated harvest in 10% sucrose (L) | 40 |
| 15% sucrose (J) | 15 |
| 35% sucrose (I) | 15 |
| 50% sucrose (H) | 20 |
| Total volume | 90 |

The sucrose gradient bottles were prepared by stratifying the individual sucrose layers. A plastic tube was attached to peristaltic pump tubing. The plastic tube was mounted on a laboratory stand using a clamp and placed into the centrifuge bottle. The nozzle of the plastic tube was touching the bottom of the bottle. Using a peristaltic pump the ZikaV material and the sucrose solutions were pumped into the cylinder. A measuring cylinder was used as feed vessel. The first solution pumped was the ZikaV material as it represented the solution of lowest density (10% sucrose (w/w)). After the ZikaV material the sucrose solutions were pumped in ascending order starting with the 15% (w/w) solution J, followed by 35% sucrose solution I and finishing with the highest density sucrose solution H (50 (w/w)). The described setup is shown in FIG. 14. After all sucrose solutions were transferred the plastic tubing was carefully removed in order not to disturb the layers.

Prior to centrifugation the centrifuge was pre-cooled to 4° C. The prepared SG bottles were carefully transferred into the pre-cooled rotor. (Note: Sudden movement of the bottles during transfer to the rotor must be avoided in order not to disturb the sucrose layers.) The bottles were centrifuged at ~11.000 RCF max at 4° C. for at least 20 hours, no brake/deceleration activated. In case a different centrifuge system with a different rotor is used the necessary speed and centrifugation times need to be calculated based on the k-factor in order to achieve comparable centrifugation efficiency.

Harvesting of the sucrose gradient was done manually using a peristaltic pump. A plastic tube attached to peristaltic pump tubing was used for harvesting the sucrose gradient. The bottle containing the gradient was mounted onto a laboratory stand in a tilted position) (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14).

Figure 21:
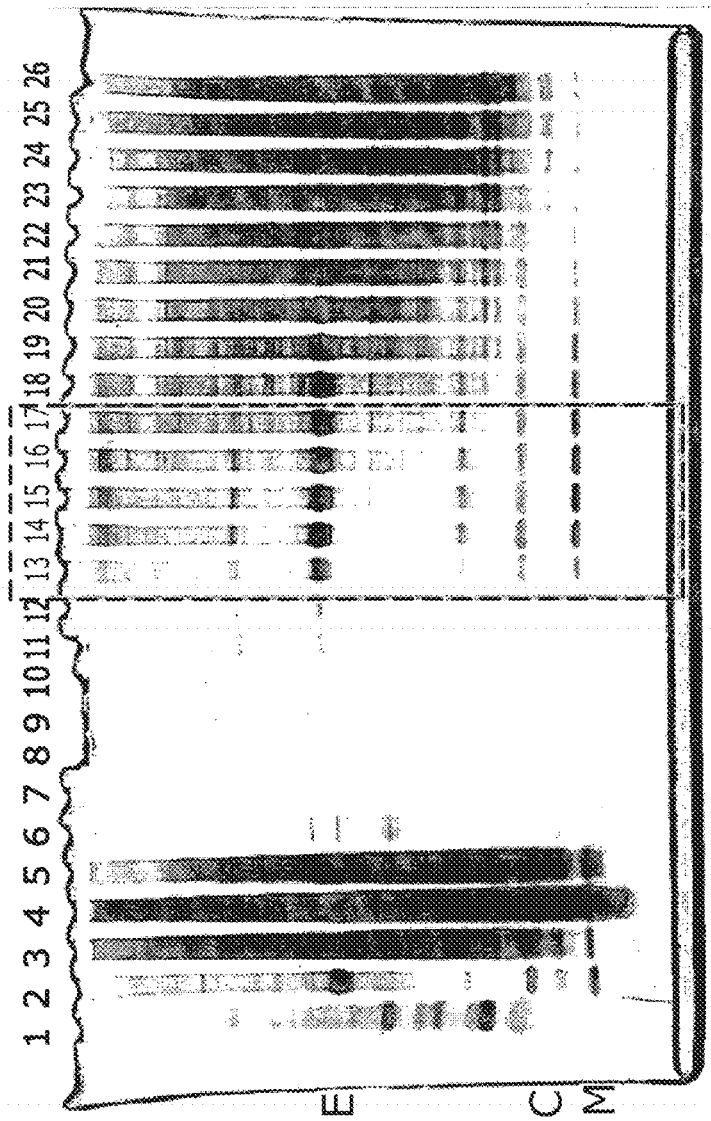
FIG. 21: Representative silver stained SDS-PAGE from the sucrose gradient harvest of a Zika virus purification is shown.

Using a peristaltic pump set to a flow rate of 30 mL per minute the gradient was harvested and manually split into 2 mL fractions. A total number of 32 fractions per bottle were harvested (~64 mL) and the remaining volume was discarded. The fractions were immediately tested by SDS-PAGE/silver stain to identify the virus containing fractions with sufficient high purity. Representative SDS-PAGE is shown in FIG. 21. Fraction 10-14 were pooled and further processed.

The purified viral solution was inactivated by incubation with 0.02% formaldehyde over a period of ten days in a 22° C. controlled-temperature incubator. The formaldehyde is neutralized by addition of sodium metabisulphite on the tenth day.

The sucrose gradient pool (~17 mL after sampling) was further diluted 3-fold with PBS to a final volume of 51 mL in a PETG container. A volume of 1% formaldehyde (10,000 ppm) solution equivalent to 1/50 of the final volume of the pre-formaldehyde pool was added to this pool resulting in an effective concentration of 200 ppm. The formaldehyde-treated solution was mixed on a magnetic stirrer for 10 minutes. After sampling, the formaldehyde-treated viral solution was placed within a cooled incubator at 22° C.±2° C. On Day 5 post addition of formaldehyde, the formaldehyde-treated viral solution was filtered through a 0.2 μm filter and then placed in the incubator at 22° C.±2° C. again. On Day 10, after removing the 10-Day inactivation final sample, a volume of 1% (of the weight of the final formaldehyde-treated viral solution) of 200 mM-sodium metabisulphite solution (2 mM final concentration) was aseptically transferred into the PETG container containing the formaldehyde-treated viral solution. After mixing for 5 minutes on a magnetic stirrer, the neutralized inactivated viral solution is held at room temperature (20 to 25° C.) for a minimum of 30 minutes. After sampling, the neutralized inactivated viral solution is stored at 5° C.±3° C. until further processing.

Inactivation by Formaldehyde

Critical parameters for this step are final formalin concentration, temperature, mixing and transfer into a new container. A preliminary acceptance criterion for maximum pfu/mL (determined by plaque assay) has been set on the diluted pool pre formaldehyde treatment.

The quality of the neutralized inactivated viral solution was monitored by the following parameters: Plaque assay on Day 10, SEC-HPLC, SDS-PAGE/Western Blot.

Interestingly, SEC-HPLC analysis of samples taken during the inactivation period followed by neutralization with bisulfite showed more or less constant peak area throughout the inactivation period. This is in contrast to JEV where losses of viral particles up to 60% are observed using the process disclosed by Srivastava et al. Vaccine 19 (2001) 4557-4565. In a scale-down model the viral losses were even much higher due to surface/area ratio at smaller scale and high losses due to unspecific adsorption. Differences of the ZikaV inactivation experiment and JEV inactivation were noticed as follows:

A) Much higher purity of ZikaV SGP pool with regard to residual PS (<2 μg/mL) compared to JEV. The 3-fold ZikaV inactivated sample contained therefore <<1 μg/mL of residual PS. Commercial JEV SGP pool contains on average ~120 μg/mL (up to 152 μg/mL possible). The average dilution to inactivation solution of ~14-fold results in a residual PS content up to ~11 μg/mL. It may be that higher amount of residual PS could cause virus precipitation due to cross-linking/reaction with formalin.

B) ZikaV inactivation sample contained ~10% sucrose (3-fold dilution of SGP pool containing ~30-35% sucrose). Sucrose might have stabilizing effect of viral ZikaV particles during treatment with formalin.

Dilution to DS and Formulation with Aluminium Hydroxide (DP)

Figure 22:
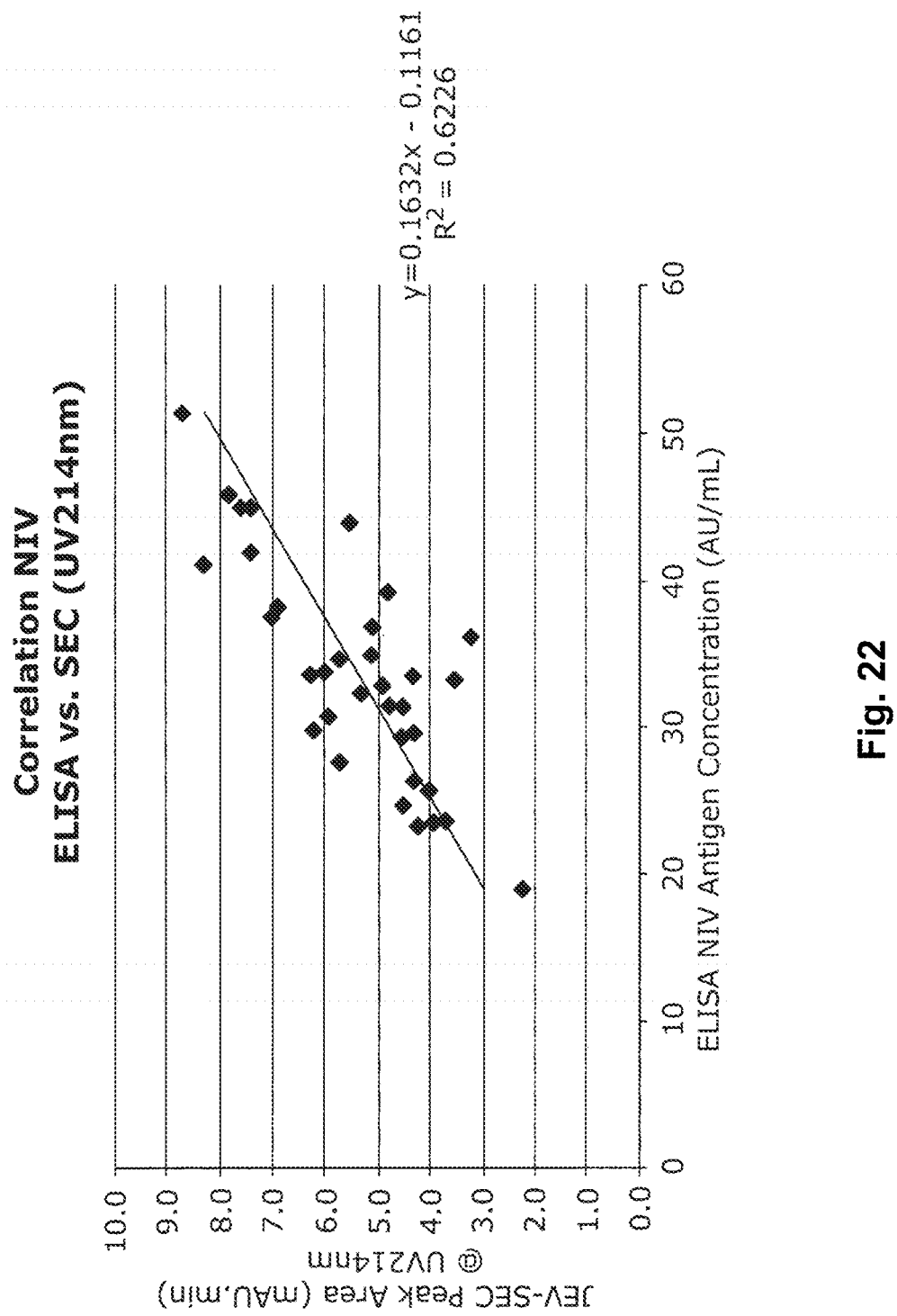
FIG. 22: Correlation between JEV antigen content in neutralized inactivated virus (NIV) analysed by ELISA and SEC-HPLC (Dionex Ultimate 3000, Superose 6 column).

For preparation of ZikaV drug substance used in mouse potency assay an antigen content (expressed as total viral particles or SEC peak area) of 5 times higher compared to Ixiaro was targeted. The basis for determination of antigen content was SEC-HPLC. Briefly, a Superose 610/300 Increase column (GE Healthcare) equilibrated with PBS+ 250 mM NaCl, pH 7.4 at 1 ml/min and 25° C., was used to detect ZikaV at 214 nm detection wavelength in harvest samples and throughout the downstream process. In the current JEV process the antigen content in NIV is determined by a specific ELISA. A good correlation was observed between antigen content determined by ELISA and SEC-HPLC. On average, the antigen content in commercial NIV samples is in the range of 33 AU/mL corresponding to ~5.2 mAU JEV peak area, see FIG. 22.

ZikaV NIV day 10 (Zika peak ~36 mAU, analysed on Waters HPLC/Superose6 Increase column) was diluted with PBS to a target of 6.3 (~5.7× dilution). Aluminium hydroxide was added to a final concentration of 0.5 mg/mL Aluminium (1/20 v/v Alum 2% stock solution added) to prepare ZikaV Drug Product (DP). The DP was gently mixed for 5 min. An aliquot of the DP was removed, Alum sedimented by centrifugation and the clear supernatant analysed by SEC-HPLC. No ZikaV peak was detected in the supernatant indicating complete adsorption (estimated as >95%) of viral particles on the mineral adjuvant. Formulated ZikaV DP was stored at 2-8° C.

The impurity profile of the inactivated Zika virus DS is comparable to the profile of JEV DS with the exception of a lower PS content (Table 8).

TABLE 8

Determination of impurity profile in Zika and JEV DS samples:

| | Specification (JEV DS) | JEV | Zika |
|---|---|---|---|
| HCP (ng/mL) | <100 LOQ 12 ng/mL | <LOQ | <LOQ |
| DNA (pg/mL) | <200 LOQ 40 pg/mL | <40 | <40 |
| Aggregates by SEC-MALLS (%) | Not specified, part of characterization LOQ 5% | <LOQ | <LOQ |
| PS (μg/mL) | Specification only at SGP pool to demonstrate consistent process performance (19-152 μg/mL), *PS content in DS calculated based on PS content | ~4* | <<LOQ |

TABLE 8-continued

Determination of impurity profile in Zika and JEV DS samples:

| Specification (JEV DS) | JEV | Zika |
|---|---|---|
| in SGP pool (~100 µg/mL) and average dilution factor (~28x) to DS; LOQ 2 µg/mL | | |

*Typical PS impurity in a JEV sample produced in accordance with protocol disclosed in Srivastava et al. Vaccine 19 (2001) 4557-4565.

SEC-MALLS Results

A representative SEC-HPLC elution profile of ZikaV NIV at 214 nm detection wave length is shown in FIG. 24. Note that BSA (50 μg/mL) was added to the sample to minimize losses in HPLC glass vial due to unspecific surface adsorption. ZikaV monomer content was estimated as ~98% with a multimer content of ~2%.

SEC-MALLS analysis (FIG. 25) of the sample confirmed the radius Rz of the monomer ZikaV population peak 1 as 21.6 nm and ~49 nm for the multimer peak 2. Cumulative particle size distribution showed that 89% of all viral particles are within a radius range between 18 to 25 nm (FIG. 26).

Results Confirm Purity and Homogeneity of ZikaV NIV.

Viral Titer by Plaque Assay

TABLE 9

Active ZikaV pfus were quantified by plaque assay throughout the process.

| Sample | Pfu/mL |
|---|---|
| Harvest day 2 (filtered) | $6.4 \times 10^7$ |
| Harvest day 3 (filtered) | $1.0 \times 10^8$ |
| Harvest day 5 (filtered) | $1.5 \times 10^8$ |
| Harvest day 7 (filtered) | $1.1 \times 10^8$ |
| PS treated harvest 300x concentrate (= SGP load) | $9.0 \times 10^8$ |
| SGP pool | $8.9 \times 10^8$ |
| Inactivation start (SGP pool 1:3 diluted) | $3.4 \times 10^8$ |
| Inactivation day 5 | <LOD |
| Inactivation day 10 | <LOD |

Comparison of PS and Benzonase on Process Performance

A direct comparison of DNA removal method of concentrated ZikaV harvest pool was done. One aliquot was treated with PS (2 mg/mL, 15 min at room temperature), the other aliquot was treated with Benzonase (50 U/mL, 2 mM MgCl2, 4 h RT, 48 h 2-8° C.). Both samples were further purified by sucrose gradient as described in this report. Interestingly, the Benzonase treated samples did not yield any pure fractions after sucrose gradient centrifugation of the treated ZikaV harvest. In those fractions where the specific virus bands were detected, a high amount of host cell protein was detected throughout the collected fractions. The PS treated material resulted in pure ZikaV containing fractions as expected. This finding may suggest that PS is not only effective for DNA removal by precipitation; in addition it improves the recovery of virus particles in the gradient by disrupting interaction of DNA (fragments) and virus particles. Benzonase treatment does not remove DNA, it only results in its fragmentation. Residual DNA fragments might still interact with virus particles and residual HCPs resulting in cross-contamination and co-purification in the sucrose gradient. Pooled SGP fractions were also analysed by SEC-HPLC. Although a large peak was detected, SDS-PAGE confirmed that this sample was highly contaminated with HCPs. A large peak might be detected at UV214 and 280 nm after SEC-HPLC analysis due to possible interaction of HCPs with large virus particles, changing the UV absorbance.

Immunogenicity of Vero Grown Zika Virus

Immunization of Mice

Prior to immunization, groups of ten 6-week-old female CD1 mice were bled via vena facialis and pre-immune sera were prepared. One intraperitoneal immunizations of 200 μL were administered. A dose titration (12 μg, 3 μg, 1 μg, 0.33 μg, 0.11 μg, 0.037 μg and 0.012 μg, equivalent to the protein amount in IXIARO) of inactivated Zika virus formulated with aluminium hydroxide (Al(OH)3) at a final concentration of 0.7%. Three weeks after immunization, blood was collected and immune sera were prepared. All animal experiments were conducted in accordance with Austrian law (BGB1 Nr. 501/1989) and approved by "Magistratsabteilung 58".

Plaque Reduction Neutralization Test (PRNT)

Twelve well plates were used for PRNT. Each well was seeded with 1 mL medium containing $4\times10^5$ Vero cells and incubated 35° C. with 5% CO2 overnight. Pools of heat inactivated sera from each dose group were tested in triplicate. The target viruses (H/PF/2013 (SEQ ID NO: 13) or MR766 (SEQ ID NO: 11)) were diluted to 100 pfu/165 μL. Equal volumes of target virus and serum dilution were incubated at 35° C. with 5% $CO_2$ for 1 hour. The cell culture medium was aspirated from the Vero cells and 330 μL of the mixture target virus/serum dilution were added to each well and the plates were rocked back and forth 5 times before incubating for 2 hours at 35° C. with 5% $CO_2$. To each well 1 mL of a 2% methylcellulose solution containing EMEM and nutrients was added, the plates were then incubated for 5 days at 35° C. with 5% $CO_2$ before staining the cells for 1 hour with crystal violet/5% formaldehyde and subsequently washed 3 times with deionized water. The plates were air dried and the numbers of plaques in each well were manually counted.

Results

Neutralization was observed with serum pools from mice immunized with inactivated Zika virus vaccine (H/PF/2013) down to 37 ng (dosing equivalent to the amount protein in IXIARO®) against Zika viruses of both the Asian (H/PF/2013) and African (MR766) lineages (FIGS. 27 and 28, respectively). Complete inhibition was seen at the 1:20 serum dilution with an immunization dose down to 110 ng (dosing equivalent to the amount protein in IXIARO®). The neutralization of both the Asian (H/PF/2013) and African (MR766) lineages of the Zika virus was equivalent, which indicates high cross-neutralization between different Zika virus strains of the inactivated Zika virus vaccine (H/PF/2013).

Another neutralization assay was performed using the microneutralization assay as described by Larocca, et al. (2016, Nature doi:10.1038/nature18952). It was found that the inactivated Zika virus of the current invention had an MN50 (microneutralization) titer of 90 at 1 μg of inactivated purified virus.

Further methods: The immunogenicity of inactivated Zika virus preparations is assessed using a mouse model of Zika infection. Groups of adult mice are immunized subcutaneously (s.c.) with 500, 50, or 5 ng of inactivated Zika virus with adjuvant (e.g. aluminium hydroxide with or without IC31®), or without adjuvant. An additional group of mice receive PBS as a negative control. Each group is administered the indicated inoculum at t=0 and in some cases also at three to four weeks later (t=3/4). Beginning approximately three weeks after administration of the last immunization, serum samples are obtained from each of the mice at regular intervals. The serum samples are tested for the presence of neutralizing antibodies using PRNT.

The in vivo protective efficacy of the inactivated Zika virus preparations is also assessed using a mouse model of Zika infection, i.e. IFN-alpha/beta receptor knock-out mice (A129) (see e.g. Dowall et al., 4 Mar. 2016, http://dx.doi.org/10.1101/042358) or blocking of the IFN-alpha/beta receptor by administration of anti-IFN-alpha/beta receptor monoclonal antibodies to C57BL/6 or BALB/c mice (see e.g. Pinto et al., 7 Dec. 2011, DOI: 10.1371/journal.ppat.1002407). For protection assays, groups of 10 three- to eight-weeks-old A129, C57BL/6 of BALB/c mice are inoculated subcutaneously in the hindquarters with inactivated Zika virus with adjuvant (aluminium hydroxide) or without adjuvant at t=0. Age-matched controls are inoculated with PBS or non-specific antigens in alum. Mice are optionally boosted with a second administration of the indicated inoculation three to four weeks later. The mice are then challenged subcutaneously at three to eight weeks post immunization by inoculation with a deadly dose of live Zika virus. One day prior to challenge of C57BL/6 and BALB/c mice, they are passively administered (intraperitoneally) anti-IFN-alpha/beta receptor monoclonal antibodies. Challenged mice are monitored daily for morbidity and mortality for up to twenty-one days. Another alternative is to challenge intracranially adult vaccinated/non-vaccinated adult mice and observe protection.

It is expected that the Zika virus produced by the process of the invention will provide very similar functional readouts in in vitro, in vivo and finally human trials as the currently licensed JEV vaccine in the EU and US and elsewhere, IXIARO®. The dosage may alter but due to the very similar impurity profile and almost identical manufacture, a very similar efficacy and safety result will be expected as was determined for the currently licensed JEV vaccine (licensed in the EU and US and elsewhere).

Discussion & Conclusion

The existing manufacturing platform for production of inactivated JEV vaccine IXIARO® was used as a basis for a manufacturing feasibility study of inactivated ZikaV vaccine candidate (Asian strain H/PF/2013). The virus was produced on Vero cells cultivated in roller bottles. The virus was purified by PS treatment followed by an optimized sucrose gradient. Inactivation was done by formalin treat (0.02%, 10 days at 22° C.). For exploratory immunization studies in mice, a DP formulated with Alum was prepared with an estimated 5-fold higher virus particle content compared to IXIARO®, the commercial JEV Vaccine. The impurity profile of the DS met all criteria as defined in the specification for IXIARO®, the commercial JEV vaccine. The neutralization of both the Asian (H/PF/2013) and African (MR766) lineages of the Zika virus was equivalent, which indicates high cross-neutralization between different Zika virus strains of the inactivated Zika virus vaccine (H/PF/2013).

The in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was higher than the recently reported inactivated Zika virus vaccine candidate (Larocca, et. al, 2016, supra.). Inactivated viruses are among the safest vaccines and especially preferred for deliver to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Example 3

Figure 29:
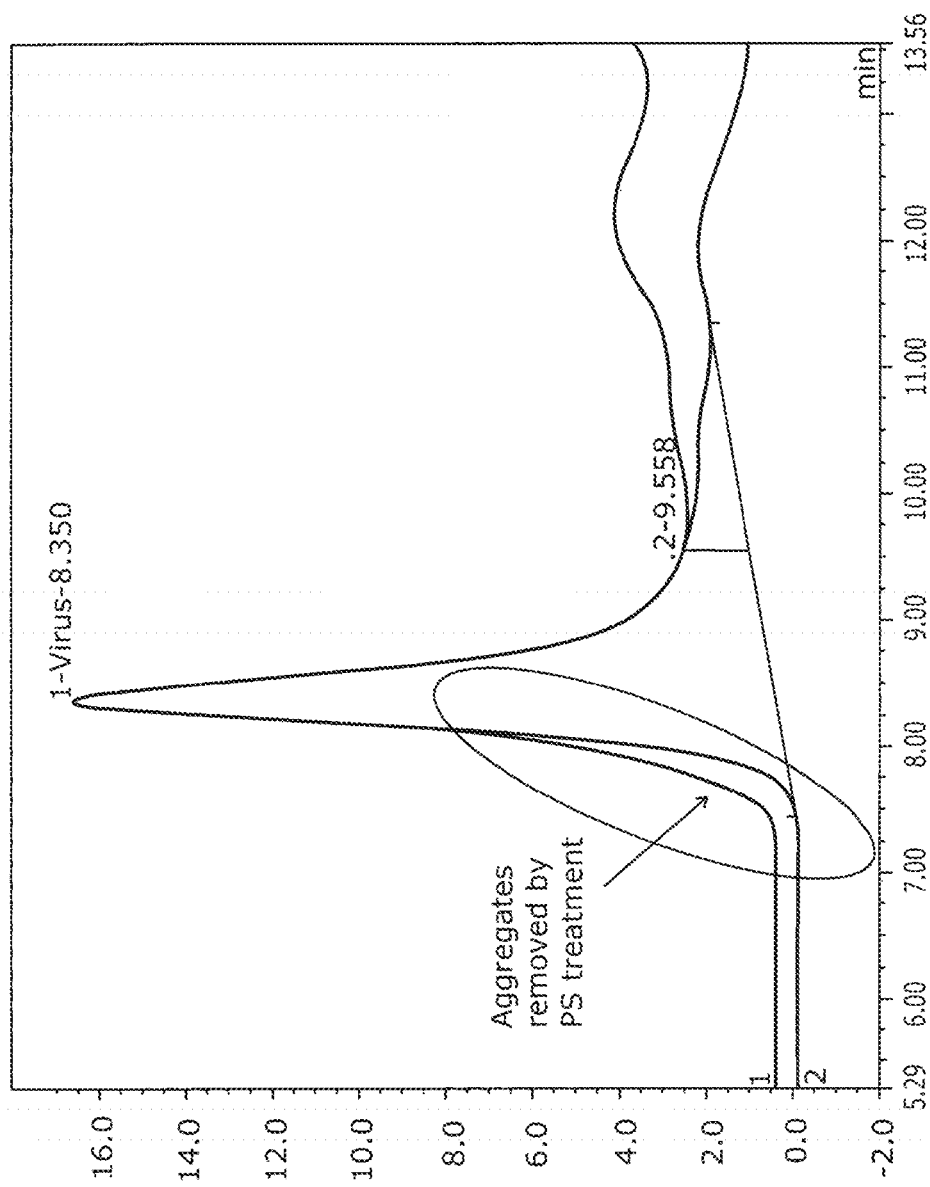
FIG. 29: Change in SEC profile of yellow fever virus peak after PS addition according to the invention showing a complete removal of large size aggregates and LMW impurities.

Development of a Purification Process for Yellow Fever Virus Vaccine Produced in Vero Cells A downstream process was developed for the purification of infectious yellow fever virus particles whereby host cell nucleic acids, non-infectious virus particles and aggregates are removed by the addition of protamine sulphate as described in Examples 1 and 2. The unexpected and novel purification properties of protamine sulphate (PS) were evaluated in purification processes for yellow fever (YF) as follows:

As before the treatment of YF-harvest with PS significantly reduces the amount of aggregates as seen with SEC for two vaccine strains currently in development (FIG. 29).

Further more detailed aspects of the invention:

A1. A Zika virus vaccine comprising an optimally inactivated Zika virus particle, wherein the Zika virus particle is able to seroconvert a subject that is administered the Zika virus vaccine with at least a 70% probability.

A2. The Zika virus vaccine of A1, wherein the Zika virus particle is able to seroconvert the subject that is administered the Zika virus vaccine with at least a 80%, 85%, 90%, or 95% probability.

A3. The vaccine of A1 or A2, wherein the Zika virus particle has a RNA genome corresponding to the DNA sequence provided by any one of the nucleic acid sequences of SEQ ID NOs: 2-13 or 78, or a variant nucleic acid sequence that is at least 88% identical to any one of SEQ ID NOs: 2-13 or 78 and able to pack a virulent Zika virus.

A4. The vaccine of any one of A1-A3, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

A5. The vaccine of any one of A1-A4, wherein the Zika virus is inactivated by chemical inactivation, thermal inactivation, pH inactivation, or UV inactivation.

A6. The vaccine of A5, wherein the chemical inactivation comprises contacting the Zika virus with a chemical inactivation agent to completely inactivate the Zika virus as measured by plaque assay.

A7. The vaccine of A6, wherein the chemical inactivation comprises contacting the Zika virus with formaldehyde.

A8. The vaccine of A7, wherein the formaldehyde inactivation comprises contacting the Zika virus with formaldehyde for between 2-10 days.

A9. The vaccine of any one of A5-A8, wherein the chemical activation is performed at about +4° C. or about +22° C.

A10. The vaccine of any one of A1-A9, further comprising an adjuvant.

A11. The vaccine of A10, wherein the adjuvant is an aluminum salt adjuvant.

A12. The vaccine of A11, wherein the aluminum salt adjuvant is aluminium hydroxide or aluminium phosphate salt.

A13. The vaccine of any one of A10-A12, wherein the vaccine comprises or further comprises an adjuvant comprising a peptide and a deoxyinosine-containing immunostimulatory oligodeoxynucleic acid molecule (I-ODN).

A14. The vaccine of A13, wherein the peptide comprises the sequence KLKL5KLK (SEQ ID NO: 71) and the I-ODN comprises oligo-d(IC)13 (SEQ ID NO: 70).

A15. The vaccine of any one of A1-A14, further comprising one or more pharmaceutically acceptable excipient.

B1. A kit comprising a Zika virus vaccine of any one of A1-A15.

B2. The kit of B1, further comprising a second vaccine.

B3. The kit of B2, wherein the second vaccine is a West Nile virus vaccine, a Japanese Encephalitis virus vaccine, a yellow fever virus vaccine, a Dengue virus vaccine or a Chikungunya virus vaccine.

C1. A method, comprising administering a first dose of a therapeutically effective amount of the Zika virus vaccine of any one of A1-A15 to a subject in need thereof.

C2. The method of C1, further comprising administering a second dose of a therapeutically effective amount of the Zika virus vaccine.

C3. The method of C1 or C2, wherein the second dose of the Zika virus vaccine is administered about 7 days after the first dose of the Zika virus vaccine.

C4. The method of C1 or C2, wherein the second dose of the Zika virus vaccine is administered about 14 days after the first dose of the Zika virus vaccine.

C5. The method of C1 or C2, wherein the second dose of the Zika virus vaccine is administered about 28 days after the first dose of the Zika virus vaccine.

C6. The method of any one of C1-C5, wherein the administering results in production of Zika virus neutralizing antibodies.

D1. A method of producing a Zika virus vaccine, comprising
(i) passaging a Zika virus on Vero cells, thereby producing a culture supernatant comprising the Zika virus;
(ii) harvesting the culture medium of (i);
(iii) precipitating the harvested culture medium of (ii), thereby producing a Zika virus supernatant; and
(iv) optimally inactivating the Zika virus in the Zika virus supernatant of (iii) thereby producing an inactivated Zika virus.

D2. The method of D1, further comprising concentrating the culture medium of (ii) prior to step (iii).

D3. The method of D1 or D2, wherein the precipitating of (iii) comprises contacting the culture medium of (ii) with protamine sulfate or benzonase.

D4. The method of any one of D1-D3, further comprising (v) dialyzing the inactivated Zika virus of (iv), thereby producing a dialyzed Zika virus.

D5. The method of D4, further comprising (vi) filtering the dialyzed Zika virus of (v).

D6. The method of any one of D1-D5, wherein the inactivating is by chemical inactivation, thermal inactivation, pH inactivation, or UV inactivation.

D7. The method of D6, wherein the chemical inactivation comprises contacting the Zika virus with a chemical inactivation agent for at least 4 days.

D8. The method of D6 or D7, wherein the chemical inactivation agent comprises formaldehyde.

D9. The method of any one of D6-D8, wherein the chemical activation is performed at about +4° C. or about +22° C.

D10. The method of D8 or D9, further comprising neutralizing the formaldehyde.

D11. The method of D10, wherein the neutralizing is performed with sodium metabisulfite.

E1. The use of the optimally inactivated Zika virus vaccine of any one of A1-A15 for the treatment and prevention of a Zika virus infection.

E2. The use of E1, wherein the inactivated Zika virus vaccine is administered in a first dose of a therapeutically effective amount to a subject in need thereof.

E3. The use of E2, wherein the inactivated Zika virus vaccine is administered in a second dose of a therapeutically effective amount to the subject.

E4. The use of E3, wherein the second dose of the inactivated Zika virus vaccine is administered about 7 days after the first dose of the Zika virus vaccine.

E5. The use of E3, wherein the second dose of the Zika virus vaccine is administered about 14 days after the first dose of the Zika virus vaccine.

E6. The use of E3, wherein the second dose of the Zika virus vaccine is administered about 28 days after the first dose of the Zika virus vaccine.

E7. The use of any one of E1-E6, wherein the vaccine administration results in production of Zika virus neutralizing antibodies.

F1. A pharmaceutical composition for use in the treatment and prevention of a Zika virus infection, wherein said pharmaceutical composition comprises the optimally inactivated Zika virus vaccine of any one of A1-A15.

F2. The pharmaceutical composition of F1, wherein the inactivated Zika virus vaccine is administered in a first dose of a therapeutically effective amount to a subject in need thereof.

F3. The use of F2, wherein the inactivated Zika virus vaccine is administered in a second dose of a therapeutically effective amount to the subject.

F4. The use of F3, wherein the second dose of the inactivated Zika virus vaccine is administered about 7 days after the first dose of the Zika virus vaccine.

F5. The use of F3, wherein the second dose of the Zika virus vaccine is administered about 14 days after the first dose of the Zika virus vaccine.

F6. The use of F3, wherein the second dose of the Zika virus vaccine is administered about 28 days after the first dose of the Zika virus vaccine.

F7. The use of any one of F1-F6, wherein the vaccine administration results in production of Zika virus neutralizing antibodies.

G1. A Chikungunya virus vaccine comprising a live attenuated Chikungunya virus particle, wherein the Chikungunya virus particle is able to seroconvert a subject that is administered the Chikungunya virus vaccine with at least a 70% probability.

G2. The Chikungunya virus vaccine of G1, wherein the Chikungunya virus particle is able to seroconvert the subject that is administered the Chikungunya virus vaccine with at least a 80%, 85%, 90%, or 95% probability.

G3. The vaccine of G1 or G2, wherein the Chikungunya virus particle has an RNA genome corresponding to the DNA sequence provided by the nucleic acid sequences of SEQ ID NOs: 77, or a variant nucleic acid sequence that is at least 88% identical to SEQ ID NO: 77 and able to pack a Chikungunya virus.

G4. The vaccine of any one of G1-G3, wherein the Chikungunya virus is inactivated by chemical inactivation, thermal inactivation, pH inactivation, or UV inactivation.

G5. The vaccine of any one of G1-G4, further comprising an adjuvant.

G6. The vaccine of G5, wherein the adjuvant is an aluminum salt adjuvant.

G7. The vaccine of G6, wherein the aluminum salt adjuvant is aluminium hydroxide or aluminium phosphate salt.

G8. The vaccine of any one of G5-G7, wherein the vaccine comprises or further comprises an adjuvant comprising a peptide and a deoxyinosine-containing immunostimulatory oligodeoxynucleic acid molecule (I-ODN).

G9. The vaccine of any one of G1-G8, further comprising one or more pharmaceutically acceptable excipient(s).

H1. A kit comprising a Chikungunya virus vaccine of any one of G1-G9.

H2. The kit of H1, further comprising a second vaccine.

H3. The kit of H2, wherein the second vaccine is a West Nile virus vaccine, a Japanese Encephalitis virus vaccine, a Yellow Fever virus vaccine, a Dengue virus vaccine or a Zika virus vaccine.

I1. A method, comprising administering a first dose of a therapeutically effective amount of the Chikungunya virus vaccine of any one of G1-G9 to a subject in need thereof.

I2. The method of I1, further comprising administering a second dose of a therapeutically effective amount of the Chikungunya virus vaccine.

I3. The method of I1, wherein a single shot is sufficient for eliciting an effective immune protection in a subject such as a human.

J1. A method of producing a Chikungunya virus vaccine, comprising
  (i) passaging a Chikungunya virus on Vero cells, thereby producing a culture supernatant comprising the Chikungunya virus;
  (ii) harvesting the culture medium of (i);
  (iii) precipitating the harvested culture medium of (ii), thereby producing a Chikungunya virus supernatant.

J2. The method of J1, further comprising concentrating the culture medium of (ii) prior to step (iii).

J3. The method of J1 or J2, wherein said precipitation of (iii) comprises contacting the culture medium of (ii) with protamine sulfate or benzonase.

K1. The use of the Chikungunya virus vaccine of any one of G1-G9 for the treatment and prevention of a Zika virus infection.

K2. The use of K1, wherein the vaccine is administered in a single shot of a therapeutically effective amount to a subject in need thereof.

K3. The use of any one of K1-K2, wherein the vaccine administration results in production of Chikungunya virus neutralizing antibodies.

L1. A pharmaceutical composition for use in the treatment and prevention of a Chikungunya virus infection, wherein said pharmaceutical composition comprises the Chikungunya virus vaccine of any one of G1-G9.

L2. The pharmaceutical composition of L1, wherein the Chikungunya virus vaccine is administered in a single shot dose of a therapeutically effective amount to a subject in need thereof.

M1. Use of protamine, preferably a protamine salt, to separate infectious virus particles from non-infectious virus particles.

M2. The use according to M1, wherein the protamine salt also facilitates the separation of infectious virus particles from host cell proteins and/or low molecular weight materials.

M3. A process of purification of infectious virus particles, comprising the steps of:
  a) providing a crude harvest (a) comprising virus particles and impurities, wherein the impurities are generated from growing said virus particles on a cell substrate;
  b) reducing impurities from said crude harvest (a) by precipitation with an agent comprising protamine, preferably a protamine salt, more preferably a protamine sulphate, even more preferably a recombinant protamine sulphate, to obtain a virus preparation (b), wherein the enrichment of infectious virus particles in the virus preparation (b) relative to total virus products in the crude harvest (a) is in the range of at least 50% to 95%, preferably at least 80%.

M4. The use of M1 or M2 or the process of M3, wherein the virus particles are selected from the group consisting of flaviviruses, e.g. yellow fever virus, Dengue virus, Japanese encephalitis virus or Zika virus, and alphaviruses, e.g. Chikungunya virus.

M5. A process of purification of infectious virus particles, comprising the steps of:
  a) providing a crude harvest (a) comprising virus particles and impurities, wherein the impurities are generated from growing said virus particles on a cell substrate;
  b) reducing impurities from said crude harvest (a) by precipitation with an agent comprising protamine, preferably a protamine salt, more preferably a protamine sulphate, even more preferably a recombinant protamine sulphate, to obtain a virus preparation (b);
  c) further purifying said virus preparation (b) by one or more size exclusion methods such as (i) a sucrose density gradient centrifugation, (ii) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles, and/or (iii) size exclusion chromatography to obtain a virus preparation (c) comprising the infectious virus particles, wherein the residual host cell DNA of the virus preparation (c) is less than 100 ng/mL and the residual host cell protein and the residual aggregates of infectious virus particles of the final virus preparation (c) is less than 1 µg/mL.

M6. The process of M5, wherein the residual host cell DNA of the virus preparation (c) is less than 10 ng/mL and the residual host cell protein of the final virus preparation (c) is less than 100 ng/mL.

M7. The process of any of M3 to M6, wherein the crude harvest (a) comprising virus particles and impurities is subjected to one or more pre-purification step(s) prior to step (b).

M8. The process of M7, wherein the one or more pre-purification step(s) comprises
  a) filtration using a filter having a pore size equal to or less than 0.2 µm; and/or
  b) digestion of host cell genomic DNA by enzymatic treatment; and/or
  c) ultra/diafiltration using a hollow fiber membrane having a pore size equal to or greater than 300 kDa, preferably equal to or greater than 100 kDa.

M9. The process of any one of M3 to M8, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml.

M10. The process of any one of M3 to M9, wherein the enrichment of infectious virus particles in the virus preparation (c) or any final virus preparation relative to total virus products in the crude harvest (a) is in the range from at least 50% to 95%, preferably at least 80%.

M11. The process of any one of M7 to M10, wherein the one or more pre-purification step(s) prior to step (b) of any of M7 to M10 is performed using a filter having a pore size equal to or less than 1 µm, preferably 0.2 µm.

M12. The process of any one of M3 to M11, wherein the residual impurity of the virus preparation (c) is less than 10%.

M13. The process of any one of M3 to M12, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

M14. The process of M13, wherein said cell line is a Vero cell line.

M15. The process of any one of M3 to M14, wherein said virus is a live virus, an attenuated live virus, a chimeric virus, a modified live virus, or a recombinant live virus.

M16. The process of any one of M3 to M15, wherein said virus is selected from the group of viruses consisting of a Zika virus, preferably a Zika virus strain of the Asian lineage or an immunogenic variant thereof; an attenuated Chikungunya virus, preferably a Chikungunya virus with a deletion mutation in the non-structural protein 3; a yellow fever virus, a Dengue virus and a Japanese Encephalitis virus.

M17. The process of any one of M3 to M16, wherein said process resulting in final virus preparation (c) is followed by an inactivation step, wherein the virus is inactivated preferably by formaldehyde.

M18. A composition comprising the virus particles obtainable or obtained by the process of any one of M3 to M17, wherein the composition contains protamine at levels below detection in size exclusion chromatography.

M19. The composition according to M18, wherein the composition contains trace amounts of protamine or fragments thereof detectable by mass spectroscopy or other sensitive methods.

M20. The composition according to M18 or M19 for treating and/or protecting from an infection.

M21. Use of the process according to any one of M3 to M17 for manufacturing a composition for immunization against a virus infection.

M22. The use according to M21, wherein said virus infection is an infection caused by the group of viruses consisting of yellow fever virus, Chikungunya virus and Zika virus.

N1. A process of purification of infectious alphavirus particles, preferably Chikungunya virus particles, comprising the steps of:
(a) providing a crude harvest (a) comprising virus particles and impurities, wherein the impurities are generated from growing said virus particles on a cell substrate;
(b) reducing impurities from the crude harvest (a) by precipitation with an agent comprising a protamine salt, preferably a protamine sulphate, even more preferably a recombinant protamine sulphate, to obtain a virus preparation (b);
(c) contacting the virus preparation (b) with (i) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and collecting the virus particles to obtain a virus preparation (d), or (ii) a solid-phase matrix comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and separating the solid-phase matrix from the virus particles by filtration to produce a virus preparation (c); and
(d) further purifying the virus preparation (c) by sucrose density gradient centrifugation to obtain a virus preparation (d) comprising the infectious virus particles, wherein the residual host cell DNA of the virus preparation (d) is less than 100 ng/mL and the residual host cell protein of the final virus preparation (d) is less than 1 µg/mL.

N2. The process of N1, wherein the residual host cell DNA of the virus preparation (d) is less than 10 ng/mL and the residual host cell protein of the final virus preparation (d) is less than 100 ng/mL.

N3. The process of N1 or 2, wherein the crude harvest (a) comprising virus particles and impurities is subjected to one or more pre-purification step(s) prior to step (b).

N4. The process of any one of N1 to 3, wherein the one or more pre-purification step(s) comprises
(a) filtration using a filter having a pore size equal to or less than 0.2 µm; and/or
(b) digestion of host cell genomic DNA by enzymatic treatment; and/or
(c) ultra/diafiltration using a hollow fiber membrane having a pore size equal to or greater than 300 kDa, preferably equal to or greater than 100 kDa.

N5. The process of any one of N1 to 4, wherein the concentration of protamine sulphate is 1 to 2 mg/ml, more preferably 1.2 to 1.8 mg/ml, more preferably 1.4 to 1.6 mg/ml, most preferably 1.6 mg/ml.

N6. The process of any one of N1 to 5, wherein the molecule entering the core of the solid-phase matrix has a molecular weight less than 700 kDa.

N7. The process of any one of N1 to 6, wherein the ligand of the ligand-activated core of the solid-phase matrix is capable of binding the molecule that enters the ligand-activated core via cationic-, anionic-, hydrophobic- or mixed interactions.

N8. The process of any one of N1 to 7, wherein the ligand of the ligand-activated core of the solid-phase matrix is octylamine.

N9. The process of any one of N1 to 8, wherein the solid-phase matrix is used as a slurry and at a final concentration between 0.5% (v/v) and 10% (v/v), preferably 0.6%, 0.7%, 0.9%, 1%, 2%, 3%, 4%, 5%, 6%, 7%, 8%, 9%, 10%, most preferably 1%.

N10. The process of any one of N1 to 9, wherein the solid-phase matrix is incubated with the protamine-treated virus preparation (b) at refrigerated temperatures (2° C. to 8° C.) with a stirring for at least 10 minutes, preferably 15 minutes, 30 minutes or 1 hour, most preferably 15 minutes.

N11. The process of any one of N1 to 10, wherein the enrichment of infectious virus particles in the final virus preparation relative to total virus products in the crude harvest (a) is in the range from at least 50% to 95%, preferably at least 80%.

N12. The process of any one of N1 to 11, wherein the filtration of step (c) of N1 is performed using a filter having a pore size equal to or less than 1 μm, preferably 0.2 μm.

N13. The process of any one of N1 to 12, wherein the residual impurity of the final virus preparation is less than 10%.

N14. The process of any one of N1 to 13, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

N15. The process of N14, wherein said cell line is a Vero cell line.

N16. The process of any one of N1 to 15, wherein the Chikungunya virus is a live virus, an attenuated live virus, a chimeric virus, a modified live virus, or a recombinant live virus.

N17. The process of any one of N1 to 16, wherein the Chikungunya virus is the Δ5nsP3 attenuated mutant or an immunogenic variant thereof.

N18. The process of any one of N1 to 17, wherein said process resulting in final virus preparation (d) is followed by an inactivation step, wherein the virus is inactivated preferably by formaldehyde.

N19. Use of the process according to any one of N1 to 18 for manufacturing a composition for immunization against a Chikungunya virus infection.

N20. The use according to N19, wherein the composition for immunization against a Chikungunya virus infection is a vaccine.

N21. A composition comprising the virus particles obtainable by the process of any one of N1 to 18 for treating and/or preventing a Chikungunya virus infection.

P1. A Zika virus vaccine comprising an optimally inactivated Zika virus particle, wherein the Zika virus particle is able to seroconvert a subject that is administered the Zika virus vaccine with at least a 70% probability.

P2. The Zika virus vaccine of P1, wherein the Zika virus particle is able to seroconvert the subject that is administered the Zika virus vaccine with at least a 80%, 85%, 90%, or 95% probability, preferably a 80% probability.

P3. The vaccine of P1 or 2, wherein the Zika virus particle has a RNA genome corresponding to the DNA sequence provided by any one of the nucleic acid sequences of SEQ ID NOs: 1-11, or a variant nucleic acid sequence that is at least 88% identical to any one of SEQ ID NOs: 1-11 and able to pack a virulent Zika virus.

P4. The vaccine of any one of P1-3, wherein the Zika virus particle has an E protein selected from the amino acid sequences provided by any one of SEQ ID NOs: 12-67, or a variant amino acid sequence that is at least 95% identical to any one of SEQ ID NOs: 12-67 and able to pack a virulent Zika virus.

P5. The vaccine of any one of P1-4, wherein the Zika virus is inactivated by chemical inactivation, thermal inactivation, pH inactivation, or UV inactivation.

P6. The vaccine of P5, wherein the chemical inactivation comprises contacting the Zika virus with a chemical inactivation agent for longer than is required to completely inactivate the Zika virus as measured by plaque assay.

P7. The vaccine of P6, wherein the chemical inactivation comprises contacting the Zika virus with formaldehyde.

P8. The vaccine of P7, wherein the formaldehyde inactivation comprises contacting the Zika virus with formaldehyde for between 2-10 days.

P9. The vaccine of any one of P5-8, wherein the chemical activation is performed at about +4° C. or about +22° C.

P10. The vaccine of any one of P1-9, further comprising an adjuvant.

P11. The vaccine of P10, wherein the adjuvant is an aluminum salt adjuvant.

P12. The vaccine of P11, wherein the aluminum salt adjuvant is aluminium hydroxide or aluminium phosphate salt.

P13. The vaccine of any one of P10-12, wherein the vaccine comprises or further comprises an adjuvant comprising a peptide and a deoxyinosine-containing immunostimulatory oligodeoxynucleic acid molecule (I-ODN).

P14. The vaccine of P13, wherein the peptide comprises the sequence KLKL5KLK (SEQ ID NO: 71) and the I-ODN comprises oligo-d(IC)13 (SEQ ID NO: 70).

P15. The vaccine of any one of P1-14, further comprising one or more pharmaceutically acceptable excipient.

Q1. A process of purification of infectious virus particles, comprising the steps of:
(a) providing a crude harvest (a) comprising virus particles and impurities, wherein the impurities are generated from growing said virus particles on a cell substrate;
(b) reducing impurities from the crude harvest (a) by precipitation with an agent comprising protamine, preferably a protamine salt, more preferably a protamine sulphate, even more preferably a recombinant protamine sulphate, to obtain a virus preparation (b);
(c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 μg/ml, preferably below 0.5 μg/mL, more preferably below 0.1 μg/mL, most preferably below 0.05 μg/mL.

Q2. The process of Q2, wherein the virus particles are selected from the group consisting of flaviviruses, e.g. yellow fever virus or Zika virus and alphaviruses, e.g. Chikungunya.

Q3. The process of Q1 or Q2, additionally comprising the step of:
(d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

Q4. The process of any of Q1 to 3, wherein the residual host cell DNA of the virus preparation (c) is less than 10 ng/mL and the residual host cell protein of the final virus preparation (c) is less than 100 ng/mL.

Q5. The process of any of Q1 to 4, wherein the crude harvest (a) comprising virus particles and impurities is subjected to one or more pre-purification step(s) prior to step (b).

Q6. The process of Q5, wherein the one or more pre-purification step(s) comprises
(a) filtration using a filter having a pore size equal to or less than 0.2 μm; and/or
(b) digestion of host cell genomic DNA by enzymatic treatment; and/or (c) ultra/diafiltration using a hollow fiber membrane having a pore size equal to or greater than 300 kDa, preferably equal to or greater than 100 kDa.

Q7. The process of any one of Q1 to 6, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

Q8. The process of any one of Q1 to 7, wherein the enrichment of infectious virus particles in the virus preparation (c) or any final virus preparation relative to total virus products in the crude harvest (a) is in the range from at least 50% to 95%, preferably at least 80%.

Q9. The process of any one of Q5 to 8, wherein the one or more pre-purification step(s) prior to step (b) of any of Q5 to 8 is performed using a filter having a pore size equal to or less than 1 µm, preferably 0.2 µm.

Q10. The process of any one of Q1 to 9, wherein the residual impurity of the virus preparation (c) is less than 10%.

Q11. The process of any one of Q1 to 10, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

Q12. The process of Q11, wherein said cell line is a Vero cell line.

Q13. The process of any one of Q1 to 12, wherein the infectious virus particles is an infectious Zika virus particle that is a live virus, an attenuated live virus, a chimeric virus, a modified live virus, or a recombinant live virus.

Q14. The process of any one of Q1 to 13, wherein the Zika virus is a Zika virus strain of the Asian lineage or an immunogenic variant thereof.

Q15. The process of any one of Q1 to 14, wherein said process resulting in final virus preparation (c) or (d) is followed by an inactivation step, wherein the virus is inactivated preferably by formaldehyde.

Q16. Use of the process according to any one of Q1 to 15 for manufacturing a composition for immunization against a virus infection.

Q17. The use according to Q16, wherein the composition for immunization against a virus infection is an infection caused by a group of viruses consisting of yellow fever virus, Chikungunya virus and Zika virus.

Q18. A composition comprising the virus particles obtainable or obtained by the process of any one of Q1 to 17 for treating and/or preventing an infection, such as e.g. a Zika virus infection.

Q19. A Zika virus vaccine comprising an inactivated Zika virus particle grown on vero cells, wherein the Zika virus particle is able to seroconvert a subject that is administered the Zika virus vaccine with at least a 70% probability and comprises minor amounts of protamine sulphate, preferably below the detection limit.

Q20. The Zika virus vaccine of Q19, wherein the Zika virus particle is able to seroconvert the subject that is administered the Zika virus vaccine with at least a 80%, 85%, 90%, or 95% probability, preferably a 80% probability.

Q21. The vaccine of Q19 or 20, wherein the Zika virus particle has a RNA genome corresponding to the DNA sequence provided by any one of the nucleic acid sequences of SEQ ID NOs: 2-13, or a variant nucleic acid sequence that is at least 88% identical to any one of SEQ ID NOs: 2-13 and able to pack a virulent Zika virus.

Q22. The vaccine of any one of Q19, 20 and 21, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

Q23. The vaccine of any one of Q19, 20 to 22, wherein the Zika virus obtained by culturing on Vero cells is purified by protamine sulfate precipitation and sucrose gradient centrifugation.

Q24. The vaccine of Q23, wherein the sucrose gradient centrifugation is an optimized sucrose gradient centrifugation.

Q25. The vaccine of Q24, wherein the optimized sucrose gradient centrifugation comprises a virus comprising fraction in a 10% (w/w) sucrose solution and three layers of sucrose with different densities, i.e. a first sucrose solution with 15% (w/w) sucrose solution, a second sucrose solution with 35% (w/w) sucrose solution, and a third sucrose solution with a 50% (w/w) sucrose solution.

Q26. The vaccine of any one of Q19, 20 to 25, wherein the Zika virus is inactivated by chemical inactivation, thermal inactivation, pH inactivation, or UV inactivation.

Q27. The vaccine of Q26, wherein the chemical inactivation comprises contacting the Zika virus with a chemical inactivation agent for longer than is required to completely inactivate the Zika virus as measured by plaque assay.

Q28. The vaccine of Q27, wherein the chemical inactivation comprises contacting the Zika virus with formaldehyde.

Q29. The vaccine of Q28, wherein the formaldehyde inactivation comprises contacting the Zika virus with formaldehyde for between 2-10 days.

Q30. The vaccine of any one of Q27-29, wherein the chemical activation is performed at about +4° C. or about +22° C.

Q31. The vaccine of any one of Q19 to 30, further comprising an adjuvant.

Q32. The vaccine of Q31, wherein the adjuvant is an aluminum salt adjuvant.

Q33. The vaccine of Q32, wherein the aluminum salt adjuvant is aluminium hydroxide or aluminium phosphate salt.

Q34. The vaccine of Q32, wherein the aluminum salt adjuvant is aluminium hydroxide with less than 1.25 ppb Cu based on the final pharmaceutical composition comprising the Zika virus, preferably the inactivated Zika virus.

Q35. The vaccine of any one of Q19 to 34, further comprising one or more pharmaceutically acceptable excipient.

R1. Use of protamine, preferably a protamine salt, to separate infectious and non-infectious virus particles, host cell proteins and/or undefined low molecular weight materials.

R2. A process of purification of infectious virus particles, comprising the steps of:
(a) providing a crude harvest (a) comprising virus particles and impurities, wherein the impurities are generated from growing said virus particles on a cell substrate;
(b) reducing impurities from the crude harvest (a) by precipitation with an agent comprising protamine, preferably a protamine salt, more preferably a protamine sulphate, even more preferably a recombinant protamine sulphate, to obtain a virus preparation (b), wherein the enrichment of infectious virus particles in the virus preparation (b) relative to total virus products in the crude harvest (a) is in the range from at least 50% to 95%, preferably at least 80%.

R3. The use of R1 or the process of R2, wherein the virus particles are selected from the group consisting of flaviviruses, e.g. yellow fever virus or Zika virus and alphaviruses, e.g. Chikungunya.

R4. A process of purification of infectious virus particles, comprising the steps of:

(a) providing a crude harvest (a) comprising virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b);

(c) further purifying the virus preparation (b) by one or more size exclusion methods such as (i) a sucrose density gradient centrifugation, (ii) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles, and/or (iii) size exclusion chromatography to obtain a virus preparation (c) comprising the infectious virus particles, wherein the residual host cell DNA of the virus preparation (c) is less than 100 ng/mL and the residual host cell protein and the residual aggregates of infectious virus particles of the final virus preparation (c) is less than 1 m/mL.

R5. The process of R4, wherein the residual host cell DNA of the virus preparation (c) is less than 10 ng/mL and the residual host cell protein of the final virus preparation (c) is less than 100 ng/mL.

R6. The process of any of R2 to 5, wherein the crude harvest (a) comprising virus particles and impurities is subjected to one or more pre-purification step(s) prior to step (b).

R7. The process of R6, wherein the one or more pre-purification step(s) comprises (a) filtration using a filter having a pore size equal to or less than 0.2 μm; and/or (b) digestion of host cell genomic DNA by enzymatic treatment; and/or (c) ultra/diafiltration using a hollow fiber membrane having a pore size equal to or greater than 300 kDa, preferably equal to or greater than 100 kDa.

R8. The process of any one of R2 to 7, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml.

R9. The process of any one of R2 to 8, wherein the enrichment of infectious virus particles in the virus preparation (c) or any final virus preparation relative to total virus products in the crude harvest (a) is in the range from at least 50% to 95%, preferably at least 80%.

R10. The process of any one of R6 to 9, wherein the one or more pre-purification step(s) prior to step (b) of any of R6 to 9 is performed using a filter having a pore size equal to or less than 1 μm, preferably 0.2 μm.

R11. The process of any one of R2 to 10, wherein the residual impurity of the virus preparation (c) is less than 10%.

R12. The process of any one of R2 to 11, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

R13. The process of R12, wherein said cell line is a Vero cell line.

R14. The process of any one of R2 to 13, wherein the Zika virus is a live virus, an attenuated live virus, a chimeric virus, a modified live virus, or a recombinant live virus.

R15. The process of any one of R2 to 14, wherein the Zika virus is a Zika virus strain of the Asian lineage or an immunogenic variant thereof.

R16. The process of any one of R2 to 15, wherein said process resulting in final virus preparation (c) is followed by an inactivation step, wherein the virus is inactivated preferably by formaldehyde.

R17. Use of the process according to any one of R1 to 16 for manufacturing a composition for immunization against a virus infection.

R18. The use according to R17, wherein the composition for immunization against a virus infection is an infection caused by a group of viruses consisting of yellow fever virus, Chikungunya virus and Zika virus.

R19. A composition comprising the virus particles obtainable or obtained by the process of any one of R2 to 16 for treating and/or preventing an infection.

What is claimed is:

1. A method for purification of infectious Chikungunya virus particles, comprising the steps of
   i) providing a crude harvest (a) comprising virus particles and impurities, wherein the impurities are generated from growing said virus particles on a cell substrate;
   ii) reducing impurities from said crude harvest (a) by precipitation with an agent comprising protamine to obtain a virus preparation (b);
   iii) further purifying said virus preparation (b) by sucrose density gradient centrifugation to obtain a Chikungunya virus preparation (c), wherein the sucrose gradient is provided such that the protamine can be completely or almost completely separated from the virus fraction; and wherein the protamine concentration in the Chikungunya virus preparation (c) is below 1 µg/ml, and wherein said sucrose gradient comprises a Chikungunya virus comprising fraction in a 10%+/−1% (w/w) sucrose solution and three further layers of sucrose solutions with different densities, wherein the three further layers of sucrose solutions comprise a first sucrose solution with 15%+/−1% (w/w) sucrose, a second sucrose solution with 35%+/−1% (w/w) sucrose, and a third sucrose solution with 50%+/−1% (w/w) sucrose.

2. The method according to claim 1, additionally comprising a further step of
  iv) further purifying said Chikungunya virus preparation (c) on a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core,
  to obtain a Chikungunya virus preparation (d).

3. The method according to claim 1, wherein said crude harvest (a) comprising Chikungunya virus particles and impurities is subjected to one or more pre-purification step(s) prior to step (ii), wherein said one or more pre-purification step(s) comprise
  a) filtration using a filter having a pore size equal to or less than 0.2 μm; and/or
  b) digestion of host cell genomic DNA by enzymatic treatment; and/or
  c) ultra/diafiltration using a hollow fiber membrane having a pore size equal to or greater than 100 kDa.

4. The method according to claim 1, wherein the residual host cell DNA content of said Chikungunya virus preparation (c) is less than 10 ng/mL and the residual host cell protein content of said Chikungunya virus preparation (c) is less than 100 ng/mL.

5. The method according to claim 1, wherein the concentration of protamine is from 0.5 mg/ml to 3 mg/ml.

6. The method according to claim 1, wherein said protamine is selected from the group consisting of a protamine salt, a protamine sulphate and a recombinant protamine sulphate.

7. The method according to claim 1, wherein the enrichment of infectious Chikungunya virus particles in said Chikungunya virus preparation (c) or any final virus preparation relative to total virus products in the crude harvest (a) is in the range of at least 50% to 95%.

8. The method according to claim 1, wherein said infectious Chikungunya virus particles are propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, an MDSK cell line, a chicken embryonic fibroblast cell line, a duck cell line and a diploid avian cell line.

9. The method according to claim 1, wherein said infectious Chikungunya virus particles are selected from the group consisting of a live virus, a live attenuated virus, a chimeric virus, a modified live virus, and a recombinant live virus.

10. The method according to claim 9, wherein said live attenuated virus has an RNA genome corresponding to the DNA sequence provided by SEQ ID NO: 77, or an immunogenic variant thereof, wherein said immunogenic variant has an RNA genome that is at least 88% identical to the corresponding DNA sequence of SEQ ID NO: 77 and is able to pack an infectious Chikungunya virus.

11. The method according to claim 1, wherein said step resulting in the Chikungunya virus preparation (c) or (d) is followed by an inactivation step.

12. The method according to claim 11, wherein said inactivation step is a formaldehyde inactivation step.

* * * * *

SEQUENCE LISTING

```
<160> NUMBER OF SEQ ID NOS: 123

<210> SEQ ID NO 1
<211> LENGTH: 32
<212> TYPE: PRT
<213> ORGANISM: Artificial Sequence
<220> FEATURE:
<223> OTHER INFORMATION: synthetic peptide

<400> SEQUENCE: 1

Pro Arg Arg Arg Arg Ser Ser Ser Arg Pro Val Arg Arg Arg Arg Arg
1               5                   10                  15

Pro Arg Val Ser Arg Arg Arg Arg Arg Arg Gly Gly Arg Arg Arg Arg
            20                  25                  30
```

<210> SEQ ID NO 2
<211> LENGTH: 10676
<212> TYPE: DNA
<213> ORGANISM: Zika virus

<400> SEQUENCE: 2
gttgttactg ttgctgactc agactgcgac agttcgagtt tgaagcgaaa gctagcaaca 60
gtatcaacag gttttatttg gatttggaaa cgagagtttc tggtcatgaa aaacccaaaa 120
aagaaatccg gaggattccg gattgtcaat atgctaaaac gcggagtagc ccgtgtgagc 180
ccctttgggg gcttgaagag gctgccagcc ggacttctgc tgggtcatgg gcccatcagg 240
atggtcttgg caattctagc ctttttgaga ttcacggcaa tcaagccatc actgggtctc 300
atcaatagat ggggttcagt ggggaaaaaa gaggctatgg aaataataaa gaagttcaag 360
aaagatctgg ctgccatgct gagaataatc aatgctagga aggagaagaa gagacggggc 420
gcagatacta gtgtcggaat tgttggcctc ctgctgacca cagctatggc agcggaggtc 480
actagacgtg ggagtgcata ctatatgtac ttggacagaa acgatgctgg ggaggccata 540
tcttttccaa ccacattggg gatgaataag tgttatatac agatcatgga tcttggacac 600
atgtgtgatg ccaccatgag ctatgaatgc cctatgctgg atgagggggt ggaaccagat 660
gacgtcgatt gttggtgcaa cacgacgtca acttgggttg tgtacggaac ctgccatcac 720
aaaaaaggtg aagcacggag atctagaaga gctgtgacgc tcccctccca ttccactagg 780
aagctgcaaa cgcggtcgca aacctggttg gaatcaagag aatacacaaa gcacttgatt 840
agagtcgaaa attggatatt caggaaccct ggcttcgcgt tagcagcagc tgccatcgct 900
tggcttttgg gaagctcaac gagccaaaaa gtcatatact tggtcatgat actgctgatt 960
gccccggcat acagcatcag gtgcatagga gtcagcaata gggactttgt ggaaggtatg 1020
tcaggtggga cttgggttga tattgtcttg gaacatggag gttgtgtcac cgtaatggca 1080
caggacaaac cgactgtcga catagagctg gttacaacaa cagtcagcaa catggcggag 1140
gtaagatcct actgctatga ggcatcaata tcagacatgg cttcggacag ccgctgccca 1200
acacaaggtg aagcctacct tgacaagcaa tcagacactc aatatgtctg caaaagaacg 1260
ttagtggaca gaggctgggg aaatggatgt ggactttttg gcaaagggag tctggtgaca 1320
tgcgctaagt ttgcatgctc caagaaaatg accgggaaga gcatccagcc agagaatctg 1380
gagtaccgga taatgctgtc agttcatggc tcccagcaca gtgggatgat cgttaatgac 1440
acaggacatg aaactgatga gaatagagcg aaggttgaga taacgcccaa ttcaccaaga 1500
gccgaagcca ccctgggggg ttttggaagc ctaggacttg attgtgaacc gaggacaggc 1560
cttgactttt cagatttgta ttacttgact atgaataaca agcactggtt ggttcacaag 1620
gagtggttcc acgacattcc attaccttgg cacgctgggg cagacaccgg aactccacac 1680
tggaacaaca aagaagcact ggtagagttc aaggacgcac atgccaaaag gcaaactgtc 1740
gtggttctag ggagtcaaga aggagcagtt cacacggccc ttgctggagc tctggaggct 1800
gagatggatg gtgcaaaggg aaggctgtcc tctggccact tgaaatgtcg cctgaaaatg 1860
gataaactta gattgaaggg cgtgtcatac tccttgtgta ccgcagcgtt cacattcacc 1920
aagatcccgg ctgaaacact gcacgggaca gtcacagtgg aggtacagta cgcagggaca 1980
gatggacctt gcaaggttcc agctcagatg gcggtggaca tgcaaactct gaccccagtt 2040
gggaggttga taaccgctaa ccccgtaatc actgaaagca ctgagaactc taagatgatg 2100
ctggaacttg atccaccatt tggggactct tacattgtca taggagtcgg ggagaagaag 2160

```
atcacccacc actggcacag gagtggcagc accattggaa aagcatttga agccactgtg    2220
agaggtgcca agagaatggc agtcttggga gacacagcct gggactttgg atcagttgga    2280
ggcgctctca actcattggg caagggcatc catcaaattt ttggagcagc tttcaaatca    2340
ttgtttggag gaatgtcctg gttctcacaa attctcattg gaacgttgct gatgtggttg    2400
ggtctgaaca caaagaatgg atctatttcc cttatgtgct tggccttagg gggagtgttg    2460
atcttcttat ccacagccgt ctctgctgat gtggggtgct cggtggactt ctcaaagaag    2520
gagacgagat gcggtacagg ggtgttcgtc tataacgacg ttgaagcctg gagggacagg    2580
tacaagtacc atcctgactc cccccgtaga ttggcagcag cagtcaagca agcctgggaa    2640
gatggtatct gcgggatctc ctctgtttca agaatggaaa acatcatgtg gagatcagta    2700
gaaggggagc tcaacgcaat cctggaagag aatggagttc aactgacggt cgttgtggga    2760
tctgtaaaaa accccatgtg gagaggtcca cagagattgc ccgtgcctgt gaacgagctg    2820
ccccacggct ggaaggcttg ggggaaatcg cacttcgtca gagcagcaaa gacaaataac    2880
agctttgtcg tggatggtga cacactgaag gaatgcccac tcaaacatag agcatggaac    2940
agctttcttg tggaggatca tgggttcggg gtatttcaca ctagtgtctg gctcaaggtt    3000
agagaagatt attcattaga gtgtgatcca gccgttattg aacagctgt taagggaaag    3060
gaggctgtac acagtgatct aggctactgg attgagagtg agaagaatga cacatggagg    3120
ctgaagaggg cccatctgat cgagatgaaa acatgtgaat ggccaaagtc ccacacattg    3180
tggacagatg gaatagaaga gagtgatctg atcatacccq agtctttagc tgggccactc    3240
agccatcaca ataccagaga gggctacagg acccaaatga agggccatg gcacagtgaa    3300
gagcttgaaa ttcggtttga ggaatgccca ggcactaagg tccacgtgga ggaaacatgt    3360
ggaacaagag gaccatctct gagatcaacc actgcaagcg gaagggtgat cgaggaatgg    3420
tgctgcaggg agtgcacaat gccccccactg tcgttccggg ctaaagatgg ctgttggtat    3480
ggaatggaga taaggcccag gaaagaacca gaaagcaact tagtaaggtc aatggtgact    3540
gcaggatcaa ctgatcacat ggatcacttc tcccttggag tgcttgtgat tctgctcatg    3600
gtgcaggaag ggctgaagaa gagaatgacc acaaagatca tcataagcac atcaatggca    3660
gtgctggtag ctatgatcct gggaggattt tcaatgagtg acctggctaa gcttgcaatt    3720
ttgatgggtg ccaccttcgc ggaaatgaac actggaggag atgtagctca tctgcgctg    3780
atagcggcat tcaaagtcag accagcgttg ctggtatctt tcatcttcag agctaattgg    3840
acaccccgtg aaagcatgct gctggccttg gcctcgtgtc ttttgcaaac tgcgatctcc    3900
gccttggaag gcgacctgat ggttctcatc aatggttttg ctttggcctg gttggcaata    3960
cgagcgatgt tgttccacg cactgataac atcaccttgg caatcctggc tgctctgaca    4020
ccactggccc ggggcacact gcttgtggcg tggagagcag gccttgctac ttgcggggg    4080
tttatgctcc tctctctgaa gggaaaaggc agtgtgaaga agaacttacc atttgtcatg    4140
gccctgggac taaccgctgt gaggctggtc gaccccatca cgtggtggg gctgctgttg    4200
ctcacaagga gtgggaagcg gagctggccc cctagcgaag tactcacagc tgttggcctg    4260
atatgcgcat tggctggagg gttcgccaag gcagatatag atgggctgg gcccatggcc    4320
gcggtcggtc tgctaattgt cagttacgtg gtctcaggaa agagtgtgga catgtacatt    4380
gaaagagcag gtgacatcac atgggaaaaa gatgcggaag tcactggaaa cagtccccgg    4440
ctcgatgtgg cgctagatga gagtggtgat ttctccctgg tggaggatga cggtcccccc    4500
atgagagaga tcatactcaa ggtggtcctg atgaccatct gtggcatgaa cccaatagcc    4560
```

```
atacccttttg cagctggagc gtggtacgta tacgtgaaga ctggaaaaag gagtggtgct    4620
ctatgggatg tgcctgctcc caaggaagta aaaaggggg  agaccacaga tggagtgtac    4680
agagtaatga ctcgtagact gctaggttca acacaagttg gagtgggagt tatgcaagag    4740
ggggtctttc acactatgtg gcacgtcaca aaaggatccg cgctgagaag cggtgaaggg    4800
agacttgatc catactgggg agatgtcaag caggatctgg tgtcatactg tggtccatgg    4860
aagctagatg ccgcctggga cgggcacagc gaggtgcagc tcttggccgt gcccccggga    4920
gagagagcga ggaacatcca gactctgccc ggaatattta agacaaagga tggggacatt    4980
ggagcggttg cgctggatta cccagcagga acttcaggat ctccaatcct agacaagtgt    5040
gggagagtga taggacttta tggcaatggg gtcgtgatca aaaatgggag ttatgttagt    5100
gccatcaccc aagggaggag ggaggaagag actcctgttg agtgcttcga gccttcgatg    5160
ctgaagaaga agcagctaac tgtcttagac ttgcatcctg gagctgggaa aaccaggaga    5220
gttcttcctg aaatagtccg tgaagccata aaaacaagac tccgtactgt gatcttagct    5280
ccaaccaggg ttgtcgctgc tgaaatggag aagcccctta gagggcttcc agtgcgttat    5340
atgacaacag cagtcaatgt cacccactct ggaacagaaa tcgtcgactt aatgtgccat    5400
gccaccttca cttcacgtct actacagcca atcagagtcc ccaactataa tctgtatatt    5460
atggatgagg cccacttcac agatccctca agtatagcag caagaggata catttcaaca    5520
agggttgaga tgggcgaggc ggctgccatc ttcatgaccg ccacgccacc aggaacccgt    5580
gacgcatttc cggactccaa ctcaccaatt atggacaccg aagtggaagt cccagagaga    5640
gcctggagct caggctttga ttgggtgacg gattattctg gaaaaacagt ttggtttgtt    5700
ccaagcgtga ggaacggcaa tgagatcgca gcttgtctga caaaggctgg aaaacgggtc    5760
atacagctca gcagaaagac ttttgagaca gagttccaga aaacaaaaca tcaagagtgg    5820
gactttgtcg tgacaactga catttcagag atgggcgcca actttaaagc tgaccgtgtc    5880
atagattcca ggagatgcct aaagccggtc atacttgatg gcgagagagt cattctggct    5940
ggacccatgc ctgtcacaca tgccagcgct gcccagagga gggggcgcat aggcaggaat    6000
cccaacaaac ctggagatga gtatctgtat ggaggtgggt gcgcagagac tgacgaagac    6060
catgcacact ggcttgaagc aagaatgctc cttgacaata tttacctcca agatggcctc    6120
atagcctcgc tctatcgacc tgaggccgac aaagtagcag ccattgaggg agagttcaag    6180
cttaggacgg agcaaaggaa gacctttgtg gaactcatga aagaggaga tcttcctgtt    6240 tggctggcct atcaggttgc atctgccgga ataacctaca cagatagaag atggtgcttt    6300
gatggcacga ccaacaacac cataatggaa gacagtgtgc cggcagaggt gtggaccaga    6360 cacgagaga  aaagagtgct caaaccgagg tggatgacg  ccagagtttg ttcagatcat    6420
gcggccctga agtcattcaa ggagtttgcc gctgggaaaa gaggagcggc ttttggagtg    6480
atggaagccc tgggaacact gccaggacac atgacagaga gattccagga agccattgac    6540
aacctcgctg tgctcatgcg ggcagagact ggaagcaggc cttacaaagc cgcggcggcc    6600
caattgccgg agaccctaga gaccattatg ctttttgggt tgctgggaac agtctcgctg    6660
ggaatctttt tcgtcttgat gaggaacaag ggcataggga gatgggctt  tggaatggtg    6720 actcttgggg ccagcgcatg gctcatgtgg ctctcggaaa ttgagccagc cagaattgca    6780
tgtgtcctca ttgttgtgtt cctattgctg gtggtgctca tacctgagcc agaaaagcaa    6840
agatctcccc aggacaacca aatggcaatc atcatcatgg tagcagtagg tcttctgggc    6900
```

```
ttgattaccg ccaatgaact cggatggttg gagagaacaa agagtgacct aagccatcta    6960
atgggaagga gagaggaggg ggcaaccatg ggattctcaa tggacattga cctgcggcca    7020
gcctcagctt gggccatcta tgctgccttg acaactttca ttaccccagc cgtccaacat    7080
gcagtgacca cttcatacaa caactactcc ttaatggcga tggccacgca agctggagtg    7140
ttgtttggta tgggcaaagg gatgccattc tacgcatggg actttggagt cccgctgcta    7200
atgataggtt gctactcaca attaacgccc ctgaccctaa tagtggccat cattttgctc    7260
gtggcgcact acatgtactt gatcccaggg ctgcaggcag cagctgcgcg tgctgcccag    7320
aagagaacgg cagctggcat catgaagaac cctgttgtgg atggaatagt ggtgactgac    7380
attgacacaa tgacaattga cccccaagtg gagaaaaaga tgggacaggt gctactcatg    7440
gcagtagccg tctccagcgc catactgtcg cggaccgcct gggggtgggg ggaggctggg    7500
gccctgatca cagccgcaac ttccactttg tgggaaggct ctccgaacaa gtactggaac    7560
tcctctacag ccacttcact gtgtaacatt tttaggggaa gttacttggc tggagcttct    7620
ctaatctaca cagtaacaag aaacgctggc ttggtcaaga cgtgggggg tggaacagga    7680
gagaccctgg gagagaaatg gaaggcccgc ttgaaccaga tgtcggccct ggagttctac    7740
tcctacaaaa agtcaggcat caccgaggtg tgcagagaag aggcccgccg cgccctcaag    7800
gacggtgtgg caacgggagg ccatgctgtg tcccgaggaa gtgcaaagct gagatggttg    7860
gtggagcggg gatacctgca gccctatgga aaggtcattg atcttggatg tggcagaggg    7920
ggctggagtt actacgccgc caccatccgc aaagttcaag aagtgaaagg atacacaaaa    7980
ggaggccctg gtcatgaaga acccgtgttg gtgcaaagct atgggtggaa catagtccgt    8040
cttaagagtg gggtggacgt cttttcatatg gcggctgagc cgtgtgacac gttgctgtgt    8100
gacataggtg agtcatcatc tagtcctgaa gtggaagaag cacggacgct cagagtcctc    8160
tccatggtgg gggattggct tgaaaaaaga ccaggagcct tttgtataaa agtgttgtgc    8220
ccatacacca gcactatgat ggaaaccctg agcgactgc agcgtaggta tggggagga    8280
ctggtcagag tgccactctc ccgcaactct acacatgaga tgtactgggt ctctggagcg    8340
aaaagcaaca ccataaaaag tgtgtccacc acgagccagc tcctcttggg gcgcatggac    8400
gggcctagga ggccagtgaa atatgaggag gatgtgaatc tcggctctgg cacgcgggct    8460
gtggtaagct gcgctgaagc tcccaacatg aagatcattg gtaaccgcat tgaaaggatc    8520
cgcagtgagc acgcggaaac gtggttcttt gacgagaacc acccatatag gacatgggct    8580
taccatggaa gctatgaggc ccccacacaa gggtcagcgt cctctctaat aaacggggtt    8640
gtcaggctcc tgtcaaaacc ctgggatgtg gtgactggag tcacaggaat agccatgacc    8700
gacaccacac cgtatggtca gcaaagagtt ttcaaggaaa agtggacac tagggtgcca    8760
gaccccaag aaggtactcg tcaggttatg agcatggtct cttcctggtt gtggaaagag    8820
ctaggcaaac acaaacggcc acgagtctgt accaaagaag agttcatcaa caaggttcgt    8880
agcaatgcag cattaggggc aatatttgaa gaggaaaaag agtggaagac tgcagtggaa    8940
gctgtgaacg atccaaggtt ctgggctcta gtggacaagg aaagagagca ccacctgaga    9000
ggagagtgcc agagttgtgt gtacaacatg atggaaaaa gagaaagaa acaagggaa    9060
tttggaaagg ccaagggcag ccgcgccatc tggtatatgt ggctaggggc tagatttcta    9120
gagttcgaag cccttggatt cttgaacgag atcactgga tggggagaga gaactcagga    9180
ggtggtgttg aagggctggg attacaaaga ctccggatatg tcctagaaga gatgagtcgc    9240
ataccaggag gaaggatgta tgcagatgac actgctggct gggacacccg catcagcagg    9300
```

-continued

| | |
|---|---|
| tttgatctgg agaatgaagc tctaatcacc aaccaaatgg agaaagggca cagggccttg | 9360 |
| gcattggcca taatcaagta cacataccaa acaaagtgg taaaggtcct tagaccagct | 9420 |
| gaaaaaggga aaacagttat ggacattatt tcgagacaag accaaggggg agcggacaa | 9480 |
| gttgtcactt acgctcttaa cacatttacc aacctagtgg tgcaactcat tcggaatatg | 9540 |
| gaggctgagg aagtcctaga gatgcaagac ttgtggctgc tgcggaggtc agagaaagtg | 9600 |
| accaactggt tgcagagcaa cggatgggat aggctcaaac gaatggcagt cagtggagat | 9660 |
| gattgcgttg tgaagccaat tgatgatagg tttgcacatg ccctcaggtt cttgaatgat | 9720 |
| atgggaaaag ttaggaagga cacacaagag tggaaaccct caactggatg ggacaactgg | 9780 |
| gaagaagttc cgttttgctc ccaccacttc aacaagctcc atctcaagga cgggaggtcc | 9840 |
| attgtggttc cctgccgcca ccaagatgaa ctgattggcc gggcccgcgt ctctccaggg | 9900 |
| gcgggatgga gcatccggga gactgcttgc ctagcaaaat catatgcgca aatgtggcag | 9960 |
| ctcctttatt tccacagaag ggacctccga ctgatggcca atgccatttg ttcatctgtg | 10020 |
| ccagttgact gggttccaac tgggagaact acctggtcaa tccatggaaa gggagaatgg | 10080 |
| atgaccactg aagacatgct tgtggtgtgg aacagagtgt ggattgagga aacgaccac | 10140 |
| atggaagaca agaccccagt tacgaaatgg acagacattc cctatttggg aaaaagggaa | 10200 |
| gacttgtggt gtggatctct catagggcac agaccgcgca ccacctgggc tgagaacatt | 10260 |
| aaaaacacag tcaacatggt gcgcaggatc ataggtgatg aagaaaagta catggactac | 10320 |
| ctatccaccc aagttcgcta cttgggtgaa aagggtcta cacctggagt gctgtaagca | 10380 |
| ccaatcttaa tgttgtcagg cctgctagtc agccacagct tggggaaagc tgtgcagcct | 10440 |
| gtgacccccc caggagaagc tgggaaacca agcctatagt caggccgaga acgccatggc | 10500 |
| acggaagaag ccatgctgcc tgtgagcccc tcagaggaca ctgagtcaaa aaccccacg | 10560 |
| cgcttggagg cgcaggatgg gaaaagaagg tggcgacctt ccccacccct caatctgggg | 10620 |
| cctgaactgg agatcagctg tggatctcca gaagagggac tagtggttag aggaga | 10676 |

<210> SEQ ID NO 3
<211> LENGTH: 10793
<212> TYPE: DNA
<213> ORGANISM: Zika virus

<400> SEQUENCE: 3

| | |
|---|---|
| ccaatctgtg aatcagactg cgacagttcg agtttgaagc gaaagctagc aacagtatca | 60 |
| acaggtttta ttttggattt ggaaacgaga gtttctggtc atgaaaaacc caaaaagaa | 120 |
| atccggagga ttccggattg tcaatatgct aaaacgcgga gtagcccgtg tgagcccctt | 180 |
| tggggggctt aagaggctgc agccggact tctgctgggt catgggccca tcaggatggt | 240 |
| cttggcgatt ctagcctttt tgagattcac ggcaatcaag ccatcactgg gtctcatcaa | 300 |
| tagatggggt tcagtgggga aaaagaggc tatggaaata ataagaagt tcaagaaaga | 360 |
| tctggctgcc atgctgagaa taatcaatgc aggaaggag aagaagagac gaggcgcaga | 420 |
| tactagtgtc ggaatcgttg gcctcctgct gaccacagct atggcagcgg aggtcactag | 480 |
| acgtgggagt gcatactata tgtacttgga cagaaacgat gctggggagg ccatatcttt | 540 |
| tccaaccaca ttggggatga ataagtgtta tatacagatc atggatcttg acacatgtg | 600 |
| tgatgccacc atgagctatg aatgccctat gctggatgag ggggtggaac cagatgacgt | 660 |
| cgattgttgg tgcaacacga cgtcaacttg ggttgtgtac ggaacctgcc atcacaaaaa | 720 |

```
aggtgaagca cggagatcta aagagctgt gacgctcccc tcccattcca ctaggaagct    780
gcaaacgcgg tcgcaaacct ggttggaatc aagagaatac acaaagcact tgattagagt    840
cgaaaattgg atattcagga accctggctt cgcgttagca gcagctgcca tcgcttggct    900
tttgggaagc tcaacgagcc aaaaagtcat atacttggtc atgatactgc tgattgcccc    960
ggcatacagc atcaggtgca taggagtcag caatagggac tttgtggaag gtatgtcagg   1020
tgggacttgg gttgatgttg tcttggaaca tgggggttgt gtcaccgtaa tggcacagga   1080
caaaccgact gtcgacatag agctggttac aacaacagtc agcaacatgg cggaggtaag   1140
atcctactgc tatgaggcat caatatcaga catggcttcg gacagccgct gcccaacaca   1200
aggtgaagcc taccttgaca agcaatcaga cactcaatat gtctgcaaaa gaacgttagt   1260
ggacagaggc tggggaaatg gatgtggact ttttggcaaa gggagcctgg tgacatgcgc   1320
taagtttgca tgctccaaga aaatgaccgg gaagagcatc cagccagaga atctggagta   1380
ccggataatg ctgtcagttc atggctccca gcacagtggg atgatcgtta atgacacagg   1440
acatgaaact gatgagaata gagcgaaggt tgagataacg cccaattcac caagagccga   1500
agccaccctg gggggttttg gaagcttagg acttgattgt gaaccgagga caggccttga   1560
cttttcagat ttgtattact tgactatgaa taacaagcac tggttggttc acaaggagtg   1620
gttccacgac attccattac cttggcacgc tggggcagac accggaactc cacactggaa   1680
caacaaagaa gcactggtag agttcaagga cgcacatgcc aaaaggcaaa ctgtcgtggt   1740
tctagggact caagaaggag cagttcacac ggcccttgct ggagctctgg aggctgagat   1800
ggatggtgca aagggaaggc tgtcctctgg ccacttgaaa tgtcgcctga aaatggataa   1860
acttagattg aagggcgtgt catactcctt gtgtaccgca gcgttcacat tcaccaagat   1920
cccggctgaa acactgcacg ggacagtcac agtggaggta cagtacgcag ggacagatgg   1980
accttgcaag gttccagctc agatggcggt ggacatgcaa actctgaccc cagttgggag   2040
gttgataacc gctaaccccg taatcactga aagcactgag aactctaaga tgatgctgga   2100
acttgatcca ccatttgggg actcttacat tgtcatagga gtcggggaga agaagatcac   2160
ccaccactgg cacaggagtg gcagcaccat tggaaaagca tttgaagcca ctgtgagagg   2220
tgccaagaga atggcagtct gggagacac agcctgggac tttggatcag ttggaggcgc   2280
tctcaactca ttgggcaagg gcatccatca aattttttgga gcagctttca atcattgtt   2340
tggaggaatg tcctggttct cacaaattct cattggaacg ttgctgatgt ggttgggtct   2400
gaacacaaag aatggatcta tttcccttat gtgcttggcc ttaggggag tgttgatctt   2460
cttatccaca gccgtctctg ctgatgtggg gtgctcggtg gacttctcaa agaaggagac   2520
gagatgtggt acagggtgt tcgtctataa cgacgttgaa gcctggaggg acaggtacaa   2580
gtaccatcct gactctcccc gtagattggc agcagcagtc aagcaagcct gggaagatgg   2640
tatctgcggg atctcctctg tttcaagaat ggaaaacatc atgtggagat cagtagaagg   2700
ggagcttaac gcaatcctgg aagagaatgg agttcaactg acggtcgttg tgggatctgt   2760
aaaaaacccc atgtggagag gtccacagag attgcccgtg cctgtgaacg agctgcccca   2820
cggctggaag gcttggggga atcgtactct cgtcagagca gcaaagacaa ataacagctt   2880
tgtcgtggat ggtgacacac tgaaggaatg cccactcaaa catagagcat ggaacagctt   2940
tcttgtggag gatcatgggt tcggggtatt tcacactagt gtctggctca aggttagaga   3000
agattattca ttagagtgtg atccagccgt tattggaaca gctgttaagg gaaaggaggc   3060
tgtacacagt gatctaggct actggattga gagtgagaag aatgacacat ggaggctgaa   3120
```

```
gagggcccat ctgatcgaga tgaaaacatg tgaatggcca aagtcccaca cattgtggac   3180
agatggaata gaagagagtg atctgatcat acccaagtct ttagctgggc cactcagcca   3240
tcacaatacc agagagggct acaggaccca aatgaaaggg ccatggcaca gtgaagagct   3300
tgaaattcgg tttgaggaat gcccaggcac taaggtccac gtggaggaaa catgtggaac   3360
aagaggacca tctctgagat caaccactgc aagcggaagg gtgatcgagg aatggtgctg   3420
cagggagtgc acaatgcccc cactgtcgtt ccgggctaaa gatggctgtt ggtatggaat   3480
ggagataagg cccaggaaag aaccagaaag caacttagta aggtcaatgg tgactgcagg   3540
atcaactgat cacatggatc acttctccct tggagtgctt gtgattctgc tcatggtgca   3600
ggaagggctg aagaagagaa tgaccacaaa gatcatcata agcacatcaa tggcagtgct   3660
ggtagctatg atcctgggag gattttcaat gagtgacctg gctaagcttg caattttgat   3720
gggtgccacc ttcgcggaaa tgaacactgg aggagatgta gctcatctgg cgctgatagc   3780
ggcattcaaa gtcagaccag cgttgctggt atctttcatc ttcagagcta attggacacc   3840
ccgtgaaagc atgctgctgg ccttggcctc gtgttttttg caaactgcga tctccgcctt   3900
ggaaggcgac ctgatggttc tcatcaatgg ttttgctttg gcctggttgg caatacgagc   3960
gatggttgtt ccacgcactg acaacatcac cttggcaatc ctggctgctc tgacaccact   4020
ggcccggggc acactgcttg tggcgtggag agcaggcctt gctacttgcg gggggtttat   4080
gctcctctct ctgaagggaa aaggcagtgt gaagaagaac ttaccatttg tcatggccct   4140
gggactaacc gctgtgaggc tggtcgaccc catcaacgtg gtgggactgc tgttgctcac   4200
aaggagtggg aagcggagct ggccccctag cgaagtactc acagctgttg gcctgatatg   4260
cgcattggct ggagggttcg ccaaggcaga tatagagatg gctgggccca tggccgcggt   4320
cggtctgcta attgtcagtt acgtggtctc aggaaagagt gtggacatgt acattgaaag   4380
agcaggtgac atcacatggg aaaaagatgc ggaagtcact ggaaacagtc ccggctcga   4440
tgtggcgcta gatgagagtg gtgacttctc cctggtggag gatgacggtc cccccatgag   4500
agagatcata ctcaaggtgg tcctgatgac catctgtggc atgaacccaa tagccatacc   4560
ctttgcagct ggagcgtggt acgtatacgt gaagactgga aaaaggagtg gtgctctatg   4620
ggatgtgcct gctcccaagg aagtaaaaaa gggggagacc acagatggag tgtacagagt   4680
aatgactcgt agactgctag gttcaacaca agttggagtg ggagttatgc aagagggggt   4740
ctttcacact atgtggcacg tcacaaaagg atccgcgctg agaagcggtg aagggagact   4800
tgatccatac tggggagatg tcaagcagga tctggtgtca tactgtggtc catggaagct   4860
agatgccgcc tgggacgggc acagcgaggt gcagctcttg gccgtgcccc ccggagagag   4920
agcgaggaac atccagactc tgcccggaat atttaagaca aaggatgggg acattggagc   4980
ggttgcgctg gattacccag caggaacttc aggatctcca atcctagaca agtgtgggag   5040
agtgatagga ctttatggca atgggtcgt gataaaaaat gggagttatg ttagtgccat   5100
cacccaaggg aggagggagg aagagactcc tgttgagtgc ttcgagcctt cgatgctgaa   5160
gaagaagcag ctaactgtct tagacttgca tcctggagct gggaaaacca ggagagttct   5220
tcctgaaata gtccgtgaag ccataaaaac aagactccgt actgtgatct tagctccaac   5280
cagggttgtc gctgctgaaa tggaggaagc ccttagaggg cttccagtgc gttatatgac   5340
aacagcagtc aatgtcaccc actctggaac agaaatcgtc gacttaatgt gccatgccac   5400
cttcacttca cgtctactac agccaatcag agtccccaac tataatctgt atattatgga   5460
```

```
tgaggcccac ttcacagatc cctcaagcat agcagcaaga ggatacattt caacaagggt    5520
tgagatgggc gaggcggctg ccatcttcat gaccgccacg ccaccaggaa cccgtgacgc    5580
atttccggac tccaactcac caattatgga caccgaagtg gaagtcccag agagagcctg    5640
gagctcaggc tttgattggg tgacggatca ttctggaaaa acagtttggt ttgttccaag    5700
cgtgaggaac ggcaatgaga tcgcagcttg tctgacaaag gctggaaaac gggtcataca    5760
gctcagcaga aagactttg agacagagtt ccagaaaaca aaacatcaag agtgggactt    5820
tgtcgtgaca actgacattt cagagatggg cgccaacttt aaagctgacc gtgtcataga    5880
ttccaggaga tgcctaaagc cggtcatact tgatggcgag agagtcattc tggctggacc    5940
catgcctgtc acacatgcca gcgctgccca gaggaggggg cgcataggca ggaatcccaa    6000
caaacctgga gatgagtacc tgtatggagg tgggtgcgca gagactgacg aagaccatgc    6060
acactggctt gaagcaagaa tgctccttga caatatttac ctccaagatg gcctcatagc    6120
ctcgctctat cgacctgagg ccgacaaagt agcagccatt gagggagagt tcaagcttag    6180
gacggagcaa aggaagacct ttgtggaact catgaaaaga ggagatcttc ctgtttggct    6240
ggcctatcag gttgcatctg ccggaataac ctacacagat agaagatggt gctttgatgg    6300
cacgaccaac aacaccataa tggaagacag tgtgccggca gaggtgtgga ccagacacgg    6360
agagaaaaga gtgctcaaac cgaggtggat ggacgccaga gtttgttcag atcatgcggc    6420
cctgaagtca ttcaaggagt ttgccgctgg gaaaagagga cggcttttg gagtgatgga    6480 agccctggga acactgccag acacatgac agagagattc caggaagcca ttgacaacct    6540
cgctgtgctc atgcgggcag agactggaag caggccttac aaagccgcgg cggcccaatt    6600
gccggagacc ctagagacca ttatgctttt ggggttgctg gaacagtct cgctgggaat    6660 cttttttcgtc ttgatgagga acaagggcat agggaagatg ggctttggaa tggtgactct    6720
tggggccagc gcatggctca tgtggctctc ggaaattgag ccagccagaa ttgcatgtgt    6780
cctcattgtt gtgttcctat tgctggtggt gctcataccct gagccagaaa agcaaagatc    6840
tccccaggac aaccaaatgg caatcatcat catggtagca gtaggtcttc tgggcttgat    6900
taccgccaat gaactcggat ggttggagag aacaaagagt gacctaagcc atctaatggg    6960
aaggagagag gaggggggcaa ccataggatt ctcaatggac attgacctgc ggccagcctc    7020
agcttgggcc atctatgctg ccttgacaac tttcattacc ccagccgtcc aacatgcagt    7080
gaccacttca tacaacaact actccttaat ggcgatggcc acgcaagctg gagtgttgtt    7140
tggtatgggc aaagggatgc cattctacgc atgggacttt ggagtcccgc tgctaatgat    7200
aggttgctac tcacaattaa cacccctgac cctaatagtg gccatcattt tgctcgtggc    7260
gcactacatg tacttgatcc cagggctgca ggcagcagct gcgcgtgctg cccagaagag    7320
aacggcagct ggcatcatga agaaccctgt tgtggatgga atagtggtga ctgacattga    7380
cacaatgaca attgacccc aagtgggaga aaagatggga caggtgctac tcatagcagt    7440
agccgtctcc agcgccatac tgtcgcggac cgcctgggg tggggggagg ctggggccct    7500
gatcacagcc gcaacttcca ctttgtggga aggctctccg aacaagtact ggaactcctc    7560
tacagccact tcactgtgta acattttag gggaagttac ttggctggag cttctctaat    7620
ctacacagta acaagaaacg ctggcttggt caagagacgt gggggtggaa caggagagac    7680
cctgggagag aaatgaagg cccgcttgaa ccagatgtcg gcctggagt tctactccta    7740 caaaaagtca ggcatcaccg aggtgtgcag agaagaggcc cgccgcgccc tcaaggacgg    7800
tgtggcaacg ggaggccatg ctgtgtcccg aggaagtgca aagctgagat ggttggtgga    7860
```

-continued

```
gcggggatac ctgcagccct atggaaaggt cattgatctt ggatgtggca gagggggctg   7920
gagttactac gccgccacca tccgcaaagt tcaagaagtg aaaggataca caaaggagg    7980 ccctggtcat gaagaacccg tgttggtgca aagctatggg tggaacatag tccgtcttaa   8040 gagtgggtg  gacgtctttc atatggcggc tgagccgtgt gacacgttgc tgtgtgacat   8100
aggtgagtca tcatctagtc ctgaagtgga agaagcacgg acgctcagag tcctctccat   8160
ggtgggggat tggcttgaaa aaagaccagg agccttttgc ataaaagtgt tgtgcccata   8220
caccagcact atgatggaaa ccctggagcg actgcagcgt aggtatgggg gaggactggt   8280
cagagtgcca ctctcccgca actctacaca tgagatgtac tgggtctctg gagcgaaaag   8340
caacaccata aaaagtgtgt ccaccacgag ccagctcctc ttggggcgca tggacgggcc   8400
taggaggcca gtgaaatatg aggaggatgt gaatctcggc tctggcacgc gggctgtggt   8460
aagctgcgct gaagctccca acatgaagat cattggtaac cgcattgaaa ggatccgcag   8520
tgagcacgcg gaaacgtggt tctttgacga aaaccaccca tataggacat gggcttacca   8580
tggaagctat gtggccccca cacaagggtc agcgtcctct ctaataaacg gggttgtcag   8640
gctcctgtca aaaccctggg atgtggtgac tggagtcaca ggaatagcca tgaccgacac   8700
cacaccgtat ggtcagcaaa gagttttcaa ggaaaaagtg gacactaggg tgccagaccc   8760
ccaagaaggc actcgtcagg ttatgagcat ggtctcttcc tggttgtgga aagagctagg   8820
caaacacaaa cgaccacgag tctgtaccaa agaagagttc atcaacaagg ttcgtagcaa   8880
tgcagcatta ggggcaatat ttgaagagga aaaagagtgg aagactgcag tggaagctgt   8940
gaacgatcca aggttctggg ctctagtgga caaggaaaga gagcaccacc tgagaggaga   9000
gtgccagagt tgtgtgtaca acatgatggg aaaaagagaa aagaaacaag gggaatttgg   9060
aaaggccaag ggcagccgcg ccatctggta tatgtggcta ggggctagat ttctagagtt   9120
cgaagccctt ggattcttga cgaggatca ctggatgggg agagagaact caggaggtgg   9180
tgttgaaggg ctgggattac aaagactcgg atatgtccta gaagagatga gtcgcatacc   9240
aggaggaagg atgtatgcag atgacactgc tggctgggac acccgcatca gcaggtttga   9300
tctggagaat gaagctctaa tcaccaacca atggagaaa  gggcacaggg ccttggcatt   9360
ggccataatc aagtacacat accaaaacaa agtggtaaag gtccttagac cagctgaaaa   9420
agggaaaaca gttatggaca ttatttcgag acaagaccaa agggggagcg acaagttgt    9480 cacttacgct cttaacacat ttaccaacct agtggtgcaa ctcattcgga atatggaggc   9540
tgaggaagtt ctagagatgc aagacttgtg gctgctgcgg aggtcagaga agtgaccaa    9600 ctggttgcag agcaacggat gggataggct caaacgaatg gcagtcagtg gagatgattg   9660
cgttgtgaag ccaattgatg ataggtttgc acatgccctc aggttcttga atgatatggg   9720
aaaagttagg aaggacacac aagagtggaa accctcaact ggatgggaca actgggaaga   9780
agttccgttt tgctcccacc acttcaacaa gctccatctc aaggacggga ggtccattgt   9840
ggttccctgc cgccaccaag atgaactgat tggccgggcc cgcgtctctc caggggcggg   9900
atggagcatc cggagactg  cttgcctagc aaaatcatat gcgcaaatgt ggcagctcct   9960
ttatttccac agaagggacc tccgactgat ggccaatgcc atttgttcat ctgtgccagt  10020
tgactgggtt ccaactggga gaactacctg gtcaatccat ggaaagggag aatggatgac  10080
cactgaagac atgcttgtgg tgtggaacag agtgtggatt gaggagaacg accacatgga  10140
agacaagacc ccagttacga aatggacaga cattccctat ttgggaaaaa gggaagactt  10200
```

```
gtggtgtgga tctctcatag ggcacagacc gcgcaccacc tgggctgaga acattaaaaa    10260
tacagtcaac atggtgcgca ggatcatagg tgatgaagaa aagtacatgg actacctatc    10320
cacccaagtt cgctacttgg gtgaagaagg gtctacacct ggagtgctgt gagcaccaat    10380
cttaatgttg tcaggcctgc tagtcagcca cagcttgggg aaagctgtgc agcctgtgac    10440
ccctccagga gaagctgggt aaccaagcct atagtcaggc cgagaacgcc atggcacgga    10500
agaagccatg ctgcctgtga gcccctcaga ggacactgag tcaaaaaacc ccacgcgctt    10560
ggaggcgcag gatgggaaaa gaaggtggcg accttcccca cccttcaatc tggggcctga    10620
actggagatc agctgtggat ctccagaaga gggactagtg gttagaggag acccccggga    10680
aaacgcaaaa cagcatattg acgctgggaa agaccagaga ctccatgagt tccaccacg     10740 ctggccgcca ggcacagatc gccgaatagc ggcggccggt gtggggaaat cca           10793
```

<210> SEQ ID NO 4
<211> LENGTH: 10675
<212> TYPE: DNA
<213> ORGANISM: Zika virus

<400> SEQUENCE: 4

```
gttgttgatc tgtgtgaatc agactgcgac agttcgagtt tgaagcgaaa gctagcaaca      60
gtatcaacag gtttatttt ggatttggaa acgagagttt ctggtcatga aaaacccaaa     120
aaagaaatcc ggaggattcc ggattgtcaa tatgctaaaa cgcggagtag cccgtgtgag     180
cccctttggg ggcttgaaga ggctgccagc cggacttctg ctgggtcatg ggcccatcag     240
gatggtcttg gcgattctag cctttttgag attcacggca atcaagccat cactgggtct     300
catcaataga tggggttcag tggggaaaaa agaggctatg gaaacaataa agaagttcaa     360
gaaagatctg gctgccatgc tgagaataat caatgctagg aaggagaaga gagacgagg     420 cgcagatact agtgtcggaa ttgttggcct cctgctgacc acagctatgg cagcggaggt     480
cactagacgt gggagtgcat actatatgta cttggacaga aacgatgctg gggaggccat     540
atcttttcca accacattgg ggatgaataa gtgttatata cagatcatgg atcttggaca     600
catgtgtgat gccaccatga gctatgaatg ccctatgctg gatgaggggg tggaaccaga     660
tgacgtcgat tgttggtgca acacgacgtc aacttgggtt gtgtacggaa cctgccatca     720 caaaaaggt gaagcacgga gatctagaag agctgtgacg ctcccctccc attccaccag     780
gaagctgcaa acgcggtcgc aaacctggtt ggaatcaaga aatacacaa agcacttgat     840 tagagtcgaa aattggatat tcaggaaccc tggcttcgcg ttagcagcag ctgccatcgc     900
ttggcttttg ggaagctcaa cgagccaaaa agtcatatac ttggtcatga tactgctgat     960
tgccccggca tacagcatca ggtgcatagg agtcagcaat agggactttg tggaaggtat    1020
gtcaggtggg acttgggttg atgttgtctt ggaacatgga ggttgtgtca ccgtaatggc    1080
acaggacaaa ccgactgtcg acatagagct ggttacaaca cagtcagca acatggcgga    1140 ggtaagatcc tactgctatg aggcatcaat atcagacatg gcttctgaca gccgctgccc    1200
aacacaaggt gaagcctacc ttgacaagca atcagacact caatatgtct gcaaaagaac    1260
gttagtggac agaggctggg gaaatggatg tggactttt ggcaaaggga gcctggtgac    1320
atgcgctaag tttgcatgct ccaagaaaat gaccgggaag agcatccagc cagagaatct    1380
ggagtaccgg ataatgctgt cagttcatgg ctcccagcac agtgggatga tcgttaatga    1440
cacaggacat gaaactgatg agaatagagc gaaagttgag ataacgccca attcaccgag    1500
agccgaagcc accctggggg gttttggaag cctaggactt gattgtgaac cgaggacagg    1560
```

```
ccttgacttt tcagatttgt attacttgac tatgaataac aagcactggt tggttcacaa    1620
ggagtggttc cacgacattc cattaccttg gcacgctggg gcagacaccg gaactccaca    1680
ctggaacaac aaagaagcac tggtagagtt caaggacgca catgccaaaa ggcaaactgt    1740
cgtggttcta gggagtcaag aaggagcagt tcacacggcc cttgctggag ctctggaggc    1800
tgagatggat ggtgcaaagg gaaggctgtc ctctggccac ttgaaatgtc gcctgaaaat    1860
ggataaactt agattgaagg gcgtgtcata ctccttgtgt actgcagcgt tcacattcac    1920
caagatcccg gctgaaacac tgcacgggac agtcacagtg gaggtacagt acgcagggac    1980
agatggacct tgcaaggttc cagctcagat ggcggtggac atgcaaactc tgaccccagt    2040
tgggaggttg ataaccgcta accccgtaat cactgaaagc actgagaact ctaagatgat    2100
gctgaaactt gatccaccat ttggggactc ttacattgtc ataggagtcg gggagaagaa    2160
gatcacccac cactggcaca ggagtggcag caccattgga aaagcatttg aagccactgt    2220
gagaggtgcc aagagaatgg cagtcttggg agacacagcc tgggactttg atcagttgg    2280
aggcgctctc aactcattgg gcaagggcat ccatcaaatt tttggagcag ctttcaaatc    2340
attgtttgga ggaatgtcct ggttctcaca aattctcatt ggaacgttgc tgatgtggtt    2400
gggtctgaac acaaagaatg gatctatttc ccttatgtgc ttggccttag ggggagtgtt    2460
gatcttctta tccacagccg tctctgctga tgtgggtgc tcggtggact tctcaaagaa    2520
ggagacgaga tgcggtacag gggtgttcgt ctataacgac gttgaagcct ggagggacag    2580
gtacaagtac catcctgact ccccccgtag attggcagca gcagtcaagc aagcctggga    2640
agatggtatc tgcgggatct cctctgtttc aagaatggaa aacatcatgt ggagatcagt    2700
agaaggggag ctcaacgcaa tcctggaaga gaatggagtt caactgacgg tcgttgtggg    2760
atctgtaaaa accccatgt ggagaggtcc acagagattg cccgtgcctg tgaacgagct    2820
gccccacggc tggaaggctt gggggaaatc gtatttcgtc agagcagcaa agacaaataa    2880
cagctttgtc gtggatggtg acacactgaa ggaatgccca ctcaaacata gagcatggaa    2940
cagctttctt gtggaggatc atgggttcgg ggtatttcac actagtgtct ggctcaaggt    3000
tagagaagat tattcattag agtgtgatcc agccgttatt ggaacagctg ttaagggaaa    3060
ggaggctgta cacagtgatc taggctactg gattgagagt gagaagaatg acacatggag    3120
gctgaagagg gcccatctga tcgagatgaa acatgtgaa tggccaaagt cccacacatt    3180
gtggacagat ggaatagaag agagtgatct gatcataccc aagtctttag ctgggccact    3240
cagccatcac aataccagag agggctacag gacccaaatg aaagggccat ggcacagtga    3300
agagcttgaa attcggtttg aggaatgccc aggcactaag gtccacgtgg aggaaacatg    3360
tggaacaaga ggaccatctc tgagatcaac cactgcaagc ggaagggtga tcagggaatg    3420
gtgctgcagg gagtgcacaa tgccccact gtcgttccgg gctaaagatg ctgttggta    3480
tggaatggag ataaggccca ggaaagaacc agaaagcaac ttagtaaggt caatggtgac    3540
tgcaggatca actgatcaca tggaccactt ctcccttgga gtgcttgtga tcctgctcat    3600
ggtgcaggaa gggctgaaga gagaatgac cacaaagatc atcataagca catcaatggc    3660
agtgctggta gctatgatcc tgggaggatt ttcaatgagt gacctggcta agcttgcaat    3720
tttgatgggt gccaccttcg cggaaatgaa cactggagga gatgtagctc atctggcgct    3780
gatagcggca ttcaaagtca gaccagcgtt gctggtatct ttcatcttca gagctaattg    3840
gacacccgt gaaagcatgc tgctggcctt ggcctcgtgt cttttgcaaa ctgcgatctc    3900
```

```
cgccttggaa ggcgacctga tggttctcat caatggtttt gctttggcct ggttggcaat    3960
acgagcgatg gttgttccac gcactgataa catcaccttg gcaatcctgg ctgctctgac    4020
accactggcc cggggcacac tgcttgtggc gtggagagca ggccttgcta cttgcggggg    4080
gtttatgctc ctctctctga agggaaaagg cagtgtgaag aagaacttac catttgtcat    4140
ggccctggga ctaaccgctg tgaggctggt cgaccccatc aacgtggtgg gactgctgtt    4200
gctcacaagg agtgggaagc ggagctggcc ccctagcgaa gtactcacag ctgttggcct    4260
gatatgcgca ttggctggag ggttcgccaa ggcagatata gagatggctg gcccatggc    4320 cgcggtcggt ctgctaattg tcagttacgt ggtctcagga aagagtgtgg acatgtacat    4380
tgaaagagca ggtgacatca catgggaaaa agatgcggaa gtcactggaa acagtccccg    4440
gctcgatgtg gcgctagatg agagtggtga tttctccctg gtggaggatg acggtccccc    4500
catgagagag atcatactca aggtggtcct gatgaccatc tgtggcatga acccaatagc    4560
catacccttt gcagctggag cgtggtacgt atacgtgaag actggaaaaa ggagtggtgc    4620
tctatgggat gtgcctgctc ccaaggaagt aaaaaagggg gagaccacag atggagtgta    4680
cagagtaatg actcgtagac tgctaggttc aacacaagtt ggagtgggag ttatgcaaga    4740
gggggtcttt cacactatgt ggcacgtcac aaaaggatcc cgctgagaa gcggtgaagg    4800 gagacttgat ccatactggg gagatgtcaa gcaggatctg gtgtcatact gtggtccatg    4860
gaagctagat gccgctgggg atgggcacag cgaggtgcag ctcttggccg tgccccccgg    4920
agagagagcg aggaacatcc agactctgcc cggaatattt aagacaaagg atggggacat    4980
tggagcggtt gcgctggatt acccagcagg aacttcagga tctccaatcc tagacaagtg    5040
tgggagagtg ataggacttt atggcaatgg ggtcgtgatc aaaaacggga gttatgttag    5100
tgccatcacc caaggaggag gggaggaaga gactcctgtt gagtgcttcg agccctcgat    5160
gctgaagaag aagcagctaa ctgtcttaga cttgcatcct ggagctggga aaaccaggag    5220
agttcttcct gaaatagtcc gtgaagccat aaaaacaaga ctccgtactg tgatcttagc    5280
tccaaccagg gttgtcgctg ctgaaatgga ggaggccctt agagggcttc cagtgcgtta    5340
tatgacaaca gcagtcaatg tcacccactc tggaacagaa atcgtcgact taatgtgcca    5400
tgccaccttc acttcacgtc tactacagcc aatcagagtc cccaactata atctgtatat    5460
tatggatgag gcccacttca cagatccctc aagtatagca gcaagaggat acatttcaac    5520
aagggttgag atgggcgagg cggctgccat cttcatgacc gccacgccac caggaacccg    5580
tgacgcattt ccggactcca actcaccaat tatggcacac gaagtggaag tcccagagag    5640
agcctggagc tcaggctttg attgggtgac ggatcattct ggaaaaacag tttggtttgt    5700
tccaagcgtg aggaacggca atgagatcgc agcttgtctg acaaaggctg aaaacgggt    5760 catacagctc agcagaaaga cttttgagac agagttccag aaaacaaaac atcaagagtg    5820
ggactttgtc gtgacaactg acatttcaga gatgggcgcc aactttaaag ctgaccgtgt    5880
catagattcc aggagatgcc taaagccggt catacttgat ggcgagagag tcattctggc    5940
tggacccatg cctgtcacac atgccagcgc tgcccagagg agggggcgca taggcaggaa    6000
tcccaacaaa cctggagatg agtatctgta tggaggtggg tgcgcagaga ctgacgaaga    6060
ccatgcacac tggcttgaag caagaatgct ccttgacaat atttacctcc aagatggcct    6120
catagcctcg ctctatcgac ctgaggccga caaagtagca gccattgagg gagagttcaa    6180
gcttaggacg gagcaaagga gacctttgt ggaactcatg aaaagaggag atcttcctgt    6240
ttggctggcc tatcaggttg catctgccgg aataacctac acagatagaa gatggtgctt    6300
```

```
tgatggcacg accaacaaca ccataatgga agacagtgtg ccggcagagg tgtggaccag    6360
acacggagag aaaagagtgc tcaaaccgag gtggatggac gccagagttt gttcagatca    6420
tgcggccctg aagtcattca aggagtttgc cgctgggaaa agaggagcgg cttttggagt    6480
gatggaagcc ctgggaacac tgccaggaca catgacagag agattccagg aagccattga    6540
caacctcgct gtgctcatgc gggcagagac tggaagcagg ccttacaaag ccgcggcggc    6600
ccaattgccg gagaccctag agaccataat gcttttgggg ttgctgggaa cagtctcgct    6660
gggaatcttc ttcgtcttga tgaggaacaa gggcataggg aagatgggct ttggaatggt    6720
gactcttggg gccagcgcat ggctcatgtg gctctcggaa attgagccag ccagaattgc    6780
atgtgtcctc attgttgtgt tcctattgct ggtggtgctc atacctgagc agaaaagca    6840 aagatctccc caggacaacc aaatggcaat catcatcatg gtagcagtag gtcttctggg    6900
cttgattacc gccaatgaac tcggatggtt ggagagaaca aagagtgacc taagccatct    6960
aatgggaagg agagaggagg gggcaaccat aggattctca atggacattg acctgcggcc    7020
agcctcagct tgggccatct atgctgcctt gacaactttc attaccccag ccgtccaaca    7080
tgcagtgacc acctcataca acaactactc cttaatggcg atggccacgc aagctggagt    7140
gttgtttggc atgggcaaag ggatgccatt ctacgcatgg gactttggag tcccgctgct    7200
aatgataggt tgctactcac aattaacacc cctgacccta atagtggcca tcattttgct    7260
cgtggcgcac tacatgtact tgatcccagg gctgcaggca gcagctgcgc gtgctgccca    7320
gaagagaacg gcagctggca tcatgaagaa ccctgttgtg gatggaatag tggtgactga    7380
cattgacaca atgacaattg acccccaagt ggagaaaaag atgggacagg tgctactcat    7440
agcagtagcc gtctccagcg ccatactgtc gcggaccgcc tgggggtggg gggaggctgg    7500
ggctctgatc acagccgcaa cttccacttt gtgggaaggc tctccgaaca agtactggaa    7560
ctcctctaca gccacttcac tgtgtaacat ttttagggga agttacttgg ctggagcttc    7620
tctaatctac acagtaacaa gaaacgctgg cttggtcaag agacgtgggg gtggaacagg    7680
agagaccctg ggagagaaat ggaaggcccg cttgaaccag atgtcggccc tggagttcta    7740
ctcctacaaa aagtcaggca tcaccgaggt gtgcagagaa gaggcccgcc gcgccctcaa    7800
ggacggtgtg gcaacgggag gccatgctgt gtcccgagga agtgcaaagc tgagatggtt    7860
ggtggagcgg ggatacctgc agccctatgg aaaggtcatt gatcttggat gtggcagagg    7920
gggctggagt tactacgtcg ccaccatccg caaagttcaa gaagtgaaag gatacacaaa    7980
aggaggccct ggtcatgaag aacccgtgtt ggtgcaaagc tatgggtgga acatagtccg    8040
tcttaagagt ggggtggacg tctttcatat ggcggctgag ccgtgtgaca cgttgctgtg    8100
tgacataggt gagtcatcat ctagtcctga agtggaagaa gcacgacgc tcagagtcct    8160 ctccatggtg ggggattggc ttgaaaaaag accaggagcc ttttgtataa aagtgttgtg    8220
cccatacacc agcactatga tggaaaccct ggagcgactg cagcgtaggt atgggggagg    8280
actggtcaga gtgccactct cccgcaactc tacacatgag atgtactggg tctctggagc    8340
gaaaagcaac accataaaaa gtgtgtccac cacgagccag ctcctcttgg ggcgcatgga    8400
cgggcctagg aggccagtga aatatgagga ggatgtgaat ctcggtctg gcacgcgggc    8460 tgtggtaagc tgcgctgaag ctcccaacat gaagatcatt ggtaaccgca ttgaaaggat    8520
ccgcagtgag cacgcggaaa cgtggttctt tgacgagaac caccatata ggacatgggc    8580 ttaccatgga agctatgagg cccccacaca agggtcagcg tcctctctaa taaacggggt    8640
```

```
tgtcaggctc ctgtcaaaac cctgggatgt ggtgactgga gtcacaggaa tagccatgac    8700
cgacaccaca ccgtatggtc agcaaagagt tttcaaggaa aaagtggaca ctagggtgcc    8760
agaccccaa gaaggcactc gtcaggttat gagcatggtc tcttcctggt tgtggaaaga    8820
gctaggcaaa cacaaacggc cacgagtctg caccaaagaa gagttcatca acaaggttcg    8880
tagcaatgca gcattagggg caatatttga agaggaaaaa gagtggaaga ctgcagtgga    8940
agctgtgaac gatccaaggt tctgggctct agtggacaag gaaagagagc accacctgag    9000
aggagagtgc cagagctgtg tgtacaacat gatgggaaaa agagaaaaga acaaggggga    9060
atttggaaag gccaagggca gccgcgccat ctggtatatg tggctagggg ctagatttct    9120
agagttcgaa gcccttggat tcttgaacga ggatcactgg atggggagag agaactcagg    9180
aggtggtgtt gaagggctgg gattacaaag actcggatat gtcctagaag agatgagtcg    9240
tataccagga ggaaggatgt atgcagatga cactgctggc tgggacaccc gcattagcag    9300
gtttgatctg gagaatgaag ctctaatcac caaccaaatg gagaaagggc acagggcctt    9360
ggcattggcc ataatcaagt acacatacca aaacaaagtg gtaaaggtcc ttagaccagc    9420
tgaaaaaggg aaaacagtta tggacattat ttcgagacaa gaccaaaggg ggagcggaca    9480
agttgtcact tacgctctta acacatttac caacctagtg gtgcaactca ttcggaatat    9540
ggaggctgag gaagttctag atgcaagga cttgtggctg ctgcggaggt cagagaaagt    9600
gaccaactgg ttgcagagca cggatgggag taggctcaaa cgaatggcag tcagtggaga    9660
tgattgcgtt gtgaagccaa ttgatgatag gtttgcacat gccctcaggt tcttgaatga    9720
tatgggaaaa gttaggaagg acacacaaga gtggaaaccc tcaactggat gggacaactg    9780
ggaagaagtt ccgttttgct cccaccactt caacaagctc catctcaagg acgggaggtc    9840
cattgtggtt ccctgccgcc accaagatga actgattggc cgggcccgcg tctctccagg    9900
ggcgggatgg agcatccggg agactgcttg cctagcaaaa tcatatgcgc aaatgtggca    9960
gctcctttat ttccacagaa gggacctccg actgatggcc aatgccattt gttcatctgt    10020
gccagttgac tgggttccaa ctgggagaac tacctggtca atccatggaa agggagaatg    10080
gatgaccact gaagacatgc ttgtggtgtg aacagagtg tggattgagg agaacgacca    10140
catggaagac aagacccag ttacgaaatg gacagacatt ccctatttgg gaaaagggga    10200
agacttgtgg tgtggatctc tcataggca cagaccgcgc accacctggg ctgagaacat    10260
taaaaacaca gtcaacatgg tgcgcaggat cataggtgat gaagaaaagt acatggacta    10320
cctatccacc caagttcgct acttgggtga agaagggtct acacctggag tgctgtaagc    10380
accaatctta atgttgtcag gcctgctagt cagccacagc ttggggaaag ctgtgcagcc    10440
tgtgaccccc ccaggagaag ctgggaaacc aagcctatag tcaggccgag aacgccatgg    10500
cacggaagaa gccatgctgc ctgtgagccc ctcagaggac actgagtcaa aaacccacac    10560
gcgcttggag gcgcaggatg ggaaaagaag tggcgacct ccccaccct tcaatctggg    10620
gcctgaactg gagatcagct gtggatctcc agaagaggga ctagtggtta gagga         10675
```

<210> SEQ ID NO 5
<211> LENGTH: 10676
<212> TYPE: DNA
<213> ORGANISM: Zika virus

<400> SEQUENCE: 5

```
gttgttactg ttgctgactc agactgcgac agttcgagtt tgaagcgaaa gctagcaaca     60
gtatcaacag gttttatttg gatttggaaa cgagagtttc tggtcatgaa aaacccaaaa    120
```

```
aagaaatccg gaggattccg gattgtcaat atgctaaaac gcggagtagc ccgtgtgagc    180
cccttTGGGG gcttgaagag gctgccagcc ggacttctgc tgggtcatgg gcccatcagg    240
atggtcttgg caattctagc ctttttgaga ttcacggcaa tcaagccatc actgggtctc    300
atcaatagat ggggttcagt ggggaaaaaa gaggctatgg aaataataaa gaagttcaag    360
aaagatctgg ctgccatgct gagaataatc aatgctagga aggagaagaa gagacgaggc    420
gcagatacta gtgtcggaat tgttggcctc ctgctgacca cagctatggc agcggaggtc    480
actagacgtg ggagtgcata ctatatgtac ttggacagaa acgatgctgg ggaggccata    540
tcttttccaa ccacattggg gatgaataag tgttatatac agatcatgga tcttggacac    600
atgtgtgatg ccaccatgag ctatgaatgc cctatgctgg atgaggggt ggaaccagat    660 gacgtcgatt gttggtgcaa cacgacgtca acttgggttg tgtacggaac ctgccatcac    720 aaaaaggtg aagcacggag atctagaaga gctgtgacgc tcccctccca ttccactagg    780
aagctgcaaa cgcggtcgca aacctggttg gaatcaagag aatacacaaa gcacttgatt    840
agagtcgaaa attggatatt caggaaccct ggcttcgcgt tagcagcagc tgccatcgct    900 tggctttgg gaagctcaac gagccaaaaa gtcatatact tggtcatgat actgctgatt    960
gccccggcat acagcatcag gtgcatagga gtcagcaata gggactttgt ggaaggtatg   1020
tcaggtggga cttgggttga tgttgtcttg gaacatggag gttgtgtcac cgtaatggca   1080
caggacaaac cgactgtcga catagagctg gttacaacaa cagtcagcaa catggcggag   1140
gtaagatcct actgctatga ggcatcaata tcagacatgg cttcggacag ccgctgccca   1200
acacaaggtg aagcctacct tgacaagcaa tcagacactc aatatgtctg caaaagaacg   1260
ttagtggaca gaggctgggg aaatggatgt ggacttttg gcaaagggag tctggtgaca   1320
tgcgctaagt ttgcatgctc caagaaaatg accgggaaga gcatccagcc agagaatctg   1380
gagtaccgga taatgctgtc agttcatggc tcccagcaca gtgggatgat cgttaatgac   1440
acaggacatg aaactgatga aatagagcg aaggttgaga taacgcccaa ttcaccaaga   1500
gccgaagcca ccctggggg ttttggaagc ctaggacttg attgtgaacc gaggacaggc   1560
cttgactttt cagatttgta ttacttgact atgaataaca agcactggtt ggttcacaag   1620
gagtggttcc acgacattcc attaccttgg cacgctgggg cagacaccgg aactccacac   1680
tggaacaaca agaagcact ggtagagttc aaggacgcac atgccaaaag gcaaactgtc   1740
gtggttctag ggagtcaaga aggagcagtt cacacggccc ttgctggagc tctggaggct   1800
gagatggatg gtgcaaaggg aaggctgtcc tctggccact tgaaatgtcg cctgaaaatg   1860
gataaactta gattgaaggg cgtgtcatac tccttgtgta ccgcagcgtt cacattcacc   1920
aagatcccgg ctgaaacact gcacgggaca gtcacagtgg aggtacagta cgcagggaca   1980
gatggacctt gcaaggttcc agctcagatg gcggtggaca tgcaaactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtccttgga gacacagcct gggactttgg atcagttgga   2280
ggcgctctca actcattggg caagggcatc catcaaattt ttggagcagc tttcaaatca   2340
ttgtttggag gaatgtcctg gttctcacaa attctcattg gaacgttgct gatgtggttg   2400
ggtctgaaca caaagaatgg atctatttcc cttatgtgct tggccttagg gggagtgttg   2460
```

```
atcttcttat ccacagccgt ctctgctgat gtggggtgct cggtggactt ctcaaagaag    2520
gagacgagat gcggtacagg ggtgttcgtc tataacgacg ttgaagcctg gagggacagg    2580
tacaagtacc atcctgactc cccccgtaga ttggcagcag cagtcaagca agcctgggaa    2640
gatggtatct gcgggatctc ctctgtttca agaatggaaa acatcatgtg gagatcagta    2700 gaagggagc tcaacgcaat cctggaagag aatggagttc aactgacggt cgttgtggga    2760
tctgtaaaaa accccatgtg gagaggtcca cagagattgc ccgtgcctgt gaacgagctg    2820
ccccacggct ggaaggcttg ggggaaatcg cacttcgtca gagcagcaaa gacaaataac    2880
agctttgtcg tggatggtga cacactgaag gaatgcccac tcaaacatag gcatggaaac    2940
agctttcttg tggaggatca tgggttcggg gtatttcaca ctagtgtctg gctcaaggtt    3000
agagaagatt attcattaga gtgtgatcca gccgttattg gaacagctgt taagggaaag    3060
gaggctgtac acagtgatct aggctactgg attgagagtg agaagaatga cacatggagg    3120
ctgaagaggg cccatctgat cgagatgaaa acatgtgaat ggccaaagtc ccacacattg    3180
tggacagatg gaatagaaga gagtgatctg atcatacccca agtctttagc tgggccactc    3240
agccatcaca ataccagaga gggctacagg acccaaatga agggccatg gcacagtgaa    3300 gagcttgaaa ttcggtttga ggaatgccca ggcactaagg tccacgtgga ggaaacatgt    3360
ggaacaagag gaccatctct gagatcaacc actgcaagcg gaaggggtgat cgaggaatgg    3420 tgctgcaggg agtgcacaat gcccccactg tcgttccggg ctaaagatgg ctgttggtat    3480
ggaatggaga taaggcccag gaaagaacca gaaagcaact tagtaaggtc aatggtgact    3540
gcaggatcaa ctgatcacat ggatcacttc tcccttggag tgcttgtgat tctgctcatg    3600
gtgcaggaag ggctgaagaa gagaatgacc acaaagatca tcataagcac atcaatggca    3660
gtgctggtag ctatgatcct gggaggattt tcaatgagtg acctggctaa gcttgcaatt    3720
ttgatgggtg ccaccttcgc ggaaatgaac actggaggag atgtagctca tctggcgctg    3780
atagcggcat tcaaagtcag accagcgttg ctggtatctt tcatcttcag agctaattgg    3840
acaccccgtg aaagcatgct gctggccttg ggcctcgtgtc ttttgcaaac tgcgatctcc    3900
gccttggaag gcgacctgat ggttctcatc aatggttttg cttttggcctg gttggcaata    3960 cgagcgatgg ttgttccacg cactgataac atcaccttgg caatcctggc tgctctgaca    4020
ccactggccc ggggcacact gcttgtggcg tggagagcag gccttgctac ttgcgggggg    4080
tttatgctcc tctctctgaa ggggaaaggc agtgtgaaga agaacttacc atttgtcatg    4140
gccctgggac taaccgctgt gaggctggtc gaccccatca cgtggtggg gctgctgttg    4200 ctcacaagga gtgggaagcg gagctggccc cctagcgaag tactcacagc tgttggcctg    4260
atatgcgcat tggctggagg gttcgccaag gcagatatag agatggctgg gcccatggcc    4320
gcggtcggtc tgctaattgt cagttacgtg gtctcaggaa agagtgtgga catgtacatt    4380
gaaagagcag gtgacatcac atgggaaaaa gatgcggaag tcactggaaa cagtccccgg    4440
ctcgatgtgg cgctagatga gagtggtgat ttctccctgg tggaggatga cggtcccccc    4500
atgagagaga tcatactcaa ggtggtcctg atgaccatct gtggcatgaa cccaatagcc    4560
ataccctttg cagctggagc gtggtacgta tacgtgaaga ctgaaaaaag gagtggtgct    4620
ctatgggatg tgcctgctcc caaggaagta aaaaaggggg agaccacaga tggagtgtac    4680
agagtaatga ctcgtagact gctaggttca acacaagttg gagtgggagt tatgcaagag    4740
ggggtctttc acactatgtg gcacgtcaca aaaggatccg cgctgagaag cggtgaaggg    4800
agacttgatc catactgggg agatgtcaag caggatctgg tgtcatactg tggtccatgg    4860
```

```
aagctagatg ccgcctggga cgggcacagc gaggtgcagc tcttggccgt gccccccgga    4920
gagagagcga ggaacatcca gactctgccc ggaatattta agacaaagga tgggacatt    4980 ggagcggttg cgctggatta cccagcagga acttcaggat ctccaatcct agacaagtgt    5040
gggagagtga taggactta tggcaatggg gtcgtgatca aaaatgggag ttatgttagt    5100
gccatcaccc aagggaggag ggaggaagag actcctgttg agtgcttcga gccttcgatg    5160
ctgaagaaga agcagctaac tgtcttagac ttgcatcctg gagctgggaa aaccaggaga    5220
gttcttcctg aaatagtccg tgaagccata aaaacaagac tccgtactgt gatcttagct    5280
ccaaccaggg ttgtcgctgc tgaaatggag gaagcccta gagggcttcc agtgcgttat    5340
atgacaacag cagtcaatgt cacccactct ggaacagaaa tcgtcgactt aatgtgccat    5400
gccaccttca cttcacgtct actacagcca atcagagtcc ccaactataa tctgtatatt    5460
atggatgagg cccacttcac agatccctca agtatagcag caagaggata catttcaaca    5520
agggttgaga tggcgaggc ggctgccatc ttcatgaccg ccacgccacc aggaacccgt    5580
gacgcatttc cggactccaa ctcaccaatt atggacaccg aagtggaagt cccagagaga    5640
gcctggagct caggctttga ttgggtgacg gattattctg gaaaacagt ttggtttgtt    5700 ccaagcgtga ggaacggcaa tgagatcgca gcttgtctga caaaggctgg aaaacgggtc    5760
atacagctca gcagaaagac ttttgagaca gagttccaga aaacaaaaca tcaagagtgg    5820
gactttgtcg tgacaactga catttcagag atgggcgcca actttaaagc tgaccgtgtc    5880
atagattcca ggagatgcct aaagccggtc atacttgatg gcgagagagt cattctggct    5940
ggacccatgc ctgtcacaca tgccagcgct gcccagagga ggggcgcat aggcaggaat    6000 cccaacaaac ctggagatga gtatctgtat ggaggtgggt gcgcagagac tgacgaagac    6060
catgcacact ggcttgaagc aagaatgctc cttgacaata tttacctcca agatggcctc    6120
atagcctcgc tctatcgacc tgaggccgac aaagtagcag ccattgaggg agagttcaag    6180
cttaggacgg agcaaaggaa gacctttgtg gaactcatga aaagaggaga tcttcctgtt    6240
tggctggcct atcaggttgc atctgccgga ataacctaca cagatagaag atggtgcttt    6300
gatggcacga ccaacaacac cataatgaa gacagtgtgc cggcagaggt gtggaccaga    6360
cacggagaga aaagagtgct caaaccgagg tggatggacg ccagagtttg ttcagatcat    6420
gcggccctga agtcattcaa ggagtttgcc gctgggaaaa gaggagcggc ttttggagtg    6480
atggaagccc tgggaacact gccaggacac atgacagaga gattccagga agccattgac    6540
aacctcgctg tgctcatgcg ggcagagact ggaagcaggc cttacaaagc cgcggcggcc    6600
caattgccgg agaccctaga gaccattatg cttttgggt tgctgggaac agtctcgctg    6660
ggaatctttt tcgtcttgat gaggaacaag gcatagga agatgggctt tggaatggtg    6720
actcttgggg ccagcgcatg gctcatgtgg ctctcggaaa ttgagccagc cagaattgca    6780
tgtgtcctca ttgttgtgtt cctattgctg gtggtgctca tacctgagcc agaaaagcaa    6840
agatctcccc aggacaacca aatggcaatc atcatcatgg tagcagtagg tcttctgggc    6900
ttgattaccg ccaatgaact cggatggttg gagagaacaa agagtgacct aagccatcta    6960
atgggaagga gagaggaggg ggcaaccatg ggattctcaa tggacattga cctgcggcca    7020
gcctcagctt gggccatcta tgctgccttg acaactttca ttaccccagc cgtccaacat    7080
gcagtgacca cttcatacaa caactactcc ttaatggcga tggccacgca agctggagtg    7140
ttgtttggta tgggcaaagg gatgccattc tacgcatggg actttggagt cccgctgcta    7200
```

```
atgataggtt gctactcaca attaacgccc ctgaccctaa tagtggccat cattttgctc    7260
gtggcgcact acatgtactt gatcccaggg ctgcaggcag cagctgcgcg tgctgcccag    7320
aagagaacgg cagctggcat catgaagaac cctgttgtgg atggaatagt ggtgactgac    7380
attgacacaa tgacaattga cccccaagtg gagaaaaaga tgggacaggt gctactcatg    7440
gcagtagccg tctccagcgc catactgtcg cggaccgcct gggggtgggg ggaggctggg    7500
gccctgatca cagccgcaac ttccactttg tgggaaggct ctccgaacaa gtactggaac    7560
tcctctacag ccacttcact gtgtaacatt tttaggggaa gttacttggc tggagcttct    7620
ctaatctaca cagtaacaag aaacgctggc ttggtcaaga gacgtggggg tggaacagga    7680
gagaccctgg gagagaaatg gaaggcccgc ttgaaccaga tgtcggccct ggagttctac    7740
tcctacaaaa agtcaggcat caccgaggtg tgcagagaag aggcccgccg cgccctcaag    7800
gacggtgtgg caacgggagg ccatgctgtg tcccgaggaa gtgcaaagct gagatggttg    7860
gtggagcggg gatacctgca gccctatgga aaggtcattg atcttggatg tggcagaggg    7920
ggctggagtt actacgccgc caccatccgc aaagttcaag aagtgaaagg atacacaaaa    7980
ggaggccctg gtcatgaaga acccgtgttg gtgcaaagct atgggtggaa catagtccgt    8040
cttaagagtg gggtggacgt cttccatatg gcggctgagc cgtgtgacac gttgctgtgt    8100
gacataggtg agtcatcatc tagtcctgaa gtggaagaag cacggacgct cagagtcctc    8160
tccatggtgg gggattggct tgaaaaaaga ccaggagcct tttgtataaa agtgttgtgc    8220
ccatacacca gcactatgat ggaaaccctg gagcgactgc agcgtaggta tgggggagga    8280
ctggtcgagag tgccactctc ccgcaactct acacatgaga tgtactgggt ctctggagcg    8340
aaaagcaaca ccataaaaag tgtgtccacc acgagccagc tcctcttggg gcgcatggac    8400
gggcctagga ggccagtgaa atatgaggag gatgtgaatc tcggctctgg cacgcgggct    8460
gtggtaagct gcgctgaagc tcccaacatg aagatcattg gtaaccgcat tgaaaggatc    8520
cgcagtgagc acgcggaaac gtggttctt gacgagaacc acccatatag gacatgggct    8580
taccatggaa gctatgaggc ccccacacaa gggtcagcgt cctctctaat aaacggggtt    8640
gtcaggctcc tgtcaaaacc ctgggatgtg gtgactggag tcacaggaat agccatgacc    8700
gacaccacac cgtatggtca gcaaagagtt ttcaaggaaa aagtggacac tagggtgcca    8760
gaccccccaag aaggcactcg tcaggttatg agcatggtct cttcctggtt gtggaaagag    8820
ctaggcaaac acaaacggcc acgagtctgt accaaagaag agttcatcaa caaggttcgt    8880
agcaatgcag cattagggc aatatttgaa gaggaaaaag agtggaagac tgcagtggaa    8940
gctgtgaacg atccaaggtt ctgggctcta gtggacaagg aaagagagca ccacctgaga    9000
ggagagtgcc agagttgtgt gtacaacatg atgggaaaaa gagaaaagaa acaagggga    9060
tttggaaagg ccaagggcag ccgcgccatc tggtatatgt ggctaggggc tagatttcta    9120
gagttcgaag cccttggatt cttgaacgag atcactggga tgggagagga gaactcagga    9180
ggtggtgttg aagggctggg attacaaaga ctcggatatg tcctagaaga gatgagtcgc    9240
ataccaggag gaaggatgta tgcagatgac actgctggct gggacacccg catcagcagg    9300
tttgatctgg agaatgaagc tctaatcacc aaccaaatgg agaaagggca gggccttg    9360
gcattggcca taatcaagta cacataccaa aacaaagtgg taaggtcct tagaccagct    9420
gaaaaaggga gacagttat ggacattatt cgagacaag accaaggggg agcggacaa    9480
gttgtcactt acgctcttaa cacatttacc aacctagtgg tgcaactcat tcggaatatg    9540
gaggctgagg aagttctaga gatgcaagac ttgtggctgc tgcggaggtc agagaaagtg    9600
```

```
accaactggt tgcagagcaa cggatgggat aggctcaaac gaatggcagt cagtggagat    9660
gattgcgttg tgaagccaat tgatgatagg tttgcacatg ccctcaggtt cttgaatgat    9720
atgggaaaag ttaggaagga cacacaagag tggaaaccct caactggatg ggacaactgg    9780
gaagaagttc cgttttgctc ccaccacttc aacaagctcc atctcaagga cgggaggtcc    9840
attgtggttc cctgccgcca ccaagatgaa ctgattggcc gggcccgcgt ctctccaggg    9900
gcgggatgga gcatccggga gactgcttgc ctagcaaaat catatgcgca aatgtggcag    9960
ctcctttatt tccacagaag ggacctccga ctgatggcca atgccatttg ttcatctgtg   10020
ccagttgact gggttccaac tgggagaact acctggtcaa tccatggaaa gggagaatgg   10080
atgaccactg aagacatgct tgtggtgtgg aacagagtgt ggattgagga aacgaccac    10140 atggaagaca gaccccagt tacgaaatgg acagacattc cctatttggg aaaaagggaa    10200
gacttgtggt gtggatctct catagggcac agaccgcgca ccacctgggc tgagaacatt   10260
aaaaacacag tcaacatggt gcgcaggatc ataggtgatg aagaaaagta catggactac   10320
ctatccaccc aagttcgcta cttgggtgaa gaagggtcta cacctggagt gctgtaagca   10380
ccaatcttaa tgttgtcagg cctgctagtc agccacagct gggggaaagc tgtgcagcct   10440 gtgaccccc caggagaagc tgggaaacca agcctatagt caggccgaga cgccatggc    10500 acggaagaag ccatgctgcc tgtgagcccc tcagaggaca ctgagtcaaa aaacccacg    10560 cgcttggagg cgcaggatgg gaaagaaggt ggcgacctt ccccacccctt caatctgggg    10620 cctgaactgg agatcagctg tggatctcca gaagagggac tagtggttag aggaga       10676

<210> SEQ ID NO 6
<211> LENGTH: 10808
<212> TYPE: DNA
<213> ORGANISM: Zika virus

<400> SEQUENCE: 6
agttgttgat ctgtgtgaat cagactgcga cagttcgagt ttgaagcgaa agctagcaac      60
agtatcaaca ggttttattt tggatttgga acgagagtt tctggtcatg aaaaacccaa     120
aaaagaaatc cggaggattc cggattgtca atatgctaaa acgcggagta gcccgtgtga     180
gcccctttgg gggcttgaag aggctgccag ccggacttct gctgggtcat gggcccatca     240
ggatggtctt ggcaattcta gccttttga gattcacggc aatcaagcca tcactgggtc     300
tcatcaatag atggggttca gtggggaaaa aagaggctat ggaataata aagaagttca     360 agaaagatct ggctgccatg ctgagaataa tcaatgctag aaggagaag aagagacgag     420 gcgcagatac tagtgtcgga attgttggcc tcctgctgac cacagctatg cagcggagg     480 tcactagacg tgggagtgca tactatatgt acttggacag aaacgatgct ggggaggcca     540
tatcttttcc aaccacattg gggatgaata gtgttatat acagatcatg gatcttggac     600
acatgtgtga tgccaccatg agctatgaat gccctatgct ggatgagggg gtggaaccag     660
atgacgtcga ttgttggtgc aacacgacgt caacttgggt tgtgtacgga acctgccatc     720
acaaaaaagg tgaagcacgg agatctgaa gagctgtgac gctccctcc cattccacta     780 ggaagctgca acgcggtcg caaacctggt tggaatcaag agaatacaca aagcacttga     840
ttagagtcga aaattggata ttcaggaacc ctggcttcgc gttagcagca gctgccatcg     900
cttggctttt gggaagctca acgagccaaa aagtcatata cttggtcatg atactgctga     960 ttgcccggc atacagcatc aggtgcatag gagtcagcaa tagggacttt gtggaaggta    1020
```

```
tgtcaggtgg gacttgggtt gatgttgtct tggaacatgg aggttgtgtc accgtaatgg    1080
cacaggacaa accgactgtc gacatagagc tggttacaac aacagtcagc aacatggcgg    1140
aggtaagatc ctactgctat gaggcatcaa tatcagacat ggcttcggac agccgctgcc    1200
caacacaagg tgaagcctac cttgacaagc aatcagacac tcaatatgtc tgcaaaagaa    1260
cgttagtgga cagaggctgg ggaaatggat gtggactttt tggcaaaggg agcctggtga    1320
catgcgctaa gtttgcatgc tccaagaaaa tgaccgggaa gagcatccag ccagagaatc    1380
tggagtaccg gataatgctg tcagttcatg gctcccagca cagtgggatg atcgttaatg    1440
acacaggaca tgaaactgat gagaatagag cgaaggttga gataacgccc aattcaccaa    1500
gagccgaagc caccctgggg ggttttggaa gcctaggact tgattgtgaa ccgaggacag    1560
gccttgactt ttcagatttg tattacttga ctatgaataa caagcactgg ttggtccaca    1620
aggagtggtt ccacgacatt ccattacctt ggcacgctgg ggcagacacc ggaactccac    1680
actggaacaa caaagaagca ctggtagagt tcaaggacgc acatgccaaa aggcaaactg    1740
tcgtggttct agggagtcaa gaaggagcag ttcacacggc ccttgctgga gctctggagg    1800
ctgagatgga tggtgcaaag ggaaggctgt cctctggcca cttgaaatgt cgcctgaaaa    1860
tggataaact tagattgaag ggcgtgtcat actccttgtg taccgcagcg ttcacattca    1920
ccaagatccc ggctgaaaca ctgcacggga cagtcacagt ggaggtacag tacgcaggga    1980 cagatgacc ttgcaaggtt ccagctcaga tggcggtgga catgcaaact ctgacccag    2040 ttgggaggtt gataaccgct aaccccgtaa tcactgaaag cactgagaac tctaagatga    2100
tgctggaact tgatccacca tttggggact cttacattgt cataggagtc ggggagaaga    2160
agatcaccca ccactggcac aggagtggca gcaccattgg aaaagcattt gaagccactg    2220
tgagaggtgc caagagaatg gcagtcttgg agacacagc ctgggacttt ggatcagttg    2280
gaggcgctct caactcattg ggcaagggca tccatcaaat ttttggagca gctttcaaat    2340 cattgttttgg aggaatgtcc tggttctcac aaatcctcat tggaacgttg ctgatgtggt    2400
tgggtctgaa cacaaagaat ggatctattt cccttatgtg cttggcctta gggggagtgt    2460
tgatcttctt atccacagcc gtctctgctg atgtggggtg ctcggtggac ttctcaaaga    2520
aggagacgag atgcggtaca ggggtgttcg tctataacga cgttgaagcc tgagggaca    2580 ggtacaagta ccatcctgac tcccccgta gattggcagc agcagtcaag caagcctggg    2640
aagatggtat ctgcgggatc tcctctgttt caagaatgga gaacatcatg tggagatcag    2700
tagaagggga gctcaacgca atcttggaag agaatggagt tcaactgacg gtcgttgtgg    2760
gatctgtaaa aaaccccatg tggagaggtc cacagagatt gcccgtgcct gtgaacgagc    2820
tgccccacgg ctggaaggct tggggaaat cgtacttcgt cagagcagca agacaaata    2880 acagctttgt cgtggatggt gacacactga aggaatgccc actcgaacat agagcatgga    2940
acagctttct tgtggaggat catgggttcg gggtatttca cactagtgtc tggctcaagg    3000
ttagagaaga ttattcatta gagtgtgatc cagccgttat tggaacagct gttaagggga    3060
aggaggctgt acacagtgat ctaggctact ggattgagag tgagaagaat gacacatgga    3120
ggctgaagag ggcccatcta atcgagatga aacatgtga atggccaaag tcccacacat    3180
tgtgggcaga tggaatagaa gagagtgatc tgatcattcc caagtcttta gctgggccac    3240
tcagccatca aataccaga gagggctaca ggacccaaat gaaagggcca tggcacagtg    3300
aagagcttga aattccggttt gaggaatgcc cgggcactaa ggtccacgtg gaggaaacat    3360
gtggaacaag aggaccatct ctgagatcaa ccactgcaag cggaaggtgg atcgaggaat    3420
```

```
ggtgctgcag ggagtgcaca atgccccac  tgtcgttccg ggctaaagat ggctgttggt   3480
atggaatgga gataaggccc aggaaagaac cagaaagcaa cttagtaagg tcagtggtga   3540
ctgcaggatc aactgatcac atggatcact tctcccttgg agtgcttgtg attctgctca   3600
tggtgcagga agggctgaag aagagaatga ccacaaagat catcataagc acatcaatgg   3660
cagtgctggt agctatgatc ctgggaggat tttcaatgag tgacctggct aagcttgcaa   3720
ttttgatggg cgccaccttc gcggaaatga acactggagg agatgtagct catctggcgc   3780
tgatagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgata acatcacctt ggcaatcctg gctgctctga   4020
caccactggc ccggggcaca ctgcttgtgg cgtggagagc aggccttgct acttgcgggg   4080
ggtttatgct cctctctctg aagggaaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc ccctagcga agtactcaca gctgttggcc   4260
tgatatgcgc attggctgga gggttcgcca aggcagatat agagatggct gggcccatgg   4320
ccgcggtcgg tctgctaatt gtcagttacg tggtctcagg aaagagtgtg acatgtaca   4380 ttgaaagagc aggtgacatc acatgggaaa agatgcgga agtcactgga aacagtcccc   4440
ggctcgatgt ggcgctagat gagagtggtg atttctccct ggtggaggat gacggtcccc   4500
ccatgagaga gatcatactc aaggtggtcc tgatgaccat ctgtggcatg aacccaatag   4560
ccataccctt tgcagctgga gcgtggtacg tatacgtgaa gactggaaaa aggagtggtg   4620
ctctatggga tgtgcctgct cccaaggaag taaaaaaggg ggagaccaca gatggagtgt   4680
acagagtaat gactcgtaga ctgctaggtt caacacaagt tggagtggga gttatgcaag   4740 aggggtctt tcacactatg tggcacgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatgggaca   4980 ttggagcggt tgcgctggat tacccagcag gaacttcagg atctccaatc ctagacaagt   5040
gtgggagagt gataggactt tatggcaatg gggtcgtgat caaaaatggg agttatgtta   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaacaag actccgtact gtgatcttag   5280
ctccaaccag ggttgtcgct gctgaaatgg aggaagccct tagagggctt ccagtgcgtt   5340
atatgacaac agcagtcaat gtcacccact ctggaacaga aatcgtcgac ttaatgtgcc   5400
atgccacctt cacttcacgt ctactacagc caatcagagt ccccaactat aatctgtata   5460
ttatggatga ggcccacttc acagatcct caagtatagc agcaagagga tacatttcaa   5520
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtttggtttg   5700
ttccaagcgt gaggaacggc aatgagatcg cagcttgtct gacaaaggct ggaaaacggg   5760
```

```
tcatacagct cagcagaaag acttttgaga cagagttcca gaaaacaaaa catcaagagt    5820
gggactttgt cgtgacaact gacatttcag agatgggcgc aactttaaa gctgaccgtg     5880
tcatagattc caggagatgc ctaaagccgg tcatacttga tggcgagaga gtcattttgg    5940
ctggacccat gcctgtcaca catgccagcg ctgcccagag gaggggcgc ataggcagga     6000
atcccaacaa acctggagat gagtatctgt atggaggtgg gtgcgcagag actgacgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagacctttg tggaactcat gaaaagagga gatcttcctg    6240
tttggctggc ctatcaggtt gcatctgccg gaataaccta cacagataga agatggtgct    6300
ttgatggcac gaccaacaac accataatgg aagacagtgt gccggcagag gtgtggacca    6360
gacacggaga gaaaagagtg ctcaaaccga ggtggatgga cgccagagtt tgttcagatc    6420
atgcggccct gaagtcattc aaggagtttg ccgctgggaa agaggagcg cttttggag      6480
tgatggaagc cctgggaaca ctgccaggac acatgacaga gagattccag gaagccattg    6540
acaacctcgc tgtgctcatg cgggcagaga ctggaagcag gccttacaaa gccgcggcgg    6600
cccaattgcc ggagacccta gagaccatta tgcttttggg gttgctggga acagtctcgc    6660
tgggaatctt tttcgtcttg atgaggaaca agggcatagg gaagatgggc tttggaatgg    6720
tgactcttgg ggccagcgca tggctcatgt ggctctcgga aattgagcca gccagaattg    6780
catgtgtcct cattgttgtg ttcctattgc tggtggtgct cataccctgag ccagaaaagc    6840
aaagatctcc ccaggacaac caaatggcaa tcatcatcat ggtagcagta ggtcttctgg    6900
gcttgattac cgccaatgaa ctcggatggt tggagagaac aaagagtgac ctaagccatc    6960
taatgggaag agagagagag ggagcaacca taggattctc aatggacatt gacctgcggc    7020
cagcctcagc ttgggccatc tatgctgcct tgacaacttt cattacccca gccgtccaac    7080
atgcagtgac cacttcatac aacaactact ccttaatggc gatggccacg caagctggag    7140
tgttgtttgg tatgggcaaa gggatgccat tctacgcatg ggactttgga gtcccgctgc    7200
taatgatagg ttgctactca caattaacac ccctgacct aatagtggcc atcattttgc     7260
tcgtggcgca ctacatgtac ttgatcccag gctgcaggc agcagctgcg cgtgctgccc     7320
agaagagaac ggcagctggc atcatgaaga accctgttgt ggatggaata gtggtgactg    7380
acattgacac aatgacaatt gaccccaag tggagaaaaa gatgggacag gtgctactca     7440
tagcagtagc agtctccagc gccatactgt cgcggaccgc ctgggggtgg ggggaggctg    7500
gggccctgat cacagccgca acttccactt tgtgggaagg ctctccgaac aagtactgga    7560
actcctctac agccacttca ctgtgtaaca ttttaggg aagttacttg gctggagctt      7620
ctctaatcta catagtaaca agaaacgctg gcttggtcaa gagacgtggg ggtggaacag    7680
gagagaccct gggagagaaa tggaaggccc gcttgaacca gatgtcggcc ctggagttct    7740
actcctacaa aaagtcaggc atcaccgagg tgtgcagaga agaggcccgc cgcgccctca    7800
aggatggtgt ggcaacggga ggccatgctg tgtcccgagg aagtgcaaag ctgagatggt    7860
tggtggagcg gggatacctg cagccctatg gaaaggtcat tgatcttgga tgtgcagag    7920
ggggctggag ttactacgcc gccaccatcc gcaaagttca agaagtgaaa ggatacacaa    7980
aggaggccc tggtcatgaa gaacccgtgt ggtgcaaag ctatgggtgg aacatagtcc      8040
gtcttaagag tgggggtggac gtcttttcata tggcggctga gccgtgtgac acgttgctgt  8100
gtgacatagg tgagtcatca tctagtcctg aagtggaaga agcacggacg ctcagagtcc    8160
```

```
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg gggcgcatgg   8400
acgggcctag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagaccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagttgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttgaacg aggatcactg gatggggaga gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
ggttcgatct ggagaatgaa gctctaatca ccaaccaaat ggagaaaggg catagggcct   9360
tggcattggc cataatcaag tacacatacc aaaacaaagt ggtaaaggtc cttagaccag   9420
ctgaaaaagg gaaaacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaagct ccatctcaag gacgggaggt   9840
ccattgtggt tccctgccgc caccaagatg aactgattgg ccgggcccgc gtctctccag   9900
gggcgggatg gagcatccgg gagactgctt gcctagcaaa atcatatgcg caaatgtggc   9960
agctccttta tttccacaga agggacctcc gactgatggc caatgccatt tgttcatctg  10020
tgccagttga ctgggttcca actgggagaa ctacctggtc aatccatgga aagggagaat  10080
ggatgaccac tgaagacatg cttgtggtgt ggaacagagt gtggattgag agaacgacc   10140 acatggaaga caagaccccca gttacgaaat ggacagacat tccctatttg ggaaaagggg  10200
aagacttgtg gtgtggatct ctcatagggc acagaccgcg caccacctgg gctgagaaca  10260
ttaaaaacac agtcaacatg gtgcgcagga tcataggtga tgaagaaaag tacatggact  10320
acctatccac ccaagttcgc tacttgggtg aagaagggtc tacacctgga gtgctgtaag  10380
caccaatctt aatgttgtca ggcctgctag tcagccacag cttggggaaa gctgtgcagc  10440
ctgtgacccc cccaggagaa gctgggaaac caagcctata gtcaggccga gaacgccatg  10500
```

```
gcacggaaga agccatgctg cctgtgagcc cctcagagga cactgagtca aaaaacccca    10560
tgcgcttgga ggcgcaggat gggaaaagaa ggtggcgacc ttccccaccc ttcaatctgg    10620
ggcctgaact ggagatcagc tgtggatctc cagaagaggg actagtggtt agaggagacc    10680
ccccggaaaa cgcaaaacag catattgacg ctgggaaaga ccagagactc catgagtttc    10740
caccacgctg gccgccaggc acagatcgcc gaatagcggc ggccggtgtg gggaaatcca    10800
tgggtctt                                                              10808

<210> SEQ ID NO 7
<211> LENGTH: 10807
<212> TYPE: DNA
<213> ORGANISM: Zika virus

<400> SEQUENCE: 7
agttgttgat ctgtgtgaat cagactgcga cagttcgagt ttgaagcgaa agctagcaac      60
agtatcaaca ggttttattt tggatttgga acgagagtt tctggtcatg aaaaacccaa     120
aaaagaaatc cggaggattc cggattgtca atatgctaaa acgcggagta gcccgtgtga     180
gccccttggg gggcttgaag aggctgccag ccggacttct gctgggtcat gggcccatca     240
ggatggtctt ggcgattcta gcctttttga gattcacggc aatcaagcca tcactgggtc     300
tcatcaatag atggggttca gtggaaaaaa agaggctat ggaataata agaagttca      360 agaaagatct ggctgccatg ctgagaataa tcaatgctag aaggagaag aagagacgag     420 gcacagatac tagtgtcgga attgttggcc tcctgctgac cacagctatg gcagcggagg     480
tcactagacg tgggagtgca tactatatgt acttggacag aagcgatgct ggggaggcca     540
tatcttttcc aaccacactg gggatgaata agtgttatat acagatcatg gatcttggac     600
acatgtgtga tgccaccatg agctatgaat gccctatgct ggatgagggg gtagaaccag     660
atgacgtcga ttgttggtgc aacacgacgt caacttgggt tgtgtacgga acctgccatc     720
acaaaaaagg tgaagcacgg agatccgaaa gagctgtgac gctccctcc cattccacta     780 ggaagctgca aacgcggtcg cagacctggt tggaatcaag agaatacaca aagcacttga     840
ttagagtcga aaattggata ttcaggaacc ctggcttcgc gttagcagca gctgccatcg     900
cttggctttt gggaagctca acgagccaaa aagtcatata cttggtcatg atactgctga     960
ttgccccggc atacagcatc aggtgcatag gagtcagtaa tagggacttt gtggaaggta    1020
tgtcaggtgg gacttgggtt gatgttgtct tggaacatgg aggttgtgtc accgtaatgg    1080
cacaggacaa accgactgtc gacatagagc tggttacaac aacagtcagc aacatggcgg    1140
aggtaagatc ctactgctat gaggcatcaa tatcggacat ggcttcggac agccgctgcc    1200
caacacaagg tgaagcctac cttgacaagc aatcagacac tcaatatgtc tgcaaaagaa    1260
cgttagtgga cagaggctgg ggaaatggat gtggactttt tggcaaaggg agcctggtga    1320
catgcgctaa gtttgcatgc tccaagaaaa tgaccgggaa gagcatccag ccagagaatc    1380
tggagtaccg gataatgctg tcagttcatg gctcccagca cagtgggatg atcgttaatg    1440
acacaggaca tgaaactgat gagaatagag cgaaggttga taacgcccc aattcaccaa    1500 gagccgaagc cacctggggg ggttttggaa gcctaggact tgattgtgaa ccgaggacag    1560
gccttgactt ttcagatttg tattacttga ctatgaacaa caagcactgg ttggttcaca    1620
aggagtggtt ccacgacatt ccattacctt ggcacactgg ggcagacacc ggaactccac    1680
actggaacaa caaagaagca ctggtagagt tcaaggacgc acatgccaaa aggcaaactg    1740
tcgtggttct agggagtcaa gaaggagcag ttcacacggc ccttgctgga gctctggagg    1800
```

```
ctgagatgga tggtgcaaag ggaaggctgt cctctggcca cttgaaatgt cgcctgaaaa    1860
tggataaact tagattgaag ggcgtgtcat actccttgtg taccgcagcg ttcacattca    1920
ccaagatccc ggctgaaaca ctgcacggga cagtcacagt ggaggtacag tacgcaggga    1980
cagatggacc ttgcaaggtt ccagctcaga tggcggtgga catgcaaact ctgacccccag   2040
ttgggaggtt gataaccgct aaccccgtaa tcactgaagg cactgagaac tctaagatga    2100
tgctggaact tgatccacca tttggggact cttacattgt cataggagtc ggggagaaga    2160
agatcaccca ccactggcac aggagtggca gcaccattgg aaaagcattt gaagccactg    2220
tgagaggtgc caagagaatg gcagtcttgg agacacagc ctgggactttt ggatcagttg    2280
gaggcgttct taactcattg ggcaagggca tccatcaaat ttttggagca gctttcaaat    2340
cattgtttgg aggaatgtcc tggttctcac aaattctcat ggaacgttg ctgatgtggt     2400
tgggtctgaa tacaaagaat ggatctattt cccttatgtg cttggcctta ggggagtgt     2460
tgatcttctt atccacagcc gtctccgctg atgtggggtg ctcggtggac ttctcaaaga    2520
aggaaacgag atgcggtaca ggggtgttcg tctataacga cgttgaagcc tggagggaca    2580
ggtacaagta ccatcctgac tcccctcgta gattggcagc agtagtcaag caagcctggg    2640
aagatggtat ctgtgggatc tcctctgttt caagaatgga aaacatcatg tggagatcag    2700
tagaagggga gctcaacgca atcctggaag agaatggagt caactgacg gtcgttgtgg     2760
gatctgtaaa aaaccccatg tggagaggtc cacagagatt gcccgtgcct gtgaacgagc    2820
tgccccacgg ctggaaggct gggggaaat cgtacttcgt cagagcagca aagacaaata    2880
acagctttgt cgtggatggt gacacactga aggaatgccc actcaaacat agagcatgga    2940
acagcttctt gtggaggat catgggttcg gggtatttca cactagtgtc tggctcaagg    3000
ttagagaaga ttattcacta gagtgtgatc cagccgtcat tggaacagct gttaagggaa    3060
aggaggctgt acacagtgat ctaggctact ggattgagag tgagaagaac gacacatgga    3120
ggctgaggag ggcccacctg atcgagatga aaacatgtga atggccaaag tcccacacat    3180
tgtggacaga tggaataaga gagagtgatc tgatcatacc caagtcttta gctgggccac    3240
tcagccatca caacaccaga gagggctaca ggacccaaat gaaagggcca tggcacagtg    3300
aagagcttga aattcggttt gaggaatgcc caggcactaa ggtccacgtg gaggaaacat    3360
gtggaacaag aggaccatct ctgagatcaa ccactgcaag cggaagggtg atcgaggaat    3420
ggtgctgcag ggagtgcaca atgcccccac tgtcgttccg ggctaaagat ggctgttggt    3480
atggaatgga gataaggccc aggaaagaac cagaaagtaa cttagtaagg tcaatggtga    3540
ctgcaggatc aactgatcac atggatcact tttcccttgg agtgcttgtg attctgctca    3600
tggtgcagga agggctgaag aagagaatga ccacaaagat catcataagc acatcaatgg    3660
cagtgctggt agctatgatc ctgggaggat tttcaatgag tgatctggct aagcttgcaa    3720
ttttgatggg tgccaccttt gcggaaatga acactggagg agatgtagct catctggcgc    3780
tggtagcggc attcaaagtc agaccagcgt tgctggtatc tttcatcttc agagctaatt    3840
ggacaccccg tgaaagcatg ctgctggcct tggcctcgtg tcttttgcaa actgcgatct    3900
ccgccttgga aggcgacctg atggttctca tcaatggttt tgcttggcc tggttggcaa    3960
tacgagcgat ggttgttcca cgcactgaca atatcacctt ggcaatcctg ctgctctga    4020
caccactggc ccggggcaca ctgcttgtgg cgtggagagc aggccttgct acttgcgggg    4080
ggttcatgct cctctctctg aaggggaaag gcagtgtgaa gaagaactta ccatttgtca   4140
```

```
tggccctggg actaaccgct gtgaggctgg tcgaccccat caacgtggtg ggactgctgt    4200
tgctcacaag gagtgggaag cggagctggc cccctagcga agtactcaca gctgttggcc    4260
tgatatgcgc attggctgga gggttcgcca aggcagatat agagatggct gggcccatgg    4320
ccgcggtcgt tctgctaatt gtcagttacg tggtctcagg aaagagtgtg acatgtaca     4380
ttgaaagagc aggtgacatc acatgggaaa agatgcgga agttactgga aacagtcccc    4440
ggctcgatgt ggcactagat gagagtggtg atttctccct ggtggaggat gacggtcccc    4500
ccatgagaga gatcatactc aaagtggtcc tgatgaccat ctgtggcatg aacccaatag    4560
ccataccctt tgcagctgga gcgtggtacg tatacgtgaa aactggaaaa aggagtggtg    4620
ctctatggga tgtgcctgct cccaaggaag taaaaaaggg ggagaccaca gatggagtgt    4680
acagagtaat gactcgtaga ctgctaggtt caacacaagt tggagtggga gttatgcaag    4740
aggggtctt tcacactatg tggcatgtca caaaaggatc cgcgctgaga agcggtgaag    4800
ggagacttga tccatactgg ggagatgtca agcaggatct ggtgtcatac tgtggtccat    4860
ggaagctaga tgccgcctgg gacgggcaca gcgaggtgca gctcttggcc gtgccccccg    4920
gagagagagc gaggaacatc cagactctgc ccggaatatt taagacaaag gatggggaca    4980
ttggagcggt tgcgctggac tatccagcag gaacttcagg atctccaatc ctagacaagt    5040
gtgggagagt gataggactc tatggcaatg gggtcgtgat caagaatggg agttatgtca    5100
gtgccatcac ccaagggagg agggaggaag agactcctgt tgagtgcttc gagccttcga    5160
tgctgaagaa gaagcagcta actgtcttag acttgcatcc tggagctggg aaaaccagga    5220
gagttcttcc tgaaatagtc cgtgaagcca taaaaacgag actccgtact gtgatcttag    5280
ctccaaccag ggttgtcgct gctgaaatgg aggaagccct tagagggctt ccagtgcgtt    5340
atatgacaac agcagtcaat gtcacccatt ctgggacaga aatcgttgac ttaatgtgcc    5400
atgccacctt cacttcacgt ctactacagc caatcagagt ccccaactat aatctgtata    5460
ttatggatga ggcccacttc acagatcct caagtatagc agcaaggagga tacatttcaa    5520
caagggttga gatgggcgag gcagctgcca tcttcatgac cgccacgcca ccaggaaccc    5580
gtgacgcatt cccggactcc aactcaccaa ttatggacac cgaagtggaa gtcccagaga    5640
gagcctggag ctcaggcttt gattgggtga cggatcattc tggaaaaaca gtttggtttg    5700
tcccaagcgt gaggaacggc aatgagatcg cagcttgtct gacaaaggct ggaaaacggg    5760
tcatacagct cagcagaaag acttttgaga cagagttcca gaaaacaaaa catcaagagt    5820
gggacttcgt cgtgacaact gacatttcag agatgggcgc caactttaaa gctgaccgtg    5880
tcatagattc caggagatgc ctaaagccgg tcatacttga tggcgagaga gtcattctgg    5940
ctggacccat gcctgtcaca catgccagcg ctgcccagag gaggggcgc ataggcagga    6000
atcccaacaa acctggagat gagtatctgt atggaggtgg gtgcgcagag actgatgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagacctttg tggaactcat gaaaagagga gatcttcctg    6240
tttggctggc ctatcaggtt gcatctgccg gaataaccta cacagataga agatggtgct    6300
ttgatggcat gaccaacaac accataatgg aagacagtgt gccggcagag gtgtggacca    6360
gacacgagaa gaaagagtg ctcaaaccga ggtggatgga cgccagagtt tgttcagatc    6420
atgcggccct gaagtcattc aaggagtttg ccgctgggaa aagaggagcg cttttggag    6480
tgatggaagc cctgggaaca ctgccaggac acatgacgga gagattccag gaagccattg    6540
```

```
acaacctcgc tgtgctcatg cgggcagaga ctggaagcag gccttacaaa gccgcggcgg    6600
cccaattgcc ggagacccta gagaccatta tgcttttggg gttgctggga acagtctcgc    6660
tgggaatctt tttcgtcttg atgcggaaca agggcatagg gaagatgggc tttggaatgg    6720
tgactcttgg ggccagcgca tggctcatgt ggctctcgga aattgagcca gccagaattg    6780
catgcgtcct cattgttgtg ttcctattgc tggtggtgct catacctgag ccagaaaagc    6840
aaagatcccc ccaggacaac caaatggcaa tcatcatcat ggtagcagta ggtcttctgg    6900
gcttgattac cgccaatgaa ctcggatggt tggagagaac aaagagtgac ctaagccatc    6960
taatgggaag gagagaggag ggggcaacca taggattctc aatggacatt gacctgcggc    7020
cagcctcggc ctgggccatc tatgctgccc tgacaacttt cattacccca gccgtccaac    7080
atgcagtgac cacttcatac aacaactact ccttaatggc gatggccacg caagctggag    7140
tgttgtttgg tatgggcaaa gggatgccat tctacgcatg ggactttgga gtcccgctgc    7200
taatgatagg ttgctactca caattaacac ccctgaccct aatagtggct atcattttgc    7260
tcgtggcgca ctacatgtac ttgatcccag gctgcaggc agcagctgcg cgtgctgccc    7320
agaagagaac ggcagctggc atcatgaaga accctgttgt ggatggaata gtggtgactg    7380
acattgacac aatgactatt gaccccccaag tggagaaaaa gatgggacag gtgctactca    7440
tagcagtagc cgtctccagc gccatactgt cgcggaccgc ctgggggtgg gggaagctg    7500 gggccctgat cacagctgca acttccactt tgtgggaagg ctctccgaac aagtactgga    7560
actcctctac agccacttca ctgtgcaaca tttttagggg aagttacttg gctggagctt    7620
ctctaatcta cacagtaaca agaaacgctg gcttggtcaa gagacgtggg ggtggaacag    7680
gagagaccct gggagagaaa tggaaggccc gcttgaacca gatgtcggcc ctggagttct    7740
actcctacaa aaagtcaggc atcaccgagg tgtgcagaga agaggcccgc cgcgccctca    7800
aggacggtgt ggcaacggga ggccatgctg tgtcccgagg aagtgcaaag ctgagatggt    7860
tggtggagcg gggatacctg cagccctatg gaaaggtcat tgatcttgga tgtggcagag    7920
ggggctggag ttactacgcc gccaccatcc gcaaagttca agaagtgaaa ggatacacaa    7980
aaggaggccc tggtcatgaa gaacccatgt tggtgcaaag ctatgggtgg aacatagtcc    8040
gtcttaagag tggggtggac gtcttttcata tggcggctga gccgtgtgac acgttgctgt    8100
gtgacatagg tgagtcatca tctagtcctg aagtggaaga agcacggacg ctcagagtcc    8160
tctccatggt gggggattgg cttgaaaaaa gaccaggagc cttttgtgta aaagtgttgt    8220
gcccatacac cagcactatg atggaaaccc tggagcgact gcagcgtagg tatgggggag    8280
gactggtcag agtgccactc tcccgcaact ctacacatga gatgtactgg gtctctggag    8340
cgaaaagcaa caccataaaa agtgtgtcca ccacgagcca gctcctcttg gggcgcatgg    8400
acgggcccag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct ttgacgagaa ccacccatat aggacatggg    8580
cttaccatgg aagctatgag gcccctacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac accagggtgc    8760 cagacccca agaaggcact cgtcaggtta tgagcatggt ctcttcctgg ttgtggaaag    8820
agctaggcaa acacaaacgg ccacgagtct gtaccaaaga gagttcatc aacaaggttc    8880
```

```
gtagcaatgc agcattaggg gcaatatttg aagaggaaaa agagtggaag accgcagtgg    8940
aagctgtgaa cgatccaagg ttctgggctc tagtggacaa ggaaagagag caccacctga    9000
gaggagagtg ccagagctgt gtgtacaaca tgatgggaaa aagagaaaag aaacaagggg    9060
aatttggaaa ggccaagggc agccgcgcca tctggtatat gtggctaggg gctagatttc    9120
tagagttcga agcccttgga ttcttaaatg aggatcactg gatggggaga gagaactcag    9180
gaggtggtgt tgaagggctg ggattacaaa gactcggata tgtcctagaa gagatgagtc    9240
gcataccagg aggaaggatg tatgcagatg acactgctgg ctgggacacc cgcatcagca    9300
ggtttgatct ggagaatgaa gctttaatca ccaaccaaat ggagaaaggg cacagggcct    9360
tagcattggc cataatcaag tacacatacc aaaacaaagt ggtaaaggtc cttagaccag    9420
ctgaaaaagg gaagacagtt atggacatta tttcaagaca agaccaaagg gggagcggac    9480
aagttgtcac ttacgctctt aacacattta ccaacctagt ggtgcaactc attcggaata    9540
tggaggctga ggaagttcta gagatgcaag acttgtggct gctgcggagg tcagagaaag    9600
tgaccaactg gttgcagagc aacggatggg ataggctcaa acgaatggca gtcagtggag    9660
atgattgcgt tgtgaagcca attgatgata ggtttgcaca tgccctcagg ttcttgaatg    9720
atatgggaaa agttaggaag gacacacaag agtggaaacc ctcaactgga tgggacaact    9780
gggaagaagt tccgttttgt tcccaccact tcaacaagct ccatctcaag gacgggaggt    9840
ccattgtggt tccctgccgc accaagatg aactgattgg ccgggcccgt gtctctccag    9900
gggcgggatg gagcatccgg gagactgctt gcctagcaaa gtcatatgcg caaatgtggc    9960
agctcccttta tttccacaga agggacctcc gactgatggc caatgccatc tgttcatctg    10020
tgccagttga ctgggttcca actgggagaa ctacctggtc aatccatgga aagggagaat    10080
ggatgaccac tgaagacatg cttgtggtgt ggaacagagt gtggattgag gagaacgacc    10140
acatggaaga caagacccca gttacgaaat ggacagacat tccctatctg ggaaaaaggg    10200
aagacttgtg gtgtgatct ctcatagggc acagaccgcg caccacctgg gctgagaaca    10260
ttaaaaacac agtcaacatg gtgcgcagga tcataggtga tgaagaaaag tacatggact    10320
acctatccac ccaagttcgc tacttgggtg aagaagggtc tacacctgga gtgctataag    10380
caccaatctt agtgttgtca ggcctgctag tcagccacag cttggggaaa gctgtgcagc    10440
ctgtgacccc cccaggagag gctgggaaac caagcccata gtcaggccga gaacgccatg    10500
gcacggaaga agccatgctg cctgtgagcc cctcaggaa cactgagtca aaaaacccca    10560
cgcgcttgga ggcgcaggat gggaaaagaa ggtggcgacc ttccccaccc ttcaatctgg    10620
ggcctgaact ggagatcagc tgtggatctc cagaagaggg actagtggtt agaggagacc    10680
ccccggaaaa cgcaaaacag catattgacg ctgggaaaga ccagagactc catgagtttc    10740
caccacgctg gccgccaggc acagatcgcc gaatagcggc ggccggtgtg gggaaatcca    10800
tgggtct                                                              10807
```

<210> SEQ ID NO 8
<211> LENGTH: 10807
<212> TYPE: DNA
<213> ORGANISM: Zika virus

<400> SEQUENCE: 8

```
agttgttgat ctgtgtgaat cagactgcga cagttcgagt ttgaagcgaa agctagcaac     60
agtatcaaca ggttttattt tggatttgga acgagagtt tctggtcatg aaaaacccaa     120
aaagaaaatc cggaggattc cggattgtca atatgctaaa acgcggagta gcccgtgtga    180
```

```
gcccctttgg gggcttgaag aggctgccag ccggacttct gctgggccat gggcccatca    240
ggatggtctt ggcgatacta gccttttgga gattcacggc aatcaagcca tcactgggtc    300
tcatcaatag atggggttca gtggggaaaa aagaggctat ggaataata aagaagttca    360 agaaagatct ggctgccatg ctgagaataa tcaatgctag gaaggagaag aagagacgag    420
gcgcagatac tagcgtcgga attgttggcc tcctcctgac cacagccatg gcagtagagg    480
tcactagacg tgggagtgca tactatatgt acttggacag aagcgatgct ggggaggcca    540 tatctttttcc aaccacactg gggatgaata agtgttacat acaaatcatg gatcttggac    600
acatgtgtga tgccaccatg agctatgaat gccctatgtt ggatgagggg gtagaaccag    660
atgacgtcga ttgctggtgc aacacgacat caacttgggt tgtgtatgga acctgccacc    720
acaaaaaagg tgaagcacgg agatctagaa gagctgtgac gctcccctcc cattccacta    780
ggaagctgca aacgcggtcg cagacctggt tggaatcaag agaatacaca aagcacctga    840
ttagagttga aaattggata ttcaggaacc ctggcttcgc gttagcagca gctgtcatcg    900
cttggctttt gggaagttca acgagccaaa aagtcatata tctggtcatg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtt accgtaatgg   1080
cacaggacaa accgactgtc gacatagagc tggttacaac aacagtcagc aacatggcgg   1140
aggtaagatc ctactgctat gaggcatcaa tatcggatat ggcttcggac agccgctgcc   1200
caacacaagg tgaggcctac cttgacaagc agtcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg ctcccagca cagtgggatg atcgttaatg   1440
acacaggaca tgaaactgat gagaatagag cgaaggttga gataacgccc aattcaccaa   1500
gagccgaagc caccctgggg ggttttggga gcctaggact tgattgtgaa ccgaggacag   1560
gccttgactt ttcagatttg tattacctga ctatgaataa caagcactgg ttggttcaca   1620
aggagtggtt ccacgacatt ccattacctt ggcatgctgg ggcagacact ggaactccac   1680
attggaacaa caagaagca ctggtagagt tcaaggacgc acatgcaaaa aggcaaactg   1740
tcgtggttct agggagtcaa gaaggagcag ttcacacggc ccttgctgga gctctggagg   1800
ctgagatgga tggagccaag ggaaggctgt cctctggcca cttgaaatgt cgcctgaaaa   1860
tggataaact tagattgaag ggcgtgtcat actccttgtg cactgcagcg ttcacattca   1920
ccaagatccc ggctgaaaca ctgcacggga cagtcacagt ggaggtacag tacgcaggga   1980 cagatgacc ttgcaaggtt ccagctcaga tggcggtgga tatgcaaact ctgacccag   2040 ttgggaggtt gataaccgct aaccctgtaa tcactgaaag caccgagaac tctaagatga   2100
tgctggaact tgatccacca tttgggact cttacattgt cataggagtc ggggagaaga   2160
agatcaccca tcactggcac aggagtggca gcaccattgg aaaagcattt gaagccactg   2220
tgagaggtgc caagagaatg gcagtcttgg gagacacagc ctgggacttt ggatcagttg   2280
ggggtgctct caactcattg ggcaagggca tccatcaaat ttttggagca gctttcaaat   2340
cattgttcgg aggaatgtcc tggttctcac aaattctcat tggaacgttg ctggtgtggt   2400
tgggtctgaa tacaaagaat ggatctattt cccttacgtg cttggcctta ggggagtgt   2460 tgatcttctt atccacagcc gtttctgctg atgtgggggtg ctcggtggac ttctcaaaga   2520
```

```
aggaaacgag atgcggtaca ggggtgttcg tctataacga cgttgaagcc tggagggaca    2580
ggtacaagta ccatcctgac tccctcgta gattggcagc agcagtcaag caagcctggg     2640
aagatgggat ctgtgggatc tcctctgtct caagaatgga aaacatcatg tggagatcag    2700
tagaagggga gctcaacgca atcctggaag agaatggagt tcaactgacg gtcgttgtgg    2760
gatctgtaaa aaaccccatg tggagaggtc cacagagatt gcccgtgcct gtgaacgagc    2820
tgccccacgg ctggaaggct gggggaaat cgtacttcgt cagagcagca aagacaaata     2880
acagctttgt cgtggatggt gacacactga aggaatgccc actcaaacat agagcatgga    2940
acagctttct tgtggaggat catgggtttg gggtatttca cactagtgtc tggctcaagg    3000
ttagagaaga ttattcatta gagtgtgatc cagccgtcat tggaacagct gctaagggaa    3060
aggaggctgt gcacagcgat ctaggctact ggattgagag tgagaagaac gacacatgga    3120
ggctgaagag ggcccacctg atcgagatga aaacatgtga atggccaaag tcccacacat    3180
tgtggacaga tggagtagaa gaaagtgatc tgatcatacc caagtctttta gctgggccac    3240 tcagccatca caacaccaga gagggctaca ggactcaaat gaagggcca tggcacagtg     3300 aagagcttga aattcggttt gaggaatgcc caggcactaa ggtccacgtg gaggaaacat    3360
gtgggacaag aggaccatcc ctgagatcaa ccactgcaag cggaagggtg atcgaggaat    3420
ggtgctgcag ggaatgcaca atgccccac tgtcgttccg agctaaagat ggctgttggt     3480
atggaatgga gataaggccc aggaaagaac cagaaagtaa cttagtaagg tcaatggtga    3540
ctgcaggatc aactgatcac atggatcact tctctcttgg agtgcttgtg attttgctca    3600
tggtgcagga agggctgaag aagagaatga ccacaaagat catcataagc acatcaatgg    3660
cagtgctggt agccatgatc ctgggaggat tttcaatgag tgacctggct aagcttgcaa    3720
ttttgatggg tgccacttc gcggaaatga acactggagg agatgtagct catttggcgc     3780
tgatagcggc attcaaagtc agacctgcgt tgctggtatc tttcatcttc agagctaatt    3840 ggacacccg tgagagcatg ctgctggcct tggcctcgtg tcttctgcaa actgcgatct     3900
ccgccttgga aggcgacctg atggttctca tcaatggttt tgctttggcc tggttggcaa    3960
tacgagcgat ggttgttcca cgcactgaca acatcaccttt ggcaatcctg ctgctctga    4020 caccactggc ccggggcaca ctgcttgtgg cgtggagagc aggccttgct acttgcgggg    4080
ggttcatgct cctctctctg aaggggaaag gcagtgtgaa gaagaaccta ccatttgtca    4140
tggccttggg actaactgct gtgaggctgg tcgacccat caacgtggtg ggactgctgt      4200
tgctcacaag gagtgggaag cggagctggc cccctagtga agtactcaca gctgttggcc    4260
tgatatgcgc attggctgga gggttcgcca aggcggatat agagatggct gggcccatgg    4320
ccgcggtcgg tctgctaatt gtcagttacg tggtctcagg aaagagtgtg acatgtaca     4380 ttgaaagagc aggtgacatc acatgggaaa agatgcgga atcactgga aacagtcccc      4440 ggctcgatgt ggcactagat gagagtggtg atttctccct agtggaggat gatggtccac    4500
ccatgagaga gatcatactc aaagtggtcc tgatgaccat ctgcggcatg aacccaatag    4560
ccataccctt tgcagctgga gcgtggtacg tgtatgtgaa gactggaaaa aggagtggtg    4620
ctctatggga tgtgcctgct cccaaggaag taaaaaaggg ggagaccaca gatgagtgt     4680 acagagtaat gactcgtaga ctgcttggtt caacacaagt tggagtggga gtcatgcaag    4740
agggggtctt ccacactatg tggcacgtca caaaaggatc cgcgctgaga agcggtgaag    4800
ggagacttga tccatactgg ggagatgtca agcaggatct ggtgtcatac tgtggtccgt    4860
ggaagctaga cgccgcctgg gacgggcaca gcgaggtgca gctcttggcc gtgccccccg    4920
```

| | |
|---|---|
| gagagagagc gaggaacatc cagactctgc ccggaacatt taagacaaag gatgggaca | 4980 |
| ttggagcagt tgcgctggac tacccagcag gaacttcagg atctccaatc ctagacaagt | 5040 |
| gtggagagt gataggactc tatggtaatg gggtcgtgat aaaaaatggg agttatgtta | 5100 |
| gtgccatcac ccaagggagg agggaggaag agactcctgt tgagtgcttc gagccttcga | 5160 |
| tgctgaagaa gaagcagcta actgtcttag acctgcatcc tggagccggg aaaaccagga | 5220 |
| gagttcttcc tgaaatagtc cgtgaagcca taaaaacaag actccgtact gtgatcttag | 5280 |
| ctccaaccag ggtcgtcgct gctgaaatgg aggaagccct tagagggctt ccagttcgtt | 5340 |
| atatgacaac agcagtcaat gtcacccatt ctgggacaga aatcgttgac ttaatgtgcc | 5400 |
| atgctacctt cacttcacgc ctactacaac caatcagagt ccccaactat aatttgtata | 5460 |
| ttatggatga ggcccacttc acagatccct caagtatagc agcaagagga tacatttcaa | 5520 |
| caagggttga gatgggcgag gcggctgcca tcttcatgac cgccacgcca ccaggaaccc | 5580 |
| gtgacgcatt cccggactcc aactcaccaa ttatggacac cgaggtggaa gtcccagaga | 5640 |
| gagcctggag cacaggcttt gattgggtga cggatcattc tgggaaaaca gtctggtttg | 5700 |
| ttccaagcgt gaggaacggc aatgagatcg cagcttgtct gacaaaggct ggaaaacggg | 5760 |
| tcatacagct cagcagaaag acttttgaga cagagttcca gaaaacgaaa aatcaagagt | 5820 |
| gggacttcgt cgtgacaacc gacatttcag agatgggcgc caactttaaa gctgaccgtg | 5880 |
| tcatagattc caggagatgc ttaaagccgg tcatacttga tggcgagaga gtcattttgg | 5940 |
| ctggacccat gcctgtcaca catgccagcg ctgctcagag gaggggcgc ataggcagga | 6000 |
| atcccaacaa acctggagat gagtatctgt atggaggtgg gtgcgcagag actgatgaag | 6060 |
| atcacgcaca ctggcttgaa gcaagaatgc ttcttgacaa catttacctc caagatggcc | 6120 |
| tcatagcttc gctctatcga cctgaggccg acaaagtagc agctattgag ggagagttca | 6180 |
| agcttaggac ggagcaaagg aagacctttg tggaactcat gaaaagagga gatcttccgg | 6240 |
| tttggttggc ctatcaggtt gcatctgccg gaataaccta cacagataga agatggtgct | 6300 |
| ttgatggcat gaccaacaac accataatgg aagacagtgt gccggcagag gtgtggacca | 6360 |
| gatacggaga gaaaagagtg ctcaaaccga ggtggatgga cgccagagtt tgttcagatc | 6420 |
| atgcggccct gaagtcattc aaagagtttg ccgctgggaa aagaggagcg cctttggag | 6480 |
| tgatagaagc cctgggaaca ctgccaggac acatgacaga gagattccag gaagccattg | 6540 |
| acaacctcgc tgtgctcatg cgggcagaga ctggaagcag gccttacaaa gccgcggcgg | 6600 |
| cccaattgcc ggagacccta gagaccatta tgctttggg gttgctggga acagtctcgc | 6660 |
| tgggaatctt tttcgtcttg atgcggaaca agggcatggg gaagatgggc tttggaatgg | 6720 |
| tgactcttgg ggcagcgca tggcttatgt ggctctcgga aattgagcca gccagaattg | 6780 |
| catgtgtcct cattgtcgtg ttcctattgc tggtggtgct cataccgag ccagaaaagc | 6840 |
| aaagatctcc tcaggacaac caaatggcaa tcatcatcat ggtagcagtg ggtcttctgg | 6900 |
| gcttgattac cgccaatgaa ctcggatggt tggagagaac aaaaagtgac ctaagccatc | 6960 |
| taatgggaag gagagaggag ggggcaacca caggattctc aatggacatt gacctgcggc | 7020 |
| cagcctcagc ttgggctatc tatgctgctc tgacaacttt catcacccca gccgtccaac | 7080 |
| atgcggtgac cacttcatac aacaactact ccttaatggc gatggccacg caagctgggg | 7140 |
| tgttgtttgg tatgggcaaa gggatgccat tctacgcatg gacttttgga gtcccgctgc | 7200 |
| taatgatggg ttgctactca caattaacac ctctgaccct aatagtggcc atcatttgc | 7260 |

```
tcgtggcgca ctacatgtac ttgatcccag ggctgcaggc agcagctgcg cgggctgccc      7320
agaagagaac ggcagctggc atcatgaaga accctgttgt ggatggaata gtggtgactg      7380
acattgacac aatgacaatt gaccccaag tggaaaaaaa gatggggcag gtgctactca       7440
tagcagtagc cgtctccagc gccatactgt cgcggaccgc ctggggggtgg ggggaggctg     7500 gggccctgat cacagctgca acttccacct tgtgggaagg ctctccgaac aagtactgga      7560
actcctccac agccacttca ctgtgtaaca ttttaggg aagttacttg gctgagctt         7620 ctctaatcta cacagtaaca agaaacgctg gcttggtcaa gagacgtggg ggtggaacgg      7680
gagagaccct gggagagaaa tggaaggccc gcctgaacca gatgtcggcc ctggagttct      7740
actcctacaa aaagtcaggc atcaccgagg tgtgcagaga agaggcccgc cgtgccctca      7800
aggacggtgt ggcaacagga ggccatgctg tgtcccgagg aagtgcaaag cttagatggc      7860
tggtggagag aggatacctg cagccctatg gaaaggtcat tgatcttgga tgtggcagag      7920
ggggctggag ttactatgcc gccaccatcc gcaaagttca ggaagtgaaa ggatacacaa      7980
aaggaggccc tggtcatgaa gaaccatgt tggtgcaaag ctatgggtgg aacatagtcc       8040
gtcttaagag tgggtggac gtctttcaca tggcggctga gccgtgtgac actttgctgt      8100
gtgatatagg tgagtcatca tctagtcctg aagtggaaga agcacggacg ctcagagtcc      8160
tctccatggt gggggattgg cttgaaaaaa gaccaggagc cttttgtata aaagtgttgt      8220
gcccatacac cagcactatg atggaaaccc tggagcgact gcagcgtagg tatggggag      8280 gactggtcag ggtgccactc tcccgcaact ctacacatga gatgtactgg gtctctggag      8340
cgaaaagcaa caccataaaa agtgtgtcca ccacagagcca gctcctcttg gggcgcatgg     8400 acggcccag gaggccagtg aaatatgagg aggatgtgaa tctcggctct ggcacgcggg       8460
ctgtggtaag ctgcgctgaa gctcccaaca tgaagatcat tggtaaccgc attgagagga     8520
tccgcagtga gcacgcggaa acgtggttct ttgacgagaa ccacccatat aggacatggg    8580
cttaccatgg aagctatgag gcccctacac aagggtcagc gtcctctcta ataaacgggg     8640
ttgtcaggct cctgtcaaaa ccctgggatg tggtgactgg agtcacagga atagccatga    8700
ctgacaccac accgtatggt cagcaaagag ttttcaagga aaaagtggac actagggtgc     8760 cagacccca agaaggcact cgtcaggtta tgagcatggt ctcttcctgg ttatggaagg      8820
agctaggcaa acacaaacgg ccacgagtct gtaccaaaga agagttcatc aacaaggttc     8880
gtagcaatgc agcattaggg gcaatatttg aagaggaaaa agagtggaag actgcagtgg    8940
aagctgtgaa tgatccaagg ttctgggctc tagtggacaa ggaaagagag catcacctga    9000
gaggagagtg tcagagctgt gtgtacaaca tgatgggaaa aagagaaaag aaacaagggg     9060
aatttggaaa ggccaaggc agccgcgcca tctggtatat gtggctaggg gctagattcc      9120
tagagttcga agcccttgga ttcttgaatg aggatcattg gatggggaga gagaattcag     9180
gaggtggtgt tgaaggactg ggattacaaa actcggata tgtcctagaa gagatgagtc      9240
gcataccagg aggaaggatg tatgcagatg atactgctgg ctgggacacc cgcatcagca    9300
ggtttgatct ggagaatgaa gctctaatca ccaaccaaat ggagaaaggg cacagggcct     9360
tggcattggc cataatcaag tacacatacc aaaacaaagt ggtaaaggtc cttagaccag    9420
ctgaaaaagg gaagacagtt atggacatta tttcaagaca agaccaaagg gggagcggac     9480
aagttgtcac ttacgctctt aatacattca ccaacctggt ggtgcagctc attcggaata    9540
tggaggctga ggaagttcta gagatgcaag acttgtggct gctgcggagg ccagagaaag    9600
tgaccaactg gttgcaaagc aacggatggg ataggctcaa aagaatggca gtcagtggag    9660
```

| | |
|---|---|
| atgattgcgt tgtgaaacca attgatgata ggtttgcaca tgccctcagg ttcttgaatg | 9720 |
| atatgggaaa agttaggaag gacacacaag agtggaaacc ctcaactgga tgggacaact | 9780 |
| gggaagaagt tccgttttgc tcccaccact tcaacaaact ccatcttaag gacgggaggt | 9840 |
| ccattgtggt tccctgccgc caccaagatg aactgattgg ccgagcccgc gtatcaccag | 9900 |
| gggcgggatg gagcatccgg gagactgctt gcctagcaaa atcatatgcg caaatgtggc | 9960 |
| agctccttta tttccacaga agggacctcc gactgatggc caatgccatt tgttcatctg | 10020 |
| tgccagttga ttgggttcca actgggagaa ctacctggtc aatccatgga agggagaat | 10080 |
| ggatgaccac tgaagacatg cttgtggtat ggaacagagt gtggattgag gaaaacgacc | 10140 |
| acatggaaga caagacccca gttacaaaat ggacagacat tccctatttg gaaaaagag | 10200 |
| aagacttgtg gtgtggatct ctcatagggc acagaccgcg tactacctgg gctgagaaca | 10260 |
| tcaaaaatac agtcaacatg atgcgcagga tcataggtga tgaagaaaag tacatggact | 10320 |
| acctatccac ccaggttcgc tacttgggtg aagaagggtc cacacctgga gtgctgtaag | 10380 |
| caccaatctt agtgttgtca ggcctgctag tcagccacag cttggggaaa gctgtgcagc | 10440 |
| ctgtgacccc cccaggagaa gctgggaaac caagcctata gtcaggccga gaacgccatg | 10500 |
| gcacggaaga agccatgctg cctgtgagcc cctcaggga cactgagtca aaaaacccca | 10560 |
| cgcgcttgga ggcgcaggat gggaaaagaa ggtggcgacc ttccccaccc ttcaatctgg | 10620 |
| ggcctgaact ggagatcagc tgtggatctc cagaagaggg actagtggtt agaggagacc | 10680 |
| ccccggaaaa cgcaaaacag catattgacg ctgggaaaga ccagagactc catgagtttc | 10740 |
| caccacgctg gccgccaggc acagatcgcc gaatagcggc ggccggtgtg gggaaatcca | 10800 |
| tgggtct | 10807 |

<210> SEQ ID NO 9
<211> LENGTH: 10648
<212> TYPE: DNA
<213> ORGANISM: Zika virus

<400> SEQUENCE: 9

| | |
|---|---|
| gacagttcga gtttgaagcg aaagctagca acagtatcaa caggttttat ttggatttgg | 60 |
| aaacgagagt ttctggtcat gaaaaaccca aaaagaaat ccggaggatt ccggattgtc | 120 |
| aatatgctaa aacgcggagt agcccgtgtg agccccttg ggggcttgaa gaggctgcca | 180 |
| gccggacttc tgctgggtca tgggcccatc aggatggtct tggcgattct agccttttg | 240 |
| agattcacgg caatcaagcc atcactgggt ctcatcaata atgggggttc agtggggaaa | 300 |
| aaagaggcta tggaaataat aaagaagttc aagaaagatc tggctgccat gctgagaata | 360 |
| atcaatgcta ggaaggagaa aagagacga ggcgcagata ctagtgtcgg aattgttggc | 420 |
| ctcctgctga ccacagctat ggcagcggag gtcactagac gtgggagtgc atactatatg | 480 |
| tacttggaca gaaacgatgc tggggaggcc atatcttttc aaccacatt ggggatgaat | 540 |
| aagtgttata tacagatcat ggatcttgga cacatgtgtg atgccaccat gagctatgaa | 600 |
| tgccctatgc tggatgaggg ggtggaacca gatgacgtcg attgttggtg caacacgacg | 660 |
| tcaacttggg ttgtgtacgg aacctgccat cacaaaaaag gtgaagcacg gagatctaga | 720 |
| agagctgtga cgctcccctc ccattccact aggaagctgc aaacgcggtc gcaaacctgg | 780 |
| ttggaatcaa gagaatacac aaagcacttg attagagtcg aaaattggat attcaggaac | 840 |
| cctggcttcg cgttagcagc agctgccatc gcttggcttt tgggaagctc aacgagccaa | 900 |

```
aaagtcatat acttggtcat gatactgctg attgccccgg catacagcat caggtgcata    960
ggagtcagca atagggactt tgtggaaggt atgtcaggtg ggacctgggt tgatgttgtc   1020
ttggaacatg gaggttgtgt caccgtaatg gcacaggaca aaccgactgt cgacatagag   1080
ctggttacaa caacagtcag caacatggcg gaggtaagat cctactgcta tgaggcatca   1140
atatcagaca tggcttcgga cagccgctgc ccaacacaag gtgaagccta ccttgacaag   1200
caatcagaca ctcaatatgt ctgcaaaaga acgttagtgg acagaggctg ggaaatgga    1260
tgtggacttt ttggcaaagg gagcctggtg acatgcgcta agtttgcatg ctccaagaaa   1320
atgaccggga gagcatcca gccagagaat ctggagtacc ggataatgct gtcagttcat    1380
ggctcccagc acagtgggat gattgttaat gacacaggac atgaaactga tgagaataga   1440
gcgaaagttg ataacgcc caattcacca agagccgaag ccaccctggg gggttttgga    1500
agcctaggac ttgattgtga accgaggaca ggccttgact tttcagattt gtattacttg   1560
actatgaata caagcactg gttggttcac aaggagtggt tccacgacat tccattacct    1620
tggcacgctg gggcagacac cggaactcca cactggaaca caaagaagc actggtagag    1680
ttcaaggacg cacatgccaa aaggcaaact gtcgtggttc tagggagtca agaaggagca   1740
gttcacacgg cccttgctgg agctctggag gctgagatgg atggtgcaaa gggaaggctg   1800
tcctctggcc acttgaaatg tcgcctgaaa atggataaac ttagattgaa gggcgtgtca   1860
tactccttgt gtactgcagc gttcacattc accaagatcc cggctgaaac actgcacggg   1920
acagtcacag tggaggtaca gtacgcaggg acagatggac cttgcaaggt tccagctcag   1980
atggcggtgg acatgcaaac tctgacccca gttgggaggt tgataaccgc taaccccgta   2040
atcactgaaa gcactgagaa ctctaagatg atgctggaac ttgatccacc atttggggac   2100
tcttacattg tcataggagt cggggagaag aagatcaccc accctggca caggagtggc   2160
agcaccattg gaaaagcatt tgaagccact gtgagaggtg ccaagagaat ggcagtcttg   2220
ggagacacag cctgggactt tggatcagtt ggaggcgctc tcaactcatt gggcaagggc   2280
atccatcaaa ttttttggagc agctttcaaa tcattgtttg gaggaatgtc ctggttctca   2340
caaattctca ttggaacgtt gctgatgtgg ttgggtctga acacaaagaa tggatctatt   2400
tcccttatgt gcttggcctt aggggagtg ttgatcttct tatccacagc cgtctctgct   2460
gatgtgggt gctcggtgga cttctcaaag aaggagacga gatgcggtac aggggtgttc   2520
gtctataacg acgttgaagc ctggagggac aggtacaagt accatcctga ctcccccgt    2580
agattggcag cagcagtcaa gcaagcctgg gaagatggta tctgcgggat ctcctctgtt   2640
tcaagaatgg aaaacatcat gtggagatca gtagaagggg agctcaacgc aatcctggaa   2700
gagaatggag ttcaactgac ggtcgttgtg ggatctgtaa aaaacccat gtggagaggt   2760
ccacagagat tgcccgtgcc tgtgaacgag ctgccccacg gctggaaggc ttggggaaaa   2820
tcgtacttcg tcagagcagc aaagacaaat aacagctttg tcgtggatgg tgacacactg   2880
aaggaatgcc cactcaaaca tagagcatgg aacagctttc ttgtggagga tcatgggttc   2940
ggggtatttc acactagtgt ctggctcaag gttagagaag attattcatt agagtgtgat   3000
ccagccgtta ttggaacagc tgttaaggga aaggaggctac acagtga tctaggctac    3060
tggattgaga gtgagaagaa tgacacatgg aggctgaaga gggcccatct gatcgagatg   3120
aaaacatgtg aatggccaaa gtcccacaca ttgtggacag atggaataga agagagtgat   3180
ctgatcatac ccaagtcttt agctgggcca ctcagccatc acaataccag agagggctac   3240
aggacccaaa tgaaagggcc atggcacagt gaagagcttg aaattcggtt tgaggaatgc   3300
```

```
ccaggcacta aggtccacgt ggaggaaaca tgtggaacaa gaggaccatc tctgagatca    3360
accactgcaa gcggaagggt gatcgaggaa tggtgctgca gggagtgcac aatgccccca    3420
ctgtcgttcc gggctaaaga tggctgttgg tatggaatgg agataaggcc caggaaagaa    3480
ccagaaagca acttagtaag gtcaatggtg actgcaggat caactgatca catgaccac     3540
ttctcccttg gagtgcttgt gattctgctc atggtgcagg aagggctgaa gaagagaatg    3600
accacaaaga tcatcataag cacatcaatg gcagtgctgg tagctatgat cctggggaga    3660
ttttcaatga gtgacctggc taagcttgca attttgatgg gtgccacctt cgcggaaatg    3720
aacactggag gagatgtagc tcatctggcg ctgatagcgg cattcaaagt cagaccagcg    3780
ttgctggtat ctttcatctt cagagctaat ggacaccccc gtgaaagcat gctgctggcc    3840
ttggcctcgt gtcttttgca aactgcgatc tccgccttgg aaggcgacct gatggttctc    3900
atcaatggtt ttgctttggc ctggttggca atacgagcga tggttgttcc acgcactgat    3960
aacatcacct tggcaatcct ggctgctctg acaccactgg cccggggcac actgcttgtg    4020
gcgtggagag caggccttgc tacttgcggg gggtttatgc tcctctctct gaagggaaaa    4080
ggcagtgtga agaagaactt accatttgtc atggcccctgg gactaaccgc tgtgaggctg    4140
gtcgacccca tcaacgtggt gggactgctg ttgctcacaa ggagtgggaa gcggagctgg    4200
cccctagcg aagtactcac agctgttggc ctgatatgcg cattggctgg agggttcgcc     4260
aaggcagata tagagatggc tgggcccatg gccgcggtcg gtctgctaat tgtcagttac    4320
gtggtctcag aaagagtgt ggacatgtac attgaaagag caggtgacat cacatgggaa     4380
aaagatgcgg aagtcactgg aaacagtccc cggctcgatg tggcgctaga tgagagtggt    4440
gatttctccc tggtggagga tgacggtccc cccatgagag agatcatact caaggtggtc    4500
ctgatgacca tctgtggcat gaacccaata gccatacct  ttgcagctgg agcgtggtac    4560
gtatacgtga agactggaaa aaggagtggt gctctatggg atgtgcctgc tcccaaggaa    4620
gtaaaaaagg gggagaccac agatggagtg tacagagtaa tgactcgtag actgctaggt    4680
tcaacacaag ttggagtggg agttatgcaa gagggggtct ttcacactat gtggcacgtc    4740
acaaaaggat ccgcgctgag aagcggtgaa gggagacttg atccatactg gggagatgtc    4800
aagcaggatc tggtgtcata ctgtggtcca tggaagctag atgccgcctg gacgggcac     4860
agcgaggtgc agctcttggc cgtgcccccc ggagagagag cgaggaacat ccagactctg    4920
cccggaatat ttaagacaaa ggatgggac attggagcgg ttgcgctgga ttacccagca     4980
ggaacttcag gatctccaat cctagacaag tgtgggagag tgataggact ttatggcaat    5040
ggggtcgtga tcaaaaatgg gagttatgtt agtgccatca cccaagggag gagggaggaa    5100
gagactcctg ttgagtgctt cgagccttcg atgctgaaga agaagcagct aactgtctta    5160
gacttgcatc ctggagctgg gaaaaccagg agagttcttc ctgaaatagt ccgtgaagcc    5220
ataaaaacaa gactccgtac tgtgatctta gctccaacca gggttgtcgc tgctgaaatg    5280
gaggaggccc ttagagggct tccagtgcgt tatatgacaa cagcagtcaa tgtcacccac    5340
tctggaacag aaatcgtcga cttaatgtgc catgccacct tcacttcacg tctactacag    5400
ccaatcagag tccccaacta taatctgtat attatggatg aggcccactt cacagatccc    5460
tcaagtatag cagcaagagg atacatttca caaggggttg agatgggcga ggcggctgcc    5520
atcttcatga ccgccacgcc accaggaacc cgtgacgcat tccggactc caactccacca    5580
attatggaca ccgaagtgga agtcccagag agagcctgga gctcaggctt tgattgggtg    5640
```

```
acggatcatt ctggaaaaac agtttggttt gttccaagcg tgaggaacgg caatgagatc    5700
gcagcttgtc tgacaaaggc tggaaaacgg gtcatacagc tcagcagaaa gacttttgag    5760
acagagttcc agaaaacaaa acatcaagag tgggactttg tcgtgacaac tgacatttca    5820
gagatgggcg ccaactttaa agctgaccgt gtcatagatt ccaggagatg cctaaagccg    5880
gtcatacttg atggcgagag agtcattctg gctggaccca tgcctgtcac acatgccagc    5940
gctgcccaga ggaggggggcg cataggcagg aatcccaaca aacctggaga tgagtatctg    6000 tatgaggtg ggtgcgcaga gactgacgaa gaccatgcac actggcttga agcaagaatg    6060
ctccttgaca atatttacct ccaagatggc ctcatagcct cgctctatcg acctgaggcc    6120
gacaaagtag cagccattga gggagagttc aagcttagga cggagcaaag gaagaccttt    6180
gtggaactca tgaaaagagg agatcttcct gtttggctgg cctatcaggt tgcatctgcc    6240
ggaataacct acacagatag aagatggtgc tttgatggca cgaccaacaa caccataatg    6300
gaagacagtg tgccggcaga ggtgtggacc agacacggag agaaaagagt gctcaaaccg    6360
aggtggatgg acgccagagt ttgttcagat catgcggccc tgaagtcatt caaggagttt    6420
gccgctggga aaagaggagc ggcttttgga gtgatggaag ccctgggaac actgccagga    6480
cacatgacag agagattcca ggaagccatt gacaacctcg ctgtgctcat gcgggcagag    6540
actggaagca ggccttacaa agccgcggcg gcccaattgc cggagaccct agagaccatt    6600
atgcttttgg ggttgctggg aacagtctcg ctgggaatct tcttcgtctt gatgaggaac    6660
aagggcatag ggaagatggg ctttggaatg gtgactcttg ggccagcgc atggctcatg    6720 tggctctcgg aaattgagcc agccagaatt gcatgtgtcc tcattgttgt gtttctattg    6780
ctggtggtgc tcataccctga gccagaaaag caaagatctc cccaggacaa ccaaatggca    6840
atcatcatca tggtagcagt aggtcttctg ggcttgatta ccgccaatga actcggatgg    6900
ttggagagaa caaagagtga cctaagccat ctaatgggaa ggagagagga gggggcaacc    6960
ataggattct caatgacat tgacctgcgg ccagcctcag cttgggccat ctatgctgcc    7020
ttgacaactt tcattacccc agccgtccaa catgcagtga ccacttcata caacaactac    7080
tccttaatgg cgatgccac gcaagctgga gtgttgtttg gtatgggcaa agggatgcca    7140
ttctacgcat gggactttgg agtccgctg ctaatgatag gttgctactc acaattaaca    7200 ccctgaccc taatagtggc catcattttg ctcgtggcgc actacatgta cttgatccca    7260
gggctgcagg cagcagctgc gcgtgctgcc cagaagagaa cggcagctgg catcatgaag    7320
aaccctgttg tggatggaat agtggtgact gacattgaca caatgacaat tgaccccaa    7380 gtggagaaaa agatgggaca ggtgctactc atagcagtag ccgtctccag cgccatactg    7440
tcgcggaccg cctgggggtg gggggaggct gggggccctga tcacagccgc aacttccact    7500
ttgtgggaag gctctccgaa caagtactgg aactcctcta cagccacttc actgtgtaac    7560 attttaggg gaagttactt ggctggagct tctctaatct acacagtaac aagaaacgct    7620
ggcttggtca agacgtgg gggtggaaca ggagagaccc tggagagaa atggaaggcc    7680 cgcttgaacc agatgtcggc cctggagttc tactcctaca aaaagtcagg catcaccgag    7740
gtgtgcagaa agaggccg ccgcgccctc aaggacggtg tggcaacggg aggccatgct    7800
gtgtcccgag gaagtgcaaa gctgagatgg ttggtggagc ggggatacct gcagccctat    7860
ggaaaggtca ttgatcttgg atgtggcaga ggggctgga gttactacgc cgccaccatc    7920
cgcaaagttc aagaagtgaa aggatacaca aaaggaggcc ctggtcatga agaacccgtg    7980
ttggtgcaaa gctatgggtg gaacatagtc cgtcttaaga gtggggtgga cgtctttcat    8040
```

```
atggcggctg agccgtgtga cacgttgctg tgtgacatag gtgagtcatc atctagtcct   8100
gaagtggaag aagcacggac gctcagagtc ctctccatgg tgggggattg gcttgaaaaa   8160
agaccaggag ccttttgtat aaaggtgttg tgcccataca ccagcactat gatggaaacc   8220
ctggagcgac tgcagcgtag gtatggggga ggactggtca gagtgccact ctcccgcaac   8280
tctacacatg agatgtattg ggtctctgga gcgaaaagca acaccataaa aagtgtgtcc   8340
accacgagcc agctcctctt ggggcgcatg acgggccta ggaggccagt gaaatatgag    8400
gaggatgtga atctcggctc tggcacgcgg gctgtggtaa gctgcgctga agctcccaac   8460
atgaagatca ttggtaaccg cattgaaagg atccgcagtg agcacgcgga aacgtggttc   8520
tttgacgaga accacccata taggacatgg gcttaccatg aagctatga ggccccaca     8580
caagggtcag cgtcctctct aataaacggg gttgtcaggc tcctgtcaaa accctgggat   8640
gtggtgactg gagtcacagg aatagccatg accgacacca caccgtatgg tcagcaaaga   8700
gttttcaagg aaaaagtgga cactaggtg ccagaccccc aagaaggcac tcgtcaggtt    8760
atgagcatgg tctcttcctg gttgtggaaa gagctaggca acacaaacg ccacgagtc     8820
tgtaccaaag aagagttcat caacaaggtt cgtagcaatg cagcattagg ggcaatattt   8880
gaagaggaaa aagagtggaa gactgcagtg gaagctgtga acgatccaag gttctgggct   8940
ctagtggata aggaaagaga gcaccacctg agaggagagt gccagagttg tgtgtacaac   9000
atgatgggaa aaagagaaaa gaaacaaggg gaatttggaa aggccaaggg cagccgcgcc   9060
atctggtata tgtggctagg gctagatttt ctagagttcg aagcccttgg attcttgaac   9120
gaggatcact ggatggggag agagaactca ggaggtggtg ttgaagggct gggattacaa   9180
agactcggat atgtcctaga agagatgagt cgtataccag gaggaaggat gtatgcagat   9240
gacactgctg gctgggacac ccgcatcagc aggtttgatc tggagaatga agctctaatc   9300
accaaccaaa tggaaaaagg gcacagggcc ttggcattgg ccataatcaa gtacacatac   9360
caaaacaaag tggtaaaggt ccttagacca gctgaaaaag ggaaaacagt tatggacatt   9420
atttcgagac aagaccaaag ggggagcgga caagttgtca cttacgctct taacacattt   9480
accaacctag tggtgcaact cattcggaat atggaggctg aggaagttct agagatgcaa   9540
gacttgtggc tgctgcggag gtcagagaaa gtgaccaact ggttgcagag caacggatgg   9600
gataggctca aacgaatggc agtcagtgga gatgattgcg ttgtgaagcc aattgatgat   9660
aggtttgcac atgccctcag gttcttgaat gatatgggaa agttaggaa ggacacacaa    9720
gagtggaaac cctcaactgg atgggacaac tgggaagaag ttccgttttg ctcccaccac   9780
ttcaacaagc tccatctcaa ggacgggagg tccattgtgg ttccctgccg ccaccaagat   9840
gaactgattg gccgggcccg cgtctctcca ggggcgggat ggagcatccg ggagactgct   9900
tgcctagcaa aatcatatgc gcaaatgtgg cagctccttt atttccacag aagggacctc   9960
cgactgatgc caatgccat tgttcatctc gtgccagttg actgggttcc aactgggaga    10020
actacctggt caatccatgg aaagggagaa tggatgacca ctgaagacat gcttgtggtg   10080
tggaacagag tgtggattga ggagaacgac cacatggaag acaagacccc agttacgaaa   10140
tggacagaca tcccctattt gggaaaaagg gaagacttgt ggtgtggatc tctcataggg   10200
cacagaccgc gcaccacctg ggctgagaac attaaaaaca cagtcaacat ggtgcgcagg   10260
atcatagtg atgaagaaaa gtacatggac tacctatcca cccaagttcg ctacttgggt    10320
gaagaagggt ctacacctgg agtgctgtaa gcaccagtct taatgttgtc aggcctgcta   10380
```

-continued

```
gtcagccaca gcttggggaa agctgtgcag cctgtgaccc ccccaggaga agctgggaaa      10440
ccaagcctat agtcaggccg agaacgccat ggcacggaag aagccatgct gcctgtgagc      10500
ccctcagagg acactgagtc aaaaaacccc acgcgcttgg aggcgcagga tgggaaaaga      10560
aggtggcgac cttccccacc cttcaatctg gggcctgaac tggagatcag ctgtggatct      10620
ccagaagagg gactagtggt tagaggag                                        10648
```

<210> SEQ ID NO 10
<211> LENGTH: 10676
<212> TYPE: DNA
<213> ORGANISM: Zika virus

<400> SEQUENCE: 10

```
gttgttactg ttgctgactc agactgcgac agttcgagtt tgaagcgaaa gctagcaaca        60
gtatcaacag gttttatttg datttggaaa cgagagtttc tggtcatgaa aacccaaaa       120 aagaaatccg gaggattccg gattgtcaat atgctaaaac gcggagtagc ccgtgtgagc       180
ccctttgggg gcttgaagag gctgccagcc ggacttctgc tgggtcatgg gcccatcagg       240
atggtcttgg caattctagc cttttttgaga ttcacggcaa tcaagccatc actgggtctc       300
atcaatagat ggggttcagt ggggaaaaaa gatgctatgg aaataataaa gaagttcaag       360
aaagatctgg ctgccatgct gagaataatc aatgctagga aggagaagaa gagacgaggc       420
gcagatacta gtgtcggaat tgttggcctc tgctgaccca cagctatggc agcggaggtc       480
actagacgtg ggagtgcata ctatatgtac ttggacagaa cgatgctggg gaggccata       540 tcttttccaa ccacattggg gatgaataag tgttatatac agatcatgga tcttggacac       600
atgtgtgatg ccaccatgag ctatgaatgc cctatgctgg atgagggggt ggaaccagat       660
gacgtcgatt gttggtgcaa cacgacgtca acttgggttg tgtacggaac ctgccatcac       720 aaaaaggtg aagcacggag atctagaaga gctgtgacgc tcccttccca ttccactagg       780
aagctgcaaa cgcggtcgca aacctggttg gaatcaagag aatacacaaa gcacttgatt       840
agagtcgaaa attggatatt caggaaccct ggcttcgcgt tagcagcagc tgccatcgct       900
tggcttttgg gaagctcaac gagccaaaaa gtcatatact tggtcatgat actgctgatt       960
gccccggcat acagcatcag gtgcatagga gtcagcaata gggactttgt ggaaggtatg      1020
tcaggtggga cttgggttga tgttgtcttg gaacatggag gttgtgtcac cgcaatggca      1080
caggacaaac cgactgtcga catagagctg gttacaacaa cagtcagcaa catggcggag      1140
gtaagatcct actgctatga ggcatcaata tcagacatgg cttcggacag ccgctgccca      1200
acacaaggtg aagcctacct tgacaagcaa tcagacactc aatatgtttg caaaagaacg      1260
ttagtggaca gaggctgggg aaatggatgt ggacttttg gcaaagggag tctggtgaca      1320
tgcgctaagt ttgcatgctc caagaaaatg accgggaaga gcatccagcc agagaatctg      1380
gagtaccgga taatgctgtc agttcatggc tcccagcaca gtgggatgct cgttaatgac      1440
acaggacatg aaactgatga aatagagcg aaggttgaga taacgcccaa ttcaccaaga      1500
gccgaagcca ccctggggg ttttggaagc ctaggacttg attgtgaacc gaggacaggc      1560
cttgactttt cagatttgta ttacttgact atgaataaca gcactggttt ggctcacaag      1620
gagtggttcc acgacattcc attaccttgg cacgctgggg cagccaccgg aactccacac      1680
tggaacaaca agaagcact ggtagagttc aaggacgcac atgccaaaag gcaaactgtc      1740
gtggttctag ggagtcaaga aggagcagtt cacacggccc ttgctgggc tctgaggct      1800 gagatggata tgtgcaaggg aaggctgtcc tctggccact tgaaatgtcg cctgaaaatg      1860
```

```
gataaactta gattgaaggg cgtgtcatac tccttgtgta ccgcagcgtt cacattcacc    1920
aagatcccgg ctgaaacagt ggacgggaca gtcacagtgg agggacagta cggagggaca    1980
gatggacctt gcaaggttcc agctcagatg gcggtggaca tgcagactct gaccccagtt    2040
gggaggttga taaccgctaa ccccgtaatc actgaaagca ctgagaactc taagatgatg    2100
ctggaacttg atccaccatt tggggactct tacattgtca taggagtcgg ggagaagaag    2160
atcacccacc actggcacag gagtggcagc accattggaa aagcatttga agccactgtg    2220
agaggtgcca agagaatggc agtcttggga gacacagcct gggactttgg atcagttgga    2280
ggcgctctca actcattggg caagggcatc catcaaatta ttggagcagc tttcaaatca    2340
ttgtttggag gaatgtcctg gttctcacaa attctcattg gacgttgct gatgtggttg     2400 ggtctgaaca caaagaatgg atctatttcc cttatgtgct tggccttagg gggagtgttg    2460
atcttcttat ccacagccgt ctcaggtggt gtggggtgct cggtggactt ctcaaagaag    2520
gagacgagat gcggtacagg ggtgttcgtc tataacgatg ttgaagcctg gagggacagg    2580
tacaagtacc atcctgactc cccccgtaga ttggcagcag cagtcaagca agcctgggaa    2640
gatggtatct gcgggatctc ctctgtttca gaatgaaaa acatcatgtg gagatcagta    2700 gaagggagc tcaacgcaat cctggaagag aatggagttc aactgacggt cgttgtggga    2760
tctgtaaaaa accccatgtg gagaggtcca cagagattgc ccgtgcctgt gaacgagctg    2820
ccccacggct ggaaggcttg ggggaaatcg tacttcgtca gagcagcaaa gacaaataac    2880
agctttgtcg tggatggtga cacactgaag gaatgcccac tcaaacatag agcatggaac    2940
agctttcttg tggaggatca tgggttcggg gtatttcaca ctagtgtctg gctcaaggtt    3000
agagaagact attggttaga gtgtgatcca gccgttattg gaacagctgt taagggaaag    3060
gaggctgtac acagtgatct aggctactgg attgagagtg agaagaatga cacatggtgg    3120
ctgaagaggg cccatctgat cgagatgaaa acatgtgaat ggccaaagtc ccacacattg    3180
tggacagatg gaatagaaga gagtgatctg atcataccca agtctttagc tgggccactc    3240
agccatcaca atgccagaga gggctacagg acccaaatga aagggccatg gcacagtgaa    3300
gagcttgaaa ttcggttga ggaatgccca ggcactaagg tccacgtgga ggaaacatgt    3360
ggaacaagag gaccatctct gagatcaacc actgcaagcg aagggtgat cgaggaatgg    3420 tgctccaggg agtgcacaat gccccactg tccttccagg ctaaagatgg ctgttggtat    3480
ggaatggaga taaggcccag gaaagaacca gaaagcaact tagtaaggtc aatggtgact    3540
gcaggatcaa ctgatcacat ggatcacttc tcccttggag tgcttgtgat tctgctcatg    3600
gtgcaggaag ggctgaagaa gagaatgacc acaaagatca tcataagcac atcaatggca    3660
gtgctggtag ctatgatcct gggaggattt tcaatgagtg acctggctaa gcttgcaatt    3720
ttgatgggtg ccaccttcgc ggaaatgaac actggaggag atgtagctca tctggcgctg    3780
atagcggcat tcaaagtcag accagcgttg ctggtatctt tcatcttcag agctaattgg    3840
acaccccgtg aaagcatgct gctggcccttg gcctcgtgtc ttttgcaaac tgcgatctcc    3900
gccttggaag gcgacctgat ggttctcatc aatggttttg cttttggcctg ttggcaata    3960 cgagcgatgg ttgttccacg cactgataac atcacccttag caatcctggc tgctctgaca    4020
ccactggccc ggggcacact gcttgtggcg tgagagcag gccttgctac ttgcgggggg    4080
tttatgctcc tctctctgaa gggaaaaggc agtgtgaaga agaacttacc atttgtcatg    4140
gccctgggac taaccgctgt gaggctggtc gaccccatca acgtgtggg actgctgttg    4200
```

```
ctcacaagga gtgggaagcg gagctggccc cctagcgaag tactcacagc tgttggcctg    4260
atatgcgcat tggctggagg gttcgccaag gcagatatag agatggctgg gcccatggcc    4320
gcggtcggtc tgctaattgt cagttacgtg gtctcaggaa agagtgtgga catgtacatt    4380
gaaagagcag gtgacatcac atgggaaaaa gatgcgaaag tcactggaaa cagtccccgg    4440
ctcgatgtgg cgctagatga gagtggtgat ttctccctgg tggaggatga cggtcccccc    4500
atgagagaga tcatactcaa ggtggtcctg atgaccatct gtggcatgaa cccaatagcc    4560
ataccctttg cagctggagc gtggtacgta tacgtgaaga ctggaaaaag gagtggtgct    4620
ctatgggatg tgcctgctcc caaggaagta aaaaagggg agaccacaga tggagtgtac    4680
agagtaatga ctcgcagact gctaggttca acacaagttg gagtgggagt tatgcaagag    4740
ggggtctttc acactatgtg gcacgtcaca aaaggatccg cgctgagaag cggtgaaggg    4800
agacttgatc catactgggg agatgtcaag caggatctgg tgtcatactg tggtccatgg    4860
aagctagatg ccgcctggga cgggcacagc gaggtgcagc tcttggccgt gccccccgga    4920
gagagagcga ggaacatcca gactctgccc ggaatatttta agcaaaggaa tggggacatt    4980
ggagcggttg cactggatta cccagcagga acttcaggat ctccaatcct agacaagtgt    5040
gggagagtga taggacttta tggcaatggg gtcgtgatca aaaatgggag ttatgttagt    5100
gccatcaccc aagggaggag ggaggaagag actcctgttg agtgcttcga gccttcgatg    5160
ctgaagaaga agcagctaac tgtcttagac ttgcatcctg gagctgggaa accaggagag    5220
gttcttcctg aaatagtccg tgaagccata aaaacaagac tccgtactgt gatcttggct    5280
ccaaccaggg ttgtcgctgc tgaaatggag gaggccctta gggcttcc agtgcgttat    5340 atgacaacag cagtcaatgt cacccactct ggaacagaaa tcgtcgactt aatgtgccat    5400
gccaccttca cttcacgtct actacagcca attagagtcc ccaactataa tctgtatatt    5460
atggatgagg cccacttcac agatccctca gtatagcag caagaggata catttcaaca    5520
agggttgaga tgggcgaggc ggctgccatc ttcatgaccg ccacgccacc aggaaccccgt    5580 gacgcatttc cggactccaa ctcaccaatt atggacaccg aagtggaagt cccagagaga    5640
gcctggagct caggctttga ttgggtgacg gagtattctg gaaaaacagt ttggtttgtt    5700
ccacgcgtga ggaacggcaa tgagatcgca gcttgtctga caaaggctgg aaaacgggtc    5760
atacagctca gcagaaagac ttttgagaca gagttccaga aaacaaaaca tcaagagtgg    5820
gactttgtcg tgacaactga catttcagag atgggcgcca actttaaagc tgaccgtgtc    5880
atagattcca ggagatgcct aaagccggtc atacttggtg gcgagagagt cattctggct    5940
ggacccatgc ctgtcacaca tgccagcgct gcccagagga gggggcgcat aggcaggaat    6000
cccaacaaac ctgagatgga gtatctgtat ggaggtgggt gcgcagagac tgacgaagac    6060
catgcacact ggcttgaagc aagaatgctc cttgacaata tttacctcca agatggcctc    6120
atagcctcgc tctatcgacc tgaggccgac aaagtagcag ccattgaggg agagttcaag    6180
cttaggacgg agcaaaggaa gacctttgtg gaactcatga aagaggaga tcttcctgtt    6240 tggctggcct atcaggttgc atctgccgga ataacctaca cagatagaag atggtgcttt    6300
gatggcacga ccaacaacac cataatgaa acagtgtgc cggcagaggt gtggaccaga    6360
cacggagaga aaagagtgct caaaccgagg tggatggacg ccagagtttg ttcagatcat    6420
gcggccctga gtcattcaa ggagtttgcc gctgggaaaa gaggagcggc ttttggagtg    6480
atggaagccc tgggaacact gccaggacac atgacagaga gattccagga agccattgac    6540
aacctcgctg tgctcatgcg ggcagagact ggaagcaggc cttacaaagc cgcggcggcc    6600
```

```
caattgccgg agaccctaga gaccattatg cttttggggt tgctgggaac agtctcgctg    6660
ggaatctttt tcgtcttgat gaggaacaag ggcataggga agatgggctt tggaatggtg    6720
actcttgggg ccagcgcatg gctcatgtgg ctctcggaaa ttgagccagc cagaattgca    6780
tgtgtcctca ttgttgtgtt cctattgctg gtggtgctca tacctgagcc agaaaagcaa    6840
agatctcccc aggacaacca aatggccatc atcatcatgg tagcagtagg tcttctgggc    6900
ttgattaccg ccaatgaact cggatggttg gagagaacaa agagtgacct aagccatcta    6960
atgggaagga gagaggaggg ggcaaccatg ggattctcaa tggacattga cctgcggcca    7020
gcctcagctt gggccatcta tcctgccttg acatctttca ttaccccagc cgtccaacat    7080
gcagtgacca cttcatacaa caactactcc ttaatggcga tggccacgca agctggagtg    7140
ttgtttggta tgggcaaagg gatgccattc tacgcatggg actttggagt cccgctgcta    7200
atgataggtt gctactcaca attaacgccc ctgaccctaa tagtggccat cattttgctc    7260
gtggcgcact acatgtactt gatcccaggg ctgcaggcag cagctgcgcg tgctgcccag    7320
aagagaacgg cagctggcat catgaagaac cctgttgtgg agggaatagt ggtgactgac    7380
attgacacaa tgacaattga cccccaagtg gagaaaaaga tgggacaggt gctactcatg    7440
gcagtagccg tctccagcgc catactgtcg aggaccgcct gggggtgggg ggaggctggg    7500
gccctgatca cagccgcaac ttccactttg tgggaaggct ctccgaacaa gtactggaac    7560
tcctctacag ccacctcact gtgtaacatt tttaggggaa gttacttggc tggagcttct    7620
ctaatctaca cagtaacaag aaacgctggc ttggtcaaga acgtgggggg tggaacagga    7680
gagaccctgg gagagaaatg gaaggcccgc ttgaaccaga tgtcggccct ggagttctac    7740
tcctacaaaa agtcaggcat caccgaggtg tgcagagaag aggcccgccg cgccctcaag    7800
gacggtgtgg caacgggagg ccatgctgtg tcccgaggaa gtgcaaagct gagatggttg    7860
gtggagcggg gatacctgca gcccctatgga aaggtcattg atcttggatg tggcagaggg    7920
ggctggagtt actacgccgc caccatccgc aaagttcaag aagtgaaagg atacacaaaa    7980
ggaggccctg gtcatgaaga acccgtgttg gtgcaaagct atgggtggaa catagtccgt    8040
cttaagagtg gggtggacgt ctttcatatg gcggctgagc cgtgtgacac gttgctgtgt    8100
gacataggtg agtcatcatc tagtcctgaa gtggaagaag cacggacgct cagagtcctc    8160
tccatggtgg gggattggct tgaaaaaaga ccaggagcct tttgtataaa agtgttgtgc    8220
ccatacacca gcactatgat ggaaaccctg gagcgactgc agcgtaggta tgggggagga    8280
ctggtcagag tgccactctc ccgcaactct acacatgaga tgtactgggt ctctggagcg    8340
aaaagcaaca ccataaaaag tgtgtccacc acgagccagc tcctcttggg gcgcatggac    8400
gggcctagga ggcagtgaa atatgaggag gatgtgaatc tcggctctgg cacgcgggct    8460
gtggtaagct gcgctgaagc tcccaacatg aagatcattg gtaaccgcat tgaaaggatc    8520
cgcgctgaga aagcggaaac gtggttctt gacgagaacc acccatatag gacatgggct    8580
taccatggaa gctatgatgc cgccacacaa gggtcagcgt cctctctaat aaacgggtt    8640 gtcaggctcc tgtcaaaacc ctgggatgtg tgactggag tcacaggaat agccatgacc    8700
gacaccacac cgtatggtca gcaaagagtt ttcaaggaaa agtggacac tagggtgcca    8760 gacccccaag aaggcactcg tcaggttatg agcatggtct cttcctggtt gtggaaagag    8820
ctaggcaaac acaaacggcc acgagtctgt accaaagaag agttcatcaa caaggttcgt    8880
agcaatgcag cattaggggc aatatttgaa gaggaaaaag agtggaagac tgcagtggaa    8940
```

```
gctgtgaacg atccaaggtt ctgggctcta gtggacaagg aaagagagca ccacctgaga    9000
ggagagtgcc agagttgtgt gtacatcaca atgggaaaaa gagaaaagaa acaaggggaa    9060
tttggaaagg ccaagggcag ccgcgccatc tggtatatgt ggctaggggc tagatttcta    9120
gagttcgaag cccttggatt cttgaacgag atcactgga tggggagaga gaactcagga    9180
ggtggtgttg aagggctggg attacaaaga ctcggatatg tcctagaaga gatgagtcgc    9240
ataccaggag aaggatgta tgcagatgac actgctggct gggacacccg catcagcagg    9300
tttgatctgg agaatgaagc tctaatcacc aaccaaatgg agaaagggca gggccttg    9360 gcattggcca taatcaagta cacataccaa acaaagtgg taaaggtcct tagaccagct    9420
gaaaaaggga agacagttat ggacattatt tcgagacaag accaaggggg agcggacaa    9480 gttgtcactt acgctctcaa cacatttacc aacctagtgg tgcaactcat tcggaatatg    9540
gaggctgagg aagttctaga gatgcaagac ttgtggctgc tgcggaggtc agagaaagtg    9600
accaactggt tgcagagcaa cggatgggat aggctcaaac gaatggcggt cagtggagat    9660
gattgcgttg tgaaaccaat tgatgatagg tttgcacatg ccctcaggtt cttgaatgat    9720 atggaaaag ttaggaagga cacacaagag tggaaaccct caactggatg ggacaactgg    9780
gaagaagttc ccttctgctc ccaccacttc aacaagctcc atctcaagga cgggaggtcc    9840
attgtggttc cctgccgcca ccaagatgaa ctgattggcc gggcccgcgt ctctccaggg    9900
gcgggatgga gcatccggga gactgcttgc ctagcaaaat catatgcgca aatgtggcag    9960
ctcctttatt tccacagaag ggacctccga ctgatggcca atgccatttg ttcatctgtg    10020
ccagttgact gggttccaac tgggagaact acctggtcaa tccatggaaa gggagaatgg    10080
atgaccactg aagacatgct tgtggcgtgg aacagagtgt ggattgagga gaacgaccac    10140
atggaagaca gaccccagt cacgaaatgg acagacattc cctatttggg aaaaagggaa    10200
gacttgtggt gtggatctct catagggcac agaccgcgca ccacctgggc tgagaacatt    10260
aaaaacacag tcaacatggt gcgcaggatc ataggtgatg aagaaaagta catggactac    10320
ctatccaccc aagttcgcta cttgggtgaa gaagggtcta cacctggagt gctgtaagca    10380
ccaatcttaa tgttgtcagg cctgctagtc agccacagct ggggaaagc tgtgcagcct    10440 gtgacccccc caggagaagc tgggaaacca gcctatagt caggccgaga acgccatggc    10500
acggaagaag ccatgctgcc tgtgagcccc tcagaggaca ctgagtcaaa aaccccacg    10560 cgcttggagg cgcaggatgg gaaaagaagg tggcgacctt ccccaccctt caatctgggg    10620
cctgaactgg agatcagctg tggatctcca gaagagggac tagtggttag aggaga       10676
```

<210> SEQ ID NO 11
<211> LENGTH: 10807
<212> TYPE: DNA
<213> ORGANISM: Zika virus

<400> SEQUENCE: 11

```
agttgttgat ctgtgtgagt cagactgcga cagttcgagt ctgaagcgag agctaacaac      60
agtatcaaca ggtttaattt ggatttggaa acgagagttt ctggtcatga aaacccaaa     120 gaagaaatcc ggaggattcc ggattgtcaa tatgctaaaa cgcggagtag cccgtgtaaa    180
ccccttggga ggtttgaaga ggttgccagc cggacttctg ctgggtcatg acccatcag     240 aatggttttg cgatactag cctttttgag atttacagca atcaagccat cactgggcct    300
tatcaacaga tggggttccg tggggaaaaa agaggctatg gaaataataa gaagttcaa    360 gaaagatctt gctgccatgt tgagaataat caatgctagg aaagagagga agagacgtgg    420
```

| | |
|---|---|
| cgcagacacc agcatcggaa tcattggcct cctgctgact acagccatgg cagcagagat | 480 |
| cactagacgc gggagtgcat actacatgta cttggatagg agcgatgccg ggaaggccat | 540 |
| ttcgtttgct accacattgg gagtgaacaa gtgccacgta cagatcatgg acctcgggca | 600 |
| catgtgtgac gccaccatga gttatgagtg ccctatgctg gatgagggag tggaaccaga | 660 |
| tgatgtcgat tgctggtgca acacgacatc aacttgggtt gtgtacggaa cctgtcatca | 720 |
| caaaaaggt gaggcacggc gatctagaag agccgtgacg ctcccttctc actctacaag | 780 |
| gaagttgcaa acgcggtcgc agacctggtt agaatcaaga aatacacga agcacttgat | 840 |
| caaggttgaa aactggatat tcaggaaccc cgggtttgcg ctagtggccg ttgccattgc | 900 |
| ctggcttttg ggaagctcga cgagccaaaa agtcatatac ttggtcatga tactgctgat | 960 |
| tgccccggca tacagtatca ggtgcattgg agtcagcaat agagacttcg tggagggcat | 1020 |
| gtcaggtggg acctgggttg atgttgtctt ggaacatgga ggctgcgtta ccgtgatggc | 1080 |
| acaggacaag ccaacagttg acatagagtt ggtcacgacg acggttagta acatggccga | 1140 |
| ggtaagatcc tattgctacg aggcatcgat atcggacatg gcttcggaca gtcgttgccc | 1200 |
| aacacaaggt gaagcctacc ttgacaagca atcagacact caatatgtct gcaaaagaac | 1260 |
| attagtggac agaggttggg gaaacggttg tggactttt ggcaaaggga gcttggtgac | 1320 |
| atgtgccaag tttacgtgtt ctaagaagat gaccgggaag agcattcaac cggaaaatct | 1380 |
| ggagtatcgg ataatgctat cagtgcatgg ctcccagcat agcgggatga ctgtcaatga | 1440 |
| tataggatat gaaactgacg aaaatagagc gaaagtcgag gttacgccta attcaccaag | 1500 |
| agcggaagca accttgggag ctttggaag cttaggactt gactgtgaac caaggacagg | 1560 |
| ccttgactt tcagatctgt attacctgac catgaacaat aagcattggt tggtgcacaa | 1620 |
| agagtggttt catgacatcc cattgccttg gcatgctggg gcagacactg gaactccaca | 1680 |
| ctggaacaac aaagaggcat tggtagaatt caaggatgcc cacgccaaga ggcaaaccgt | 1740 |
| cgtcgttctg gggagccagg aaggagccgt tcacacggct ctcgctggag ctctagaggc | 1800 |
| tgagatggat ggtgcaaagg gaaagctgtt ctctggccat ttgaaatgcc gcctaaaaat | 1860 |
| ggacaagctt agattgaagg gcgtgtcata ttccttgtgc actgcggcat tcacattcac | 1920 |
| caaggtccca gctgaaacac tgcatggaac agtcacagtg gaggtgcagt atgcagggac | 1980 |
| agatggaccc tgcaagatcc cagtccagat ggcggtggac atgcagaccc tgaccccagt | 2040 |
| tggaaggctg ataaccgcca accccgtgat tactgaaagc actgagaact caaagatgat | 2100 |
| gttggagctt gacccaccat tgggggattc ttacattgtc ataggagttg gggacaagaa | 2160 |
| aatcacccac cactggcata ggagtggtag caccatcgga aaggcatttg aggccactgt | 2220 |
| gagaggcgcc aagagaatgg cagtcctggg ggatacagcc tgggacttcg gatcagtcgg | 2280 |
| gggtgtgttc aactcactgg gtaagggcat tcaccagatt ttttggagcag ccttcaaatc | 2340 |
| actgtttgga ggaatgtcct ggttctcaca gatcctcata ggcacgctgc tagtgtggtt | 2400 |
| aggtttgaac acaaagaatg gatctatctc cctcacatgc ttggcctgg ggggagtgat | 2460 |
| gatcttcctc tccacggctg tttctgctga cgtggggtgc tcagtggact tctcaaaaaa | 2520 |
| ggaaacgaga tgtggcacgg gggtattcat ctataatgat gttgaagcct ggaggaccg | 2580 |
| gtacaagtac catcctgact ccccccgcag attggcagca gcagtcaagc aggcctggga | 2640 |
| agagggggatc tgtgggatct catccgtttc aagaatggaa acatcatgt ggaaatcagt | 2700 |
| agaaggggag ctcaatgcta tcctagagga gaatggagtt caactgacag ttgttgtggg | 2760 |

```
atctgtaaaa aacccccatgt ggagaggtcc acaaagattg ccagtgcctg tgaatgagct    2820
gccccatggc tggaaagcct gggggaaatc gtattttgtt agggcggcaa agaccaacaa    2880
cagttttgtt gtcgacggtg acacactgaa ggaatgtccg cttgagcaca gagcatggaa    2940
tagttttctt gtggaggatc acgggtttgg agtcttccac accagtgtct ggcttaaggt    3000
cagagaagat tactcattag aatgtgaccc agccgtcata ggaacagctg ttaagggaag    3060
ggaggccgcg cacagtgatc tgggctattg gattgaaagt gaaaagaatg acacatggag    3120
gctgaagagg gcccacctga ttgagatgaa aacatgtgaa tggccaaagt ctcacacatt    3180
gtggacagat ggagtagaag aaagtgatct tatcatacccc aagtctttag ctggtccact    3240
cagccaccac aacaccagag agggttacag aacccaagtg aaagggccat ggcacagtga    3300
agagcttgaa atccggtttg aggaatgtcc aggcaccaag gtttacgtgg aggagacatg    3360
cggaactaga ggaccatctc tgagatcaac tactgcaagt ggaagggtca ttgaggaatg    3420
gtgctgtagg gaatgcacaa tgcccccact atcgtttcga gcaaaagacg gctgctggta    3480
tggaatggag ataaggccca ggaaagaacc agagagcaac ttagtgaggt caatggtgac    3540
agcggggtca accgatcata tggaccactt ctctcttgga gtgcttgtga ttctactcat    3600
ggtgcaggag gggttgaaga agagaatgac cacaaagatc atcatgagca catcaatggc    3660
agtgctggta gtcatgatct tgggaggatt ttcaatgagt gacctggcca agcttgtgat    3720
cctgatgggt gctactttcg cagaaatgaa cactggagga gatgtagctc acttggcatt    3780
ggtagcggca tttaaagtca gaccagcctt gctggtctcc ttcattttca gagccaattg    3840
gacaccccgt gagagcatgc tgctagcccct ggcttcgtgt cttctgcaaa ctgcgatctc    3900
tgctcttgaa ggtgacttga tggtcctcat taatggattt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtggagg    4080
gatcatgctc ctctccctga agggaaagg tagtgtgaag aagaacctgc catttgtcat    4140 ggcccctggga ttgacagctg tgagggtagt agaccctatt aatgtggtag actactgtt    4200 actcacaagg agtgggaagc ggagctggcc ccctagtgaa gttctcacag ccgttggcct    4260
gatatgtgca ctggccggag ggtttgccaa ggcagacatt gagatggctg acccatggc    4320 tgcagtaggc ttgctaattg tcagctatgt ggtctcggga aagagtgtgg acatgtacat    4380
tgaaagagca ggtgacatca catgggaaaa ggacgcggaa gtcactggaa acagtcctcg    4440
gcttgacgtg gcactggatg agagtggtga tttctccttg gtagaggaag atggtccacc    4500
catgagagag atcatactta aggtggtcct gatggccatc tgtggcatga acccaatagc    4560
tatacctttt gctgcaggag cgtggtatgt gtatgtgaag actgggaaaa ggagtggcgc    4620
cctctgggac gtgcctgctc ccaaagaagt gaagaaagga gagccacag atggagtgta    4680 cagagtgatg actcgcagac tgctaggttc aacacaggtt ggagtgggag tcatgcaaga    4740
gggagtcttc cacaccatgt ggcacgttac aaaaggagcc gcactgagga gcggtgaggg    4800
aagacttgat ccatactggg gggatgtcaa gcaggacttg gtgtcatact gtgggccttg    4860
gaagttggat gcagcttggg atggactcag cgaggtacag cttttggccg tacctccgg    4920 agagagggcc agaaacattc agaccctgcc tggaatattc aagacaaagg acgggggacat    4980 cggagcagtt gctctggact accctgcagg gacctcagga tctccgatcc tagacaaatg    5040
tggaagagtg ataggactct atggcaatgg ggttgtgatc aagaatgaa gctatgttag    5100 tgctataacc caggggaaga gggaggagga gactccggtt gaatgtttcg aaccctcgat    5160
```

```
gctgaagaag aagcagctaa ctgtcttgga tctgcatcca ggagccggaa aaaccaggag    5220
agttcttcct gaaatagtcc gtgaagccat aaaaaagaga ctccggacag tgatcttggc    5280
accaactagg gttgtcgctg ctgagatgga ggaggccttg agaggacttc cggtgcgtta    5340
catgacaaca gcagtcaacg tcacccattc tgggacagaa atcgttgatt tgatgtgcca    5400
tgccactttc acttcacgct tactacaacc catcagagtc cctaattaca atctctacat    5460
catggatgaa gcccacttca cagacccctc aagtatagct gcaagaggat atatatcaac    5520
aagggttgaa atgggcgagg cggctgccat ttttatgact gccacaccac caggaacccg    5580
tgatgcgttt cctgactcta actcaccaat catggacaca gaagtggaag tcccagagag    5640
agcctggagc tcaggctttg attgggtgac agaccattct gggaaaacag tttggttcgt    5700
tccaagcgtg agaaacggaa atgaaatcgc agcctgtctg acaaaggctg aaagcgggt     5760 catacagctc agcaggaaga cttttgagac agaatttcag aaaacaaaaa atcaagagtg    5820
ggactttgtc ataacaactg acatctcaga gatgggcgcc aacttcaagg ctgaccgggt    5880
catagactct aggagatgcc taaaaccagt catacttgat ggtgagagag tcatcttggc    5940
tgggcccatg cctgtcacgc atgctagtgc tgctcagagg agaggacgta taggcaggaa    6000
ccctaacaaa cctggagatg agtacatgta tggaggtggg tgtgcagaga ctgatgaagg    6060
ccatgcacac tggcttgaag caagaatgct tcttgacaac atctacctcc aggatggcct    6120
catagcctcg ctctatcggc ctgaggccga taaggtagcc gccattgagg gagagtttaa    6180
gctgaggaca gagcaaagga agaccttcgt ggaactcatg aagagaggag accttcccgt    6240
ctggctagcc tatcaggttg catctgccgg aataacttac acagacagaa gatggtgctt    6300
tgatggcaca accaacaaca ccataatgga agacagcgta ccagcagagg tgtggacaaa    6360
gtatggagag aagagagtgc tcaaaccgag atggatggat gctagggtct gttcagacca    6420
tgcggccctg aagtcgttca aagaattcgc cgctggaaaa agaggagcgg ctttgggagt    6480
aatggaggcc ctgggaacac tgccaggaca catgacagag aggtttcagg aagccattga    6540
caacctcgcc gtgctcatgc gagcagagac tggaagcagg ccttataagg cagcggcagc    6600
ccaactgccg gagaccctag agaccattat gctcttaggt ttgctgggaa cagtttcact    6660
ggggatcttc ttcgtcttga tgcggaataa gggcatcggg aagatgggct ttggaatggt    6720
aaccctttgg gccagtgcat ggctcatgtg gctttcggaa attgaaccag ccagaattgc    6780
atgtgtcctc attgttgtgt ttttattact ggtggtgctc atacccgagc cagagaagca    6840
aagatctccc caagataacc agatggcaat tatcatcatg gtggcagtgg gccttctagg    6900
tttgataact gcaaacgaac ttggatggct ggaaagaaca aaaaatgaca tagctcatct    6960
aatgggaagg agagaagaag gagcaaccat gggattctca atggacattg atctgcggcc    7020
agcctccgcc tgggctatct atgccgcatt gacaactctc atcacccag ctgtccaaca    7080 tgcggtaacc acttcataca acaactactc cttaatggcg atggccacac aagctggagt    7140
gctgtttggc atgggcaaag gatgccatt ttatgcatgg gaccttggag tcccgctgct    7200
aatgatgggt tgctattcac aattaacacc cctgactctg atagtagcta tcattctgct    7260
tgtggcgcac tacatgtact tgatcccagg cctacaagcg gcagcagcgc gtgctgccca    7320
gaaaaggaca gcagctggca tcatgaagaa tcccgttgtg gatggaatag tggtaactga    7380
cattgacaca atgacaatag accccaggt ggagaagaag atgggacaag tgttactcat    7440
agcagtagcc atctccagtg ctgtgctgct gcggaccgcc tggggatggg gggaggctgg    7500
```

```
agctctgatc acagcagcga cctccacctt gtgggaaggc tctccaaaca aatactggaa    7560
ctcctctaca gccacctcac tgtgcaacat cttcagagga agctatctgg caggagcttc    7620
ccttatctat acagtgacga gaaacgctgg cctggttaag agacgtggag gtgggacggg    7680
agagactctg ggagagaagt ggaaagctcg tctgaatcag atgtcggccc tggagttcta    7740
ctcttataaa aagtcaggta tcactgaagt gtgtagagag gaggctcgcc gtgccctcaa    7800
ggatggagtg gccacaggag acatgccgt atcccgggga agtgcaaagc tcagatggtt     7860
ggtggagaga ggatatctgc agccctatgg gaaggttgtt gacctcggat gtggcagagg    7920
gggctggagc tattatgccg ccaccatccg caaagtgcag gaggtgagag gatacacaaa    7980
gggaggtccc ggtcatgaag aacccatgct ggtgcaaagc tatgggtgga acatagttcg    8040
tctcaagagt ggagtggacg tcttccacat ggcggctgag ccgtgtgaca ctctgctgtg    8100
tgacataggt gagtcatcat ctagtcctga agtggaagag acacgaacac tcagagtgct    8160
ctctatggtg ggggactggc ttgaaaaaag accaggggcc ttctgtataa aggtgctgtg    8220
cccatacacc agcactatga tggaaaccat ggagcgactg caacgtaggc atggggagg    8280 attagtcaga gtgccattgt ctcgcaactc cacacatgag atgtactggg tctctggggc    8340
aaagagcaac atcataaaaa gtgtgtccac cacaagtcag ctcctcctgg gacgcatgga    8400
tggccccagg aggccagtga aatatgagga ggatgtgaac ctcggctcgg gtacacgagc    8460
tgtggcaagc tgtgctgagg ctcctaacat gaaaatcatc ggcaggcgca ttgagagaat    8520
ccgcaatgaa catgcagaaa catggttct tgatgaaaac cacccataca ggacatgggc    8580
ctaccatggg agctacgaag cccccacgca aggatcagcg tcttccctcg tgaacggggt    8640
tgttagactc ctgtcaaagc cttgggacgt ggtgactgga gttacaggaa tagccatgac    8700
tgacaccaca ccatcggcc aacaaagagt cttcaaagaa aaagtggaca ccagggtgcc    8760
agatccccaa gaaggcactc gccaggtaat gaacatagtc tcttcctggc tgtggaagga    8820
gctggggaaa cgcaagcggc cacgcgtctg caccaaagaa gagtttatca acaaggtgcg    8880
cagcaatgca gcactgggag caatatttga agaggaaaaa gaatggaaga cggctgtgga    8940
agctgtgaat gatccaagg t tttgggcccct agtggatagg gagagagaac accacctgag    9000
aggagagtgt cacagctgtg tgtacaacat gatgggaaaa agagaaaaga gcaaggaga    9060 gttcggaaa gcaaaggta gccgcgccat ctggtacatg tggttgggag ccagattctt    9120
ggagtttgaa gcccttggat tcttgaacga ggaccattgg atgggaagag aaaactcagg    9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaaggc acagaactct    9360 ggcgttggcc gtgattaat acacatacca aaacaaagtg gtgaaggttc tcagaccagc    9420
tgaaggagga aaaacagtta tggacatcat ttcaagacaa gaccagagag ggagtggaca    9480
agttgtcact tatgctctca acacattcac caacttggtg gtgcagctta tccggaacat    9540
ggaagctgag gaagtgttag agatgcaaga cttatggttg ttgaggaagc agagaaagt    9600 gaccagatgt tgcagagca atggatggga tagactcaaa cgaatggcgg tcagtggaga    9660
tgactgcgtt gtgaagccaa tcgatgatag gtttgcacat gccctcaggt tcttgaatga    9720
catgggaaaa gttaggaaag acacacagga gtggaaaccc tcgactggat ggagcaattg    9780
ggaagaagtc ccgttctgct cccaccactt caacaagctg tacctcaagg atgggagatc    9840
cattgtggtc ccttgccgcc accaagatga actgattggc cgagctcgcg tctcaccagg    9900
```

```
ggcaggatgg agcatccggg agactgcctg tcttgcaaaa tcatatgcgc agatgtggca    9960
gctcctttat ttccacagaa gagaccttcg actgatggct aatgccattt gctcggctgt   10020
gccagttgac tgggtaccaa ctgggagaac cacctggtca atccatggaa agggagaatg   10080
gatgaccact gaggacatgc tcatggtgtg gaatagagtg tggattgagg agaacgacca   10140
tatggaggac aagactcctg taacaaaatg gacagacatt ccctatctag gaaaaaggga   10200
ggacttatgg tgtggatccc ttatagggca gaccccgcac caccttggg ctgaaaacat    10260
caaagacaca gtcaacatgg tgcgcaggat cataggtgat gaagaaaagt acatggacta   10320
tctatccacc caagtccgct acttgggtga ggaagggtcc acacccggag tgttgtaagc   10380
accaattta gtgttgtcag gcctgctagt cagccacagt ttggggaaag ctgtgcagcc    10440
tgtaaccccc ccaggagaag ctgggaaacc aagctcatag tcaggccgag aacgccatgg   10500
cacggaagaa gccatgctgc ctgtgagccc ctcagaggac actgagtcaa aaaccccac    10560
gcgcttggaa gcgcaggatg gaaaagaag gtggcgacct tccccaccct tcaatctggg    10620
gcctgaactg gagactagct gtgaatctcc agcagaggga ctagtggtta gaggagaccc   10680
cccggaaaac gcaaaacagc atattgacgc tgggaaagac cagagactcc atgagtttcc   10740
accacgctgg ccgccaggca cagatcgccg aacagcggcg gccggtgtgg ggaaatccat   10800
ggtttct                                                             10807

<210> SEQ ID NO 12
<211> LENGTH: 10794
<212> TYPE: DNA
<213> ORGANISM: Zika virus

<400> SEQUENCE: 12
agttgttgat ctgtgtgagt cagactgcga cagttcgagt ctgaagcgag agctaacaac     60
agtatcaaca ggtttaattt ggatttggaa acgagagttt ctggtcatga aaacccccaa    120
agaagaaatc cggaggatcc ggattgtcaa tatgctaaaa cgcggagtag cccgtgtaaa    180
ccccttggga ggtttgaaga ggttgccagc cggacttctg ctgggtcatg gacccatcag    240
aatggttttg gcgatactag ccttttttgag atttacagca atcaagccat cactgggcct    300
tatcaacaga tggggttccg tggggaaaaa agaggctatg gaaataataa gaagttcaa     360
gaaagatctt gctgccatgt tgagaataat caatgctagg aaagagagga agagacgtgg    420
cgcagacacc agcatcggaa tcattggcct cctgctgact acagccatgg cagcagagat    480
cactagacgg gggagtgcat actacatgta cttggatagg agcgatgccg ggaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720
caaaaaggt gaggcacggc gatctagaag agccgtgacg ctcccttctc actctacaag    780
gaagttgcaa acgcggtcgc agacctggtt agaatcaaga gaatacacga agcacttgat    840
caaggttgaa aactgatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctggggttg atgttgtctt ggaacatgga ggctgcgtta ccgtgatggc    1080
acaggacaag ccaacagtcg acatagagtt ggtcacgacg acggttagta acatggccga   1140
```

-continued

```
ggtaagatcc tattgctacg aggcatcgat atcggacatg gcttcggaca gtcgttgccc    1200
aacacaaggt gaagcctacc ttgacaagca atcagacact caatatgtct gcaaaagaac    1260
attagtggac agaggttggg gaaacggttg tggactttt ggcaaaggga gcttggtgac     1320
atgtgccaag tttacgtgtt ctaagaagat gaccgggaag agcattcaac cggaaaatct    1380
ggagtatcgg ataatgctat cagtgcatgg ctcccagcat agcgggatga ttggatatga    1440
aactgacgaa gatagagcga aagtcgaggt tacgcctaat tcaccaagag cggaagcaac    1500
cttgggaggc tttggaagct taggacttga ctgtgaacca aggacaggcc ttgactttc     1560 agatctgtat tacctgacca tgaacaataa gcattggttg gtgcacaaag agtggtttca    1620
tgacatccca ttgccttggc atgctgggc agacaccgga actccacact ggaacaacaa     1680
agaggcattg gtagaattca aggatgccca cgccaagagg caaaccgtcg tcgttctggg    1740
gagccaggaa ggagccgttc acacggctct cgctggagct ctagaggctg agatggatgg    1800
tgcaaaggga aggctgttct ctggccattt gaaatgccgc ctaaaaatgg acaagcttag    1860
attgaagggc gtgtcatatt ccttgtgcac tgcggcattc acattcacca aggtcccagc    1920
tgaaacactg catggaacag tcacagtgga ggtgcagtat gcaggacag atggaccctg     1980 caagatccca gtccagatgg cggtggacat gcagaccctg accccagttg aaggctgat     2040 aaccgccaac cccgtgatta ctgaaagcac tgagaactca agatgatgt tggagcttga    2100 cccaccattt ggggattctt acattgtcat aggagttggg gacaagaaaa tcacccacca    2160
ctggcatagg agtggtagca ccatcggaaa ggcatttgag gccactgtga gaggcgccaa    2220
gagaatggca gtcctggggg atacagcctg ggacttcgga tcagtcgggg gtgtgttcaa    2280
ctcactgggt aagggcattc accagatttt tggagcagcc ttcaaatcac tgttggagg    2340 aatgtcctgg ttctcacaga tcctcatagg cacgctgcta gtgtggttag gtttgaacac    2400
aaagaatgga tctatctccc tcacatgctt ggccctgggg ggagtgatga tcttcctctc    2460
cacggctgtt tctgctgacg tggggtgctc agtggacttc tcaaaaaagg aaacgagatg    2520
tggcacgggg gtattcatct ataatgatgt tgaagcctgg agggaccggt acaagtacca    2580
tcctgactcc ccccgcagat tggcagcagc agtcaagcag gcctgggaag aggggatctg    2640
tgggatctca tccgtttcaa gaatggaaaa catcatgtgg aaatcagtag aagggagct     2700 caatgctatc ctagaggaga atggagttca actgacagtt gttgtgggat ctgtaaaaaa    2760
ccccatgtgg agaggtccac aaagattgcc agtgcctgtg aatgagctgc ccatggctg     2820 gaaagcctgg gggaaatcgt attttgttag ggcggcaaag accaacaaca gttttgttgt    2880
cgacggtgac acactgaagg aatgtccgct tgagcacaga gcatggaata gttttcttgt    2940
ggaggatcac ggttttggag tcttccacac cagtgtctgg cttaaggtca gagaagatta    3000
ctcattagaa tgtgacccag ccgtcatagg aacagctgtt aagggaaggg aggccgcgca    3060
cagtgatctg ggctattgga ttgaaagtga aagaatgac acatggaggc tgaagaggggc    3120 ccacctgatt gagatgaaaa catgtgaatg gccaaagtct cacacattgt ggacagatgg    3180
agtagaagaa agtgatctta tcatacccaa gtctttagct ggtccactca gccaccacaa    3240
caccagagag ggttacagaa cccaagtgaa agggccatgg cacagtgaag agcttgaaat    3300
ccggtttgag gaatgtccag gcaccaaggt ttacgtggag agacatgcg gaactagagg     3360 accatctctg agatcaacta ctgcaagtgg aaggttcatt gaggaatggt gctgtagga     3420 atgcacaatg cccccactat cgtttcgagc aaaagacggc tgctggtatg gaatggagat    3480
aaggcccagg aaagaaccag agagcaactt agtgaggtca atggtgacag cggggtcaac    3540
```

```
cgatcatatg gaccacttct ctcttggagt gcttgtgatt ctactcatgg tgcaggaggg   3600
gttgaagaag agaatgacca caaagatcat catgagcaca tcaatggcag tgctggtagt   3660
catgatcttg ggaggatttt caatgagtga cctggccaag cttgtgatcc tgatgggtgc   3720
tactttcgca gaaatgaaca ctggaggaga tgtagctcac ttggcattgg tagcggcatt   3780
taaagtcaga ccagccttgc tggtctcctt cattttcaga gccaattgga caccccgtga   3840
gagcatgctg ctagccctgg cttcgtgtct tctgcaaact gcgatctctg ctcttgaagg   3900
tgacttgatg gtcctcatta atggatttgc tttggcctgg ttggcaattc gagcaatggc   3960
cgtgccacgc actgacaaca tcgctctacc aatcttggct gctctaacac cactagctcg   4020
aggcacactg ctcgtggcat ggagagcggg cctggctact tgtggaggga tcatgctcct   4080
ctccctgaaa gggaaggta gtgtgaagaa gaacctgcca tttgtcatgg ccctgggatt   4140
gacagctgtg agggtagtag accctattaa tgtggtagga ctactgttac tcacaaggag   4200
tgggaagcgg agctggcccc ctagtgaagt tctcacagcc gttggcctga tatgtgcact   4260
ggccggaggg tttgccaagg cagacattga gatggctgga cccatggctg cagtaggctt   4320
gctaattgtc agctatgtgg tctcgggaaa gagtgtggac atgtacattg aaagagcagg   4380
tgacatcaca tgggaaaagg acgcggaagt cactggaaac agtcctcggc ttgacgtggc   4440
actggatgag agtggtgact tctccttggt agaggaagat ggtccaccca tgagagagat   4500
catactcaag gtggtcctga tggccatctg tggcatgaac ccaatagcta ccttttgc    4560 tgcaggagcg tggtatgtgt atgtgaagac tgggaaaagg agtggcgccc tctgggacgt   4620
gcctgctccc aaagaagtga agaaaggaga gaccacagat ggagtgtaca gagtgatgac   4680
tcgcagactg ctaggttcaa cacaggttgg agtgggagtc atgcaagagg gagtcttcca   4740
caccatgtgg cacgttacaa aaggagccgc actgaggagc ggtgagggaa gacttgatcc   4800
atactggggg gatgtcaagc aggacttggt gtcatactgt gggccttgga agttggatgc   4860
agcttgggat ggactcagcg aggtacagct tttggccgta cctcccggag agagggccag   4920
aaacattcag accctgcctg gaatattcaa gacaaaggac ggggacatcg agcagttgc    4980 tctggactac cctgcaggga cctcaggatc tccgatccta gacaaatgtg gaagagtgat   5040
aggactctat ggcaatgggg ttgtgatcaa gaatggaagc tatgttagtg ctataaccca   5100
gggaaagagg gaggaggaga ctccggttga atgtttcgaa ccctcgatgc tgaagaagaa   5160
gcagctaact gtcttggatc tgcatccagg agccggaaaa accaggagag ttcttcctga   5220
aatagtccgt gaagccataa aaagagact ccggacagtg atcttggcac caactagggt   5280
tgtcgctgct gagatggagg aggccttgag aggacttccg gtgcgttaca tgacaacagc   5340
agtcaacgtc acccattctg ggacagaaat cgttgatttg atgtgccatg ccactttcac   5400
ttcacgctta ctacaaccca tcagagtccc taattacaat ctcaacatca tggatgaagc   5460
ccacttcaca gaccctcaa gtatagctgc aagaggatac atatcaacaa gggttgaaat   5520
gggcgaggcg gctgccattt ttatgactgc cacaccacca ggaacccgtg atgcgtttcc   5580
tgactctaac tcaccaatca tggacacaga agtggaagtc ccagagagag cctggagctc   5640
aggctttgat tgggtgacag accattctgg gaaaacagtt tggttcgttc caagcgtgag   5700
aaacggaaat gaaatcgcag cctgtctgac aaaggctgga aagcgggtca tacagctcag   5760
caggaagact tttgagacag aatttcagaa aacaaaaaat caagagtggg acttttgtcat   5820 aacaactgac atctcagaga tgggcgccaa cttcaaggct gaccgggtca tagactctag   5880
```

-continued

```
gagatgccta aaaccagtca tacttgatgg tgagagagtc atcttggctg ggcccatgcc    5940
tgtcacgcat gctagtgctg ctcagaggag aggacgtata ggcaggaacc ctaacaaacc    6000
tggagatgag tacatgtatg gaggtgggtg tgcagagact gatgaaggcc atgcacactg    6060
gcttgaagca agaatgcttc ttgacaacat ctacctccag gatggcctca tagcctcgct    6120
ctatcggcct gaggccgata aggtagccgc cattgaggga gagtttaagc tgaggacaga    6180
gcaaaggaag accttcgtgg aactcatgaa gagaggagcc cttcccgtct ggctagccta    6240
tcaggttgca tctgccggaa taacttacac agacagaaga tggtgctttg atggcacaac    6300
caacaacacc ataatggaag acagtgtacc agcagaggtt tggacaaagt atggagagaa    6360
gagagtgctc aaaccgagat ggatggatgc tagggtctgt tcagaccatg cggccctgaa    6420
gtcgttcaaa gaattcgccg ctggaaaaag aggagcggct ttgggagtaa tggaggccct    6480
gggaacactg ccaggacaca tgacagagag gtttcaggaa gccattgaca acctcgccgt    6540
gctcatgcga gcagagactg gaagcaggcc ttataaggca gcggcagccc aactgccgga    6600
gaccctagag accattatgc tcttaggttt gctgggaaca gtttcactgg ggatcttctt    6660
cgtcttgatg cggaataagg gcatcgggaa gatgggcttt ggaatggtaa cccttgggc    6720
cagtgcatgg ctcatgtggc tttcggaaat tgaaccagcc agaattgcat gtgtcctcat    6780
tgttgtgttt ttattactgg tggtgctcat acccgagcca gagaagcaaa gatctcccca    6840
agataaccag atggcaatta tcatcatggt ggcagtgggc cttctaggtt tgataactgc    6900
aaacgaactt ggatggctgg aaagaacaaa aaatgacata gctcatctaa tgggaaggag    6960
agaagaagga gcaaccatgg gattctcaat ggacattgat ctgcggccag cctccgcctg    7020
ggctatctat gccgcattga acaactctcat caccccagct gtccaacatg cggtaaccac    7080
ttcatacaac aactactcct taatggcgat ggccacacaa gctggagtgc tgtttggcat    7140
gggcaaaggg atgccatttta tgcatgggga ccttggagtc ccgctgctaa tgatgggttg    7200
ctattcacaa ttaacccccc tgactctgat agtagctatc attctgcttg tggcgcacta    7260
catgtacttg atcccaggcc tacaagcggc agcagcgcgt gctgcccaga aaaggacagc    7320
agctggcatc atgaagaatc ccgttgtgga tggaatagtg gtaactgaca ttgacacaat    7380
gacaatagac ccccaggtgg agaagaagat gggacaagtg ttactcatag cagtagccat    7440
ctccagtgct gtgctgctgc ggaccgcctg gggatggggg gaggctggag ctctgatcac    7500
agcagcgacc tccaccttgt gggaaggctc tccaaacaaa tactgaaact cctctacagc    7560
cacctcactg tgcaacatct tcagaggaag ctatctggca ggagcttccc ttatctatac    7620
agtgacgaga aacgctggcc tggttaagag acgtggaggt gggacgggag agactctggg    7680
agagaagtgg aaagctcgtc tgaatcagat gtcggccctg gagttctact cttataaaaa    7740
gtcaggtatc actgaagtgt gtagagagga ggctcgccgt gccctcaagg atggagtggc    7800
cacaggagga catgccgtat cccgggaag tgcaaagatc agatggttgg aggagagagg    7860
atatctgcag ccctatggga aggttgttga cctcggatgt ggcagagggg gctggagcta    7920
ttatgccgcc accatccgca aagtgcagga ggtgagagga tacacaaagg gaggtcccgg    7980
tcatgaagaa cccatgctgg tgcaaagcta tgggtggaac atagttcgtc tcaagagtgg    8040
agtggacgtc ttccacatgg cggctgagcc gtgtgacact ctgctgtgtg acataggtga    8100
gtcatcatct agtcctgaag tggaagagac acgaacactc agagtgctct ctatggtggg    8160
ggactggctt gaaaaaagac cagggggcctt ctgtataaag gtgctgtgcc catacaccag    8220
cactatgatg gaaaccatgg agcgactgca acgtaggcat gggggaggat tagtcagagt    8280
```

| | |
|---|---|
| gccattgtgt cgcaactcca cacatgagat gtactgggtc tctgggcaa agagcaacat | 8340 |
| cataaaaagt gtgtccacca caagtcagct cctcctggga cgcatggatg gccccaggag | 8400 |
| gccagtgaaa tatgaggagg atgtgaacct cggctcgggt acacgagctg tggcaagctg | 8460 |
| tgctgaggct cctaacatga aaatcatcgg caggcgcatt gagagaatcc gcaatgaaca | 8520 |
| tgcagaaaca tggtttcttg atgaaaacca cccatacagg acatgggcct accatgggag | 8580 |
| ctacgaagcc cccacgcaag gatcagcgtc ttccctcgtg aacggggttg ttagactcct | 8640 |
| gtcaaagcct tgggacgtgg tgactggagt tacaggaata gccatgactg acaccacacc | 8700 |
| atacggccaa caaagagtct tcaaagaaaa agtggacacc agggtgccag atccccaaga | 8760 |
| aggcactcgc caggtaatga acatagtctc ttcctggctg tggaaggagc tggggaaacg | 8820 |
| caagcggcca cgcgtctgca ccaaagaaga gtttatcaac aaggtgcgca gcaatgcagc | 8880 |
| actgggagca atatttgaag aggaaaaaga atggaagacg gctgtggaag ctgtgaatga | 8940 |
| tccaaggttt tgggcctag tggataggga gagagaacac cacctgagag gagagtgtca | 9000 |
| cagctgtgtg tacaacatga tgggaaaaag agaaaagaag caaggagagt cgggaaagc | 9060 |
| aaaaggtagc cgcgccatct ggtacatgtg gttgggagcc agattcttgg agtttgaagc | 9120 |
| ccttggattc ttgaacgagg accattggat gggaagagaa aactcaggag gtggagtcga | 9180 |
| agggttagga ttgcaaagac ttggatacat tctagaagaa atgaatcggg caccaggagg | 9240 |
| aaagatgtac gcagatgaca ctgctggctg ggacacccgc attagtaagt ttgatctgga | 9300 |
| gaatgaagct ctgattacca accaaatgga ggaagggcac agaactctgg cgttggccgt | 9360 |
| gattaaatac acataccaaa acaaagtggt gaaggttctc agaccagctg aaggaggaaa | 9420 |
| aacagttatg gacatcattt caagacaaga ccagagaggg agtggacaag ttgtcactta | 9480 |
| tgctctcaac acattcacca acttggtggt gcagcttatc cggaacatgg aagctgagga | 9540 |
| agtgttagag atgcaagact tatggttgtt gaggaagcca gagaaagtga ccagatggtt | 9600 |
| gcagagcaat ggatgggata gactcaaacg aatggcggtc agtggagatg actgcgttgt | 9660 |
| gaagccaatc gatgataggt ttgcacatgc cctcaggttc ttgaatgaca tgggaaaagt | 9720 |
| taggaaagac acacaggagt ggaaaccctc gactggatgg agcaattggg aagaagtccc | 9780 |
| gttctgctcc caccacttca acaagctgta cctcaaggat gggagatcca ttgtggtccc | 9840 |
| ttgccgccac caagatgaac tgattggccg agctcgcgtc tcaccagggg caggatggag | 9900 |
| catccgggag actgcctgtc ttgcaaaatc atatgcgcag atgtggcagc tcctttattt | 9960 |
| ccacagaaga gaccttcgac tgatggctaa tgccatttgc tcggctgtgc cagttgactg | 10020 |
| ggtaccaact gggagaacca cctggtcaat ccatggaaag ggagaatgga tgaccactga | 10080 |
| ggacatgctc atggtgtgga atagagtgtg gattgaggag aacgaccata tggaggacaa | 10140 |
| gactcctgta acaaaatgga cagacattcc ctatctagga aaagggagg acttatggtg | 10200 |
| tggatccctt ataggcaca gaccccgcac cacttgggct gaaaacatca agacacagt | 10260 |
| caacatggtg cgcaggatca taggtgatga agaaaagtac atggactatc tatccaccca | 10320 |
| agtccgctac ttgggtgagg aagggtccac acccggagtg ttgtaagcac caattttagt | 10380 |
| gttgtcaggc ctgctagtca gccacagttt ggggaaagct gtgcagcctg taaccccccc | 10440 |
| aggagaagct gggaaaccaa gctcatagtc aggccgagaa cgccatggca cggaagaagc | 10500 |
| catgctgcct gtgagcccct cagaggacac tgagtcaaaa accccacgc gcttggaagc | 10560 |
| gcaggatggg aaaagaaggt ggcgaccttc cccaccttc aatctggggc ctgaactgga | 10620 |

```
gactagctgt gaatctccag cagagggact agtggttaga ggagaccccc cggaaaacgc    10680
aaaacagcat attgacgtgg gaaagaccag agactccatg agtttccacc acgctggccg    10740
ccaggcacag atcgccgaac ttcggcggcc ggtgtgggga aatccatggt ttct          10794

<210> SEQ ID NO 13
<211> LENGTH: 10617
<212> TYPE: DNA
<213> ORGANISM: Zika virus

<400> SEQUENCE: 13
agtatcaaca ggttttattt tggatttgga acgagagtt tctggtcatg aaaaacccaa      60
aaaagaaatc cggaggattc cggattgtca atatgctaaa acgcggagta gcccgtgtga    120
gcccctttgg gggcttgaag aggctgccag ccggacttct gctgggtcat gggcccatca    180
ggatggtctt ggcgattcta gcctttttga gattcacggc aatcaagcca tcactgggtc    240
tcatcaatag atggggttca gtggggaaaa aagaggctat ggaataata aagaagttca    300 agaaagatct ggctgccatg ctgagaataa tcaatgctag gaaggagaag aagagacgag    360
gcgcagatac tagtgtcgga attgttggcc tcctgctgac cacagctatg cagcggagg    420 tcactagacg tgggagtgca tactatatgt acttggacaa aaacgacgct ggggaggcca    480
tatcttttcc aaccacattg gggatgaata gtgttatat acagatcatg gatcttggac    540
acatgtgtga tgccaccatg agctatgaat gccctatgct ggatggggg gtggaaccag    600 atgacgtcga ttgttggtgc aacacgacgt caacttgggt tgtgtacgga acctgccatc    660
acaaaaaagg tgaagcacgg atctagaa gagctgtgac gctcccctcc cattccacta    720
ggaagctgca aacgcggtcg caaacctggt tggaatcaag agaatacaca aagcacttga    780
ttagagtcga aaattggata ttcaggaacc ctggcttcgc gttagcagca gctgccatcg    840
cttggctttt gggaagctca acgagccaaa aagtcatata cttggtcatg atactgctga    900
ttgccccggc atacagcatc aggtgcatag gagtcagcaa tagggacttt gtggaaggta    960
tgtcaggtgg gacttgggtt gatgttgtct ggaacatgg aggttgtgtc accgtaatgg    1020
cacaggacaa accgactgtc gacatagagc tggttacaac aacagtcagc aacatggcgg    1080
aggtaagatc ctactgctat gaggcatcaa tatcggacat ggcttcggac agccgctgcc    1140
caacacaagg tgaagcctac cttgacaagc aatcagacac tcaatatgtc tgcaaaagaa    1200
cgttagtgga cagaggctgg ggaaatggat gtggactttt tggcaaaggg agcctggtga    1260
catgcgctaa gtttgcatgc tccaagaaaa tgaccgggaa gagcatccag ccagagaatc    1320
tggagtaccg gataatgctg tcagttcatg gctcccagca cagtgggatg atcgttaatg    1380
acacaggaca tgaaactgat gagaatagag cgaaggttga gaatcgccc aattcaccaa    1440 gagccgaagc caccctgggg ggttttggaa gcctaggact tgattgtgaa ccgaggacag    1500
gccttgactt ttcagatttg tattacttga ctatgaataa caagcactgg ttggttcaca    1560
aggagtggtt ccacgacatt ccattacctt ggcacgctgg ggcagacacc ggaactccac    1620
actggaacaa caaagaagca ctggtagagt tcaaggacgc acatgccaaa aggcaaactg    1680
tcgtggttct agggagtcaa gaaggagcag ttcacacggc ccttgctgga gctctggagg    1740
ctgagatgga tggtgcaaag ggaaggctgt cctctggcca cttgaaatgt cgcctgaaaa    1800
tggataaact tagattgaag ggcgtgtcat actccttgtg taccgcagcg ttcacattca    1860
ccaagatccc ggctgaaaca ctgcacggga cagtcacagt ggaggtacag tacgcaggga    1920
cagatggacc ttgcaaggtt ccagctcaga tggcggtgga catgcaaact ctgaccccag    1980
```

```
ttgggaggtt gataaccgct aaccccgtaa tcactgaaag cactgagaac tctaagatga   2040
tgctggaact tgatccacca tttggggact cttacattgt cataggagtc ggggagaaga   2100
agatcaccca ccactggcac aggagtggca gcaccattgg aaaagcattt gaagccactg   2160
tgagaggtgc caagagaatg gcagtcttgg agacacagc ctgggacttt ggatcagttg    2220
gaggcgctct caactcattg ggcaagggca tccatcaaat ttttggagca gctttcaaat   2280
cattgtttgg aggaatgtcc tggttctcac aaattctcat ggaacgttg ctgatgtggt    2340 tgggtctgaa cacaaagaat ggatctattt cccttatgtg cttggcctta ggggagtgt    2400 tgatcttctt atccacagct gtctctgctg atgtggggtg ctcggtggac ttctcaaaga   2460
aggagacgag atgcggtaca ggggtgttcg tctataacga cgttgaagcc tggagggaca   2520
ggtacaagta ccatcctgac tccccccgta gattggcagc agcagtcaag caagcctggg   2580
aagatggtat ctgtgggatc tcctctgttt caagaatgga aaacatcatg tggagatcag   2640
tagaagggga gctcaacgca atcctggaag agaatggagt tcaactgacg gtcgttgtgg   2700
gatctgtaaa aaaccccatg tggagaggtc cacagagatt gcccgtgcct gtgaacgagc   2760
tgccccacgg ctggaaggct tgggggaaat cgtacttcgt cagagcagca aagacaaata   2820
acagctttgt cgtggatggt gacacactga aggaatgccc actcaaacat agagcatgga   2880 acagcttttct tgtggaggat catgggttcg gggtatttca cactagtgtc tggctcaagg   2940
ttagagaaga ttattcatta gagtgtgatc cagccgttat tggaacagct gttaagggaa   3000
aggaggctgt acacagtgat ctaggctact ggattgagag tgagaagaat gacacatgga   3060
ggctgaagag ggcccatctg atcgagatga aaacatgtga atggccaaag tcccacacat   3120
tgtggacaga tggaatagaa gagagtgatc tgatcatacc caagtcttta gctgggccac   3180
tcagccatca caataccaga gagggctaca ggacccaaat gaaagggcca tggcacagtg   3240
aagagcttga aattcggttt gaggaatgcc caggcactaa ggtccacgtg gaggaaacat   3300
gtggaacaag aggaccatct ctgagatcaa ccactgcaag cggaagggtg atcgaggaat   3360
ggtgctgcag ggagtgcaca atgccccac tgtcgttccg ggctaaagat ggctgttggt    3420
atggaatgga gataaggccc aggaaagaac cagaaagtaa cttagtaagg tcaatggtga   3480
ctgcaggatc aactgatcac atggatcact tctcccttgg agtgcttgtg attctgctca   3540
tggtgcagga agggctgaag aagagaatga ccacaaagat catcataagc acatcgatgg   3600
cagtgctggt agctatgatc ctgggaggat tttcaatgag tgacctggct aagcttgcaa   3660
ttttgatggg tgccaccttc gcggaaatga acactggagg agatgtagct catctggcgc   3720
tgatagcggc attcaaagtc agaccagcgt tgctggtatc tttcatcttc agagctaatt   3780
ggacaccccg tgaaagcatg ctgctggcct tggcctcgtg tcttttgcaa actgcgatct   3840
ccgccttgga aggcgacctg atggttctca tcaatggttt tgctttggcc tggttggcaa   3900
tacgagcgat ggttgttcca cgcactgata acatcacctt ggcaatcctg ctgctctga    3960 caccactggc ccggggcaca ctgcttgtgg cgtggagagc aggccttgct acttgcgggg   4020
ggtttatgct cctctctctg aagggaaaag gcagtgtgaa gaagaactta ccatttgtca   4080
tggcccctgg gactaaccgct gtgaggctgg tcgaccccat caacgtggtg gactgctgt    4140 tgctcacaag gagtgggaag cggagctggc cccctagcga agtactcaca gctgttggcc   4200
tgatatgcgc attggctgga gggttcgcca aggcagatat agagatggct gggcccatgg   4260
ccgcggtcgg tctgctaatt gtcagttacg tggtctcagg aaagagtgtg gacatgtaca   4320
```

```
ttgaaagagc aggtgacatc acatgggaaa aagatgcgga agtcactgga aacagtcccc    4380
ggctcgatgt ggcgctagat gagagtggtg atttctccct ggtggaggat gacggtcccc    4440
ccatgagaga gatcatactc aaggtggtcc tgatgaccat ctgtggcatg aacccaatag    4500
ccataccctt tgcagctgga gcgtggtacg tatacgtgaa gactggaaaa aggagtggtg    4560
ctctatggga tgtgcctgct cccaaggaag taaaaaaggg ggagaccaca gatggagtgt    4620
acagagtaat gactcgtaga ctgctaggtt caacacaagt tggagtggga gttatgcaag    4680
aggggggtctt tcacactatg tggcacgtca caaaaggatc cgcgctgaga agcggtgaag    4740
ggagacttga tccatactgg ggagatgtca agcaggatct ggtgtcatac tgtggtccat    4800
ggaagctaga tgccgcctgg gacgggcaca gcgaggtgca gctcttggcc gtgcccccg     4860
gagagagagc gaggaacatc cagactctgc ccggaatatt taagacaaag gatgggaca    4920
ttggagcggt tgcgctggat tacccagcag gaacttcagg atctccaatc ctagacaagt   4980
gtgggagagt gataggactt tatgcaatg gggtcgtgat caaaaatggg agttatgtta    5040
gtgccatcac ccaagggagg agggaggaag agactcctgt tgagtgcttc gagccttcga    5100
tgctgaagaa gaagcagcta actgtcttag acttgcatcc tggagctggg aaaaccagga    5160
gagttcttcc tgaaatagtc cgtgaagcca taaaaacaag actccgtact gtgatcttag    5220
ctccaaccag ggttgtcgct gctgaaatgg aggaagccct tagagggctt ccagtgcgtt    5280
atatgacaac agcagtcaat gtcacccact ctggaacaga aatcgtcgac ttaatgtgcc    5340
atgccacctt cacttcacgt ctactacagc caatcagagt ccccaactat aatctgtata    5400
ttatggatga ggcccacttc acagatcctt caagtatagc agcaagagga tacatttcaa    5460
caagggttga gatgggcgag gcggctgcca tcttcatgac cgccacgcca ccaggaaccc    5520
gtgacgcatt tccggactcc aactcaccaa ttatggacac cgaagtggaa gtcccagaga    5580
gagcctggag ctcaggcttt gattgggtga cggatcattc tggaaaaaca gtttggtttg    5640
ttccaagcgt gaggaacggc aatgagatcg cagcttgtct gacaaaggct ggaaaacggg    5700
tcatacagct cagcagaaag actttgaga cagagttcca gaaaacaaaa catcaagagt     5760
gggactttgt cgtgacaact gacatttcag agatgggcgc caactttaaa gctgaccgtg    5820
tcatagattc caggagatgc ctaaagccgg tcatacttga tggcgagaga gtcattctgg    5880
ctggacccat gcctgtcaca catgccagcg ctgcccagag gaggggggcgc ataggcagga    5940
atcccaacaa acctggagat gagtatctgt atggaggtgg gtgcgcagag actgacgaag    6000
accatgcaca ctggcttgaa gcaagaatgc tccttgacaa tatttacctc caagatggcc    6060
tcatagcctc gctctatcga cctgaggccg acaaagtagc agccattgag ggagagttca    6120
agcttaggac ggagcaaagg aagaccttg tggaactcat gaaaagagga gatcttcctg    6180
tttggctggc ctatcaggtt gcatctgccg gaataaccta cacagataga agatggtgct    6240
ttgatggcac gaccaacaac accataatgg aagacagtgt gccggcagag gtgtggacca    6300
gacacggaga gaaagagtg ctcaaaccga ggtggatgga cgccagagtt tgttcagatc    6360
atgcggccct gaagtcattc aaggagtttg ccgctggaa aagaggagcg cttttggag    6420
tgatggaagc cctgggaaca ctgccaggac acatgacaga gagattccag gaagccattg    6480
acaacctcgc tgtgctcatg cgggcagaga ctggaagcag gccttacaaa gccgcggcgg    6540
cccaattgcc ggagacccta gagaccatta tgcttttggg gttgctggga acagtctcgc    6600
tgggaatctt tttcgtcttg atgaggaaca agggcatagg gaagatgggc tttgaatgg    6660
tgactcttgg ggccagcgca tggctcatgt ggctctcgga aattgagcca gccagaattg    6720
```

```
catgtgtcct cattgttgtg ttcctattgc tggtggtgct catacctgag ccagaaaagc    6780
aaagatctcc ccaggacaac caaatggcaa tcatcatcat ggtagcagta ggtcttctgg    6840
gcttgattac cgccaatgaa ctcggatggt tggagagaac aaagagtgac ctaagccatc    6900
taatgggaag gagagaggag ggggcaacca taggattctc aatggacatt gacctgcggc    6960
cagcctcagc ttgggccatc tatgctgcct tgacaactttt cattacccca gccgtccaac    7020
atgcagtgac cacttcatac aacaactact ccttaatggc gatggccacg caagctggag    7080
tgttgtttgg tatgggcaaa gggatgccat tctacgcatg ggactttgga gtcccgctgc    7140
taatgatagg ttgctactca caattaacac ccctgaccct aatagtggcc atcattttgc    7200
tcgtggcgca ctacatgtac ttgatcccag gctgcaggc agcagctgcg cgtgctgccc    7260
agaagagaac ggcagctggc atcatgaaga accctgttgt ggatggaata gtggtgactg    7320
acattgacac aatgacaatt gaccccccaag tggagaaaaa gatgggacag gtgctactca    7380
tagcagtagc cgtctccagc gccatactgt cgcggaccgc ctgggggtgg ggggaggctg    7440
gggccctgat cacagcggca acttccactt tgtgggaagg ctctccgaac aagtactgga    7500
actcctctac agccacttca ctgtgtaaca tttttagggg aagttacttg gctggagctt    7560
ctctaatcta cacagtaaca agaaacgctg gcttggtcaa gagacgtggg ggtggaacag    7620
gagagaccct gggagagaaa tggaaggccc gcttgaacca gatgtcggcc ctggagttct    7680
actcctacaa aaagtcaggc atcaccgagg tgtgcagaga agaggcccgc cgcgccctca    7740
aggacggtgt ggcaacggga ggccatgctg tgtcccgagg aagtgcaaag ctgagatggt    7800
tggtggagcg gggatacctg cagccctatg gaaaggtcat tgatcttgga tgtggcagag    7860
ggggctggag ttactacgcc gccaccatcc gcaaagttca agaagtgaaa ggatacacaa    7920
aaggaggccc tggtcatgaa gaacccatgt tggtgcaaag ctatgggtgg aacatagtcc    7980
gtcttaagag tgggtggac gtctttcata tggcggctga gccgtgtgac acgttgctgt    8040
gtgacatagg tgagtcatca tctagtcctg aagtggaaga agcacggacg ctcagagtcc    8100
tctccatggt gggggattgg cttgaaaaaa gaccaggagc cttttgtata aaagtgttgt    8160
gcccatacac cagcactatg atggaaaccc tggagcgact gcagcgtagg tatgggggag    8220
gactggtcag agtgccactc tcccgcaact ctacacatga gatgtactgg gtctctggag    8280
cgaaaagcaa caccataaaa agtgtgtcca ccacgagcca gctcctcttg gggcgcatgg    8340
acgggcccag gaggccagtg aaatatgagg aggatgtgaa tctcggctct ggcacgcggg    8400
ctgtggtaag ctgcgctgaa gctcccaaca tgaagatcat tggtaaccgc attgaaagga    8460
tccgcagtga gcacgcggaa acgtggttct ttgacgagaa ccacccatat aggacatggg    8520
cttaccatga aagctatgag gccccacaca aagggtcagc gtcctctcta ataaacgggg    8580
ttgtcaggct cctgtcaaaa ccctgggata tggtgactgg agtcacagga atagccatga    8640
ccgacaccac accgtatggt cagcaaagag ttttcaagga aaaagtggac actagggtgc    8700 cagacccca gaaggcact cgtcaggtta tgagcatggt ctcttcctgg ttgtggaaag    8760
agctaggcaa acacaaacgg ccacgagtct gtaccaaaga agagttcatc aacaaggttc    8820
gtagcaatgc agcattaggg gcaatatttg aagaggaaaa agagtggaag actgcagtgg    8880
aagctgtgaa cgatccaagg ttctgggctc tagtggacaa ggaaagagag caccacctga    8940
gaggagagtg ccagagttgt gtgtacaaca tgatgggaaa aagagaaaag aaacaagggg    9000
aatttggaaa ggccaagggc agccgcgcca tctggtatat gtggctaggg gctagatttc    9060
```

```
tagagttcga agcccttgga ttcttgaacg aggatcactg gatggggaga gagaactcag    9120
gaggtggtgt tgaagggctg ggattacaaa gactcggata tgtcctagaa gagatgagtc    9180
gcataccagg aggaaggatg tatgcagatg acactgctgg ctgggacacc cgcatcagca    9240
ggtttgatct ggagaatgaa gctctaatca ccaaccaaat ggagaaaggg cacagggcct    9300
tggcattggc cataatcaag tacacatacc aaaacaaagt ggtaaaggtc cttagaccag    9360
ctgaaaaagg gaagacagtt atggacatta tttcgagaca agaccaaagg gggagcggac    9420
aagttgtcac ttacgctctt aacacattta ccaacctagt ggtgcaactc attcggaata    9480
tggaggctga ggaagttcta gagatgcaag acttgtggct gctgcggagg tcagagaaag    9540
tgaccaactg gttgcagagc aacggatggg ataggctcaa cgaatggca gtcagtggag    9600
atgattgcgt tgtgaagcca attgatgata ggtttgcaca tgccctcagg ttcttgaatg    9660
atatgggaaa agttaggaag gacacacaag agtgaaacc ctcaactgga tgggacaact    9720
gggaagaagt tccgttttgc tcccaccact tcaacaagct ccatctcaag gacgggaggt    9780
ccattgtggt tccctgccgc caccaagatg aactgattgg ccgggccgc gtctctccag    9840
gggcgggatg gagcatccgg gagactgctt gcctagcaaa atcatatgcg caaatgtggc    9900
agctcccttta tttccacaga agggacctcc gactgatggc caatgccatt tgttcatctg    9960
tgccagttga ctgggttcca actgggagaa ctacctggtc aatccatgga agggagaat    10020
ggatgaccac tgaagacatg cttgtggtgt ggaacagagt gtggattgag gagaacgacc    10080
acatggaaga caagaccccca gttacgaaat ggacagacat tccctatttg ggaaaaaggg    10140
aagacttgtg gtgtggatct ctcataggc acagaccgcg caccacctgg gctgagaaca    10200
ttaaaaacac agtcaacatg gtgcgcagga tcataggtga tgaagaaaag tacatggact    10260
acctatccac ccaagttcgc tacttgggtg aagaagggtc tacacctgga gtgctgtaag    10320
caccaatctt agtgttgtca ggcctgctag tcagccacag cttggggaaa gctgtgcagc    10380
ctgtgaccc cccaggagaa gctgggaaac caagcctata gtcaggccga aacgccatg    10440
gcacggaaga agccatgctg cctgtgagcc cctcagagga cactgagtca aaaaacccca    10500
cgcgcttgga ggcgcaggat gggaaaagaa ggtggcgacc ttccccaccc ttcaatctgg    10560
ggcctgaact ggagatcagc tgtggatctc cagaagaggg actagtggtt agaggag    10617
```

<210> SEQ ID NO 14
<211> LENGTH: 498
<212> TYPE: PRT
<213> ORGANISM: Zika virus

<400> SEQUENCE: 14

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser

```
                    100                 105                 110
Leu Val Thr Cys Ala Lys Phe Thr Cys Ser Lys Lys Met Thr Gly Lys
                115                 120                 125

Ser Ile Gln Pro Glu Asn Leu Glu Tyr Arg Ile Met Leu Ser Val His
            130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
            195                 200                 205

Lys Glu Trp Phe His Asp Ile Pro Leu Pro Trp His Ala Gly Ala Asp
            210                 215                 220

Thr Gly Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
                260                 265                 270

Gly Ala Lys Gly Arg Leu Phe Ser Gly His Leu Lys Cys Arg Leu Lys
                275                 280                 285

Met Asp Lys Leu Arg Leu Lys Gly Val Ser Tyr Ser Leu Cys Thr Ala
            290                 295                 300

Ala Phe Thr Phe Thr Lys Val Pro Ala Glu Thr Leu His Gly Thr Val
305                 310                 315                 320

Thr Val Glu Val Gln Tyr Ala Gly Thr Asp Gly Pro Cys Lys Val Pro
                325                 330                 335

Ala Gln Met Ala Val Asp Met Gln Thr Leu Thr Pro Val Gly Arg Leu
                340                 345                 350

Ile Thr Ala Asn Pro Val Ile Thr Glu Ser Thr Glu Asn Ser Lys Met
            355                 360                 365

Met Leu Glu Leu Asp Pro Pro Phe Gly Asp Ser Tyr Ile Val Ile Gly
            370                 375                 380

Val Gly Asp Lys Lys Ile Thr His His Trp His Arg Ser Gly Ser Thr
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
                420                 425                 430

Asn Ser Leu Gly Lys Gly Ile His Gln Ile Phe Gly Ala Ala Phe Lys
            435                 440                 445

Ser Leu Phe Gly Gly Met Ser Trp Phe Ser Gln Ile Leu Ile Gly Thr
            450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala

<210> SEQ ID NO 15
<211> LENGTH: 498
```

<212> TYPE: PRT
<213> ORGANISM: Zika virus

<400> SEQUENCE: 15

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ser Gly Ala Asp
    210                 215                 220

Thr Glu Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Ser Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300

Ala Phe Thr Phe Thr Lys Val Pro Ala Glu Thr Leu His Gly Thr Val
305                 310                 315                 320

Thr Val Glu Val Gln Tyr Ala Gly Arg Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
        355                 360                 365

Met Leu Glu Leu Asp Pro Pro Phe Gly Asp Ser Tyr Ile Val Ile Gly
    370                 375                 380

Val Gly Asp Lys Lys Ile Thr His His Trp His Arg Ser Gly Ser Ile
385                 390                 395                 400
```

-continued

```
Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala

<210> SEQ ID NO 16
<211> LENGTH: 504
<212> TYPE: PRT
<213> ORGANISM: Zika virus
<220> FEATURE:
<221> NAME/KEY: misc_feature
<222> LOCATION: (156)..(162)
<223> OTHER INFORMATION: X=any amino acid

<400> SEQUENCE: 16

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Xaa Xaa Xaa Xaa Xaa
145                 150                 155                 160

Xaa Xaa Asn Arg Ala Glu Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
```

245                 250                 255
Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 17
<211> LENGTH: 504
<212> TYPE: PRT
<213> ORGANISM: Zika virus
<220> FEATURE:
<221> NAME/KEY: misc_feature
<222> LOCATION: (152)..(156)
<223> OTHER INFORMATION: X=any amino acid

<400> SEQUENCE: 17

Ile Arg Cys Ile Gly Val Ser Asn Arg Asp Phe Val Glu Gly Met Ser
1               5

```
Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
            115                 120                 125

Ser Ile Gln Pro Glu Asn Leu Glu Tyr Arg Ile Met Leu Ser Val His
130                 135                 140

Gly Ser Gln His Ser Gly Met Xaa Xaa Xaa Xaa Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
            195                 200                 205

Lys His Arg Leu Val Arg Lys Glu Trp Phe His Asp Ile Pro Leu Pro
        210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Asp Lys Lys Ile Thr His His Trp
385                 390                 395                 400

Leu Lys Lys Gly Ser Ser Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500
```

<210> SEQ ID NO 18
<211> LENGTH: 504
<212> TYPE: PRT
<213> ORGANISM: Zika virus

<400> SEQUENCE: 18

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380
```

```
Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
        420                 425                 430

Ser Val Gly Gly Val Phe Asn Ser Leu Gly Lys Gly Ile His Gln Ile
            435                 440                 445

Phe Gly Ala Ala Phe Lys Ser Leu Phe Gly Gly Met Ser Trp Phe Ser
        450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
            485                 490                 495

Phe Leu Ser Thr Ala Val Ser Ala
            500

<210> SEQ ID NO 19
<211> LENGTH: 504
<212> TYPE: PRT
<213> ORGANISM: Zika virus

<400> SEQUENCE: 19

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
```

```
                    245                 250                 255

Val Leu Gly Ser Gln Glu Gly Ala Val His Thr Ala Leu Ala Gly Ala
                260                 265                 270

Leu Glu Ala Glu Met Asp Gly Ala Lys Gly Arg Leu Phe Ser Gly His
                275                 280                 285

Leu Lys Cys Arg Leu Lys Met Asp Lys Leu Arg Leu Lys Gly Val Ser
            290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
                340                 345                 350

Thr Pro Val Gly Arg Leu Ile Thr Ala Asn Pro Val Ile Thr Glu Ser
                355                 360                 365

Thr Glu Asn Ser Lys Met Met Leu Glu Leu Asp Pro Pro Phe Gly Asp
            370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
                420                 425                 430

Ser Val Gly Gly Val Phe Asn Ser Leu Gly Lys Gly Ile His Gln Ile
                435                 440                 445

Phe Gly Ala Ala Phe Lys Ser Leu Phe Gly Gly Met Ser Trp Phe Ser
            450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
                500

<210> SEQ ID NO 20
<211> LENGTH: 504
<212> TYPE: PRT
<213> ORGANISM: Zika virus

<400> SEQUENCE: 20

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
                100                 105                 110
```

```
Leu Val Thr Cys Ala Lys Phe Thr Cys Ser Lys Lys Met Thr Gly Lys
            115                 120                 125

Ser Ile Gln Pro Glu Asn Leu Glu Tyr Arg Ile Met Leu Ser Val His
        130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 21
<211> LENGTH: 504
<212> TYPE: PRT
```

<213> ORGANISM: Zika virus

<400> SEQUENCE: 21

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400
```

-continued

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 22
<211> LENGTH: 504
<212> TYPE: PRT
<213> ORGANISM: Zika virus

<400> SEQUENCE: 22

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

-continued

```
Leu Glu Ala Glu Met Asp Gly Ala Lys Gly Arg Leu Phe Ser Gly His
            275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
                340                 345                 350

Thr Pro Val Gly Arg Leu Ile Thr Ala Asn Pro Val Ile Thr Glu Ser
                355                 360                 365

Thr Glu Asn Ser Lys Met Met Leu Glu Leu Asp Pro Pro Phe Gly Asp
370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
                420                 425                 430

Ser Val Gly Gly Val Phe Asn Ser Leu Gly Lys Gly Ile His Gln Ile
                435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
                500

<210> SEQ ID NO 23
<211> LENGTH: 504
<212> TYPE: PRT
<213> ORGANISM: Zika virus

<400> SEQUENCE: 23

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
                100                 105                 110

Leu Val Thr Cys Ala Lys Phe Thr Cys Ser Lys Lys Met Thr Gly Lys
            115                 120                 125

Ser Ile Gln Pro Glu Asn Leu Glu Tyr Arg Ile Met Leu Ser Val His
```

```
                130               135                140
Gly Ser Gln His Ser Gly Met Thr Val Asn Asp Ile Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 24
<211> LENGTH: 504
<212> TYPE: PRT
<213> ORGANISM: Zika virus

<400> SEQUENCE: 24
```

-continued

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Thr Val Asn Asp Ile Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
```

```
                    420                 425                 430
Ser Val Gly Gly Val Phe Asn Ser Leu Gly Lys Gly Ile His Gln Ile
                435                 440                 445

Phe Gly Ala Ala Phe Lys Ser Leu Phe Gly Gly Met Ser Trp Phe Ser
            450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 25
<211> LENGTH: 504
<212> TYPE: PRT
<213> ORGANISM: Zika virus

<400> SEQUENCE: 25

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285
```

```
Leu Lys Cys Arg Leu Lys Met Asp Lys Leu Arg Leu Lys Gly Val Ser
            290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                    325                 330                 335

Gly Pro Cys Lys Ile Pro Val Gln Met Ala Val Asp Met Gln Thr Leu
                340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                    405                 410                 415

Gly Ala Lys Arg Met Ala Val Leu Gly Asp Thr Ala Trp Asp Phe Gly
                420                 425                 430

Ser Val Gly Gly Val Phe Asn Ser Leu Gly Lys Gly Ile His Gln Ile
            435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                    485                 490                 495

Phe Leu Ser Thr Ala Val Ser Ala
            500

<210> SEQ ID NO 26
<211> LENGTH: 504
<212> TYPE: PRT
<213> ORGANISM: Zika virus

<400> SEQUENCE: 26

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Ile Gly His Glu Thr
145                 150                 155                 160
```

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Val Cys Thr Ala Ala Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 27
<211> LENGTH: 500
<212> TYPE: PRT
<213> ORGANISM: Zika virus

<400> SEQUENCE: 27

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr

```
            20                  25                  30
Val Met Ala Gln Asp Lys Pro Thr Val Asp Ile Glu Leu Val Thr Thr
        35                  40                  45
Thr Val Ser Asn Met Ala Glu Val Arg Ser Tyr Cys Tyr Glu Ala Ser
 50                  55                  60
Ile Ser Asp Met Ala Ser Asp Ser Arg Cys Pro Thr Gln Gly Glu Ala
 65                  70                  75                  80
Tyr Leu Asp Lys Gln Ser Asp Thr Gln Tyr Val Cys Lys Arg Thr Leu
                 85                  90                  95
Val Asp Arg Gly Trp Gly Asn Gly Cys Gly Leu Phe Gly Lys Gly Ser
            100                 105                 110
Leu Val Thr Cys Ala Lys Phe Thr Cys Ser Lys Lys Met Thr Gly Lys
            115                 120                 125
Ser Ile Gln Pro Glu Asn Leu Glu Tyr Arg Ile Met Leu Ser Val His
            130                 135                 140
Gly Ser Gln His Ser Gly Met Ile Gly Tyr Glu Thr Asp Glu Asp Arg
145                 150                 155                 160
Ala Lys Val Glu Val Thr Pro Asn Ser Pro Arg Ala Glu Ala Thr Leu
                165                 170                 175
Gly Gly Phe Gly Ser Leu Gly Leu Asp Cys Glu Pro Arg Thr Gly Leu
            180                 185                 190
Asp Phe Ser Asp Leu Tyr Tyr Leu Thr Met Asn Asn Lys His Trp Leu
            195                 200                 205
Val His Lys Glu Trp Phe His Asp Ile Pro Leu Pro Trp His Ala Gly
            210                 215                 220
Ala Asp Thr Gly Thr Pro His Trp Asn Asn Lys Glu Ala Leu Val Glu
225                 230                 235                 240
Phe Lys Asp Ala His Ala Lys Arg Gln Thr Val Val Val Leu Gly Ser
                245                 250                 255
Gln Glu Gly Ala Val His Thr Ala Leu Ala Gly Ala Leu Glu Ala Glu
            260                 265                 270
Met Asp Gly Ala Lys Gly Arg Leu Phe Ser Gly His Leu Lys Cys Arg
            275                 280                 285
Leu Lys Met Asp Lys Leu Arg Leu Lys Gly Val Ser Tyr Ser Leu Cys
            290                 295                 300
Thr Ala Ala Phe Thr Phe Thr Lys Val Pro Ala Glu Thr Leu His Gly
305                 310                 315                 320
Thr Val Thr Val Glu Val Gln Tyr Ala Gly Thr Asp Gly Pro Cys Lys
                325                 330                 335
Ile Pro Val Gln Met Ala Val Asp Met Gln Thr Leu Thr Pro Val Gly
            340                 345                 350
Arg Leu Ile Thr Ala Asn Pro Val Ile Thr Glu Ser Thr Glu Asn Ser
            355                 360                 365
Lys Met Met Leu Glu Leu Asp Pro Pro Phe Gly Asp Ser Tyr Ile Val
            370                 375                 380
Ile Gly Val Gly Asp Lys Lys Ile Thr His His Trp His Arg Ser Gly
385                 390                 395                 400
Ser Thr Ile Gly Lys Ala Phe Glu Ala Thr Val Arg Gly Ala Lys Arg
                405                 410                 415
Met Ala Val Leu Gly Asp Thr Ala Trp Asp Phe Gly Ser Val Gly Gly
            420                 425                 430
Val Phe Asn Ser Leu Gly Lys Gly Ile His Gln Ile Phe Gly Ala Ala
            435                 440                 445
```

```
Phe Lys Ser Leu Phe Gly Gly Met Ser Trp Phe Ser Gln Ile Leu Ile
    450                 455                 460
Gly Thr Leu Leu Val Trp Leu Gly Leu Asn Thr Lys Asn Gly Ser Ile
465                 470                 475                 480
Ser Leu Thr Cys Leu Ala Leu Gly Gly Val Met Ile Phe Leu Ser Thr
            485                 490                 495
Ala Val Ser Ala
            500

<210> SEQ ID NO 28
<211> LENGTH: 500
<212> TYPE: PRT
<213> ORGANISM: Zika virus

<400> SEQUENCE: 28

Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
                20                  25                  30
Val Met Ala Gln Asp Lys Pro Thr Val Asp Ile Glu Leu Val Thr Thr
            35                  40                  45
Thr Val Ser Asn Met Ala Glu Val Arg Ser Tyr Cys Tyr Glu Ala Ser
50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
            100                 105                 110
Leu Val Thr Cys Ala Lys Phe Thr Cys Ser Lys Lys Met Thr Gly Lys
        115                 120                 125
Ser Ile Gln Pro Glu Asn Leu Glu Tyr Arg Ile Met Leu Ser Val His
    130                 135                 140
Gly Ser Gln His Ser Gly Met Ile Gly Tyr Glu Thr Asp Glu Asp Arg
145                 150                 155                 160
Ala Lys Val Glu Val Thr Pro Asn Ser Pro Arg Ala Glu Ala Thr Leu
                165                 170                 175
Gly Gly Phe Gly Ser Leu Gly Leu Asp Cys Glu Pro Arg Thr Gly Leu
            180                 185                 190
Asp Phe Ser Asp Leu Tyr Tyr Leu Thr Met Asn Asn Lys His Trp Leu
        195                 200                 205
Val His Lys Glu Trp Phe His Asp Ile Pro Leu Pro Trp His Ala Gly
    210                 215                 220
Ala Asp Thr Gly Thr Pro His Trp Asn Asn Lys Glu Ala Leu Val Glu
225                 230                 235                 240
Phe Lys Asp Ala His Ala Lys Arg Gln Thr Val Val Val Leu Gly Ser
                245                 250                 255
Gln Glu Gly Ala Val His Thr Ala Leu Ala Gly Ala Leu Glu Ala Glu
            260                 265                 270
Met Asp Gly Ala Lys Gly Arg Leu Phe Ser Gly His Leu Lys Cys Arg
        275                 280                 285
Leu Lys Met Asp Lys Leu Arg Leu Lys Gly Val Ser Tyr Ser Leu Cys
    290                 295                 300
Thr Ala Ala Phe Thr Phe Thr Lys Val Pro Ala Glu Thr Leu His Gly
```

```
            305                 310                 315                 320
    Thr Val Thr Val Glu Val Gln Tyr Ala Gly Thr Asp Gly Pro Cys Lys
                    325                 330                 335

Ile Pro Val Gln Met Ala Val Asp Met Gln Thr Leu Thr Pro Val Gly
                    340                 345                 350

Arg Leu Ile Thr Ala Asn Pro Val Ile Thr Glu Ser Thr Glu Asn Ser
                    355                 360                 365

Lys Met Met Leu Glu Leu Asp Pro Pro Phe Gly Asp Ser Tyr Ile Val
                    370                 375                 380

Ile Gly Val Gly Asp Lys Lys Ile Thr His His Trp His Arg Ser Gly
    385                 390                 395                 400

Ser Thr Ile Gly Lys Ala Phe Glu Ala Thr Val Arg Gly Ala Lys Arg
                    405                 410                 415

Met Ala Val Leu Gly Asp Thr Ala Trp Asp Phe Gly Ser Val Gly Gly
                    420                 425                 430

Val Phe Asn Ser Leu Gly Lys Gly Ile His Gln Ile Phe Gly Ala Ala
                    435                 440                 445

Phe Lys Ser Leu Phe Gly Gly Met Ser Trp Phe Ser Gln Ile Leu Ile
                    450                 455                 460

Gly Thr Leu Leu Val Trp Leu Gly Leu Asn Thr Lys Asn Gly Ser Ile
    465                 470                 475                 480

Ser Leu Thr Cys Leu Ala Leu Gly Gly Val Met Ile Phe Leu Ser Thr
                    485                 490                 495

Ala Val Ser Ala
                    500

<210> SEQ ID NO 29
<211> LENGTH: 500
<212> TYPE: PRT
<213> ORGANISM: Zika virus

<400> SEQUENCE: 29

Ile Arg Cys Ile Gly Val Ser Asn Arg Asp Phe Val Glu Gly Met Ser
    1               5                   10                  15

Gly Gly Thr Trp Val Asp Val Val Leu Glu His Gly Gly Cys Val Thr
                    20                  25                  30

Val Met Ala Gln Asp Lys Pro Thr Val Asp Ile Glu Leu Val Thr Thr
                    35                  40                  45

Thr Val Ser Asn Met Ala Glu Val Arg Ser Tyr Cys Tyr Glu Ala Ser
                    50                  55                  60

Ile Ser Asp Met Ala Ser Asp Ser Arg Cys Pro Thr Gln Gly Glu Ala
    65                  70                  75                  80

Tyr Leu Asp Lys Gln Ser Asp Thr Gln Tyr Val Cys Lys Arg Thr Leu
                    85                  90                  95

Val Asp Arg Gly Trp Gly Asn Gly Cys Gly Leu Phe Gly Lys Gly Ser
                    100                 105                 110

Leu Val Thr Cys Ala Lys Phe Thr Cys Ser Lys Lys Met Thr Gly Lys
                    115                 120                 125

Ser Ile Gln Pro Glu Asn Leu Glu Tyr Arg Ile Met Leu Ser Val His
                    130                 135                 140

Gly Ser Gln His Ser Gly Met Ile Gly Tyr Glu Thr Asp Glu Asp Arg
    145                 150                 155                 160

Ala Lys Val Glu Val Thr Pro Asn Ser Pro Arg Ala Glu Ala Thr Leu
                    165                 170                 175
```

-continued

```
Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500

<210> SEQ ID NO 30
<211> LENGTH: 504
<212> TYPE: PRT
<213> ORGANISM: Zika virus

<400> SEQUENCE: 30

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45
```

```
Thr Val Ser Asn Met Ala Glu Val Arg Ser Tyr Cys Tyr Glu Ala Ser
     50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                 85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Thr Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Gly
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460
```

```
Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
            485                 490                 495

Phe Leu Ser Thr Ala Val Ser Ala
            500

<210> SEQ ID NO 31
<211> LENGTH: 504
<212> TYPE: PRT
<213> ORGANISM: Zika virus

<400> SEQUENCE: 31

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
210                 215                 220

Trp His Thr Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335
```

```
Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Gly
            355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Leu Asn Ser Leu Gly Lys Gly Ile His Gln Ile
            435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 32
<211> LENGTH: 504
<212> TYPE: PRT
<213> ORGANISM: Zika virus

<400> SEQUENCE: 32

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
```

```
            195                 200                 205
Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 33
<211> LENGTH: 504
<212> TYPE: PRT
<213> ORGANISM: Zika virus

<400> SEQUENCE: 33

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Le

```
Ile Ser Asp Met Ala Ser Asp Ser Arg Cys Pro Thr Gln Gly Glu Ala
 65                  70                  75                  80

Tyr Leu Asp Lys Gln Ser Asp Thr Gln Tyr Val Cys Lys Arg Thr Leu
                 85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
```

-continued

Phe Leu Ser Thr Ala Val Ser Ala
                500

<210> SEQ ID NO 34
<211> LENGTH: 504
<212> TYPE: PRT
<213> ORGANISM: Zika virus

<400> SEQUENCE: 34

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

```
Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
    435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 35
<211> LENGTH: 504
<212> TYPE: PRT
<213> ORGANISM: Zika virus

<400> SEQUENCE: 35

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220
```

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
            245                 250                 255

Val Leu Gly Ser Gln Glu Gly Ala Val His Thr Ala Leu Ala Gly Ala
        260                 265                 270

Leu Glu Ala Glu Met Asp Gly Ala Lys Gly Arg Leu Ser Ser Gly His
    275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
            325                 330                 335

Gly Pro Cys Lys Val Pro Ala Gln Met Ala Val Asp Met Gln Thr Leu
        340                 345                 350

Thr Pro Val Gly Arg Leu Ile Thr Ala Asn Pro Val Ile Thr Glu Ser
    355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
        420                 425                 430

Ser Val Gly Gly Ala Leu Asn Ser Leu Gly Lys Gly Ile His Gln Ile
    435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
            485                 490                 495

Phe Leu Ser Thr Ala Val Ser Ala
            500

<210> SEQ ID NO 36
<211> LENGTH: 504
<212> TYPE: PRT
<213> ORGANISM: Zika virus

<400> SEQUENCE: 36

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu

```
                85                  90                  95
Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
            115                 120                 125

Ser Ile Gln Pro Glu Asn Leu Glu Tyr Arg Ile Met Leu Ser Val His
            130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
            210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
            275                 280                 285

Leu Lys Cys Arg Leu Lys Met Asp Lys Leu Arg Leu Lys Gly Val Ser
            290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
            370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
            450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 37
<211> LENGTH: 504
<212> TYPE: PRT
<213> ORGANISM: Zika virus

<400> SEQUENCE: 37

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
```

```
            370                 375                 380
Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 38
<211> LENGTH: 504
<212> TYPE: PRT
<213> ORGANISM: Zika virus

<400> SEQUENCE: 38

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240
```

```
Ala Leu Val Glu Phe Lys Asp Ala His Ala Lys Arg Gln Thr Val Val
            245                 250                 255

Val Leu Gly Ser Gln Glu Gly Ala Val His Thr Ala Leu Ala Gly Ala
        260                 265                 270

Leu Glu Ala Glu Met Asp Gly Ala Lys Gly Arg Leu Ser Ser Gly His
    275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 39
<211> LENGTH: 504
<212> TYPE: PRT
<213> ORGANISM: Zika virus

<400> SEQUENCE: 39

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110
```

Leu Val Thr Cys Ala Lys Phe Ala Cys Ser Lys Lys Met Thr Gly Lys
            115                 120                 125

Ser Ile Gln Pro Glu Asn Leu Glu Tyr Arg Ile Met Leu Ser Val His
        130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 40
<211> LENGTH: 504

```
<212> TYPE: PRT
<213> ORGANISM: Zika virus

<400> SEQUENCE: 40

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400
```

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
        420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
            485                 490                 495

Phe Leu Ser Thr Ala Val Ser Ala
            500

<210> SEQ ID NO 41
<211> LENGTH: 504
<212> TYPE: PRT
<213> ORGANISM: Zika virus

<400> SEQUENCE: 41

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala

```
                260                 265                 270
Leu Glu Ala Glu Met Asp Gly Ala Lys Gly Arg Leu Ser Ser Gly His
            275                 280                 285

Leu Lys Cys Arg Leu Lys Met Asp Lys Leu Arg Leu Lys Gly Val Ser
            290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
            370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
            450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 42
<211> LENGTH: 504
<212> TYPE: PRT
<213> ORGANISM: Zika virus

<400> SEQUENCE: 42

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
50              55                  60

Ile Ser Asp Met Ala Ser Asp Ser Arg Cys Pro Thr Gln Gly Glu Ala
65              70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
            115                 120                 125
```

```
Ser Ile Gln Pro Glu Asn Leu Glu Tyr Arg Ile Met Leu Ser Val His
    130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
    290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
            420                 425                 430
Ser Val Gly Gly Ala Leu Asn Ser Leu Gly Lys Gly Ile His Gln Ile
        435                 440                 445
Phe Gly Ala Ala Phe Lys Ser Leu Phe Gly Gly Met Ser Trp Phe Ser
    450                 455                 460
Gln Ile Leu Ile Gly Thr Leu Leu Met Trp Leu Gly Leu Asn Thr Lys
465                 470                 475                 480
Asn Gly Ser Ile Ser Leu Met Cys Leu Ala Leu Gly Gly Val Leu Ile
                485                 490                 495
Phe Leu Ser Thr Ala Val Ser Ala
            500

<210> SEQ ID NO 43
<211> LENGTH: 504
<212> TYPE: PRT
<213> ORGANISM: Zika virus

<400> SEQUENCE: 43
```

```
Ile Arg Cys Ile Gly Val Ser Asn Arg Asp Phe Val Glu Gly Met Ser
1               5                   10                  15
Gly Gly Thr Trp Val Asp Val Leu Glu His Gly Cys Val Thr
            20                  25              30
Val Met Ala Gln Asp Lys Pro Thr Val Asp Ile Glu Leu Val Thr Thr
        35              40                  45
Thr Val Ser Asn Met Ala Glu Val Arg Ser Tyr Cys Tyr Glu Ala Ser
    50              55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
                100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
                180                 185                 190
Arg Thr Gly Leu Asp Phe Ser Asp Leu Tyr Tyr Leu Thr Met Asn Asn
                195                 200                 205
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
                260                 265                 270
Leu Glu Ala Glu Met Asp Gly Ala Lys Gly Arg Leu Ser Ser Gly His
                275                 280                 285
Leu Lys Cys Arg Leu Lys Met Asp Lys Leu Arg Leu Lys Gly Val Ser
    290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
                340                 345                 350
Thr Pro Val Gly Arg Leu Ile Thr Ala Asn Pro Val Ile Thr Glu Ser
                355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
```

```
Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 44
<211> LENGTH: 504
<212> TYPE: PRT
<213> ORGANISM: Zika virus

<400> SEQUENCE: 44

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285
```

-continued

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
            325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
            485                 490                 495

Phe Leu Ser Thr Ala Val Ser Ala
            500

<210> SEQ ID NO 45
<211> LENGTH: 504
<212> TYPE: PRT
<213> ORGANISM: Zika virus

<400> SEQUENCE: 45

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr

```
              145                 150                 155                 160
Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 46
<211> LENGTH: 504
<212> TYPE: PRT
<213> ORGANISM: Zika virus

<400> SEQUENCE: 46

Ile Arg Cys Ile Gly Val Ser Asn Arg Asp Phe Val Glu Gly Met Ser
1               5                   10                  15
```

-continued

```
Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
```

```
            435                 440                 445
Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 47
<211> LENGTH: 504
<212> TYPE: PRT
<213> ORGANISM: Zika virus

<400> SEQUENCE: 47

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
    115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
    195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
    275                 280                 285

Leu Lys Cys Arg Leu Lys Met Asp Lys Leu Arg Leu Lys Gly Val Ser
290                 295                 300
```

```
Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 48
<211> LENGTH: 504
<212> TYPE: PRT
<213> ORGANISM: Zika virus

<400> SEQUENCE: 48

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175
```

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 49
<211> LENGTH: 504
<212> TYPE: PRT
<213> ORGANISM: Zika virus

<400> SEQUENCE: 49

Ile Arg Cys Ile Gly Val Ser Asn Arg Asp Phe Val Glu Gly Met Ser
1               5                   10                  15

Gly Gly Thr Trp Val Asp Ile Val Leu Glu His Gly Gly Cys Val Thr
            20                  25                  30

Val Met Ala Gln Asp Lys Pro Thr Val Asp Ile Glu Leu Val Thr Thr

-continued

```
                35                  40                  45
Thr Val Ser Asn Met Ala Glu Val Arg Ser Tyr Cys Tyr Glu Ala Ser
                50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
                100                 105                 110
Leu Val Thr Cys Ala Lys Phe Ala Cys Ser Lys Lys Met Thr Gly Lys
                115                 120                 125
Ser Ile Gln Pro Glu Asn Leu Glu Tyr Arg Ile Met Leu Ser Val His
                130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
                180                 185                 190
Arg Thr Gly Leu Asp Phe Ser Asp Leu Tyr Tyr Leu Thr Met Asn Asn
                195                 200                 205
Lys His Trp Leu Val His Lys Glu Trp Phe His Asp Ile Pro Leu Pro
                210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
                260                 265                 270
Leu Glu Ala Glu Met Asp Gly Ala Lys Gly Arg Leu Ser Ser Gly His
                275                 280                 285
Leu Lys Cys Arg Leu Lys Met Asp Lys Leu Arg Leu Lys Gly Val Ser
                290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
                340                 345                 350
Thr Pro Val Gly Arg Leu Ile Thr Ala Asn Pro Val Ile Thr Glu Ser
                355                 360                 365
Thr Glu Asn Ser Lys Met Met Leu Glu Leu Asp Pro Pro Phe Gly Asp
                370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
                420                 425                 430
Ser Val Gly Gly Ala Leu Asn Ser Leu Gly Lys Gly Ile His Gln Ile
                435                 440                 445
Phe Gly Ala Ala Phe Lys Ser Leu Phe Gly Gly Met Ser Trp Phe Ser
                450                 455                 460
```

```
Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 50
<211> LENGTH: 504
<212> TYPE: PRT
<213> ORGANISM: Zika virus

<400> SEQUENCE: 50

Ile Arg Cys Ile Gly Val Ser Asn Arg Asp Phe Val Glu Gly Met Ser
1               5                   10                  15

Gly Gly Thr Trp Val Asp Ile Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
        290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
```

```
                       325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 51
<211> LENGTH: 504
<212> TYPE: PRT
<213> ORGANISM: Zika virus

<400> SEQUENCE: 51

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Ile Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190
```

```
Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 52
<211> LENGTH: 504
<212> TYPE: PRT
<213> ORGANISM: Zika virus

<400> SEQUENCE: 52

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
50                  55                  60
```

```
Ile Ser Asp Met Ala Ser Asp Ser Arg Cys Pro Thr Gln Gly Glu Ala
 65                  70                  75                  80

Tyr Leu Asp Lys Gln Ser Asp Thr Gln Tyr Val Cys Lys Arg Thr Leu
                 85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Thr Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480
```

```
Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 53
<211> LENGTH: 504
<212> TYPE: PRT
<213> ORGANISM: Zika virus

<400> SEQUENCE: 53

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Thr Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350
```

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
        370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
        450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 54
<211> LENGTH: 504
<212> TYPE: PRT
<213> ORGANISM: Zika virus

<400> SEQUENCE: 54

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro

```
                210                 215                 220
Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
                260                 265                 270

Leu Glu Ala Glu Met Asp Gly Ala Lys Gly Arg Leu Ser Ser Gly His
                275                 280                 285

Leu Lys Cys Arg Leu Lys Met Asp Lys Leu Arg Leu Lys Gly Val Ser
                290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
                340                 345                 350

Thr Pro Val Gly Arg Leu Ile Thr Ala Asn Pro Val Ile Thr Glu Ser
                355                 360                 365

Thr Glu Asn Ser Lys Met Met Leu Glu Leu Asp Pro Pro Phe Gly Asp
                370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Arg Arg Met Ala Val Leu Gly Asp Thr Ala Trp Asp Phe Gly
                420                 425                 430

Ser Val Gly Gly Ala Leu Asn Ser Leu Gly Lys Gly Ile His Gln Ile
                435                 440                 445

Phe Gly Ala Ala Phe Lys Ser Leu Phe Gly Gly Met Ser Trp Phe Ser
                450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
                500

<210> SEQ ID NO 55
<211> LENGTH: 504
<212> TYPE: PRT
<213> ORGANISM: Zika virus

<400> SEQUENCE: 55

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
                35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80
```

```
Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
            115                 120                 125

Ser Ile Gln Pro Glu Asn Leu Glu Tyr Arg Ile Met Leu Ser Val His
        130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
        210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
            275                 280                 285

Leu Lys Cys Arg Leu Lys Met Asp Lys Leu Arg Leu Lys Gly Val Ser
        290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
        370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
        450                 455                 460

Gln Ile Leu Ile Gly Thr Leu Leu Val Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
```

500

<210> SEQ ID NO 56
<211> LENGTH: 504
<212> TYPE: PRT
<213> ORGANISM: Zika virus

<400> SEQUENCE: 56

| Ile | Arg | Cys | Ile | Gly | Val | Ser | Asn | Arg | Asp | Phe | Val | Glu | Gly | Met | Ser |
|---|---|---|---|---|---|---|---|---|---|---|---|---|---|---|---|
| 1 | | | | 5 | | | | | 10 | | | | | 15 | |

| Gly | Gly | Thr | Trp | Val | Asp | Val | Val | Leu | Glu | His | Gly | Gly | Cys | Val | Thr |
| | | | 20 | | | | | 25 | | | | | 30 | | |

| Val | Met | Ala | Gln | Asp | Lys | Pro | Thr | Val | Asp | Ile | Glu | Leu | Val | Thr | Thr |
| | | 35 | | | | | 40 | | | | | 45 | | | |

| Thr | Val | Ser | Asn | Met | Ala | Glu | Val | Arg | Ser | Tyr | Cys | Tyr | Glu | Ala | Ser |
| | 50 | | | | | 55 | | | | | 60 | | | | |

| Ile | Ser | Asp | Met | Ala | Ser | Asp | Ser | Arg | Cys | Pro | Thr | Gln | Gly | Glu | Ala |
| 65 | | | | | 70 | | | | | 75 | | | | | 80 |

| Tyr | Leu | Asp | Lys | Gln | Ser | Asp | Thr | Gln | Tyr | Val | Cys | Lys | Arg | Thr | Leu |
| | | | | 85 | | | | | 90 | | | | | 95 | |

| Val | Asp | Arg | Gly | Trp | Gly | Asn | Gly | Cys | Gly | Leu | Phe | Gly | Lys | Gly | Ser |
| | | | 100 | | | | | 105 | | | | | 110 | | |

| Leu | Val | Thr | Cys | Ala | Lys | Phe | Ala | Cys | Ser | Lys | Lys | Met | Thr | Gly | Lys |
| | | 115 | | | | | 120 | | | | | 125 | | | |

| Ser | Ile | Gln | Pro | Glu | Asn | Leu | Glu | Tyr | Arg | Ile | Met | Leu | Ser | Val | His |
| 130 | | | | | 135 | | | | | 140 | | | | | |

| Gly | Ser | Gln | His | Ser | Gly | Met | Ile | Val | Asn | Asp | Thr | Gly | His | Glu | Thr |
| 145 | | | | | 150 | | | | | 155 | | | | | 160 |

| Asp | Glu | Asn | Arg | Ala | Lys | Val | Glu | Ile | Thr | Pro | Asn | Ser | Pro | Arg | Ala |
| | | | | 165 | | | | | 170 | | | | | 175 | |

| Glu | Ala | Thr | Leu | Gly | Gly | Phe | Gly | Ser | Leu | Gly | Leu | Asp | Cys | Glu | Pro |
| | | | 180 | | | | | 185 | | | | | 190 | | |

| Arg | Thr | Gly | Leu | Asp | Phe | Ser | Asp | Leu | Tyr | Tyr | Leu | Thr | Met | Asn | Asn |
| | | 195 | | | | | 200 | | | | | 205 | | | |

| Lys | His | Trp | Leu | Val | His | Lys | Glu | Trp | Phe | His | Asp | Ile | Pro | Leu | Pro |
| 210 | | | | | 215 | | | | | 220 | | | | | |

| Trp | His | Ala | Gly | Ala | Asp | Thr | Gly | Thr | Pro | His | Trp | Asn | Asn | Lys | Glu |
| 225 | | | | | 230 | | | | | 235 | | | | | 240 |

| Ala | Leu | Val | Glu | Phe | Lys | Asp | Ala | His | Ala | Lys | Arg | Gln | Thr | Val | Val |
| | | | | 245 | | | | | 250 | | | | | 255 | |

| Val | Leu | Gly | Ser | Gln | Glu | Gly | Ala | Val | His | Thr | Ala | Leu | Ala | Gly | Ala |
| | | | 260 | | | | | 265 | | | | | 270 | | |

| Leu | Glu | Ala | Glu | Met | Asp | Gly | Ala | Lys | Gly | Arg | Leu | Ser | Ser | Gly | His |
| | | 275 | | | | | 280 | | | | | 285 | | | |

| Leu | Lys | Cys | Arg | Leu | Lys | Met | Asp | Lys | Leu | Arg | Leu | Lys | Gly | Val | Ser |
| 290 | | | | | 295 | | | | | 300 | | | | | |

| Tyr | Ser | Leu | Cys | Thr | Ala | Ala | Phe | Thr | Phe | Thr | Lys | Ile | Pro | Ala | Glu |
| 305 | | | | | 310 | | | | | 315 | | | | | 320 |

| Thr | Leu | His | Gly | Thr | Val | Thr | Val | Glu | Val | Gln | Tyr | Ala | Gly | Thr | Asp |
| | | | | 325 | | | | | 330 | | | | | 335 | |

| Gly | Pro | Cys | Lys | Val | Pro | Ala | Gln | Met | Ala | Val | Asp | Met | Gln | Thr | Leu |
| | | | 340 | | | | | 345 | | | | | 350 | | |

| Thr | Pro | Val | Gly | Arg | Leu | Ile | Thr | Ala | Asn | Pro | Val | Ile | Thr | Glu | Ser |
| | | | 355 | | | | | 360 | | | | | 365 | | |

```
Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
                420                 425                 430

Ser Val Gly Gly Ala Leu Asn Ser Leu Gly Lys Gly Ile His Gln Ile
                435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
                500

<210> SEQ ID NO 57
<211> LENGTH: 504
<212> TYPE: PRT
<213> ORGANISM: Zika virus

<400> SEQUENCE: 57

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
                35                  40                  45

Thr Val Ser Asn Met Ala Glu Val Arg Ser Tyr Cys Tyr Glu Ala Ser
            50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
                100                 105                 110

Leu Val Thr Cys Ala Lys Phe Ala Cys Ser Lys Lys Met Thr Gly Lys
                115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
                180                 185                 190

Arg Thr Gly Leu Asp Phe Ser Asp Leu Tyr Tyr Leu Thr Met Asn Asn
                195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240
```

```
Ala Leu Val Glu Phe Lys Asp Ala His Ala Lys Arg Gln Thr Val Val
            245                 250                 255

Val Leu Gly Ser Gln Glu Gly Ala Val His Thr Ala Leu Ala Gly Ala
        260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
        290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
            325                 330                 335

Gly Pro Cys Lys Val Pro Ala Gln Met Ala Val Asp Met Gln Thr Leu
        340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
        370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
        420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
        450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
            485                 490                 495

Phe Leu Ser Thr Ala Val Ser Ala
            500

<210> SEQ ID NO 58
<211> LENGTH: 504
<212> TYPE: PRT
<213> ORGANISM: Zika virus

<400> SEQUENCE: 58

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
```

```
            100                 105                 110
Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Thr Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 59
```

```
<211> LENGTH: 504
<212> TYPE: PRT
<213> ORGANISM: Zika virus

<400> SEQUENCE: 59

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Gly Thr His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
```

```
                385                 390                 395                 400
His Arg Ser Gly Ser Thr Ile Gly Lys Ala Phe Glu Ala Thr Val Arg
                    405                 410                 415

Gly Ala Lys Arg Met Ala Val Leu Gly Asp Thr Ala Trp Asp Phe Gly
                    420                 425                 430

Ser Val Gly Gly Ala Leu Asn Ser Leu Gly Lys Gly Ile His Gln Ile
                    435                 440                 445

Phe Gly Ala Ala Phe Lys Ser Leu Phe Gly Gly Met Ser Trp Phe Ser
                    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                    485                 490                 495

Phe Leu Ser Thr Ala Val Ser Ala
                    500

<210> SEQ ID NO 60
<211> LENGTH: 504
<212> TYPE: PRT
<213> ORGANISM: Zika virus

<400> SEQUENCE: 60

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
                35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
                100                 105                 110

Leu Val Thr Cys Ala Lys Phe Ala Cys Ser Lys Lys Met Thr Gly Lys
                115                 120                 125

Ser Ile Gln Pro Glu Asn Leu Glu Tyr Arg Ile Met Leu Ser Val His
                130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
                180                 185                 190

Arg Thr Gly Leu Asp Phe Ser Asp Leu Tyr Tyr Leu Thr Met Asn Asn
                195                 200                 205

Lys His Trp Leu Val His Lys Glu Trp Phe His Asp Ile Pro Leu Pro
                210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255
```

-continued

```
Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Leu Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 61
<211> LENGTH: 504
<212> TYPE: PRT
<213> ORGANISM: Zika virus

<400> SEQUENCE: 61

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Ala Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125
```

```
Ser Ile Gln Pro Glu Asn Leu Glu Tyr Arg Ile Met Leu Ser Val His
        130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
            420                 425                 430
Ser Val Gly Gly Ala Leu Asn Ser Leu Gly Lys Gly Ile His Gln Ile
        435                 440                 445
Phe Gly Ala Ala Phe Lys Ser Leu Phe Gly Gly Met Ser Trp Phe Ser
450                 455                 460
Gln Ile Leu Ile Gly Thr Leu Leu Val Trp Leu Gly Leu Asn Thr Lys
465                 470                 475                 480
Asn Gly Ser Ile Ser Leu Thr Cys Leu Ala Leu Gly Gly Val Leu Ile
                485                 490                 495
Phe Leu Ser Thr Ala Val Ser Ala
            500

<210> SEQ ID NO 62
<211> LENGTH: 504
<212> TYPE: PRT
<213> ORGANISM: Zika virus
```

<400> SEQUENCE: 62

```
Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
            20                  25                  30
Val Met Ala Gln Asp Lys Pro Thr Val Asp Ile Glu Leu Val Thr Thr
        35                  40                  45
Thr Val Ser Asn Met Ala Glu Val Arg Ser Tyr Cys Tyr Glu Ala Ser
    50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
    290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
```

-continued

Gly Ala Lys Arg Met Ala Val Leu Gly Asp Thr Ala Trp Asp Phe Gly
                420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
        450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
                500

<210> SEQ ID NO 63
<211> LENGTH: 504
<212> TYPE: PRT
<213> ORGANISM: Zika virus

<400> SEQUENCE: 63

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His

```
                275                 280                 285
Leu Lys Cys Arg Leu Lys Met Asp Lys Leu Arg Leu Lys Gly Val Ser
    290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
            420                 425                 430
Ser Val Gly Gly Ala Leu Asn Ser Leu Gly Lys Gly Ile His Gln Ile
        435                 440                 445
Phe Gly Ala Ala Phe Lys Ser Leu Phe Gly Gly Met Ser Trp Phe Ser
    450                 455                 460
Gln Ile Leu Ile Gly Thr Leu Leu Val Trp Leu Gly Leu Asn Thr Lys
465                 470                 475                 480
Asn Gly Ser Ile Ser Leu Thr Cys Leu Ala Leu Gly Gly Val Leu Ile
                485                 490                 495
Phe Leu Ser Thr Ala Val Ser Ala
            500

<210> SEQ ID NO 64
<211> LENGTH: 504
<212> TYPE: PRT
<213> ORGANISM: Zika virus

<400> SEQUENCE: 64

Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
            20                  25                  30
Val Met Ala Gln Asp Lys Pro Thr Val Asp Ile Glu Leu Val Ser Thr
        35                  40                  45
Thr Val Ser Asn Met Ala Glu Val Arg Ser Tyr Cys Tyr Glu Ala Thr
    50                  55                  60
Ile Ser Asp Ile Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
```

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
            165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
            210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Ala Val
            245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
            275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
            325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
            370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
            485                 490                 495

Phe Leu Ser Thr Ala Val Ser Ala
            500

<210> SEQ ID NO 65
<211> LENGTH: 504
<212> TYPE: PRT
<213> ORGANISM: Zika virus
<220> FEATURE:
<221> NAME/KEY: misc_feature
<222> LOCATION: (1)..(504)
<223> OTHER INFORMATION: X=any amino acid

<400> SEQUENCE: 65

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Xaa Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

Xaa Arg Ser Gly Ser Thr Ile Gly Lys Ala Phe Glu Ala Thr Val Arg
                405                 410                 415
```

```
Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500
```

<210> SEQ ID NO 66
<211> LENGTH: 504
<212> TYPE: PRT
<213> ORGANISM: Zika virus

<400> SEQUENCE: 66

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Ala Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Leu Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Ala His Lys Glu Trp Phe His Asp Ile Pro Leu Pro
210                 215                 220

Trp His Ala Gly Ala Ala Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
```

```
            275                 280                 285
Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Val Asp Gly Thr Val Thr Val Glu Gly Gln Tyr Gly Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Ile Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Gly
            500

<210> SEQ ID NO 67
<211> LENGTH: 504
<212> TYPE: PRT
<213> ORGANISM: Zika virus

<400> SEQUENCE: 67

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Ala Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140
```

```
Gly Ser Gln His Ser Gly Met Leu Val Asn Asp Thr Gly His Glu Thr
145                 150                 155                 160

Asp Glu Asn Arg Ala Lys Val Glu Ile Thr Pro Asn Ser Pro Arg Ala
            165                 170                 175

Glu Ala Thr Leu Gly Gly Phe Gly Ser Leu Gly Leu Asp Cys Glu Pro
        180                 185                 190

Arg Thr Gly Leu Asp Phe Ser Asp Leu Tyr Tyr Leu Thr Met Asn Asn
    195                 200                 205

Lys His Trp Leu Ala His Lys Glu Trp Phe His Asp Ile Pro Leu Pro
210                 215                 220

Trp His Ala Gly Ala Ala Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Val Asp Gly Thr Val Thr Val Glu Gly Gln Tyr Gly Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Ile Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Gly
            500

<210> SEQ ID NO 68
<211> LENGTH: 504
<212> TYPE: PRT
<213> ORGANISM: Zika virus

<400> SEQUENCE: 68

Ile Ser Cys Ile Gly Val Ser Asn Arg Asp Leu Val Glu Gly Met Ser
1               5                   10                  15
```

-continued

Gly Gly Thr Trp Val Asp Val Leu Glu His Gly Gly Cys Val Thr
            20              25              30

Glu Met Ala Gln Asp Lys Pro Thr Val Asp Ile Glu Leu Val Thr Met
        35              40              45

Thr Val Ser Asn Met Ala Glu Val Arg Ser Tyr Cys Tyr Glu Ala Ser
50              55              60

Leu Ser Asp Met Ala Ser Ala Ser Arg Cys Pro Thr Gln Gly Glu Pro
65              70              75              80

Ser Leu Asp Lys Gln Ser Asp Thr Gln Ser Val Cys Lys Arg Thr Leu
            85              90              95

Gly Asp Arg Gly Trp Gly Asn Gly Cys Gly Ile Phe Gly Lys Gly Ser
            100             105             110

Leu Val Thr Cys Ser Lys Phe Thr Cys Lys Lys Met Pro Gly Lys
            115             120             125

Ser Ile Gln Pro Glu Asn Leu Glu Tyr Arg Ile Met Leu Pro Val His
    130             135             140

Gly Ser Gln His Ser Gly Met Ile Val Asn Asp Ile Gly His Glu Thr
145             150             155             160

Asp Glu Asn Arg Ala Lys Val Glu Val Thr Pro Asn Ser Pro Arg Ala
                165             170             175

Glu Ala Thr Leu Gly Gly Phe Gly Ser Leu Gly Leu Asp Cys Glu Pro
            180             185             190

Arg Thr Gly Leu Asp Phe Ser Asp Leu Tyr Tyr Leu Thr Met Asn Asn
            195             200             205

Lys His Trp Leu Val His Lys Glu Trp Phe His Asp Ile Pro Leu Pro
    210             215             220

Trp His Ala Gly Ala Asp Thr Gly Thr Pro His Trp Asn Asn Lys Glu
225             230             235             240

Ala Leu Val Glu Phe Lys Asp Ala His Ala Lys Arg Gln Thr Val Val
            245             250             255

Val Leu Gly Ser Gln Glu Gly Ala Val His Thr Ala Leu Ala Gly Ala
            260             265             270

Leu Glu Ala Glu Met Asp Gly Ala Lys Gly Arg Leu Phe Ser Gly His
            275             280             285

Leu Lys Cys Arg Leu Lys Met Asp Lys Leu Arg Leu Lys Gly Val Ser
    290             295             300

Tyr Ser Leu Cys Thr Ala Ala Phe Thr Phe Thr Lys Val Pro Ala Glu
305             310             315             320

Thr Leu His Gly Thr Val Thr Val Glu Val Gln Ser Ala Gly Thr Asp
            325             330             335

Gly Pro Cys Lys Val Pro Ala Gln Met Ala Val Asp Met Gln Thr Leu
            340             345             350

Thr Pro Val Gly Arg Leu Ile Thr Ala Asn Pro Val Ile Thr Glu Ser
            355             360             365

Thr Glu Asn Ser Lys Met Met Leu Glu Leu Asp Pro Pro Phe Gly Asp
            370             375             380

Ser Tyr Ile Val Ile Gly Val Gly Asp Lys Lys Ile Thr His His Trp
385             390             395             400

His Arg Ser Gly Ser Thr Ile Gly Lys Ala Phe Glu Ala Thr Val Arg
                405             410             415

Gly Ala Lys Arg Met Ala Val Leu Gly Asp Thr Ala Trp Asp Phe Gly
            420             425             430

```
Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
                500

<210> SEQ ID NO 69
<211> LENGTH: 498
<212> TYPE: PRT
<213> ORGANISM: Zika virus

<400> SEQUENCE: 69

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ala Gly Ala Asp
    210                 215                 220

Thr Gly Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Phe Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300
```

```
Ala Phe Thr Phe Thr Lys Val Pro Ala Glu Thr Leu His Gly Thr Val
305                 310                 315                 320

Thr Val Glu Val Gln Tyr Ala Gly Thr Asp Gly Pro Cys Lys Val Pro
            325                 330                 335

Ala Gln Met Ala Val Asp Met Gln Thr Leu Thr Pro Val Gly Arg Leu
        340                 345                 350

Ile Thr Ala Asn Pro Val Ile Thr Glu Ser Thr Glu Asn Ser Lys Met
    355                 360                 365

Met Leu Glu Leu Asp Pro Pro Phe Gly Asp Ser Tyr Ile Val Ile Gly
370                 375                 380

Val Gly Asp Lys Lys Ile Thr His His Trp His Arg Ser Gly Ser Thr
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
    450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala

<210> SEQ ID NO 70
<211> LENGTH: 26
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(26)
<223> OTHER INFORMATION: n=inosine

<400> SEQUENCE: 70
ncncncncnc ncncncncnc ncncnc                                      26

<210> SEQ ID NO 71
<211> LENGTH: 11
<212> TYPE: PRT
<213> ORGANISM: Artificial Sequence
<220> FEATURE:
<223> OTHER INFORMATION: synthetic peptide

<400> SEQUENCE: 71

Lys Leu Lys Leu Leu Leu Leu Lys Leu Lys
1               5                   10

<210> SEQ ID NO 72
<211> LENGTH: 11840
<212> TYPE: DNA
<213> ORGANISM: Chikungunya virus

<400> SEQUENCE: 72
atggctgcgt gagacacacg tagcctacca gtttcttact gctctactct gcaaagcaag    60
agattaataa cccatcatgg atcctgtgta cgtggacata gacgctgaca cgcgcctttt   120
```

```
gaaggccctg caacgtgcgt accccatgtt tgaggtggaa ccaaggcagg tcacaccgaa    180
tgaccatgct aatgctagag cgttctcgca tctagctata aaactaatag agcaggaaat    240
tgaccccgac tcaaccatcc tggatatcgg cagtgcgcca gcaaggagga tgatgtcgga    300
caggaagtac cactgcgtct gcccgatgcg cagtgcggaa gatcccgaga gactcgccaa    360
ttatgcgaga aagctagcat ctgccgcagg aaaagtcctg gacagaaaca tctctggaaa    420
gatcggggac ttacaagcag taatggccgt gccagacacg gagacgccaa cattctgctt    480
acacacagac gtctcatgta gacagagagc agacgtcgct ataccaagac gtctatgc     540 tgtacacgca cccacgtcgc tataccacca ggcgattaaa ggggtccgag tggcgtactg    600
ggttgggttc gacacaaccc cgttcatgta caatgccatg gcgggtgcct acccctcata    660
ctcgacaaac tgggcagatg agcaggtact gaaggctaag aacataggat tatgttcaac    720
agacctgacg gaaggtagac gaggcaagtt gtctattatg agagggaaaa agctaaaacc    780
gtgcgaccgt gtgctgttct cagtagggtc aacgctctac ccggaaagcc gcaagctact    840
taagagctgg cacctgccat cggtgttcca tttaaagggc aaactcagct tcacatgccg    900
ctgtgataca gtggtttcgt gtgagggcta cgtcgttaag agaataacga tgagcccagg    960
cctttatgga aaaccacag ggtatgcggt aacccaccac gcagacggat tcctgatgtg   1020
caagactacc gacacggttg acggcgaaag artgtcattc tcggtgtgca catacgtgcc   1080
ggcgaccatt tgtgatcaaa tgaccggcat ccttgctaca gaagtcacgc cggaggatgc   1140
acagaagctg ttggtggggc tgaaccgag aatagtggtt aacggcagaa cgcaacggaa    1200
tacgaacacc atgaaaaatt atctgcttcc cgtggtcgcc caagccttca gtaagtgggc   1260
aaaggagtgc cggaaagaca tggaagatga aaaactcctg ggggtcagag aaagaacact   1320
gacctgctgc tgtctatggg cattcaagaa gcagaaaaca cacacggtct acaagaggcc   1380
tgatacccag tcaattcaga aggttcaggc cgagtttgac agctttgtgg taccgagtct   1440
gtggtcgtcc gggttgtcaa tcccttttgag gactagaatc aaatggttgt taagcaaggt   1500
gccaaaaacc gacctgatcc catacagcgg agacgcccga gaagcccggg acgcagaaaa   1560
agaagcagag gaagaacgag aagcagaact gactcgcgaa gccctaccac ctctacaggc   1620
agcacaggaa gatgttcagg tcgaaatcga cgtggaacag cttgaggaca gagcgggcgc   1680
aggaataata gagactccga gaggagctat caaagttact gcccaaccaa cagaccacgt   1740
cgtgggagag tacctggtac tctccccgca gaccgtacta cgtagccaga agctcagtct   1800
gattcacgct ttggcggagc aagtgaagac gtgcacgcac aacggacgag cagggaggta   1860
tgcggtcgaa gcgtacgacg gccgagtcct agtgccctca ggctatgcaa tctcgcctga   1920
agacttccag agtctaagcg aaagcgcaac gatggtgtat aacgaaagag agttcgtaaa   1980
cagaaagcta caccatattg cgatgcacgg accagccctg aacaccgacg aagagtcgta   2040
tgagctggtg agggcagaga ggacagaaca cgagtacgtc tacgacgtgg atcagagaag   2100
atgctgtaag aaggaagaag ccgcaggact ggtactggtg ggcgacttga ctaatccgcc   2160
ctaccacgaa ttcgcatatg aagggctaaa aatccgccct gcctgcccat acaaaattgc   2220
agtcatagga gtcttcggag taccgggatc tggcaagtca gctattatca gaacctagt    2280 taccaggcag gacctggtga ctagcggaaa gaaagaaaac tgccaagaaa tcaccaccga   2340
cgtgatgaga cagagaggtc tagagatatc tgcacgtacg gttgactcgc tgctcttgaa   2400
tggatgcaac agaccagtcg acgtgttgta cgtagacgag gcgtttgcgt gccactctgg   2460
```

```
aacgctactt gctttgatcg ccttggtgag accaaggcag aaagttgtac tttgtggtga   2520
cccgaagcag tgcggcttct tcaatatgat gcagatgaaa gtcaactata atcacaacat   2580
ctgcacccaa gtgtaccaca aaagtatctc caggcggtgt acactgcctg tgaccgccat   2640
tgtgtcatcg ttgcattacg aaggcaaaat gcgcactacg aatgagtaca caagccgat    2700 tgtagtggac actacaggct caacaaaacc tgaccctgga gacctcgtgt taacgtgctt   2760
cagagggtgg gttaaacaac tgcaaattga ctatcgtgga tacgaggtca tgacagcagc   2820
cgcatcccaa gggttaacca gaaaaggagt ttacgcagtt agacaaaaag ttaatgaaaa   2880
cccgctctat gcatcaacgt cagagcacgt caacgtactc ctaacgcgta cggaaggtaa   2940
actggtatgg aagacacttt ccggcgaccc gtggataaag acgctgcaga acccaccgaa   3000
aggaaacttc aaagcaacta ttaaggagtg ggaggtggag catgcatcaa taatggcggg   3060
catctgcagt caccaaatga ccttcgatac attccaaaat aaagccaacg tttgttgggc   3120
taagagcttg gtccctatcc tcgaaacagc ggggataaaa ctaaatgata ggcagtggtc   3180
tcagataatt caagccttca agaagacaa agcatactca cctgaagtag ccctgaatga    3240
aatatgtacg cgcatgtatg gggtggatct agacagcggg ctattttcta aaccgttggt   3300
gtctgtgtat tacgcggata accactggga taataggcct ggagggaaaa tgttcggatt   3360
taaccccgag gcagcatcca ttctagaaag aaagtatcca ttcacaaaag ggaagtggaa   3420
catcaacaag cagatctgcg tgactaccag gaggatagaa gactttaacc ctaccaccaa   3480
catcataccg gccaacagga gactaccaca ctcattagtg gccgaacacc gcccagtaaa   3540 agggaaaga atggaatggc tggttaacaa gataaacggc caccacgtgc tcctggtcag    3600
tggctataac cttgcactgc ctactaagag agtcacttgg gtagcgccgt taggtgtccg   3660
cggagcggac tacacataca acctagagtt gggtctgcca gcaacgcttg gtaggtatga   3720
cctagtggtc ataaacatcc acacaccttt tcgcatacac cattaccaac agtgcgtcga   3780
ccacgcaatg aaaactgcaaa tgctcggggg tgactcattg agactgctca accgggcgg   3840 ctctctattg atcagagcat atggttacgc agatagaacc agtgaacgag tcatctgcgt   3900
attgggacgc aagtttagat cgtctagagc gttgaaacca ccatgtgtca ccagcaacac   3960
tgagatgttt ttcctattca gcaactttga caatggcaga aggaatttca caactcatgt   4020
catgaacaat caactgaatg cagccttcgt aggacaggtc acccgagcag atgtgcacc    4080 gtcgtaccgg gtaaaacgca tggacatcgc gaagaacgat gaagagtgcg tagtcaacgc   4140
cgctaaccct cgcgggttac cgggtgtcgg tgtttgcaag gcagtataca aaaatggcc    4200 ggagtccttt aagaacagtg caacaccagt gggaaccgca aaaacagtta tgtgcggtac   4260
gtatccagta atccacgctg ttggaccaaa cttctctaat tattcggagt ctgaagggga   4320
ccgggaattg gcagctgcct atcgagaagt cgcaaaggaa gtaactaggc tgggagtaaa   4380
tagtgtagct atacctctcc tctccacagg tgtatactca ggagggaaag acaggctgac   4440
ccagtcactg aaccacctct ttacagccat ggactcgacg gatgcagacg tggtcatcta   4500
ctgccgcgac aaagaatggg agaagaaaat atctgaggcc atacagatgc ggacccaagt   4560
agagctgctg gatgagcaca tctccataga ctgcgatatt gttcgcgtgc accctgacag   4620
cagcttggca ggcagaaaag gatacagcac cacggaaggc gcactgtact catatctaga   4680 agggaccccgt tttcatcaga cggctgtgga tatggcggag atacatacta tgtggccaaa   4740
gcaaacagag gccaatgagc aagtctgcct atatgccctg ggggaaagta ttgaatcgat   4800
caggcagaaa tgcccggtgg atgatgcaga cgcatcatct ccccccaaaa ctgtcccgtg   4860
```

-continued

```
cctttgccgt tacgctatga ctccagaacg cgtcacccgg cttcgcatga accacgtcac    4920
aagcataatt gtgtgttctt cgtttcccct cccaaagtac aaaatagaag gagtgcaaaa    4980
agtcaaatgc tctaaggtaa tgctatttga ccacaacgtg ccatcgcgcg taagtccaag    5040
ggaatataka tcttcccagg agtctgcaca ggaggcgagt acaatcacgt cactgacgca    5100
tagtcaattc gacctaagcg ttgatggcga gatactgccc gtcccgtcag acctggatgc    5160
tgacgcccca gccctagaac cagcactaga cgacggggcg acacacacgc tgccatccac    5220
aaccggaaac cttgcggccg tgtctgattg ggtaatgagc accgtacctg tcgcgccgcc    5280
cagaagaagg cgagggagaa acctgactgt gacatgtgac gagagagaag ggaatataac    5340
acccatggct agcgtccgat tctttagggc agagctgtgt ccggtcgtac aagaaacagc    5400
ggagacgcgt gacacagcaa tgtctcttca ggcaccaccg agtaccgcca cggaaccgaa    5460
tcatccgccg atctccttcg gagcatcaag cgagacgttc cccattacat ttggggactt    5520
caacgaagga gaaatcgaaa gcttgtcttc tgagctacta actttcggag acttcttacc    5580
aggagaagtg gatgacttga cagacagcga ctggtccacg tgctcagaca cggacgacga    5640
gttatgacta gacagggcag gtgggtatat attctcgtcg acaccggtc caggtcattt    5700 acaacagaag tcagtacgcc agtcagtgct gccggtgaac accctggagg aagtccacga    5760
ggagaagtgt tacccaccta agctggatga agcaaaggag caactattac ttaagaaact    5820
ccaggagagt gcatccatgg ccaacagaag caggtatcag tcgcgcaaag tagaaaacat    5880
gaaagcagca atcatccaga gactaaagag aggctgtaga ctatacttaa tgtcagagac    5940
cccaaaagtc cctacttacc ggactacata tccggcgcct gtgtactcgc ctccgatcaa    6000
cgtccgattg tccaatcccg agtccgcagt ggcagcatgc aatgagttct tagctagaaa    6060
ctatccaact gtctcatcat accaaattac cgacgagtat gatgcatatc tagacatggt    6120
ggacgggtcg gagagttgcc tggaccgagc gacattcaat ccgtcaaaac tcaggagcta    6180
cccgaaacag cacgcttacc acgcgccctc catcagaagc gctgtaccgt ccccattcca    6240
gaacacacta cagaatgtac tggcagcagc cacgaaaaga aactgcaacg tcacacagat    6300
gagggaatta cccactttgg actcagcagt attcaacgtg gagtgtttca aaaaattcgc    6360
atgcaaccaa gaatactggg aagaatttgc tgccagccct attaggataa caactgagaa    6420
tttagcaacc tatgttacta aactaaaagg gccaaaagca gcagcgctat cgcaaaaac    6480 ccataatcta ctgccactac aggaagtacc aatggatagg ttcacagtag atatgaaaag    6540
ggacgtaaag gtgactcctg gtacaaagca tacagaggaa agacctaagg tgcaggttat    6600
acaggcggct gaaccttggc gacagcata cctatgtggg attcacagag agctggttag    6660
gaggctgaac gccgtcctcc tacccaatgt acatacacta tttgacatgt ctgccgagga    6720
tttcgatgcc atcatagccg cacactttaa gccaggagac actgttttgg aaacggacat    6780
agcctccttt gataagagcc aagatgattc acttgcgctt actgctttga tgctgttaga    6840
ggatttaggg gtggatcact ccctgctgga cttgatagag gctgctttcg agagatttc    6900 cagctgtcac ctaccgacag gtacgcgctt caagttcggc gccatgatga aatcaggtat    6960
gttcctaact ctgttcgtca acacattgtt aaacatcacc atcgccagcc gagtgctgga    7020
agatcgtctg acaaaatccg cgtgcgcggc cttcatcggc gacgacaaca taatacatgg    7080
agtcgtctcc gatgaattga tggcagccag atgtgccact tggatgaaca tggaagtgaa    7140
gatcatagat gcagttgtat ccttgaaagc cccttacttt tgtggagggt ttatactgca    7200
```

```
cgatactgtg acaggaacag cttgcagagt ggcagacccg ctaaaaaggc ttttaaaact    7260
gggcaaaccg ctagcggcag gtgacgaaca agatgaagat agaagacgag cgctggctga    7320
cgaagtgatc agatggcaac gaacagggct aattgatgag ctggagaaag cggtatactc    7380
taggtacgaa gtgcagggta tatcagttgt ggtaatgtcc atggccacct ttgcaagctc    7440
cagatccaac ttcgagaagc tcagaggacc cgtcataact ttgtacggcg gtcctaaata    7500
ggtacgcact acagctacct attttgcaga agccgacagc aagtatctaa acactaatca    7560
gctacaatgg agttcatccc aacccaaact ttttacaata ggaggtacca gcctcgaccc    7620
tggactccgc gccctactat ccaagtcatc aggcccagac cgcgccctca gaggcaagct    7680
gggcaacttg cccagctgat ctcagcagtt aataaactga caatgcgcgc ggtaccccaa    7740
cagaagccac gcaggaatcg gaagaataag aagcaaaagc aaaaacaaca ggcgccacaa    7800
aacaacacaa atcaaaagaa gcagccacct aaaagaaac cggctcaaaa gaaaagaag    7860 ccgggccgca gagagaggat gtgcatgaaa atcgaaaatg attgtatttt cgaagtcaag    7920
cacgaaggta aggtaacagg ttacgcgtgc ctggtggggg acaaagtaat gaaaccagca    7980
cacgtaaagg ggaccatcga taacgcggac ctggccaaac tggcctttaa gcggtcatct    8040
aagtatgacc ttgaatgcgc gcagataccc gtgcacatga agtccgacgc ttcgaagttc    8100
acccatgaga aaccggaggg gtactacaac tggcaccacg gagcagtaca gtactcagga    8160
ggccggttca ccatccctac aggtgctggc aaaccagggg acagcggcag accgatcttc    8220
gacaacaagg gacgcgtggt ggccatagtc ttaggaggag ctaatgaagg agcccgtaca    8280
gccctctcgg tggtgacctg gaataaagac attgtcacta aaatcacccc cgagggggcc    8340
gaagagtgga gtcttgccat cccagttatg tgcctgttgg caaacaccac gttccccctgc    8400 tcccagcccc cttgcacgcc ctgctgctac gaaaaggaac cggaggaaac cctacgcatg    8460
cttgaggaca acgtcatgag acctgggtac tatcagctgc tacaagcatc cttaacatgt    8520
tctccccacc gccagcgacg cagcaccaag gacaacttca atgtctataa agccacaaga    8580
ccatacttag ctcactgtcc cgactgtgga gaagggcact cgtgccatag tcccgtagca    8640
ctagaacgca tcagaaatga agcgacagac gggacgctga aaatccaggt ctccttgcaa    8700
atcggaataa agacggatga cagccacgat tggaccaagc tgcgttatat ggacaaccac    8760
atgccagcag acgcagagag ggcggggcta tttgtaagaa catcagcacc gtgtacgatt    8820
actggaacaa tgggacactt catcctggcc cgatgtccaa aaggggaaac tctgacggtg    8880
ggattcactg acagtaggaa gattagtcac tcatgtacgc acccatttca ccacgaccct    8940
cctgtgatag gtcgggaaaa attccattcc cgaccgcagc acggtaaaga gctaccttgc    9000
agcacgtacg tgcagagcac cgccgcaact accgaggaga tagaggtaca catgcccca    9060 gacacccctg atcgcacatt aatgtcacaa cagtccggca acgtaaagat cacagtcaat    9120
ggccagacgg tgcggtacaa gtgtaattgc ggtggctcaa atgaaggact aacaactaca    9180
gacaaagtga ttaataactg caaggttgat caatgtcatg ccgcggtcac caatcacaaa    9240
aagtggcagt ataactcccc tctggtcccg cgtaatgctg aacttgggga ccgaaaagga    9300
aaaattcaca tcccgtttcc gctggcaaat gtaacatgca gggtgcctaa agcaaggaac    9360
cccaccgtga cgtacgggaa aaaccaagtc atcatgctac tgtatcctga ccacccaaca    9420
ctcctgtcct accggaatat gggagaagaa ccaaactatc aagaagagtg ggtgatgcat    9480
aagaaggaag tcgtgctaac cgtgccgact gaagggctcg aggtcacgtg gggcaacaac    9540
gagccgtata agtattggcc gcagttatct acaaacggta cagcccatgg ccacccgcat    9600
```

```
gagataattc tgtattatta tgagctgtac cccactatga ctgtagtagt tgtgtcagtg    9660
gccacgttca tactcctgtc gatggtgggt atggcagcgg ggatgtgcat gtgtgcacga    9720
cgcagatgca tcacaccgta tgaactgaca ccaggagcta ccgtcccttt cctgcttagc    9780
ctaatatgct gcatcagaac agctaaagcg gccacatacc aagaggctgc gatatacctg    9840
tggaacgagc agcaaccttt gttttggcta caagccctta ttccgctggc agccctgatt    9900
gttctatgca actgtctgag actcttacca tgctgctgta aaacgttggc ttttttagcc    9960
gtaatgagcg tcggtgccca cactgtgagc gcgtacgaac acgtaacagt gatcccgaac   10020
acggtgggag taccgtataa gactctagtc aatagacctg gctacagccc catggtattg   10080
gagatggaac tactgtcagt cactttggag ccaacactat cgcttgatta catcacgtgc   10140
gagtacaaaa ccgtcatccc gtctccgtac gtgaagtgct gcggtacagc agagtgcaag   10200
gacaaaaacc tacctgacta cagctgtaag gtcttcaccg gcgtctaccc atttatgtgg   10260
ggcggcgcct actgcttctg cgacgctgaa aacacgcagt tgagcgaagc acacgtggag   10320
aagtccgaat catgcaaaac agaatttgca tcagcataca gggctcatac cgcatctgca   10380
tcagctaagc tccgcgtcct ttaccaagga ataacatca ctgtaactgc ctatgcaaac    10440
ggcgaccatg ccgtcacagt taaggacgcc aaattcattg tggggccaat gtcttcagcc   10500
tggacacctt tcgacaacaa aattgtggtg tacaaaggtg acgtctataa catggactac   10560
ccgccctttg gcgcaggaag accaggacaa tttggcgata tccaaagtcg cacacctgag   10620
agtaaagacg tctatgctaa tacacaactg gtactgcaga gaccggctgt gggtacggta   10680
cacgtgccat actctcaggc accatctggc tttaagtatt ggctaaaaga acgcggggcg   10740
tcgctgcagc acacagcacc atttggctgc caaatagcaa caaacccggt aagagcggtg   10800
aactgcgccg tagggaacat gcccatctcc atcgacatac cggaagcggc cttcactagg   10860
gtcgtcgacg cgccctcttt aacgacatg tcgtgcgagg taccagcctg cacccattcc    10920
tcagactttg ggggcgtcgc cattattaaa tatgcagcca gcaagaaagg caagtgtgcg   10980
gtgcattcga tgactaacgc cgtcactatt cgggaagctg agatagaagt tgaagggaat   11040
tctcagctgc aaatctcttt ctcgacggcc ttagccagcg ccgaattccg cgtacaagtc   11100
tgttctacac aagtacactg tgcagccgag tgccaccccc cgaaggacca catagtcaac   11160
tacccggcgt cacataccac cctcggggtc caggacatct ccgctacggc gatgtcatgg   11220
gtgcagaaga tcacgggagg tgtgggactg gttgttgctg ttgccgcact gattctaatc   11280
gtggtgctat gcgtgtcgtt cagcaggcac taacttgaca attaagtatg aaggtatatg   11340
tgtcccctaa gagacacact gtacatagca aataatctat agatcaaagg gctacgcaac   11400
ccctgaatag taacaaaata caaatcact aaaaattata aaaacagaaa aatacataaa    11460
taggtatacg tgtcccctaa gagacacatt gtatgtaggt gataagtata gatcaaaggg   11520
ccgaataacc cctgaatagt aacaaatat gaaaatcaat aaaaatcata aaatagaaaa    11580
accataaaca gaagtagttc aaagggctat aaaacccctg aatagtaaca aacataaaa    11640 ttaataaaaa tcaaatgaat accataattg gcaaacggaa gagatgtagg tacttaagct   11700
tcctaaaagc agccgaactc actttgagaa gtaggcatag cataccgaac tcttccacga   11760
ttctccgaac ccacagggac gtaggagatg ttattttgtt tttaatattt caaaaaaaaa   11820
aaaaaaaaaa aaaaaaaaa                                                11840
```

<210> SEQ ID NO 73

```
<211> LENGTH: 10863
<212> TYPE: DNA
<213> ORGANISM: Japanese encephalitis virus

<400> SEQUENCE: 73
tttaaacagt tttttagaac ggaagataac catgactaaa aaaccaggag ggcccggtaa      60
aaaccgggct atcaatatgc tgaaacgcgg cctaccccgc gtattcccac tagtgggagt     120
gaagagggta gtaatgagct tgttggacgg cagagggcca gtacgtttcg tgctggctct     180
tatcacgttc ttcaagttta cagcattagc cccgaccaag gcgcttttag gccgatggaa     240
agcagtggaa aagagtgtgg caatgaaaca tcttactagt ttcaaacgag aacttggaac     300
actcattgac gccgtgaaca gcggggcag aaagcaaaac aaaagaggag gaaatgaagg     360
ctcaatcatg tggctcgcga gcttggcagt tgtcatagct tgtgcaggag ccatgaagtt     420
gtcgaatttc caggggaagc ttttgatgac catcaacaac acggacattg cagacgttat     480
cgtgattccc acctcaaaag gagagaacag atgctgggtc cggcaatcg acgtcggcta     540 catgtgtgag gacactatca cgtacgaatg tcctaagctt accatgggca atgatccaga     600
ggatgtggat tgctggtgtg acaaccaaga agtctacgtc caatatggac ggtgcacgcg     660
gaccaggcat tccaagcgaa gcaggagatc cgtgtcggtc caaacacatg gggagagttc     720
actagtgaat aaaaagagg cttggctgga ttcaacgaaa gccacacgat atctcatgaa     780
aactgagaac tggatcataa ggaatcctgg ctatgctttc ctggcggcgg tacttggctg     840
gatgcttggc agtaacaacg gtcaacgcgt ggtatttacc atcctcctgc tgttggtcgc     900
tccggcttac agttttaatt gtctgggaat gggcaatcgt gacttcatag aaggagccag     960
tggagccact tgggtggact tggtgctaga aggagatagc tgcttgacaa tcatggcaaa    1020
cgacaaacca acattggacg tccgcatgat taacatcgaa gctagccaac ttgctgaggt    1080
cagaagttac tgctatcatg cttcagtcac tgacatctcg acggtggctc ggtgccccac    1140
gactggagaa gcccacaacg agaagcgagc tgatagtagc tatgtgtgca aacaaggctt    1200
cactgaccgt gggtggggca acggatgtgg actttttcggg aagggaagca ttgacacatg    1260
tgcaaaattc tcctgcacca gtaaagcgat tgggagaaca atccagccag aaaacatcaa    1320
atacgaagtt ggcattttg tgcatggaac caccacttcg gaaaaccatg gaattattc    1380 agcgcaagtt ggggcgtccc agcggcaaa gtttacagta acacccaatg ctccttcgat    1440
aaccctcaaa cttggtgact acggagaagt cacactggac tgtgagccaa ggagtggact    1500
gaacactgaa gcgttttacg tcatgaccgt ggggtcaaag tcatttctgg tccatagga    1560 gtggtttcat gacctcgctc tccctggac gtccccttcg agcacagcgt ggagaaacag    1620
agaactcctc atggaatttg aagggcgca cgccacaaaa cagtccgttg ttgctcttgg    1680
gtcacaggaa ggaggcctcc atcaggcgtt ggcaggagcc atcgtggtgg agtactcaag    1740
ctcagtgaag ttaacatcag gccacctgaa atgtaggctg aaaatggaca aactggctct    1800
gaaaggcaca acctatggca tgtgtacaga aaaattctcg ttcgcgaaaa atccggcgga    1860
cactggtcac ggaacagttg tcattgaact ctcctactct gggagtgatg gcccctgcaa    1920
aattccgatt gtttccgttg cgagcctcaa tgacatgacc cccgtgggc ggctggtgac    1980 agtgaacccc ttcgtcgcga cttccagtgc caactcaaag gtgctggtcg agatggaacc    2040
ccccttcgga gactcctaca tcgtagttgg aaggggagac aagcagatca accaccattg    2100
gcacaaagct ggaagcacgc tgggcaaggc ctttttcaaca acttttgaagg gagctcaaag    2160 actggcagcg ttgggcgaca cagcctggga ctttggctct attggagggg tcttcaactc    2220
```

```
cataggaaaa gccgttcacc aagtgtttgg tggtgccttc agaacactct ttgggggaat   2280
gtcttggatc acacaagggc taatgggtgc cctactgctc tggatgggcg tcaacgcacg   2340
agaccgatca attgctttgg ccttcttagc cacagggggt gtgctcgtgt tcttagcgac   2400
caatgtgcat gctgacactg gatgtgccat tgacatcaca agaaaagaga tgagatgtgg   2460
aagtggcatc ttcgtgcaca acgacgtgga agcctgggtg gataggtata aatatttgcc   2520
agaaacgccc agatccctag cgaagatcgt ccacaaagcg cacaaggaag gcgtgtgcgg   2580
agtcagatct gtcactagac tggagcacca aatgtgggaa gccgtacggg acgaattgaa   2640
cgtcctgctc aaagagaatg cagtggacct cagtgtggtt gtgaacaagc ccgtgggaag   2700
atatcgctca gccctaaac gcctatccat gacgcaagag aagtttgaaa tgggctggaa   2760
agcatgggga aaaagcattc tctttgcccc ggaattggct aactccacat tgtcgtaga   2820
tggacctgag acaaggaat gccctgatga gcacagagct tggaacagca tgcaaatcga   2880
agacttcggc tttggcatca catcaacccg tgtgtggctg aaaattagag aggagagcac   2940
tgacgagtgt gatggagcga tcataggcac ggctgtcaaa ggacatgtgg cagtccatag   3000
tgacttgtcg tactggattg agagtcgcta caacgacaca tggaaacttg agagggcagt   3060
ctttggagag gtcaaatctt gcacttggcc agagacacac acccctttggg gagatgatgt   3120
tgaggaaagt gaactcatca ttccgcacac catagccgga ccaaaaagca agcacaatcg   3180
gagggaaggg tataagacac aaaaccaggg accttgggat gagaatggca tagtcttgga   3240
ctttgattat tgcccaggga caaaagtcac cattacagag gattgtgca agagaggccc   3300
ttcggtcaga accactactg acagtggaaa gttgatcact gactggtgct gtcgcagttg   3360
ctcccttccg cccctacgat tccgacaga aaatggctgc tggtacggaa tggaaatcag   3420
acctgttagg catgatgaaa caacactcgt cagatcacag gttgatgctt tcaatggtga   3480
aatggttgac ccttttcagc tgggccttct ggtgatgttt ctggccaccc aggaggtcct   3540
tcgcaagagg tggacggcca gattgaccat tcctgcggtt ttgggggccc tacttgtgct   3600
gatgcttggg ggcatcactt acactgattt ggcgaggtat gtggtgctag tcgctgctgc   3660
tttcgcagag gccaacagtg gaggagacgt cctgcacctt gctttgattg ccgttttaa   3720
gatccaacca gcatttctag tgatgaacat gcttagcacg agatggacga accaagaaaa   3780
cgtggttctg gtcctagggg ctgcctttt ccaattggcc tcagtagatc tgcaaatagg   3840
agtccacgga atcctgaatg ccgccgctat agcatggatg attgtccgag cgatcacctt   3900
ccccacaacc tcctccgtca ccatgccagt cttagcgctt ctaactccgg ggatgagggc   3960
tctataccta gacacttaca gaatcatcct cctcgtcata gggatttgct ccctgctgca   4020
cgagaggaaa aagaccatgg caaaaaagaa aggagctgta ctcttgggct agcgctcac   4080
atccactgga tggttctcgc ccaccactat agctgccgga ctaatggtct gcaacccaaa   4140
caagaagaga gggtggccag ctactgagtt tttgtcggca gttggattga tgtttgccat   4200
cgtaggtggt ttggccgagt tggatattga atccatgtca ataccttca tgctggcagg   4260
tctcatggca gtgtcctacg tggtgtcagg aaaagcaaca gatatgtggc ttgaacgggc   4320
cgccgacatc agctgggaga tggatgctgc aatcacagga agcagtcgga ggctggatgt   4380
gaaactggat gatgacggag attttcactt gattgatgat cccggtgttc catggaaggt   4440
ctgggtcctg cgcatgtctt gcattggctt agccgccctc acgccttggg ccatcgttcc   4500
cgccgctttc ggttattggc tcactttaaa aacaacaaaa agaggggcg tgttttggga   4560
```

```
cacgccatcc ccaaaaccctt gctcaaaagg agacaccact acaggagtct accgaattat    4620
ggctagaggg attcttggca cttaccaggc cggcgtcgga gtcatgtacg agaatgtttt    4680
ccacacacta tggcacacaa ctagaggagc agccattatg agtggagaag gaaaattgac    4740
gccatactgg ggtagtgtga gagaagaccg catagcttac ggaggcccat ggaggtttga    4800
ccgaaaatgg aatggaacag atgacgtgca agtgatcgtg gtagaaccgg ggaaggctgc    4860
agtaaacatc cagacaaaac caggagtgtt tcggactccc ttcggggagg ttggggctgt    4920
tagtctggat tacccgcgag gaacatccgg ctcacccatt ctggattcca atggagacat    4980
tataggccta tacggcaatg gagttgagct tggcgatggc tcatacgtca gcgccatcgt    5040
gcagggtgac cgtcaggagg aaccagtccc agaagcttac accccaaaca tgttgagaaa    5100
gagacagatg actgtgctag atttgcaccc tggttcaggg aaaaccagga aaattctgcc    5160
acaaataatt aaggacgcta tccagcagcg cctaagaaca gctgtgttgg caccgacgcg    5220
ggtggtagca gcagaaatgg cagaagcttt gagagggctc ccagtacgat atcaaacttc    5280
agcagtgcag agagagcacc aagggaatga aatagtggat gtgatgtgcc acgccactct    5340
gacccataga ctgatgtcac cgaacagagt gcccaactac aacctatttg tcatggatga    5400
agctcatttc accgacccag ccagtatagc cgcacgagga tacattgcta ccaaggtgga    5460
attaggggag gcagcagcca tctttatgac agcgaccccg cctggaacca cggatccttt    5520
tcctgactca aatgccccaa tccatgattt gcaagatgag ataccagaca gggcatggag    5580
cagtggatac gaatggatca cagaatatgc gggtaaaacc gtgtggtttg tggcgagcgt    5640
aaaaatgggg aatgagattg caatgtgcct ccaaagagcg gggaaaaagg tcatccaact    5700
caaccgcaag tcctatgaca cagaatacccc aaaatgtaag aatggagact gggattttgt    5760
cattaccacc gacatctctg aaatgggggc caacttcggt gcgagcaggg tcatcgactg    5820
tagaaagagc gtgaaaccca ccatcttaga agagggagaa ggcagagtca tcctcggaaa    5880
cccatctccc ataaccagtg caagcgcagc tcaacggagg ggcagagtag cagaaaccc    5940 caaccaagtt ggagatgaat accactatgg gggggctacc agtgaagatg acagtaacct    6000 agccattgg acagaggcaa agatcatgtt agacaacata cacatgccca atggactggt    6060
ggcccagctc tatggaccag agagggaaaa ggctttcaca atggatggcg aataccgtct    6120
cagaggtgaa gaaagaaaaa acttcttaga gctgcttagg acggctgacc tcccggtgtg    6180
gctggcctac aaggtggcgt ccaatggcat tcagtacacc gacagaaagt ggtgttttga    6240
tgggccgcgt acgaatgcca tactggagga caacaccgag gtagagatag tcacccggat    6300
gggtgagagg aaaatcctca gccgagatg gcttgatgca agagtttatg cagatcacca    6360
agccctcaag tggttcaaag actttgcagc agggaagaga tcagccgtta gcttcatagaa    6420 ggtgctcggt cgcatgcctg agcatttcat gggaaagacg cgggaagctt tagacaccat    6480
gtacttggtt gcaacggctg agaaaggtgg gaaagcacac cgaatggctc tcgaagagct    6540
gccagatgca ctggaaacca tcacacttat tgtcgccatt actgtgatga caggaggatt    6600
cttcctacta atgatgcagc gaaagggtat agggaagatg ggtcttggag ctctagtgct    6660
cacgctagct accttcttcc tgtgggcgg agaggttcct ggaaccaaaa tagcagggac    6720
cctgctgatc gccctgctgc tgatggtggt tctcatccca gaaccggaaa acagaggtc    6780 acagacagat aaccaactgg cggtgttct catctgtgtc ttgaccgtgg ttggagtggt    6840
ggcagcaaac gagtacgggat gctagaaaa aaccaaagca gatctcaaga gcatgtttgg    6900
cggaaagacg caggcatcag gactgactgg attgccaagc atggcactgg acctgcgtcc    6960
```

```
agccacagcc tgggcactgt atgggggag cacagtcgtg ctaaccccctc ttctgaagca    7020 cctgatcacg tcggaatacg tcaccacatc gctagcctca attaactcac aagctggctc    7080
attattcgtc ttgccacgag gcgtgccttt taccgaccta gacttgaccg ttggcctcgt    7140
cttccttggc tgttggggtc aaatcaccct cacaacgttt ctgacagcca tggttctggc    7200
gacacttcac tatgggtaca tgctccctgg atggcaagca aagcactca gggctgccca     7260 gagaaggaca gcggctggaa taatgaagaa tgccgttgtt gacggaatgg tcgccactga    7320
tgtgcctgaa ctggaaagga ctactcctct gatgcaaaag aaagtcggac aggtgctcct    7380 catagggta agcgtggcag cgttcctcgt caaccctaat gtcaccactg tgagagaagc     7440
aggggtgttg gtgacggcgg ctacgcttac tttgtgggac aatggagcca gtgccgtttg    7500
gaattccacc acagccacgg gactctgcca tgtcatgcga ggtagctacc tggctggagg    7560
ctccattgct tggactctca tcaagaacgc tgataagccc tccttgaaaa ggggaaggcc    7620
tgggggcagg acgctagggg agcagtggaa ggaaaaacta aatgccatga gcagagaaga    7680
gttttttaaa taccggagag aggccataat cgaggtggac cgcactgaag cacgcagggc    7740
cagacgtgaa ataacatag tgggaggaca tccggtttcg cgaggctcag caaaactccg      7800
ttggctcgtg gagaaaggat ttgtctcgcc aataggaaaa gtcattgatc tagggtgtgg    7860
gcgtggagga tggagctact acgcagcaac cctgaagaag gtccaggaag tcagaggata    7920
cacgaaaggt ggggcgggac atgaagaacc gatgctcatg cagagctacg gctggaaccct   7980 ggtctccctg aagagtggag tggacgtgtt ttacaaacct tcagagccca gtgcaccct     8040 gttctgtgac atagggaat cctccccaag tccagaagta aagaacaac gcacactacg      8100 cgtcctagag atgacatctg actggttgca ccgaggacct agagagttct gcattaaagt    8160
tctctgccct tacatgccca aggttataga aaaaatggaa gttctgcagc gccgcttcgg    8220
aggtgggcta gtgcgtctcc ccctgtcccg aaactccaat cacgagatgt attgggttag    8280
tggagccgct ggcaatgtgg tgcacgctgt gaacatgacc agccaggtac tactggggcg    8340
aatggatcgc acagtgtgga gagggccaaa gtatgaggaa gatgtcaacc tagggagcgg    8400
aacaagagcc gtgggaaagg gagaagtcca tagcaatcag gagaaaatca agaagagaat    8460
ccagaagctt aaagaagaat tcgccacaac gtggcacaaa gaccctgagc atccataccg    8520
cacttggaca taccacggaa gctatgaagt gaaggctact ggctcagcca gctctctcgt    8580
caacggagtg gtgaagctca tgagcaaacc ttgggacgcc attgccaacg tcaccaccat    8640
ggccatgact gacaccaccc cttttggaca gcaaagagtt ttcaaggaga agttgacac     8700 gaaggctcct gagccaccag ctggagccaa ggaagtgctc aacgagacca ccaactggct    8760
gtgggcccac ttgtcacggg aaaaaagacc ccgcttgtgc accaaggaag aattcataaa    8820
gaaagtcaac agcaacgcgg ctcttggagc agtgttcgct gaacagaatc aatggagcac    8880
ggcgcgtgag gctgtggatg acccgcggtt tgggagatg gttgatgaag agagggaaa      8940 ccatctgcga ggagagtgtc acacatgtat ctacaacatg atgggaaaaa gagagaagaa    9000
gcctggagag tttggaaaag ctaaaggaag cagggccatt tggttcatgt ggcttggagc    9060
acggtatcta gagtttgaag cttttgggtt cctgaatgaa gaccattggc tgagccgaga    9120
gaattcagga ggtggagtgg aaggctcagg cgtccaaaag ctgggataca tcctccgtga    9180
catagcagga aagcaaggag ggaaaatgta cgctgatgat accgccgggt gggacactag    9240
aattaccaga actgatttag aaaatgaagc taaggtactg gagctcctag acggtgaaca    9300
```

```
ccgcatgctc gcccgagcca taattgaact gacttacagg cacaaagtgg tcaaggtcat    9360
gagacctgca gcagaaggaa agaccgtgat ggacgtgata tcaagagaag atcaaagggg    9420
gagtggacag gtggtcactt atgctcttaa cactttcacg aacatcgctg tccagctcgt    9480
caggctgatg gaggctgagg gggtcattgg accacaacac ttggaacagc tacctaggaa    9540
aaacaagata gctgtcagga cctggctctt tgagaatgga gaggagagag tgaccaggat    9600
ggcgatcagc ggagacgact gtgtcgtcaa gccgctggac gacagattcg ccacagccct    9660
ccacttcctc aacgcaatgt caaaggtcag aaaagacatc caggaatgga gccttcgca    9720 tggctggcac gattgcagc aagttcccct ctgctctaac cattttcagg agattgtgat    9780
gaaagatgga aggagtatag ttgtcccgtg cagaggacag gatgagctga taggcagggc    9840
tcgcatctct ccaggagctg gatggaatgt gaaggacaca gcttgcctgg ccaaagcata    9900
tgcacagatg tggctactcc tatacttcca tcgcagggac ttgcgtctca tggcaaatgc    9960
gatttgctca gcagtgccag tggattgggt gcccacaggc aggacatcct ggtcaataca   10020
ctcgaaagga gagtggatga ccacggaaga catgctgcag gtctggaaca gagtctggat   10080
tgaagaaaat gaatggatga tggacaagac tccaatcaca agctggacag acgttccgta   10140
tgtgggaaag cgtgaggaca tctggtgtgg cagcctcatc ggaacgcgat ccagagcaac   10200
ctgggctgag aacatctatg cggcgataaa ccaggttaga gctgtcattg ggaaagaaaa   10260
ttatgttgac tacatgacct cactcaggag atacgaagac gtcttgatcc aggaagacag   10320
ggtcatctag tgtgatttaa ggtagaaaag tagactatgt aaataatgta aatgagaaaa   10380
tgcatgcata tggagtcagg ccagcaaaag ctgccaccgg atactgggta gacggtgctg   10440
cctgcgtctc agtcccagga ggactgggtt aacaaatctg acaacagaaa gtgagaaagc   10500
cctcagaacc gtctcggaag taggtccctg ctcactggaa gttgaaagac caacgtcagg   10560
ccacaaattt gtgccactcc gctagggagt gcggcctgcg cagccccagg aggactgggt   10620
taccaaagcc gttgaggccc ccacggccca agcctcgtct aggatgcaat agacgaggtg   10680
taaggactag aggttagagg agaccccgtg gaaacaacaa catgcggccc aagcccctc    10740 gaagctgtag aggaggtgga aggactagag gttagaggag accccgcatt tgcatcaaac   10800
agcatattga cacctgggaa tagactggga gatcttctgc tctatctcaa catcagctac   10860
tag                                                                10863
```

<210> SEQ ID NO 74
<211> LENGTH: 10977
<212> TYPE: DNA
<213> ORGANISM: Japanese encephalitis virus

<400> SEQUENCE: 74

```
agaagtttat ctgtgtgaac ttcttggctt agtatcgtag agaagaatcg agagattagt      60
gcagtttaaa cagttttta gaacggaaga taaccatgac taaaaaacca ggagggcccg     120
gtaaaaaccg ggctatcaat atgctgaaac gcggcctacc ccgcgtattc ccactagtgg     180
gagtgaagag ggtagtaatg agcttgttgg acggcagagg gccagtacgt ttcgtgctgg     240
ctcttatcac gttcttcaag tttacagcat tagccccgac caaggcgctt tcaggccgat     300
ggaaagcagt ggaaaagagt gtggcaatga acatcttac tagtttcaaa cgagaacttg     360
gaacactcat tgacgccgtg aacaagcggg gcagaaagca aaacaaaaga ggaggaaatg     420
aaggctcaat catgtggctc gcgagcttgg cagttgtcat agcttgtgca ggagccatga     480
agttgtcgaa tttccagggg aagcttttga tgaccatcaa caacacggac attgcagacg     540
```

```
ttatcgtgat tcccacctca aaaggagaga acagatgctg ggtccgggca atcgacgtcg    600
gctacatgtg tgaggacact atcacgtacg aatgtcctaa gcttaccatg ggcaatgatc    660
cagaggatgt ggattgctgg tgtgacaacc aagaagtcta cgtccaatat ggacggtgca    720
cgcggaccag gcattccaag cgaagcagga gatccgtgtc ggtccaaaca catggggaga    780
gttcactagt gaataaaaaa gaggcttggc tggattcaac gaaagccaca cgatatctca    840
tgaaaactga gaactggatc ataaggaatc ctggctatgc tttcctggcg gcggtacttg    900
gctggatgct tggcagtaac aacggtcaac gcgtggtatt taccatcctc ctgctgttgg    960
tcgctccggc ttacagtttt aattgtctgg gaatgggcaa tcgtgacttc atagaaggag   1020
ccagtggagc cacttgggtg gacttggtgc tagaaggaga cagctgcttg acaatcatgg   1080
caaacgacaa accaacattg gacgtccgca tgattaacat cgaagctagc caacttgctg   1140
aggtcagaag ttactgctat catgcttcag tcactgacat ctcgacggtg gctcggtgcc   1200
ccacgactgg agaagcccac aacgagaagc gagctgatag tagctatgtg tgcaaacaag   1260
gcttcactga ccgtgggtgg ggcaacggat gtggattttt cgggaaggga agcattgaca   1320
catgtgcaaa attcctctgc accagtaaag cgattgggag aacaatccag ccagaaaaca   1380
tcaaatacaa agttggcatt tttgtgcatg gaaccaccac ttcggaaaac catgggaatt   1440
attcagcgca gtggggcg tcccaggcgg caaagtttac agtaacaccc aatgctcctt   1500
cggtagccct caaacttggt gactacggag aagtcacact ggactgtgag ccaaggagtg   1560
gactgaacac tgaagcgttt tacgtcatga ccgtggggtc aaagtcattt ctggtccata   1620
gggagtggtt tcatgacctc gctctcccct ggacgtcccc ttcgagcaca gcgtggagaa   1680
acagagaact cctcatggaa tttgaagggg cgcacgccac aaaacagtcc gttgttgctc   1740
ttgggtcaca ggaaggaggc ctccatcatg cgttggcagg agccatcgtg gtggagtact   1800
caagctcagt gatgttaaca tcaggccacc tgaaatgtag gctgaaaatg gacaaactgg   1860
ctctgaaagg cacaacctat ggcatgtgta cagaaaaatt ctcgttcgcg aaaaatccgg   1920
tggacactgg tcacggaaca gttgtcattg aactctccta ctctgggagt gatggcccct   1980
gcaaaattcc gattgtttcc gttgcgagcc tcaatgacat gaccccgtt gggcggctgg   2040 tgacagtgaa ccccttcgtc gcgacttcca gtgccaactc aaaggtgctg gtcgagatgg   2100
aacccccctt cggagactcc tacatcgtag ttggaagggg agacaagcag atcaaccacc   2160
attggcacaa agctggaagc acgctgggca aggcctttc aacaactttg aagggagctc   2220 aaagactgg agcgttgggc gacacagcct gggactttgg ctctattgga ggggtcttca   2280
actccatagg aagagccgtt caccaagtgt ttggtggtgc cttcagaaca ctctttgggg   2340
gaatgtcttg gatcacacaa gggctaatgg gtgccctact gctctggatg ggcgtcaacg   2400
cacgagaccg atcaattgct ttggccttct tagccacagg aggtgtgctc gtgttcttag   2460
cgaccaatgt gcatgctgac actggatgtg ccattgacat cacaagaaaa gagatgagat   2520
gtggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg ggaagccgta agggacgaat   2700
tgaacgtcct gctcaaagag aatgcagtgg acctcagtgt ggttgtgaac aagcccgtgg   2760
gaagatatcg ctcagcccct aaacgccat ccatgacgca agagaagttt gaatgggct   2820 ggaaagcatg gggaaaaagc atcctctttg ccccggaatt ggctaactcc acatttgtcg   2880
```

-continued

```
tagatggacc tgagacaaag gaatgccctg atgagcacag agcttggaac agcatgcaaa    2940
tcgaagactt cggctttggc atcacatcaa cccgtgtgtg gctgaaaatt agagaggaga    3000
gcactgacga gtgtgatgga gcgatcatag gcacggctgt caaaggacat gtggcagtcc    3060
atagtgactt gtcgtactgg attgagagtc gctacaacga cacatggaaa cttgagaggg    3120
cagtctttgg agaggtcaaa tcttgcactt ggccagagac acacacccct tggggagatg    3180
atgttgagga aagtgaactc atcattccgc acaccatagc cggaccaaaa agcaagcaca    3240
atcggaggga agggtataag acacaaaacc agggaccttg ggatgagaat ggcatagtct    3300
tggactttga ttattgccca gggacaaaag tcaccattac agaggattgt agcaagagag    3360
gcccttcggt cagaaccact actgacagtg aaagttgat cactgactgg tgctgtcgca    3420
gttgctccct tccgccccta cgattccgga cagaaaatgg ctgctggtac ggaatggaaa    3480
tcagacctgt tatgcatgat gaaacaacac tcgtcagatc acaggttcat gctttcaaag    3540
gtgaaatggt tgacccttt cagctgggcc ttctggtgat gtttctggcc acccaggaag    3600
tccttcgcaa gaggtggacg gccagattga ccattcctgc ggttttgggg gtcctacttg    3660
tgctgatgct tgggggtatc acttacactg atttggcgag gtatgtggtg ctagtcgctg    3720
ctgctttcgc agaggccaac agtggaggag acgtcctgca ccttgctttg attgctgttt    3780
ttaagatcca accagcattt ttagtgatga acatgcttag cacgagatgg acgaaccaag    3840
aaaacgtggt tctggtccta ggggctgcct ttttccaatt ggcctcagta gatctgcaaa    3900
taggagtcca cggaatcctg aatgccgccg ctatagcatg gatgattgtc cgagcgatca    3960
ccttccccac aacctcctcc gtcaccatgc cagtcttagc gcttctaact ccggggatga    4020
gggctctata cctagacact tacagaatca tcctcctcgt catagggatt gctccctgc    4080
tgcacgagag gaaaaagacc atggcgaaaa agaaaggagc tgtactcttg gcttagcgc    4140
tcacatccac tggatggttc tcgcccacca ctatagctgc cggactaatg gtctgcaacc    4200
caaacaagaa gagagggtgg ccagctactg agttttttgtc ggcagttgga ttgatgtttg    4260
ccatcgtagg tggtttggcc gagttggata ttgaatccat gtcaatacccc ttcatgctgg    4320
caggtctcat ggcagtgtcc tacgtggtgt caggaaaagc aacagatatg tggcttgaac    4380
gggccgccga catcagctgg gatatgggtg ctgcaatcac aggaagcagt cggaggctgg    4440
atgtgaaact ggatgatgac ggagattttc acttgattga tgatcccggt gttccatgga    4500
aggtctgggt cctgcgcatg tcttgcattg gcttagccgc cctcacgcct tgggccatcg    4560
ttcccgccgc tttcggttat tggctcactt taaaaacaac aaaaagaggg ggcgtgtttt    4620
gggacacgcc atccccaaaa ccttgctcaa aaggagacac cactacagga gtctaccgaa    4680
ttatggctag agggattctt ggcacttacc aggccggcgt cggagtcatg tacgagaatg    4740
ttttccacac actatggcac acaactagag gagcagccat tgtgagtgga aaggaaaat    4800
tgacgccata ctggggtagt gtgaaagaag accgcatagc ttacggaggc ccatggaggt    4860
ttgaccgaaa atggaatgga acagatgacg tgcaagtgat cgtggtagaa ccgggaaggg    4920
gcgcagtaaa catccagaca aaaccaggag tgtttcggac tcccttcggg gaggttgggg    4980
ctgttagtct ggattacccg cgaggaacat ccggctcacc cattctggat ccaatggag    5040
acattatagg cctatacggc aatggagttg agcttggcga tggctcatac gtcagcgcca    5100
tcgtgcaggg tgaccgtcag gaggaaccag tcccagaagc ttacacccca aacatgttga    5160
gaaagagaca gatgactgtg ctagatttgc accctggttc agggaaaacc aggaaaattc    5220
tgccacaaat aattaaggac gctatccagc agcgcctaag aacagctgtg ttggcaccga    5280
```

```
cgcgggtggt agcagcagaa atggcagaag ctttgagagg gctcccagta cgatatcaaa   5340
cttcagcagt gcagagagag caccaaggga atgaaatagt ggatgtgatg tgccacgcca   5400
ctctgaccca tagactgatg tcaccgaaca gagtgcccaa ctacaaccta tttgtcatgg   5460
atgaagctca tttcaccgac ccagccagta tagccgcacg aggatacatt gctaccaagg   5520
tggaattagg ggaggcagca gccatcttta tgacagcgac cccgcctgga accacggatc   5580
cttttcctga ctcaaatgcc ccaatccatg atttgcaaga tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcggggaaa aaggtcatcc   5760
aactcaaccg caagtcctat gacacagaat acccaaaatg taagaatgga gactgggatt   5820
ttgtcattac caccgacatc tctgaaatgg gggccaactt cggtgcgagc agggtcatcg   5880
actgtagaaa gagcgtgaaa cccaccatct tagaagaggg agaaggcaga gtcatcctcg   5940
gaaacccatc tcccataacc agtgcaagcg cagctcaacg gaggggcaga gtaggcagaa   6000
accccaatca agttggagat gaataccact atgggggggc taccagtgaa gatgacagta   6060
acctagccca ttggacagag gcaaagatca tgttagacaa catacacatg cccaatggac   6120
tggtggccca gctctatgga ccagagaggg aaaaggcttt cacaatggat ggcgaatacc   6180
gtctcagagg tgaagaaaag aaaaacttct tagagctgct taggacggct gacctcccgg   6240
tgtggctggc ctacaaggtg gcgtccaatg gcattcagta caccgacaga aagtggtgtt   6300
ttgatgggcc gcgtacgaat gccatactgg aggacaacac cgaggtagag atagtcaccc   6360
ggatgggtga gaggaaaatc ctcaagccga gatggcttga tgcaagagtt tatgcagatc   6420
accaggccct caagtggttc aaagactttg cagcagggaa gagatcagcc gttagcttca   6480
tagaggtgct cggtcgcatg cctgagcatt tcatgggaaa gacgcgggaa gctttagaca   6540
ccatgtactt ggttgcaacg gctgagaaag gtgggaaagc acaccgaatg gctctcgaag   6600
agctgccaga tgcactggaa accatcacac ttattgtcgc cattactgtg atgacaggag   6660
gattcttcct actaatgatg cagcgaaagg gtataggaaa gatgggtctt ggagctctag   6720
tgctcacact agctaccttc ttcctgtggg cggcagaggt tcctggaacc aaaatagcag   6780 ggacccttgct gatcgccctg ctgctgatgg tggttctcat cccagaaccg gaaaaacaga   6840
ggtcacagac agataaccaa ctggcggtgt ttctcatctg tgtcttgacc gtggttggag   6900
tggtggcagc aaacgagtac gggatgctag aaaaaaccaa agcggatctc aagagcatgt   6960
ttggcggaaa gacgcaggca tcaggactga ctggattgcc aagcatggca ctggacctgc   7020
gtccagccac agcctgggca ctgtatgggg ggagcacagt cgtgctaacc cctcttctga   7080
agcacctgat cacgtcggaa tacgtcacca catcgctagc ttcaattaac tcacaagctg   7140
gctcattatt cgtcttgcca cgaggcgtgc cttttaccga cctagacttg actgttggcc   7200
tcgtcttcct tggctgttgg ggtcaagtca ccctcacaac gtttctgaca gccatggttc   7260
tggcgacact tcactatggg tacatgctcc ctggatggca agcagaagca ctcagggctg   7320
cccagagaag gacagcggct ggaataatga agaatgccgt tgttgacgga atggtcgcca   7380
ctgatgtgcc tgaactggaa aggactactc ctctgatgca aagaaagtc ggacaggtgc   7440 tcctcatagg ggtaagcgtg gcagcgttcc tcgtcaaccc taatgtcacc actgtgagag   7500
aagcaggggt gttggtgacg gcggctacgc ttacttgtgt ggacaatgga gccagtgccg   7560
tttggaattc caccacagcc acgggactct gccatgtcat gcgaggtagc tacctggctg   7620
```

```
gaggctccat tgcttggact ctcatcaaga acgctgataa gccctccttg aaaagggaa      7680 ggcctggggg caggacgcta ggggagcagt ggaaggaaaa actaaatgcc atgagtagag      7740
aagagttttt taaataccgg agagaggcca taatcgaggt ggaccgcact gaagcacgca      7800
gggccagacg tgaaaataac atagtgggag gacatccggt ttcgcgaggc tcagcaaaac      7860
tccgttggct cgtggagaaa ggatttgtct cgccaatagg aaaagtcatt gatctagggt      7920
gtgggcgtgg aggatggagc tactacgcag caaccctgaa gaaggtccag gaagtcagag      7980
gatacacgaa aggtggggcg ggacatgaag aaccgatgct catgcagagc tacggctgga      8040
acctggtctc cctgaagagt ggagtggacg tgttttacaa accttcagag cccagtgata      8100
ccctgttctg tgacataggg gaatcctccc caagtccaga agtagaagaa caacgcacac      8160
tacgcgtcct agagatgaca tctgactggt tgcaccgagg acctagagag ttctgcatta      8220
aagttctctg cccttacatg cccaaggtta tagaaaaaat ggaagttctg cagcgtcgct      8280
tcggaggtgg gctagtgcgt ctcccctgt cccgaaactc caatcacgag atgtattggg      8340
ttagtggagc cgctggcaat gtggtgcacg ctgtgaacat gaccagccag gtattactgg      8400
ggcgaatgga tcgcacagtg tggagagggc caaagtatga ggaagatgtc aacctaggga      8460
gcggaacaag agccgtggga aagggagaag tccatagcaa tcaggagaaa atcaagaaga      8520
gaatccagaa gcttaaagaa gaattcgcca caacgtggca caaagaccct gagcatccat      8580
accgcacttg gacataccac ggaagctatg aagtgaaggc tactggctca gccagctctc      8640
tcgtcaacgg agtggtgaag ctcatgagca aaccttggga cgccattgcc aacgtcacca      8700
ccatggccat gactgacacc accccttttg gacagcaaag agttttcaag gagaaagttg      8760
acacgaaggc tcctgagcca ccagctggag ccaaggaagt gctcaacgag accaccaact      8820
ggctgtgggc ctacttgtca cgggaaaaaa gaccccgctt gtgcaccaag gaagaattca      8880
ttaagaaagt taacagcaac gcggctcttg gagcagtgtt cgctgaacag aatcaatgga      8940
gcacggcgcg tgaggctgtg gatgacccgc ggttttggga gatggttgat gaagagaggg      9000
aaaaccatct gcgaggagag tgtcacacat gtatctacaa catgatggga aaaagagaga      9060
agaagcctgg agagtttgga aaagctaaag gaagcagggc catttggttc atgtggcttg      9120
gagcacggta tctagagttt gaagctttgg ggttcctgaa tgaagaccat tggctgagcc      9180
gagagaattc aggaggtgga gtggaaggct caggcgtcca aaagctggga tacatcctcc      9240
gtgacatagc aggaaagcaa ggagggaaaa tgtacgctga tgataccgcc gggtgggaca      9300
ctagaattac cagaactgat ttagaaaatg aagctaaggt actggagctc ctagacggtg      9360
aacaccgcat gctcgcccga gccataattg aactgactta caggcacaaa gtggtcaagg      9420
tcatgagacc tgcagcagaa ggaaagaccg tgatggacgt gatatcaaga gaagatcaaa      9480
gggggagtgg acaggtggtc acttatgctc ttaacacttt cacgaacatc gctgtccagc      9540
tcgtcaggct gatggaggct gagggggtca ttggaccaca acacttggaa catctaccta      9600
ggaaaaacaa gatagctgtc aggacctggc tctttgagaa tggagaggag agagtgacca      9660
ggatggcgat cagcggagac gactgtgccg tcaaaccgct ggacgacaga ttcgccacag      9720
ccctccactt cctcaacgca atgtcaaagg tcagaaaaga catccaggaa tggaagcctt      9780
cgcatggctg gcacgattgg cagcaagttc ccttctgttc taaccatttt caggagattg      9840
tgatgaaaga tggaaggagt atagttgtcc cgtgcagagg acaggatgag ctgataggca      9900
gggctcgcat ctctcctgga gctggatgga atgtgaagga cacagcttgc ctggccaaag      9960
catatgcaca gatgtggcta ctcctatact tccatcgcag ggacttgcgt ctcatggcaa     10020
```

-continued

```
atgcgatttg ctcagcagtg ccagtagatt gggtgcccac aggcaggaca tcctggtcaa    10080
tacactcgaa aggagagtgg atgaccacgg aagacatgct gcaggtctgg aacagagttt    10140
ggattgaaga aaatgaatgg atgatggaca agactccaat cacaagctgg acagacgttc    10200
cgtatgtggg aaagcgcgag acatctggt gtggcagcct catcggaacg cgatccagag    10260
caacctgggc tgagaacatc tatgcggcga taaaccaggt tagagctgtc attgggaaag    10320
aaaattatgt tgactacatg acctcactca ggagatacga agacgtcttg atccaggaag    10380
acagggtcat ctagtgtgat ttaaggtaga aaagtagact atgtaaacaa tgtaaatgag    10440
aaaatgcatg catatggagt caggccagca aaagctgcca ccggatactg ggtagacggt    10500
gctgcctgcg tctcagtccc aggaggactg ggttaacaaa tctgacaaca gaaagtgaga    10560
aagccctcag aaccgtctcg gaagtaggtc cctgctcact ggaagttgaa agaccaacgt    10620
caggccacaa atttgtgcca ctccgctagg gagtgcggcc tgcgcagccc caggaggact    10680
gggttaccaa agccgttgag gcccccacgg cccaagcctc gtctaggatg caatagacga    10740
ggtgtaagga ctagaggtta gaggagaccc cgtggaaaca caacatgcg cccaagccc     10800 cctcgaagct gtagaggagg tggaaggact agaggttaga ggagacccg catttgcatc     10860 aaacagcata ttgacacctg gaatagact gggagatctt ctgctctatc tcaacatcag     10920
ctactaggca cagagcgccg aagtatgtag ctggtggtga ggaagaacac aggatct       10977
```

<210> SEQ ID NO 75
<211> LENGTH: 10976
<212> TYPE: DNA
<213> ORGANISM: Japanese encephalitis virus

<400> SEQUENCE: 75

```
agaagtttat ctgtgtgaac ttcttggctt agtatcgtag agaagaatcg agagattagt      60
gcagtttaaa cagtttttta gaacggaaga taaccatgac taaaaaacca ggagggcccg     120
gtaaaaaccg ggctatcaat atgctgaaac gcggcctacc ccgcgtattc ccactagtgg     180
gagtgaagag ggtagtaatg agcttgttgg acggcagagg gccagtacgt ttcgtgctgg     240
ctcttatcac gttcttcaag tttacagcat tagccccgac caaggcgctt tcaggccgat     300
ggaaagcagt ggaaaagagt gtggcaatga acatcttac tagtttcaaa cgagaacttg     360
gaacactcat tgacgccgtg aacaagcggg gcagaaagca aaacaaaaga ggaggaaatg     420
aaggctcaat catgtggctc gcgagcttgg cagttgtcat agcttgtgca ggagccatga     480
agttgtcgaa tttccagggg aagcttttga tgaccatcaa caacacgac attgcagacg     540 ttatcgtgat tcccacctca aaaggagaga acagatgctg ggtccgggca atcgacgtcg     600
gctacatgtg tgaggacact atcacgtacg aatgtcctaa gcttaccatg ggcaatgatc     660
cagaggatgt ggattgctgg tgtgacaacc aagaagtcta cgtccaatat ggacggtgca     720
cgcggaccag gcattccaag cgaagcagga atccgtgtc ggtccaaaca catggggaga     780
gttcactagt gaataaaaaa gaggcttggc tggattcaac gaaagccaca cgatatctca     840
tgaaaactga gaactggatc ataaggaatc ctggctatgc tttcctggcg gcggtacttg     900
gctggatgct tggcagtaac aacggtcaac gcgtggtatt taccatcctc ctgctgttgg     960
tcgctccggc ttacagtttt aattgtctgg gaatgggcaa tcgtgacttc atagaaggag     1020
ccagtggagc cacttgggtg gacttggtgc tagaaggaga cagctgcttg acaatcatgg     1080
caaacgacaa accaacattg gacgtccgca tgattaacat cgaagctagc caacttgctg     1140
```

```
aggtcagaag ttactgctat catgcttcag tcactgacat ctcgacggtg gctcggtgcc    1200
ccacgactgg agaagcccac aacgagaagc gagctgatag tagctatgtg tgcaaacaag    1260
gcttcactga ccgtgggtgg ggcaacggat gtggattttt cgggaaggga agcattgaca    1320
catgtgcaaa attctcctgc accagtaaag cgattgggag aacaatccag ccagaaaaca    1380
tcaaatacaa agttggcatt tttgtgcatg gaaccaccac ttcggaaaac catgggaatt    1440
attcagcgca agtggggcg tcccaggcgg caaagtttac agtaacaccc aatgctcctt    1500
cggtagccct caaacttggt gactacggag aagtcacact ggactgtgag ccaaggagtg    1560
gactgaacac tgaagcgttt tacgtcatga ccgtggggtc aaagtcattt ctggtccata    1620
gggagtggtt tcatgacctc gctctcccct ggacgtcccc ttcgagcaca gcgtggagaa    1680
acagagaact cctcatggaa tttgaagggg cgcacgccac aaaacagtcc gttgttgctc    1740
ttgggtcaca ggaaggaggc ctccatcatg cgttggcagg agccatcgtg gtggagtact    1800
caagctcagt gatgttaaca tcaggccacc tgaaatgtag gctgaaaatg dacaaactgg    1860
ctctgaaagg cacaacctat ggcatgtgta cagaaaaatt ctcgttcgcg aaaaatccgg    1920
tggacactgg tcacggaaca gttgtcattg aactctccta ctctgggagt gatggcccct    1980
gcaaaattcc gattgtttcc gttgcgagcc tcaatgacat gaccccgtt gggcggctgg    2040 tgacagtgaa ccccttcgtc gcgacttcca gtgccaactc aaaggtgctg gtcgagatgg    2100 aaccccctt cggagactcc tacatcgtag ttggaagggg agacaagcag atcaaccacc    2160
attggcacaa agctggaagc acgctgggca aggccttttc aacaactttg aagggagctc    2220
aaaagactgg cagcgttggc gacacagcct gggactttgg ctctattgga ggggtcttca    2280
actccatagg aagagccgtt caccaagtgt ttggtgatgc cttcagaaca ctctttgggg    2340
gaatgtcttg gatcacacaa gggctaatgg gtgccctact gctctggatg ggcgtcaacg    2400
cacgagaccg atcaattgct ttggccttct tagccacagg aggtgtgctc gtgttcttag    2460
cgaccaatgt gcatgctgac actggatgtg ccattgacat cacaagaaaa gagatgagat    2520
gtggaagtgg catcttcgtg cacaacgacg tggaagcctg ggtggatagg tataaatatt    2580
tgccagaaac gcccagatcc ctagcgaaga tcgtccacaa agcgcacaag aaggcgtgt    2640 gcggagtcag atctgtcact agactggagc accaaatgtg ggaagccgta agggacgaat    2700
tgaacgtcct gctcaaagag aatgcagtgg acctcagtgt ggttgtgaac aagcccgtgg    2760
gaagatatcg ctcagcccct aaacgcctat ccatgacgca agagaagttt gaaatgggct    2820
ggaaagcatg gggaaaaagc atcctctttg ccccggaatt ggctaactcc acatttgtcg    2880
tagatggacc tgagacaaag gaatgccctg atgagcacag agcttggaac agcatgcaaa    2940
tcgaagactt cggcttttggc atcacatcaa cccgtgtgtg gctgaaaatt agagaggaga    3000
gcactgacga gtgtgatgga gcgatcatag gcacggctgt caaaggacat gtggcagtcc    3060
atagtgactt gtcgtactgg attgagagtc gctacaacga cacatggaaa cttgagaggg    3120
cagtctttgg agaggtcaaa tcttgcactt ggccagagac acacacctt tggggagatg    3180 atgttgagga aagtgaactc atcattccgc acaccatagc cggaccaaaa agcaagcaca    3240
atcggaggga agggtataag acacaaaacc agggaccttg gatgagaat ggcatagtct    3300 tggactttga ttattgccca gggacaaaag tcaccattac agaggattgt agcaagagag    3360
gcccttcggt cagaaccact actgacagtg gaaagttgat cactgactgg tgctgtcgca    3420
gttgctccct tccgccccta cgattccgga cagaaaatgg ctgctggtac ggaatggaaa    3480
tcagacctgt tatgcatgat gaaacaacac tcgtcagatc acaggttcat gctttcaaag    3540
```

```
gtgaaatggt tgacccttttt cagctgggcc ttctggtgat gtttctggcc acccaggaag    3600
tccttcgcaa gaggtggacg gccagattga ccattcctgc ggttttgggg gtcctacttg    3660
tgctgatgct tgggggtatc acttacactg atttggcgag gtatgtggtg ctagtcgctg    3720
ctgctttcgc agaggccaac agtggaggag acgtcctgca ccttgctttg attgctgttt    3780
ttaagatcca accagcattt ttagtgatga acatgcttag cacgagatgg acgaaccaag    3840
aaaacgtggt tctggtccta ggggctgcct ttttccaatt ggcctcagta gatctgcaaa    3900
taggagtcca cggaatcctg aatgccgccg ctatagcatg gatgattgtc cgagcgatca    3960
ccttccccac aacctcctcc gtcaccatgc cagtcttagc gcttctaact ccggggatga    4020
gggctctata cctagacact tacagaatca tcctcctcgt catagggatt tgctccctgc    4080
tgcacgagag gaaaaagacc atggcgaaaa agaaaggagc tgtactcttg gcttagcgc     4140 tcacatccac tggatggttc tcgcccacca ctatagctgc cggactaatg gtctgcaacc    4200
caaacaagaa gagagggtgg ccagctactg agttttttgtc ggcagttgga ttgatgtttg    4260
ccatcgtagg tggtttggcc gagttggata ttgaatccat gtcaataccc ttcatgctgg    4320
caggtctcat ggcagtgtcc tacgtggtgt caggaaaagc aacagatatg tggcttgaac    4380
gggccgccga catcagctgg gatatgggtg ctgcaatcac aggaagcagt cggaggctgg    4440
atgtgaaact ggatgatgac ggagattttc acttcattga tgatcccggt gttccatgga    4500
aggtctgggt cctgcgcatg tcttgcattg gcttagccgc cctcacgcct tgggccatcg    4560
ttcccgccgc tttcggttat tggctcactt taaaaacaac aaaaagaggg ggcgtgtttt    4620
gggacacgcc atccccaaaa ccttgctcaa aaggagacac cactacagga gtctaccgaa    4680
ttatggctag agggattctt ggcacttacc aggccggcgt cggagtcatg tacgagaatg    4740
ttttccacac actatggcac acaactagag gagcagccat tgtgagtgga gaaggaaaat    4800
tgacgccata ctggggtagt gtgaaagaag accgcatagc ttacggaggc ccatggaggt    4860
ttgaccgaaa atggaatgga acagatgacg tgcaagtgat cgtggtagaa ccggggaagg    4920
gcgcagtaaa catccagaca aaaccaggag tgtttcggac tcccttcggg gaggttgggg    4980
ctgttagtct ggattacccg cgaggaacat ccggctcacc cattctggat ccaatggag    5040 acattatagg cctatacggc aatggagttg agcttggcga tggctcatac gtcagcgcca    5100
tcgtgcaggg tgaccgtcag gaggaaccag tcccagaagc ttacacccca acatgttga    5160 gaaagagaca gatgactgtg ctagatttgc accctggttc agggaaaacc aggaaaattc    5220
tgccacaaat aattaaggac gctatccagc agcgcctaag aacagctgtg ttggcaccga    5280
cgcgggtggt agcagcagaa atggcagaag ttttgagagg ctcccagta cgatatcaaa    5340 cttcagcagt gcagagagag caccaaggga atgaaatagt ggatgtgatg tgccacgcca    5400
ctctgaccca tagactgatg tcaccgaaca gagtgcccaa ctacaaccta tttgtcatgg    5460
atgaagctca tttcaccgac ccagccagta tagccgcacg aggatacatt gctaccaagg    5520
tggaattagg ggaggcagca gccatctttta tgacagcgac cccgcctgga accacggatc    5580 ctttttcctga ctcaaatgcc ccaatccatg atttgcaaga tgagataccca gacagggcat    5640 ggagcagtgg atacgaatgg atcacagaat atgcgggtaa aaccgtgtgg tttgtggcga    5700
gcgtaaaaat ggggaatgag attgcaatgt gcctccaaag agcggggaaa aaggtcatcc    5760
aactcaaccg caagtcctat gacacagaat acccaaaatg taagaatgga gactgggatt    5820
ttgtcattac caccgacatc tctgaaatgg gggccaactt cggtgcgagc agggtcatcg    5880
```

```
actgtagaaa gagcgtgaaa cccaccatct tagaagaggg agaaggcaga gtcatcctcg    5940
gaaacccatc tcccataacc agtgcaagcg cagctcaacg gaggggcaga gtaggcagaa    6000
accccaatca agttggagat gaataccact atgggggggc taccagtgaa gatgacagta    6060
acctagccca ttggacagag gcaaagatca tgttagacaa catacacatg cccaatggac    6120
tggtggccca gctctatgga ccagagaggg aaaaggcttt cacaatggat ggcgaatacc    6180
gtctcagagg tgaagaaaag aaaaacttct tagagctgct taggacggct gacctcccgg    6240
tgtggctggc ctacaaggtg gcgtccaatg gcattcagta caccgacaga agtggtgtt     6300
ttgatgggcc gcgtacgaat gccatactgg aggacaacac cgaggtagag atagtcaccc    6360
ggatgggtga gaggaaaatc ctcaagccga gatggcttga tgcaagagtt tatgcagatc    6420
accaggccct caagtggttc aaagactttg cagcagggaa gagatcagcc gttagcttca    6480
tagaggtgct cggtcgcatg cctgagcatt tcatgggaaa gacgcgggaa gctttagaca    6540
ccatgtactt ggttgcaacg gctgagaaag gtgggaaagc acaccgaatg gctctcgaag    6600
agctgccaga tgcactggaa accatcacac ttattgtcgc cattactgtg atgacaggag    6660
gattcttcct actaatgatg cagcgaaagg gtataggaaa gatgggtctt ggagctctag    6720
tgctcacact agctaccttc ttcctgtggg cggcagaggt tcctggaacc aaaatagcag    6780
ggaccctgct gatcgccctg ctgctgatgg tggttctcat cccagaaccg gaaaaacaga    6840
ggtcacagac agataaccaa ctggcggtgt tctcatctg tgtcttgacc gtggttggag      6900
tggtggcagc aaacgagtac gggatgctag aaaaaaccaa agcggatctc aagagcatgt    6960
ttggcggaaa gacgcaggca tcaggactga ctggattgcc aagcatggca ctggacctgc    7020
gtccagccac agcctgggca ctgtatgggg ggagcacagt cgtgctaacc cctcttctga    7080
agcacctgat cacgtcggaa tacgtcacca catcgctagc ttcaattaac tcacaagctg    7140
gctcattatt cgtcttgcca cgaggcgtgc cttttaccga cctagacttg actgttggcc    7200
tcgtcttcct tggctgttgg ggtcaagtca ccctcacaac gtttctgaca gccatggttc    7260
tggcgacact tcactatggg tacatgctcc ctggatggca agcagaagca ctcagggctg    7320
cccagagaag gacagcggct ggaataatga agaatgccgt tgttgacgga atggtcgcca    7380
ctgatgtgcc tgaactggaa aggactactc ctctgatgca aagaaagtc ggacaggtgc      7440
tcctcatagg ggtaagcgtg gcagcgttcc tcgtcaaccc taatgtcacc actgtgagag    7500
aagcagggt gttggtgacg gcggctacgc ttacttgtg ggacaatgga gccagtgccg       7560
tttgaattc caccacagcc acgggactct gccatgtcat gcgaggtagc tacctggctg     7620
gaggctccat tgcttggact ctcatcaaga cgctgataa gccctccttg aaaaggggaa      7680
ggcctggggg caggacgcta ggggagcagt ggaaggaaaa actaaatgcc atgagtagag    7740
aagagttttt taaataccgg agagagggca taatcgaggt ggaccgcact gaagcacgca    7800
gggccagaag tgaaaataac atagtgggag acatccggt ttcgcgaggc tcagcaaaac      7860
tccgttggct tgtggagaaa ggatttgtct cgccaatagg aaaagtcatt gatctagggt    7920
gtgggcgtgg aggatggagc tactacgcag caaccctgaa gaaggtccag gaagtcagag    7980
gatacacgaa aggtggggcg ggacatgaag aaccgatgct catgcagagc tacggctgga   8040
acctggtctc cctgaagagt ggagtggacg tgttttacaa accttcagag cccagtgata    8100
ccctgttctg tgacataggg gaatcctccc caagtccaga agtagaagaa caacgcacac    8160
tacgcgtcct agagatgaca tctgactggt tgcaccgagg acctagagag ttctgcatta    8220
aagttctctg cccttacatg cccaaggtta tagaaaaaat tgaagttctg cagcgccgct    8280
```

```
tcggaggtgg gctagtgcgt ctcccctgt cccgaaactc caatcacgag atgtattggg    8340
ttagtggagc cgctggcaat gtggtgcacg ctgtgaacat gaccagccag gtattactgg    8400
ggcgaatgga tcgcacagtg tggagagggc caaagtatga ggaagatgtc aacctaggga    8460
gcggaacaag agccgtggga aagggagaag tccatagcaa tcaggagaaa atcaagaaga    8520
gaatccagaa gcttaaagaa gaattcgcca caacgtggca caaagaccct gagcatccat    8580
accgcacttg gacataccac ggaagctatg aagtgaaggc tactggctca gccagctctc    8640
tcgtcaacgg agtggtgaag ctcatgagca accttggga cgccattgcc aacgtcacca    8700
ccatggccat gactgacacc accccttttg gacagcaaag agttttcaag gagaaagttg    8760
acacgaaggc tcctgagcca ccagctggag ccaaggaagt gctcaacgag accaccaact    8820
ggctgtgggc ctacttgtca cgggaaaaaa gaccccgctt gtgcaccaag gaagaattca    8880
ttaagaaagt taacagcaac gcggctcttg gagcagtgtt cgctgaacag aatcaatgga    8940
gcacggcgcg tgaggctgtg gatgacccgc ggttttggga gatggttgat gaagagaggg    9000
aaaaccatct gcgaggagag tgtcacacat gtatctacaa catgatggga aaaagagaga    9060
agaagcctgg agagtttgga aaagctaaag gaagcagggc catttggttc atgtggcttg    9120
gagcacggta tctagagttt gaagctttgg ggttcctgaa tgaagaccat tggctgagcc    9180
gagagaattc aggaggtgga gtggaaggct caggcgtcca aaagctggga tacatcctcc    9240
gtgacatagc aggaaagcaa ggagggaaaa tgtacgctga tgataccgcc gggtgggaca    9300
ctagaattac cagaactgat ttagaaaatg aagctaaggt actggagctc ctagacggtg    9360
aacaccgcat gctcgcccga gccataattg aactgactta caggcacaaa gtggtcaagg    9420
tcatgagacc tgcagcagaa ggaaagaccg tgatggacgt gatatcaaga gaagatcaaa    9480
gggggagtgg acaggtggtc acttatgctc ttaacacttt cacgaacatc gctgtccagc    9540
tcgtcaggct gatggaggct gagggggtca ttgaccacac acttgaa catctaccta    9600 ggaaaaacaa gatagctgtc aggacctggc tctttgagaa tggagaggag agagtgacca    9660
ggatggcgat cagcggagac gactgtgccg tcaaaccgct ggacgacaga ttcgccacag    9720
ccctccactt cctcaacgca atgtcaaagg tcagaaaaga catccaggaa tggaagcctt    9780
cgcatggctg gcacgattgg cagcaagttc ccttctgttc taaccatttt caggagattg    9840
tgatgaaaga tggaaggagt atagttgtcc cgtgcagagg acaggatgag ctgataggca    9900
gggctcgcat ctctccagga gctggatgga atgtgaagga cacagcttgc ctgcccaaag    9960
catatgcaca aatgtgggta ctcctatact tccaccgcag ggacttgcgt ctcatggcaa   10020
atgcgatttg ctcagcagtg ccagtagatt gggtgcccac aggcaggaca tcctggtcaa   10080
tacactcgaa aggagagtgg atgaccacg aagacatgct gcaggtctgg aacagagttt   10140
ggattgaaga aaatgaatgg atgatggaca agactccaat cacaagctgg acagacgttc   10200
cgtatgtggg aaagcgcgag gacatctggt gtggcagcct catcggaacg cgatccagag   10260
caacctgggc tgagaacatc tatgcggcga taaaccaggt tagagctgtc attgggaaag   10320
aaaattatgt tgactacatg acctcactca ggagatacga agacgtcttg atccaggaag   10380 acaggggtcat ctagtgtgat ttaaggtaga aaagtagact atgtaaacaa tgtaaatgag   10440
aaaatgcatg catatggagt caggccagca aaagctgcca ccggatactg ggtagacggt   10500
gctgcctgcg tctcagtccc aggaggactg ggttaacaaa tctgacaaca gaaagtgaga   10560
aagccctcag aactgtctcg gaagtaggtc cctgctcact ggaagttgaa agaccaacgt   10620
```

| | |
|---|---:|
| caggccacaa atttgtgcca ctccgctagg gagtgcggcc tgcgcagccc caggaggact | 10680 |
| gggttaccaa agccgttgag cccccacggc ccaagcctcg tctaggatgc aatagacgag | 10740 |
| gtgtaaggac tagaggttag aggagacccc gtggaaacaa caacatgcgg cccaagcccc | 10800 |
| ctcgaagctg tagaggaggt ggaaggacta gaggttagag gagacccgc atttgcatca | 10860 |
| aacagcatat tgacacctgg aatagactg ggagatcttc tgctctatct caacatcagc | 10920 |
| tactaggcac agagcgccga agtatgtacg tggtggtgag aagaacaca ggatct | 10976 |

<210> SEQ ID NO 76
<211> LENGTH: 10838
<212> TYPE: DNA
<213> ORGANISM: Yellow fever virus

<400> SEQUENCE: 76

| | |
|---|---:|
| gtgctaattg aggtgcattg gtctgcaaat cgagttgcta ggcaataaac acatttggat | 60 |
| taattttaat cgttcgttga gcgattagca gagaactgac cagaacatgt ctggtcgtaa | 120 |
| agctcaggga aaaaccctgg gcgtcaatat ggtacgacga ggagttcgct ccttgtcaaa | 180 |
| caaaataaaa caaaaaacaa aacaaattgg aaacagacct ggaccttcaa gaggtgttca | 240 |
| aggatttatc tttttctttt tgttcaacat tttgactgga aaaaagatca cagcccacct | 300 |
| aaagaggttg tggaaaatgc tggacccaag acaaggcttg gctgttctaa ggaaagtcaa | 360 |
| gagagtggtg gccagtttga tgagaggatt gtcctcaagg aaacgccgtt cccatgatgt | 420 |
| tctgactgtg caattcctaa ttttgggaat gctgttgatg acgggtggag tgaccttggt | 480 |
| gcggaaaaac agatggttgc tcctaaatgt gacatctgag gacctcggga aaacattctc | 540 |
| tgtgggcaca ggcaactgca caacaaacat tttggaagcc aagtactggt gcccagactc | 600 |
| aatggaatac aactgtccca atctcagtcc aagagaggag ccagatgaca ttgattgctg | 660 |
| gtgctatggg gtggaaaacg ttagagtcgc atatggtaag tgtgactcag caggcaggtc | 720 |
| taggaggtca agaagggcca ttgacttgcc tacgcatgaa aaccatggtt tgaagacccg | 780 |
| gcaagaaaaa tggatgactg gaagaatggg tgaaaggcaa ctccaaaaga ttgagagatg | 840 |
| gttcgtgagg aaccccttt tgcagtgac ggctctgacc attgcctacc ttgtgggaag | 900 |
| caacatgacg caacgagtcg tgattgccct actggtcttg gctgttggtc cggcctactc | 960 |
| agctcactgc attggaatta ctgacaggga tttcattgag ggggtgcatg gaggaacttg | 1020 |
| ggtttcagct accctggagc aagacaagtg tgtcactgtt atggcccctg acaagccttc | 1080 |
| attggacatc tcactagaga cagtagccat tgatagacct gctgaggtga ggaaagtgtg | 1140 |
| ttacaatgca gttctcactc atgtgaagat taatgacaag tgccccagca ctggagaggc | 1200 |
| ccacctagct gaagagaacg aaggggacaa tgcgtgcaag cgcacttatt ctgatagagg | 1260 |
| ctggggcaat ggctgtggcc tatttgggaa agggagcatt gtggcatgcg ccaaattcac | 1320 |
| ttgtgccaaa tccatgagtt tgtttgaggt tgatcagacc aaaattcagt atgtcatcag | 1380 |
| agcacaattg catgtagggg ccaagcagga aaattgact accgacatta agactctcaa | 1440 |
| gtttgatgcc ctgtcaggct cccaggaagt cgagttcatt gggtatggaa agctacact | 1500 |
| ggaatgccag gtgcaaactg cggtggactt tggtaacagt tacatcgctg agatggaaac | 1560 |
| agagagctgg atagtggaca gacagtgggc ccaggacttg accctgccat ggcagagtgg | 1620 |
| aagtggcggg gtgtggagag agatgcatca tcttgtcgaa tttgaacctc gcatgccgc | 1680 |
| cactatcaga gtactggccc tgggaaacca ggaaggctcc ttgaaaacag ctcttactgg | 1740 |
| cgcaatgagg gttacaaagg acacaaatga caacaacctt tacaaactac atggtggaca | 1800 |

```
tgtttcttgc agagtgaaat tgtcagcttt gacactcaag gggacatcct acaaaatatg    1860
cactgacaaa atgttttttg tcaagaaccc aactgacact ggccatggca ctgttgtgat    1920
gcaggtgaaa gtgtcaaaag gagcccctg caggattcca gtgatagtag ctgatgatct    1980
tacagcggca atcaataaag gcattttggt tacagttaac cccatcgcct caaccaatga    2040
tgatgaagtg ctgattgagg tgaacccacc ttttggagac agctacatta tcgttgggag    2100
aggagattca cgtctcactt accagtggca caaagaggga agctcaatag gaaagttgtt    2160
cactcagacc atgaaaggcg tggaacgcct ggccgtcatg ggagacaccg cctgggattt    2220
cagctccgct ggagggttct tcacttcggt tgggaaagga attcatacgg tgtttggctc    2280
tgcctttcag gggctatttg cggcttgaa ctggataaca aaggtcatca tggggcggt    2340 acttatatgg gttggcatca acacaagaaa catgacaatg tccatgagca tgatcttggt    2400
aggagtgatc atgatgtttt tgtctctagg agttggggcg atcaaggat gcgccatcaa    2460 ctttggcaag agagagctca gtgcggaga tggtatcttc atatttagag actctgatga    2520
ctggctgaac aagtactcat actatccaga agatcctgtg aagcttgcat caatagtgaa    2580
agcctctttt gaagaaggga agtgtggcct aaattcagtt gactcccttg agcatgagat    2640
gtggagaagc agggcagatg agatcaatgc cattttgag gaaaacgagg tggacatttc    2700
tgttgtcgtg caggatccaa agaatgtta ccagagagga actcatccat tttccagaat    2760
tcgggatggt ctgcagtatg gttggaagac ttggggtaag aaccttgtgt ctccccagg    2820 gaggaagaat ggaagcttca tcatagatgg aaagtccagg aaagaatgcc cgttttcaaa    2880
ccgggtctgg aattctttcc agatagagga gtttgggacg ggagtgttca ccacacgcgt    2940
gtacatggac gcagtctttg aatacaccat agactgcgat ggatctatct tgggtgcagc    3000
ggtgaacgga aaaagagtg cccatggctc tccaacattt tggatgggaa gtcatgaagt    3060
aaatgggaca tggatgatcc acaccttgga ggcattagat tacaaggagt gtgagtggcc    3120
actgacacat acgattggaa catcagttga agagagtgaa atgttcatgc cgagatcaat    3180
cggaggccca gttagctctc acaatcatat ccctggatac aaggttcaga cgaacgacc    3240 ttggatgcag gtaccactag aagtgaagag agaagcttgc ccagggacta gcgtgatcat    3300
tgatggcaac tgtgatggac ggggaaaatc aaccagatcc accacggata gcgggaaagt    3360
tattcctgaa tggtgttgcc gctcctgcac aatgccgcct gtgagcttcc atggtagtga    3420
tgggtgttgg tatcccatgg aaattaggcc aaggaaaacg catgaaagcc atctggtgcg    3480
ctcctgggtt acagctggag aaatacatgc tgtcccttt ggtttggtga gcatgatgat    3540
agcaatggaa gtggtcctaa ggaaaagaca gggaccaaag caaatgttgg ttggaggagt    3600
agtgctcttg gagcaatgc tggtcggca gtaactctc cttgatttgc tgaaactcac    3660
agtggctgtg ggattgcatt tccatgagat gaacaatgga ggagacgcca tgtatatggc    3720
gttgattgct gccttttcaa tcagaccagg gctgctcatc ggctttggc tcaggaccct    3780 atggagccct cgggaacgcc ttgtgctgac cctaggagca gccatggtgg agattgcctt    3840
gggtggcgtg atgggcggcc tgtggaagta tctaaatgca gttctctct gcatcctgac    3900 aataaatgct gttgcttcta ggaaagcatc aaataccatc ttgcccctca tggctctgtt    3960
gacacctgtc actatggctg aggtgagact tgccgcaatg ttcttttgtg ccgtggttat    4020 catagggtc cttcaccaga atttcaagga cacctccatg cagaagacta tacctctggt    4080
ggccctcaca ctcacatctt acctgggctt gacacaacct ttttgggcc tgtgtgcatt    4140
```

```
tctggcaacc cgcatatttg ggcgaaggag tatcccagtg aatgaggcac tcgcagcagc    4200
tggtctagtg ggagtgctgg caggactggc ttttcaggag atggagaact tccttggtcc    4260
gattgcagtt ggaggactcc tgatgatgct ggttagcgtg gctgggaggg tggatgggct    4320
agagctcaag aagcttggtg aagtttcatg ggaagaggag gcggagatca gcggagttc    4380
cgcccgctat gatgtggcac tcagtgaaca aggggagttc aagctgcttt ctgaagagaa    4440
agtgccatgg gaccaggttg tgatgacctc gctggccttg gttggggctg ccctccatcc    4500
atttgctctt ctgctggtcc ttgctgggtg gctgtttcat gtcaggggag ctaggagaag    4560
tggggatgtc ttgtgggata ttcccactcc taagatcatc gaggaatgtg aacatctgga    4620
ggatgggatt tatggcatat ccagtcaac cttcttgggg gcctcccagc gaggagtggg    4680
agtggcacag ggaggggtgt tccacacaat gtggcatgtc acaagaggag ctttccttgt    4740
caggaatggc aagaagttga ttccatcttg ggcttcagta aaggaagacc ttgtcgccta    4800
tggtggctca tggaagttgg aaggcagatg ggatggagag gaagaggtcc agttgatcgc    4860
ggctgttcca ggaaagaacg tggtcaacgt ccagacaaaa ccgagcttgt tcaaagtgag    4920
gaatggggga gaaatcgggg ctgtcgctct tgactatccg agtggcactt caggatctcc    4980
tattgttaac aggaacggag aggtgattgg gctgtacggc aatggcatcc ttgtcggtga    5040
caactccttc gtgtccgcca tatcccagac tgaggtgaag gaagaaggaa aggaggagct    5100
ccaagagatc ccgacaatgc taaagaaagg aatgacaact gtccttgatt tcatcctgg    5160
agctgggaag acaagacgtt tcctcccaca gatcttggcc gagtgcgcac ggagacgctt    5220
gcgcactctt gtgttggccc ccaccagggt tgttctttct gaaatgaagg aggcttttca    5280
cggcctggac gtgaaattcc acacacaggc ttttccgct cacggcagcg ggagagaagt    5340
cattgatgct atgtgccatg ccaccctaac ttacaggatg ttggaaccaa ctagggttgt    5400
taactgggaa gtgatcatta tggatgaagc ccatttttg gatccagcta gcatagccgc    5460
tagaggttgg gcagcgcaca gagctagggc aaatgaaagt gcaacaatct tgatgacagc    5520
cacaccgcct gggactagtg atgaatttcc acattcaaat ggtgaaatag aagatgttca    5580
aacggacata cccagtgagc cctggaacac agggcatgac tggatcctgg ctgacaaaag    5640
gcccacggca tggttccttc catccatcag agctgcaaat gtcatggctg cctcttcgcg    5700
taaggctgga aagagtgtgg tggtcctgaa caggaaaacc tttgagagag atacccccac    5760
gataaagcag aagaaacctg actttatatt ggccactgac atagctgaaa tgggagccaa    5820
cctttgcgtg gagcgagtgc tggattgcag gacggctttt aagcctgtgc ttgtggatga    5880
agggaggaag gtggcaataa aagggccact tcgtatctcc gcatcctctg ctgctcaaag    5940
gaggggggcgc attgggagaa atcccaacag agatggagac tcatactact attctgagcc    6000
tacaagtgaa aataatgccc accacgtctg ctggttggag gcctcaatgc tcttggacaa    6060
catgagggtg aggggtggaa tggtcgcccc actctatggc gttgaaggaa ctaaaacacc    6120
agtttccccct ggtgaaatga gactgaggga tgaccagagg aaaagtcttca gagaactagt    6180
gaggaattgt gacctgcccg tttggcttc gtggcaagtg gccaaggctg gtttgaagac    6240
gaatgatcgt aagtggtgtt ttgaaggcc tgaggaacat gagatcttga atgacagcgg    6300
tgaaacagtg aagtgcaggg ctcctggagg agcaaagaag cctctgcgcc caaggtggtg    6360
tgatgaaagg gtgtcatctg accagagtgc gctgtctgaa tttattaagt tgctgaagg    6420
taggagggga gctgctgaag tgctagttgt gctgagtgaa ctccctgatt tcctggctaa    6480
aaaaggtgga gaggcaatgg ataccatcag tgtgtttctc cactctgagg aaggctctag    6540
```

```
ggcttaccgc aatgcactat caatgatgcc tgaggcaatg acaatagtca tgctgtttat    6600
actggctgga ctactgacat cgggaatggt catcttttc atgtctccca aaggcatcag     6660
tagaatgtct atggcgatgg gcacaatggc cggctgtgga tatctcatgt tccttggagg    6720
cgtcaaaccc actcacatct cctatatcat gctcatattc tttgtcctga tggtggttgt    6780
gatccccgag ccagggcaac aaaggtccat ccaagacaac caagtggcat acctcattat    6840
tggcatcctg acgctggttt cagcggtggc agccaacgag ctaggcatgc tggagaaaac    6900
caaagaggac ctctttggga agaagaactt aattccatct agtgcttcac cctggagttg    6960
gccggatctt gacctgaagc caggagctgc ctggacagtg tacgttggca ttgttacaat    7020
gctctctcca atgttgcacc actggatcaa agtcgaatat ggcaacctgt ctctgtctgg    7080
aatagcccag tcagcctcag tcctttcttt catggacaag gggataccat tcatgaagat    7140
gaatatctcg gtcataatgc tgctggtcag tggctggaat tcaataacag tgatgcctct    7200
gctctgtggc atagggtgcg ccatgctcca ctggtctctc attttacctg gaatcaaagc    7260
gcagcagtca aagcttgcac agagaagggt gttccatggc gttgccaaga accctgtggt    7320
tgatgggaat ccaacagttg acattgagga agctcctgaa atgcctgccc tttatgagaa    7380
gaaactggct ctatatctcc ttcttgctct cagcctagct tctgttgcca tgtgcagaac    7440 gccctttca ttggctgaag gcattgtcct agcatcagct gccctagggc cgctcataga    7500
gggaaacacc agccttcttt ggaatggacc catggctgtc tccatgacag gagtcatgag    7560
ggggaatcac tatgcttttg tgggagtcat gtacaatcta tggaagatga aaactggacg    7620
ccgggggagc gcgaatggaa aaactttggg tgaagtctgg aagagggaac tgaatctgtt    7680
ggacaagcga cagtttgagt tgtataaaag accgacatt gtggaggtgg atcgtgatac     7740
ggcacgcagg catttggccg aagggaaggt ggacaccggg gtggcggtct ccaggggac     7800 cgcaaagtta aggtggttcc atgagcgtgg ctatgtcaag ctggaaggta gggtgattga    7860
cctggggtgt ggccgcggag ctggtgttac tacgctgct gcgcaaaagg aagtgagtgg     7920
ggtcaaagga tttactcttg aagagacgcc ccatgagaaa cccatgaatg tgcaaagtct    7980
gggatggaac atcatcacct tcaaggacaa aactgatatc caccgcctag aaccagtgaa    8040
atgtgacacc ctttgtgtg acattggaga gtcatcatcg tcatcggtca cagagggga     8100 aaggaccgtg agagttcttg atactgtaga aaatggctg gcttgtgggg ttgacaactt     8160
ctgtgtgaag gtgttagctc catacatgcc agatgttctc gagaaactgg aattgctcca    8220
aaggaggttt ggcggaacag tgatcaggaa ccctctctcc aggaattcca ctcatgaaat    8280
gtactacgtg tctggagccc gcagcaatgt cacatttact gtgaaccaaa catcccgcct    8340
cctgatgagg agaatgaggc gtccaactgg aaaagtgacc ctggaggctg acgtcatcct    8400
cccaattggg acacgcagtg ttgagacaga caagggaccc ctggacaaag aggccataga    8460
agaaagggtt gagaggataa aatctgagta catgacctct tggttttatg acaatgacaa    8520
cccctacagg acctggcact actgtggctc ctatgtcaca aaaacctcag gaagtgcggc    8580
gagcatggta aatggtgtta ttaaaattct gacatatcca tgggacagga tagaggaggt    8640
cacaagaatg gcaatgactg acacaacccc ttttggacag caaagagtgt ttaaagaaaa    8700
agttgacacc agagcaaagg atccaccagc gggaactagg aagatcatga agttgtcaa     8760 caggtggctg ttccgccacc tggccagaga aaagaacccc agactgtgca caaaggaaga    8820
atttattgca aaagtccgaa gtcatgcagc cattggagct tacctggaag aacaagaaca    8880
```

| gtggaagact gccaatgagg ctgtccaaga cccaaagttc tgggaactgg tggatgaaga | 8940 |
| aaggaagctg caccaacaag gcaggtgtcg gacttgtgtg tacaacatga tggggaaaag | 9000 |
| agagaagaag ctgtcagagt ttgggaaagc aaagggaagc cgtgccatat ggtatatgtg | 9060 |
| gctgggagcg cggtatcttg agtttgaggc cctgggattc ctgaatgagg accattgggc | 9120 |
| ttccagggaa aactcaggag gaggagtgga aggcattggc ttacaatacc taggatatgt | 9180 |
| gatcagagac ctggctgcaa tggatggtgg tggattctac gcggatgaca ccgctggatg | 9240 |
| ggacacgcgc atcacagagg cagaccttga tgatgaacag gagatcttga actacatgag | 9300 |
| cccacatcac aaaaaactgg cacaagcagt gatggaaatg acatacaaga caaagtggt | 9360 |
| gaaagtgttg agaccagccc caggagggaa agcctacatg gatgtcataa gtcgacgaga | 9420 |
| ccagagagga tccgggcagg tagtgactta tgctctgaac accatcacca acttgaaagt | 9480 |
| ccaattgatc agaatggcag aagcagagat ggtgatacat caccaacatg ttcaagattg | 9540 |
| tgatgaatca gttctgacca ggctggaggc atggctcact gagcacggat gtaacagact | 9600 |
| gaagaggatg gcggtgagtg gagacgactg tgtggtccgg cccatcgatg acaggttcgg | 9660 |
| cctggccctg tcccatctca acgccatgtc caaggttaga aaggacatat ctgaatggca | 9720 |
| gccatcaaaa gggtggaatg attggagaa tgtgccttc tgttcccacc acttccatga | 9780 |
| actacagctg aaggatggca ggaggattgt ggtgccttgc cgagaacagg acgagctcat | 9840 |
| tgggagagga agggtgtctc caggaaacgg ctggatgatc aaggaaacag cttgcctcag | 9900 |
| caaagcctat gccaacatgt ggtcactgat gtattttcac aaaagggaca tgaggctact | 9960 |
| gtcattggct gtttcctcag ctgttcccac ctcatgggtt ccacaaggac gcacaacatg | 10020 |
| gtcgattcat gggaaagggg agtggatgac cacggaagac atgcttgagg tgtggaacag | 10080 |
| agtatggata accaacaacc cacacatgca ggacaagaca atggtgaaaa atggagaga | 10140 |
| tgtcccttat ctaaccaaga gacaagacaa gctgtgcgga tcactgattg gaatgaccaa | 10200 |
| tagggccacc tgggcctccc acatccattt ggtcatccat cgtatccgaa cgctgattgg | 10260 |
| acaggagaaa tacactgact acctaacagt catggacagg tattctgtgg atgctgacct | 10320 |
| gcaactgggt gagcttatct gaaacaccat ctaacaggaa taaccgggat acaaaccacg | 10380 |
| ggtggagaac cggactcccc acaacctgaa accgggatat aaaccacggc tggagaaccg | 10440 |
| gactccgcac ttaaaatgaa acagaaaccg ggataaaaac tacggatgga gaaccggact | 10500 |
| ccacacattg agacagaaga gttgtcagc ccagaacccc acacgagttt tgccactgct | 10560 |
| aagctgtgag gcagtgcagg ctgggacagc cgacctccag gttgcgaaaa acctggtttc | 10620 |
| tgggacctcc caccccagag taaaagaac ggagcctccg ctaccaccct cccacgtggt | 10680 |
| ggtagaaaga cggggtctag aggttagagg agaccctcca gggaacaaat agtgggacca | 10740 |
| tattgacgcc agggaaagac cggagtggtt ctctgctttt cctccagagg tctgtgagca | 10800 |
| cagtttgctc aagaataagc agacctttgg atgacaaa | 10838 |

<210> SEQ ID NO 77
<211> LENGTH: 11674
<212> TYPE: DNA
<213> ORGANISM: Chikungunya virus

<400> SEQUENCE: 77

| gatggctgcg tgagacacac gtagcctacc agtttcttac tgctctactc tgcaaagcaa | 60 |
| gagattaata acccatcatg gatcctgtgt acgtggacat agacgctgac agcgcctttt | 120 |
| tgaaggccct gcaacgtgcg taccccatgt ttgaggtgga accaaggcag gtcacaccga | 180 |

```
atgaccatgc taatgctaga gcgttctcgc atctagctat aaaactaata gagcaggaaa    240
ttgaccccga ctcaaccatc ctggatatcg gcagtgcgcc agcaaggagg atgatgtcgg    300
acaggaagta ccactgcgtc tgcccgatgc gcagtgcgga agatcccgag agactcgcca    360
attatgcgag aaagctagca tctgccgcag gaaaagtcct ggacagaaac atctctggaa    420
agatcgggga cttacaagca gtaatggccg tgccagacac ggagacgcca acattctgct    480
tacacacaga cgtctcatgt agacagagag cagacgtcgc tatataccaa gacgtctatg    540
ctgtacacgc acccacgtcg ctataccacc aggcgattaa aggggtccga gtggcgtact    600
gggttgggtt cgacacaacc ccgttcatgt acaatgccat ggcgggtgcc tacccctcat    660
actcgacaaa ctgggcagat gagcaggtac tgaaggctaa gaacatagga ttatgttcaa    720
cagacctgac ggaaggtaga cgaggcaagt tgtctattat gagagggaaa aagctaaaac    780
cgtgcgaccg tgtgctgttc tcagtagggt caacgctcta cccggaaagc cgcaagctac    840
ttaagagctg gcacctgcca tcggtgttcc atttaaaggg caaactcagc ttcacatgcc    900
gctgtgatac agtggtttcg tgtgagggct acgtcgttaa gagaataacg atgagcccag    960
gcctttatgg aaaaaccaca gggtatgcgg taacccacca cgcagacgga ttcctgatgt    1020
gcaagactac cgacacggtt gacggcgaaa gaatgtcatt ctcggtgtgc acatacgtgc    1080
cggcgaccat ttgtgatcaa atgaccggca tccttgctac agaagtcacg ccggaggatg    1140
cacagaagct gttggtgggg ctgaaccaga gaatagtggt taacggcaga acgcaacgga    1200
atacgaacac catgaaaaat tatctgcttc ccgtggtcgc ccaagccttc agtaagtggg    1260
caaaggagtg ccggaaagac atggaagatg aaaaactcct gggggtcaga gaaagaacac    1320
tgacctgctg ctgtctatgg gcattcaaga agcagaaaac acacacgtc tacaagaggc    1380 ctgatacccca gtcaattcag aaggttcagg ccgagtttga cagctttgtg gtaccgagtc    1440
tgtggtcgtc cggttgtca atcccttga ggactagaat caaatggttg ttaagcaagg    1500
tgccaaaaac cgacctgatc ccatacagcg gagacgcccg agaagcccgg gacgcagaaa    1560
aagaagcaga ggaagaacga gaagcagaac tgactcgcga agccctacca cctctacagg    1620
cagcacagga agatgttcag gtcgaaatcg acgtggaaca gcttgaggac agagcgggcg    1680
caggaataat agagactccg agaggagcta tcaaagttac tgcccaacca acagaccacg    1740
tcgtgggaga gtacctggta ctctcccccgc agaccgtact acgtagccag aagctcagtc    1800
tgattcacgc tttggcggag caagtgaaga cgtgcacgca caacggacga gcaggaggt    1860 atgcggtcga agcgtacgac ggccgagtcc tagtgcccctc aggctatgca atctcgcctg    1920
aagacttcca gagtctaagc gaaagcgcaa cgatggtgta taacgaaaga gagttcgtaa    1980
acagaaagct acaccatatt gcgatgcacg gaccagccct gaacaccgac gaagagtcgt    2040
atgagctggt gagggcagag aggacagaac acgagtacgt ctacgacgtg gatcagagaa    2100
gatgctgtaa gaaggaagaa gccgcaggac tggtactggt gggcgacttg actaatccgc    2160
cctaccacga attcgcatat gaagggctaa aaatccgccc tgcctgccca tacaaaattg    2220
cagtcatagg agtcttcgga gtaccgggat ctggcaagtc agctattatc aagaacctag    2280
ttaccaggca ggacctggtg actagcggaa agaaagaaaa ctgccaagaa atcaccaccg    2340
acgtgatgag acagagaggt ctagagatat ctgcacgtac ggttgactcg ctgctcttga    2400
atggatgcaa cagaccagtc gacgtgttgt acgtagacga ggcgttcgcg tgccactctg    2460
gaacgctact tgctttgatc gccttggtga gaccaaggca gaaagttgta ctttgtggtg    2520
```

```
acccgaagca gtgcggcttc ttcaatatga tgcagatgaa agtcaactat aatcacaaca    2580
tctgcaccca agtgtaccac aaaagtatct ccaggcggtg tacactgcct gtgaccgcca    2640
ttgtgtcatc gttgcattac gaaggcaaaa tgcgcactac gaatgagtac aacaagccga    2700
ttgtagtgga cactacaggc tcaacaaaac ctgaccctgg agacctcgtg ttaacgtgct    2760
tcagagggtg ggttaaacaa ctgcaaattg actatcgtgg atacgaggtc atgacagcag    2820
ccgcatccca agggttaacc agaaaaggag tttacgcagt tagacaaaaa gttaatgaaa    2880
acccgctcta tgcatcaacg tcagagcacg tcaacgtact cctaacgcgt acggaaggta    2940
aactggtatg gaagacactt tccggcgacc cgtggataaa gacgctgcag acccaccga    3000
aaggaaactt caaagcaact attaaggagt gggaggtgga gcatgcatca ataatggcgg    3060
gcatctgcag tcaccaaatg accttcgata cattccaaaa taaagccaac gtttgttggg    3120
ctaagagctt ggtccctatc ctcgaaacag cggggataaa actaaatgat aggcagtggt    3180
ctcagataat tcaagccttc aaagaagaca aagcatactc acctgaagta gccctgaatg    3240
aaatatgtac gcgcatgtat ggggtggatc tagacagcgg gctatttttct aaaccgttgg    3300
tgtctgtgta ttacgcggat aaccactggg ataataggcc tggagggaaa atgttcggat    3360
ttaaccccga ggcagcatcc attctagaaa gaaagtatcc attcacaaaa gggaagtgga    3420
acatcaacaa gcagatctgc gtgactacca ggaggataga agactttaac cctaccacca    3480
acatcatacc ggccaacagg agactaccac actcattagt ggccgaacac cgcccagtaa    3540
aaggggaaag aatggaatgg ctggttaaca agataaacgg ccaccacgtg ctcctggtca    3600
gtggctataa ccttgcactg cctactaaga gagtcacttg ggtagcgccg ttaggtgtcc    3660
gcggagcgga ctacacatac aacctagagt tgggtctgcc agcaacgctt ggtaggtatg    3720
acctagtggt cataaacatc cacacacctt ttcgcataca ccattaccaa cagtgcgtcg    3780
accacgcaat gaaactgcaa atgctcgggg gtgactcatt gagactgctc aaaccgggcg    3840
gctctctatt gatcagagca tatggttacg cagatagaac cagtgaacga gtcatctgcg    3900
tattgggacg caagtttaga tcgtctagag cgttgaaacc accatgtgtc accagcaaca    3960
ctgagatgtt tttcctattc agcaactttg acaatggcag aaggaatttc acaactcatg    4020
tcatgaacaa tcaactgaat gcagccttcg taggacaggt cacccgagca ggatgtgcac    4080
cgtcgtaccg ggtaaaacgc atggacatcg cgaagaacga tgaagagtgc gtagtcaacg    4140
ccgctaaccc tcgcgggtta ccgggtggcg tgtttgcaa ggcagtatac aaaaaatggc    4200
cggagtcctt taagaacagt gcaacaccag tgggaaccgc aaaaacagtt atgtgcggta    4260
cgtatccagt aatccacgct gttggaccaa acttctctaa ttattcggag tctgaagggg    4320
accgggaatt ggcagctgcc tatcgagaag tcgcaaagga agtaactagg ctgggagtaa    4380
atagtgtagc tatacctctc ctctccacag gtgtatactc aggagggaaa gacaggctga    4440
cccagtcact gaaccacctc tttacagcca tggactcgac ggatgcagac gtggtcatct    4500
actgccgcga caaagaatgg gagaagaaaa tatctgaggc catacagatg cggacccaag    4560
tagagctgct ggatgagcac atctccatag actgcgatat tgttcgcgtg caccctgaca    4620
gcagcttggc aggcagaaaa ggatacagca ccacggaagg cgcactgtac tcatatctag    4680
aagggacccg ttttcatcag acggctgtgg atatggcgga gatacatact atgtggccaa    4740
agcaaacaga ggccaatgag caagtctgcc tatatgccct gggggaaagt attgaatcga    4800
tcaggcagaa atgcccggtg gatgatgcag acgcatcatc tccccccaaa actgtcccgt    4860
gcctttgccg ttacgctatg actccagaac gcgtcacccg gcttcgcatg aaccacgtca    4920
```

```
caagcataat tgtgtgttct tcgtttcccc tcccaaagta caaaatagaa ggagtgcaaa    4980
aagtcaaatg ctctaaggta atgctatttg accacaacgt gccatcgcgc gtaagtccaa    5040
gggcttatag aggtgccgct gccggtaacc ttgcggccgt gtctgattgg gtaatgagca    5100
ccgtacctgt cgcgccgccc agaagaaggc gagggagaaa cctgactgtg acatgtgacg    5160
agagagaagg gaatataaca cccatggcta gcgtccgatt ctttagggca gagctgtgtc    5220
cggtcgtaca agaaacagcg gagacgcgtg acacagcaat gtctcttcag gcaccaccga    5280
gtaccgccac ggaaccgaat catccgccga tctccttcgg agcatcaagc gagacgttcc    5340
ccattacatt tggggacttc aacgaaggag aaatcgaaag cttgtcttct gagctactaa    5400
ctttcggaga cttcttacca ggagaagtgg atgacttgac agacagcgac tggtccacgt    5460
gctcagacac ggacgacgag ttaagactag acagggcagg tgggtatata ttctcgtcgg    5520
acaccggtcc aggtcattta caacagaagt cagtacgcca gtcagtgctg ccggtgaaca    5580
ccctggagga agtccacgag gagaagtgtt acccacctaa gctggatgaa gcaaaggagc    5640
aactattact taagaaactc caggagagtg catccatggc caacagaagc aggtatcagt    5700
cgcgcaaagt agaaaacatg aaagcagcaa tcatccagag actaaagaga ggctgtagac    5760
tatacttaat gtcagagacc ccaaaagtcc ctacttaccg gactacatat ccggcgcctg    5820
tgtactcgcc tccgatcaac gtccgattgt ccaatcccga gtccgcagtg gcagcatgca    5880
atgagttctt agctagaaac tatccaactg tctcatcata ccaaattacc gacgagtatg    5940
atgcatatct agacatggtg gacgggtcgg agagttgcct ggaccgagcg acattcaatc    6000
cgtcaaaact caggagctac ccgaaacagc acgcttacca cgcgccctcc atcagaagcg    6060
ctgtaccgtc cccattccag aacacactac agaatgtact ggcagcagcc acgaaaagaa    6120
actgcaacgt cacacagatg agggaattac ccactttgga ctcagcagta ttcaacgtgg    6180
agtgtttcaa aaaattcgca tgcaaccaag aatactggga agaatttgct gccagcccta    6240
ttaggataac aactgagaat ttagcaacct atgttactaa actaaagggg ccaaaagcag    6300
cagcgctatt cgcaaaaacc cataatctac tgccactaca ggaagtacca atggataggt    6360
tcacagtaga tatgaaaagg gacgtaaagg tgactcctgg tacaaagcat acagaggaaa    6420
gacctaaggt gcaggttata caggcggctg aacccttggc gacagcatac ctatgtggga    6480
ttcacagaga gctggttagg aggctgaacg ccgtcctcct acccaatgta catacactat    6540
ttgacatgtc tgccgaggat ttcgatgcca tcatagccgc cacttttaag ccaggagaca    6600
ctgttttgga aacggacata gcctcctttg ataagagcca agatgattca cttgcgctta    6660
ctgctttgat gctgttagag gatttagggg tggatcactc cctgctggac ttgatagagg    6720
ctgctttcgg agagatttcc agctgtcacc taccgacagg tacgcgcttc aagttcggcg    6780
ccatgatgaa atcaggtatg ttcctaactc tgttcgtcaa cacattgtta aacatcacca    6840
tcgccagccg agtgctggaa gatcgtctga caaaatccgc gtgcgcggcc ttcatcggcg    6900
acgacaacat aatacatgga gtcgtctccg atgaattgat ggcagccaga tgtgccactt    6960
ggatgaacat ggaagtgaag atcatagatg cagttgtatc cttgaaagcc ccttactttt    7020
gtggagggtt tatactgcac gatactgtga caggaacagc ttgcagagtg cagaccgc      7080 taaaaaggct ttttaaactg gcaaaccgc tagcggcagg tgacgaacaa gatgaagata    7140
gaagacgagc gctggctgac gaagtgatca gatggcaacg aacagggcta attgatgagc    7200
tggagaaagc ggtatactct aggtacgaag tgcagggtat atcagttgtg gtaatgtcca    7260
```

```
tggccacctt tgcaagctcc agatccaact tcgagaagct cagaggaccc gtcataactt    7320
tgtacggcgg tcctaaatag gtacgcacta cagctaccta ttttgcagaa gccgacagca    7380
agtatctaaa cactaatcag ctacaatgga gttcatccca acccaaactt tttacaatag    7440
gaggtaccag cctcgaccct ggactccgcg ccctactatc caagtcatca ggcccagacc    7500
gcgccctcag aggcaagctg gcaacttgc ccagctgatc tcagcagtta ataaactgac    7560
aatgcgcgcg gtaccacaac agaagccacg caggaatcgg aagaataaga agcaaaagca    7620
aaacaacag gcgccacaaa acaacacaaa tcaaagaag cagccaccta aaagaaacc      7680
ggctcaaaag aaaagaagc cgggccgcag agagaggatg tgcatgaaaa tcgaaaatga    7740
ttgtattttc gaagtcaagc acgaaggtaa ggtaacaggt tacgcgtgcc tggtggggga    7800
caaagtaatg aaaccagcac acgtaaaggg gaccatcgat aacgcggacc tggccaaact    7860
ggcctttaag cggtcatcta agtatgacct tgaatgcgcg cagatacccg tgcacatgaa    7920
gtccgacgct tcgaagttca cccatgagaa accggagggg tactacaact ggcaccacgg    7980
agcagtacag tactcaggag gccggttcac catccctaca ggtgctggca accaggga     8040
cagcggcaga ccgatcttcg acaacaaggg acgcgtggtg gccatagtct taggaggagc    8100
taatgaagga gcccgtacag ccctctcggt ggtgacctgg aataaagaca ttgtcactaa    8160
aatcaccccc gaggggccg aagagtggag tcttgccatc ccagttatgt gcctgttggc     8220
aaacaccacg ttcccctgct cccagccccc ttgcacgccc tgctgctacg aaaaggaacc    8280
ggaggaaacc ctacgcatgc ttgaggacaa cgtcatgaga cctgggtact atcagctgct    8340
acaagcatcc ttaacatgtt ctccccaccg ccagcgacgc agcaccaagg acaacttcaa    8400
tgtctataaa gccacaagac catacttagc tcactgtccc gactgtggag aagggcactc    8460
gtgccatagt cccgtagcac tagaacgcat cagaaatgaa gcgacagacg ggacgctgaa    8520
aatccaggtc tccttgcaaa tcggaataaa gacggatgac agccacgatt ggaccaagct    8580
gcgttatatg gacaaccaca tgccagcaga cgcagagagg gcgggctat ttgtaagaac     8640
atcagcaccg tgtacgatta ctggaacaat gggacacttc atcctggccc gatgtccaaa    8700
aggggaaact ctgacggtgg gattcactga cagtaggaag attagtcact catgtacgca    8760
cccatttcac cacgaccctc ctgtgatagg tcgggaaaaa ttccattccc gaccgcagca    8820
cggtaaagag ctaccttgca gcacgtacgt gcagagcacc gccgcaacta ccgaggagat    8880
agaggtacac atgcccccag acacccctga tcgcacatta atgtcacaac agtccggcaa    8940
cgtaaagatc acagtcaatg gccagacggt gcggtacaag tgtaattgcg gtggctcaaa    9000
tgaaggacta acaactacag acaaagtgat taataactgc aaggttgatc aatgtcatgc    9060
cgcggtcacc aatcacaaaa agtggcagta taactccccct ctggtcccgc gtaatgctga    9120
acttgggac cgaaaggaa aaattcacat cccgtttccg ctggcaaatg taacatgcag     9180
ggtgcctaaa gcaaggaacc ccaccgtgac gtacggaaaa accaagtca tcatgctact    9240
gtatcctgac cacccaacac tcctgtccta ccggaatatg ggagaagaac caaactatca    9300
agaagagtgg gtgatgcata agaaggaagt cgtgctaacc gtgccgactg aagggctcga    9360
ggtcacgtgg ggcaacaacg agccgtataa gtattggccg cagttatcta caaacggtac    9420
agcccatggc caccgcatg agataattct gtattattat gagctgtacc ccactatgac    9480
tgtagtagtt gtgtcagtgg ccacgttcat actcctgtcg atggtgggta tggcagcggg    9540
gatgtgcatg tgtgcacgac gcagatgcat cacaccgtat gaactgacac caggagctac    9600
cgtcccttc ctgcttagcc taatatgctg catcagaaca gctaaagcgg ccacatacca    9660
```

```
agaggctgcg atatacctgt ggaacgagca gcaacctttg ttttggctac aagcccttat    9720
tccgctggca gccctgattg ttctatgcaa ctgtctgaga ctcttaccat gctgctgtaa    9780
aacgttggct tttttagccg taatgagcgt cggtgcccac actgtgagcg cgtacgaaca    9840
cgtaacagtg atcccgaaca cggtgggagt accgtataag actctagtca atagacctgg    9900
ctacagcccc atggtattgg agatggaact actgtcagtc actttggagc caacactatc    9960
gcttgattac atcacgtgcg agtacaaaac cgtcatcccg tctccgtacg tgaagtgctc   10020
cggtacagca gagtgcaagg acaaaaacct acctgactac agctgtaagg tcttcaccgg   10080
cgtctaccca tttatgtggg gcggcgccta ctgcttctgc gacgctgaaa acacgcagtt   10140
gagcgaagca cacgtggaga agtccgaatc atgcaaaaca gaatttgcat cagcatacag   10200
ggctcatacc gcatctgcat cagctaagct ccgcgtcctt taccaaggaa ataacatcac   10260
tgtaactgcc tatgcaaacg cgaccatgc cgtcacagtt aaggacgcca aattcattgt   10320
ggggccaatg tcttcagcct ggacaccttt cgacaacaaa attgtggtgt acaaaggtga   10380
cgtctataac atggactacc cgcccttttgg cgcaggaaga ccaggacaat tggcgatat   10440
ccaaagtcgc acacctgaga gtaaagacgt ctatgctaat acacaactgg tactgcagag   10500
accggctgtg ggtacggtac acgtgccata ctctcaggca ccatctggct ttaagtattg   10560
gctaaaagaa cgcggggcgt cgctgcagca cacagcacca tttggctgcc aaatagcaac   10620
aaacccggta gagcggtga actgcgccgt agggaacatg cccatctcca tcgacatacc   10680
ggaagcggcc ttcactaggg tcgtcgacgc gccctcttta acggacatgt cgtgcgaggt   10740
accagcctgc acccattcct cagactttgg gggcgtcgcc attattaaat atgcagccag   10800
caagaaaggc aagtgtgcgg tgcattcgat gactaacgcc gtcactattc gggaagctga   10860
gatagaagtt gaagggaatt ctcagctgca atctctttc tcgacggcct tagccagcgc   10920
cgaattccgc gtacaagtct gttctacaca agtacactgt gcagccgagt gccacccccc   10980
gaaggaccac atagtcaact acccggcgtc acataccacc ctcggggtcc aggacatctc   11040
cgctacggcg atgtcatggg tgcagaagat cacgggaggt gtgggactgg ttgttgctgt   11100
tgccgcactg attctaatcg tggtgctatg cgtgtcgttc agcaggcact aacttgacaa   11160
ttaagtatga aggtatatgt gtcccctaag agacacactg tacatagcaa ataatctata   11220
gatcaaaggg ctacgcaacc cctgaatagt aacaaaatac aaaatcacta aaattataa   11280
aaacagaaaa atacataaat aggtatacgt gtcccctaag agacacattg tatgtaggtg   11340
ataagtatag atcaaagggc cgaataaccc ctgaatagta acaaaatatg aaatcaata   11400
aaaatcataa aatagaaaaa ccataaacag aagtagttca aagggctata aaacccctga   11460
atagtaacaa aacataaaat taataaaaat caaatgaata ccataattgg caaacggaag   11520
agatgtaggt acttaagctt cctaaaagca gccgaactca ctttgagaag taggcatagc   11580
ataccgaact cttccacgat tctccgaacc cacagggacg taggagatgt tattttgttt   11640
ttaatatttc aaaaaaaaaa aaaaaaaaa aaaa                                 11674
```

<210> SEQ ID NO 78
<211> LENGTH: 10773
<212> TYPE: DNA
<213> ORGANISM: Zika virus

<400> SEQUENCE: 78

```
cagactgcga cagttcgagt ttgaagcgaa agctagcaac agtatcaaca ggttttattt      60
```

```
tggatttgga aacgagagtt tctggtcatg aaaaacccaa aaaagaaatc cggaggattc    120
cggattgtca atatgctaaa acgcggagta gcccgtgtga gcccctttgg gggcttgaag    180
aggctgccag ccggacttct gctgggtcat gggcccatca ggatggtctt ggcgattcta    240 gccttttga gattcacggc aatcaagcca tcactgggtc tcatcaatag atggggttca    300
gtggggaaaa aagaggctat ggaaataata aagaagttca agaaagatct ggctgccatg    360
ctgagaataa tcaatgctag gaaggagaag aagagacgag gcgcagatac tagtgtcgga    420
attgttggcc tcctgctgac cacagctatg gcagcggagg tcactagacg tgggagtgca    480
tactatatgt acttggacag aaacgacgct ggggaggcca tatctttcc aaccacattg    540 gggatgaata agtgttatat acagatcatg gatcttggac acatgtgtga tgccaccatg    600
agctatgaat gccctatgct ggatgagggg gtggaaccag atgacgtcga ttgttggtgc    660
aacacgacgt caacttgggt tgtgtacgga acctgccatc acaaaaaagg tgaagcacgg    720
agatctagaa gagctgtgac gctcccctcc cattccacta ggaagctgca aacgcggtcg    780
caaacctggt tggaatcaag agaatacaca aagcacttga ttagagtcga aaattggata    840
ttcaggaacc ctggcttcgc gttagcagca gctgccatcg cttggcttt gggaagctca    900 acgagccaaa aagtcatata cttggtcatg atactgctga ttgccccggc atacagcatc    960
aggtgcatag gagtcagcaa tagggacttt gtggaaggta tgtcaggtgg acttgggtt   1020 gatgttgtct tggaacatgg aggttgtgtc accgtaatgg cacaggacaa accgactgtc   1080
gacatagagc tggttacaac aacagtcagc aacatggcgg aggtaagatc ctactgctat   1140
gaggcatcaa tatcggacat ggcttcggac agccgctgcc caacacaagg tgaagcctac   1200
cttgacaagc aatcagacac tcaatatgtc tgcaaaagaa cgttagtgga cagaggctgg   1260
ggaaatggat gtggactttt tggcaaaggg agcctggtga catgcgctaa gtttgcatgc   1320
tccaagaaaa tgaccgggaa gagcatccag ccagagaatc tggagtaccg ataatgctg   1380 tcagttcatg gctcccagca cagtgggatg atcgttaatg acacaggaca tgaaactgat   1440
gagaatagag cgaaggttga gataacgccc aattcaccaa gagccgaagc caccctgggg   1500
ggttttggaa gcctaggact tgattgtgaa ccgaggacag gccttgactt ttcagatttg   1560
tattacttga ctatgaataa caagcactgg ttggttcaca ggagtggtt ccacgacatt   1620 ccattacctt ggcacgctgg ggcagacacc ggaactccac actggaacaa caaagaagca   1680
ctggtagagt tcaaggacgc acatgccaaa aggcaaactg tcgtggttct agggagtcaa   1740
gaaggagcag ttcacacggc ccttgctgga gctctggagg ctgagatgga tggtgcaaag   1800
ggaaggctgt cctctggcca cttgaaatgt cgcctgaaaa tggataaact tagattgaag   1860
ggcgtgtcat actccttgtg taccgcagcg ttcacattca caagatccc ggctgaaaca   1920 ctgcacggga cagtcacagt ggaggtacag tacgcaggga cagatggacc ttgcaaggtt   1980
ccagctcaga tggcggtgga catgcaaact ctgaccccag ttgggaggtt gataaccgct   2040
aaccccgtaa tcactgaaag cactgagaac tctaagatga tgctggaact tgatccacca   2100 tttgggact cttacattgt cataggagtc ggggagaaga gatcaccca ccactggcac   2160 aggagtggca gcaccattgg aaaagcattt gaagccactg tgagaggtgc aagagaatg   2220 gcagtcttgg gagacacagc ctgggactt ggatcagttg gaggcgctct caactcattg   2280
ggcaagggca tccatcaaat tttggagca gctttcaaat cattgtttgg aggaatgtcc   2340
tggttctcac aaattctcat tggaacgttg ctgatgtggt tgggtctgaa cacaaagaat   2400
ggatctattt cccttatgtg cttggcctta gggggagtgt tgatcttctt atccacagct   2460
```

```
gtctctgctg atgtggggtg ctcggtggac ttctcaaaga aggagacgag atgcggtaca    2520
ggggtgttcg tctataacga cgttgaagcc tggagggaca ggtacaagta ccatcctgac    2580
tcccccgta  gattggcagc agcagtcaag caagcctggg aagatggtat ctgtgggatc    2640
tcctctgttt caagaatgga aaacatcatg tggagatcag tagaagggga gctcaacgca    2700
atcctggaag agaatggagt tcaactgacg gtcgttgtgg gatctgtaaa aaaccccatg    2760
tggagaggtc cacagagatt gcccgtgcct gtgaacgagc tgccccacgg ctggaaggct    2820
tgggggaaat cgtacttcgt cagagcagca aagacaaata acagctttgt cgtggatggt    2880
gacacactga aggaatgccc actcaaacat agagcatgga acagcttcct tgtggaggat    2940
catgggttcg gggtatttca cactagtgtc tggctcaagg ttagagaaga ttattcatta    3000
gagtgtgatc cagccgttat tggaacagct gttaagggaa aggaggctgt acacagtgat    3060
ctaggctact ggattgagag tgagaagaat gacacatgga ggctgaagag ggcccatctg    3120
atcgagatga aacatgtgaa atggccaaag tcccacacat tgtggacaga tggaatagaa    3180
gagagtgatc tgatcatacc caagtctta  gctgggccac tcagccatca caataccaga    3240
gagggctaca ggacccaaat gaaagggcca tggcacagtg aagagcttga aattcggttt    3300
gaggaatgcc caggcactaa ggtccacgtg gaggaaacat gtggaacaag aggaccatct    3360
ctgagatcaa ccactgcaag cggaagggtg atcgaggaat ggtgctgcag ggagtgcaca    3420
atgccccac  tgtcgttccg ggctaaagat ggctgttggt atggaatgga gataaggccc    3480
aggaaagaac cagaaagtaa cttagtaagg tcaatggtga ctgcaggatc aactgatcac    3540
atggatcact tctcccttgg agtgcttgtg attctgctca tggtgcagga agggctgaag    3600
aagagaatga ccacaaagat catcataagc acatcgatgg cagtgctggt agctatgatc    3660
ctgggaggat tttcaatgag tgacctggct aagcttgcaa ttttgatggg tgccaccttc    3720
gcggaaatga acactggagg agatgtagct catctggcgc tgatagcggc attcaaagtc    3780
agaccagcgt tgctggtatc tttcatcttc agagctaatt ggacaccccg tgaaagcatg    3840
ctgctggcct tggcctcgtg tctttttgcaa actgcgatct ccgccttgga aggcgacctg    3900
atggttctca tcaatggttt tgcttggcc  tggttggcaa tacgagcgat ggttgttcca    3960
cgcactgata acatcacctt ggcaatcctg gctgctctga caccactggc ccggggcaca    4020
ctgcttgtgg cgtggagagc aggccttgct acttgcgggg ggtttatgct cctctctctg    4080
aagggaaaag gcagtgtgaa gaagaactta ccatttgtca tggccctggg actaaccgct    4140
gtgaggctgc tcgaccccat caacgtggtg ggactgctgt tgctcacaag gagtgggaag    4200
cggagctggc cccctagcga agtactcaca gctgttggcc tgatatgcgc attggctgga    4260
gggttcgcca aggcagatat agagatggct gggcccatgg ccgcggtcgg tctgctaatt    4320
gtcagttacg tggtctcagg aaagagtgtg gacatgtaca ttgaaagagc aggtgacatc    4380
acatgggaaa aagatgcgga agtcactgga aacagtcccc ggctcgatgt ggcgctagat    4440
gagagtggtg atttctccct ggtggaggat gacggtcccc ccatgagaga gatcatactc    4500
aaggtggtcc tgatgaccat ctgtggcatg aacccaatag ccatacccct tgcagctgga    4560
gcgtggtacg tatacgtgaa gactggaaaa aggagtggtg ctctatggga tgtgcctgct    4620
cccaaggaag taaaaagggg ggagaccaca gatggagtgt acagagtaat gactcgtaga    4680
ctgctaggtt caacacaagt tggagtggga gttatgcaag agggggtctt tcacactatg    4740
tggcacgtca caaaaggatc cgcgctgaga agcggtgaag ggagacttga tccatactgg    4800
```

```
ggagatgtca agcaggatct ggtgtcatac tgtggtccat ggaagctaga tgccgcctgg    4860
gacgggcaca gcgaggtgca gctcttggcc gtgcccccg gagagagagc gaggaacatc     4920
cagactctgc ccggaatatt taagacaaag gatggggaca ttggagcggt tgcgctggat    4980
tacccagcag gaacttcagg atctccaatc ctagacaagt gtgggagagt gataggactt    5040
tatggcaatg gggtcgtgat caaaaatggg agttatgtta gtgccatcac ccaagggagg    5100
agggaggaag agactcctgt tgagtgcttc gagccttcga tgctgaagaa gaagcagcta    5160
actgtcttag acttgcatcc tggagctggg aaaaccagga gagttcttcc tgaaatagtc    5220
cgtgaagcca taaaaacaag actccgtact gtgatcttag ctccaaccag ggttgtcgct    5280
gctgaaatgg aggaagccct tagagggctt ccagtgcgtt atatgacaac agcagtcaat    5340
gtcacccact ctggaacaga aatcgtcgac ttaatgtgcc atgccacctt cacttcacgt    5400
ctactacagc caatcagagt ccccaactat aatctgtata ttatggatga ggcccacttc    5460
acagatccct caagtatagc agcaagagga tacatttcaa caagggttga gatgggcgag    5520
gcggctgcca tcttcatgac cgccacgcca ccaggaaccc gtgacgcatt tccggactcc    5580
aactcaccaa ttatggacac cgaagtggaa gtcccagaga gagcctggag ctcaggcttt    5640
gattgggtga cggatcattc tggaaaaaca gtttggtttg ttccaagcgt gaggaacggc    5700
aatgagatcg cagcttgtct gacaaaggct ggaaaacggg tcatacagct cagcagaaag    5760 actttttgaga cagagttcca gaaaacaaaa catcaagagt gggactttgt cgtgacaact    5820
gacatttcag agatgggcgc caactttaaa gctgaccgtg tcatagattc caggagatgc    5880
ctaaagccgg tcatacttga tggcgagaga gtcattctgg ctggacccat gcctgtcaca    5940
catgccagcg ctgcccagag gaggggggcgc ataggcagga atcccaacaa acctggagat    6000
gagtatctgt atggaggtgg gtgcgcagag actgacgaag accatgcaca ctggcttgaa    6060
gcaagaatgc tccttgacaa tatttacctc caagatggcc tcatagcctc gctctatcga    6120
cctgaggcca caaagtagc agccattgag ggagagttca gcttaggac ggagcaaagg    6180 aagacctttg tggaactcat gaaaagagga gatcttcctg tttggctggc ctatcaggtt    6240
gcatctgccg gaataaccta cacagataga agatggtgct tgatggcac gaccaacaac    6300 accataatgg aagacagtgt gccggcagag gtgtggacca gacacggaga gaaaagagtg    6360
ctcaaaccga ggtggatgga cgccagagtt tgttcagatc atgcggccct gaagtcattc    6420
aaggagtttg ccgctgggaa aagaggagcg gcttttggag tgatggaagc cctgggaaca    6480
ctgccaggac acatgacaga gagattccag gaagccattg acaacctcgc tgtgctcatg    6540
cgggcagaga ctggaagcag gccttacaaa gccgcggcgg cccaattgcc ggagacccta    6600
gagaccatta tgcttttggg gttgctggga acagtctcgc tgggaatctt tttcgtcttg    6660
atgaggaaca agggcatagg gaagatgggc tttggaatgg tgactcttgg ggccagcgca    6720
tggctcatgt ggctctcgga aattgagcca gccagaattg catgtgtcct cattgttgtg    6780
ttcctattgc tggtggtgct catacctgag ccagaaaagc aaagatctcc ccaggacaac    6840
caaatggcaa tcatcatcat ggtagcagta ggtcttctgg gcttgattac cgccaatgaa    6900
ctcggatggt tggagagaac aaaagtgac ctaagccatc taatgggaag agagaggag    6960 ggggcaacca taggattctc aatggacatt gacctgcggc cagcctcagc ttgggccatc    7020
tatgctgcct tgacaacttt cattacccca gccgtccaac atgcagtgac cacttcatac    7080
aacaactact cctaatggc gatggccacg caagctggag tgttgttgg tatgggcaaa    7140 gggatgccat tctacgcatg ggacttttgga gtcccgctgc taatgatagg ttgctactca    7200
```

```
caattaacac ccctgaccct aatagtggcc atcattttgc tcgtggcgca ctacatgtac   7260
ttgatcccag ggctgcaggc agcagctgcg cgtgctgccc agaagagaac ggcagctggc   7320
atcatgaaga accctgttgt ggatggaata gtggtgactg acattgacac aatgacaatt   7380 gaccccaag tggagaaaaa gatgggacag gtgctactca tagcagtagc cgtctccagc   7440
gccatactgt cgcggaccgc ctgggggtgg ggggaggctg ggccctgat cacagcggca    7500 acttccactt tgtgggaagg ctctccgaac aagtactgga actcctctac agccacttca   7560
ctgtgtaaca tttttagggg aagttacttg gctggagctt ctctaatcta cacagtaaca   7620
agaaacgctg gcttggtcaa gagacgtggg ggtggaacag gagagaccct gggagagaaa   7680
tggaaggccc gcttgaacca gatgtcggcc ctggagttct actcctacaa aaagtcaggc   7740
atcaccgagg tgtgcagaga agaggcccgc cgcgccctca aggacggtgt ggcaacggga   7800
ggccatgctg tgtcccgagg aagtgcaaag ctgagatggt tggtggagcg gggatacctg   7860 cagcccatg gaaaggtcat tgatcttgga tgtggcagag ggggctggag ttactacgcc     7920
gccaccatcc gcaaagttca agaagtgaaa ggatacacaa aggaggccc tggtcatgaa    7980 gaacccatgt tggtgcaaag ctatgggtgg aacatagtcc gtcttaagag tggggtggac   8040
gtctttcata tggcggctga gccgtgtgac acgttgctgt gtgacatagg tgagtcatca   8100
tctagtcctg aagtggaaga agcacggacg ctcagagtcc tctccatggt gggggattgg   8160
cttgaaaaaa gaccaggagc cttttgtata aaagtgttgt gcccatacac cagcactatg   8220
atggaaaccc tggagcgact gcagcgtagg tatgggggag gactggtcag agtgccactc   8280
tcccgcaact ctacacatga gatgtactgg gtctctggag cgaaaagcaa caccataaaa   8340
agtgtgtcca ccacgagcca gctcctcttg gggcgcatgg acgggcccag gaggccagtg   8400
aaatatgagg aggatgtgaa tctcggctct ggcacgcggg ctgtggtaag ctgcgctgaa   8460
gctcccaaca tgaagatcat tggtaaccgc attgaaagga tccgcagtga gcacgcggaa   8520
acgtggttct ttgacgagaa ccacccatat aggacatggg cttaccatgg aagctatgag   8580 gccccacac aagggtcagc gtcctctcta ataaacgggg ttgtcaggct cctgtcaaaa     8640
ccctgggatg tggtgactgg agtcacagga atagccatga ccgacaccac accgtatggt   8700
cagcaaagag ttttcaagga aaaagtggac actagggtgc cagacccca agaaggcact    8760 cgtcaggtta tgagcatggt ctcttcctgg ttgtggaaag agctaggcaa acacaaacgg   8820
ccacgagtct gtaccaaaga agagttcatc aacaaggttc gtagcaatgc agcattaggg   8880
gcaatatttg aagaggaaaa agagtggaag actgcagtgg aagctgtgaa cgatccaagg   8940
ttctgggctc tagtggacaa ggaaagagag caccacctga gaggagagtg ccagagttgt   9000
gtgtacaaca tgatgggaaa aagagaaaag aaacaagggg aatttggaaa ggccaagggc   9060
agccgcgcca tctggtatat gtggctaggg ctagatttc tagagttcga agcccttgga    9120
ttcttgaacg aggatcactg gatggggaga gagaactcag gaggtggtgt gaagggctg     9180 ggattacaaa gactcggata tgtcctagaa gagatgagtc gcataccagg aggaaggatg   9240
tatgcagatg acactgctgg ctgggacacc cgcatcagca ggtttgatct ggagaatgaa   9300
gctctaatca ccaaccaaat ggagaaaggg cacagggcct tggcattggc cataatcaag   9360
tacacatacc aaaacaaagt ggtaaaggtc cttagaccag ctgaaaaagg gaagacagtt   9420
atggacatta tttcgagaca agaccaaagg gggagcggac aagttgtcac ttacgctctt   9480
aacacattta ccaacctagt ggtgcaactc attcggaata tggaggctga ggaagttcta   9540
```

-continued

```
gagatgcaag acttgtggct gctgcggagg tcagagaaag tgaccaactg gttgcagagc    9600
aacggatggg ataggctcaa acgaatggca gtcagtggag atgattgcgt tgtgaagcca    9660
attgatgata ggtttgcaca tgccctcagg ttcttgaatg atatgggaaa agttaggaag    9720
gacacacaag agtggaaacc ctcaactgga tgggacaact gggaagaagt tccgttttgc    9780
tcccaccact tcaacaagct ccatctcaag gacgggaggt ccattgtggt tccctgccgc    9840
caccaagatg aactgattgg ccgggcccgc gtctctccag gggcgggatg gagcatccgg    9900
gagactgctt gcctagcaaa atcatatgcg caaatgtggc agctcctta tttccacaga    9960 agggacctcc gactgatggc caatgccatt tgttcatctg tgccagttga ctgggttcca   10020
actgggagaa ctacctggtc aatccatgga aagggagaat ggatgaccac tgaagacatg   10080
cttgtggtgt ggaacagagt gtggattgag gagaacgacc acatggaaga caagacccca   10140
gttacgaaat ggacagacat tccctatttg gaaaaaggg aagacttgtg gtgtggatct   10200 ctcataggc acagaccgcg caccacctgg gctgagaaca ttaaaaacac agtcaacatg   10260
gtgcgcagga tcataggtga tgaagaaag tacatggact acctatccac ccaagttcgc   10320
tacttgggtg aagaagggtc tacacctgga gtgctgtaag caccaatctt agtgttgtca   10380
ggcctgctag tcagccacag cttggggaaa gctgtgcagc ctgtgacccc cccaggaaaa   10440
gctgggaaac caagcctata gtcaggccga aacgccatg gcacggaaga agccatgctg   10500
cctgtgagcc cctcagagga cactgagtca aaaaacccca cgcgcttgga ggcgcaggat   10560
gggaaaagaa ggtggcgacc ttccccaccc ttcaatctgg ggcctgaact ggagatcagc   10620
tgtggatctc cagaagaggg actagtggtt agaggagacc ccccggaaaa cgcaaaacag   10680
catattgacg ctgggaaaga ccagagactc catgagtttc caccacgctg gccgccaggc   10740
acagatcgcc gaatagcggc ggccggtgtg ggg                                10773
```

<210> SEQ ID NO 79
<211> LENGTH: 3423
<212> TYPE: PRT
<213> ORGANISM: Zika virus

<400> SEQUENCE: 79

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160
```

```
Met Asp Leu Gly His Met Cys Asp Ala Thr Met Ser Tyr Glu Cys Pro
            165                 170                 175

Met Leu Asp Glu Gly Val Glu Pro Asp Val Asp Cys Trp Cys Asn
        180                 185                 190

Thr Thr Ser Thr Trp Val Val Tyr Gly Thr Cys His His Lys Lys Gly
            195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
            245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
            275                 280                 285

Tyr Ser Ile Arg Cys Ile Gly Val Ser Asn Arg Asp Phe Val Glu Gly
            290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
            325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
            355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
            405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
    435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
            485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
            515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
            565                 570                 575
```

```
Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
        835                 840                 845

Cys Gly Ile Ser Ser Val Ser Arg Met Glu Asn Ile Met Trp Arg Ser
850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
        915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys  Asn Asp Thr Trp Arg  Leu Lys Arg
```

|  |  |  | 995 |  |  | 1000 |  |  | 1005 |  |
|---|---|---|---|---|---|---|---|---|---|---|

Ala His Leu Ile Glu Met Lys Thr Cys Glu Trp Pro Lys Ser His
    1010                1015                1020

Thr Leu Trp Thr Asp Gly Ile Glu Ser Asp Leu Ile Ile Pro
    1025                1030                1035

Lys Ser Leu Ala Gly Pro Leu Ser His Asn Thr Arg Glu Gly
    1040                1045                1050

Tyr Arg Thr Gln Met Lys Gly Pro Trp His Ser Glu Glu Leu Glu
    1055                1060                1065

Ile Arg Phe Glu Glu Cys Pro Gly Thr Lys Val His Val Glu Glu
    1070                1075                1080

Thr Cys Gly Thr Arg Gly Pro Ser Leu Arg Ser Thr Thr Ala Ser
    1085                1090                1095

Gly Arg Val Ile Glu Glu Trp Cys Cys Arg Glu Cys Thr Met Pro
    1100                1105                1110

Pro Leu Ser Phe Arg Ala Lys Asp Gly Cys Trp Tyr Gly Met Glu
    1115                1120                1125

Ile Arg Pro Arg Lys Glu Pro Glu Ser Asn Leu Val Arg Ser Met
    1130                1135                1140

Val Thr Ala Gly Ser Thr Asp His Met Asp His Phe Ser Leu Gly
    1145                1150                1155

Val Leu Val Ile Leu Leu Met Val Gln Glu Gly Leu Lys Lys Arg
    1160                1165                1170

Met Thr Thr Lys Ile Ile Ile Ser Thr Ser Met Ala Val Leu Val
    1175                1180                1185

Ala Met Ile Leu Gly Gly Phe Ser Met Ser Asp Leu Ala Lys Leu
    1190                1195                1200

Ala Ile Leu Met Gly Ala Thr Phe Ala Glu Met Asn Thr Gly Gly
    1205                1210                1215

Asp Val Ala His Leu Ala Leu Ile Ala Ala Phe Lys Val Arg Pro
    1220                1225                1230

Ala Leu Leu Val Ser Phe Ile Phe Arg Ala Asn Trp Thr Pro Arg
    1235                1240                1245

Glu Ser Met Leu Leu Ala Leu Ala Ser Cys Leu Leu Gln Thr Ala
    1250                1255                1260

Ile Ser Ala Leu Glu Gly Asp Leu Met Val Leu Ile Asn Gly Phe
    1265                1270                1275

Ala Leu Ala Trp Leu Ala Ile Arg Ala Met Val Val Pro Arg Thr
    1280                1285                1290

Asp Asn Ile Thr Leu Ala Ile Leu Ala Ala Leu Thr Pro Leu Ala
    1295                1300                1305

Arg Gly Thr Leu Leu Val Ala Trp Arg Ala Gly Leu Ala Thr Cys
    1310                1315                1320

Gly Gly Phe Met Leu Leu Ser Leu Lys Gly Lys Gly Ser Val Lys
    1325                1330                1335

Lys Asn Leu Pro Phe Val Met Ala Leu Gly Leu Thr Ala Val Arg
    1340                1345                1350

Leu Val Asp Pro Ile Asn Val Val Gly Leu Leu Leu Leu Thr Arg
    1355                1360                1365

Ser Gly Lys Arg Ser Trp Pro Pro Ser Glu Val Leu Thr Ala Val
    1370                1375                1380

Gly Leu Ile Cys Ala Leu Ala Gly Gly Phe Ala Lys Ala Asp Ile
    1385                1390                1395

-continued

```
Glu Met Ala Gly Pro Met Ala Ala Val Gly Leu Leu Ile Val Ser
    1400            1405                1410
Tyr Val Val Ser Gly Lys Ser Val Asp Met Tyr Ile Glu Arg Ala
    1415            1420                1425
Gly Asp Ile Thr Trp Glu Lys Asp Ala Glu Val Thr Gly Asn Ser
    1430            1435                1440
Pro Arg Leu Asp Val Ala Leu Asp Glu Ser Gly Asp Phe Ser Leu
    1445            1450                1455
Val Glu Asp Asp Gly Pro Pro Met Arg Glu Ile Ile Leu Lys Val
    1460            1465                1470
Val Leu Met Thr Ile Cys Gly Met Asn Pro Ile Ala Ile Pro Phe
    1475            1480                1485
Ala Ala Gly Ala Trp Tyr Val Tyr Val Lys Thr Gly Lys Arg Ser
    1490            1495                1500
Gly Ala Leu Trp Asp Val Pro Ala Pro Lys Glu Val Lys Lys Gly
    1505            1510                1515
Glu Thr Thr Asp Gly Val Tyr Arg Val Met Thr Arg Arg Leu Leu
    1520            1525                1530
Gly Ser Thr Gln Val Gly Val Gly Val Met Gln Glu Gly Val Phe
    1535            1540                1545
His Thr Met Trp His Val Thr Lys Gly Ser Ala Leu Arg Ser Gly
    1550            1555                1560
Glu Gly Arg Leu Asp Pro Tyr Trp Gly Asp Val Lys Gln Asp Leu
    1565            1570                1575
Val Ser Tyr Cys Gly Pro Trp Lys Leu Asp Ala Ala Trp Asp Gly
    1580            1585                1590
His Ser Glu Val Gln Leu Leu Ala Val Pro Pro Gly Glu Arg Ala
    1595            1600                1605
Arg Asn Ile Gln Thr Leu Pro Gly Ile Phe Lys Thr Lys Asp Gly
    1610            1615                1620
Asp Ile Gly Ala Val Ala Leu Asp Tyr Pro Ala Gly Thr Ser Gly
    1625            1630                1635
Ser Pro Ile Leu Asp Lys Cys Gly Arg Val Ile Gly Leu Tyr Gly
    1640            1645                1650
Asn Gly Val Val Ile Lys Asn Gly Ser Tyr Val Ser Ala Ile Thr
    1655            1660                1665
Gln Gly Arg Arg Glu Glu Glu Thr Pro Val Glu Cys Phe Glu Pro
    1670            1675                1680
Ser Met Leu Lys Lys Lys Gln Leu Thr Val Leu Asp Leu His Pro
    1685            1690                1695
Gly Ala Gly Lys Thr Arg Arg Val Leu Pro Glu Ile Val Arg Glu
    1700            1705                1710
Ala Ile Lys Thr Arg Leu Arg Thr Val Ile Leu Ala Pro Thr Arg
    1715            1720                1725
Val Val Ala Ala Glu Met Glu Glu Ala Leu Arg Gly Leu Pro Val
    1730            1735                1740
Arg Tyr Met Thr Thr Ala Val Asn Val Thr His Ser Gly Thr Glu
    1745            1750                1755
Ile Val Asp Leu Met Cys His Ala Thr Phe Thr Ser Arg Leu Leu
    1760            1765                1770
Gln Pro Ile Arg Val Pro Asn Tyr Asn Leu Tyr Ile Met Asp Glu
    1775            1780                1785
```

```
Ala His Phe Thr Asp Pro Ser Ser Ile Ala Arg Gly Tyr Ile
1790                1795                1800

Ser Thr Arg Val Glu Met Gly Glu Ala Ala Ile Phe Met Thr
1805                1810                1815

Ala Thr Pro Pro Gly Thr Arg Asp Ala Phe Pro Asp Ser Asn Ser
1820                1825                1830

Pro Ile Met Asp Thr Glu Val Glu Val Pro Glu Arg Ala Trp Ser
1835                1840                1845

Ser Gly Phe Asp Trp Val Thr Asp His Ser Gly Lys Thr Val Trp
1850                1855                1860

Phe Val Pro Ser Val Arg Asn Gly Asn Glu Ile Ala Ala Cys Leu
1865                1870                1875

Thr Lys Ala Gly Lys Arg Val Ile Gln Leu Ser Arg Lys Thr Phe
1880                1885                1890

Glu Thr Glu Phe Gln Lys Thr Lys His Gln Glu Trp Asp Phe Val
1895                1900                1905

Val Thr Thr Asp Ile Ser Glu Met Gly Ala Asn Phe Lys Ala Asp
1910                1915                1920

Arg Val Ile Asp Ser Arg Arg Cys Leu Lys Pro Val Ile Leu Asp
1925                1930                1935

Gly Glu Arg Val Ile Leu Ala Gly Pro Met Pro Val Thr His Ala
1940                1945                1950

Ser Ala Ala Gln Arg Arg Gly Arg Ile Gly Arg Asn Pro Asn Lys
1955                1960                1965

Pro Gly Asp Glu Tyr Leu Tyr Gly Gly Gly Cys Ala Glu Thr Asp
1970                1975                1980

Glu Asp His Ala His Trp Leu Glu Ala Arg Met Leu Leu Asp Asn
1985                1990                1995

Ile Tyr Leu Gln Asp Gly Leu Ile Ala Ser Leu Tyr Arg Pro Glu
2000                2005                2010

Ala Asp Lys Val Ala Ala Ile Glu Gly Glu Phe Lys Leu Arg Thr
2015                2020                2025

Glu Gln Arg Lys Thr Phe Val Glu Leu Met Lys Arg Gly Asp Leu
2030                2035                2040

Pro Val Trp Leu Ala Tyr Gln Val Ala Ser Ala Gly Ile Thr Tyr
2045                2050                2055

Thr Asp Arg Arg Trp Cys Phe Asp Gly Thr Thr Asn Asn Thr Ile
2060                2065                2070

Met Glu Asp Ser Val Pro Ala Glu Val Trp Thr Arg His Gly Glu
2075                2080                2085

Lys Arg Val Leu Lys Pro Arg Trp Met Asp Ala Arg Val Cys Ser
2090                2095                2100

Asp His Ala Ala Leu Lys Ser Phe Lys Glu Phe Ala Ala Gly Lys
2105                2110                2115

Arg Gly Ala Ala Phe Gly Val Met Glu Ala Leu Gly Thr Leu Pro
2120                2125                2130

Gly His Met Thr Glu Arg Phe Gln Glu Ala Ile Asp Asn Leu Ala
2135                2140                2145

Val Leu Met Arg Ala Glu Thr Gly Ser Arg Pro Tyr Lys Ala Ala
2150                2155                2160

Ala Ala Gln Leu Pro Glu Thr Leu Glu Thr Ile Met Leu Leu Gly
2165                2170                2175

Leu Leu Gly Thr Val Ser Leu Gly Ile Phe Phe Val Leu Met Arg
```

```
                        2180                    2185                    2190

Asn  Lys  Gly  Ile  Gly  Lys  Met  Gly  Phe  Gly  Met  Val  Thr  Leu  Gly
          2195                    2200                    2205

Ala  Ser  Ala  Trp  Leu  Met  Trp  Leu  Ser  Glu  Ile  Glu  Pro  Ala  Arg
          2210                    2215                    2220

Ile  Ala  Cys  Val  Leu  Ile  Val  Val  Phe  Leu  Leu  Leu  Val  Val  Leu
          2225                    2230                    2235

Ile  Pro  Glu  Pro  Glu  Lys  Gln  Arg  Ser  Pro  Gln  Asp  Asn  Gln  Met
          2240                    2245                    2250

Ala  Ile  Ile  Ile  Met  Val  Ala  Val  Gly  Leu  Leu  Gly  Leu  Ile  Thr
          2255                    2260                    2265

Ala  Asn  Glu  Leu  Gly  Trp  Leu  Glu  Arg  Thr  Lys  Ser  Asp  Leu  Ser
          2270                    2275                    2280

His  Leu  Met  Gly  Arg  Arg  Glu  Glu  Gly  Ala  Thr  Ile  Gly  Phe  Ser
          2285                    2290                    2295

Met  Asp  Ile  Asp  Leu  Arg  Pro  Ala  Ser  Ala  Trp  Ala  Ile  Tyr  Ala
          2300                    2305                    2310

Ala  Leu  Thr  Thr  Phe  Ile  Thr  Pro  Ala  Val  Gln  His  Ala  Val  Thr
          2315                    2320                    2325

Thr  Ser  Tyr  Asn  Asn  Tyr  Ser  Leu  Met  Ala  Met  Ala  Thr  Gln  Ala
          2330                    2335                    2340

Gly  Val  Leu  Phe  Gly  Met  Gly  Lys  Gly  Met  Pro  Phe  Tyr  Ala  Trp
          2345                    2350                    2355

Asp  Phe  Gly  Val  Pro  Leu  Leu  Met  Ile  Gly  Cys  Tyr  Ser  Gln  Leu
          2360                    2365                    2370

Thr  Pro  Leu  Thr  Leu  Ile  Val  Ala  Ile  Ile  Leu  Leu  Val  Ala  His
          2375                    2380                    2385

Tyr  Met  Tyr  Leu  Ile  Pro  Gly  Leu  Gln  Ala  Ala  Ala  Ala  Arg  Ala
          2390                    2395                    2400

Ala  Gln  Lys  Arg  Thr  Ala  Ala  Gly  Ile  Met  Lys  Asn  Pro  Val  Val
          2405                    2410                    2415

Asp  Gly  Ile  Val  Val  Thr  Asp  Ile  Asp  Thr  Met  Thr  Ile  Asp  Pro
          2420                    2425                    2430

Gln  Val  Glu  Lys  Lys  Met  Gly  Gln  Val  Leu  Leu  Ile  Ala  Val  Ala
          2435                    2440                    2445

Val  Ser  Ser  Ala  Ile  Leu  Ser  Arg  Thr  Ala  Trp  Gly  Trp  Gly  Glu
          2450                    2455                    2460

Ala  Gly  Ala  Leu  Ile  Thr  Ala  Ala  Thr  Ser  Thr  Leu  Trp  Glu  Gly
          2465                    2470                    2475

Ser  Pro  Asn  Lys  Tyr  Trp  Asn  Ser  Ser  Thr  Ala  Thr  Ser  Leu  Cys
          2480                    2485                    2490

Asn  Ile  Phe  Arg  Gly  Ser  Tyr  Leu  Ala  Gly  Ala  Ser  Leu  Ile  Tyr
          2495                    2500                    2505

Thr  Val  Thr  Arg  Asn  Ala  Gly  Leu  Val  Lys  Arg  Arg  Gly  Gly  Gly
          2510                    2515                    2520

Thr  Gly  Glu  Thr  Leu  Gly  Glu  Lys  Trp  Lys  Ala  Arg  Leu  Asn  Gln
          2525                    2530                    2535

Met  Ser  Ala  Leu  Glu  Phe  Tyr  Ser  Tyr  Lys  Lys  Ser  Gly  Ile  Thr
          2540                    2545                    2550

Glu  Val  Cys  Arg  Glu  Glu  Ala  Arg  Arg  Ala  Leu  Lys  Asp  Gly  Val
          2555                    2560                    2565

Ala  Thr  Gly  Gly  His  Ala  Val  Ser  Arg  Gly  Ser  Ala  Lys  Leu  Arg
          2570                    2575                    2580
```

-continued

Trp Leu Val Glu Arg Gly Tyr Leu Gln Pro Tyr Gly Lys Val Ile
2585                2590                2595

Asp Leu Gly Cys Gly Arg Gly Gly Trp Ser Tyr Tyr Ala Ala Thr
2600                2605                2610

Ile Arg Lys Val Gln Glu Val Lys Gly Tyr Thr Lys Gly Gly Pro
2615                2620                2625

Gly His Glu Glu Pro Met Leu Val Gln Ser Tyr Gly Trp Asn Ile
2630                2635                2640

Val Arg Leu Lys Ser Gly Val Asp Val Phe His Met Ala Ala Glu
2645                2650                2655

Pro Cys Asp Thr Leu Leu Cys Asp Ile Gly Glu Ser Ser Ser Ser
2660                2665                2670

Pro Glu Val Glu Glu Ala Arg Thr Leu Arg Val Leu Ser Met Val
2675                2680                2685

Gly Asp Trp Leu Glu Lys Arg Pro Gly Ala Phe Cys Ile Lys Val
2690                2695                2700

Leu Cys Pro Tyr Thr Ser Thr Met Met Glu Thr Leu Glu Arg Leu
2705                2710                2715

Gln Arg Arg Tyr Gly Gly Gly Leu Val Arg Val Pro Leu Ser Arg
2720                2725                2730

Asn Ser Thr His Glu Met Tyr Trp Val Ser Gly Ala Lys Ser Asn
2735                2740                2745

Thr Ile Lys Ser Val Ser Thr Thr Ser Gln Leu Leu Leu Gly Arg
2750                2755                2760

Met Asp Gly Pro Arg Arg Pro Val Lys Tyr Glu Glu Asp Val Asn
2765                2770                2775

Leu Gly Ser Gly Thr Arg Ala Val Val Ser Cys Ala Glu Ala Pro
2780                2785                2790

Asn Met Lys Ile Ile Gly Asn Arg Ile Glu Arg Ile Arg Ser Glu
2795                2800                2805

His Ala Glu Thr Trp Phe Phe Asp Glu Asn His Pro Tyr Arg Thr
2810                2815                2820

Trp Ala Tyr His Gly Ser Tyr Glu Ala Pro Thr Gln Gly Ser Ala
2825                2830                2835

Ser Ser Leu Ile Asn Gly Val Val Arg Leu Leu Ser Lys Pro Trp
2840                2845                2850

Asp Val Val Thr Gly Val Thr Gly Ile Ala Met Thr Asp Thr Thr
2855                2860                2865

Pro Tyr Gly Gln Gln Arg Val Phe Lys Glu Lys Val Asp Thr Arg
2870                2875                2880

Val Pro Asp Pro Gln Glu Gly Thr Arg Gln Val Met Ser Met Val
2885                2890                2895

Ser Ser Trp Leu Trp Lys Glu Leu Gly Lys His Lys Arg Pro Arg
2900                2905                2910

Val Cys Thr Lys Glu Glu Phe Ile Asn Lys Val Arg Ser Asn Ala
2915                2920                2925

Ala Leu Gly Ala Ile Phe Glu Glu Lys Glu Trp Lys Thr Ala
2930                2935                2940

Val Glu Ala Val Asn Asp Pro Arg Phe Trp Ala Leu Val Asp Lys
2945                2950                2955

Glu Arg Glu His His Leu Arg Gly Glu Cys Gln Ser Cys Val Tyr
2960                2965                2970

Asn Met Met Gly Lys Arg Glu Lys Lys Gln Gly Glu Phe Gly Lys
2975                    2980                    2985

Ala Lys Gly Ser Arg Ala Ile Trp Tyr Met Trp Leu Gly Ala Arg
2990                    2995                    3000

Phe Leu Glu Phe Glu Ala Leu Gly Phe Leu Asn Glu Asp His Trp
3005                    3010                    3015

Met Gly Arg Glu Asn Ser Gly Gly Val Glu Gly Leu Gly Leu
3020                    3025                    3030

Gln Arg Leu Gly Tyr Val Leu Glu Glu Met Ser Arg Ile Pro Gly
3035                    3040                    3045

Gly Arg Met Tyr Ala Asp Asp Thr Ala Gly Trp Asp Thr Arg Ile
3050                    3055                    3060

Ser Arg Phe Asp Leu Glu Asn Glu Ala Leu Ile Thr Asn Gln Met
3065                    3070                    3075

Glu Lys Gly His Arg Ala Leu Ala Leu Ala Ile Lys Tyr Thr
3080                    3085                    3090

Tyr Gln Asn Lys Val Val Lys Val Leu Arg Pro Ala Glu Lys Gly
3095                    3100                    3105

Lys Thr Val Met Asp Ile Ile Ser Arg Gln Asp Gln Arg Gly Ser
3110                    3115                    3120

Gly Gln Val Val Thr Tyr Ala Leu Asn Thr Phe Thr Asn Leu Val
3125                    3130                    3135

Val Gln Leu Ile Arg Asn Met Glu Ala Glu Glu Val Leu Glu Met
3140                    3145                    3150

Gln Asp Leu Trp Leu Leu Arg Arg Ser Glu Lys Val Thr Asn Trp
3155                    3160                    3165

Leu Gln Ser Asn Gly Trp Asp Arg Leu Lys Arg Met Ala Val Ser
3170                    3175                    3180

Gly Asp Asp Cys Val Val Lys Pro Ile Asp Asp Arg Phe Ala His
3185                    3190                    3195

Ala Leu Arg Phe Leu Asn Asp Met Gly Lys Val Arg Lys Asp Thr
3200                    3205                    3210

Gln Glu Trp Lys Pro Ser Thr Gly Trp Asp Asn Trp Glu Glu Val
3215                    3220                    3225

Pro Phe Cys Ser His His Phe Asn Lys Leu His Leu Lys Asp Gly
3230                    3235                    3240

Arg Ser Ile Val Val Pro Cys Arg His Gln Asp Glu Leu Ile Gly
3245                    3250                    3255

Arg Ala Arg Val Ser Pro Gly Ala Gly Trp Ser Ile Arg Glu Thr
3260                    3265                    3270

Ala Cys Leu Ala Lys Ser Tyr Ala Gln Met Trp Gln Leu Leu Tyr
3275                    3280                    3285

Phe His Arg Arg Asp Leu Arg Leu Met Ala Asn Ala Ile Cys Ser
3290                    3295                    3300

Ser Val Pro Val Asp Trp Val Pro Thr Gly Arg Thr Thr Trp Ser
3305                    3310                    3315

Ile His Gly Lys Gly Glu Trp Met Thr Thr Glu Asp Met Leu Val
3320                    3325                    3330

Val Trp Asn Arg Val Trp Ile Glu Glu Asn Asp His Met Glu Asp
3335                    3340                    3345

Lys Thr Pro Val Thr Lys Trp Thr Asp Ile Pro Tyr Leu Gly Lys
3350                    3355                    3360

Arg Glu Asp Leu Trp Cys Gly Ser Leu Ile Gly His Arg Pro Arg

```
                3365                3370                3375
       Thr  Thr  Trp  Ala  Glu  Asn  Ile  Lys  Asn  Thr  Val  Asn  Met  Val  Arg
            3380                3385                3390

Arg  Ile  Ile  Gly  Asp  Glu  Glu  Lys  Tyr  Met  Asp  Tyr  Leu  Ser  Thr
       3395                3400                3405

Gln  Val  Arg  Tyr  Leu  Gly  Glu  Glu  Gly  Ser  Thr  Pro  Gly  Val  Leu
            3410                3415                3420
```

<210> SEQ ID NO 80
<211> LENGTH: 28
<212> TYPE: DNA
<213> ORGANISM: Artificial Sequence
<220> FEATURE:
<223> OTHER INFORMATION: primer

<400> SEQUENCE: 80
ttaggatccg ttgttgatct gtgtgaat                                    28

<210> SEQ ID NO 81
<211> LENGTH: 26
<212> TYPE: DNA
<213> ORGANISM: Artificial Sequence
<220> FEATURE:
<223> OTHER INFORMATION: primer

<400> SEQUENCE: 81
taactcgagc gtacacaacc caagtt                                      26

<210> SEQ ID NO 82
<211> LENGTH: 27
<212> TYPE: DNA
<213> ORGANISM: Artificial Sequence
<220> FEATURE:
<223> OTHER INFORMATION: primer

<400> SEQUENCE: 82
ttaggatcct cactagacgt gggagtg                                     27

<210> SEQ ID NO 83
<211> LENGTH: 29
<212> TYPE: DNA
<213> ORGANISM: Artificial Sequence
<220> FEATURE:
<223> OTHER INFORMATION: primer

<400> SEQUENCE: 83
taactcgaga agccatgtcy gatattgat                                   29

<210> SEQ ID NO 84
<211> LENGTH: 26
<212> TYPE: DNA
<213> ORGANISM: Artificial Sequence
<220> FEATURE:
<223> OTHER INFORMATION: primer

<400> SEQUENCE: 84
ttaggatccg catacagcat caggtg                                      26

<210> SEQ ID NO 85
<211> LENGTH: 27
<212> TYPE: DNA
<213> ORGANISM: Artificial Sequence
<220> FEATURE:
<223> OTHER INFORMATION: primer

```
<400> SEQUENCE: 85
taactcgagt gtggagttcc ggtgtct                                27

<210> SEQ ID NO 86
<211> LENGTH: 31
<212> TYPE: DNA
<213> ORGANISM: Artificial Sequence
<220> FEATURE:
<223> OTHER INFORMATION: primer

<400> SEQUENCE: 86
ttaggatccg aatagagcga argttgagat a                           31

<210> SEQ ID NO 87
<211> LENGTH: 28
<212> TYPE: DNA
<213> ORGANISM: Artificial Sequence
<220> FEATURE:
<223> OTHER INFORMATION: primer

<400> SEQUENCE: 87
taactcgagt ggtgggtgat cttcttct                               28

<210> SEQ ID NO 88
<211> LENGTH: 31
<212> TYPE: DNA
<213> ORGANISM: Artificial Sequence
<220> FEATURE:
<223> OTHER INFORMATION: primer

<400> SEQUENCE: 88
ttaggatcca gtcacagtgg aggtacagta c                           31

<210> SEQ ID NO 89
<211> LENGTH: 27
<212> TYPE: DNA
<213> ORGANISM: Artificial Sequence
<220> FEATURE:
<223> OTHER INFORMATION: primer

<400> SEQUENCE: 89
taactcgagc rcagatacca tcttccc                                27

<210> SEQ ID NO 90
<211> LENGTH: 28
<212> TYPE: DNA
<213> ORGANISM: Artificial Sequence
<220> FEATURE:
<223> OTHER INFORMATION: primer

<400> SEQUENCE: 90
ttaggatccc ttatgtgctt ggccttag                               28

<210> SEQ ID NO 91
<211> LENGTH: 26
<212> TYPE: DNA
<213> ORGANISM: Artificial Sequence
<220> FEATURE:
<223> OTHER INFORMATION: primer

<400> SEQUENCE: 91
taactcgagt cttcagcctc catgtg                                 26

<210> SEQ ID NO 92
<211> LENGTH: 29
```

```
<212> TYPE: DNA
<213> ORGANISM: Artificial Sequence
<220> FEATURE:
<223> OTHER INFORMATION: primer

<400> SEQUENCE: 92
ttaggatcca atgcccactc aaacataga                                29

<210> SEQ ID NO 93
<211> LENGTH: 30
<212> TYPE: DNA
<213> ORGANISM: Artificial Sequence
<220> FEATURE:
<223> OTHER INFORMATION: primer

<400> SEQUENCE: 93
taactcgagt cattctcttc ttcagcccett                              30

<210> SEQ ID NO 94
<211> LENGTH: 26
<212> TYPE: DNA
<213> ORGANISM: Artificial Sequence
<220> FEATURE:
<223> OTHER INFORMATION: primer

<400> SEQUENCE: 94
ttaggatcca agggtgatcg aggaat                                   26

<210> SEQ ID NO 95
<211> LENGTH: 29
<212> TYPE: DNA
<213> ORGANISM: Artificial Sequence
<220> FEATURE:
<223> OTHER INFORMATION: primer

<400> SEQUENCE: 95
taactcgagt tcccttcaga gagaggagc                                29

<210> SEQ ID NO 96
<211> LENGTH: 28
<212> TYPE: DNA
<213> ORGANISM: Artificial Sequence
<220> FEATURE:
<223> OTHER INFORMATION: primer

<400> SEQUENCE: 96
ttaggatcct cttttgcaaa ctgcgatc                                 28

<210> SEQ ID NO 97
<211> LENGTH: 27
<212> TYPE: DNA
<213> ORGANISM: Artificial Sequence
<220> FEATURE:
<223> OTHER INFORMATION: primer

<400> SEQUENCE: 97
taactcgagt ccagctgcaa agggtat                                  27

<210> SEQ ID NO 98
<211> LENGTH: 28
<212> TYPE: DNA
<213> ORGANISM: Artificial Sequence
<220> FEATURE:
<223> OTHER INFORMATION: primer

<400> SEQUENCE: 98
```

```
ttaggatccg tgtggacatg tacattga                                28

<210> SEQ ID NO 99
<211> LENGTH: 26
<212> TYPE: DNA
<213> ORGANISM: Artificial Sequence
<220> FEATURE:
<223> OTHER INFORMATION: primer

<400> SEQUENCE: 99
taactcgagc ccattgccat aaagtc                                  26

<210> SEQ ID NO 100
<211> LENGTH: 28
<212> TYPE: DNA
<213> ORGANISM: Artificial Sequence
<220> FEATURE:
<223> OTHER INFORMATION: primer

<400> SEQUENCE: 100
ttaggatcct catactgtgg tccatgga                                28

<210> SEQ ID NO 101
<211> LENGTH: 26
<212> TYPE: DNA
<213> ORGANISM: Artificial Sequence
<220> FEATURE:
<223> OTHER INFORMATION: primer

<400> SEQUENCE: 101
taactcgagg cccatctcaa cccttg                                  26

<210> SEQ ID NO 102
<211> LENGTH: 26
<212> TYPE: DNA
<213> ORGANISM: Artificial Sequence
<220> FEATURE:
<223> OTHER INFORMATION: primer

<400> SEQUENCE: 102
ttaggatcct agagggcttc cagtgc                                  26

<210> SEQ ID NO 103
<211> LENGTH: 31
<212> TYPE: DNA
<213> ORGANISM: Artificial Sequence
<220> FEATURE:
<223> OTHER INFORMATION: primer

<400> SEQUENCE: 103
taactcgaga tactcatctc caggtttgtt g                            31

<210> SEQ ID NO 104
<211> LENGTH: 30
<212> TYPE: DNA
<213> ORGANISM: Artificial Sequence
<220> FEATURE:
<223> OTHER INFORMATION: primer

<400> SEQUENCE: 104
ttaggatccg aaaacaaaac atcaagagtg                              30

<210> SEQ ID NO 105
<211> LENGTH: 31
<212> TYPE: DNA
<213> ORGANISM: Artificial Sequence
```

<220> FEATURE:
<223> OTHER INFORMATION: primer

<400> SEQUENCE: 105
taactcgagg aatctctctg tcatgtgtcc t					31

<210> SEQ ID NO 106
<211> LENGTH: 26
<212> TYPE: DNA
<213> ORGANISM: Artificial Sequence
<220> FEATURE:
<223> OTHER INFORMATION: primer

<400> SEQUENCE: 106
ttaggatcct tgatggcacg accaac					26

<210> SEQ ID NO 107
<211> LENGTH: 28
<212> TYPE: DNA
<213> ORGANISM: Artificial Sequence
<220> FEATURE:
<223> OTHER INFORMATION: primer

<400> SEQUENCE: 107
ttaggatccg ttgttgatct gtgtgaat					28

<210> SEQ ID NO 108
<211> LENGTH: 26
<212> TYPE: DNA
<213> ORGANISM: Artificial Sequence
<220> FEATURE:
<223> OTHER INFORMATION: primer

<400> SEQUENCE: 108
taactcgagc aggtcaatgt ccattg					26

<210> SEQ ID NO 109
<211> LENGTH: 30
<212> TYPE: DNA
<213> ORGANISM: Artificial Sequence
<220> FEATURE:
<223> OTHER INFORMATION: primer

<400> SEQUENCE: 109
ttaggatcct gttgtgttcc tattgctggt					30

<210> SEQ ID NO 110
<211> LENGTH: 25
<212> TYPE: DNA
<213> ORGANISM: Artificial Sequence
<220> FEATURE:
<223> OTHER INFORMATION: primer

<400> SEQUENCE: 110
taactcgagt gatcagrgcc ccagc					25

<210> SEQ ID NO 111
<211> LENGTH: 26
<212> TYPE: DNA
<213> ORGANISM: Artificial Sequence
<220> FEATURE:
<223> OTHER INFORMATION: primer

<400> SEQUENCE: 111
ttaggatcct gctgcccaga agagaa					26

<210> SEQ ID NO 112
<211> LENGTH: 26
<212> TYPE: DNA
<213> ORGANISM: Artificial Sequence
<220> FEATURE:
<223> OTHER INFORMATION: primer

<400> SEQUENCE: 112
taactcgagc accaacaygg gttctt                                          26

<210> SEQ ID NO 113
<211> LENGTH: 25
<212> TYPE: DNA
<213> ORGANISM: Artificial Sequence
<220> FEATURE:
<223> OTHER INFORMATION: primer

<400> SEQUENCE: 113
ttaggatcct caaggacggt gtggc                                           25

<210> SEQ ID NO 114
<211> LENGTH: 28
<212> TYPE: DNA
<213> ORGANISM: Artificial Sequence
<220> FEATURE:
<223> OTHER INFORMATION: primer

<400> SEQUENCE: 114
taactcgagc aatgatcttc atgttggg                                        28

<210> SEQ ID NO 115
<211> LENGTH: 26
<212> TYPE: DNA
<213> ORGANISM: Artificial Sequence
<220> FEATURE:
<223> OTHER INFORMATION: primer

<400> SEQUENCE: 115
ttaggatcct atgggggagg actggt                                          26

<210> SEQ ID NO 116
<211> LENGTH: 25
<212> TYPE: DNA
<213> ORGANISM: Artificial Sequence
<220> FEATURE:
<223> OTHER INFORMATION: primer

<400> SEQUENCE: 116
taactcgagc ccagaacctt ggatc                                           25

<210> SEQ ID NO 117
<211> LENGTH: 25
<212> TYPE: DNA
<213> ORGANISM: Artificial Sequence
<220> FEATURE:
<223> OTHER INFORMATION: primer

<400> SEQUENCE: 117
ttaggatcca gaccccaag aaggc                                            25

<210> SEQ ID NO 118
<211> LENGTH: 26
<212> TYPE: DNA
<213> ORGANISM: Artificial Sequence
<220> FEATURE:
<223> OTHER INFORMATION: primer

```
<400> SEQUENCE: 118
taactcgagc ccctttggtc ttgtct                                          26

<210> SEQ ID NO 119
<211> LENGTH: 29
<212> TYPE: DNA
<213> ORGANISM: Artificial Sequence
<220> FEATURE:
<223> OTHER INFORMATION: primer

<400> SEQUENCE: 119
ttaggatcca ggaaggatgt atgcagatg                                       29

<210> SEQ ID NO 120
<211> LENGTH: 30
<212> TYPE: DNA
<213> ORGANISM: Artificial Sequence
<220> FEATURE:
<223> OTHER INFORMATION: primer

<400> SEQUENCE: 120
taactcgaga catttgcgca tatgattttg                                      30

<210> SEQ ID NO 121
<211> LENGTH: 28
<212> TYPE: DNA
<213> ORGANISM: Artificial Sequence
<220> FEATURE:
<223> OTHER INFORMATION: primer

<400> SEQUENCE: 121
ttaggatcca ggaaggacac acaagagt                                        28

<210> SEQ ID NO 122
<211> LENGTH: 26
<212> TYPE: DNA
<213> ORGANISM: Artificial Sequence
<220> FEATURE:
<223> OTHER INFORMATION: primer

<400> SEQUENCE: 122
taactcgaga caggctgcac agcttt                                          26

<210> SEQ ID NO 123
<211> LENGTH: 28
<212> TYPE: DNA
<213> ORGANISM: Artificial Sequence
<220> FEATURE:
<223> OTHER INFORMATION: primer

<400> SEQUENCE: 123
ttaggatcct ctctcatagg gcacagac                                        28
```